US008703726B2

(12) United States Patent
Cao et al.

(10) Patent No.: US 8,703,726 B2
(45) Date of Patent: Apr. 22, 2014

(54) METHODS FOR TREATING PROSTATE CONDITIONS

(75) Inventors: Liangxian Cao, Parlin, NJ (US); Thomas W. Davis, South Orange, NJ (US); Samit Hirawat, Chatham, NJ (US); Harry H. Miao, Wellsley, MA (US); Langdon Miller, Seattle, WA (US); Charles M. Romfo, Easton, PA (US); Marla L. Weetall, Morristown, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 13/321,213

(22) PCT Filed: May 27, 2010

(86) PCT No.: PCT/US2010/036345
§ 371 (c)(1),
(2), (4) Date: Mar. 23, 2012

(87) PCT Pub. No.: WO2010/138685
PCT Pub. Date: Dec. 2, 2010

(65) Prior Publication Data
US 2012/0178707 A1 Jul. 12, 2012

Related U.S. Application Data

(60) Provisional application No. 61/181,649, filed on May 27, 2009.

(51) Int. Cl.
*A61K 31/437* (2006.01)
(52) U.S. Cl.
USPC .......................................................... 514/35
(58) Field of Classification Search
USPC .......................................................... 514/35
See application file for complete search history.

(56) References Cited

U.S. PATENT DOCUMENTS

| | | | |
|---|---|---|---|
| 3,328,412 A | 6/1967 | Atkinson et al. | |
| 5,206,377 A | 4/1993 | McAfee | |
| 5,314,908 A | 5/1994 | McAfee | |
| 5,500,431 A | 3/1996 | Audia et al. | |
| 5,760,051 A | 6/1998 | Audia et al. | |
| 5,866,587 A | 2/1999 | de Nanteuil et al. | |
| 6,090,945 A | 7/2000 | Audia et al. | |
| 6,093,723 A | 7/2000 | Miao et al. | |
| 6,720,331 B2 | 4/2004 | Yeh et al. | |
| 7,341,749 B2* | 3/2008 | Hall et al. | 424/725 |
| 7,601,840 B2 | 10/2009 | Moon et al. | |
| 7,767,689 B2 | 8/2010 | Moon et al. | |
| 7,872,133 B2 | 1/2011 | Ohmoto et al. | |
| 8,076,352 B2 | 12/2011 | Cao et al. | |
| 8,076,353 B2 | 12/2011 | Cao et al. | |
| 8,367,694 B2 | 2/2013 | Moon et al. | |
| 8,372,860 B2 | 2/2013 | Moon et al. | |
| 2003/0040527 A1 | 2/2003 | Yeh et al. | |
| 2003/0130293 A1 | 7/2003 | Bamdad | |
| 2004/0116458 A1 | 6/2004 | Sawyer et al. | |
| 2005/0143371 A1 | 6/2005 | Meyers et al. | |
| 2005/0282849 A1 | 12/2005 | Moon et al. | |
| 2006/0241084 A1 | 10/2006 | Roifman et al. | |
| 2007/0254878 A1* | 11/2007 | Cao et al. | 514/232.8 |
| 2008/0103164 A1 | 5/2008 | Gudmundsson et al. | |
| 2008/0103213 A1 | 5/2008 | Kurzrock et al. | |
| 2008/0293766 A1 | 11/2008 | Diamond et al. | |

(Continued)

FOREIGN PATENT DOCUMENTS

| | | |
|---|---|---|
| EP | 0357122 A2 | 3/1990 |
| EP | 0549916 A2 | 7/1993 |
| FR | 2662940 A1 | 12/1991 |
| JP | 3-287586 | 12/1991 |
| JP | 4275221 | 9/2002 |
| WO | WO 91/18604 | 12/1991 |
| WO | WO 94/10175 | 5/1994 |
| WO | WO 95/26723 | 10/1995 |
| WO | WO 97/37658 | 10/1997 |
| WO | WO 02/062339 A1 | 8/2002 |
| WO | WO 02/064590 A2 | 8/2002 |
| WO | WO 02/064591 A2 | 8/2002 |
| WO | WO 03/020279 A2 | 3/2003 |
| WO | WO 03/033496 A1 | 4/2003 |
| WO | WO 03/099821 A1 | 12/2003 |

(Continued)

OTHER PUBLICATIONS

U.S. Appl. No. 13/274,412, filed Oct. 17, 2011, Cao et al.
Begum et al., 1996, "Chemistry and biological activity of a tryptamine and beta-carboline series of bases", Drug Research; 12(46):1163-1168.
Berrougui et al., 2005, "Cytotoxic activity of methanolic extract and two alkaloids extracted from seeds of *Peganum harmala* L", Journal of Natural Remedies; 5(1):41-45.
Boyer et al., 2002, "Small molecule inhibitors of KDR (VEGFR-2) kinase: an overview of structure activity relationships", Current Topics in Medicinal Chemistry; 2(9):973-1000.
Cao et al., 2005, "Synthesis and in vitro cytotoxic evaluation of 1,3-disubstituted and 1,3,9-trisubstituted beta-carboline derivatives", European Journal of Medicinal Chemistry; 40(3):249-257.
Database WPI Accession No. 1992-376264, Abstract of JP 4275221, 1992, Taisho Pharm. Co., Ltd.

(Continued)

*Primary Examiner* — Wu-Cheng Winston Shen
*Assistant Examiner* — Yih-Horng Shiao
(74) *Attorney, Agent, or Firm* — Jones Day

(57) ABSTRACT

Methods for treating prostate cancer involving the administration of a compound that selectively inhibits pathological production of human vascular endothelial growth factor (VEGF) are described. Methods for treating benign prostatic hyperplasia involving the administration of a compound that selectively inhibits pathological production of human VEGF are also described. The compound may be administered as a single-agent therapy or in combination with one or more additional therapies to a human in need of such treatment.

15 Claims, 41 Drawing Sheets

(56) References Cited

U.S. PATENT DOCUMENTS

Figure 1:
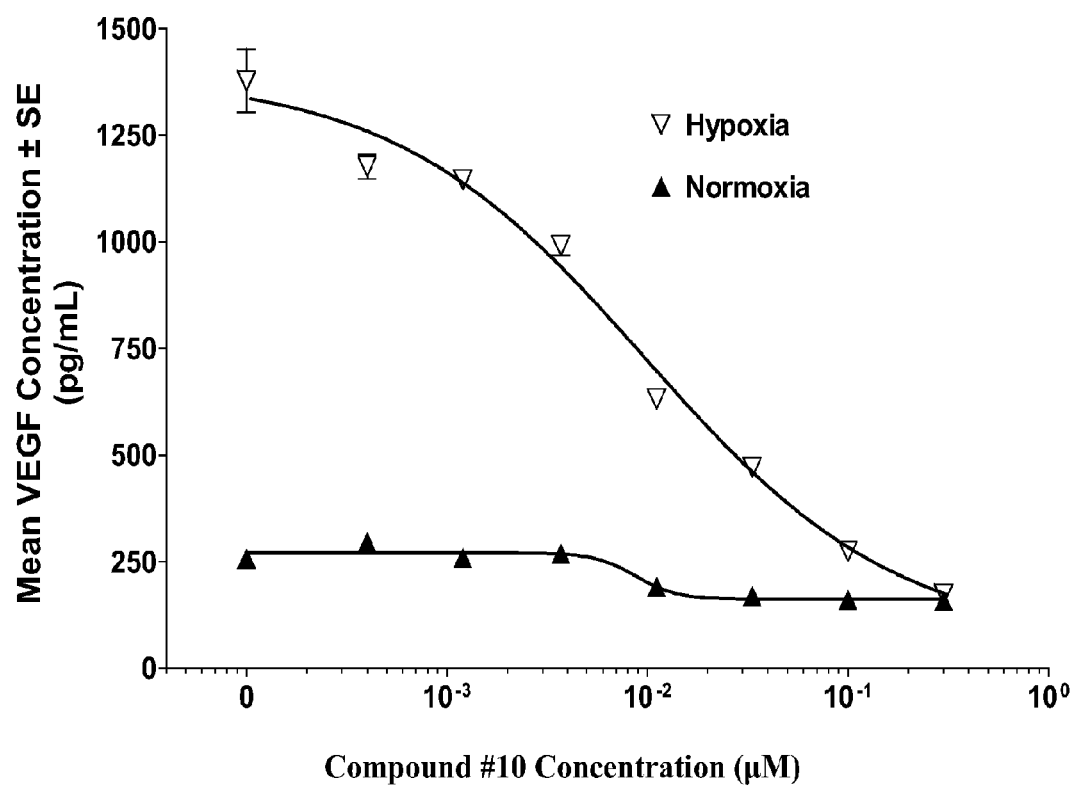

| | | |
|---|---|---|
| 2009/0017021 A1 | 1/2009 | Davis et al. |
| 2010/0125065 A1 | 5/2010 | Moon et al. |
| 2010/0158858 A1 | 6/2010 | Cao et al. |
| 2010/0179132 A1 | 7/2010 | Moon et al. |
| 2011/0160190 A1 | 6/2011 | Moon et al. |
| 2012/0157400 A1 | 6/2012 | Cao et al. |
| 2012/0157401 A1 | 6/2012 | Cao et al. |
| 2012/0157402 A1 | 6/2012 | Cao et al. |
| 2012/0202763 A1 | 8/2012 | Almstead et al. |
| 2012/0202801 A1 | 8/2012 | Cao et al. |

FOREIGN PATENT DOCUMENTS

| | | | |
|---|---|---|---|
| WO | WO 2004/113336 A1 | 12/2004 | |
| WO | WO 2005/007672 A2 | 1/2005 | |
| WO | WO 2005/009370 A2 | 2/2005 | |
| WO | WO 2005/070930 A2 | 8/2005 | |
| WO | WO 2005/089764 A1 | 9/2005 | |
| WO | WO 2005/115470 A2 | 12/2005 | |
| WO | WO 2006/015035 A1 | 2/2006 | |
| WO | WO 2006/058088 A2 | 6/2006 | |
| WO | WO 2006/113703 A2 | 10/2006 | |
| WO | WO 2007/002051 A1 | 1/2007 | |
| WO | WO 2008/127714 A1 | 10/2008 | |

OTHER PUBLICATIONS

Fuhrmann-Benzakein et al., 2000, "Elevated levels of angiogenic cytokines in the plasma of cancer patients", International Journal of Cancer; 85(1):40-45.

Hirawat et al., 2006, "51 Poster Phase 1 single-dose safety, PK, and food-effect study of PTC299, a novel VEGF expression inhibitor for treatment of solid tumors", European Journal of Cancer, Suppl; 4(12):19-20.

Hirawat et al., 2007, "Phase 1 studies assessing the safety, PK, and VEGF-modulating effects of PTC299, a novel VEGF expression inhibitor", Journal of Clinical Oncology ASCO Annual Meeting Proceedings Part 1; 25(18s):Abstract 3562.

International Search Report of International application PCT/US2010/036345, mailedJul. 16, 2010.

Ishida et al., 1999, "Antitumor Agents 201. Cytotoxicity of harmine and beta-carboline analogs", Bioorganic & Medicinal Chemistry Letters; 9(23):3319-3324.

Nicolaus et al., 1983, "Symbiotic approach to drug design", Decision Making in Drug Research; pp. 173-186.

Venkov et al., 1999, "Synthesis of 2-acyltetrahydro-β-carbolines by an intramolecular α-amidoalkylation reaction", Synthetic Communications; 29(3):487-494.

Written Opinion of International application PCT/US2010/036345, mailed Jul. 16, 2010.

Ardill et al., 1990, "X=Y-ZH compounds as potential 1,3-dipoles. Part 29. The iminium ion route to azomethine ylides. Reaction of cyclic secondary amines with mono- and bi-functional aldehydes," Tetrahedron 46(18):6449-6466.

Audia et al., 1996, "Potent, Selective Tetrahydro-beta-carboline Antagonists of the Serotonin 2B ($5HT_{2B}$) Contractile Receptor in the Rat Stomach Fundus," J. Med. Chem. 39:2773-2780.

Belzil, 2006, "Therapeutic Potential for Inhibition of HIV Activation", Lethbridge Undergrad. Res. J. 1(2):1-12.

Cleaveland et al., "Identification of a Novel Inhibitor (NSC 665564) of Dihydroorotate Dehydrogenase with a Potency Equivalent to Brequinar," Biochemical and Biophysical Research Communications 223(3):654-659 (1996).

Database Accession No. 84862, 570837, 578504, 585452, 690268 (XRN) accompanied by Aghbalian et al., 1972, "Synthesis Based on Harmine and Tetrahydroharmine," Armyanskii Khimicheskii Zhurnal 25:689-692; Partial European Search Report for EP11178488 dated May 9, 2012, p. 4.

Database Reaxys [Online], Elsevier Information Systems GmbH, Frankfurt/Main; XP002675485, Database Accession No. 84862, 230057, 306267 (XRN), accompanied by Fischer, 1897, "Über Harmin und Harmalin," Ber. Dtsch. Chem. Ges. 30(3):2481-2489; Fischer, 1901, "Chemische Studien der Alkaloide der Steppenraute (Peganum Harmala)," Chem. Zentralbl. 72(1):957-959; Partial European Search Report for EP11178488 dated May 9, 2012, p. 2.

Database Reaxys [Online], Elsevier Information Systems GmbH, Frankfurt/Main; XP002675486, Database Accession No. 207280, 3918373 (XRN), accompanied by Fischer, 1914, "Über Harmin und Harmalin," Ber. Dtsch. Chem. Ges. 47:99-107 ; Partial European Search Report for EP11178488 dated May 9, 2012, p. 3.

Formagio et al., 2009, "Synthesis and antiviral activity of β-carboline derivatives bearing a substituted carbohydrazide at C-3 against poliovirus and herpes simplex virus (HSV-1)," Eur. J. Med. Chem. 44:4695-4701.

Hino et al., 1990, "2-Hydroxy-1-substituted-1,2,3,4-tetrahydro-β-carbolines. The Pictet-Spengler Reaction of N-Hydroxytryptamine with Aldehydes," Chem. Pharm. Bull. 38(1):59-64.

Iakhontov et al., 1958, "Reduction of Derivatives of Harmine with Sodium Borohydride to Derivatives of Py-Tetrahydroharmine" Zhurnal Obshchei Khimii 28(11):3139-3141.

Ishida et al., 1999, "Antitumor agents 201. Cytotoxicity of harmine and beta-carboline analogs," Bioorganic Med. Chem. Letters; 9: 3319-3324.

Jiang et al., 2003, "Potassium Superoxide as an Alternative Reagent for Winterfeldt Oxidation of β-Carbolines," Organic Letters 5(1):43-46.

Kawashima et al., 1995, "Synthesis and Pharmacological Evaluation of 1,2,3,4-Tetrahydro-β-Carboline Derivatives," Chem. Pharm. Bull. 43(5):783-787.

Kawate et al., 1999, "Chiral Auxiliary Approach to the Asymmetric Pictet-Spengler Reaction of Tryptamines," Heterocycles 50(2):1033-1039.

Lehmann et al., 1987, "Lactamisation of 4.9-Dihydropyrano [3.4-b] indol-1(3H)-ones. —A New Synthetic Route to the beta-Carboline Ring System," Archiv der Pharmazie 320(1):30-36.

Lehnert et al., 1994, "DNA topoisomerase II inhibition by substituted 1,2,3,4-tetrahydro-β-carboline derivatives," Bioorganic & Medicinal Chemistry Letters 4(20):2411-2416.

McNulty et al., 1991, "Diastereoselective Pictet-Spengler reaction of L-(Boc) prolinal: a biomimetic synthesis of eudistomins H and I, and woodinine," Tetrahedron Letters 32(37):4875-4878.

Miller et al., 2010, "Substituted tetrahydro-β-carbolines as potential agents for the treatment of human papillomavirus infection," Bioorg. Med. Chem. Lett. 20:256-259.

Rubtsov et al., 1959, "Synthesis of Py-N-Alkyltetrahydroharmines" Zhurnal Obshchei Khimii 29.3232-3235.

Saiga et al., 1987, "Synthesis of 1,2,3,4-tetrahydro-beta-carboline derivatives as hepatoprotective agents. III. Introduction of substituents onto methyl 1,2,3,4-tetrahydro-beta-carboline-2-carbodithioate," Chem. Pharm. Bull. 35(8), 3284-3291.

Schoenenberger et al., 1986, "Fragmentation of Optically Active (1-Phenylethyl)- and (1-Naphthylethyl) ureas in Refluxing Alcohols: Easy Preparation of Optically Active Amines of High Optical Purity," Helvetica Chimica Acta 69(6):1486-1497.

Siddiqui et al., 1992, "Preparation of Tetrahydroharmine Analogues—Their Antibacterial, Bronchodilator and Cytotoxic Activity and Effect on Central Nervous System," Proc. Pakistan Acad. Sci. 29(4):285-298.

Soe et al., 1995, "Asymmetric Pictet-Spengler Reaction with a Chiral N-(β-3-indolyl)-ethyl-l-methylbenzylamine," Tetrahedron Letters 36(11):1857-1860.

Solomina et al., 1990, "Synthesis and Pharmacological Properties of 1-R-2-[3'-R'-Amino-2-Hydroxypropyl]-1,2,3,4-Tetrahydro-β-Carbolines," Pharmaceutical Chemistry Journal. 24(4):272-275.

Tsuji et al., 2002, "Pictet-Spengler Reaction of Nitrones and Imines Catalyzed by $Yb(OTf)_3$-TMSCl," Chem. Lett. 4: 428-429.

Wu et al., 2002, "A Versatile Linkage Strategy for Solid-Phase Synthesis of N,N-Dimethyltryptamines and β-Carbolines," Organic Letters 4(23):4033-4036.

(56) References Cited

OTHER PUBLICATIONS

Yamada et al., 1998, "Chiral Lewis Acid-Mediated Enantioselective Pictet-Spengler Reaction of $N_b$-Hydroxytryptamine with Aldehydes," J. Org. Chem. 63(18):6348-6354.

Notice of Allowance mailed Nov. 7, 2013 for U.S. Appl. No. 13/321,233.

Office Action mailed Apr. 25, 2013 for U.S. Appl. No. 13/321,233, filed Mar. 9, 2012.

Office Action mailed Oct. 8, 2013 for U.S. Appl. No. 13/321,271, filed Mar. 23, 2012.

Office Action mailed Sep. 9, 2013 for U.S. Appl. No. 13/321,257, filed Apr. 25, 2012.

Saaristo et al., 2000, "Mechanisms of angiogenesis and their use in the inhibition of tumor growth and metastasis," Oncogene 19:6122-6129.

Corrected Notice of Allowability mailed Nov. 18, 2013 for U.S. Appl. No. 13/321,233.

* cited by examiner

A.

B.

A.

B.

A   Percentage of Cells Which Incorporated BrdU

B   Levels of BrdU/Cell

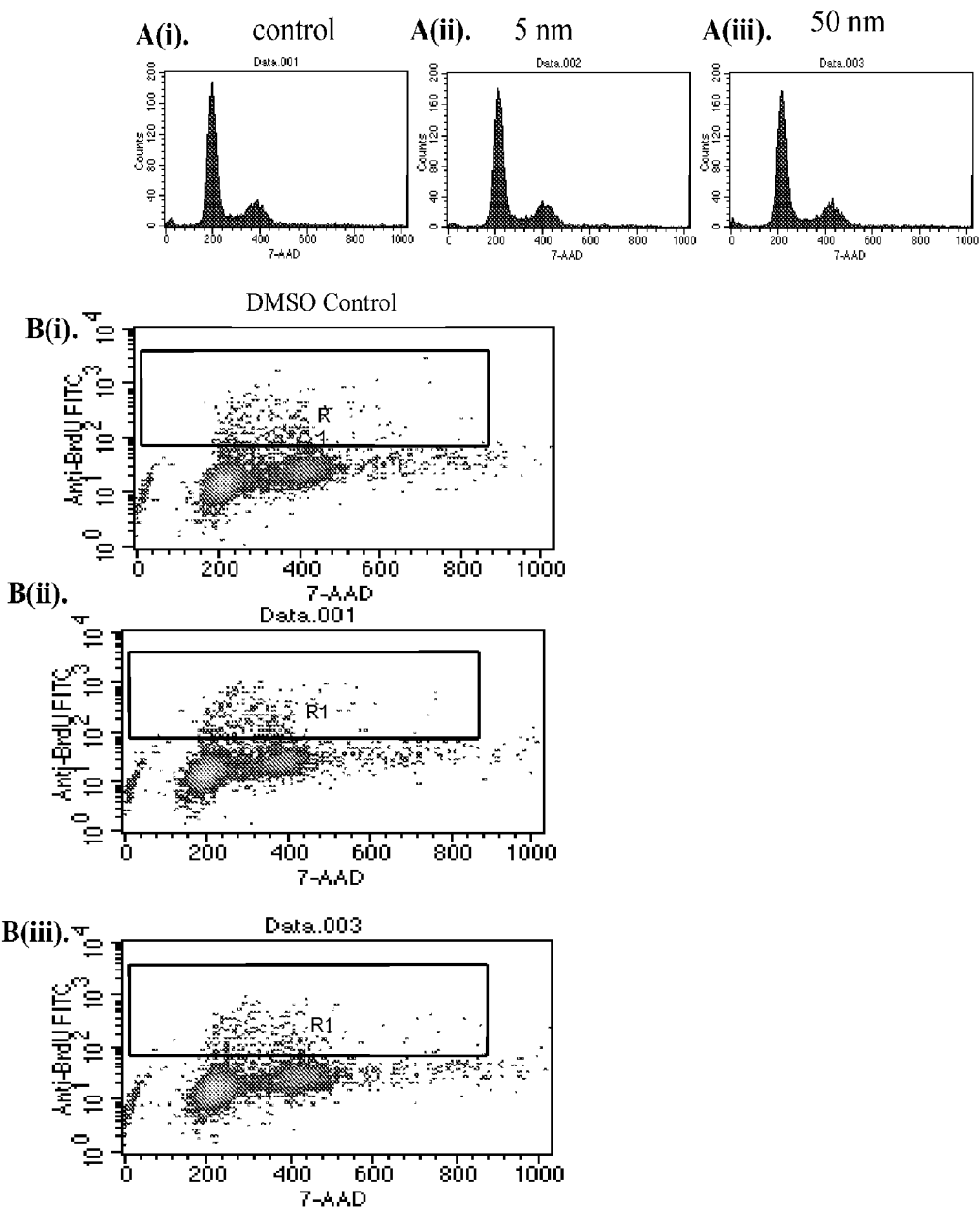
Fig. 31A-B

C.

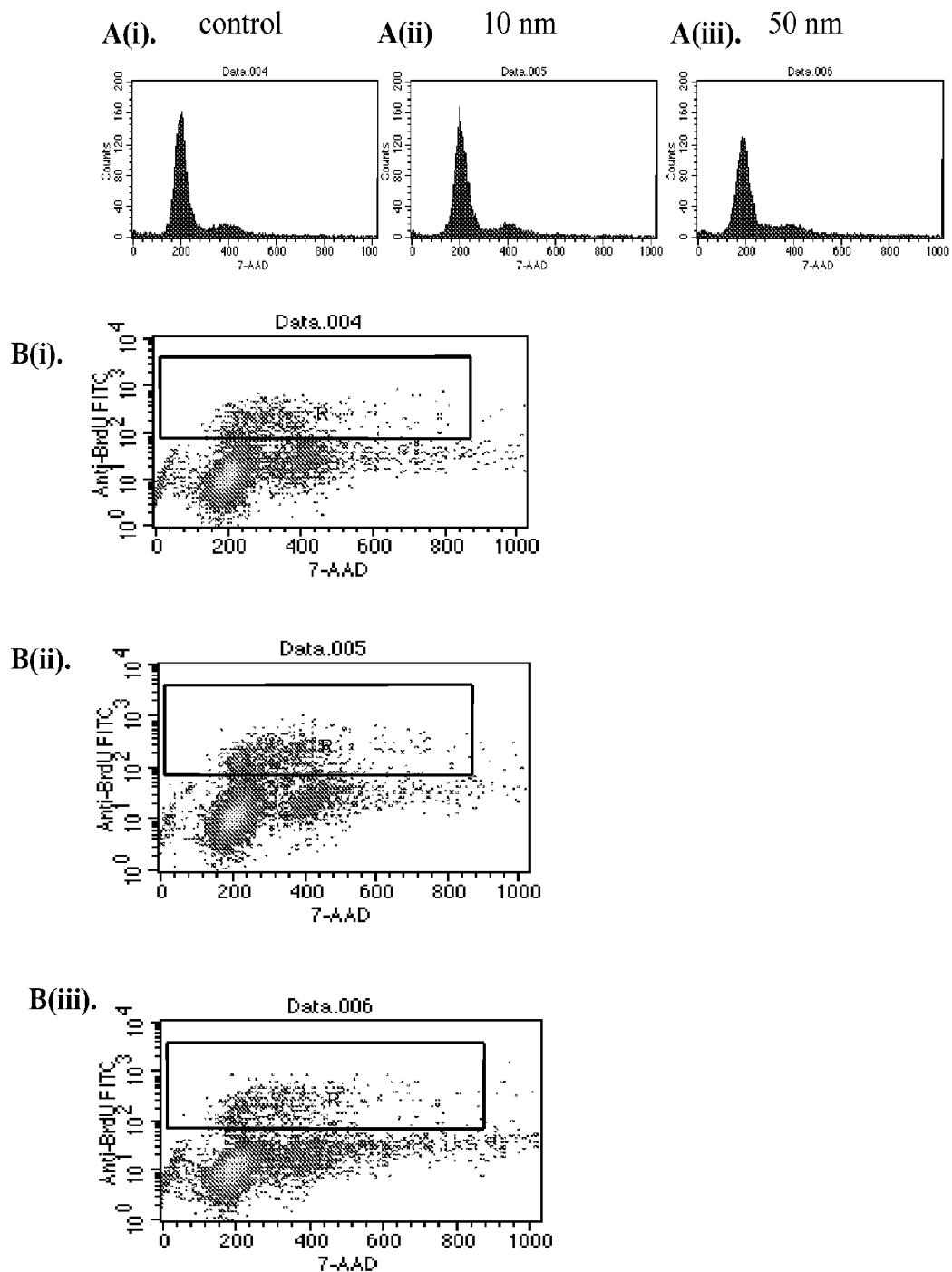
Fig. 32A-B

METHODS FOR TREATING PROSTATE CONDITIONS

CROSS REFERENCE TO RELATED APPLICATIONS

This application is a national stage application of International Application No. PCT/US 2010/036345, filed May 27, 2010, which claims the benefit of priority to U.S. Provisional Patent Application No. 61/181,649, filed May 27, 2009, each of which is incorporated herein by reference in its entirety and for all purposes.

1. INTRODUCTION

Methods for treating prostate cancer involving the administration of a compound that selectively inhibits pathological production of human vascular endothelial growth factor (VEGF) are described. Methods for treating benign prostatic hyperplasia involving the administration of a compound that selectively inhibits pathological production of human VEGF are also described. The compound may be administered as a single-agent therapy or in combination with one or more additional therapies to a human in need of such treatment.

2. BACKGROUND

2.1 Prostate Cancer

Prostate cancer represents the most commonly diagnosed cancer in males and is the second leading cause of cancer-related death in North American men. Prostate cancer is classified in four stages. Stage I prostate cancer is found in the prostate only and cannot be felt during a digital rectal exam nor is it visible by imaging. In stage II prostate cancer, the tumor has grown inside the prostate but has not extended beyond it, whereas in stage III, the cancer has spread outside the prostate, but to a minimal extent. Often, prostate cancer in stage III will have spread only to nearby tissues, such as the seminal vesicles. Finally, in stage IV, the cancer has spread outside the prostate to other tissues, such as the lymph nodes, bones, liver, and/or lungs.

Despite its high prevalence, treatment options for men having prostate cancer remain relatively limited and typically depend on the stage of the cancer. Treatment options include surgical treatments such as radical prostatectomy, in which the prostate is completely removed and radiation, applied through an external beam that directs the dose to the prostate from outside the body or via low-dose radioactive seeds that are implanted within the prostate to kill cancer cells locally. Anti-androgen hormone therapy also is used in the treatment of prostate cancer, either alone or in conjunction with surgery or radiation. Hormone therapy typically aims at blocking the pituitary from producing hormones that stimulate testosterone production by use of castration or administration of hormone analogs (e.g., luteinizing hormone-releasing hormone analogs) and requires that patients have injections of these hormone analogs for protracted periods (often for the rest of their lives). Finally, chemotherapeutic approaches have been used to treat advanced prostate cancer, usually as a last resort when other approaches have failed.

Although these treatments for prostate cancer can be somewhat effective in treating local tumors, each is accompanied by problematic or life-changing side effects. Radiation therapy can result in pain while urinating, localized hair loss, and impotence in those receiving treatment; surgery can cause permanent impotence and urinary incontinence; chemotherapy can result in a multitude of painful side effects, causing substantial morbidity; and hormone therapy can cause loss of sexual desire, impotence, nausea, and swelling of the breasts.

Moreover, none of these treatments are curative and prostate cancer often will progress despite surgical and hormonal-based therapies, resulting in so-called castration resistant prostate cancer (CRPC), which is characterized by progressive disease and rising levels of serum prostate-specific antigen (PSA).

Clinical disease manifestations of CRPC are commonly related to bone metastases and may include pain, pathologic fractures, and spinal cord compression, with local recurrences that may be associated with pelvic discomfort, renal dysfunction due to ureteral compression, bladder outlet obstruction, and sexual dysfunction (Damber et al. Lancet. 2008 May 17; 371(9625):1710-21). Further, while bone cancer is the predominant result of CRPC, patients may develop soft-tissue metastases in liver, lung, brain, and other organs (Damber et al. Lancet. 2008 May 17; 371(9625):1710-21; Petrylak et al. N Engl J Med. 2004 Oct. 7; 351(15):1513-20; Tannock et al. N Engl J Med. 2004 Oct. 7; 351(15):1502-12).

Patients with CRPC are minimally responsive to chemotherapy and the majority of patients die due to progressive prostate cancer within 20 months of initiating treatment (Tannock et al. J Clin Oncol. 1996 June; 14(6):1756-64). Indeed, in certain patients with CRPC, expectant management and symptom control are considered reasonable alternatives to chemotherapy (Basch et al. J Clin Oncol. 2007 Nov. 20; 25(33):5313-8).

Thus, prostate cancer can be a serious, progressive, disabling, and life-threatening disorder. CRPC, in particular, has with few adequate treatment options. It is clear that development of a therapy that can safely address a component of the pathogenesis of the disease would address a high unmet medical need. Text.

2.2 Benign Prostatic Hyperplasia

Benign prostatic hyperplasia (BPH) refers to the increase in size of the prostate in middle-aged and elderly men. BPH is characterized by hyperplasia of prostatic stromal and epithelial cells, resulting in the formation of large, fairly discrete nodules in the periurethral region of the prostate. When sufficiently large, the nodules compress the urethral canal to cause partial, or sometimes virtually complete, obstruction of the urethra, which interferes with the normal flow of urine.

Symptoms of BPH include urinary hesitancy, frequent urination, dysuria (painful urination), increased risk of urinary tract infections and urinary retention. Although prostate specific antigen levels may be elevated in these patients because of increased organ volume and inflammation due to urinary tract infections, BPH is not considered to be a pre-malignant lesion.

BPH-associated adenomatous prostatic growth is believed to begin in men of approximately 30 years of age. An estimated 50% of men have histologic evidence of BPH by the time they reach 50 years old, and that number increases to 75% in men aged 80 and older.

Onset of BPH is believed to be caused by androgens such as testosterone and its metabolites and other hormones. Thus, current treatment options work by targeting these androgens. However, these treatments are not always curative, and patients often need to undergo invasive therapies such as are transurethral microwave thermotherapy and transurethral needle ablation, which deliver energy to the area of the prostate in an attempt create sufficient heat to cause cell death by necrosis in the prostate. Other patients require transurethral resection of prostate surgery, which involves removing part of the prostate through the urethra or other surgical approaches involving lasers.

Thus, there remains a need for effective non-invasive BPH therapies.

3. SUMMARY

Methods for treating prostate conditions (i.e., prostate cancer or BPH), are described involving the administration of compounds having the formulas set forth herein ("Compound") to a human subject in need of such treatment. Preferably, the Compound used in the therapeutic method demonstrates one or more of the following activities as determined in cell culture and/or animal model systems, such as those described herein: (a) selective inhibition of the pathological production of human VEGF; (b) inhibition of angiogenesis, tumor- or BPH-related inflammation, tumor- or BPH-related edema, and/or tumor or BPH growth; (c) prolongation of the G1/S phase of the cell cycle of cells of prostatic or prostate-derived tissue; (d) reduction in prostate-specific markers (e.g., PSA); and/or (e) reduction in prostate-derived circulating tumor cells (CTCs).

The Compound can be administered as a single-agent therapy to a human in need of such treatment. Alternatively, the Compound can be administered in combination with one or more additional therapies to a human in need of such treatment. Such therapies may include the use of anti-cancer agents (e.g., cytotoxic agents, anti-angiogenesis agents, tyrosine kinase inhibitors, or other enzyme inhibitors) or anti-BPH agents.

Despite the differences in the basis for prostate cancer and BPH, the therapies described herein may be effective because they are aimed at interfering with basic mechanisms (such as angiogenesis) required for manifestation of each disease—e.g., uncontrolled cell proliferation or hyperplastic or tumor growth or inflammation or edema associated with uncontrolled cell proliferation or hyperplastic or tumor growth. While not bound by any theory, the therapies described are based, in part, on the pharmacodynamic activities of the Compounds as measured in cell culture and in animal models; in particular, these include: (a) selective inhibition of the pathological production of human VEGF; (b) inhibition of angiogenesis, tumor- or BPH-related inflammation, and/or tumor or BPH growth; and/or (c) prolongation of the G1/S phase of the cell cycle of cells of prostatic or prostate-derived tissue.

These pharmacologic activities contribute to limiting growth of prostate tissue or prostate-derived tissue or tumor- or BPH-related inflammation or edema in several ways. For example, inhibition of pathological production of human VEGF by the tumor or BPH will inhibit tumor or BPH angiogenesis, thereby limiting vascularization and further growth of the tissue (e.g., the tumor or BPH). An additional benefit is achieved for tumors or BPH that respond to VEGF as a growth factor—in such cases, the Compound can limit proliferation of such cells independent of their angiogenic status, that is angiogenesis and vascularization need not be present for the Compound to limit proliferation of the prostatic or prostate-derived cells. Because the process of tumorigenesis or hyperplasia can result in inflammation and edema, a Compound may limit such inflammation or edema. Finally, the prolongation of cell cycle may contribute to the induction of apoptotic death of the tumor or BPH cells, and/or allow for increased efficacy when the Compound is used in combination with a therapy or therapies for treatment of prostate cancer (e.g., chemotherapeutic agents or radiation) that interfere with nucleic acid synthesis during the cell cycle (e.g., G1/S phase) or BPH.

Thus, in specific embodiments, the methods for treating a prostate condition such as prostate cancer or BPH can result in inhibition or reduction of the pathological production of human VEGF (including intratumoral VEGF production), thus reducing human VEGF concentrations in biological specimens of an afflicted subject; inhibition of angiogenesis, tumor- or BPH-related inflammation or edema, and/or tumor or BPH growth in the subject; stabilization or reduction of tumor or BPH volume or tumor or BPH burden in the subject; stabilization or reduction of peritumoral or peri-BPH inflammation or edema in the subject; reduction of the concentrations of angiogenic or inflammatory mediators in biological specimens (e.g., plasma, serum, cerebral spinal fluid, urine, or any other biofluids); and/or a delayed or prolonged G1/S phase of the cell cycle (i.e., the period between the late resting or pre-DNA synthesis phase, and the early DNA synthesis phase) in prostatic or prostate-derived cells of the subject.

In specific embodiments, the methods for treating prostate cancer or BPH can result in reduction or slowing of progression based on evaluation of prostate-specific markers (e.g., PSA).

In specific embodiments, the methods for treating prostate cancer or BPH can result in reduction or slowing of progression based on evaluation of prostate-derived CTCs.

Existing antiangiogenic therapies that have been developed for other diseases (e.g., certain cancers, retinopathies including macular degeneration and the like) are directed at neutralizing VEGF activity (e.g., using anti-VEGF antibodies), or inhibiting downstream effects of VEGF signaling (e.g., using tyrosine kinase inhibitors to block the signaling activity of the VEGF receptor). As a result, these existing antiangiogenic therapies neutralize or inhibit "physiological" or homeostatic VEGF, as well as pathologically produced human VEGF, activity resulting in side effects that, while tolerated for the treatment of life-threatening cancers or to prevent or slow the development of blindness, may not be acceptable for the treatment of prostate cancer or BPH. Since the Compounds used in the therapeutic methods described herein selectively inhibit pathologic production of human VEGF (e.g., by the tumor), and do not disturb the production of human VEGF under physiological conditions, side effects that are unacceptable for the treatment of prostate cancer or BPH should be reduced.

The efficacy of the therapeutic intervention is supported by the data presented herein, demonstrating that: the Compounds inhibit the pathological production of human VEGF (see Section 9.1 et. seq., infra); the Compounds inhibit tumor angiogenesis and tumor growth (see Section 9.2 et. seq., infra); the Compounds delay cell cycle by prolonging the G1/S phase (see Section 9.3 et. seq., infra); the Compounds can be administered safely to human subjects (see Section 10.2 et. seq., infra); and the Compounds inhibit the growth of xenograft human prostate cancer tumors in animal model systems (see Section 9.2.5 et. seq., and Section 12 et. seq., infra).

3.1 Definitions

Unless specified otherwise, as used hereinafter, the term "prostate condition" refers to either prostate cancer, BPH or both.

As used herein, the term "effective amount" in the context of administering a Compound to a subject with prostate cancer refers to the amount of a Compound that results in a beneficial or therapeutic effect. In specific embodiments, an "effective amount" of a Compound refers to an amount of a Compound which is sufficient to achieve at least one, two, three, four or more of the following effects: (i) the reduction or amelioration of the severity of prostate cancer and/or one or more symptoms associated therewith; (ii) the reduction in the duration of one or more symptoms associated with prostate cancer; (iii) the prevention in the recurrence of a tumor (e.g., prostate tumor) or one or more symptoms associated with prostate cancer; (iv) the regression of prostate cancer and/or one or more symptoms associated therewith; (v) the reduction in hospitalization of a subject; (vi) the reduction in hospitalization length; (vii) the increase in the survival of a subject; (viii) the inhibition of the progression of prostate cancer and/or one or more symptoms associated therewith; (ix) the enhancement or improvement of the therapeutic effect of another therapy; (x) a reduction or elimination in the prostate cancer cell population; (xi) a reduction in the growth of a prostate tumor or neoplasm; (xii) a decrease in prostate tumor size (e.g., volume or diameter); (xiii) a reduction in the formation of a newly formed prostate tumor; (xiv) eradication, removal, or control of primary, regional and/or metastatic cancer; (xv) ease in removal of a prostate tumor by reducing tumor and/or edema-related vascularization prior to surgery; (xvi) a decrease in the number or size of metastases; (xvii) a reduction in mortality; (xviii) an increase in tumor-free survival rate of patients; (xvix) an increase in relapse free survival; (xx) an increase in the number of patients in remission; (xxi) a decrease in hospitalization rate; (xxii) the size of the prostate tumor is maintained and does not increase or increases by less than the increase of a prostate tumor after administration of a standard therapy as measured by conventional methods available to one of skill in the art, such as evaluation of PSA concentrations, digital rectal exam, ultrasound (e.g., transrectal ultrasound), bone scan, computed tomography (CT) scan, magnetic resonance imaging (MRI), dynamic contrast-enhanced MRI (DCE-MRI), or a positron emission tomography (PET) scan; (xxiii) the prevention of the development or onset of one or more symptoms associated prostate cancer; (xxiv) an increase in the length of remission in patients; (xxv) the reduction in the number of symptoms associated with prostate cancer; (xxvi) an increase in symptom-free survival of prostate cancer patients; (xxvii) a decrease in PSA levels in a subject with prostate cancer; (xxviii) a decrease in the concentration of VEGF or other angiogenic or inflammatory mediators (e.g., cytokines or interleukins) in biological specimens (e.g., plasma, serum, cerebral spinal fluid, urine, or any other biofluids) of a subject with prostate cancer; (xxix) a decrease in circulating tumor cells (CTCs) in the blood of a subject with prostate cancer; (xxx) stabilization or reduction of prostate tumor or peritumoral inflammation or edema; (xxxi) inhibition or decrease in tumor metabolism or perfusion; (xxxii) inhibition or decrease in angiogenesis or vascularization; (xxxiii) a decrease in the concentration of VEGF-C, VEGF-D, P1GF, VEGFR-1, VEGFR-2, IL-6 and/or IL-8 in biological specimens (e.g., plasma, serum, cerebral spinal fluid, urine, or any other biofluids) of a subject with prostate cancer; and/or (xxxiv) improvement in the quality of life as assessed by methods well known in the art, e.g., questionnaires. In specific embodiments, an "effective amount" of a Compound refers to an amount of a Compound specified herein, e.g., in section 5.4 below.

As used herein, the term "effective amount" in the context of administering a Compound to a subject with BPH refers to the amount of a Compound that results in a beneficial or therapeutic effect. In specific embodiments, an "effective amount" of a Compound refers to an amount of a Compound which is sufficient to achieve at least one, two, three, four or more of the following effects: (i) the reduction or amelioration of the severity of BPH and/or one or more symptoms associated therewith; (ii) the reduction in the duration of one or more symptoms associated with BPH; (iii) the prevention in the recurrence of one or more symptoms associated with BPH; (iv) the regression of BPH and/or one or more symptoms associated therewith; (v) the inhibition of the progression of BPH and/or one or more symptoms associated therewith; (vi) the enhancement or improvement the therapeutic effect of another therapy; (vii) a reduction in the growth of the prostate; (viii) a decrease in prostate size; (ix) the size of the prostate is maintained and does not increase or increases by less after administration of a standard therapy as measured by conventional methods available to one of skill in the art, such as PSA concentrations, digital rectal exam, ultrasound (e.g., transrectal ultrasound), CT Scan, MRI, and DCE-MRI; (x) the prevention of the development or onset of one or more symptoms associated with BPH; (xi) the reduction in the number of symptoms associated with BPH; (xii) a decrease in PSA levels or CTC levels in a subject with BPH; (xiii) a decrease in prostate, stromal, or epithelial cell hyperplasia; (xiv) a decrease in the concentration of VEGF or other angiogenic or inflammatory mediators (e.g., cytokines or interleukins) in biological specimens (e.g., plasma, serum, cerebral spinal fluid, urine, or any other biofluids) of a subject with BPH; and/or (xv) improvement in the quality of life as assessed by methods well known in the art, e.g., questionnaires. In specific embodiments, an "effective amount" of a Compound refers to an amount of a Compound specified herein, e.g., in section 5.4 below.

As used herein, the term "elderly human" refers to a male human 65 years or older.

As used herein, the term "human adult" refers to a male human that is 18 years or older.

As used herein, the term "middle-aged human" refers to a male human between the ages of 30 and 64.

As used herein, the term "subject" and "patient" are used interchangeably to refer to an individual. In a specific embodiment, the individual is a human male. See Section 5.3 infra for more information concerning patients treated for prostate cancer or BPH in accordance with the methods provided herein.

As used herein, the terms "therapies" and "therapy" can refer to any protocol(s), method(s), compositions, formulations, and/or agent(s) that can be used in the prevention, treatment, management, or amelioration of a condition or disorder or symptom thereof (e.g., cancer or one or more symptoms or condition associated therewith; prostate cancer or one or more symptoms or condition associated therewith; BPH or one or more symptoms or condition associated therewith). In certain embodiments, the terms "therapies" and "therapy" refer to drug therapy, adjuvant therapy, radiation, surgery, biological therapy, supportive therapy, and/or other therapies useful in treatment, management, prevention, or amelioration of a condition or disorder or one or more symptoms thereof (e.g., cancer or one or more symptoms or condition associated therewith; prostate cancer or one or more symptoms or condition associated therewith; BPH or one or more symptoms or condition associated therewith). In certain embodiments, the term "therapy" refers to a therapy other than a Compound or pharmaceutical composition thereof. In specific embodiments, an "additional therapy" and "additional therapies" refer to a therapy other than a treatment using a Compound or pharmaceutical composition. In a specific embodiment, a therapy includes the use of a Compound as an adjuvant therapy. For example, using a Compound in conjunction with a drug therapy, biological therapy, surgery, and/or supportive therapy.

Concentrations, amounts, cell counts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Compounds provided herein include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, Remington's Pharmaceutical Sciences, 18$^{th}$ eds., Mack Publishing, Easton Pa. (1990) or Remington: The Science and Practice of Pharmacy, 19$^{th}$ eds., Mack Publishing, Easton Pa. (1995).

As used herein, the term "alkyl" generally refers to saturated hydrocarbyl radicals of straight or branched configuration including, but not limited to methyl, ethyl, n-propyl, isopropyl, n-butyl, isobutyl, sec-butyl, tert-butyl, n-pentyl, n-hexyl, n-heptyl, octyl, n-octyl, and the like. In some embodiments, alkyl substituents can be $C_1$ to $C_8$, $C_1$ to $C_6$, or $C_1$ to $C_4$ alkyl. Alkyl may be optionally substituted where allowed by available valences, for example, with one or more halogen or alkoxy substituents. For instance, halogen substituted alkyl may be selected from haloalkyl, dihaloalkyl, trihaloalkyl and the like.

As used herein, the term "cycloalkyl" generally refers to a saturated or partially unsaturated non-aromatic carbocyclic ring. Representative examples of cycloalkyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, indanyl and the like. Cycloalkyl may be optionally substituted where allowed by available valences. In certain embodiments, cycloalkyl is selected from $C_3$-$C_{20}$cycloalkyl, $C_3$-$C_{14}$cycloalkyl, $C_5$-$C_8$cycloalkyl, $C_3$-$C_8$cycloalkyl and the like.

As used herein, the term "alkenyl" generally refers to linear or branched alkyl radicals having one or more carbon-carbon double bonds, such as $C_2$ to $C_8$ and $C_2$ to $C_6$ alkenyl, including 3-propenyl and the like, and may be optionally substituted where allowed by available valences.

As used herein, the term "alkynyl" generally refers to linear or branched alkyl radicals having one or more carbon-carbon triple bonds, such as $C_2$ to $C_8$ and $C_2$ to $C_6$ alkynyl, including hex-3-yne and the like and may be optionally substituted where allowed by available valences.

As used herein, the term "aryl" refers to a monocarbocyclic, bicarbocyclic or polycarbocyclic aromatic ring structure. Included in the scope of aryl are aromatic rings having from six to twenty carbon atoms. Aryl ring structures include compounds having one or more ring structures, such as mono-, bi-, or tricyclic compounds. Examples of aryl include phenyl, tolyl, anthracenyl, fluorenyl, indenyl, azulenyl, phenanthrenyl (i.e., phenanthrene), napthyl (i.e., napthalene) and the like. In certain embodiments, aryl may be optionally substituted where allowed by available valences. In one embodiment, aryl is an optionally substituted phenyl or naphthyl.

As used herein, the term "heteroaryl" refers to monocyclic, bicyclic or polycyclic aromatic ring structures in which one or more atoms in the ring, is an element other than carbon (heteroatom). Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, heteroaryl may be selected from ring structures that contain one or more heteroatoms, two or more heteroatoms, three or more heteroatoms, or four or more heteroatoms. In one embodiment, the heteroaryl is a 5 to 10 membered or 5 to 12 membered heteroaryl. Heteroaryl ring structures may be selected from those that contain five or more atoms, six or more atoms, or eight or more atoms. Examples of heteroaryl ring structures include, but are not limited to: acridinyl, benzimidazolyl, benzoxazolyl, benzofuranyl, benzothiazolyl, benzothienyl, 1,3-diazinyl, 1,2-diazinyl, 1,2-diazolyl, 1,4-diazanaphthalenyl, furanyl, furazanyl, imidazolyl, indazolyl, indolyl, isoxazolyl, isoquinolinyl, isothiazolyl, isoindolyl, oxadiazolyl, oxazolyl, purinyl, pyridazinyl, pyrazolyl, pyridinyl, pyrazinyl, pyrimidinyl, pyrrolyl, quinazolinyl, quinolinyl, quinoxalinyl, thiazole-2 (3H)imine, 1,3,4,-thiadiazole-2(3H)-imine-yl, thiazolyl, thiophenyl, 1,3,5-triazinyl, 1,2,4-triazinyl, 1,2,3-triazinyl, tetrazolyl and the like. In certain embodiments, heteroaryl may be optionally substituted where allowed by available valences.

As used herein, the term "heteroaryl" refers to monocyclic, bicyclic or polycyclic aromatic ring structures in which one or more atoms in the ring, is an element other than carbon (heteroatom). Heteroatoms are typically O, S or N atoms. Included within the scope of heteroaryl, and independently selectable, are O, N, and S heteroaryl ring structures. The ring structure may include compounds having one or more ring structures, such as mono-, bi-, or tricyclic compounds. In some embodiments, heteroaryl may be selected from ring structures that contain one or more heteroatoms, two or more heteroatoms, three or more heteroatoms, or four or more heteroatoms. In one embodiment, the heteroaryl is a 5 to 10 membered or 5 to 12 membered heteroaryl. Heteroaryl ring structures may be selected from those that contain five or more atoms, six or more atoms, or eight or more atoms. Examples of heteroaryl ring structures include, but are not limited to: acridinyl, benzimidazolyl, benzoxazolyl, benzofuranyl, benzothiazolyl, benzothienyl, 1,3-diazinyl, 1,2-diazinyl, 1,2-diazolyl, 1,4-diazanaphthalenyl, furanyl, furazanyl, imidazolyl, indazolyl, indolyl, isoxazolyl, isoquinolinyl, isothiazolyl, isoindolyl, oxadiazolyl, oxazolyl, purinyl, pyridazinyl, pyrazolyl, pyridinyl, pyrazinyl, pyrimidinyl, pyrrolyl, quinazolinyl, quinolinyl, quinoxalinyl, thiazole-2 (3H)imine, 1,3,4,-thiadiazole-2(3H)-imine-yl, thiazolyl, thiophenyl, 1,3,5-triazinyl, 1,2,4-triazinyl, 1,2,3-triazinyl, tetrazolyl and the like. In certain embodiments, heteroaryl may be optionally substituted where allowed by available valences.

As used herein, the term "alkoxy" generally refers to a structure of the formula: —O—R. In certain embodiments, R may be an optionally substituted straight or branched alkyl, such as a $C_1$ to $C_5$ alkyl.

As used herein, the term "alkylthio" generally refers to a structure of the formula: —S—R. In certain embodiments, R may be an optionally substituted straight or branched alkyl, such as a $C_1$ to $C_5$ alkyl.

As used herein, the term "amino" generally refers to a structure of the formula: —NRR'. In certain embodiments, R and R' independently may be H or an optionally substituted straight or branched alkyl, such as a $C_1$ to $C_5$ alkyl. In one embodiment, "thiazoleamino" refers to an amino, wherein at least one of R or R' is a 2-thiazolyl, 3-thiazolyl or 4-thiazolyl. In one embodiment, "alkylamino" refers to an amino, wherein at least one of R or R' is an optionally substituted straight or branched $C_1$ to $C_5$ alkyl.

As used herein, the term "acetamino" generally refers to a structure of the formula: —NR(C(=O)CH$_3$), wherein R may be H or an optionally substituted straight or branched alkyl, such as a $C_1$ to $C_5$ alkyl.

As used herein, the term "acetamide" generally refers to a structure of the formula: C(=O)NH$_2$.

As used herein, the term "sulfonyl" generally refers to a structure of the formula: —SO$_2$R, wherein R can be H or an optional substituent including, but not limited to straight or branched $C_1$ to $C_6$ alkyl, aryl, heteroaryl, cycloalkyl, or heterocycle. In one embodiment, "alkylsulfonyl" refers to a structure of the formula: —SO$_2$R, wherein R is an optionally substituted straight or branched $C_1$ to $C_6$ alkyl.

As used herein, the term "oxo" generally refers to a structure of the formula: (=O).

As used herein, the term "phenyloxy" generally refers to a structure of the formula: —O-phenyl, wherein phenyl can be optionally substituted.

For the purposes of this disclosure, the terms "halogen" or "halo" refer to substituents independently selected from fluorine, chlorine, bromine, and iodine.

As used herein, the terms "Compound" or "Compound provided herein" generally refer to a compound described in Section 5.1 or Example 6. In one embodiment, the terms refer to a compound of Formula I, II, III or IV. In another embodiment, the terms refer to a compound of Formula Ia, IIa, IIa or IVa. In a specific embodiment, the terms refer to a compound depicted in Table 1. In one embodiment, the terms refer to a Compound disclosed in WO2005/089764, e.g., Compounds in the table on pages 26-98; WO2006/113703, e.g., Compounds in the table on pages 29-102; WO2008/127715, e.g., Compounds in the table on pages 52-126; WO2008/127714, e.g., Compounds in the table on pages 48-123; and U.S. Provisional Patent Application 61/181,653, entitled: METHODS FOR TREATING CANCER AND NON-NEOPLASTIC CONDITIONS, filed May 27, 2009, all of which are herewith incorporated by reference in their entirety. In one embodiment, the terms refer to a particular enantiomer, such as an R or S enantiomer of a "Compound" or "Compound provided herein". In one embodiment, the terms refer to an R or S enantiomer of a compound of Formula I, II, III or IV. In another embodiment, the terms refer to an R or S enantiomer of a compound of Formula Ia, IIa, IIIa or IVa. In a specific embodiment, the terms refer to an R or S enantiomer of a compound depicted in Table 1. The "Compound" or "Compound provided herein" may comprise one or more asymmetric carbon atoms, i.e. n asymmetric carbon atoms, having either R or S configuration as determined by a person skilled in the art. It is understood that the terms "Compound" or "Compound provided herein" encompass all possible stereoisomers that may be generated based on all asymmetric carbon atoms. For example, if a Compound has two (n=2) assymetric carbon atoms, the terms "Compound" or "Compound provided herein" encompass all four, i.e. $2^n=2^2=4$, stereoisomers (R,S; R,R; S,S; S;R). The "Compound" or "Compound provided herein" may be a substantially pure (e.g., about 90%, about 95%, about 98%, about 99%, or about 99.9% pure) single stereoisomer or a mixture of two or more stereoisomers.

As used herein, the terms "self-microemulsifying drug delivery system" (SMEDDS) or "self-emulsifying drug delivery system" (SEDDS) mean a composition that contains an active agent herein defined in intimate admixture with pharmaceutically acceptable excipients such that the system is capable of dissolving the active agent to the desired concentration and producing colloidal structures by spontaneously forming a microemulsion when diluted with an aqueous medium, for example water, or in gastric juices. The colloidal structures can be solid or liquid particles including droplets and nanoparticles. In a SEDDS or SMEDDS system the type of microemulsion produced will be either clear or turbid depending on drug loading and the type of surfactant used.

As used herein, "microemulsion" means a slightly opaque, opalescent, non-opaque or substantially non-opaque colloidal dispersion (i.e. "clear") that is formed spontaneously or substantially spontaneously when its components are brought into contact with an aqueous medium. A microemulsion is thermodynamically stable and typically contains dispersed droplets of a mean diameter less than about 200 nm (2000 Å). Generally microemulsions comprise droplets or liquid nanoparticles that have a mean diameter of less than about 150 nm (1500 Å); typically less than 100 nm, generally greater than 10 nm, wherein the dispersion may be thermodynamically stable over a time period of up to about 24 hours.

As used herein, the terms "pathologic," "pathological" or "pathologically-induced," in the context of the production of VEGF described herein, refer to the stress-induced expression of VEGF protein. In one embodiment, oncongenic transformation-induced expression of VEGF protein by tumor cells or other cells in the tumor environment is encompassed by the terms. In another embodiment, hypoxia-induced expression of VEGF protein in a chronic or traumatic inflammatory condition is encompassed by the terms. In another embodiment, in response to environmental stimuli, cells that disregulate or overproduce VEGF protein is also encompassed by the terms. As applicable, expression of VEGF protein supports inflammation, angiogenesis and tumor growth. The inhibition or reduction in pathological production of VEGF protein by a Compound can be assessed in cell culture and/or animal models as described herein.

As used herein, the term "about" means a range around a given value wherein the resulting value is substantially the same as the expressly recited value. In one embodiment, "about" means within 25% of a given value or range. For example, the phrase "about 70% by weight" comprises at least all values from 52% to 88% by weight. In another embodiment, the term "about" means within 10% of a given value or range. For example, the phrase "about 70% by weight" comprises at least all values from 63% to 77% by weight. In another embodiment, the term "about" means within 7% of a given value or range. For example, the phrase "about 70% by weight" comprises at least all values from 65% to 75% by weight.

4. DESCRIPTION OF FIGURES

FIG. 1. ELISA Evaluation of Inhibition of Soluble VEGF$_{121/165}$ Production by Compound #10 during Hypoxia or Normoxia in HeLa Cells. The results shown are from assays performed in triplicate. The acronyms have the following definitions:
ELISA=enzyme-linked immunosorbent assay; SE=standard error of the mean; and, VEGF=vascular endothelial growth factor.

Figure 2:
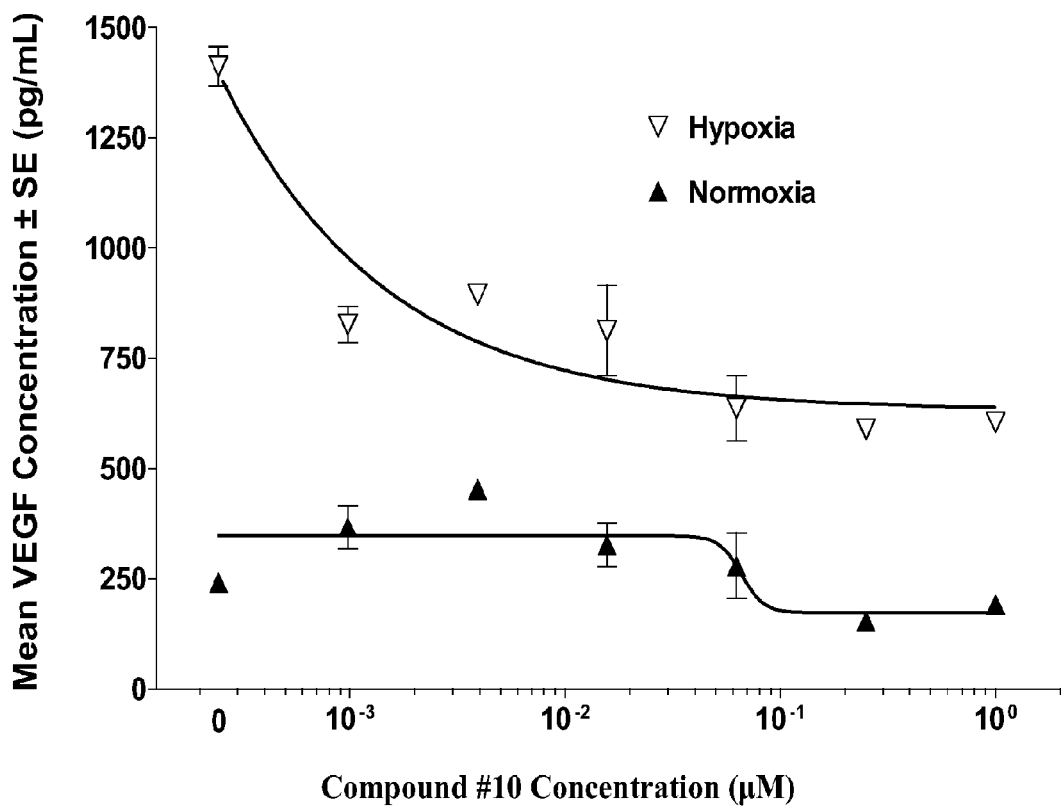

FIG. 2. ELISA Evaluation of Inhibition of Soluble VEGF$_{121/165}$ Production by Compound #10 during Hypoxia or Normoxia in Keratinocytes. The results shown are from assays performed in duplicate. The acronyms have the following definitions:
ELISA=enzyme-linked immunosorbent assay; SE=standard error of the mean; and, VEGF=vascular endothelial growth factor.

Figure 3:
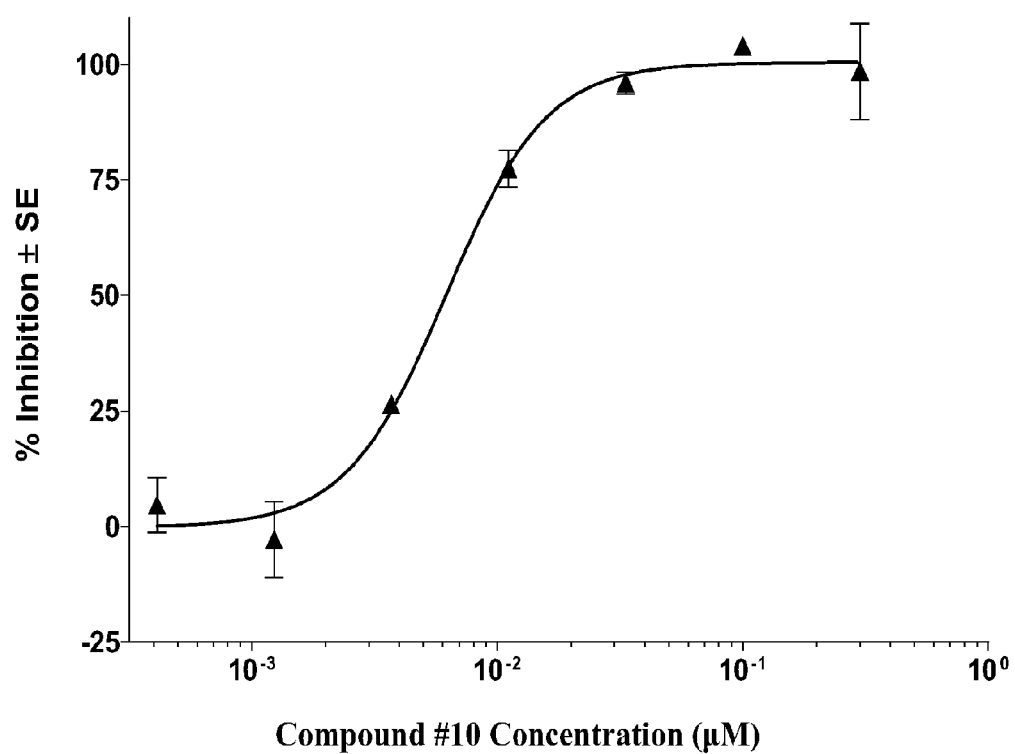

FIG. 3. In Cell Western Evaluation of Inhibition of Matrix Associated VEGF$_{189/206}$ Production in HT1080 Cells. The results shown are from assays performed in duplicate. The acronyms have the following definitions: SE=standard error of the mean; and,
VEGF=vascular endothelial growth factor.

Figure 4:
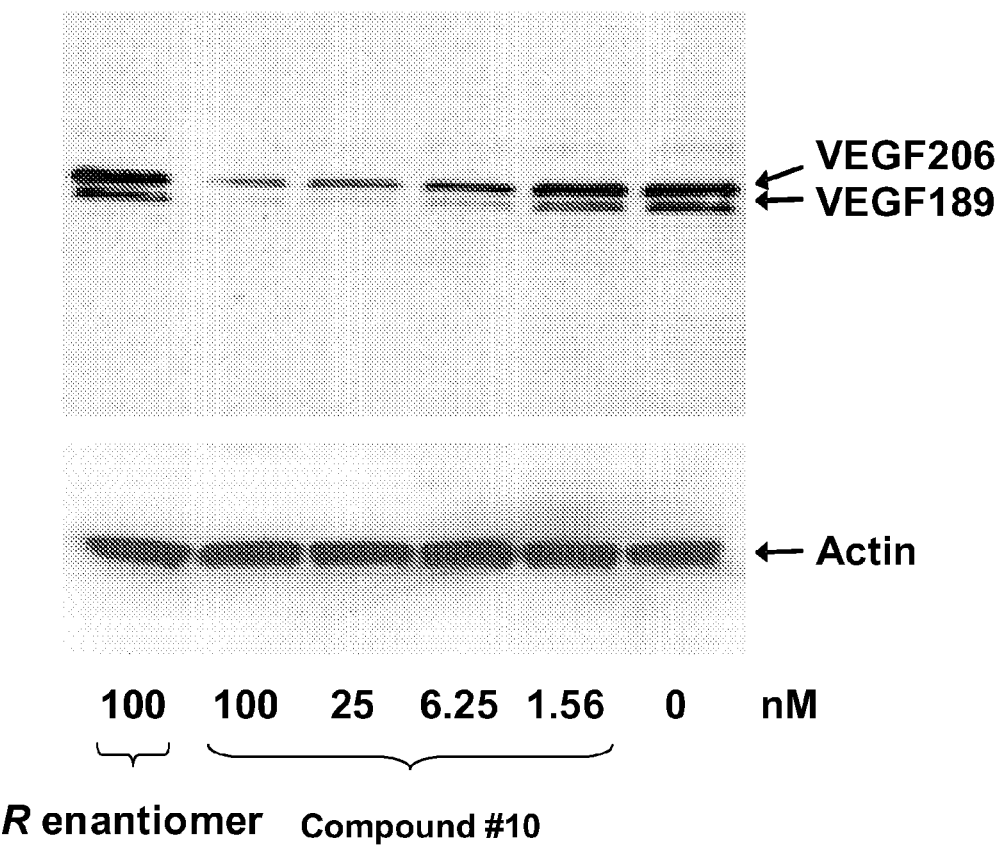

FIG. 4. Western Blot Evaluation of Inhibition of Matrix Associated VEGF$_{189/206}$ Production in HT1080 Cells.

Figure 5:
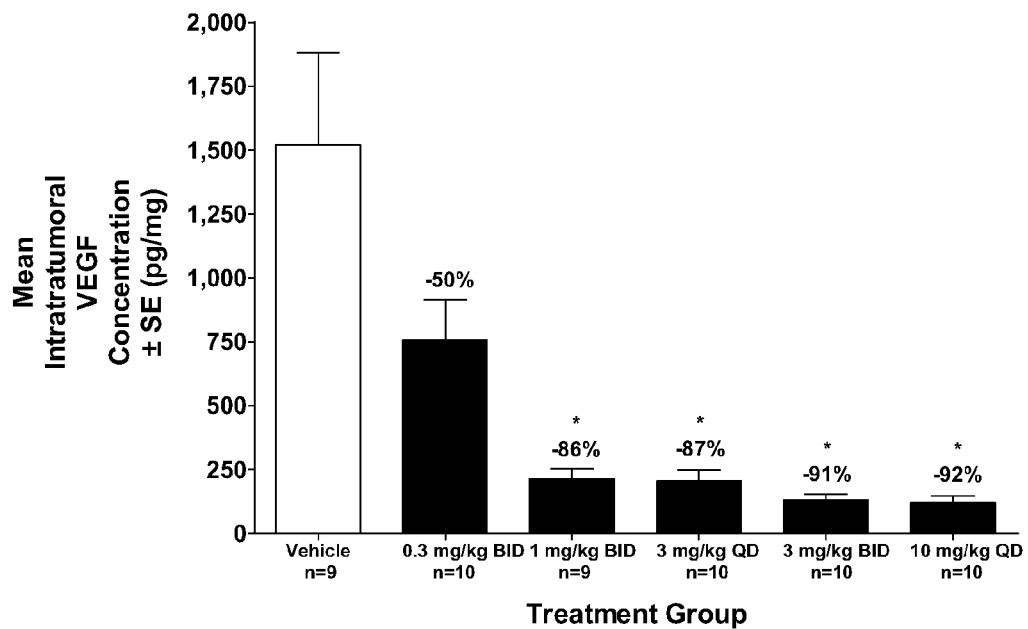

FIG. 5. Reduction of Intratumoral VEGF by Compound #10 in Nude Mice Bearing HT1080 Xenografts. The symbol "*" represents a p value of p<0.05, signifying that the differences in treated mice were significantly different from tumor size in vehicle-treated mice (ANOVA, followed by individual comparisons to vehicle). The acronyms have the following definitions: ANOVA=analysis of variance; BID=2 times per day; QD=1 time per day; SE=standard error of the mean; and, VEGF=vascular endothelial growth factor.

Figure 6:
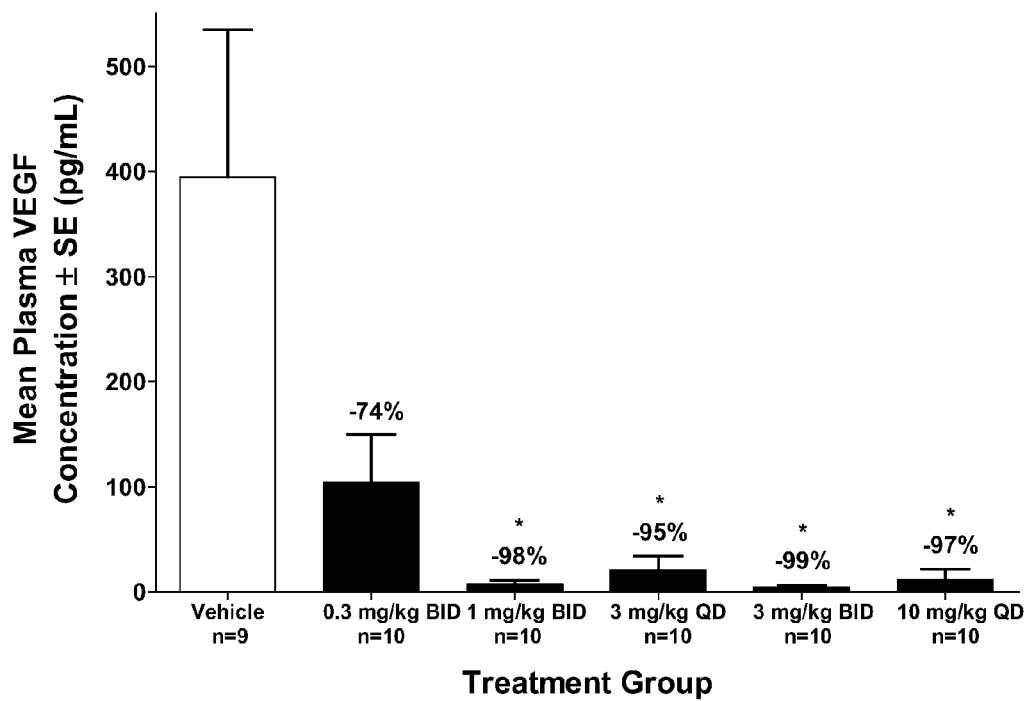

FIG. 6. Reduction of Tumor Induced Plasma VEGF by Compound #10 in Nude Mice Bearing HT1080 Xenografts. The symbol "*" represents a p value of p<0.05, signifying that the differences in treated mice were significantly different from tumor size in vehicle-treated mice (ANOVA, followed by individual comparisons to vehicle). The acronyms have the following definitions: ANOVA=analysis of variance; BID=2 times per day; QD=1 time per day; SE=standard error of the mean; and, VEGF=vascular endothelial growth factor.

Figure 7:
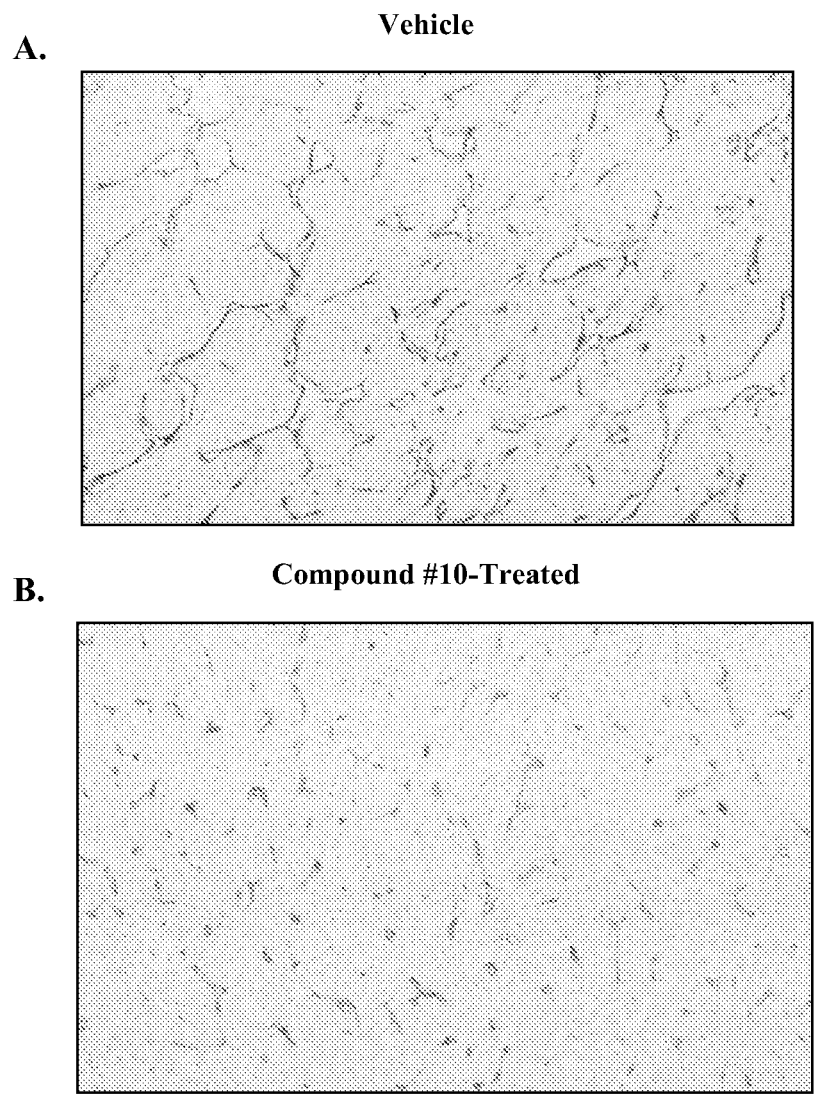

FIG. 7A-B. Inhibition of Tumor Angiogenesis by Compound #10 in Nude Mice Bearing HT1080 Xenografts. FIG. 7A. The effect of vehicle on an immunostain using an anti-murine CD31 antibody specific for endothelial cells. FIG. 7B. The effect of Compound #10 on an immunostain using an anti-murine CD31 antibody specific for endothelial cells.

Figure 8:
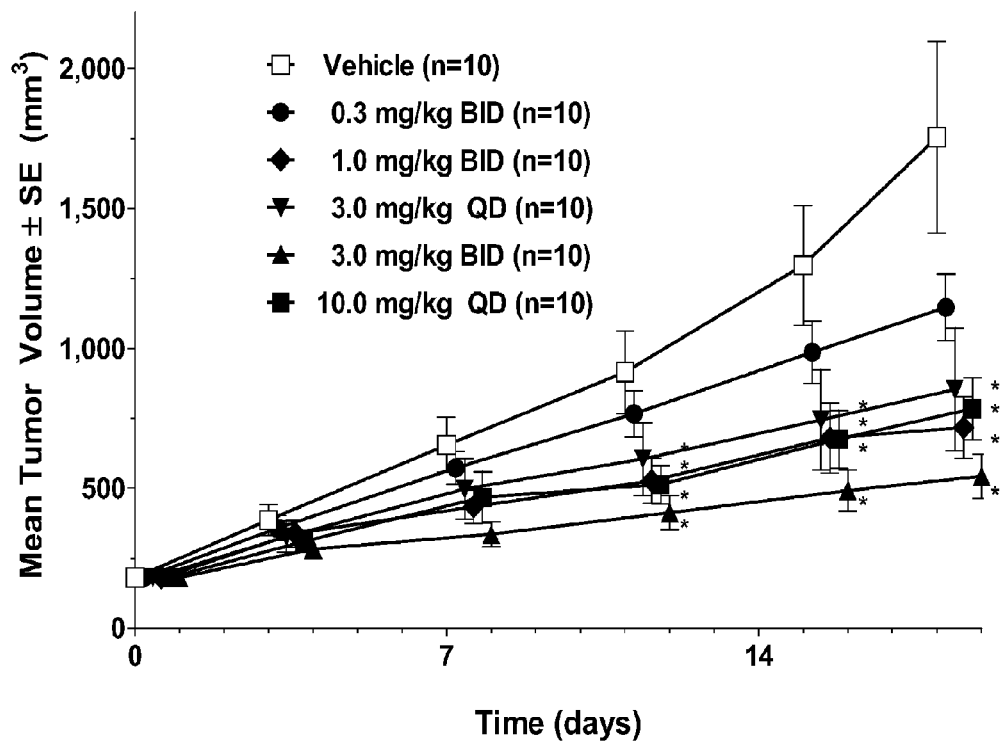

FIG. 8. Inhibition of Tumor Growth by Compound #10 in Nude Mice Bearing HT1080 Xenografts. The symbol "*" represents a p value of p<0.05, signifying that the differences in treated mice were significantly different from tumor size in vehicle-treated mice (ANOVA, followed by individual comparisons to vehicle). The acronyms have the following definitions: ANOVA=analysis of variance; BID=2 times per day; QD=1 time per day; and, SE=standard error of the mean.

Figure 9:
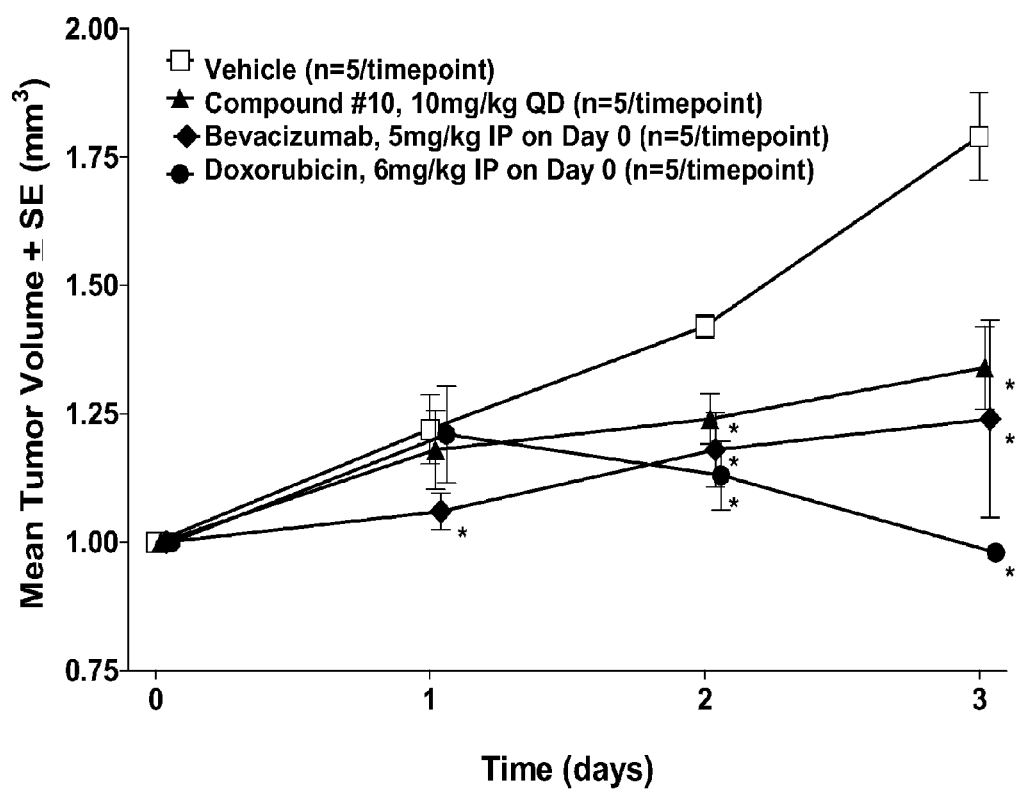

FIG. 9. Time Course of Inhibition of Tumor Growth by Compound #10, Bevacizumab, and Doxorubicin in Nude Mice Bearing HT1080 Xenografts. The symbol "*" represents a p value of p<0.05, signifying that the differences in treated mice were significantly different from tumor size in vehicle-treated mice (ANOVA, followed by individual comparisons to vehicle). The acronyms have the following definitions: ANOVA=analysis of variance; IP=intraperitoneal; QD=1 time per day; and, SE=standard error of the mean.

Figure 10:
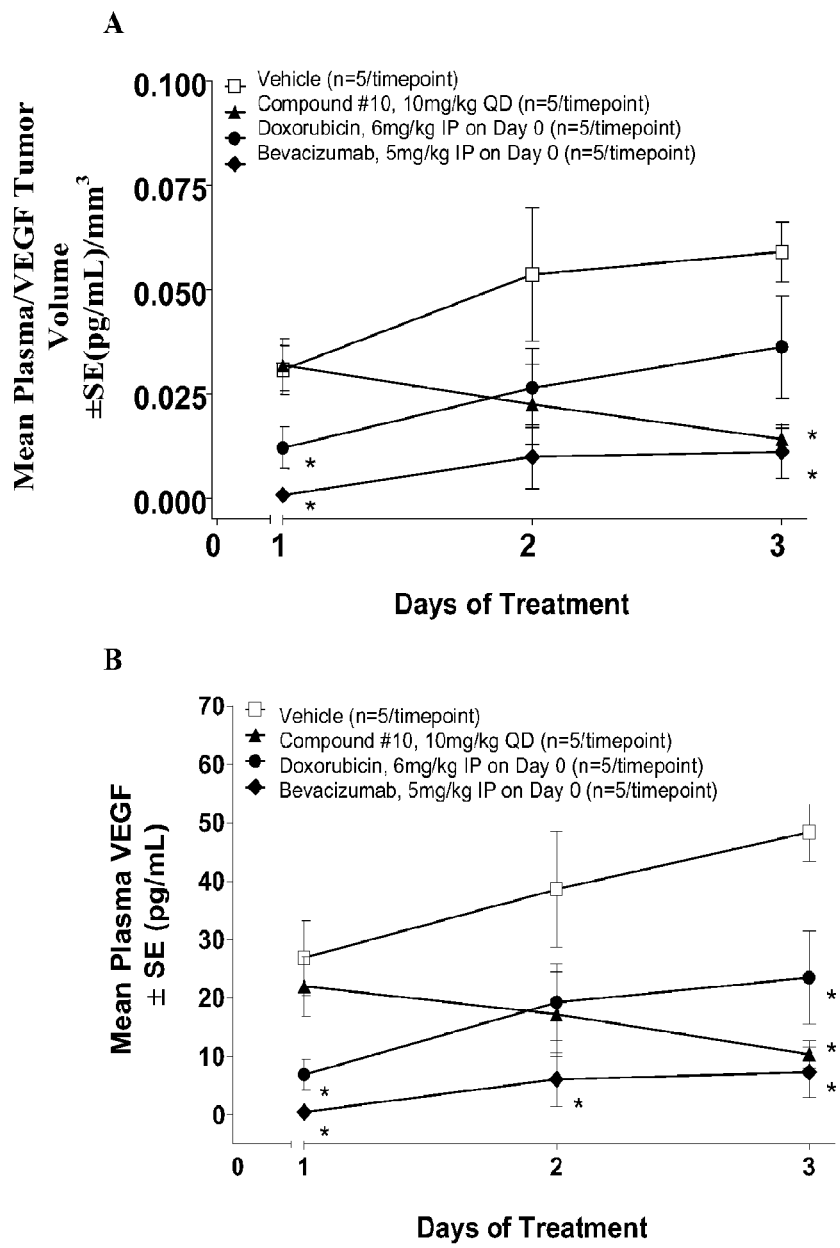

FIG. 10A-B. Time Course of Inhibition of Tumor Induced Plasma VEGF Concentrations by Compound #10, Bevacizumab, and Doxorubicin in Nude Mice Bearing HT1080 Xenografts. FIG. 10A. The effect on absolute values of plasma human VEGF concentrations. FIG. 10A. The effect on values of plasma human VEGF concentrations expressed as a ratio relative to tumor volume. The symbol "*" represents a p value of p<0.05, signifying that the differences in treated mice were significantly different from tumor size in vehicle-treated mice (ANOVA, followed by individual comparisons to vehicle). The acronyms have the following definitions: IP=intraperitoneal; QD=once per day;
SE=standard error of the mean; and, VEGF=vascular endothelial growth factor.

Figure 11:
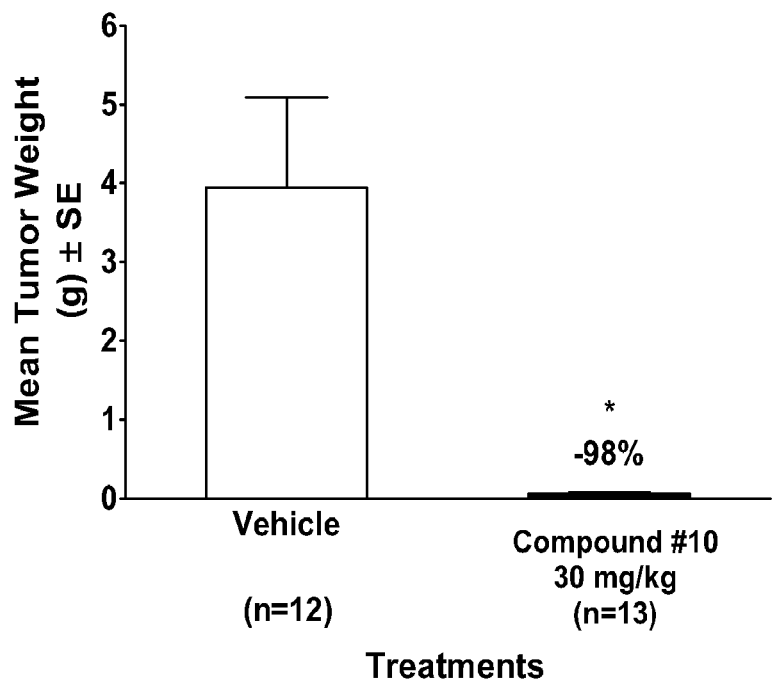
Figure 11:
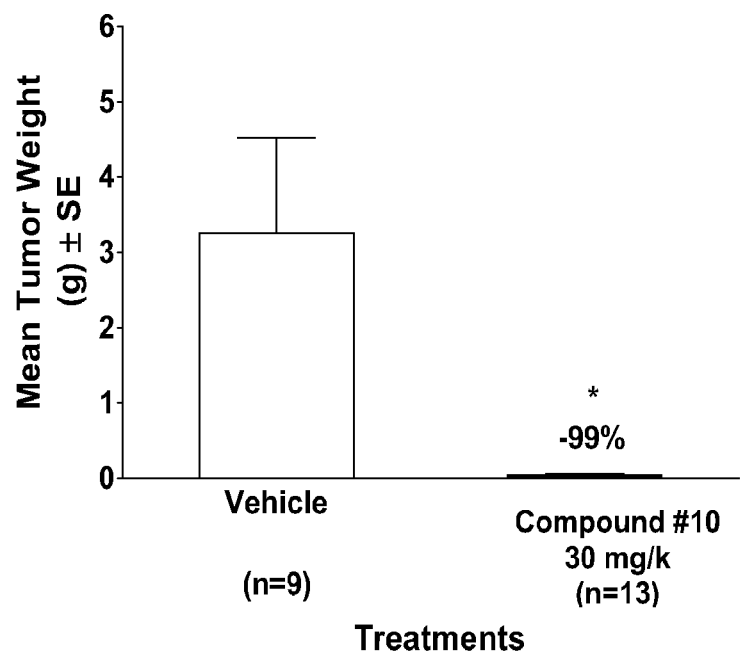

FIG. 11A-B. Inhibition of Tumor Growth by Compound #10 at 5 Weeks in Nude Mice Bearing Orthotopically Implanted SKNEP or SY5Y Xenograft. FIG. 11A. The effect on weight of an SY5Y tumor for mice treated with vehicle and Compound #10. FIG. 11B. The effect on weight of an SKNEP tumor for mice treated with vehicle and Compound #10. The symbol "*" represents a p value of p<0.05, signifying that the differences in treated mice were significantly different from tumor size in vehicle-treated mice (Student's t-test). The acronyms have the following definitions: SE=standard error of the mean.

FIG. 12A-G. Cell Cycle Effects in HT1080 Cells by Compound #10 Concentration. Histograms depicting relative DNA content in HT1080 cells under normoxic conditions after treatment with varying concentrations of Compound #10 compared to vehicle. FIG. 12A. Histogram showing the effect of treatment with vehicle. FIG. 12B-G. Histograms showing the effect of treatment with Compound #10 at 0.3 nm, 1 nm, 3 nm, 10 nm, 30 nm and 100 nm, respectively. The acronyms have the following definitions: $G_1$=gap 1 phase (resting or pre-DNA synthesis phase—2 chromosomes present); $G_2$=gap 2 phase (gap between DNA synthesis and mitosis—4 chromosomes present); S=synthesis phase (DNA synthesis ongoing); and, PI=propidium iodide.

FIG. 13A-F. Cell Cycle Effects in HT1080 Cells by Time from Discontinuation of Compound #10. Histograms depicting relative DNA content in HT1080 cells under normoxic conditions after discontinuation of treatment with Compound #10 compared to vehicle. FIG. 13A. Histogram showing the effect of treatment with vehicle. FIGS. 13B-F. Histograms showing the effect of discontinuation of treatment with Compound #10 at 0 hours, 2 hours, 5 hours, 8 hours and 26 hours, respectively. The acronyms have the following definitions: $G_1$=gap 1 phase (resting or pre-DNA synthesis phase—2 chromosomes present); $G_2$=gap 2 phase (gap between DNA synthesis and mitosis—4 chromosomes present); S=synthesis phase (DNA synthesis ongoing); and, PI=propidium iodide.

Figure 14:
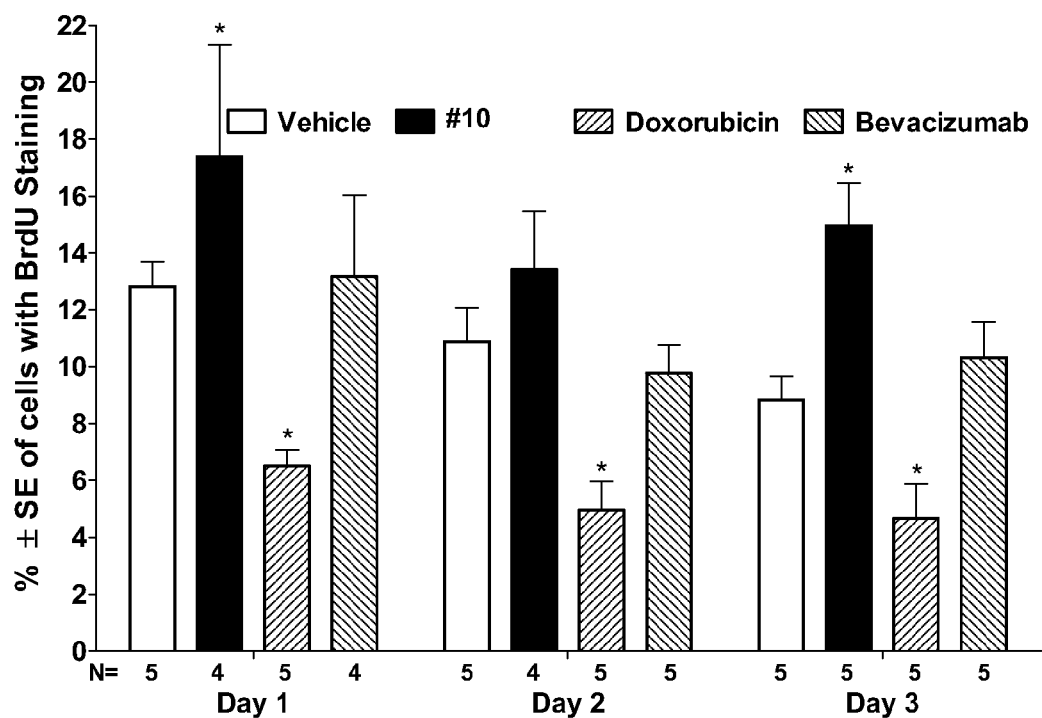

FIG. 14. BrdU Labeling of Cells from HT1080 Xenografts Grown in Nude Mice. The effect of treatment with Compound #10 compared to vehicle and a positive and negative control, doxorubicin and bevcizumab, respectively. The tumors with adequate BrdU staining (≥3%) were included in analyses. The symbol "*" represents a p value of p<0.05, signifying that the differences in treated mice were significantly different from tumor size in vehicle-treated mice (ANOVA, followed by Dunnett's test relative to vehicle). The acronyms have the following definitions: ANOVA=analysis of variance; BrdU=bromodeoxyuridine; and, SE=standard error of the mean.

Figure 15:
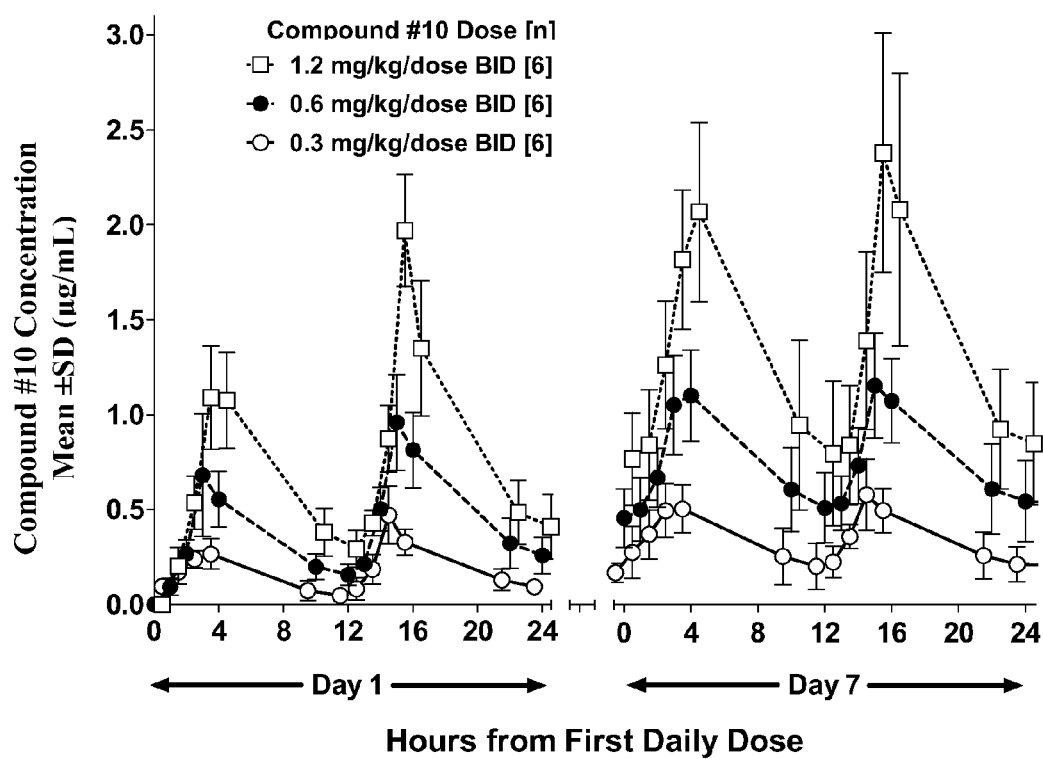

FIG. 15. Plasma Concentrations of Compound #10 by Dose Level after Stage 1 of a Study in Healthy Volunteers. The acronyms have the following definitions: BID=2 times per day; and, SD=standard deviation.

Figure 16:
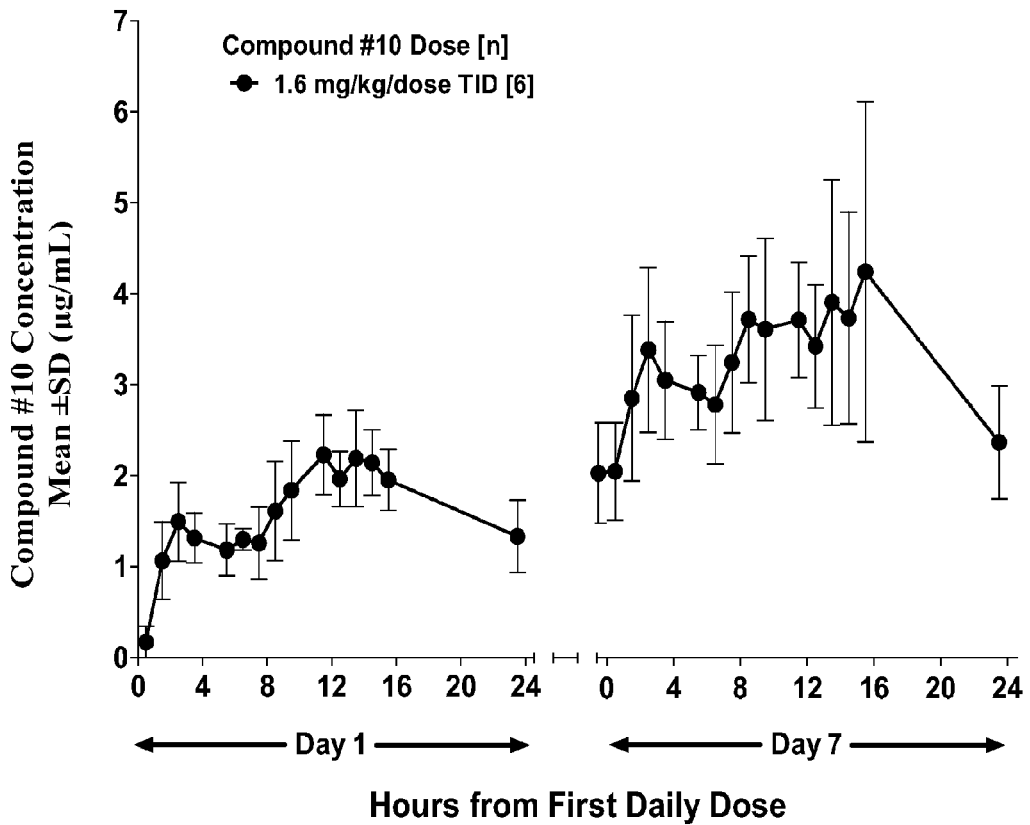

FIG. 16. Plasma Concentrations of Compound #10 by Dose Level after Stage 2 of a Study in Healthy Volunteers. The acronyms have the following definitions: TID=3 times per day; and, SD=standard deviation.

Figure 17:
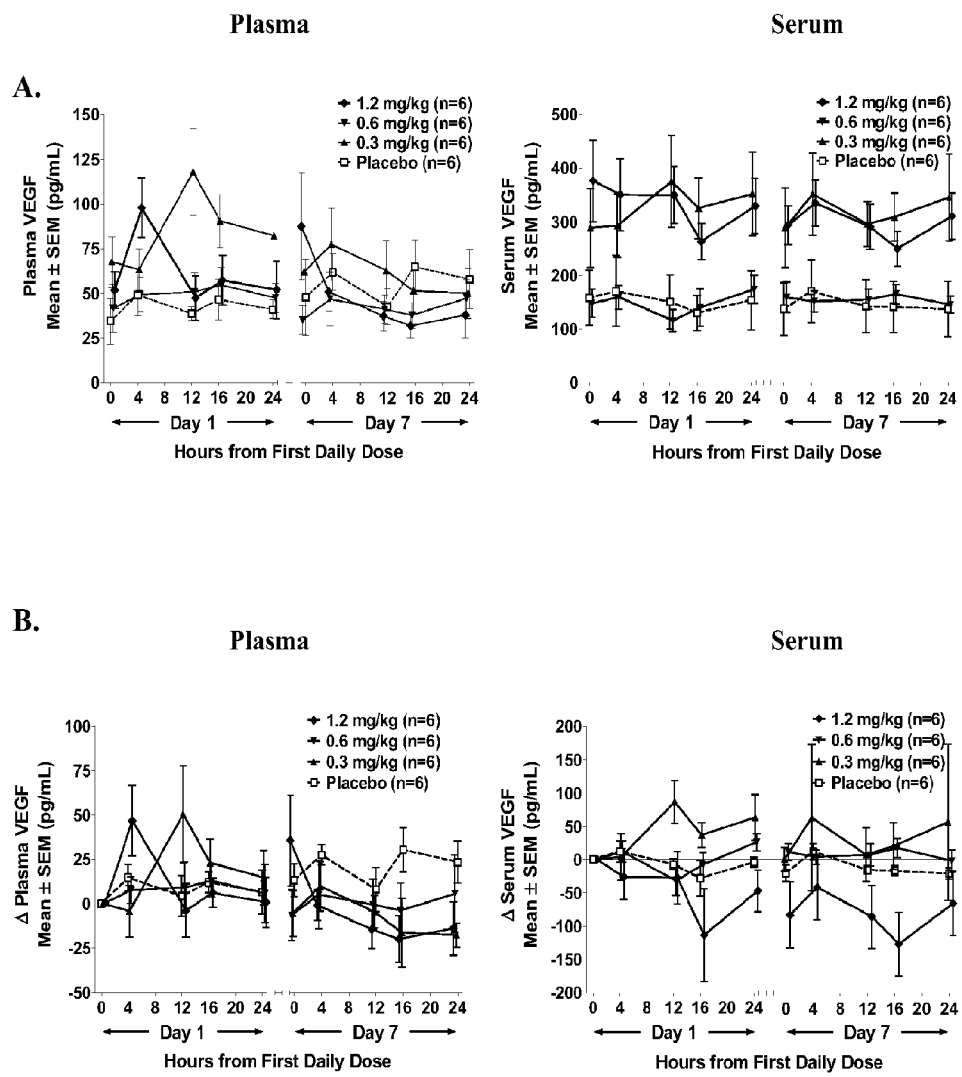

FIG. 17A-B. FIG. 17A: Absolute Physiologic VEGF A Plasma and Serum Concentrations: Stage 1 of Multiple dose Study; FIG. 17B: Change from Baseline in Physiologically-Induced VEGF-A Plasma and Serum VEGF Concentrations: Stage 1 of Multiple-dose Study. The acronyms have the following definitions: VEGF=vascular endothelial growth factor; and, SEM=standard error of the mean.

Figure 18:
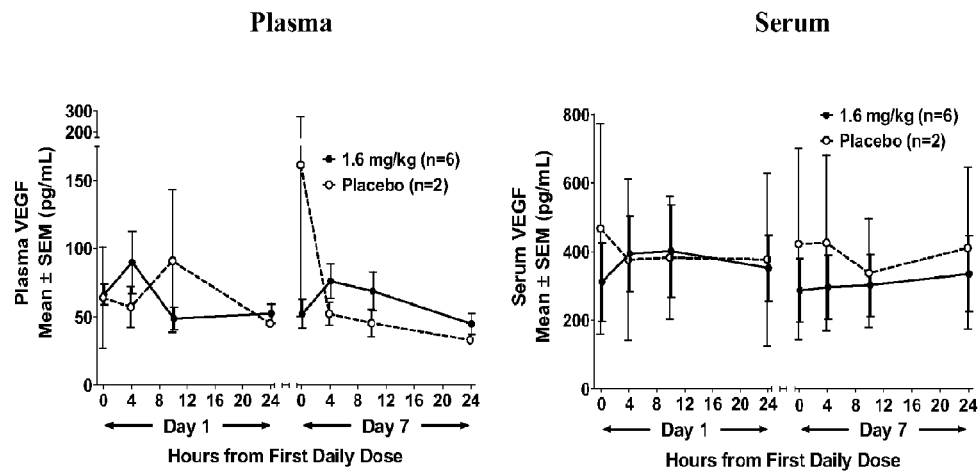
Figure 18:
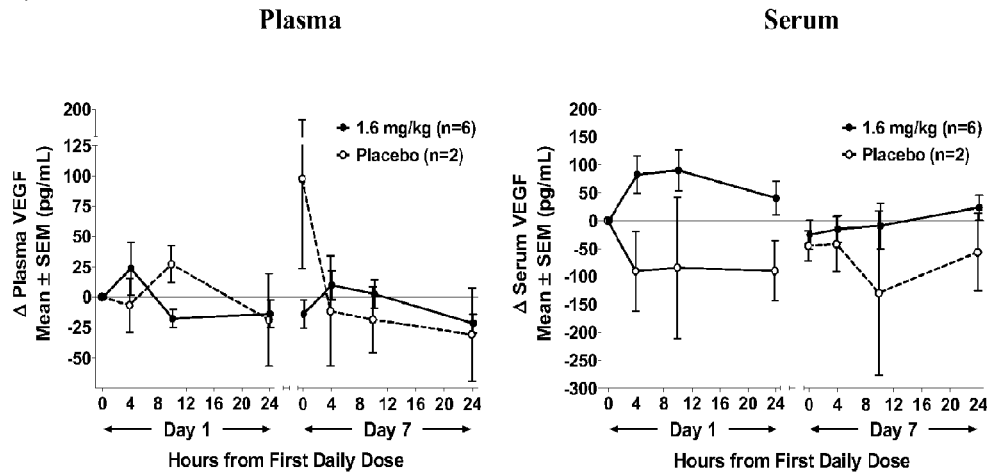

FIG. 18A-B. FIG. 18A: Absolute VEGF-A Plasma and Serum Concentrations: Stage 2 of Multiple-dose Study; FIG. 18B: Change from Baseline in VEGF-A Plasma and Serum VEGF Concentrations: Stage 2 of Multiple-dose Study. The acronyms have the following definitions: VEGF=vascular endothelial growth factor; and, SEM=standard error of the mean.

Figure 19:
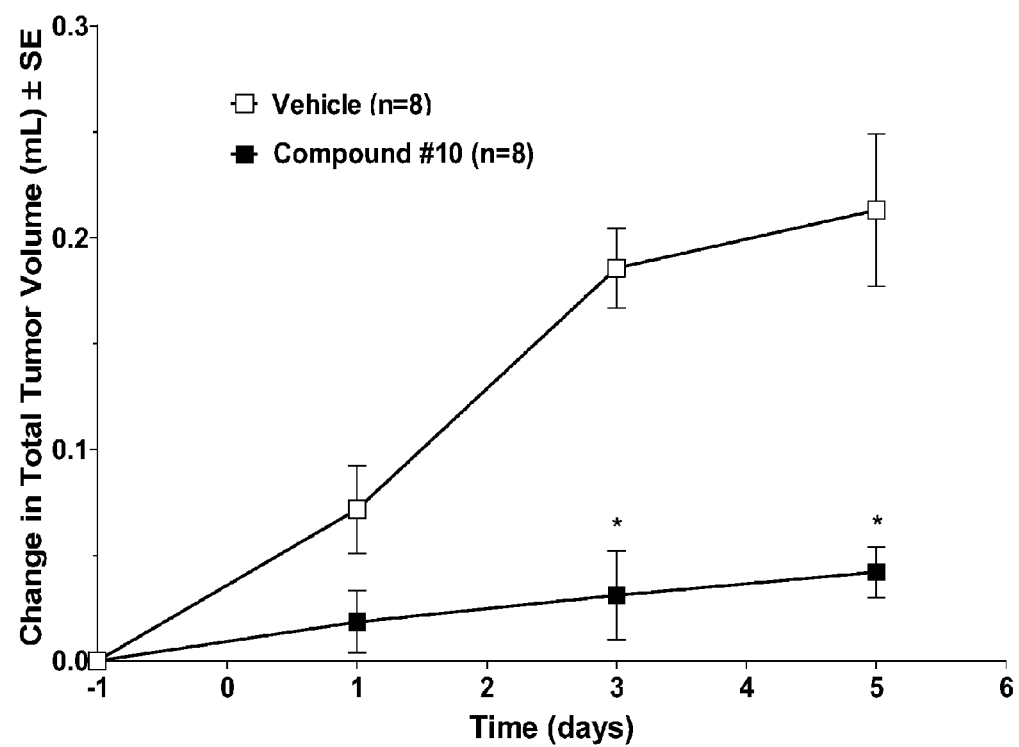

FIG. 19. Change in Total Tumor Volume Induced by Compound #10 in Nude Mice Bearing MDA-MB-468 Xenografts. The symbol "*" represents a p value of p<0.01, signifying that the differences in treated mice were significantly different from tumor size in vehicle-treated mice (Student's t-test). The acronyms have the following definitions: SE=standard error of the mean.

Figure 20:
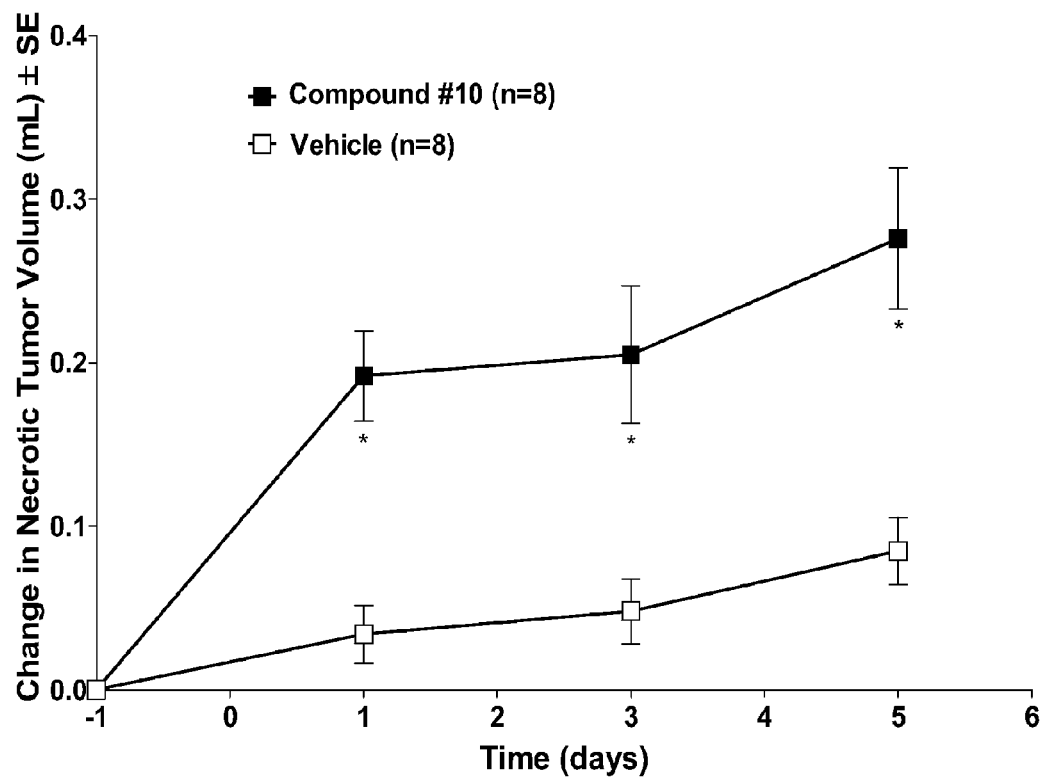

FIG. 20. Change in Necrotic Tumor Volume Induced by Compound #10 in Nude Mice Bearing MDA-MB-468 Xenografts. The symbol "*" represents a p value of p<0.01, signifying that the differences in treated mice were significantly different from tumor size in vehicle-treated mice (Student's t-test). The acronyms have the following definitions: SE=standard error of the mean.

Figure 21:
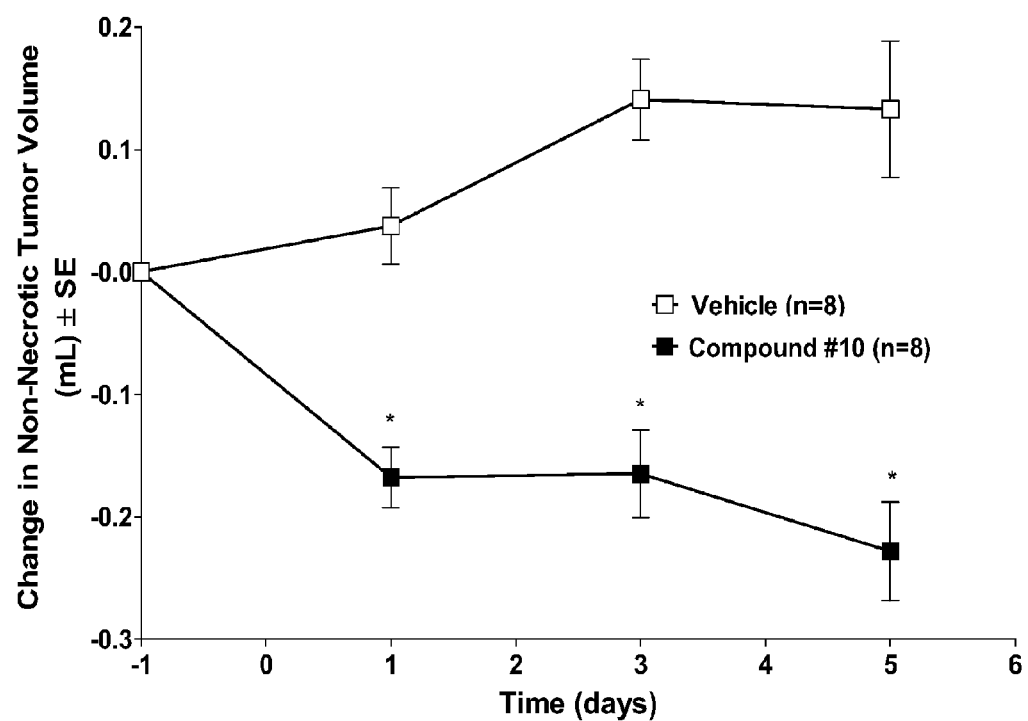

FIG. 21. Change in Non-Necrotic Tumor Volume Induced by Compound #10 in Nude Mice Bearing MDA-MB-468 Xenografts. The symbol "*" represents a p value of p<0.01, signifying that the differences in treated mice were significantly different from tumor size in vehicle-treated mice (Student's t-test). The acronyms have the following definitions: SE=standard error of the mean.

Figure 22:
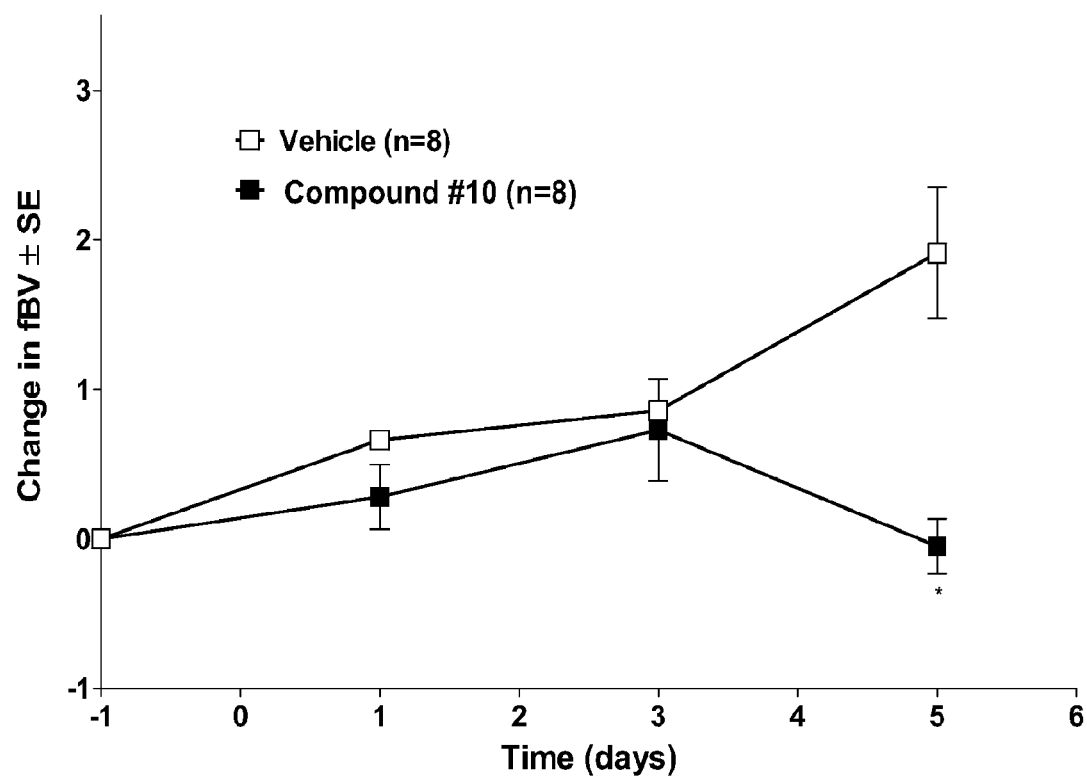

FIG. 22. Change in fBV Induced by Compound #10 in Non Necrotic Tissue in Nude Mice Bearing MDA-MB-468 Xenografts. The symbol "**" represents a p value of p<0.01, signifying that the differences in treated mice were significantly different from tumor size in vehicle-treated mice (Student's t-test). The acronyms have the following definitions: fBV=fractional blood volume; and, SE=standard error of the mean.

Figure 23:
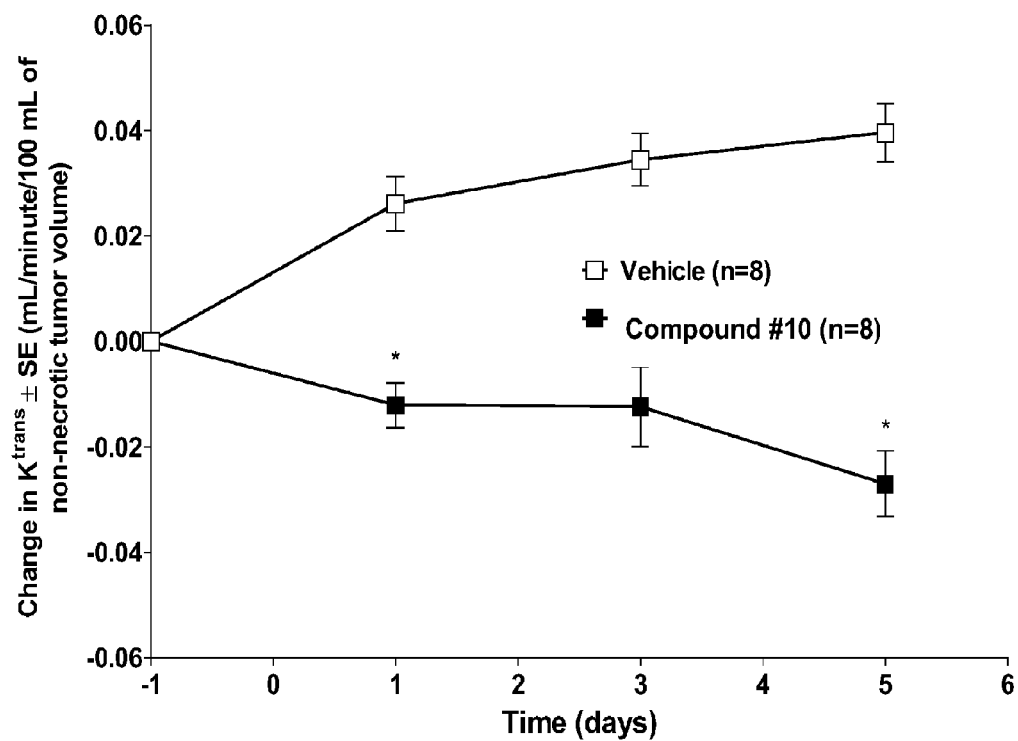

FIG. 23. Change in $K_{trans}$ Induced by Compound #10 in Non Necrotic Tissue in Nude Mice Bearing MDA-MB-468 Xenografts. The symbol "*" represents a p value of p<0.01, signifying that the differences in treated mice were significantly different from tumor size in vehicle-treated mice (Student's t-test). The acronyms have the following definitions: $K_{trans}$=volume transfer coefficient; and, SE=standard error of the mean.

Figure 24:
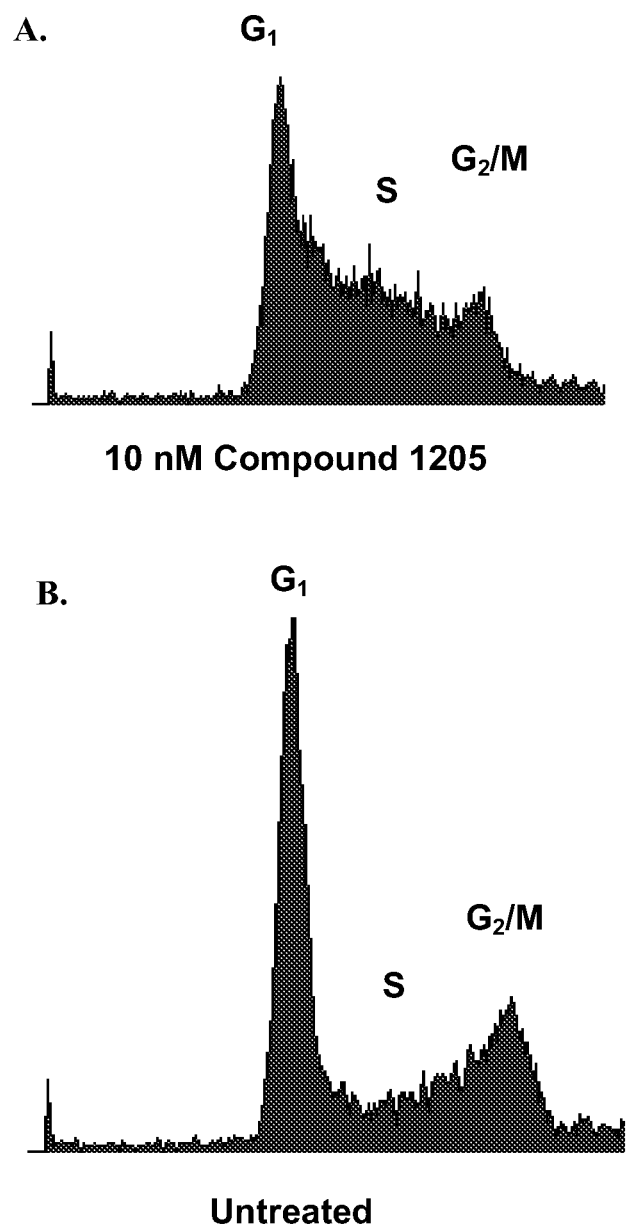

FIG. 24A-B. Cell Cycle Delay After Overnight Exposure to Compound 1205. Histograms depicting relative DNA content in HT1080 cells under normoxic conditions after treatment with Compound 1205 compared to vehicle. FIG. 24A. Histogram showing the effect of treatment with Compound 1205 at 10 nm. FIG. 24B. Histogram showing the effect of treatment with vehicle.

Figure 25:
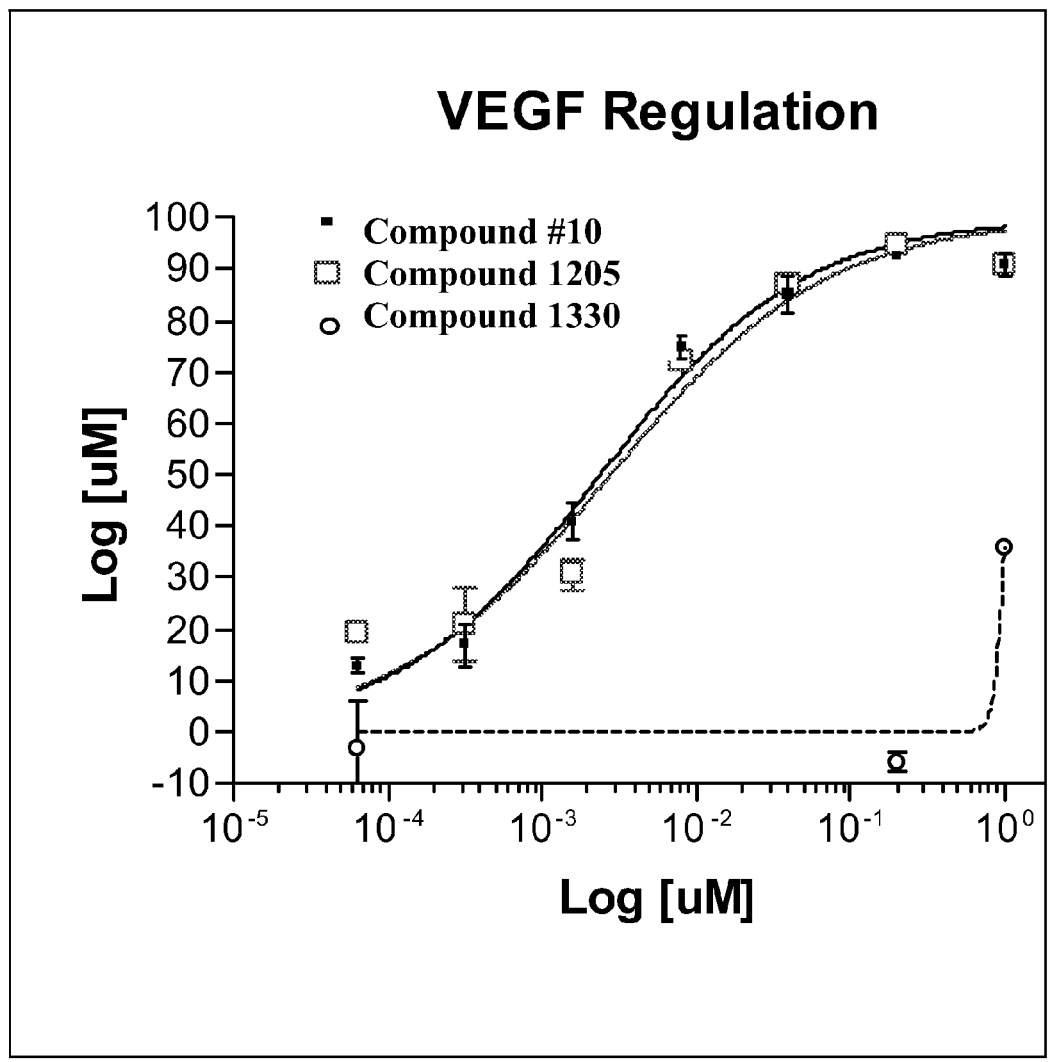

FIG. 25. Dose Response of Compound 1205 and Compound #10: Inhibition of the Production of Hypoxia-Induced VEGF in HeLa Cells.

Figure 26:
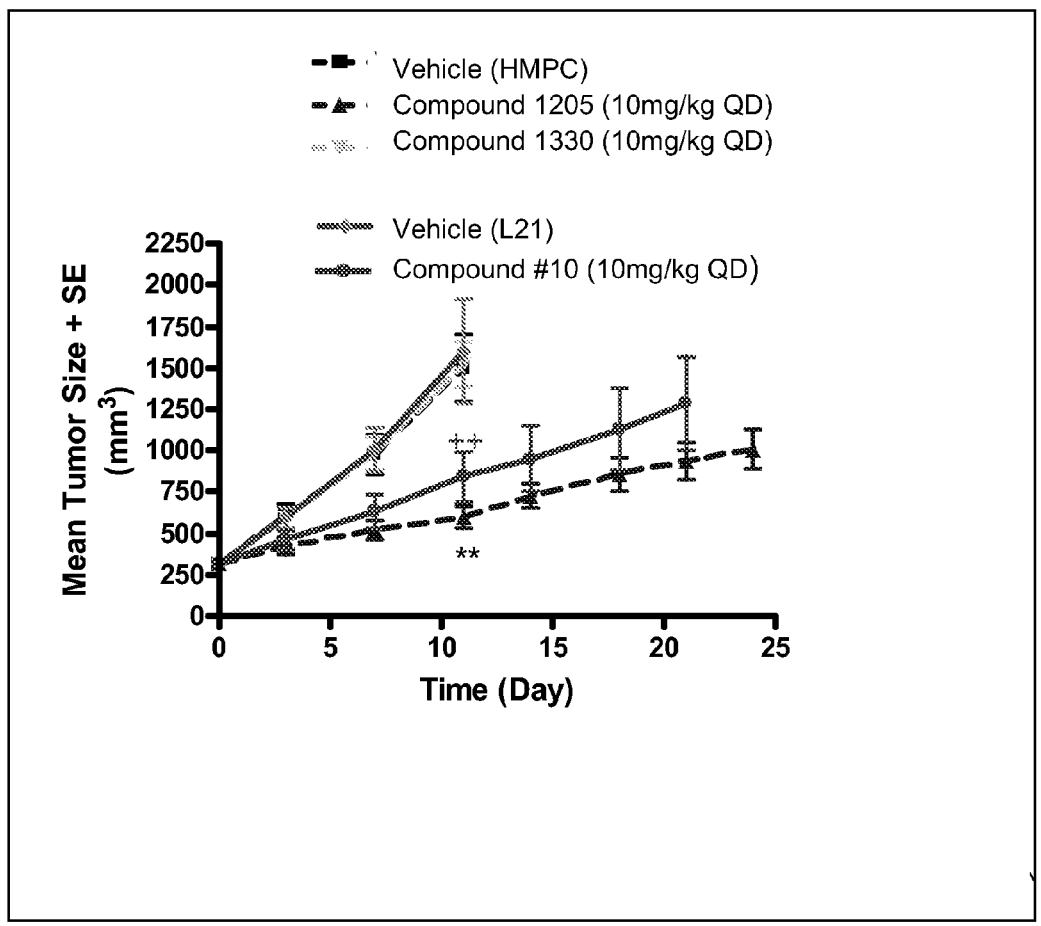

FIG. 26. Inhibition of HT1080 Tumor Growth by Compound #10, 1205 and 1330. The symbol "++" represents a p value of p=0.051, signifying the difference in tumor size in Compound #10 treated mice from tumor size in vehicle-treated mice (Student's t-test) on Day 11. The symbol "**" represents a p value of p<0.05, signifying that the differences in tumor size in Compound 1205 (S,S diastereoisomer) treated mice were significantly different from tumor size in vehicle-treated mice and that the differences in tumor size in Compound 1205 (S,S diastereoisomer) treated mice were significantly different from tumor size in Compound 1330 (R,S diastereoisomer)-treated mice (ANOVA, multiple comparisons).

Figure 27:
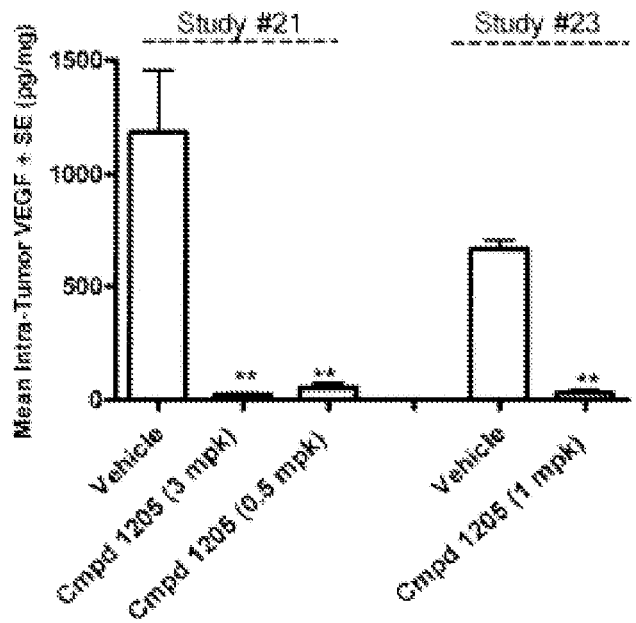
Figure 27:
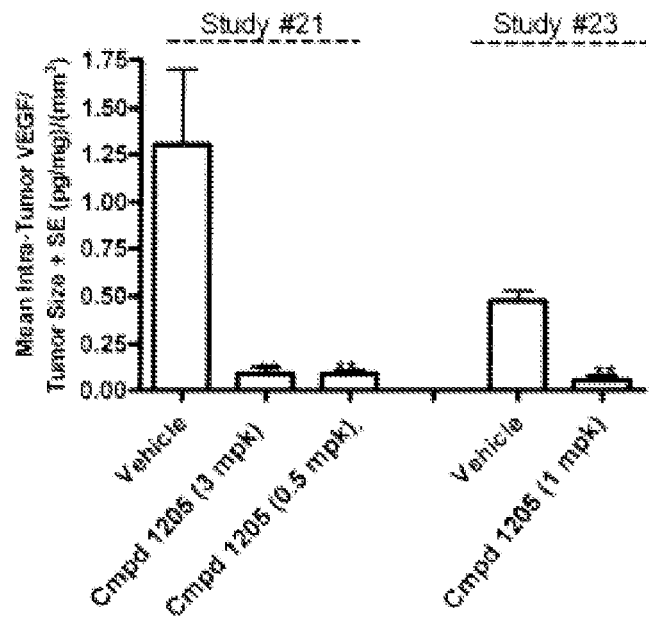

FIG. 27A-B. Effect of Compound 1205 on Intra-Tumor Human VEGF Levels. FIG. 27A. Effect of treatment with vehicle and Compound 1205 on intra-tumor VEGF levels for Study #21 (target tumor size: 1200 $mm^3$) and Study #23 (target tumor size: 1500 $mm^3$). FIG. 27B. Intra-tumor VEGF levels normalized to tumor size.

Figure 28:
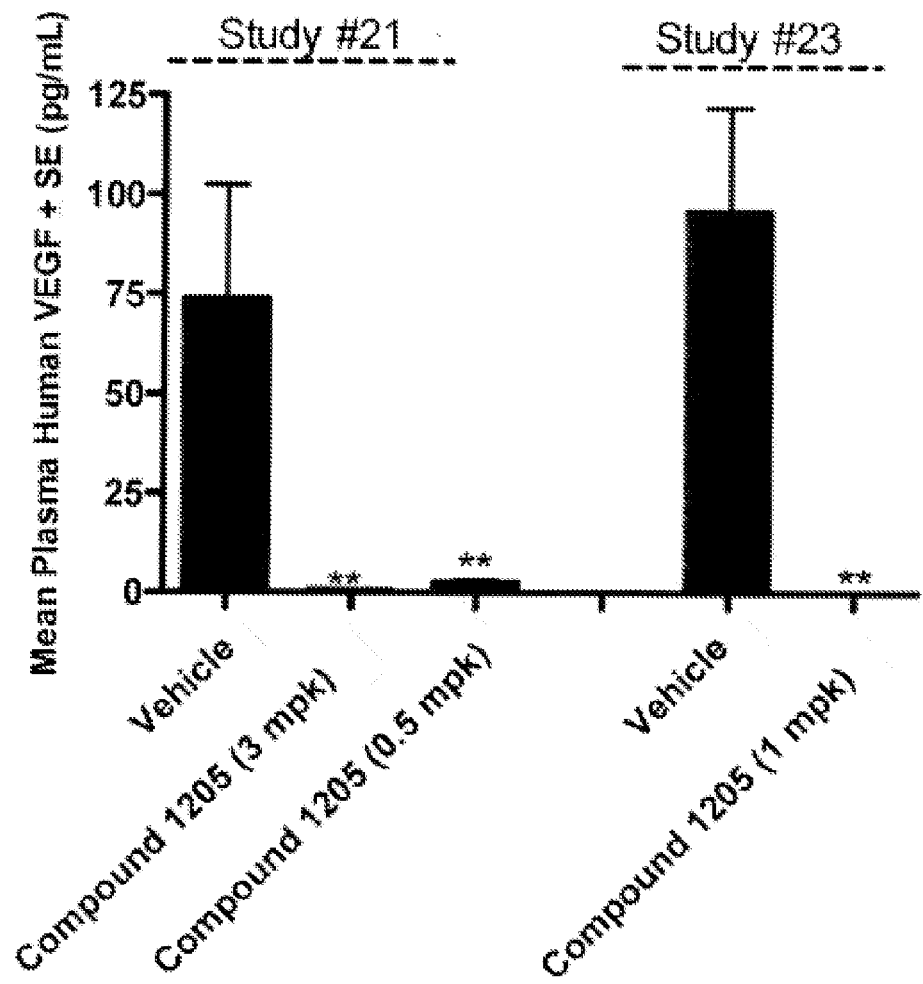

FIG. 28. Effect of Compound 1205 on Levels of Homeostatic Plasma Human VEGF for Study #21 and Study #23.

Figure 29:
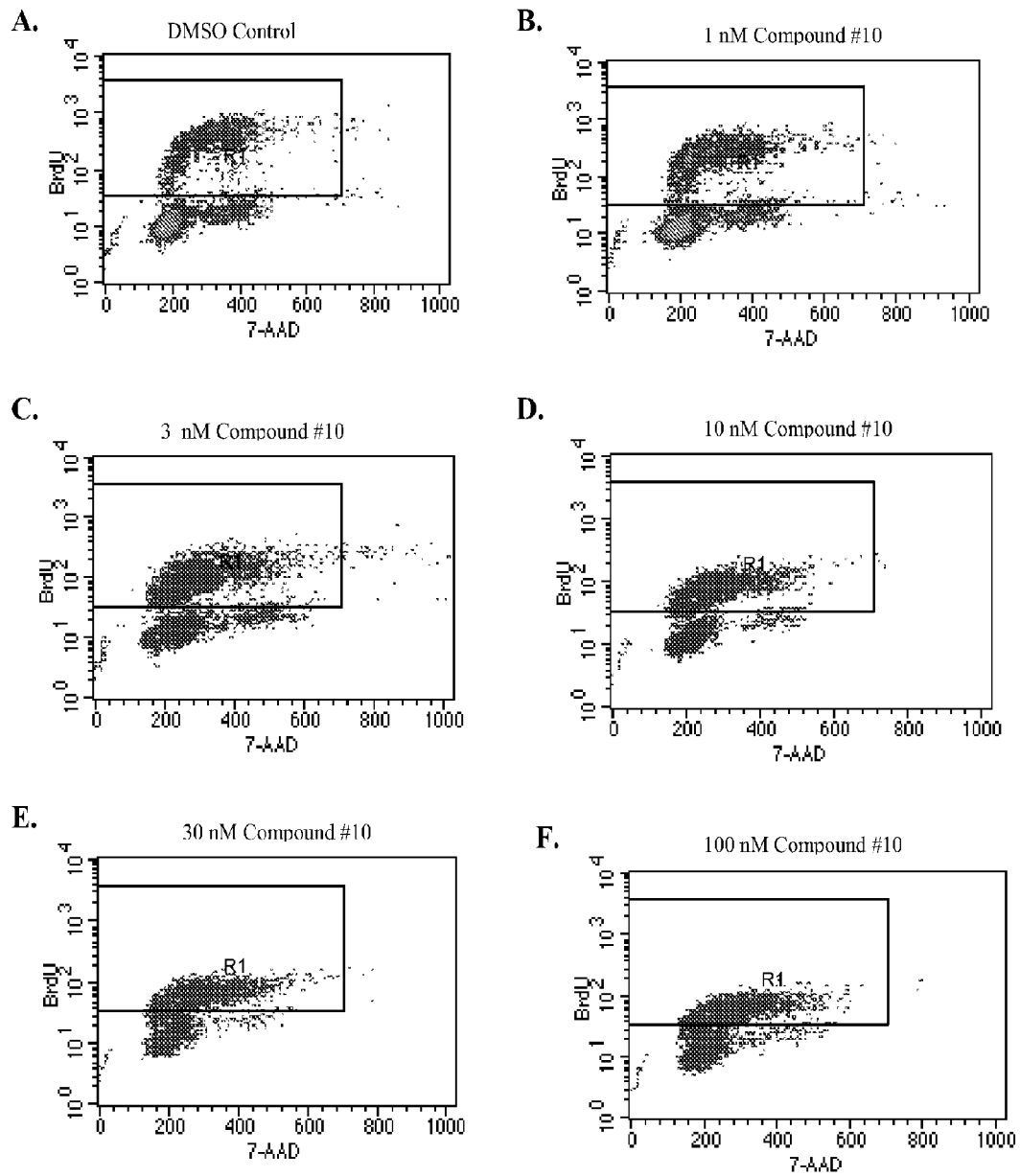

FIG. 29A-F. Treatment of BrdU labeled HT1080 cells with increasing doses of Compound #10. FIG. 29A. The effect of DMSO control on percentage of cells residing in S-phase. FIGS. 29B-F. The effect of increasing concentration of Compound #10 at 1 nm, 3 nm, 10 nm, 30 nm and 100 nm, respectively, on percentage of cells residing in S-phase.

Figure 30:
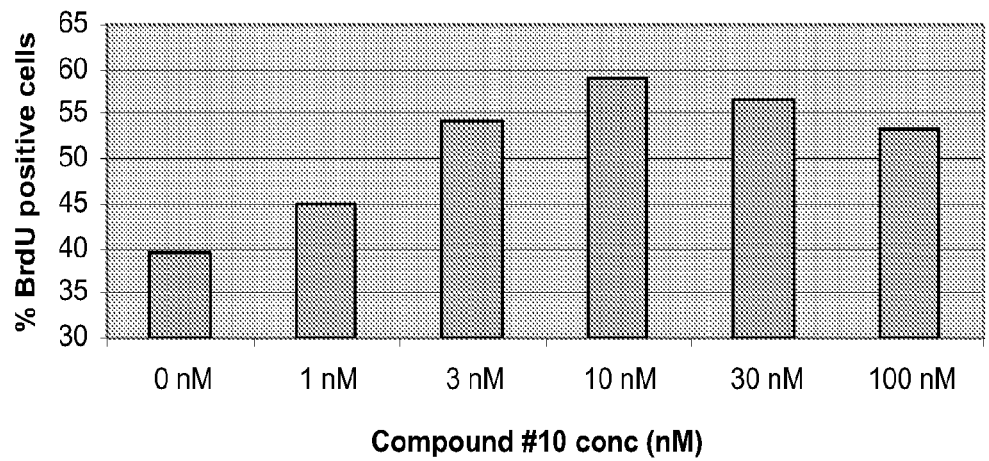
Figure 30:
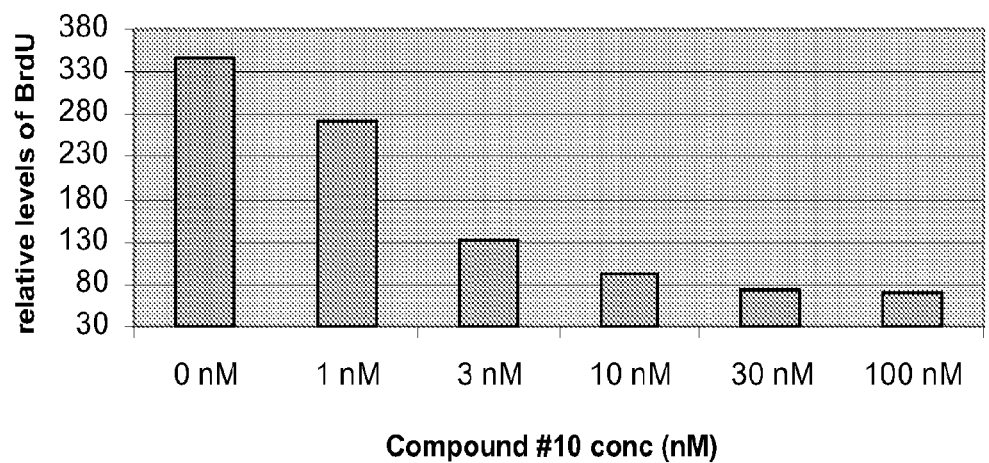

FIG. 30A-B. FIG. 30A. The percentage of cells incorporating BrdU. FIG. 30B. The relative level of BrdU at each Compound #10 concentration.

Figure 31C:
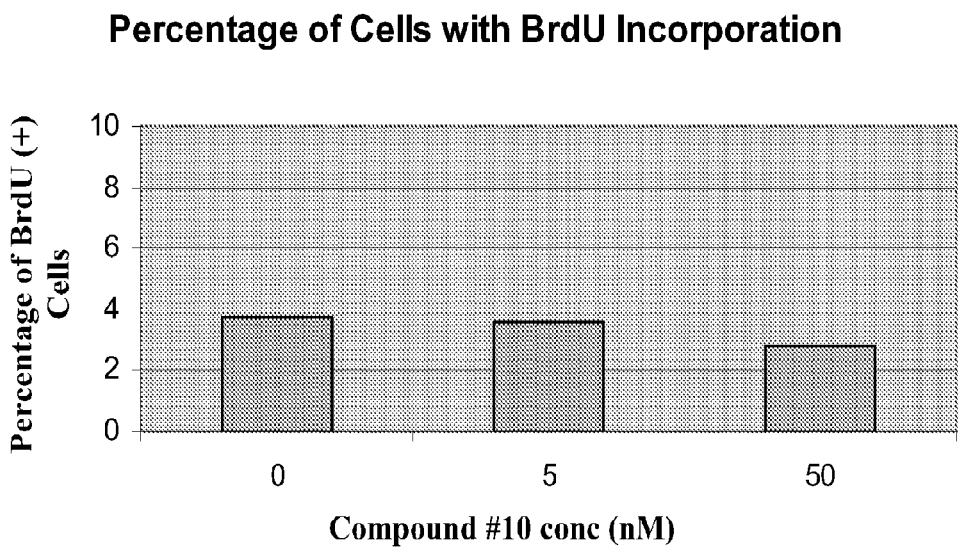

FIG. 31A-B-C. BrdU Histogram and Quantification: FIG. 31(A). Histograms of DNA content demonstrating that the cell cycle distribution for HT1080 spheroids treated for 24 hours is not affected by exposure to Compound #10; FIG. 31(A)(i). Data.001 shows the control results; FIG. 31(A)(ii). Data.002 shows the results of exposure at 5 nm Compound #10; and, FIG. 31(A)(iii). Data.003 shows the results of exposure at 50 nm Compound #10. FIG. 31(B). BrdU quantification indicating the fraction of cells actively synthesizing DNA; FIG. 31(B)(i). The effect of the DMSO control; FIG. 31(B)(ii). Represents the Data.001 results; and, FIG. 31(B)(iii). Represents the Data.003 results. FIG. 31(C) A graphical representation of the percentage of cells that incorporated BrdU (i.e., the cells in S-phase) after treatment with Compound #10 at various concentrations.

Figure 32C:
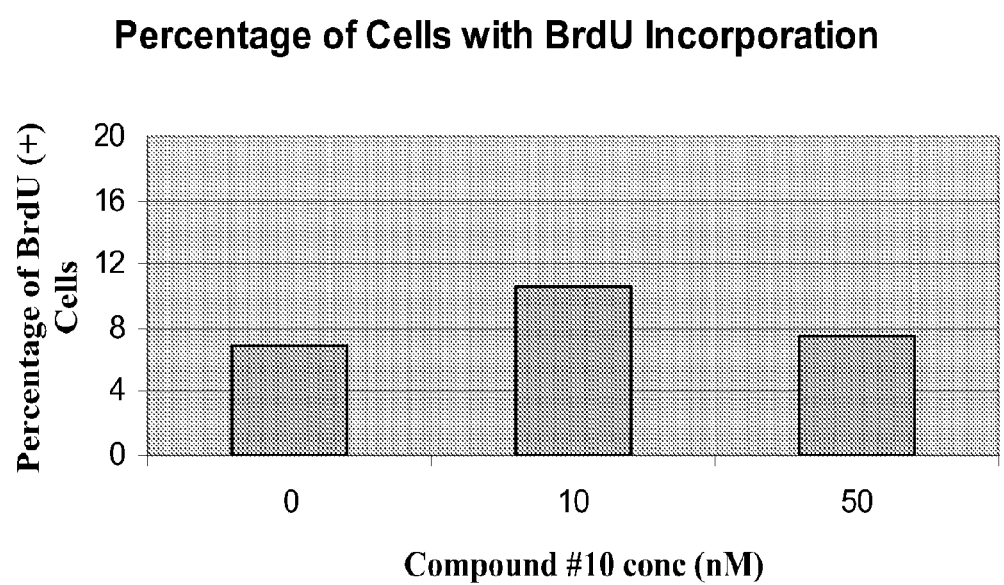

FIG. 32A-B-C. BrdU Histogram and Quantification: FIG. 32(A). Histograms of DNA content demonstrating that the cell cycle distribution for HT1080 spheroids treated for 48 hours is not affected by exposure to Compound #10; FIG. 32(A)(i). Data.004 shows the control results; FIG. 32(A)(ii). Data.005 shows the results of exposure at 10 nm Compound #10; and, FIG. 32(A)(iii). Data.006 shows the results of exposure at 50 nm Compound #10. FIG. 32(B). BrdU quantification indicating the fraction of cells actively synthesizing DNA; FIG. 32(B)(i). Represents the Data.004 results; FIG. 32(B)(ii). Represents the Data.005 results; and, FIG. 32(B) (iii). Represents the Data.006 results. FIG. 32(C) A graphical representation of the percentage of cells that incorporated BrdU (i.e., the cells in S-phase) after treatment with Compound #10 at various concentrations.

Figure 33:
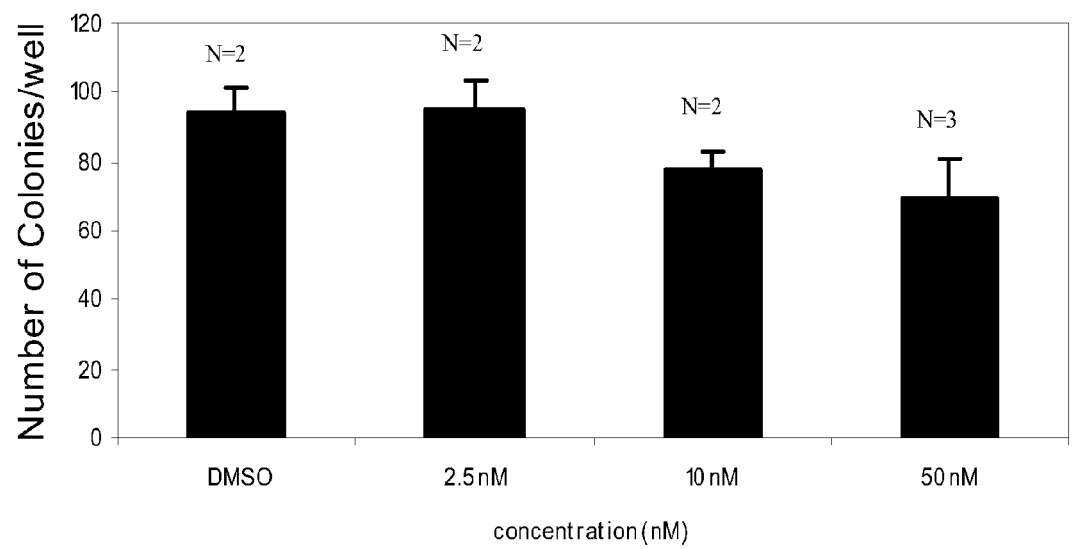

FIG. 33. The effect of Compound #10 on Anchorage Independent Colony Formation.

Figure 34:
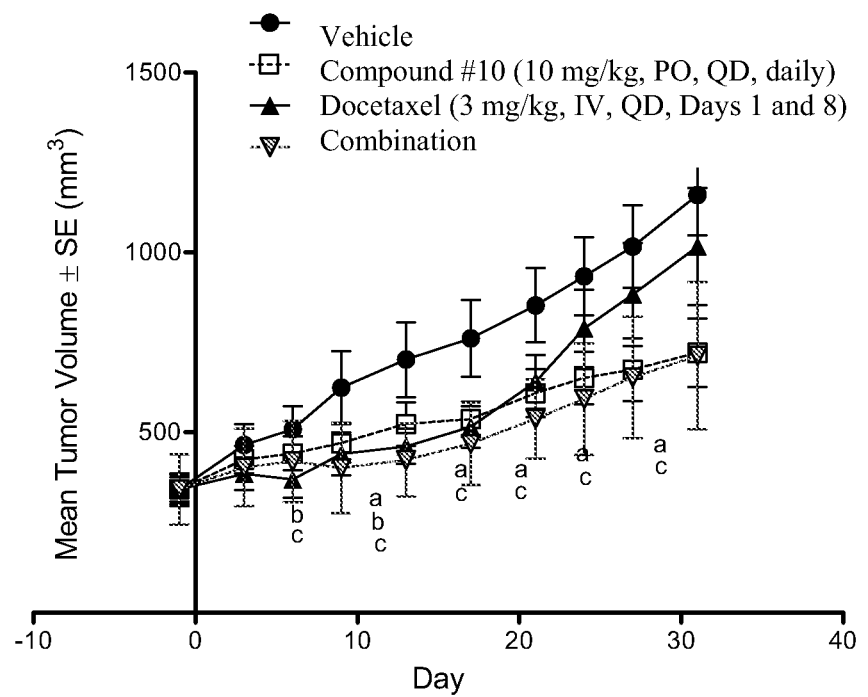

FIG. 34. Mean changes in tumor volume over time in C.B.17 SCID mice inoculated with LNCaP prostate tumor cells following administration of vehicle alone, Compound #10 (10 mg/kg, PO, QD, daily), docetaxel (3 mg/kg, QD, Days 1 and 8), or the combination of Compound #10 (10 mg/kg, PO, QD, daily) and docetaxel (3 mg/kg, QD, Days 1 and 8). The "a" symbol represents measurable lesions only; the "b" symbol represents measurable lesions not followed as target lesions or non-measurable lesions; the "c" symbol represents measurable or non-measurable lesions.

Figure 35:
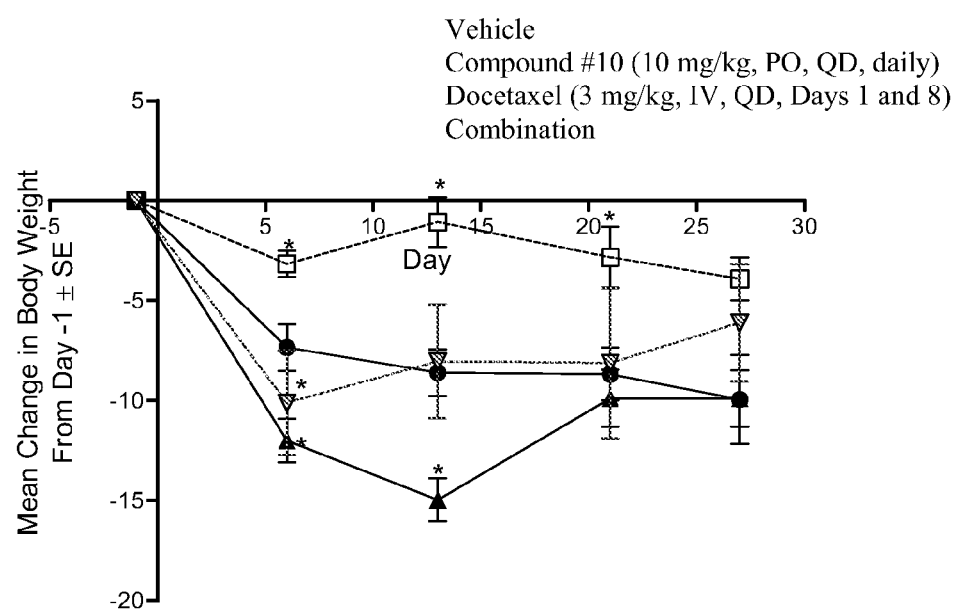

FIG. 35. Mean changes in body weight over time in C.B.17 SCID mice inoculated with LNCaP prostate tumor cells following administration of vehicle alone, Compound #10 (10 mg/kg, PO, QD, daily), docetaxel (3 mg/kg, QD, Days 1 and 8), or the combination of Compound #10 (10 mg/kg, PO, QD, daily) and docetaxel (3 mg/kg, QD, Days 1 and 8). The initial weights were obtained the day before the study was started, where the symbol "*" represents a p value of $p<0.05$, signifying that the differences in treated mice were significantly different from vehicle-treated mice (ANOVA, multiple comparisons to vehicle). The acronyms have the following definitions: have the following definitions: IV=intravenous; PO=oral; QD=once per day; SE=standard error of the mean.

Figure 36:
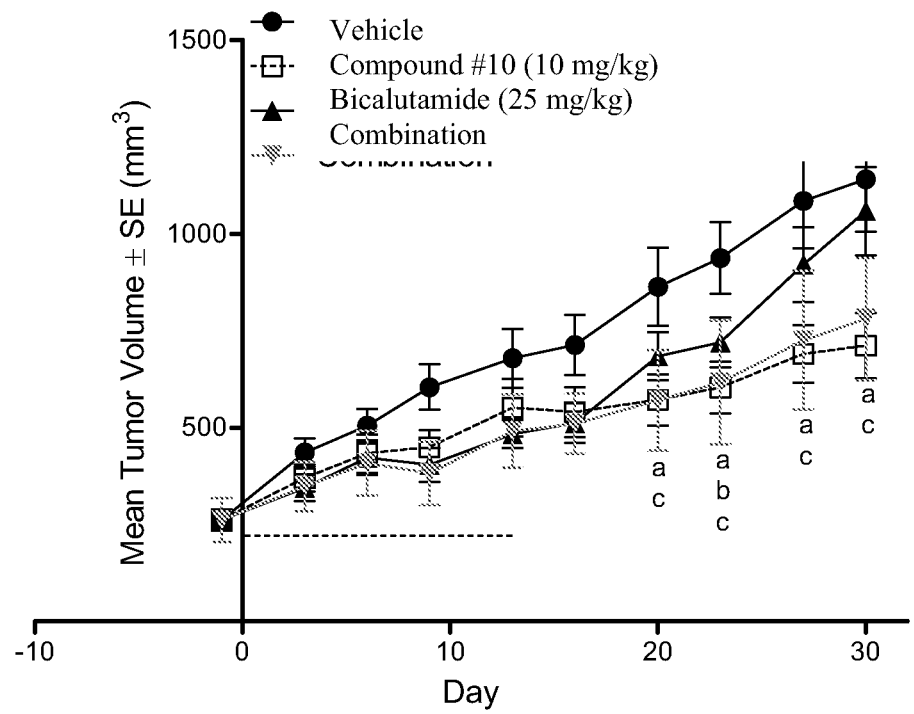

FIG. 36. Mean changes in tumor volume over time in C.B.17 SCID mice inoculated with LNCaP prostate tumor cells following administration of vehicle alone, Compound #10 (10 mg/kg, PO, QD, daily), bicalutamide (25 mg/kg, QD, Days 0, 1, 2, 3, 6, 7, 8, 9, and 10), or the combination of Compound #10 (10 mg/kg, PO, QD, daily) and bicalutamide (25 mg/kg, QD, Days 0, 1, 2, 3, 6, 7, 8, 9, and 10). The "a" symbol represents measurable lesions only; the "b" symbol represents measurable lesions not followed as target lesions or non-measurable lesions; the "c" symbol represents measurable or non-measurable lesions.

Figure 37:
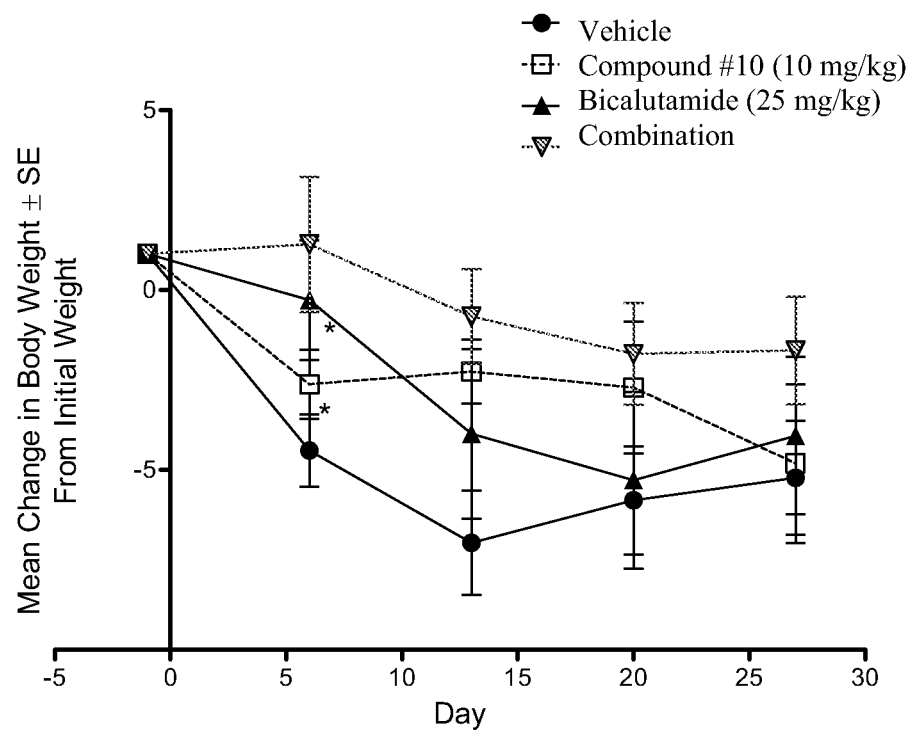

FIG. 37. Mean changes in body weight over time in C.B.17 SCID mice inoculated with LNCaP prostate tumor cells following administration of vehicle alone, Compound #10 (10 mg/kg, PO, QD, daily), bicalutamide (25 mg/kg, QD, Days 0, 1, 2, 3, 6, 7, 8, 9, and 10), or the combination of Compound #10 (10 mg/kg, PO, QD, daily) and bicalutamide (25 mg/kg, QD, Days 0, 1, 2, 3, 6, 7, 8, 9, and 10). The initial weights were obtained the day before the study was started, where the symbol "*" represents a p value of $p<0.05$, signifying that the differences in treated mice were significantly different from vehicle-treated mice (ANOVA, multiple comparisons to vehicle). The acronyms have the following definitions: have the following definitions: IV=intravenous; PO=oral; QD=once per day; SE=standard error of the mean.

FIG. 38A-B. FIG. 38A: The effect on mean tumor growth over the study time period for nude mice bearing PC3 Xenografts treated by oral gavage with Compound #10 at 10 mg/kg QD (once per day), 10 mg/kg BID (twice per day) and 3 mg/kg BID. FIG. 38B: The effect on mean tumor growth over the study time period for nude mice bearing PC3 Xenografts treated by oral gavage with Compound #10 (10 mg/kg QD), docetaxel (3 mg/kg IV Day 1, and at 8 and 10 mg/kg Day 29) and the combination of Compound #10 and docetaxel. Symbols represent the average tumor±SE of 10-13 mice per group.

Figure 39:
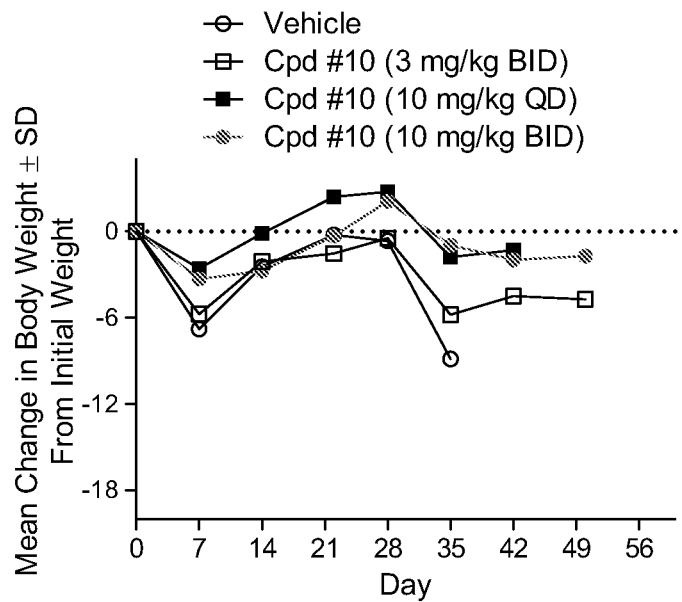
Figure 39:
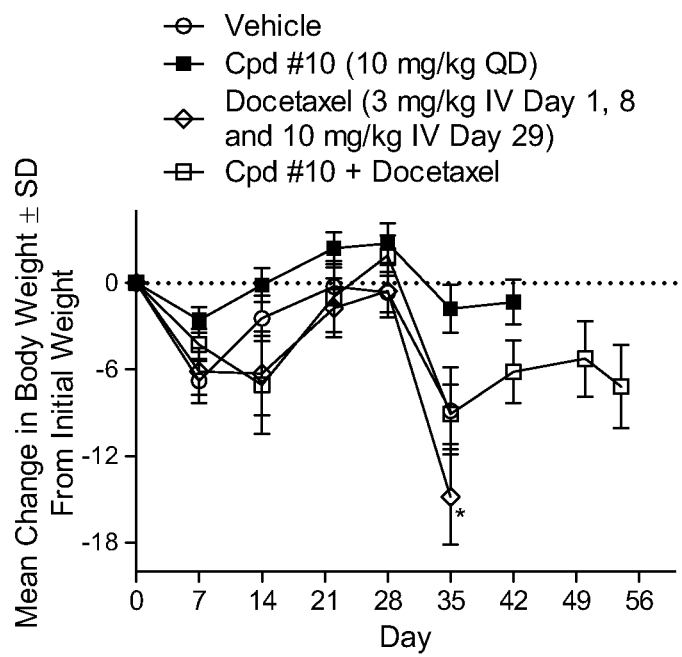

FIG. 39A-B. FIG. 39A: Mean changes in body weight over the study time period for nude mice bearing PC3 Xenografts treated by oral gavage with various doses of Compound #10 (10 mg/kg QD, 10 mg/kg BID and 3 mg/kg BID). FIG. 39B: The effect on body weight over the study time period for nude mice bearing PC3 Xenografts treated by oral gavage with Compound #10 (10 mg/kg QD), docetaxel (3 mg/kg IV Day 1, and at 8 and 10 mg/kg Day 29) and the combination of Compound #10 and docetaxel.

5. DETAILED DESCRIPTION

Presented herein are methods for treating a prostate condition. In one aspect, the methods for treating a prostate condition (e.g., prostate cancer or BPH) involve the administration of a Compound, as a single-agent therapy, to a patient in need thereof. In a specific embodiment, presented herein is a method for treating a prostate condition, comprising administering to a patient in need thereof an effective amount of a Compound, as a single agent. In another embodiment, presented herein is a method for treating a prostate condition, comprising administering to a patient in need thereof a pharmaceutical composition comprising a Compound, as the single active ingredient, and a pharmaceutically acceptable carrier, excipient or vehicle.

In another aspect, the methods for treating a prostate condition involve the administration of a Compound in combination with another therapy (e.g., one or more additional therapies that do not comprise a Compound, or that comprise a different Compound) to a patient in need thereof. Such methods may involve administering a Compound prior to, concurrent with, or subsequent to administration of the additional therapy. In certain embodiments, such methods have an additive or synergistic effect. In a specific embodiment, presented herein is a method for treating a prostate condition, comprising administering to a patient in need thereof an effective amount of a Compound and an effective amount of another therapy.

In certain embodiments, the concentration of VEGF or other angiogenic or inflammatory mediators in biological specimens (e.g., plasma, serum, cerebral spinal fluid, urine, or any other biofluids) of a patient is monitored before, during and/or after a course of treatment involving the administration of a Compound or a pharmaceutical composition thereof to the patient. In certain embodiments, the tumoral or BPH blood flow or metabolism, or peritumoral or peri-BPH inflammation or edema in a patient is monitored before, during and/or after a course of treatment involving the administration of a Compound or a pharmaceutical composition. The dosage, frequency and/or length of administration of a Compound or a pharmaceutical composition thereof to a patient may also be modified as a result of the concentration of VEGF or other angiogenic or inflammatory mediators, or of tumoral or BPH blood flow or metabolism, or peritumoral or peri-BPH inflammation or edema, as assessed by imaging techniques. Alternatively, the changes in one or more of these monitoring parameters (e.g., concentration of VEGF or other angiogenic or inflammatory mediators, or tumoral or BPH blood flow or metabolism, or peritumoral or peri-BPH inflammation or edema) may indicate that the course of treatment involving the administration of the Compound or pharmaceutical composition thereof is effective in treating the prostate condition.

In a specific embodiment, presented herein is a method for treating a prostate condition, comprising: (a) administering to a patient in need thereof one or more doses of a Compound or a pharmaceutical composition thereof; and (b) monitoring the concentration of VEGF or other angiogenic mediators, inflammatory mediators, or a prostate-specific marker (e.g., detected in biological specimens such as plasma, serum, cerebral spinal fluid, urine or other biofluids), before and/or after step (a). In specific embodiments, step (b) comprises monitoring the concentration of one or more inflammatory mediators including, but not limited to, cytokines or interleukins such as IL-6 and IL-8. In particular embodiments, step (b) comprises monitoring the concentration of VEFG, VEGF-R, P1GF, VEGF-C, and/or VEGF-D. In some embodiments, step (b) comprises monitoring the concentration of PSA. In certain embodiments, the monitoring step (b) is carried out before and/or after a certain number of doses (e.g., 1, 2, 4, 6, 8, 10, 12, 14, 15, or 20 doses, or more doses; or 2 to 4, 2 to 8, 2 to 20 or 2 to 30 doses) or a certain time period (e.g., 1, 2, 3, 4, 5, 6, or 7 days; or 1, 2, 3, 4, 5, 10, 15, 20, 30, 40, 45, 48, or 50 weeks) of administering the Compound. In certain embodiments, one or more of these monitoring parameters are detected prior to administration of the Compound or pharmaceutical composition thereof. In specific embodiments, a decrease in the concentration of VEGF or other angiogenic mediators, inflammatory mediators, and/or prostate-specific markers following administration of the Compound or pharmaceutical composition thereof indicates that the course of treatment is effective for treating the prostate condition. In some embodiments, a change in the concentration of VEGF or other angiogenic mediators, inflammatory mediators, and/or prostate-specific markers following administration of the Compound or pharmaceutical composition thereof may indicate that the dosage, frequency and/or length of administration of the Compound or a pharmaceutical composition thereof may be adjusted (e.g., increased, reduced or maintained).

In a specific embodiment, presented herein is a method for treating a prostate condition, comprising: (a) administering to a patient in need thereof one or more doses of a Compound or a pharmaceutical composition thereof; and (b) monitoring the concentration of VEGF, other angiogenic mediators, inflammatory mediators, and/or one or more prostate-specific markers (e.g., detected in biological specimens such as plasma, serum, cerebral spinal fluid, urine or other biofluids), tumoral or BPH blood flow or metabolism, or peritumoral or peri-BPH inflammation or edema, before and/or after step (a). In certain embodiments, the monitoring step (b) is carried out before and/or after a certain number of doses (e.g., 1, 2, 4, 6, 8, 10, 12, 14, 2 to 4, 2 to 8, 2 to 20 or 2 to 30 doses) or a certain time period (e.g., 1, 2, 3, 4, 5, 6, or 7 days; 1, 2, 3, or 4 weeks) of administering the Compound. In certain embodiments, one or more of these monitoring parameters are detected prior to administration of the Compound or pharmaceutical composition thereof. In specific embodiments, a decrease in the concentration of VEGF, other angiogenic mediators, inflammatory mediators, and/or a prostate-specific marker, or a change in tumoral or BPH blood flow or metabolism, or peritumoral or peri-BPH inflammation or edema following administration of the Compound or pharmaceutical composition thereof indicates that the course of treatment is effective for treating the prostate condition. In some embodiments, a decrease in the concentration of VEGF or other angiogenic mediators, inflammatory mediators, and/or a prostate-specific marker, or a change in tumoral or BPH blood flow or metabolism, or peritumoral or peri-BPH inflammation or edema following administration of the Compound or pharmaceutical composition thereof may indicate that the dosage, frequency and/or length of administration of the Compound or a pharmaceutical composition thereof may be adjusted (e.g., increased, reduced or maintained).

The concentration of VEGF, other angiogenic mediators, inflammatory mediators, or prostate-specific markers, and a change in tumor or BPH blood flow or metabolism, or peritumoral or peri-BPH inflammation or edema of a patient may be detected by any technique known to one of skill in the art. In certain embodiments, the method for detecting the concentration of VEGF or other angiogenic or inflammatory mediators, or of prostate-specific markers (e.g., PSA) of a patient involves obtaining a biological sample (e.g., tissue or fluid sample) from the patient and detecting the concentration of VEGF, other angiogenic mediators, inflammatory mediators, or prostate-specific markers (e.g., PSA) in the biological sample (e.g., from plasma serum sample, cerebral spinal fluid, urine, or other biofluids), that has been subjected to certain types of treatment (e.g., centrifugation), and detection by use of immunological techniques, such as ELISA. In a specific embodiment, an ELISA described herein, e.g., in the working examples in Section 9 et seq. may be used to detect the concentration of VEGF or other angiogenic or inflammatory mediators, in a biological sample (e.g., from plasma serum, cerebral spinal fluid, urine, or other biofluids) that has been subjected to certain types of treatment (e.g., centrifugation). Other techniques known in the art that may be used to detect the concentration of VEGF, other angiogenic mediators, inflammatory mediators, and prostate-specific markers (e.g., PSA) in a biological sample, include multiplex or proteomic assays. The levels of prostate-derived CTCs may be detected by immunomagnetic capture techniques. In a specific embodiment, a CT scan, an MRI scan, or a PET scan may be used to detect the tumor or BPH blood flow or metabolism, or peritumoral or peri-BPH inflammation or edema.

In specific embodiments, the methods for treating a prostate condition provided herein alleviate or manage one, two or more symptoms associated with the prostate condition. Alleviating or managing one, two or more symptoms of a prostate condition may be used as a clinical endpoint for efficacy of a Compound for treating the prostate condition. In some embodiments, the methods for treating a prostate condition provided herein reduce the duration and/or severity of one or more symptoms associated with the prostate condition. In some embodiments, the methods for treating a prostate condition provided herein inhibit the onset, progression and/or recurrence of one or more symptoms associated with the prostate condition. In some embodiments, the methods for treating a prostate condition provided herein reduce the number of symptoms associated with the prostate condition. In a specific embodiment, the prostate condition is prostate cancer. In another specific embodiment, the prostate condition is BPH.

Symptoms associated with prostate cancer include, but are not limited to: frequent urination, waking at night to urinate, unable to postpone urination, feeling of being unable to empty bladder, delay in starting to urinate, weak urinary stream-straining, intermittent stream-stopping and starting urination, incontinence (loss of urinary control), painful urination, blood in urine, inability to empty bladder (acute urinary retention), inability to urinate, painful ejaculation, continuing pain in the bones, pain in the lower back, hips or upper thighs, liver pain, shortness of breath, loss of appetite, weight loss, cachexia, nausea, vomiting, fatigue, weakness, spinal cord compression, impaired brain function due to central nervous system metastases, prostate enlargement, and elevated PSA levels.

Symptoms associated with BPH include, but are not limited to: frequent urination, waking at night to urinate, unable to postpone urination, feeling of being unable to empty bladder, delay in starting to urinate, weak urinary stream-straining, intermittent stream-stopping and starting urination, incontinence (loss of urinary control), painful urination, blood in urine, inability to empty bladder (acute urinary retention), prostate enlargement, and elevated PSA.

The methods for treating a prostate condition provided herein inhibit or reduce pathological production of human VEGF. In specific embodiments, the methods for treating a prostate condition provided herein selectively inhibit pathologic production of human VEGF (e.g., by the tumor), but do not disturb the physiological activity of human VEGF protein. Preferably, the methods for treating a prostate condition provided herein do not significantly inhibit or reduce physiological or homeostatic production of human VEGF. For example, blood pressure, protein levels in urine, and bleeding are maintained within normal ranges in treated subjects. In a specific embodiment, the treatment does not result in adverse events as defined in Cancer Therapy Evaluation Program, Common Terminology Criteria for Adverse Events, Version 3.0, DCTD, NCI, NIH, DHHS Mar. 31, 2003 (cstep.cancer.gov), publish date Aug. 9, 2006, which is incorporated by reference herein in its entirety. In other embodiments, the methods for treating a prostate condition provided herein do not result in adverse events of grade 2 or greater as defined in the Cancer Therapy Evaluation Program, Common Terminology Criteria for Adverse Events, Version 3.0, supra.

In specific embodiments, the methods for treating a prostate condition provided herein inhibit or decrease pathological production of VEGF by at least about 5%, 10%, 15%, 20%, 25%, 30%, 35%, 40%, 45%, 50%, 55%, 60%, 65%, 80%, 85%, 90%, 95%, or 100%, relative to the pathological production of VEFG prior to administration of a Compound, as assessed by methods well known in the art. In particular embodiments, the methods for treating a prostate condition provided herein inhibit or decrease pathological production of VEGF in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the pathological production of VEFG prior to administration of a Compound, as assessed by methods well known in the art.

In specific aspects, the methods for treating a prostate condition provided herein decrease the concentration of VEGF or other angiogenic or inflammatory mediators (e.g., cytokines or interleukins, such as IL-6) of a subject as assessed by methods well known in the art, e.g., ELISA. In specific embodiments, the methods for treating a prostate condition provided herein decrease the concentration of VEGF or other angiogenic or inflammatory mediators (e.g., cytokines or interleukins, such as IL-6) of a subject by at least about 5%, 10%, 15%, 20%, 25%, 30%, 35%, 40%, 45%, 50%, 55%, 60%, 65%, 80%, 85%, 90%, 95%, or 100%, relative to the respective concentration prior to administration of a Compound, as assessed by methods well known in the art, e.g., ELISA. In particular embodiments, the methods for treating a prostate condition provided herein decrease the concentration of VEGF or other angiogenic or inflammatory mediators (e.g., cytokines or interleukins, such as IL-6) of a subject in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the respective concentration prior to administration of a Compound, as assessed by methods well known in the art, e.g., ELISA.

In specific aspects, the methods for treating a prostate condition provided herein decrease the concentrations of P1GF, VEGF-C, VEGF-D, VEGFR-1, VEGFR-2, IL-6 and/or IL-8 of a subject as assessed by methods well known in the art, e.g., ELISA. In specific embodiments, the methods for treating a prostate condition provided herein decrease the concentrations of P1GF, VEGF-C, VEGF-D, VEGFR-1, VEGFR-2, IL-6 and/or IL-8 of a subject by at least about 5%, 10%, 15%, 20%, 25%, 30%, 35%, 40%, 45%, 50%, 55%, 60%, 65%, 80%, 85%, 90%, 95%, or 100%, relative to the respective concentration prior to administration of a Compound, as assessed by methods well known in the art, e.g., ELISA. In particular embodiments, the methods for treating a prostate condition provided herein decrease the concentrations P1GF, VEGF-C, VEGF-D, VEGFR-1, VEGFR-2, IL-6 and/or IL-8 of a subject in the range of about 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the respective concentration prior to administration of a Compound, as assessed by methods well known in the art, e.g., ELISA.

In specific embodiments, the methods for treating a prostate condition provided herein inhibit or decrease PSA by at least about 5%, 10%, 15%, 20%, 25%, 30%, 35%, 40%, 45%, 50%, 55%, 60%, 65%, 80%, 85%, 90%, 95%, or 100%, relative to the PSA prior to administration of a Compound, as assessed by methods well known in the art, e.g., ELISA. In particular embodiments, the methods for treating a prostate condition provided herein inhibit or decrease PSA in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the PSA level prior to administration of a Compound, as assessed by methods well known in the art, e.g., ELISA.

In certain embodiments, the methods for treating a prostate condition provided herein inhibit or reduce pathological angiogenesis or vascularization. In a specific embodiment, a CT scan, an MRI scan, or a PET scan may be used to detect angiogenesis or vascularization. In specific embodiments, the methods for treating a prostate condition provided herein inhibit or reduce angiogenesis or vascularization, by at least about 5%, 10%, 15%, 20%, 25%, 30%, 35%, 40%, 45%, 50%, 55%, 60%, 65%, 80%, 85%, 90%, 95%, or 100%, relative to the pathological angiogenesis or vascularization prior to administration of a Compound, as assessed by methods well known in the art, e.g., CT scan, MRI scan, or PET scan. In particular embodiments, the methods for treating a prostate condition provided herein inhibit or reduce angiogenesis or vascularization, in the range of about 5% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the pathological angiogenesis or vascularization prior to administration of a Compound, as assessed by methods well known in the art, e.g., CT scan, MRI scan, or PET scan.

In certain embodiments, the methods for treating a prostate condition provided herein prolong or delay the G1/S or late G1/S phase of cell cycle (i.e., the period between the late resting or pre-DNA synthesis phase, and the early DNA synthesis phase).

In some embodiments, the methods for treating a prostate condition provided herein reduce, ameliorate, or alleviate the severity and/or frequency of the prostate condition and/or one or more symptoms thereof. In other embodiments, the methods for treating a prostate condition provided herein reduce hospitalization (e.g., the frequency or duration of hospitalization) of a subject diagnosed with the prostate condition. In some embodiments, the methods for treating a prostate condition provided herein reduce hospitalization length of a subject diagnosed with the prostate condition. In certain embodiments, the methods provided herein increase the survival of a subject diagnosed with a prostate condition. In specific embodiments, the methods provided herein increase the survival of a subject diagnosed with a prostate condition by about 6 months or more, about 7 months or more, about 8 months or more, about 9 months or more, or about 12 months or more. In particular embodiments, the methods for treating a prostate condition provided herein inhibit or reduce the progression of the prostate condition or one or more symptoms associated therewith. In specific embodiments, the methods for treating a prostate condition provided herein enhance or improve the therapeutic effect of another therapy (e.g., an anti-cancer agent, radiation, drug therapy such as chemotherapy, antiandrogen therapy or surgery). In certain embodiments, the methods for treating a prostate condition provided herein involve the use of a Compound as an adjuvant therapy. In certain embodiments, the methods for treating a prostate condition provided herein improve the ease in removal of tumors (e.g., enhance resectability of the tumors) by reducing vascularization prior to surgery. In particular embodiments, the methods for treating a prostate condition provided herein reduce vascularization after surgery, for example, reduce vascularization of the remaining tumor mass not removed by surgery. In some embodiments, the methods for treating a prostate condition provided herein prevent recurrence, e.g., recurrence of vascularization and/or tumor growth. In some embodiments, the methods for treating a prostate condition provided herein decrease or inhibit prostate, stromal, or epithelial cell hyperplasia.

In particular embodiments, the methods for treating a prostate condition provided herein reduce the mortality of subjects diagnosed with the prostate condition. In certain embodiments, the methods for treating a prostate condition provided herein increase the number of patients in remission or decrease the hospitalization rate. In other embodiments, the methods for treating a prostate condition provided herein prevent the development, onset or progression of a prostate condition, or one or more symptoms associated therewith. In particular embodiments, the methods for treating a prostate condition provided herein increase symptom-free survival of prostate condition patients. In some embodiments, the methods for treating a prostate condition provided herein do not cure the prostate condition in patients, but prevent the progression or worsening of the disease.

In particular embodiments, the methods for treating a prostate condition provided herein inhibit, reduce, diminish, arrest, or stabilize the prostatic tumor or BPH. In other embodiments, the methods for treating a prostate condition provided herein inhibit, reduce, diminish, arrest, or stabilize the blood flow or metabolism of a tumor or BPH, or tumor-related or BPH-related inflammation or edema associated with the prostate condition or one or more symptoms thereof. In specific embodiments, the methods for treating a prostate condition provided herein cause the regression of the size, blood flow, or metabolism of a tumor or BPH, or peritumoral or peri-BPH inflammation or edema, and/or one or more symptoms associated with the prostate condition. In other embodiments, the methods for treating the prostate condition provided herein maintain the size of a tumor or BPH so that it does not increase, or so that it increases by less than the increase of a tumor or BPH after administration of a standard therapy as measured by conventional methods available to one of skill in the art, such as PSA concentrations, digital rectal exam, ultrasound (e.g., transrectal ultrasound), CT Scan, and MRI. In specific embodiments, the methods for treating a prostate condition provided herein decrease the size of a tumor or BPH. In certain embodiments, the methods for treating a prostate condition provided herein reduce the formation of a newly formed tumor or BPH. In certain embodiments, the methods for treating a prostate condition provided herein eradicate, remove, or control primary, regional and/or metastatic tumors associated with prostate cancer or eradicate, remove, or control BPH. In some embodiments, the methods for treating a prostate condition such as prostate cancer provided herein decrease the number or size of metastases associated with prostate cancer. In specific embodiments, the methods for treating a prostate condition achieve stabilization or reduction of peritumoral or peri-BPH inflammation or edema. In specific embodiments, the methods for treating a prostate condition achieve one or more of the following: (i) inhibition or reduction in pathological production of VEGF; (ii) reduction of the concentration of VEGF or other angiogenic or inflammatory mediators (e.g., cytokines or interleukins) in biological specimens (e.g., plasma, serum, cerebral spinal fluid, urine, or any other biofluids); (iii) reduction of the concentration of P1GF, VEGF-C, VEGF-D, VEGFR, IL-6, and/or IL-8 in biological specimens (e.g., plasma, serum, cerebral spinal fluid, urine, or any other biofluids), and (iv) reduction of the concentration of prostate-specific markers such as PSA in biological specimens (e.g., plasma, serum, cerebral spinal fluid, urine, or any other biofluids).

In certain embodiments, the methods for treating a prostate condition provided herein reduce the size (e.g., volume or diameter) of a tumor or BPH in a subject by at least about 5%, 10%, 15%, 20%, 25%, 30%, 35%, 40%, 45%, 50%, 55%, 60%, 65%, 80%, 85%, 90%, 95%, 99%, or 100%, relatiave to the size prior to administration of a Compound, as assessed by methods well known in the art, e.g., CT Scan or MRI. In particular embodiments, the methods for treating a prostate condition provided herein reduce the size (e.g., volume or diameter) of a tumor or BPH in a subject by an amount in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the size prior to administration of a Compound, as assessed by methods well known in the art, e.g., CT Scan or MRI.

In particular aspects, the methods for treating a prostate condition provided herein inhibit or decrease tumor or BPH perfusion in a subject as assessed by methods well known in the art, e.g., DCE-MRI. Standard protocols for DCE-MRI have been described (see., e.g., Morgan et al., J. Clin. Oncol., Nov. 1, 2003, 21(21):3955-64; Leach et al., Br. J. Cancer, May 9, 2005, 92(9):1599-610; Liu et al., J. Clin. Oncol., August 2005, 23(24): 5464-73; and Thomas et al., J. Clin. Oncol., Jun. 20, 2005, 23(18):4162-71) and can be applied in the methods provided herein. In specific embodiments, the methods for treating a prostate condition provided herein inhibit or decrease tumor or BPH perfusion in a subject by at least about 5%, 10%, 15%, 20%, 25%, 30%, 35%, 40%, 45%, 50%, 55%, 60%, 65%, 80%, 85%, 90%, 95%, or 100%, relative to tumor or BPH perfusion prior to administration of a Compound, as assessed by methods well known in the art, e.g., DCE-MRI. In particular embodiments, the methods for treating a prostate condition provided herein inhibit or decrease tumor or BPH perfusion in a subject by an amount in the range of 5% to 20%, 10% to 30%, 15% to 40%, 15% to 50%, 20% to 95%, 30% to 100%, or any range in between, relative to tumor or BPH perfusion prior to administration of a Compound, as assessed by methods well known in the art, e.g., DCE-MRI.

In particular aspects, the methods for treating a prostate condition provided herein inhibit or decrease tumor or BPH metabolism in a subject as assessed by methods well known in the art, e.g., PET scanning Standard protocols for PET scanning have been described and can be applied in the methods provided herein. In specific embodiments, the methods for treating a prostate condition provided herein inhibit or decrease tumor or BPH metabolism in a subject by at least about 5%, 10%, 15%, 20%, 25%, 30%, 35%, 40%, 45%, 50%, 55%, 60%, 65%, 80%, 85%, 90%, 95%, or 100%, relative to tumor metabolism or BPH prior to administration of a Compound, as assessed by methods well known in the art, e.g., PET scanning. In particular embodiments, the methods for treating a prostate condition provided herein inhibit or decrease tumor or BPH metabolism in a subject in the range of about 10% to 100%, or any range in between, relative to tumor metabolism prior to administration of a Compound, as assessed by methods well known in the art, e.g., PET scan.

In specific aspects, the methods for treating a prostate condition provided herein decrease the concentration of PSA in the blood of a subject as assessed by methods well known in the art, e.g., ELISA. In specific embodiments, the methods for treating a prostate condition provided herein decrease the concentration of PSA in the blood of a subject by at least about 5%, 10%, 15%, 20%, 25%, 30%, 35%, 40%, 45%, 50%, 55%, 60%, 65%, 80%, 85%, 90%, 95%, 99%, or 100%, relative to the concentration of PSA prior to administration of a Compound, as assessed by methods well known in the art, e.g., ELISA. In particular embodiments, the methods for treating a prostate condition provided herein decrease the concentration of PSA in the blood of a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the concentration of PSA prior to administration of a Compound, as assessed by methods well known in the art, e.g., ELISA.

In specific embodiments, the methods for treating prostate cancer provided herein decrease the number of CTCs in the blood of the subject as assessed by methods known in the art, e.g., CellSearch immunomagnetic-capture. In specific embodiments, the methods for treating prostate cancer provided herein decrease the number of CTCs in the blood of a subject by at least about 5%, 10%, 15%, 20%, 25%, 30%, 35%, 40%, 45%, 50%, 55%, 60%, 65%, 80%, 85%, 90%, 95%, 99%, or 100%, relative to the number of CTCs prior to administration of a Compound, as assessed by methods well known in the art, e.g., CellSearch immunomagnetic-capture. In particular embodiments, the methods for treating prostate cancer provided herein decrease the number of CTCs in the blood of a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the number of CTCs prior to administration of a Compound, as assessed by methods well known in the art, e.g., CellSearch immunomagnetic-capture.

In specific embodiments, the methods for treating a prostate condition provided herein decrease [$^{18}$F]-2-fluorodeoxyglucose (FDG) or [$^{11}$C]-choline uptake as detected by a techniques known to one of skill in the art, such as [$^{18}$F]-2-fluorodeoxyglucose or [$^{11}$C]-choline positron emission tomography (FDG- or choline-PET) (see, e.g., Tuncel et al., Nucl Med. Biol. 2008 August; 35(6):689-95). In specific embodiments, the methods for treating a prostate condition provided herein decrease FDG or [$^{11}$C]-choline uptake in a subject by at least about 5%, 10%, 15%, 20%, 25%, 30%, 35%, 40%, 45%, 50%, 55%, 60%, 65%, 80%, 85%, 90%, 95%, 99%, or 100%, relative to the FDG or [$^{11}$C]-choline uptake prior to administration of a Compound, as assessed by methods well known in the art, e.g., FDG- or choline-PET. In particular embodiments, the methods for treating a prostate condition provided herein decrease FDG or [$^{11}$C]-choline uptake in a subject in the range of about 5% to 20%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 95%, 30% to 99%, 30% to 100%, or any range in between, relative to the FDG or [$^{11}$C]-choline uptake prior to administration of a Compound, as assessed by methods well known in the art, e.g., FDG- or choline-PET.

In specific embodiments, the methods for treating a prostate condition provided herein inhibit or reduce inflammation, by at least about 5%, 10%, 15%, 20%, 25%, 30%, 35%, 40%, 45%, 50%, 55%, 60%, 65%, 80%, 85%, 90%, 95%, 99%, or 100%, or any percentage in between, relative to the inflammation prior to administration of a Compound, as assessed by methods well known in the art. In particular embodiments, the methods for treating a prostate condition provided herein inhibit or reduce inflammation, in the range of about 5% to 15%, 10% to 20%, 10% to 30%, 15% to 40%, 15% to 50%, 20% to 30%, 20% to 40%, 20% to 50%, 30% to 60%, 30% to 70%, 30% to 80%, 30% to 90%, 30% to 99%, 30% to 100%, or any range in between, relative to the inflammation prior to administration of a Compound, as assessed by methods well known in the art.

In certain embodiments, the methods for treating prostate cancer provided herein increase the tumor-free survival rate of patients diagnosed with prostate cancer. In some embodiments, the methods for treating prostate cancer provided herein increase relapse-free survival. In certain embodiments, the methods for treating prostate cancer provided herein increase the number of patients in remission. In other embodiments, the methods for treating prostate cancer provided herein increase the length of remission in patients. In specific embodiments, the methods for treating prostate cancer achieve one or more of the clinical endpoints set forth in the working examples in Section 11 et seq.

In particular embodiments, the methods for treating BPH provided herein inhibit, reduce, diminish, or stabilize the size of the prostate or one or more symptoms thereof as measured by a technique known to one of skill in the art, such as digital rectal exam, ultrasound (e.g., transrectal ultrasound), or cytoscopy.

In specific embodiments, the methods for treating a prostate condition provided herein minimize the severity and/or frequency of one or more side effects observed with current anti-angiogenesis therapies. In certain embodiments, the methods for treating a prostate condition provided herein do not cause one or more side effects observed with current anti-angiogenesis therapies. Such side effects include, but are not limited to, bleeding, arterial and venous thrombosis, hypertension, delayed wound healing, asymptomatic proteinuria, nasal septal perforation, reversible posterior leukoencephalopathy syndrome in association with hypertension, light-headedness, ataxia, headache, hoarseness, nausea, vomiting, diarrhea, rash, subungual hemorrhage, myelosuppression, fatigue, hypothyroidism, QT interval prolongation, and heart failure.

In a specific embodiment, treatment of prostate cancer with a Compound prevents tumor-induced cachexia. In another specific embodiment, when treatment of prostate cancer comprises administration of a Compound in combination with one or more additional therapies, cachexia induced by the one or more additional therapies is reduced due to administration of a Compound.

5.1 Compounds

In one embodiment, provided herein are Compounds having Formula (I):

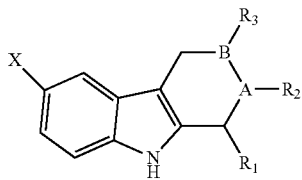

or a pharmaceutically acceptable salt, racemate or stereoisomer thereof, wherein, X is hydrogen; $C_1$ to $C_6$ alkyl optionally substituted with one or more halogen substituents; hydroxyl; halogen; or $C_1$ to $C_5$ alkoxy optionally substituted with aryl;

A is CH or N;

B is CH or N, with the proviso that at least one of A or B is N, and that when A is N, B is CH;

$R_1$ is hydroxyl; $C_1$ to $C_8$ alkyl optionally substituted with alkylthio, 5 to 10 membered heteroaryl, or aryl optionally substituted with one or more independently selected $R_o$ substituents; $C_2$ to $C_8$ alkenyl; $C_2$ to $C_8$ alkynyl; 3 to 12 membered heterocycle optionally substituted with one or more substituents independently selected from halogen, oxo, amino, alkylamino, acetamino, thio, or alkylthio; 5 to 12 membered heteroaryl optionally substituted with one or more substituents independently selected from halogen, oxo, amino, alkylamino, acetamino, thio, or alkylthio; or aryl, optionally substituted with one or more independently selected $R_o$ substituents;

$R_o$ is a halogen; cyano; nitro; sulfonyl optionally substituted with $C_1$ to $C_6$ alkyl or 3 to 10 membered heterocycle; amino optionally substituted with $C_1$ to $C_6$ alkyl, —C(O)—$R_b$, —C(O)O—$R_b$, sulfonyl, alkylsulfonyl, 3 to 10 membered heterocycle optionally substituted with —C(O)O—$R_n$; —C(O)—NH—$R_b$; 5 to 6 membered heterocycle; 5 to 6 membered heteroaryl; $C_1$ to $C_6$ alkyl optionally substituted with one or more substituents independently selected from hydroxyl, halogen, amino, or 3 to 12 membered heterocycle wherein amino and 3 to 12 membered heterocycle are optionally substituted with one or more $C_1$ to $C_4$ alkyl substituents optionally substituted with one or more substituents independently selected from $C_1$ to $C_4$ alkoxy, amino, alkylamino, or 5 to 10 membered heterocycle; —C(O)—$R_n$; or —OR$_a$;

$R_a$ is hydrogen; $C_2$ to $C_8$ alkylene; —C(O)—$R_n$; —C(O)O—$R_b$; —C(O)—NH—$R_b$; $C_3$-$C_{14}$cycloalkyl; aryl; heteroaryl; heterocyclyl; $C_1$ to $C_8$ alkyl optionally substituted with one or more substituents independently selected from hydroxyl, halogen, $C_1$ to $C_4$ alkoxy, amino, alkylamino, acetamide, —C(O)—$R_b$, —C(O)O—$R_b$, aryl, 3 to 12 membered heterocycle, or 5 to 12 membered heteroaryl, further wherein the alkylamino is optionally substituted with hydroxyl, $C_1$ to $C_4$ alkoxy, or 5 to 12 membered heteroaryl optionally substituted with $C_1$ to $C_4$ alkyl, further wherein the acetamide is optionally substituted with $C_1$ to $C_4$ alkoxy, sulfonyl, or alkylsulfonyl, further wherein the 3 to 12 membered heterocycle is optionally substituted with $C_1$ to $C_4$ alkyl optionally substituted with hydroxyl, —C(O)—$R_n$, —C(O)O—$R_a$, or oxo, further wherein the amino is optionally substituted with $C_1$ to $C_4$ alkoxycarbonyl, imidazole, isothiazole, pyrazole, pyridine, pyrazine, pyrimidine, pyrrole, thiazole or sulfonyl substituted with $C_1$ to $C_6$ alkyl, wherein pyridine and thiazole are each optionally substituted with $C_1$ to $C_4$ alkyl;

$R_b$ is hydroxyl; amino; alkylamino optionally substituted with hydroxyl, amino, alkylamino, $C_1$ to $C_4$ alkoxy, 3 to 12 membered heterocycle optionally substituted with one or more independently selected $C_1$ to $C_6$ alkyl, oxo, —C(O)O—$R_a$, or 5 to 12 membered heteroaryl optionally substituted with $C_1$ to $C_4$ alkyl; $C_1$ to $C_4$ alkoxy; $C_2$ to $C_8$ alkenyl; $C_2$ to $C_8$ alkynyl; aryl, wherein the aryl is optionally substituted with one or more substituents independently selected from halogen or $C_1$ to $C_4$ alkoxy; 5 to 12 membered heteroaryl; 3 to 12 membered heterocycle optionally substituted with one or more substituents independently selected from acetamide, —C(O)O—$R_n$, 5 to 6 membered heterocycle, or $C_1$ to $C_6$ alkyl optionally substituted with hydroxyl, $C_1$ to $C_4$ alkoxy, amino, or alkylamino; or $C_1$ to $C_8$ alkyl optionally substituted with one or more substituents independently selected from $C_1$ to $C_4$ alkoxy, aryl, amino, or 3 to 12 membered heterocycle, wherein the amino and 3 to 12 membered heterocycle are optionally substituted with one or more substituents independently selected from $C_1$ to $C_6$ alkyl, oxo, or —C(O)O—$R_n$;

$R_2$ is hydrogen; hydroxyl; 5 to 10 membered heteroaryl; $C_1$ to $C_8$ alkyl optionally substituted with hydroxyl, $C_1$ to $C_4$ alkoxy, 3 to 10 membered heterocycle, 5 to 10 membered heteroaryl, or aryl; —C(O)—$R_c$; —C(O)O—$R_d$; —C(O)—N($R_dR_d$); —C(S)—N($R_dR_d$); —C(S)—O—$R_e$; —S(O$_2$)—$R_e$; —C(NR$_e$)—S—$R_e$; or —C(S)—S—$R_f$;

$R_c$ is hydrogen; amino optionally substituted with one or more substituents independently selected from $C_1$ to $C_6$ alkyl or aryl; aryl optionally substituted with one or more substituents independently selected from halogen, haloalkyl, hydroxyl, $C_1$ to $C_4$ alkoxy, or $C_1$ to $C_6$ alkyl; —C(O)—$R_n$; 5 to 6 membered heterocycle optionally substituted with —C(O)—$R_n$; 5 to 6 membered heteroaryl; thiazoleamino; $C_1$ to $C_8$ alkyl optionally substituted with one or more substituents independently selected from halogen, $C_1$ to $C_4$ alkoxy, phenyloxy, aryl, —C(O)—$R_n$, —O—C(O)—$R_n$, hydroxyl, or amino optionally substituted with —C(O)O—$R_n$;

$R_d$ is independently hydrogen; $C_2$ to $C_8$ alkenyl; $C_2$ to $C_8$ alkynyl; aryl optionally substituted with one or more substituents independently selected from halogen, nitro, $C_1$ to $C_6$ alkyl, —C(O)O—$R_e$, or —OR$_e$; or $C_1$ to $C_8$ alkyl optionally substituted with one or more substituents independently selected from halogen, $C_1$ to $C_4$ alkyl, $C_1$ to $C_4$ alkoxy, phenyloxy, aryl, 5 to 6 membered heteroaryl, —C(O)—$R_n$, —C(O)O—$R_n$, or hydroxyl, wherein the aryl is optionally substituted with one or more substituents independently selected from halogen or haloalkyl;

$R_e$ is hydrogen; $C_1$ to $C_6$ alkyl optionally substituted with one or more substituents independently selected from halogen or alkoxy; or aryl optionally substituted with one or more substituents independently selected from halogen or alkoxy;

$R_f$ is $C_1$ to $C_6$ alkyl optionally substituted with one or more substituents independently selected from halogen, hydroxyl, $C_1$ to $C_4$ alkoxy, cyano, aryl, or —C(O)—$R_n$, wherein the alkoxy is optionally substituted with one or more $C_1$ to $C_4$ alkoxy substituents and the aryl is optionally substituted with one or more substituents independently selected from halogen, hydroxyl, $C_1$ to $C_4$ alkoxy, cyano, or $C_1$ to $C_6$ alkyl;

$R_n$ is hydroxyl, $C_1$ to $C_4$ alkoxy, amino, or $C_1$ to $C_6$ alkyl;

$R_3$ is hydrogen or —C(O)—$R_g$; and $R_g$ is hydroxyl; amino optionally substituted with cycloalkyl or 5 to 10 membered heteroaryl; or 5 to 10 membered heterocycle, wherein the 5 to 10 membered heterocycle is optionally substituted with —C(O)—R$_n$.

In one embodiment, the compound of Formula (I) is other than:

- (R)-1-(benzo[d][1,3]dioxol-5-yl)-2,3,4,9-tetrahydro-1H-pyrido[3,4-b]indole,
- 1-(benzo[d][1,3]dioxol-5-yl)-N-benzyl-3,4-dihydro-1H-pyrido[3,4-b]indole-2(9H)-carbothioamide,
- (R)-1-(benzo[d][1,3]dioxol-5-yl)-N-benzyl-3,4-dihydro-1H-pyrido[3,4-b]indole-2(9H)-carbothioamide,
- 1-phenyl-2,3,4,9-tetrahydro-1H-pyrido[3,4-b]indole,
- (R)-1-(benzo[d][1,3]dioxol-5-yl)-N-benzyl-3,4-dihydro-1H-pyrido[3,4-b]indole-2(9H)-carboxamide,
- N-benzyl-1-phenyl-3,4-dihydro-1H-pyrido[3,4-b]indole-2(9H)-carboxamide,
- N,1-diphenyl-3,4-dihydro-1H-pyrido[3,4-b]indole-2(9H)-carboxamide,
- N-(naphthalen-1-yl)-1-phenyl-3,4-dihydro-1H-pyrido[3,4-b]indole-2(9H)-carboxamide,
- 1-(benzo[d][1,3]dioxol-5-yl)-N-cyclohexyl-3,4-dihydro-1H-pyrido[3,4-b]indole-2(9H)-carboxamide,
- 1-(benzo[d][1,3]dioxol-5-yl)-N-phenyl-3,4-dihydro-1H-pyrido[3,4-b]indole-2(9H)-carboxamide,
- 1-(3-chloro-4-methoxyphenyl)-N-phenyl-3,4-dihydro-1H-pyrido[3,4-b]indole-2(9H)-carboxamide,
- (R)-1-(benzo[d][1,3]dioxol-5-yl)-N—((R)-1-phenylethyl)-3,4-dihydro-1H-pyrido[3,4-b]indole-2(9H)-carboxamide,
- (R)-1-(benzo[d][1,3]dioxol-5-yl)-N—((S)-1-phenylethyl)-3,4-dihydro-1H-pyrido[3,4-b]indole-2(9H)-carboxamide,
- (R)-1-(benzo[d][1,3]dioxol-5-yl)-N-benzoyl-3,4-dihydro-1H-pyrido[3,4-b]indole-2(9H)-carboxamide,
- (R)—N-(1-(benzo[d][1,3]dioxol-5-yl)-2,3,4,9-tetrahydro-1H-pyrido[3,4-b]indole-2-carbonothioyl)benzamide,
- benzyl 1-(benzo[d][1,3]dioxol-5-yl)-3,4-dihydro-1H-pyrido[3,4-b]indole-2(9H)-carboxylate,
- (R)-benzyl 1-(benzo[d][1,3]dioxol-5-yl)-3,4-dihydro-1H-pyrido[3,4-b]indole-2(9H)-carboxylate,
- methyl 1-phenyl-3,4-dihydro-1H-pyrido[3,4-b]indole-2(9H)-carboxylate,
- methyl 5-oxo-5-(1-phenyl-3,4-dihydro-1H-pyrido[3,4-b]indol-2(9H)-yl)pentanoate,
- 5-(1-(3-chloro-4-methoxyphenyl)-3,4-dihydro-1H-pyrido[3,4-b]indol-2(9H)-yl)-5-oxopentanoic acid,
- 5-(1-(benzo[d][1,3]dioxol-5-yl)-3,4-dihydro-1H-pyrido[3,4-b]indol-2(9H)-yl)-5-oxopentanoic acid,
- 3-(2-aminophenyl)-1-(1-(benzo[d][1,3]dioxol-5-yl)-3,4-dihydro-1H-pyrido[3,4-b]indol-2(9H)-yl)propan-1-one,
- (R)-1-(benzo[d][1,3]dioxol-5-yl)-N-(2-chlorobenzyl)-3,4-dihydro-1H-pyrido[3,4-b]indole-2(9H)-carbothioamide,
- (R)-1-(benzo[d][1,3]dioxol-5-yl)-N-(2,4-dichlorobenzyl)-3,4-dihydro-1H-pyrido[3,4-b]indole-2(9H)-carbothioamide,
- (R)-1-(benzo[d][1,3]dioxol-5-yl)-N-(2-fluorobenzyl)-3,4-dihydro-1H-pyrido[3,4-b]indole-2(9H)-carbothioamide,
- (R)-1-(benzo[d][1,3]dioxol-5-yl)-N—((S)-1-phenylethyl)-3,4-dihydro-1H-pyrido[3,4-b]indole-2(9H)-carbothioamide,
- (R)-4-((1-(benzo[d][1,3]dioxol-5-yl)-2,3,4,9-tetrahydro-1H-pyrido[3,4-b]indole-2-carbothioamido)methyl)benzoic acid,
- (R)-methyl 4-((1-(benzo[d][1,3]dioxol-5-yl)-2,3,4,9-tetrahydro-1H-pyrido[3,4-b]indole-2-carbothioamido)methyl)benzoate,
- (R)-3-((1-(benzo[d][1,3]dioxol-5-yl)-2,3,4,9-tetrahydro-1H-pyrido[3,4-b]indole-2-carbothioamido)methyl)benzoic acid,
- (R)-methyl 3-((1-(benzo[d][1,3]dioxol-5-yl)-2,3,4,9-tetrahydro-1H-pyrido[3,4-b]indole-2-carbothioamido)methyl)benzoate,
- (R)-1-(benzo[d][1,3]dioxol-5-yl)-N-(4-chloro-3-(trifluoromethyl)phenyl)-3,4-dihydro-1H-pyrido[3,4-b]indole-2(9H)-carbothioamide,
- (R)-1-(benzo[d][1,3]dioxol-5-yl)-N-(2-(trifluoromethyl)phenyl)-3,4-dihydro-1H-pyrido[3,4-b]indole-2(9H)-carbothioamide,
- (R)-1-(benzo[d][1,3]dioxol-5-yl)-N-(3-fluorobenzyl)-3,4-dihydro-1H-pyrido[3,4-b]indole-2(9H)-carbothioamide,
- (R)-1-(benzo[d][1,3]dioxol-5-yl)-N-(4-chlorobenzyl)-3,4-dihydro-1H-pyrido[3,4-b]indole-2(9H)-carbothioamide,
- (R)-1-(benzo[d][1,3]dioxol-5-yl)-N-(3,4-dichlorobenzyl)-3,4-dihydro-1H-pyrido[3,4-b]indole-2(9H)-carbothioamide,
- (R)-1-(benzo[d][1,3]dioxol-5-yl)-N-(4-fluorobenzyl)-3,4-dihydro-1H-pyrido[3,4-b]indole-2(9H)-carbothioamide,
- (R)-1-(benzo[d][1,3]dioxol-5-yl)-N-(3,4-dimethylbenzyl)-3,4-dihydro-1H-pyrido[3,4-b]indole-2(9H)-carbothioamide,
- (R)-1-(benzo[d][1,3]dioxol-5-yl)-N-(3-chlorobenzyl)-3,4-dihydro-1H-pyrido[3,4-b]indole-2(9H)-carbothioamide,
- (R)-1-(benzo[d][1,3]dioxol-5-yl)-N-(naphthalen-1-ylmethyl)-3,4-dihydro-1H-pyrido[3,4-b]indole-2(9H)-carbothioamide,
- (3,4-difluorophenyl)-(1-phenyl-1,3,4,9-tetrahydro-β-carbolin-2-yl)-methanone,
- 6-methoxy-1,2,3,4-tetrahydronorharmane,
- 1,2,3,4-tetrahydronorharman-3-carboxylic acid,
- 6-methoxy-1,2,3,4-tetrahydronorharman-1-carboxylic acid,
- 1-(4-methoxyphenyl)-1,2,3,4-tetrahydronorharman-3-carboxylic acid,
- 1-methyl-1,2,3,4-tetrahydronorharman-3-carboxylic acid,
- 1-methyl-1,2,3,4-tetrahydronorharman-1,3-dicarboxylic acid,
- 1-(diethylmethyl)-1,2,3,4-tetrahydronorharman-3-carboxylic acid,
- (6-bromo-1,2,3,4-tetrahydronorharman-1-yl)-3-propionic acid,
- 1-isobutyl-1,2,3,4-tetrahydronorharman-3-carboxylic acid,
- 1-phenyl-1,2,3,4-tetrahydronorharman-3-carboxylic acid,
- 1-propyl-1,2,3,4-tetrahydronorharman-3-carboxylic acid,
- 1-methyl-1-methoxycarbonyl-6-benzyloxy-1,2,3,4-tetrahydronorharmane,
- 1-methyl-1-methoxycarbonyl-6-methoxy-1,2,3,4-tetrahydronorharmane,
- 1-methyl-1-methoxycarbonyl-6-hydroxy-1,2,3,4-tetrahydronorharmane,
- 1-methyl-1-methoxycarbonyl-6-chloro-1,2,3,4-tetrahydronorharmane,
- 1-methyl-1-methoxycarbonyl-6-bromo-1,2,3,4-tetrahydronorharmane,
- 1-methyl-2-N-acetyl-6-methoxy-1,2,3,4-tetrahydro-β-carboline,
- 2-N-acetyl-1,2,3,4-tetrahydro-β-carboline,
- 1-methyl-2-N-acetyl-6-methoxy-1,2,3,4-tetrahydro-β-carboline,
- 4-chlorobenzyl (1S,3R)-1-(2,4-dichlorophenyl)-1,2,3,4-tetrahydro-β-carboline-3-carboxamide,
- (3R)-1-(1-benzylindol-3-yl)-2-tert-butoxycarbonyl-1,2,3,4-tetrahydro-β-carboline-3-carboxylic acid,
- (3R)-1-(1-butylindol-3-yl)-2-tert-butoxycarbonyl-1,2,3,4-tetrahydro-β-carboline-3-carboxylic acid,
- (1S,3R)-1-(indol-3-yl)-2-tert-butoxycarbonyl-1,2,3,4-tetrahydro-β-carboline-3-carboxylic acid, (1S,3R)-1-(1-methylindol-3-yl)-2-tert-butoxycarbonyl-1,2,3,4-tetrahydro-β-carboline-3-carboxylic acid,
benzothiazol-2-yl (1S,3R)-1-cyclohexyl-2-tert-butoxycarbonyl-1,2,3,4-tetrahydro-β-carboline-3-carboxylic acid,
benzothiazol-2-yl (1S,3R)-1-cyclohexyl-1,2,3,4-tetrahydro-β-carboline-3-carboxylic acid,
1-(4-chlorophenyl)-1,2,3,4-tetrahydro-β-carboline,
1-(4-bromophenyl)-1,2,3,4-tetrahydro-β-carboline,
1-(4-nitrophenyl)-1,2,3,4-tetrahydro-β-carboline,
1-(4-dimethylaminophenyl)-1,2,3,4-tetrahydro-β-carboline,
1-(4-diethylaminophenyl)-1,2,3,4-tetrahydro-β-carboline,
1-(2,4-dimethoxyphenyl)-1,2,3,4-tetrahydro-β-carboline,
1-(3,4-dimethoxyphenyl)-1,2,3,4-tetrahydro-β-carboline,
1-(2,5-dimethoxyphenyl)-1,2,3,4-tetrahydro-β-carboline,
1-(3,5-dimethoxyphenyl)-1,2,3,4-tetrahydro-β-carboline,
1-(3,4,5-trimethoxyphenyl)-1,2,3,4-tetrahydro-β-carboline,
1-(4-nitrobenzo[d][1,3]dioxol-5-yl)-1,2,3,4-tetrahydro-β-carboline,
1-(2-fluorenyl)-1,2,3,4-tetrahydro-β-carboline,
1-(9-ethyl-9H-carbazol-3-yl)-1,2,3,4-tetrahydro-β-carboline,
6-chloro-1-(4-methylphenyl)-2,3,4,9-tetrahydro-1H-β-carboline,
methyl 6-chloro-1-(4-methylphenyl)-1,3,4,9-tetrahydro-2H-β-carboline-2-carboxylate,
6-chloro-1-(4-methylphenyl)-2-(3-phenylpropanoyl)-2,3,4,9-tetrahydro-1H-β-carboline,
phenylmethyl 6-chloro-1-(4-methylphenyl)-1,3,4,9-tetrahydro-2H-β-carboline-2-carboxylate,
6-fluoro-1-(4-methylphenyl)-2,3,4,9-tetrahydro-1H-β-carboline,
methyl 6-fluoro-1-(4-methylphenyl)-1,3,4,9-tetrahydro-2H-β-carboline-2-carboxylate,
6-fluoro-1-(4-methylphenyl)-2-(3-phenylpropanoyl)-2,3,4,9-tetrahydro-1H-β-carboline,
phenylmethyl 6-fluoro-1-(4-methylphenyl)-1,3,4,9-tetrahydro-2H-β-carboline-2-carboxylate,
6-bromo-1-(4-methylphenyl)-2,3,4,9-tetrahydro-1H-β-carboline,
methyl 6-bromo-1-(4-methylphenyl)-1,3,4,9-tetrahydro-2H-β-carboline-2-carboxylate,
6-bromo-1-(4-methylphenyl)-2-(3-phenylpropanoyl)-2,3,4,9-tetrahydro-1H-β-carboline,
phenylmethyl 6-bromo-1-(4-methylphenyl)-1,3,4,9-tetrahydro-2H-β-carboline-2-carboxylate,
(1R)-6-chloro-1-(4-methylphenyl)-2-(3-phenylpropanoyl)-2,3,4,9-tetrahydro-1H-β-carboline,
(1S)-6-chloro-1-(4-methylphenyl)-2-(3-phenylpropanoyl)-2,3,4,9-tetrahydro-1H-β-carboline,
1-(4-methylphenyl)-2-(methylsulfonyl)-2,3,4,9-tetrahydro-1H-β-carboline,
2-acetyl-1-(4-methylphenyl)-2,3,4,9-tetrahydro-1H-β-carboline,
1-(4-methylphenyl)-2-(3-phenylpropanoyl)-2,3,4,9-tetrahydro-1H-β-carboline,
6-(methyloxy)-1-(4-methylphenyl)-2-(3-phenylpropanoyl)-2,3,4,9-tetrahydro-1H-β-carboline,
6-methyl-1-(4-methylphenyl)-2-(3-phenylpropanoyl)-2,3,4,9-tetrahydro-1H-β-carboline,
(1R/1S)-1-(2,3-dihydro-1-benzofuran-5-yl)-2,3,4,9-tetrahydro-1H-β-carboline, or
1-(1,3-benzodioxol-5-yl)-2-(2-pyrimidinyl)-2,3,4,9-tetrahydro-1H-β-carboline.

As will be evident to one of skill in the art, Compounds provided herein comprise at least one stereocenter, and may exist as a racemic mixture or as an enantiomerically pure composition. In one embodiment, a Compound provided herein is the (S) isomer, in an enantiomerically pure composition. In certain embodiments, the enantiomeric excess (e.e.) is about 90%, about 95%, about 99% or about 99.9% or greater.

In another embodiment, provided herein are Compounds having Formula (II):

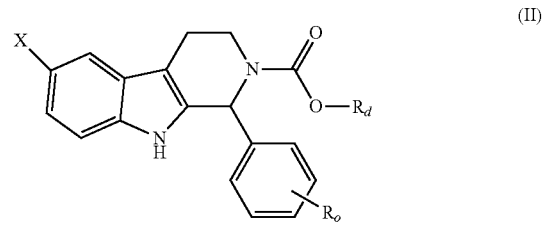

(II)

or a pharmaceutically acceptable salt, racemate or stereoisomer thereof, wherein, X is hydrogen; $C_1$ to $C_6$ alkyl optionally substituted with one or more halogen substituents; hydroxyl; halogen; or $C_1$ to $C_5$ alkoxy optionally substituted with phenyl;

$R_o$ is halogen; cyano; nitro; sulfonyl substituted with $C_1$ to $C_6$ alkyl or morpholinyl; amino optionally substituted with $C_1$ to $C_6$ alkyl, $C(O)R_b$, —$C(O)O$—$R_b$, alkylsulfonyl, morpholinyl or tetrahydropyranyl; $C_1$ to $C_6$ alkyl optionally substituted with one or more substituents independently selected from hydroxyl, halogen or amino; $C(O)$—$R_a$; or —$OR_a$;

$R_a$ is hydrogen; $C_2$ to $C_8$ alkenyl; —$C(O)$—$R_n$; —$C(O)O$—$R_b$; —$C(O)$—NH—$R_b$; $C_1$ to $C_8$ alkyl optionally substituted with one or more substituents independently selected from hydroxyl, halogen, $C_1$ to $C_4$ alkoxy, $C_1$ to $C_4$ alkoxy $C_1$ to $C_4$ alkoxy, amino, alkylamino, dialkylamino, acetamide, —$C(O)$—$R_b$, —$C(O)O$—$R_b$, aryl, morpholinyl, thiomorpholinyl, pyrrolidinyl, piperidinyl, piperazinyl, 1,3-dioxolan-2-one, oxiranyl, tetrahydrofuranyl, tetrahydropyranyl, 1,2,3-triazole, 1,2,4-triazole, furan, imidazole, isoxazole, isothiazole, oxazole, pyrazole, thiazole, thiophene or tetrazole;

wherein amino is optionally substituted with $C_1$ to $C_4$ alkoxycarbonyl, imidazole, isothiazole, pyrazole, pyridine, pyrazine, pyrimidine, pyrrole, thiazole or sulfonyl substituted with $C_1$ to $C_6$ alkyl, wherein pyridine and thiazole are each optionally substituted with $C_1$ to $C_4$ alkyl;

wherein alkylamino and dialkylamino are each optionally substituted on alkyl with hydroxyl, $C_1$ to $C_4$ alkoxy, imidazole, pyrazole, pyrrole or tetrazole; and, wherein morpholinyl, thiomorpholinyl, pyrrolidinyl, piperidinyl, piperazinyl and oxiranyl are each optionally substituted with —$C(O)$—$R_n$, —$C(O)O$—$R_n$ or $C_1$ to $C_4$ alkyl, wherein $C_1$ to $C_4$ alkyl is optionally substituted with hydroxyl;

$R_b$ is hydroxyl; amino; alkylamino, optionally substituted on alkyl with hydroxyl, amino, alkylamino or $C_1$ to $C_4$ alkoxy; $C_1$ to $C_4$ alkoxy; $C_2$ to $C_8$ alkenyl; $C_2$ to $C_8$ alkynyl; aryl optionally substituted with one or more substituents independently selected from halogen and $C_1$ to $C_4$ alkoxy; furan; or $C_1$ to $C_8$ alkyl optionally substituted with one or more substituents independently selected from $C_1$ to $C_4$ alkoxy, aryl, amino, morpholinyl, piperidinyl or piperazinyl;

$R_d$ is aryl optionally substituted with one or more substituents independently selected from halogen, nitro, $C_1$ to $C_6$ alkyl, —C(O)O—$R_e$, and —$OR_e$;

$R_e$ is hydrogen; $C_1$ to $C_6$ alkyl optionally substituted with one or more substituents independently selected from halogen and alkoxy; or phenyl, wherein phenyl is optionally substituted with one or more substituents independently selected from halogen and alkoxy; and $R_n$ is hydroxyl, $C_1$ to $C_4$ alkoxy, amino or $C_1$ to $C_6$ alkyl.

In another embodiment, provided herein are Compounds having Formula (II):

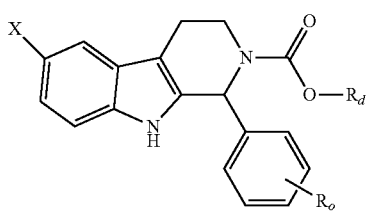

(II)

or a pharmaceutically acceptable salt, racemate or stereoisomer thereof, wherein, X is halogen;

$R_o$ is halogen, substituted or unsubstituted $C_1$ to $C_8$ alkyl or $OR_a$;

$R_a$ is H, $C_1$ to $C_8$ alkyl optionally substituted with one or more substituents independently selected from hydroxyl and halogen; and $R_d$ is phenyl optionally substituted with one or more alkoxy or halogen substituents.

In one embodiment, X is chloro or bromo.

In one embodiment, $R_d$ is chloro or bromo.

In one embodiment, $R_o$ is $OR_a$.

In one embodiment, $R_a$ is methyl, ethyl, propyl, isopropyl, butyl, or pentyl, each optionally substituted with one or more hydroxyl substituents.

In another embodiment, provided herein are Compounds having Formula (II):

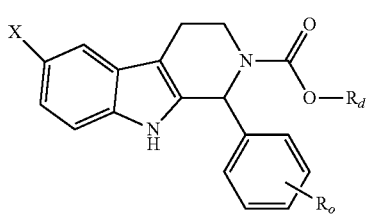

(II)

or a pharmaceutically acceptable salt, racemate or stereoisomer thereof, wherein, X is halogen;

$R_o$ is halogen, substituted or unsubstituted $C_1$ to $C_8$ alkyl or $OR_a$;

$R_a$ is H, or $C_1$ to $C_8$ alkyl optionally substituted with one or more substituents independently selected from hydroxyl and halogen; and $R^d$ is phenyl optionally substituted with one or more halogen substituents.

In another embodiment, provided herein are Compounds having Formula (III):

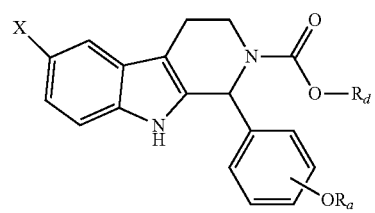

(III)

or a pharmaceutically acceptable salt, racemate or stereoisomer thereof, wherein, X is halogen;

$R_a$ is H, $C_1$ to $C_8$ alkyl optionally substituted with one or more substituents independently selected from hydroxyl and halogen; and $R_d$ is phenyl substituted with one or more halogen substituents.

In another embodiment, provided herein are Compounds having Formula (IV):

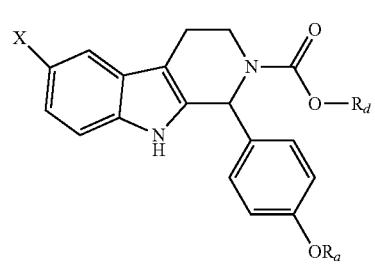

(IV)

or a pharmaceutically acceptable salt, racemate or stereoisomer thereof, wherein, X is halogen;

$R_a$ is H, $C_1$ to $C_8$ alkyl optionally substituted with one or more substituents independently selected from hydroxyl and halogen; and $R_d$ is phenyl substituted with one or more halogen substituents.

In another embodiment, provided herein are Compounds having Formula (IV):

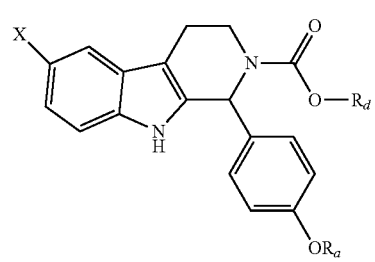

(IV)

or a pharmaceutically acceptable salt, racemate or stereoisomer thereof, wherein, X is halogen;

$R_a$ is H, $C_1$ to $C_8$ alkyl optionally substituted with one or more substituents independently selected from hydroxyl and halogen; and $R_d$ is phenyl substituted on a para position with a halogen substituent.

In another embodiment, the Compounds set forth above having a formula selected from Formula (Ia), Formula (IIa), Formula (IIIa) and Formula (IVa):

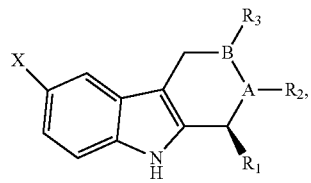
(Ia)

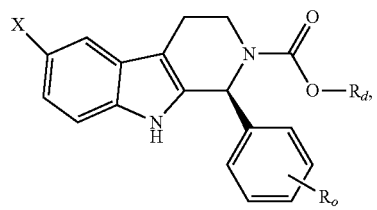
(IIa)

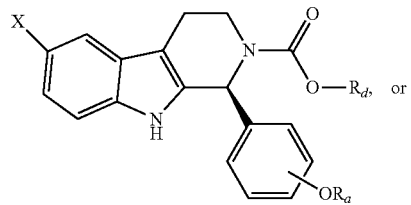
(IIIa)

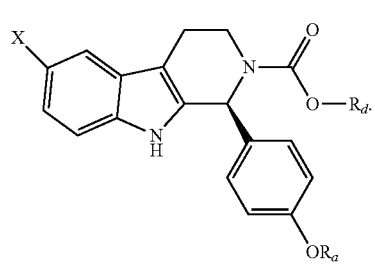
(IVa)

Illustrative examples of Compounds or a pharmaceutically acceptable salt, racemate or stereoisomer thereof provided herein include:

TABLE 1

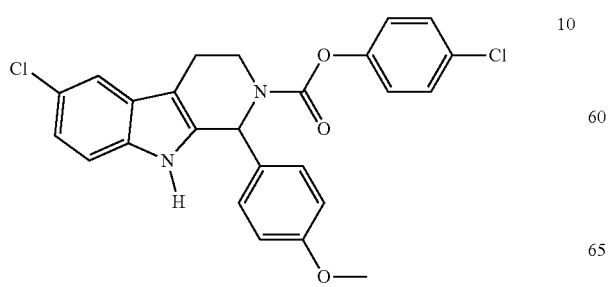
10

TABLE 1-continued

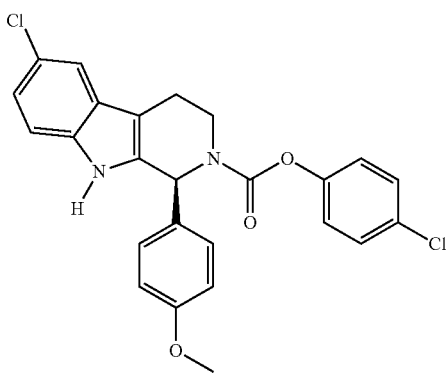 [SMILES: COc1ccc([C@H]2c3[nH]c4ccc(Cl)cc4c3CCN2C(=O)Oc2ccc(Cl)cc2)cc1]
10

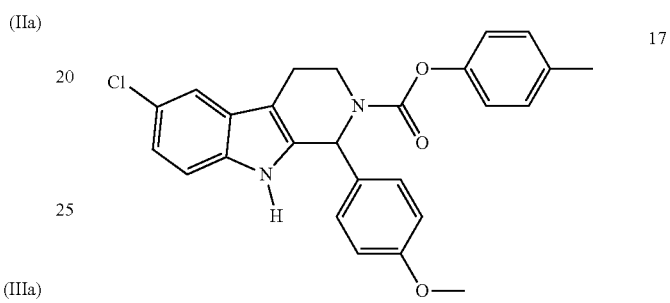
17

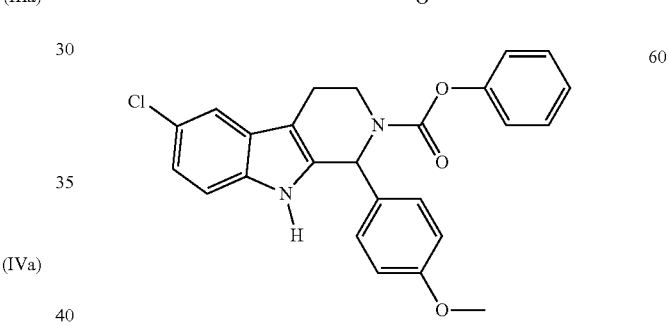
60

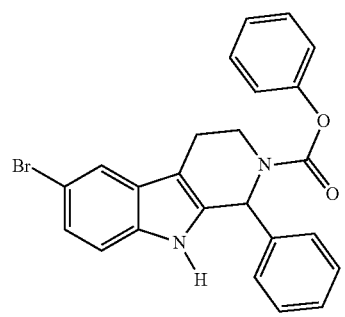
76

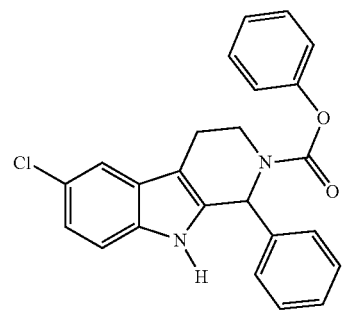 [SMILES: O=C(Oc1ccccc1)N1CCc2c([nH]c3ccc(Cl)cc23)C1c1ccccc1]
121

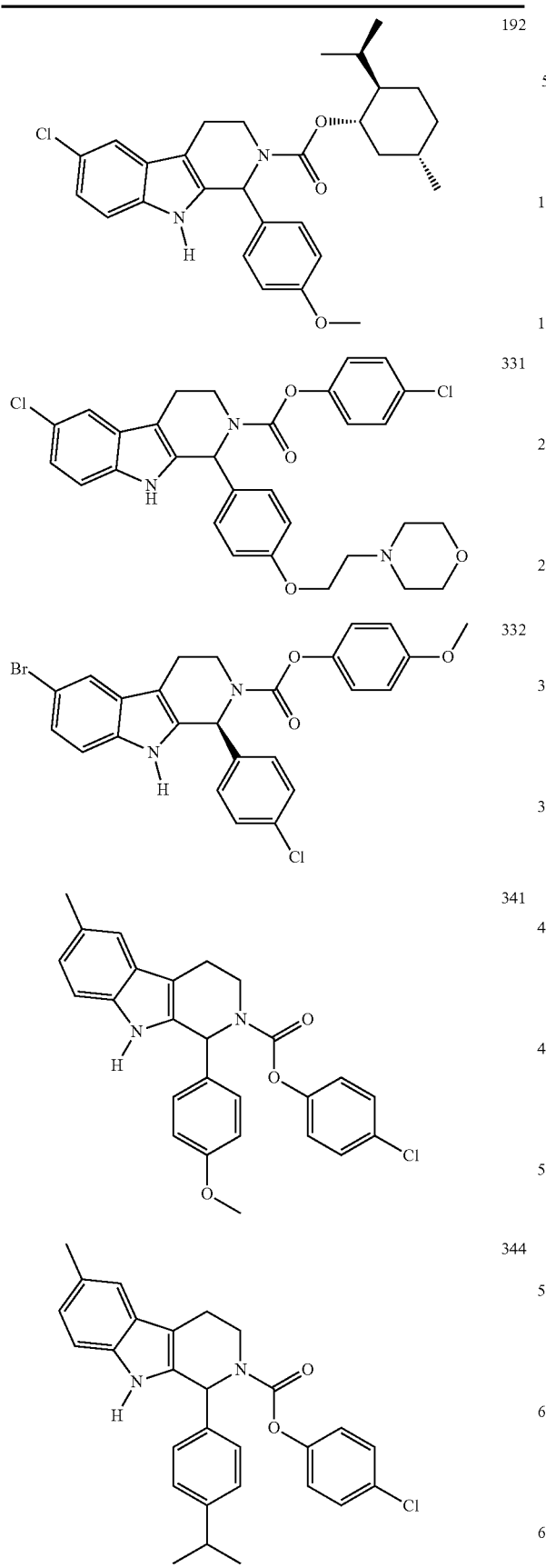
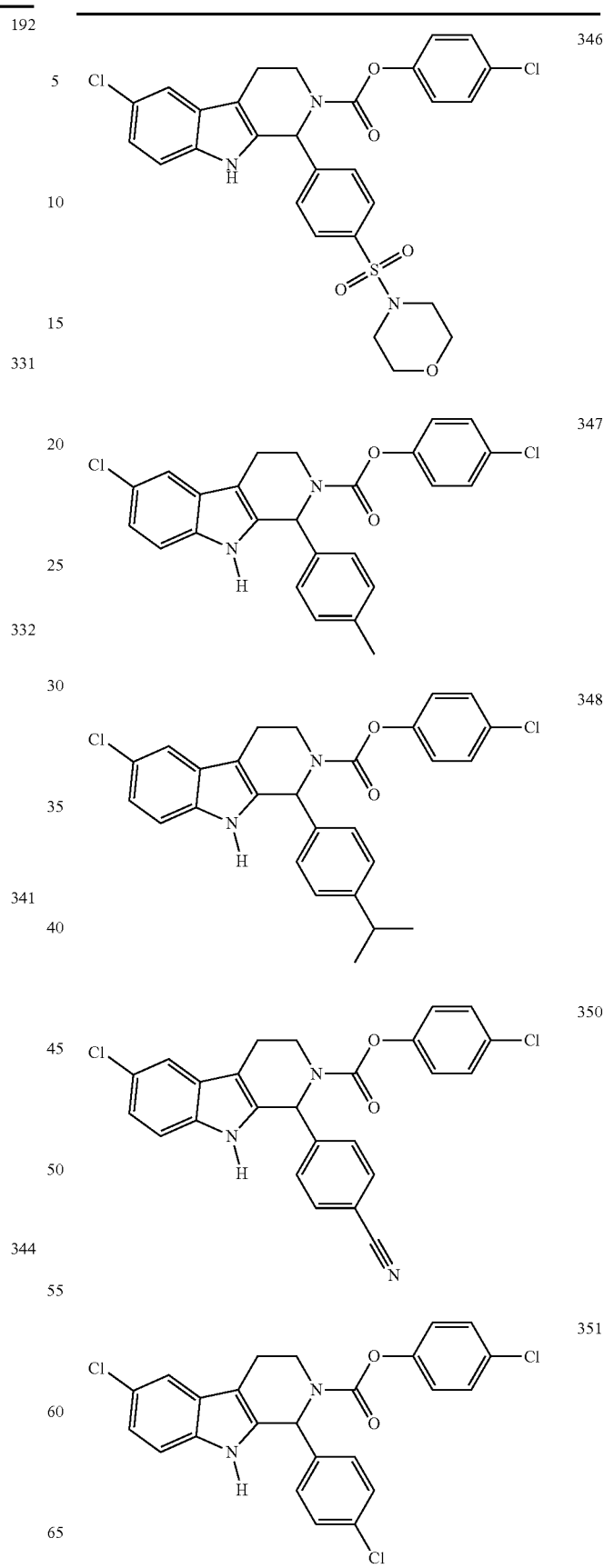

TABLE 1-continued
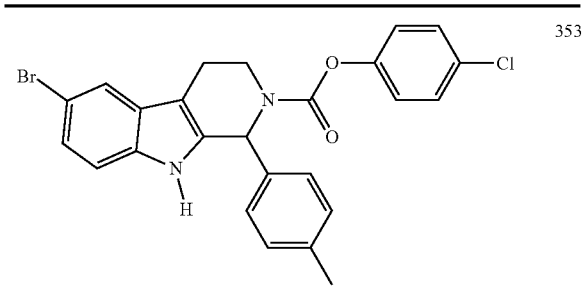
353
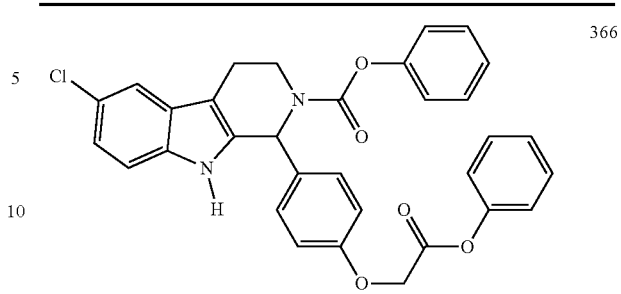
366
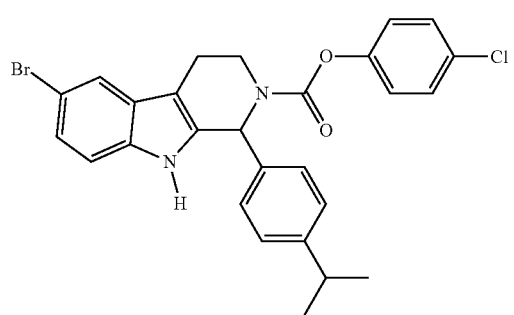 [SMILES: CC(C)c1ccc(C2c3[nH]c4ccc(Br)cc4c3CCN2C(=O)Oc2ccc(Cl)cc2)cc1]
354
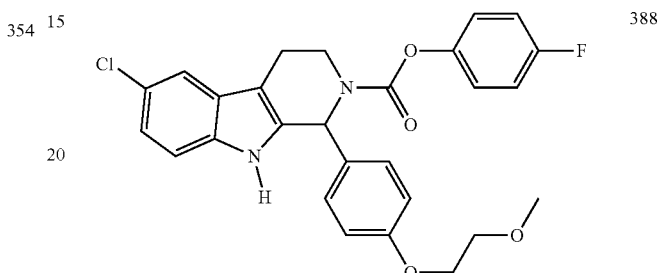
388
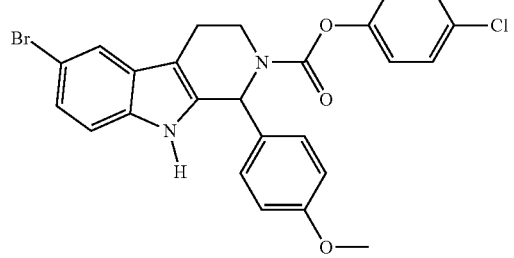
355
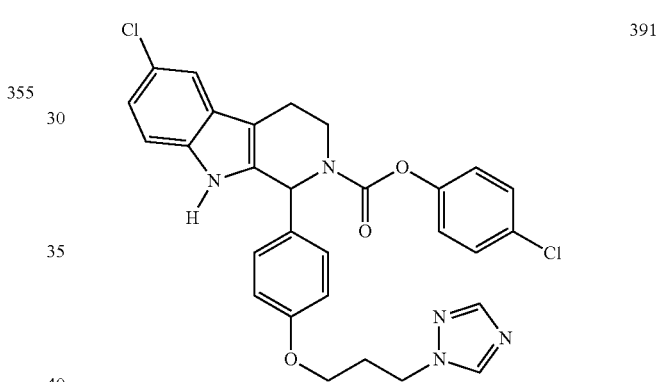
391
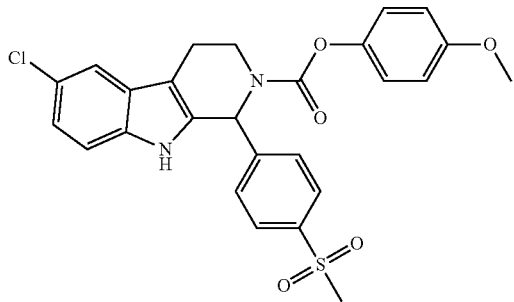 [SMILES: COc1ccc(OC(=O)N2CCc3c([nH]c4ccc(Cl)cc34)C2c2ccc(S(C)(=O)=O)cc2)cc1]
359
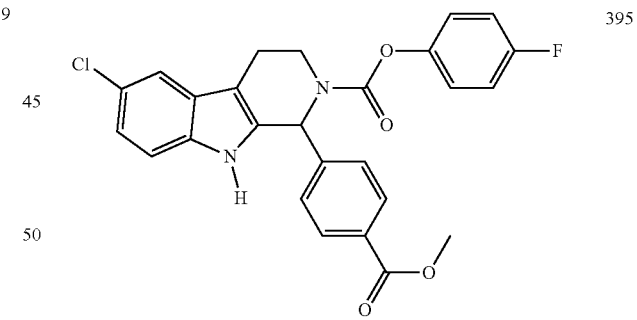
395
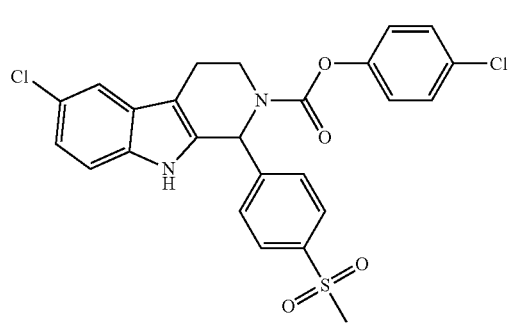 [SMILES: CS(=O)(=O)c1ccc(C2c3[nH]c4ccc(Cl)cc4c3CCN2C(=O)Oc2ccc(Cl)cc2)cc1]
360
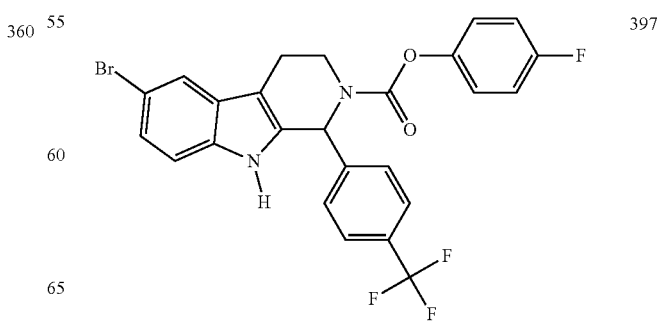
397

TABLE 1-continued
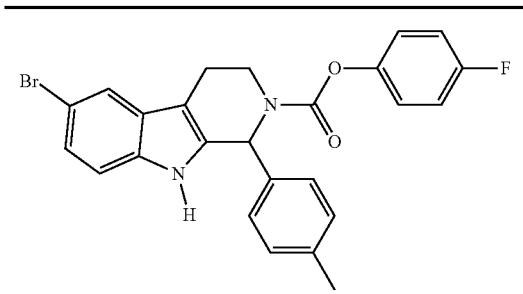 398
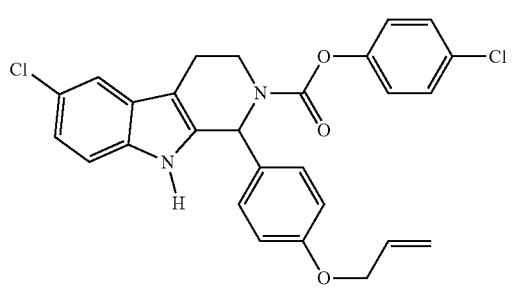 [SMILES: C=CCOc1ccc(C2c3[nH]c4ccc(Cl)cc4c3CCN2C(=O)Oc2ccc(Cl)cc2)cc1] 400
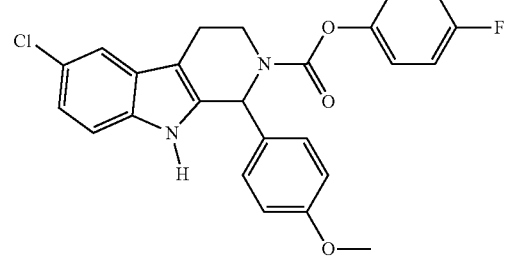 401
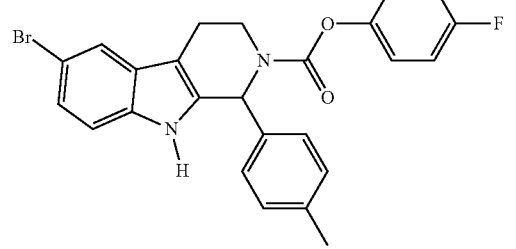 403
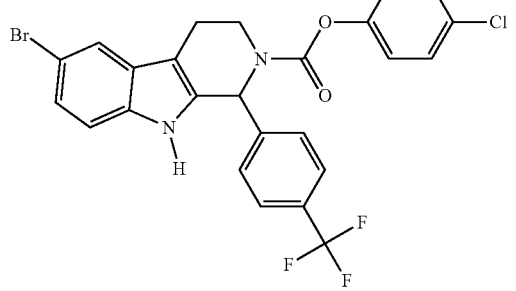 405
TABLE 1-continued
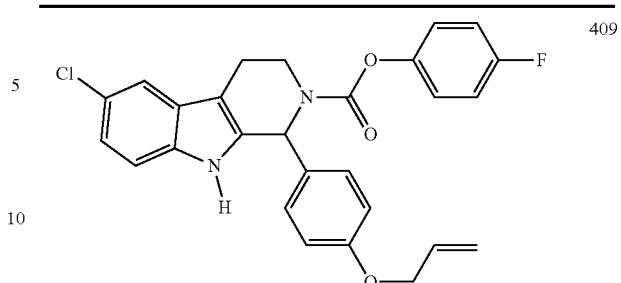 409
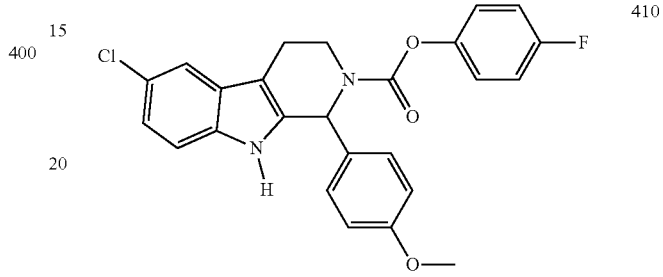 410
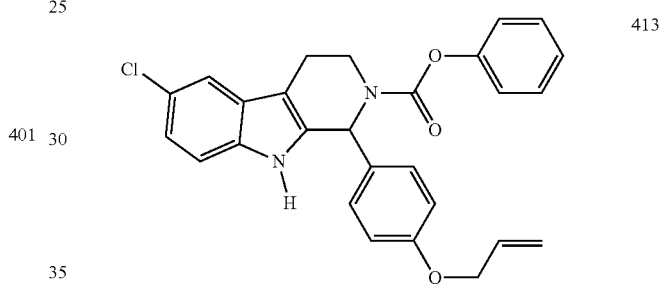 413
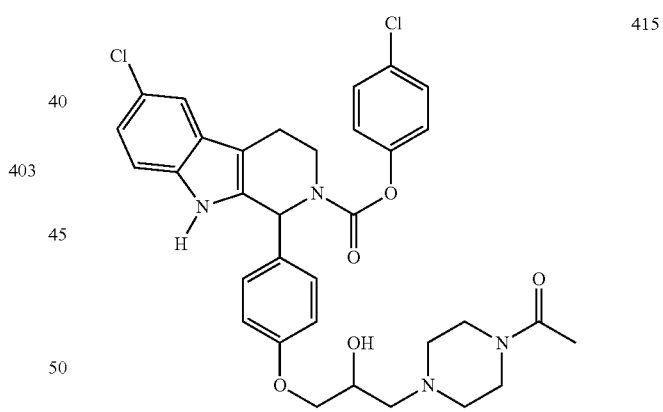 415
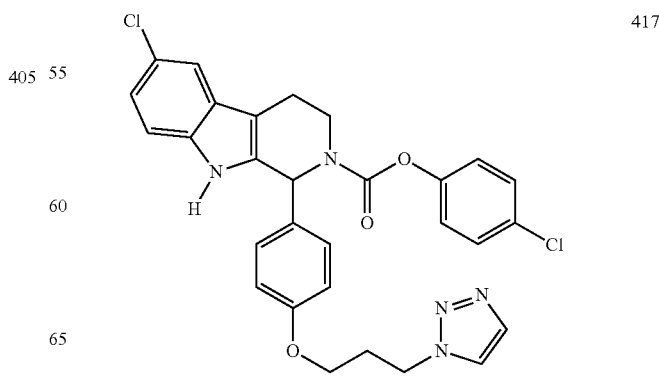 417

TABLE 1-continued
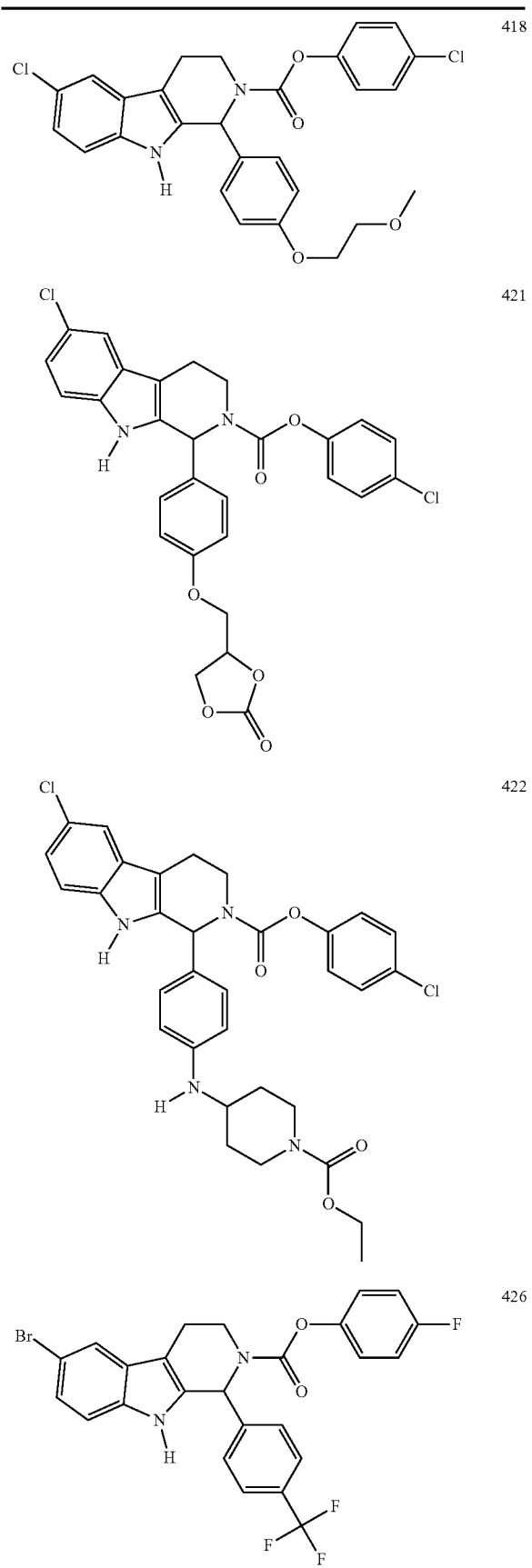
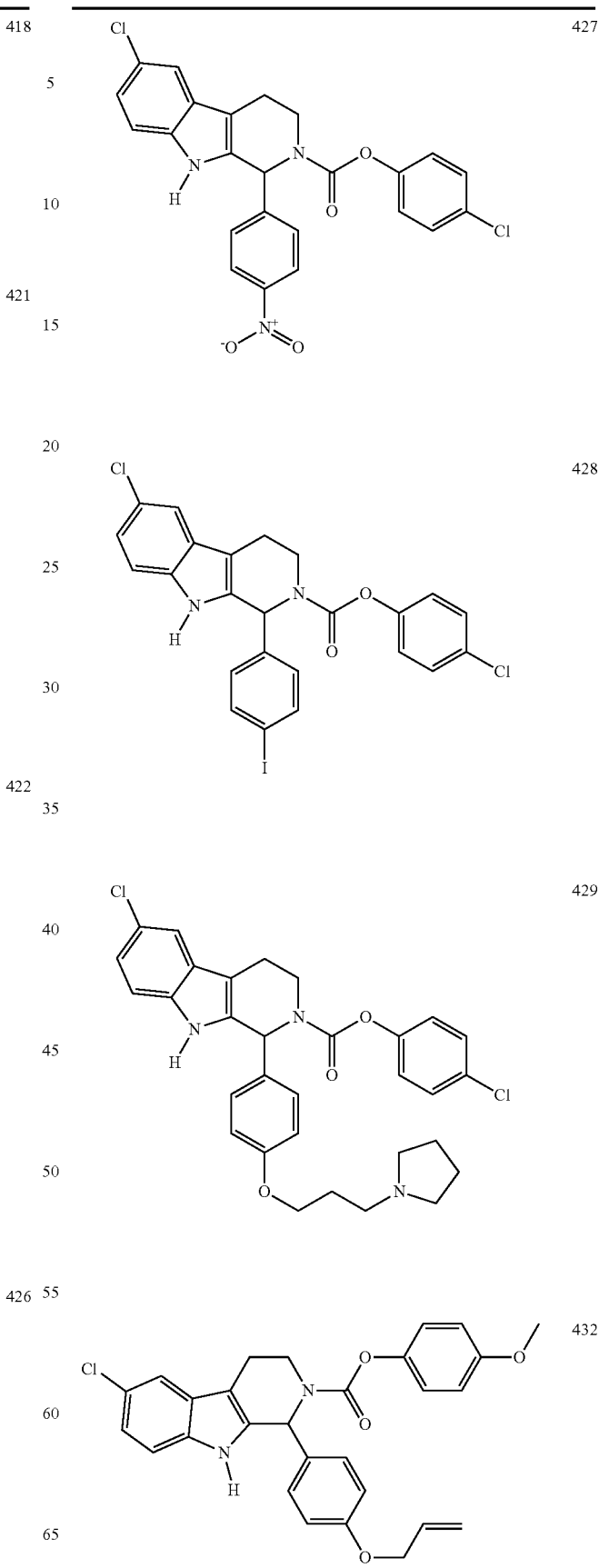

TABLE 1-continued
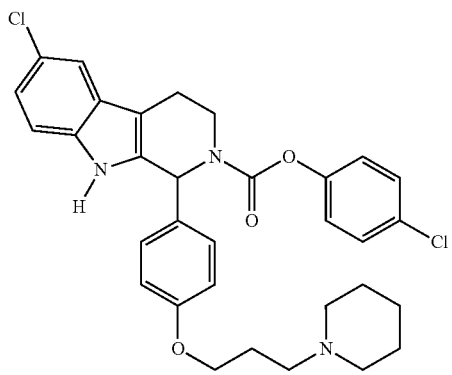 [SMILES: O=C(Oc1ccc(Cl)cc1)N1CCc2c([nH]c3ccc(Cl)cc23)C1c1ccc(OCCCN2CCCCC2)cc1]
433
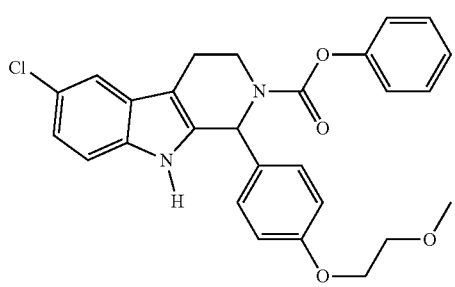 [SMILES: COCCOc1ccc(C2c3[nH]c4ccc(Cl)cc4c3CCN2C(=O)Oc2ccccc2)cc1]
436
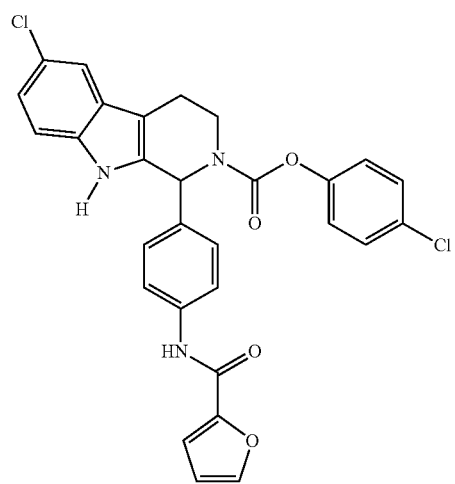 [SMILES: O=C(Nc1ccc(C2c3[nH]c4ccc(Cl)cc4c3CCN2C(=O)Oc2ccc(Cl)cc2)cc1)c1ccco1]
437
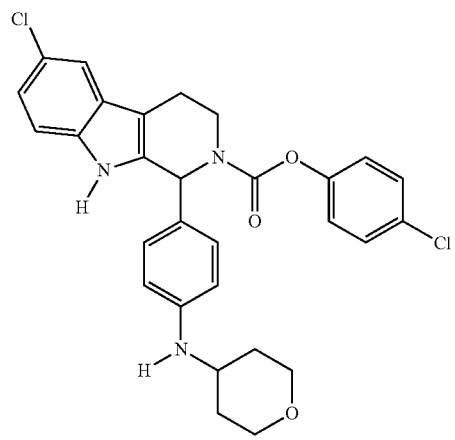 [SMILES: O=C(Oc1ccc(Cl)cc1)N1CCc2c([nH]c3ccc(Cl)cc23)C1c1ccc(NC2CCOCC2)cc1]
440
TABLE 1-continued
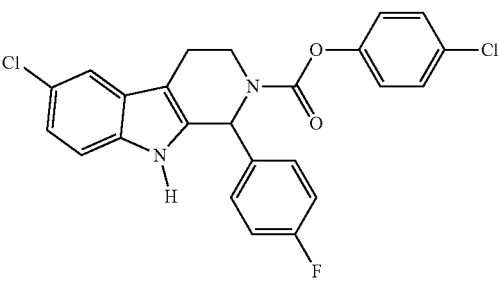 [SMILES: O=C(Oc1ccc(Cl)cc1)N1CCc2c([nH]c3ccc(Cl)cc23)C1c1ccc(F)cc1]
444
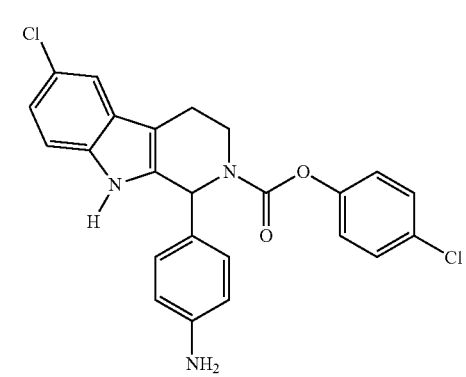 [SMILES: Nc1ccc(C2c3[nH]c4ccc(Cl)cc4c3CCN2C(=O)Oc2ccc(Cl)cc2)cc1]
446
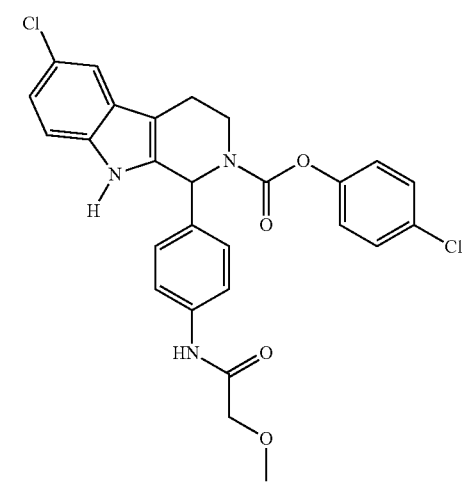 [SMILES: COCC(=O)Nc1ccc(C2c3[nH]c4ccc(Cl)cc4c3CCN2C(=O)Oc2ccc(Cl)cc2)cc1]
448
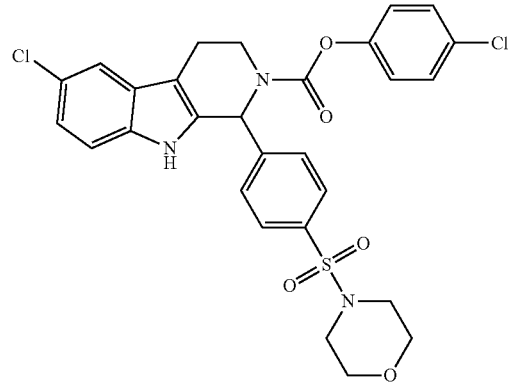 [SMILES: O=C(Oc1ccc(Cl)cc1)N1CCc2c([nH]c3ccc(Cl)cc23)C1c1ccc(S(=O)(=O)N2CCOCC2)cc1]
450

TABLE 1-continued
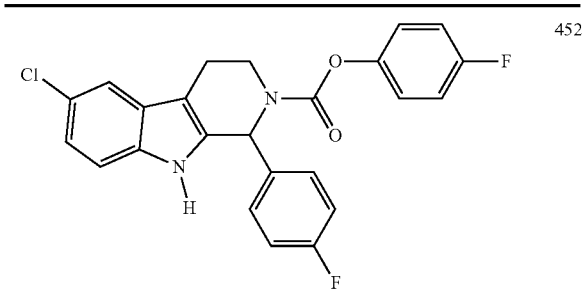 452
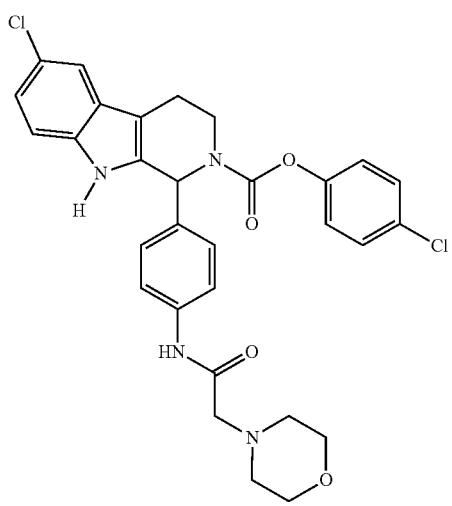 [SMILES: O=C(CN1CCOCC1)Nc1ccc(C2c3[nH]c4ccc(Cl)cc4c3CCN2C(=O)Oc2ccc(Cl)cc2)cc1] 454
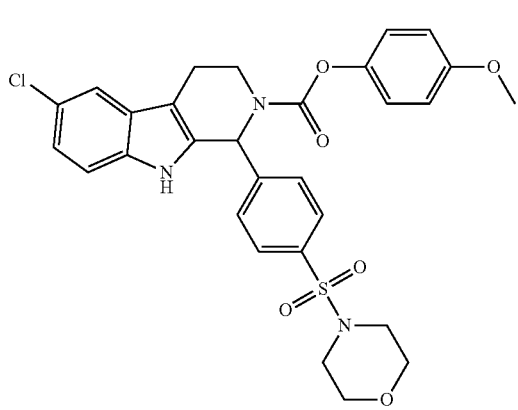 [SMILES: COc1ccc(OC(=O)N2CCc3c([nH]c4ccc(Cl)cc34)C2c2ccc(S(=O)(=O)N3CCOCC3)cc2)cc1] 455
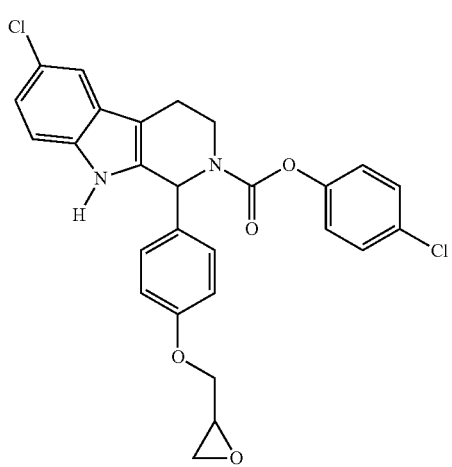 [SMILES: O=C(Oc1ccc(Cl)cc1)N1CCc2c([nH]c3ccc(Cl)cc23)C1c1ccc(OCC2CO2)cc1] 460
TABLE 1-continued
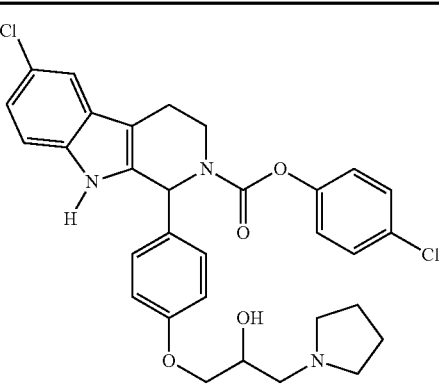 462
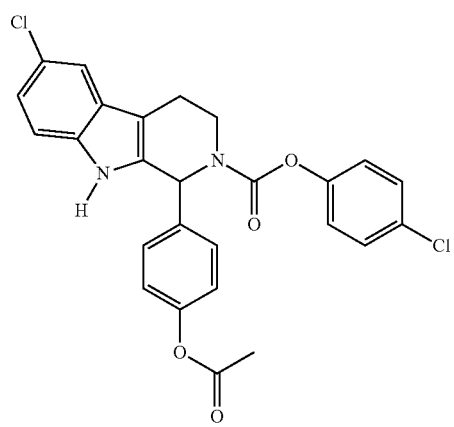 [SMILES: CC(=O)Oc1ccc(C2c3[nH]c4ccc(Cl)cc4c3CCN2C(=O)Oc2ccc(Cl)cc2)cc1] 463
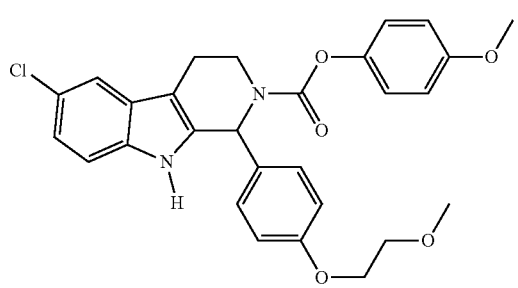 [SMILES: COCCOc1ccc(C2c3[nH]c4ccc(Cl)cc4c3CCN2C(=O)Oc2ccc(OC)cc2)cc1] 465
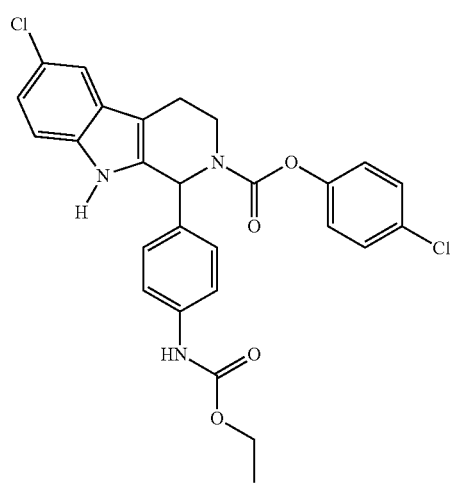 [SMILES: CCOC(=O)Nc1ccc(C2c3[nH]c4ccc(Cl)cc4c3CCN2C(=O)Oc2ccc(Cl)cc2)cc1] 467

TABLE 1-continued
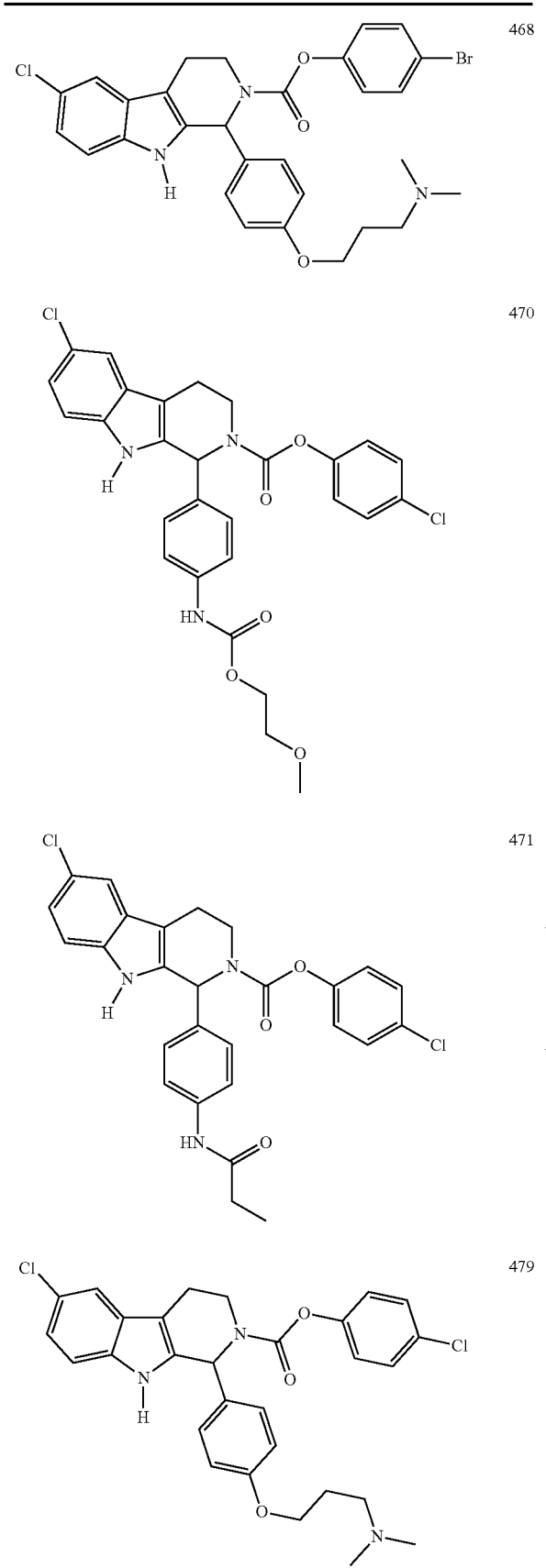
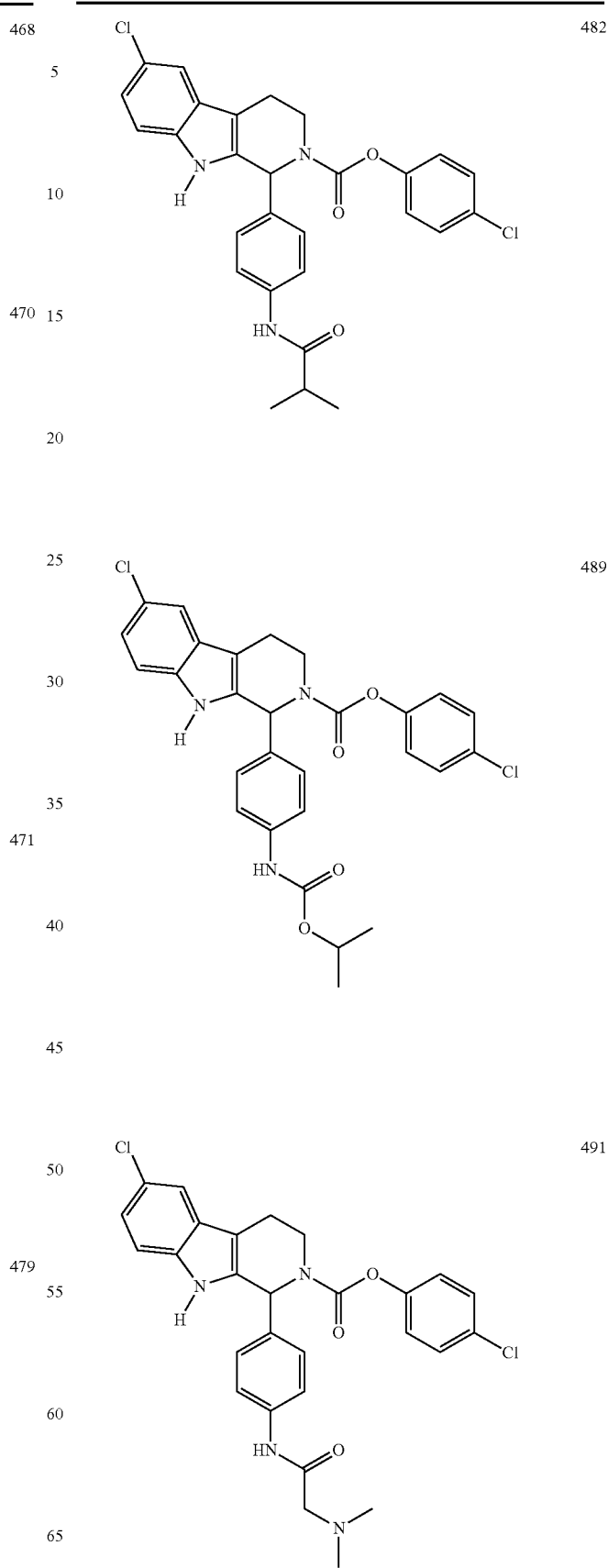

TABLE 1-continued
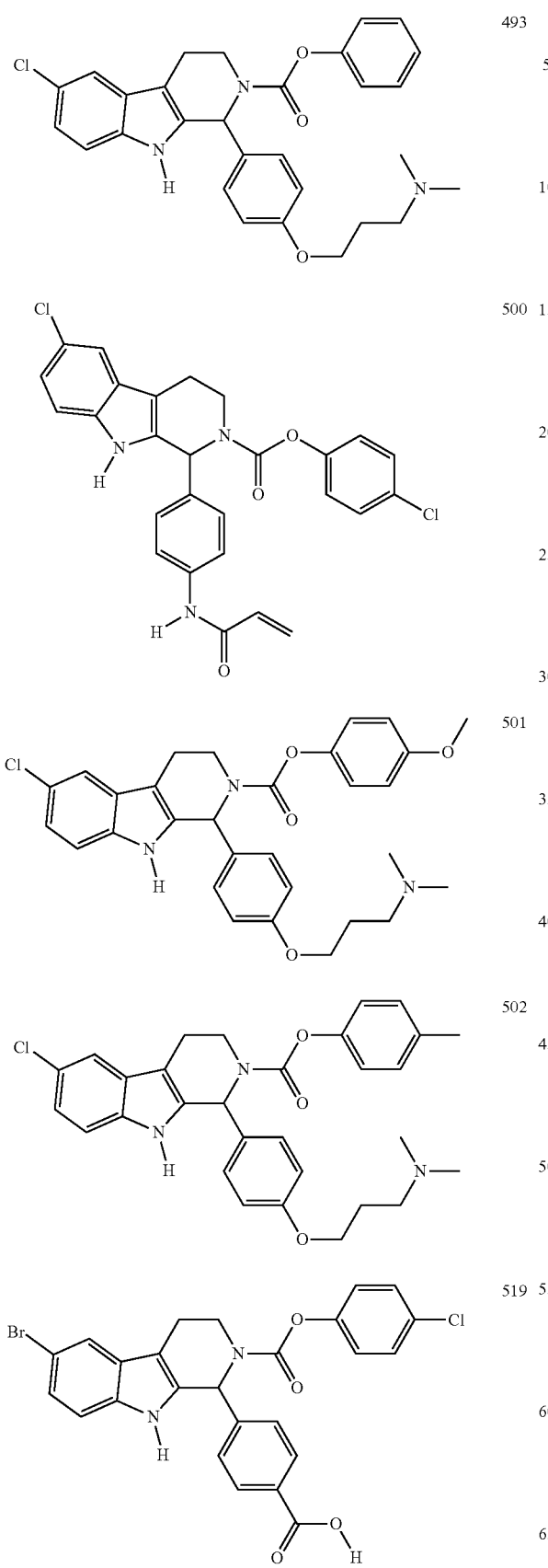
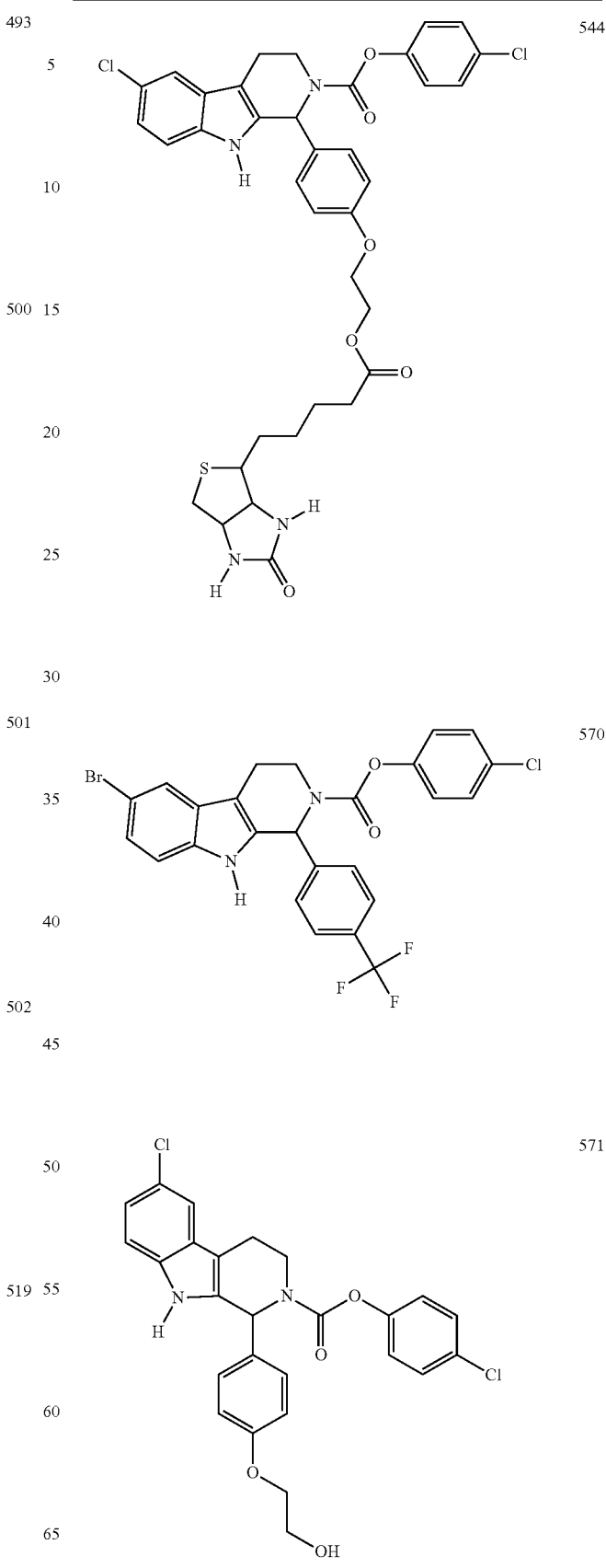

TABLE 1-continued
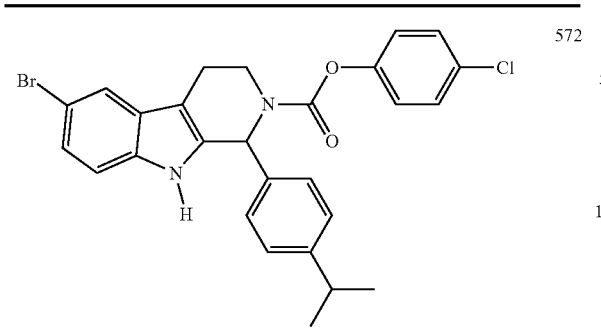
572
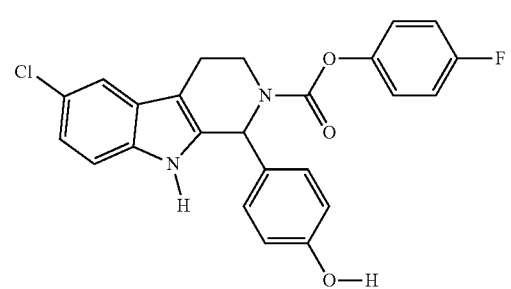 [SMILES: O=C(Oc1ccc(F)cc1)N1CCc2c([nH]c3ccc(Cl)cc23)C1c1ccc(O)cc1]
575
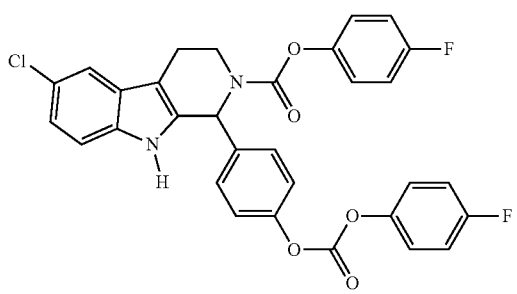 [SMILES: O=C(Oc1ccc(F)cc1)Oc1ccc(C2c3[nH]c4ccc(Cl)cc4c3CCN2C(=O)Oc2ccc(F)cc2)cc1]
576
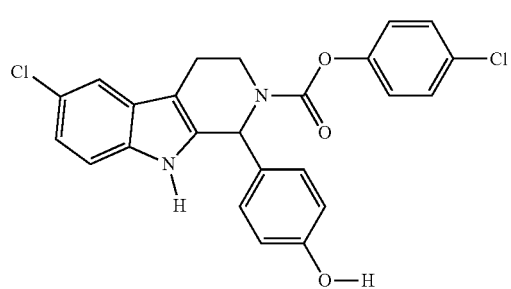
577
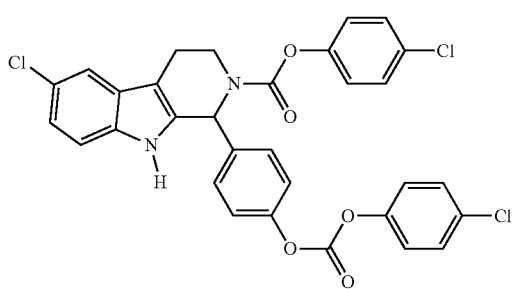 [SMILES: O=C(Oc1ccc(Cl)cc1)Oc1ccc(C2c3[nH]c4ccc(Cl)cc4c3CCN2C(=O)Oc2ccc(Cl)cc2)cc1]
578
TABLE 1-continued
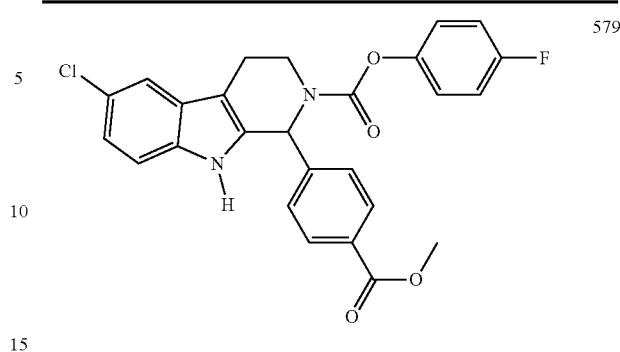
579
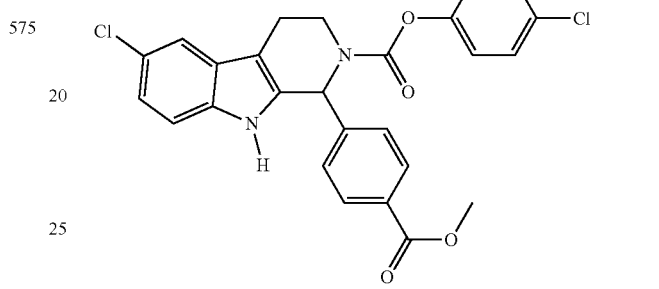
580
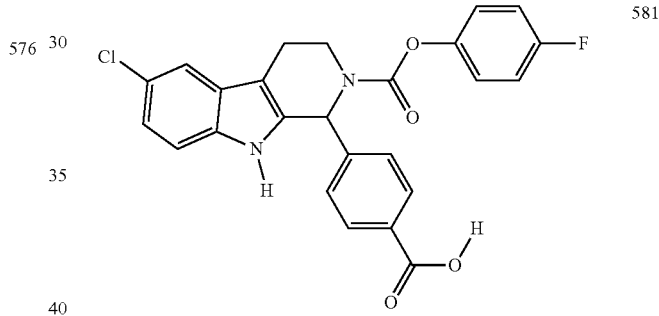
581
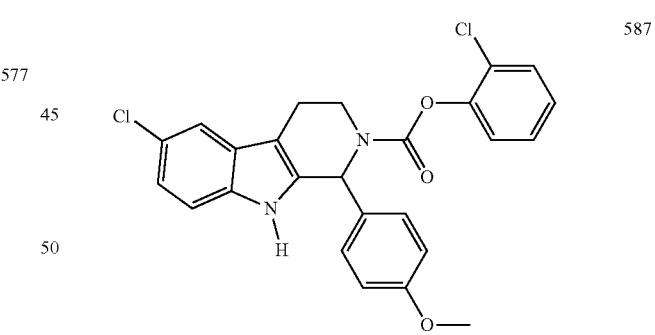
587
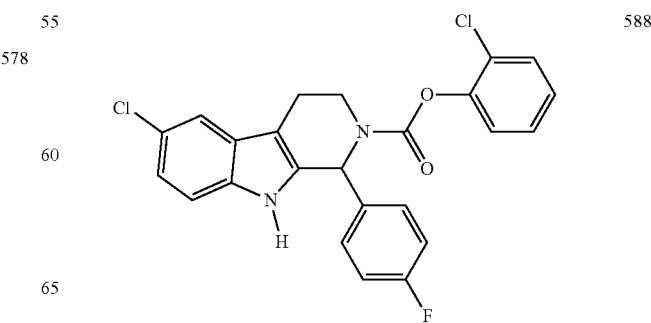
588

TABLE 1-continued
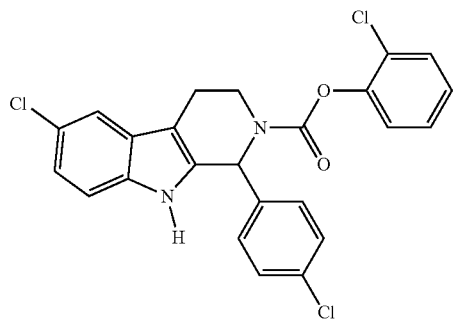 [SMILES: O=C(Oc1ccccc1Cl)N1CCc2c([nH]c3ccc(Cl)cc23)C1c1ccc(Cl)cc1]
589
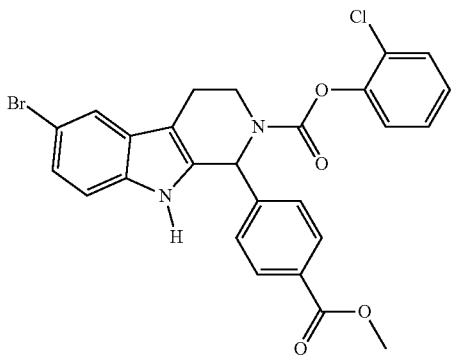
593
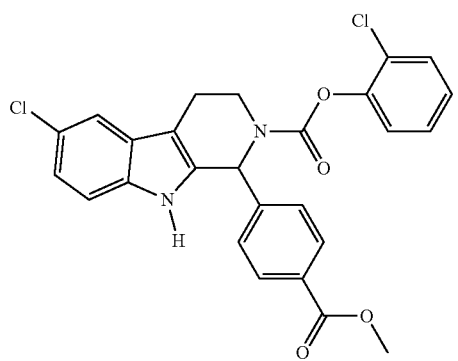 [SMILES: COC(=O)c1ccc(C2c3[nH]c4ccc(Cl)cc4c3CCN2C(=O)Oc2ccccc2Cl)cc1]
590
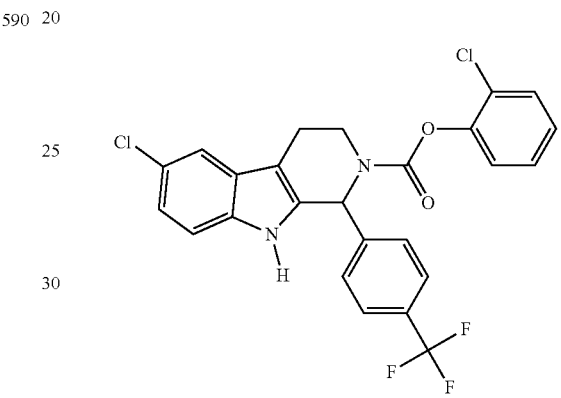
594
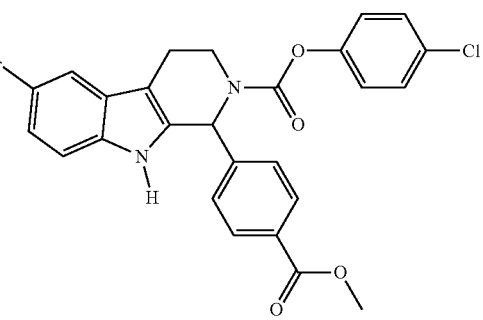
591
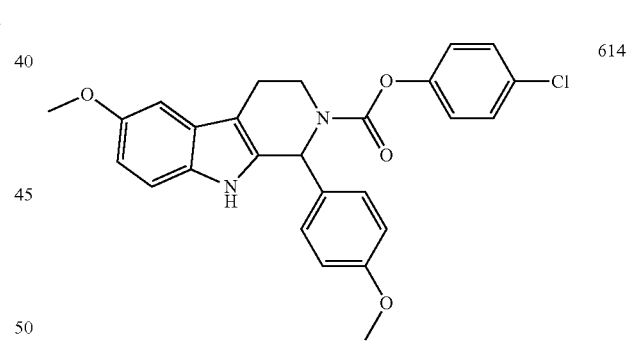
614
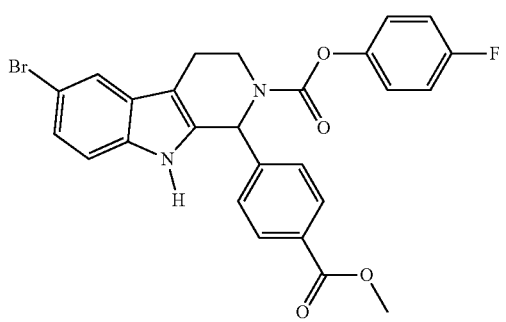 [SMILES: COC(=O)c1ccc(C2c3[nH]c4ccc(Br)cc4c3CCN2C(=O)Oc2ccc(F)cc2)cc1]
592
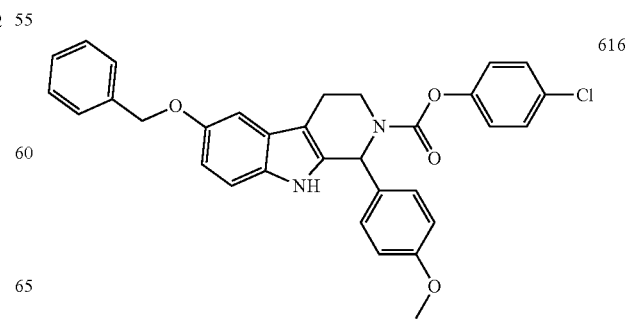
616

TABLE 1-continued
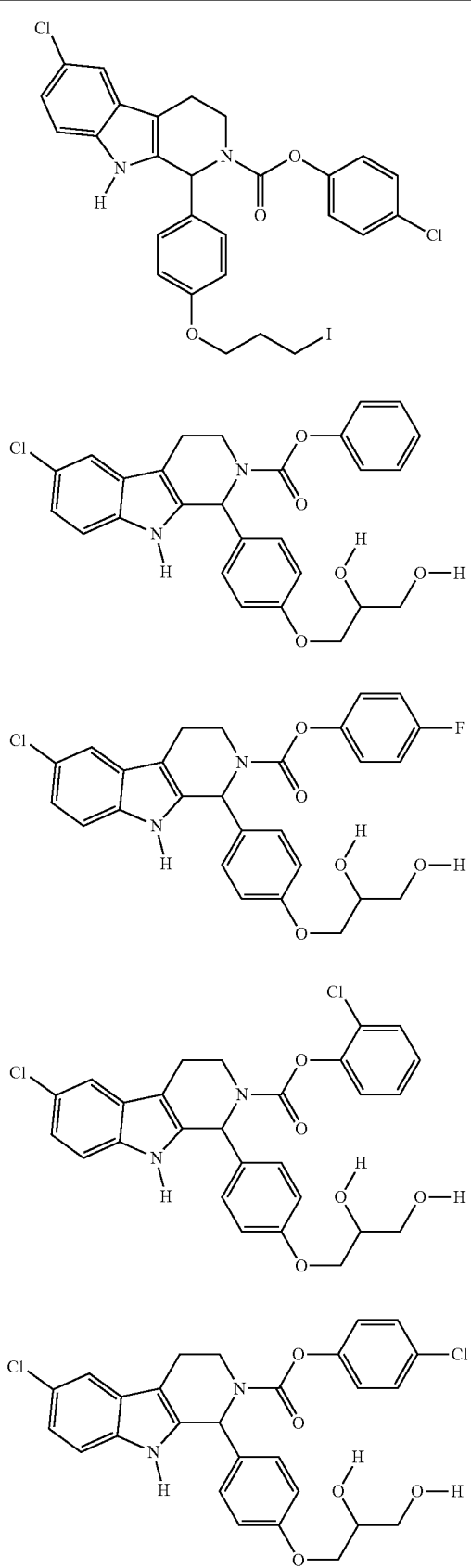
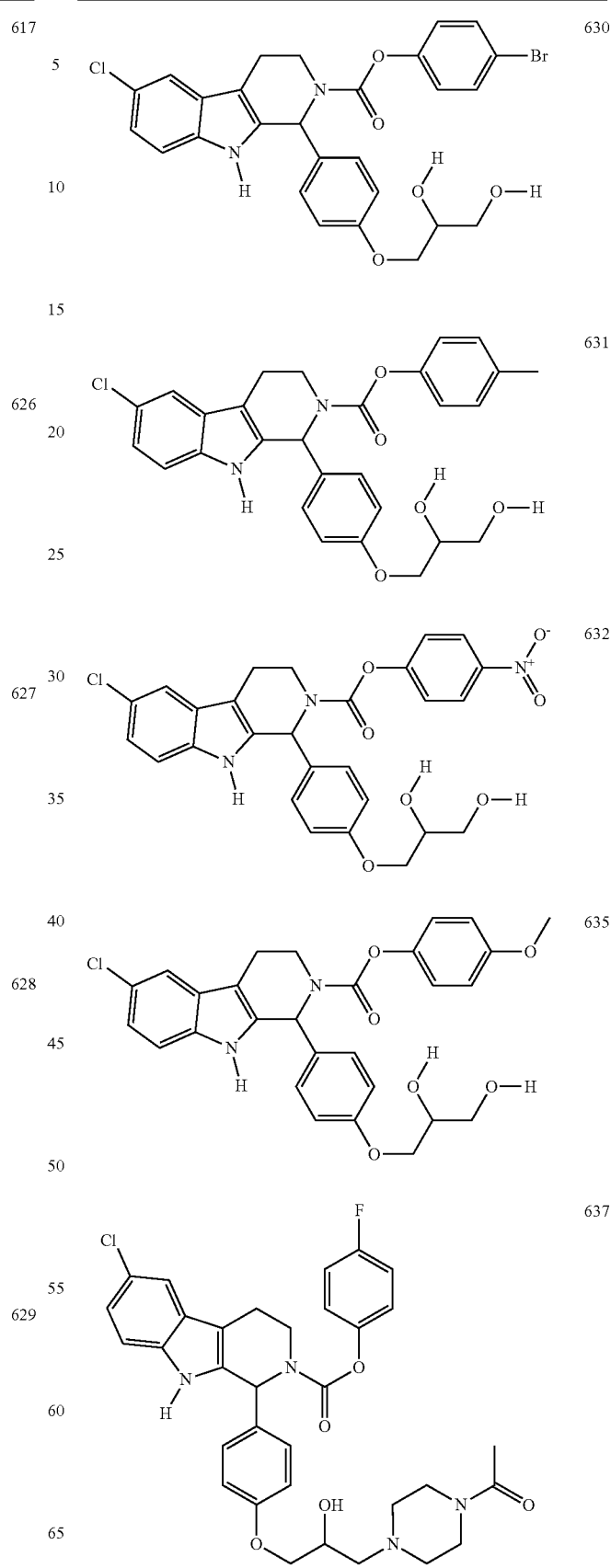

TABLE 1-continued
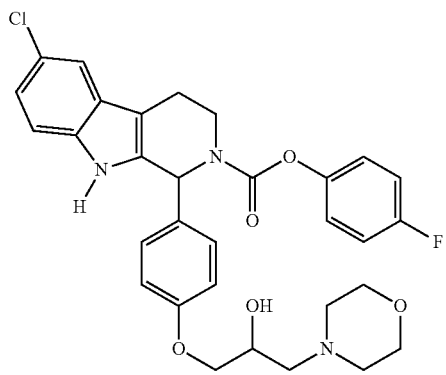 [SMILES: O=C(Oc1ccc(F)cc1)N1CCc2c([nH]c3ccc(Cl)cc23)C1c1ccc(OCC(O)CN2CCOCC2)cc1]
638
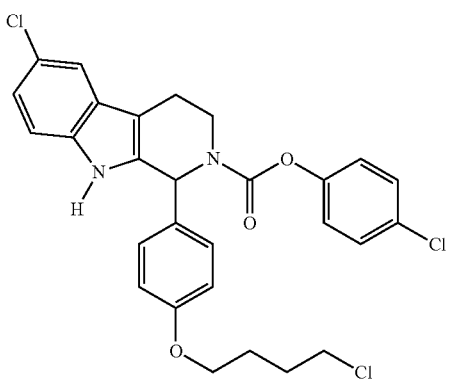 [SMILES: O=C(Oc1ccc(Cl)cc1)N1CCc2c([nH]c3ccc(Cl)cc23)C1c1ccc(OCCCCCl)cc1]
660
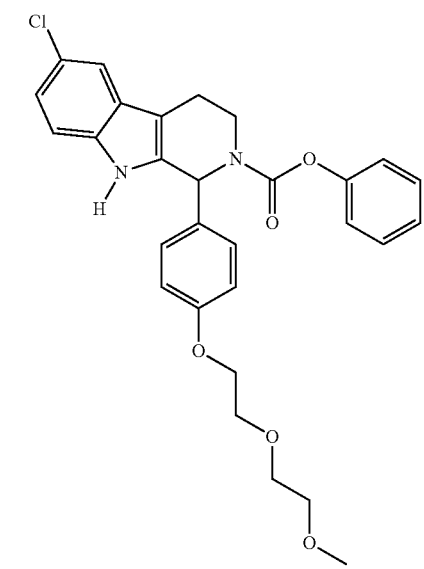 [SMILES: COCCOCCOc1ccc(C2c3[nH]c4ccc(Cl)cc4c3CCN2C(=O)Oc2ccccc2)cc1]
670
TABLE 1-continued
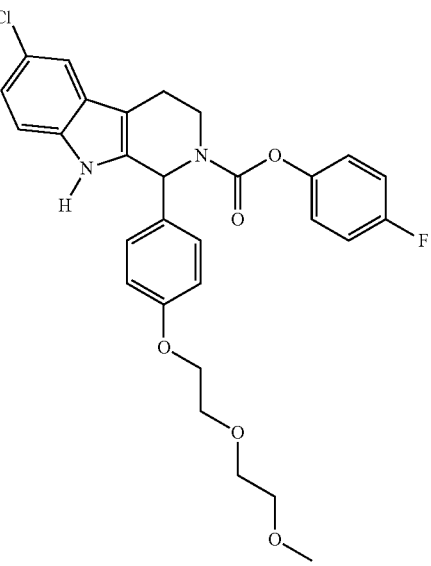
673
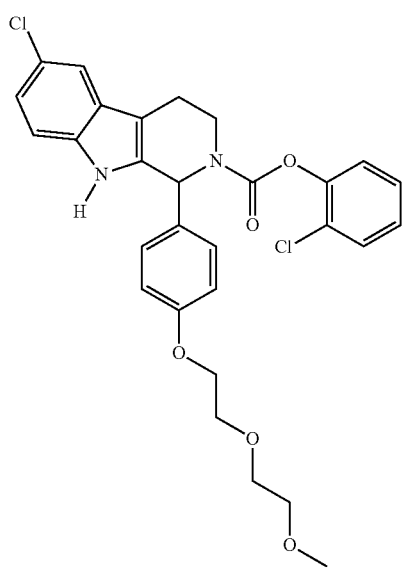 [SMILES: COCCOCCOc1ccc(C2c3[nH]c4ccc(Cl)cc4c3CCN2C(=O)Oc2ccccc2Cl)cc1]
674

TABLE 1-continued
675
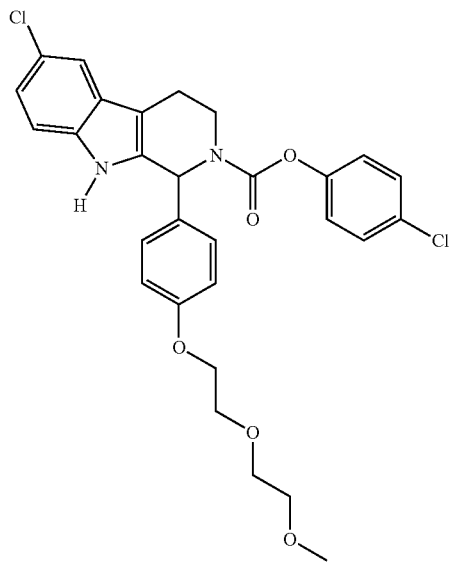 [SMILES: COCCOCCOc1ccc(C2c3[nH]c4ccc(Cl)cc4c3CCN2C(=O)Oc2ccc(Cl)cc2)cc1]
677
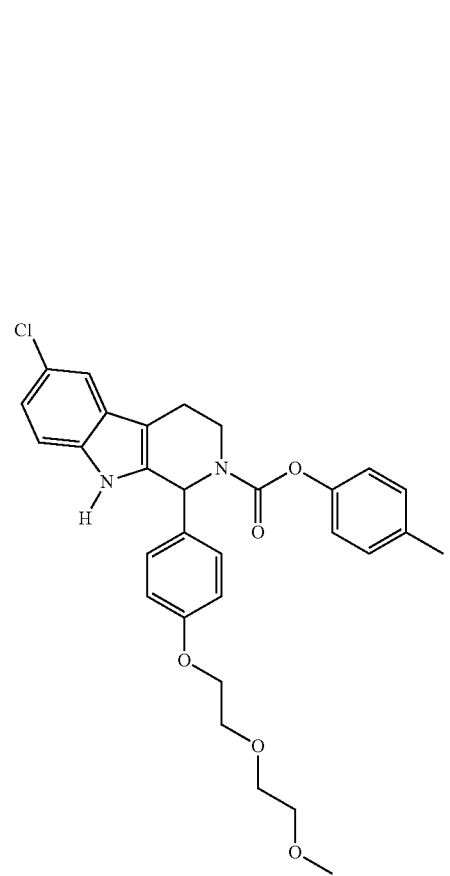 [SMILES: COCCOCCOc1ccc(C2c3[nH]c4ccc(Cl)cc4c3CCN2C(=O)Oc2ccc(C)cc2)cc1]
TABLE 1-continued
678
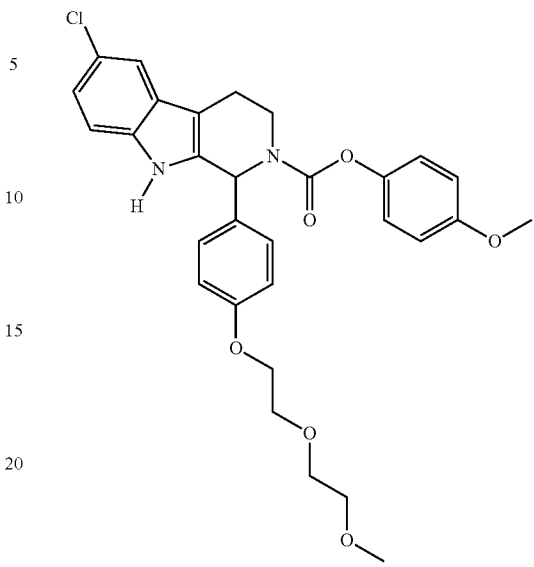
680
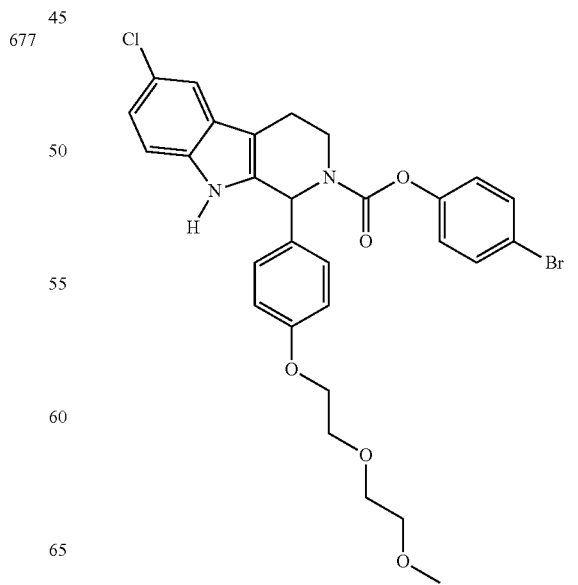

TABLE 1-continued
681
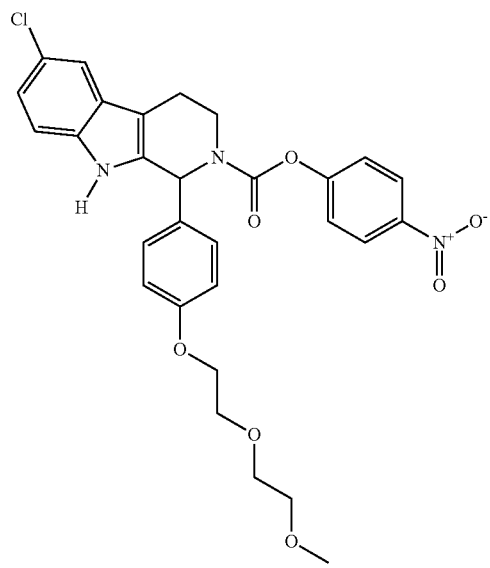 [SMILES: COCCOCCOc1ccc(C2c3[nH]c4ccc(Cl)cc4c3CCN2C(=O)Oc2ccc([N+](=O)[O-])cc2)cc1]
698
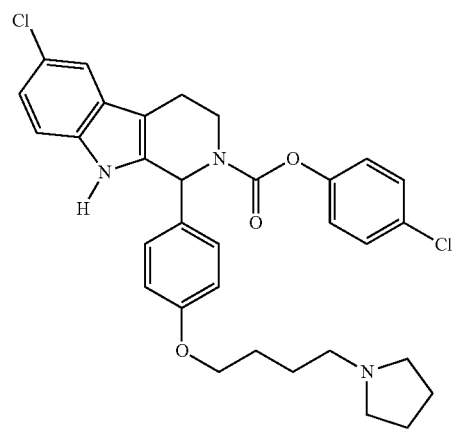 [SMILES: O=C(Oc1ccc(Cl)cc1)N1CCc2c([nH]c3ccc(Cl)cc23)C1c1ccc(OCCCCN2CCCC2)cc1]
699
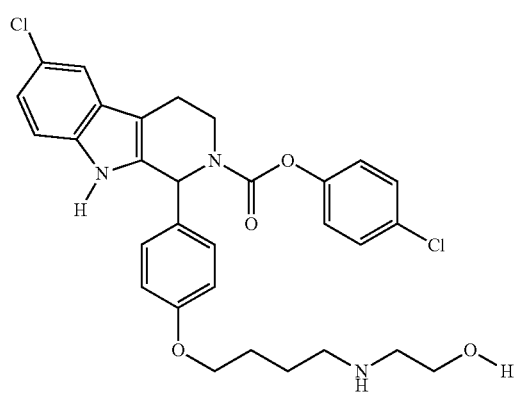 [SMILES: O=C(Oc1ccc(Cl)cc1)N1CCc2c([nH]c3ccc(Cl)cc23)C1c1ccc(OCCCCNCCO)cc1]
TABLE 1-continued
700
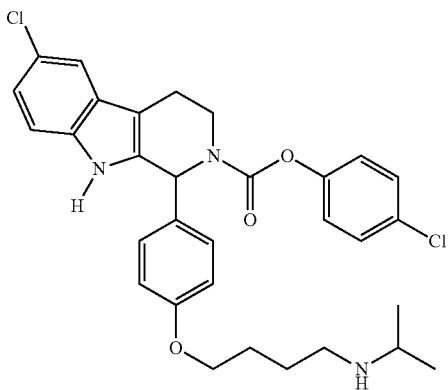 [SMILES: CC(C)NCCCCOc1ccc(C2c3[nH]c4ccc(Cl)cc4c3CCN2C(=O)Oc2ccc(Cl)cc2)cc1]
701
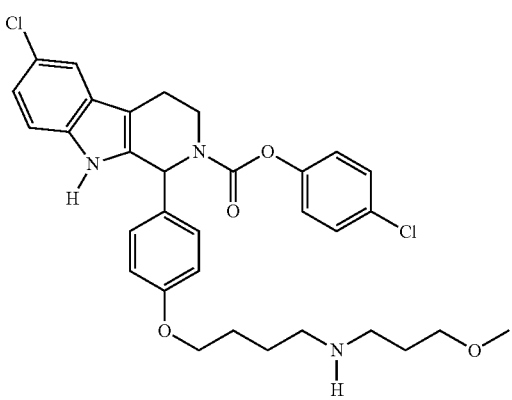 [SMILES: COCCCNCCCCOc1ccc(C2c3[nH]c4ccc(Cl)cc4c3CCN2C(=O)Oc2ccc(Cl)cc2)cc1]
702
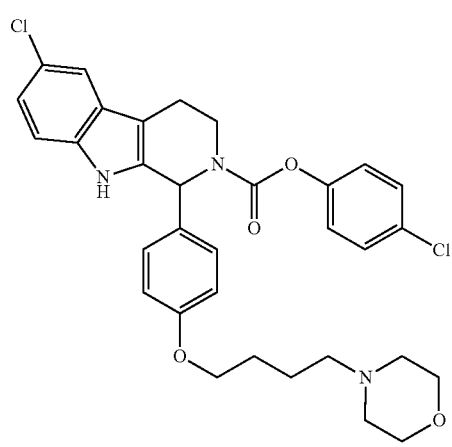 [SMILES: O=C(Oc1ccc(Cl)cc1)N1CCc2c([nH]c3ccc(Cl)cc23)C1c1ccc(OCCCCN2CCOCC2)cc1]
703
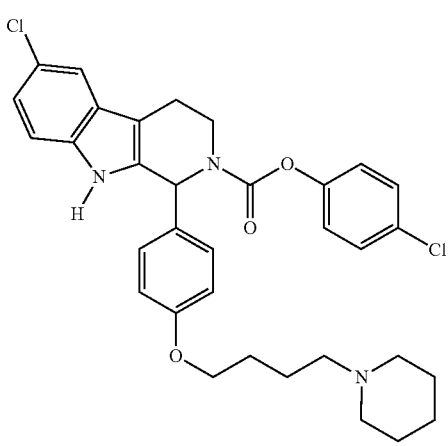 [SMILES: O=C(Oc1ccc(Cl)cc1)N1CCc2c([nH]c3ccc(Cl)cc23)C1c1ccc(OCCCCN2CCCCC2)cc1]

TABLE 1-continued
704 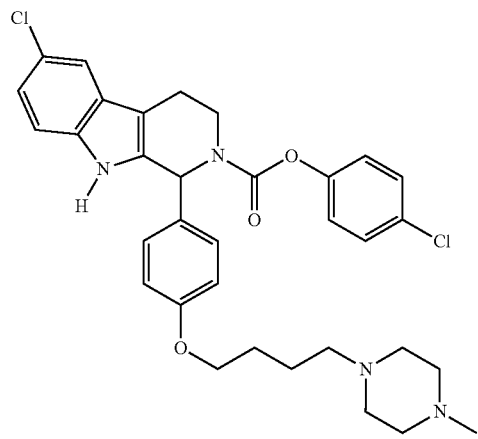
705 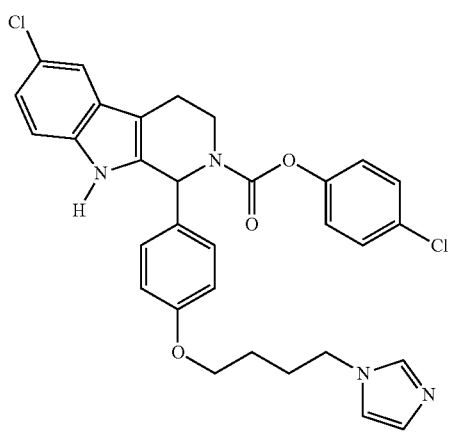 [SMILES: O=C(Oc1ccc(Cl)cc1)N1CCc2c([nH]c3ccc(Cl)cc23)C1c1ccc(OCCCCn2ccnc2)cc1]
706 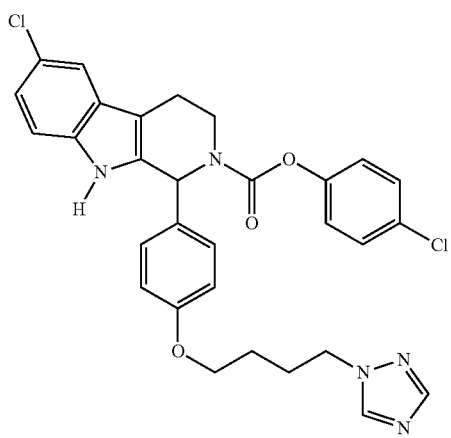 [SMILES: O=C(Oc1ccc(Cl)cc1)N1CCc2c([nH]c3ccc(Cl)cc23)C1c1ccc(OCCCCn2cncn2)cc1]
710 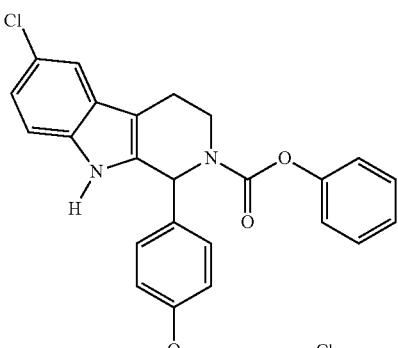
712 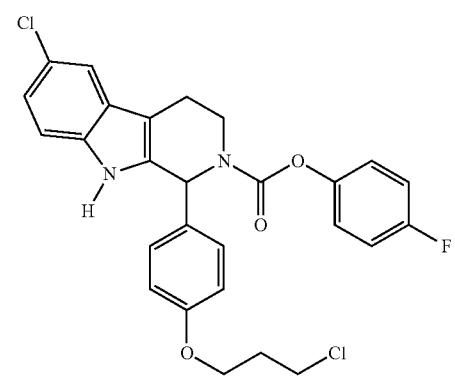 [SMILES: O=C(Oc1ccc(F)cc1)N1CCc2c([nH]c3ccc(Cl)cc23)C1c1ccc(OCCCCl)cc1]
713 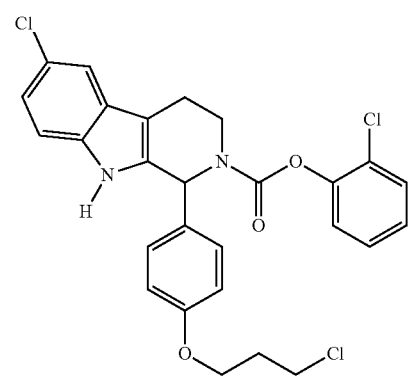 [SMILES: O=C(Oc1ccccc1Cl)N1CCc2c([nH]c3ccc(Cl)cc23)C1c1ccc(OCCCCl)cc1]
719 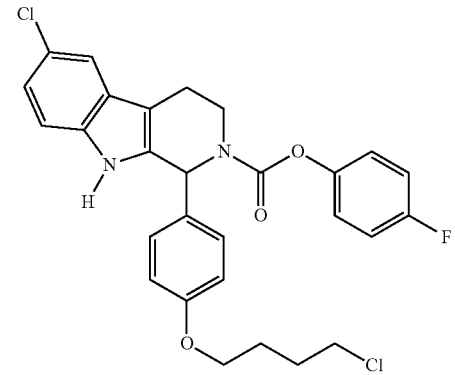 [SMILES: O=C(Oc1ccc(F)cc1)N1CCc2c([nH]c3ccc(Cl)cc23)C1c1ccc(OCCCCCl)cc1]

TABLE 1-continued
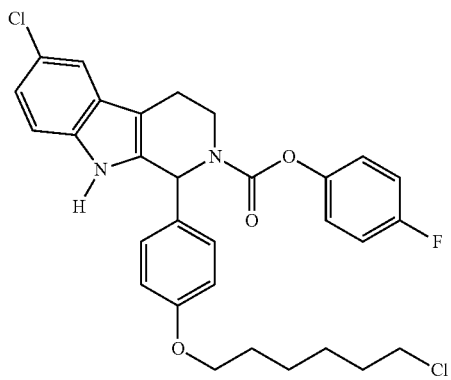 [SMILES: O=C(Oc1ccc(F)cc1)N1CCc2c([nH]c3ccc(Cl)cc23)C1c1ccc(OCCCCCCCl)cc1]
723
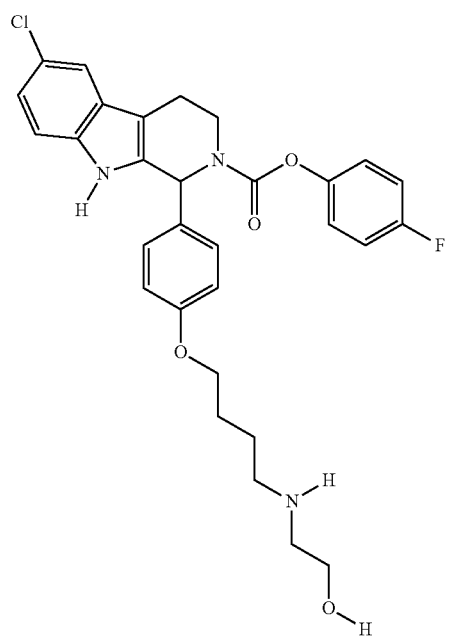 [SMILES: O=C(Oc1ccc(F)cc1)N1CCc2c([nH]c3ccc(Cl)cc23)C1c1ccc(OCCCCNCCO)cc1]
735
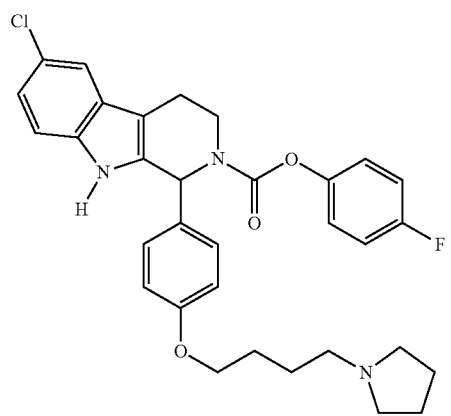 [SMILES: O=C(Oc1ccc(F)cc1)N1CCc2c([nH]c3ccc(Cl)cc23)C1c1ccc(OCCCCN2CCCC2)cc1]
736
TABLE 1-continued
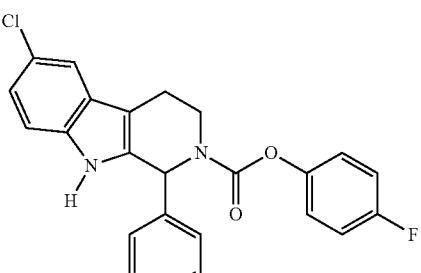
737
738
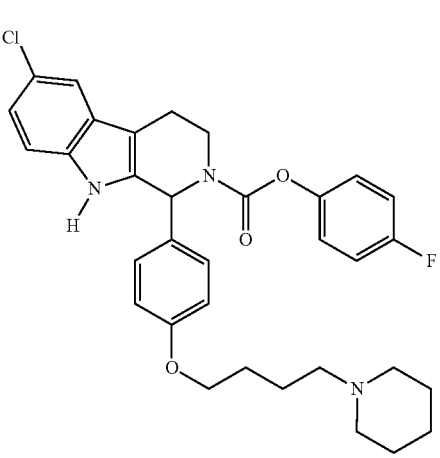 [SMILES: O=C(Oc1ccc(F)cc1)N1CCc2c([nH]c3ccc(Cl)cc23)C1c1ccc(OCCCCN2CCCCC2)cc1]
739

TABLE 1-continued
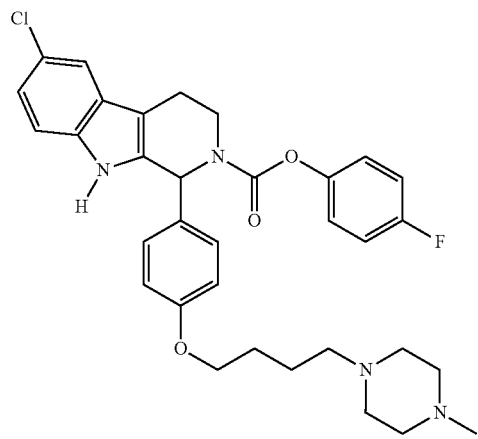 [SMILES: CN1CCN(CCCCOc2ccc(C3c4[nH]c5ccc(Cl)cc5c4CCN3C(=O)Oc3ccc(F)cc3)cc2)CC1]
740
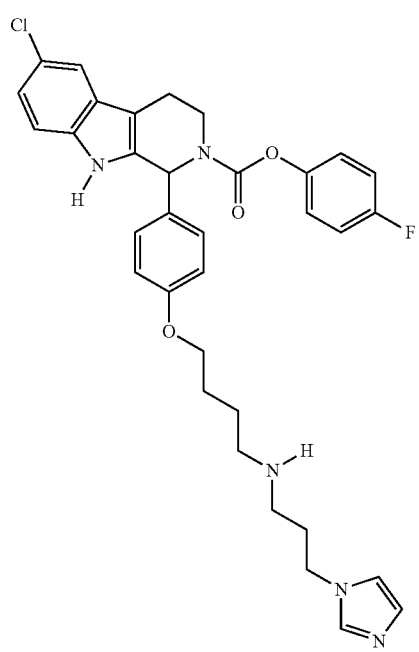 [SMILES: O=C(Oc1ccc(F)cc1)N1CCc2c([nH]c3ccc(Cl)cc23)C1c1ccc(OCCCCNCCCn2ccnc2)cc1]
741
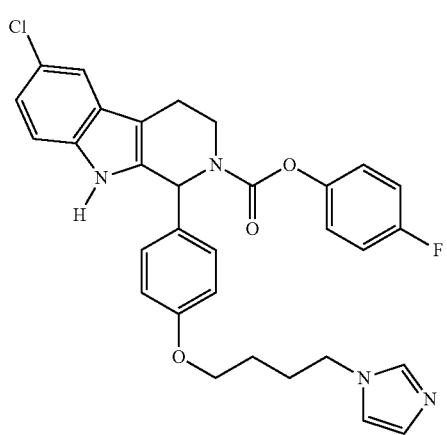 [SMILES: O=C(Oc1ccc(F)cc1)N1CCc2c([nH]c3ccc(Cl)cc23)C1c1ccc(OCCCCn2ccnc2)cc1]
742
TABLE 1-continued
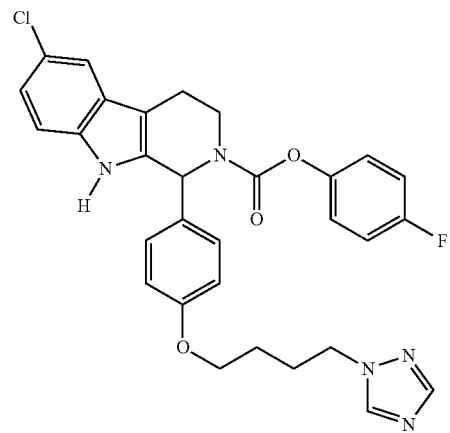 [SMILES: O=C(Oc1ccc(F)cc1)N1CCc2c([nH]c3ccc(Cl)cc23)C1c1ccc(OCCCCn2cncn2)cc1]
743
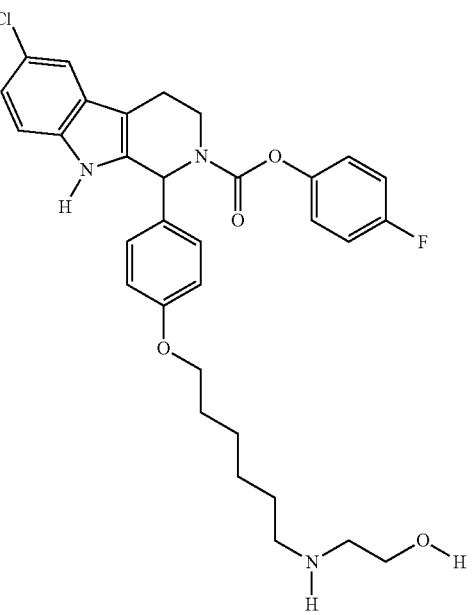
772
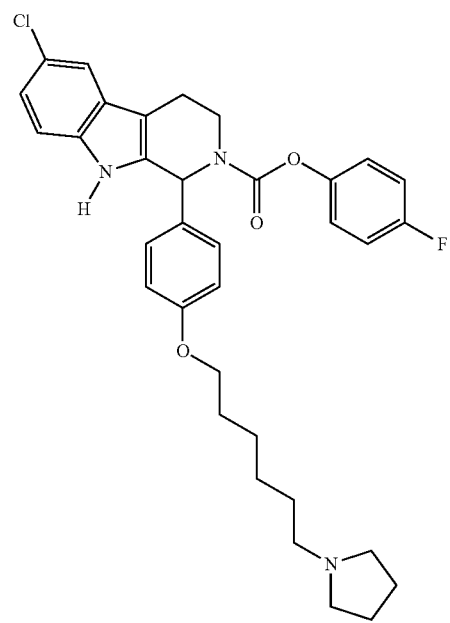 [SMILES: O=C(Oc1ccc(F)cc1)N1CCc2c([nH]c3ccc(Cl)cc23)C1c1ccc(OCCCCCCN2CCCC2)cc1]
773

TABLE 1-continued
774
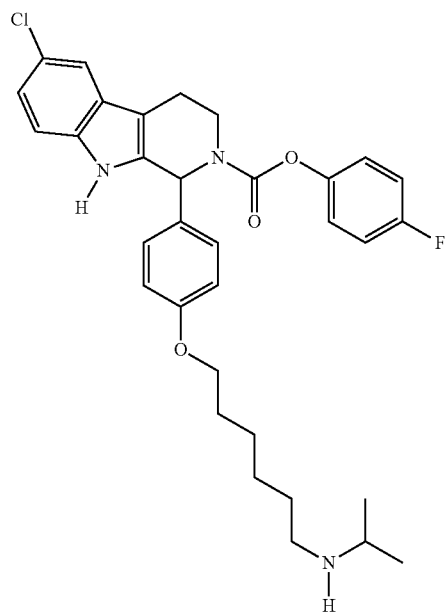 [SMILES: CC(C)NCCCCCCOc1ccc(C2c3[nH]c4ccc(Cl)cc4c3CCN2C(=O)Oc2ccc(F)cc2)cc1]
776
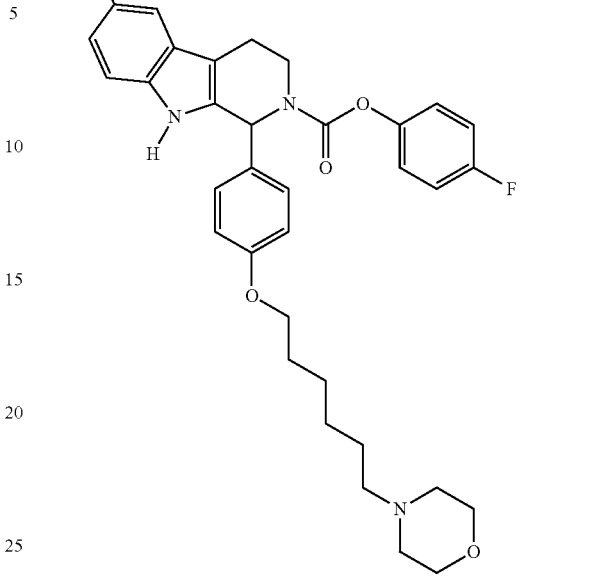
775
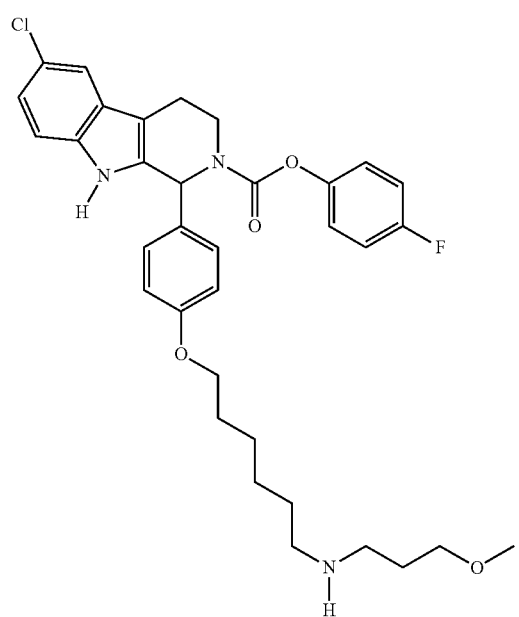 [SMILES: COCCCNCCCCCCOc1ccc(C2c3[nH]c4ccc(Cl)cc4c3CCN2C(=O)Oc2ccc(F)cc2)cc1]
777
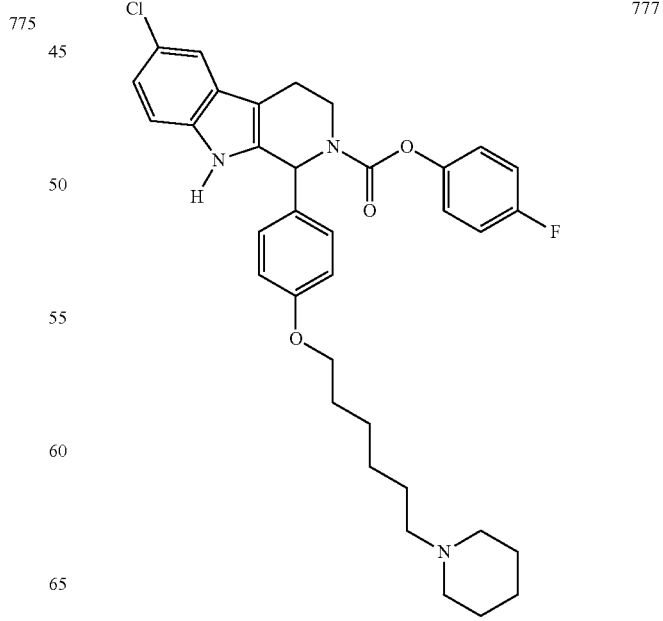

TABLE 1-continued
778
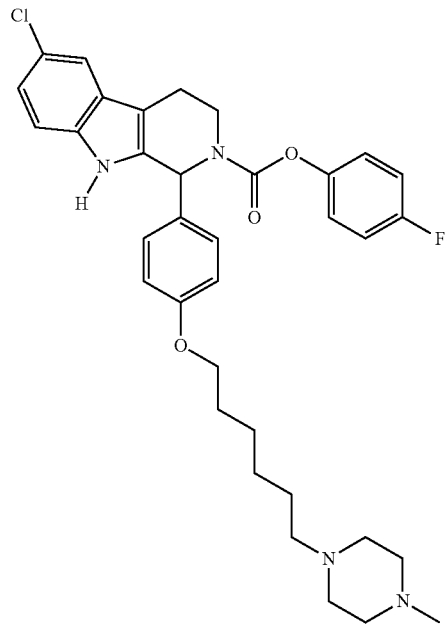 [SMILES: CN1CCN(CCCCCCOc2ccc(C3c4[nH]c5ccc(Cl)cc5c4CCN3C(=O)Oc3ccc(F)cc3)cc2)CC1]
779
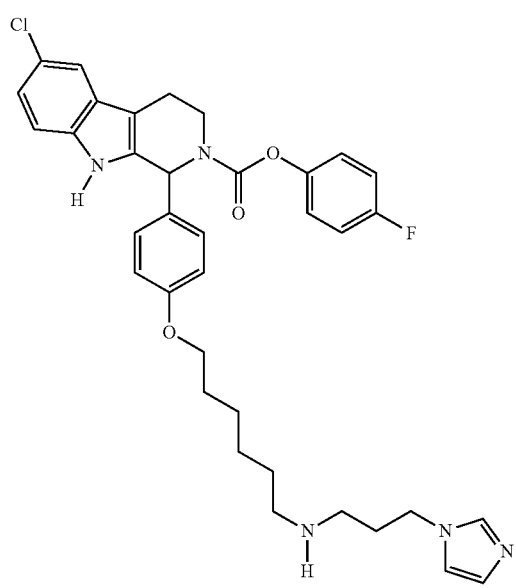 [SMILES: O=C(Oc1ccc(F)cc1)N1CCc2c([nH]c3ccc(Cl)cc23)C1c1ccc(OCCCCCCNCCCn2ccnc2)cc1]
TABLE 1-continued
780
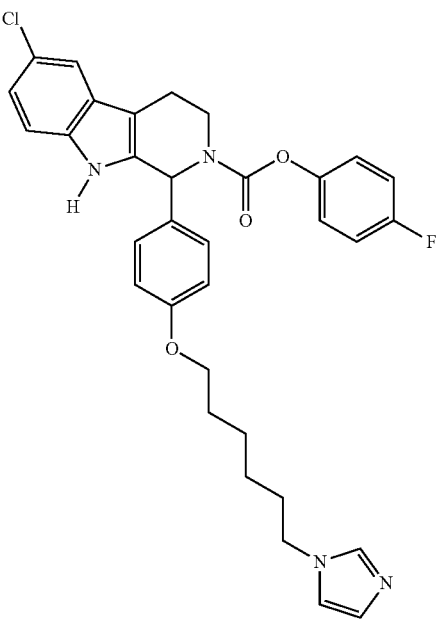 [SMILES: O=C(Oc1ccc(F)cc1)N1CCc2c([nH]c3ccc(Cl)cc23)C1c1ccc(OCCCCCCn2ccnc2)cc1]
781
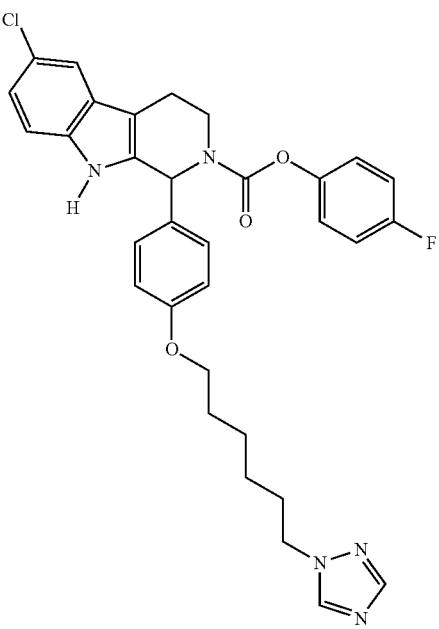 [SMILES: O=C(Oc1ccc(F)cc1)N1CCc2c([nH]c3ccc(Cl)cc23)C1c1ccc(OCCCCCCn2cncn2)cc1]

TABLE 1-continued
| 73 | 782 |
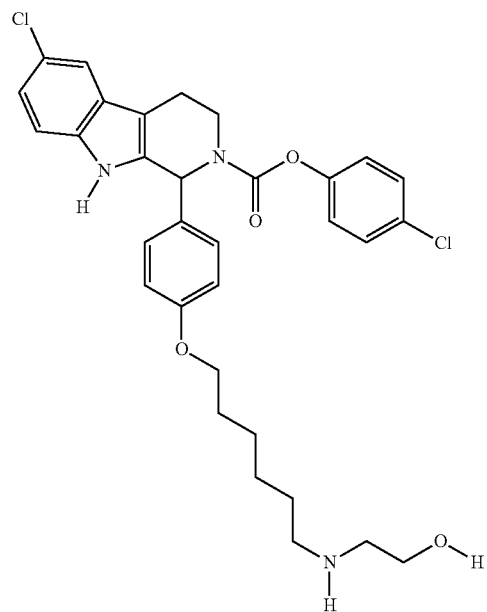
| 74 | 784 |
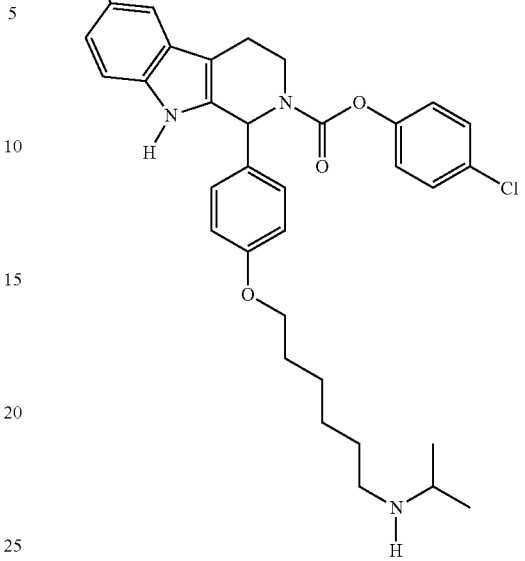
| | 783 |
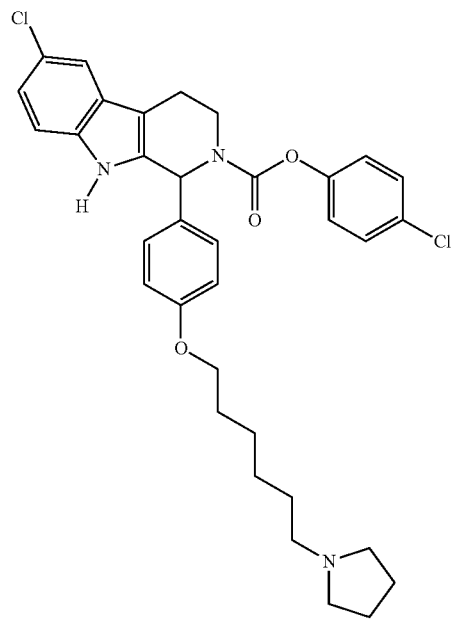 [SMILES: O=C(Oc1ccc(Cl)cc1)N1CCc2c([nH]c3ccc(Cl)cc23)C1c1ccc(OCCCCCCN2CCCC2)cc1]
| | 785 |
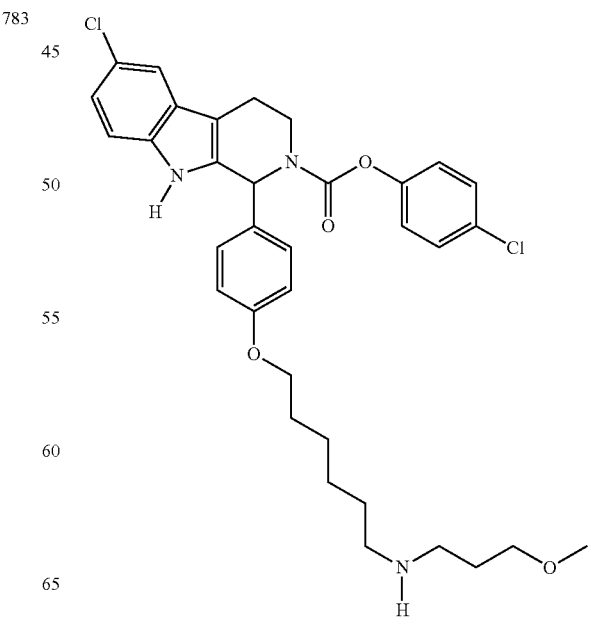

TABLE 1-continued
786 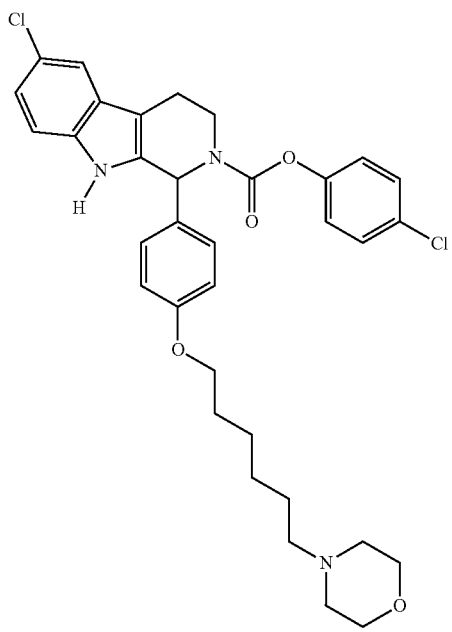 [SMILES: O=C(Oc1ccc(Cl)cc1)N1CCc2c([nH]c3ccc(Cl)cc23)C1c1ccc(OCCCCCCN2CCOCC2)cc1]
787 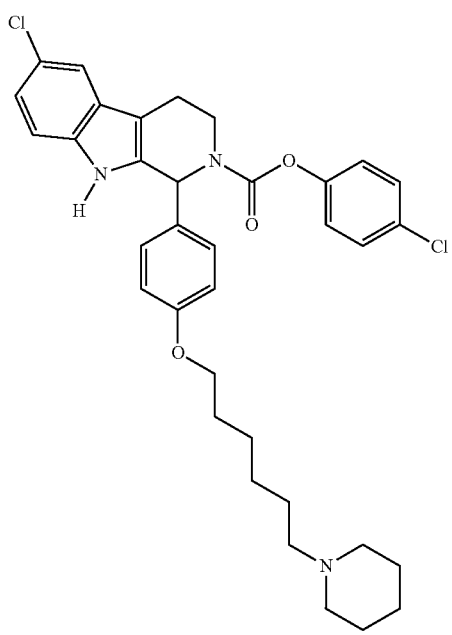 [SMILES: O=C(Oc1ccc(Cl)cc1)N1CCc2c([nH]c3ccc(Cl)cc23)C1c1ccc(OCCCCCCN2CCCCC2)cc1]
788 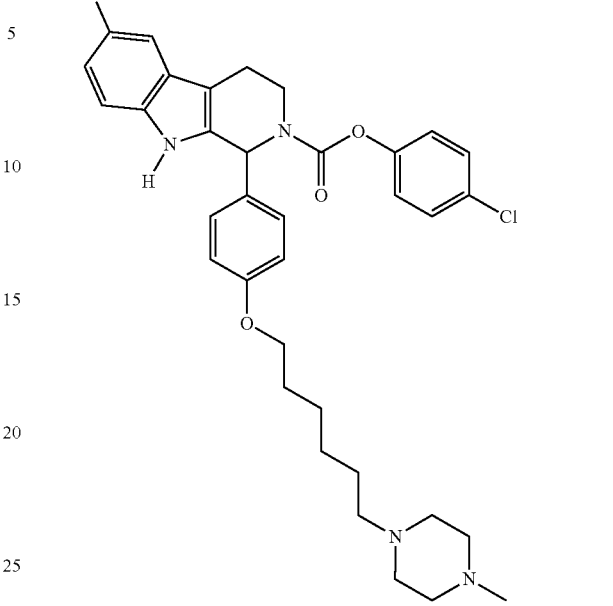
789 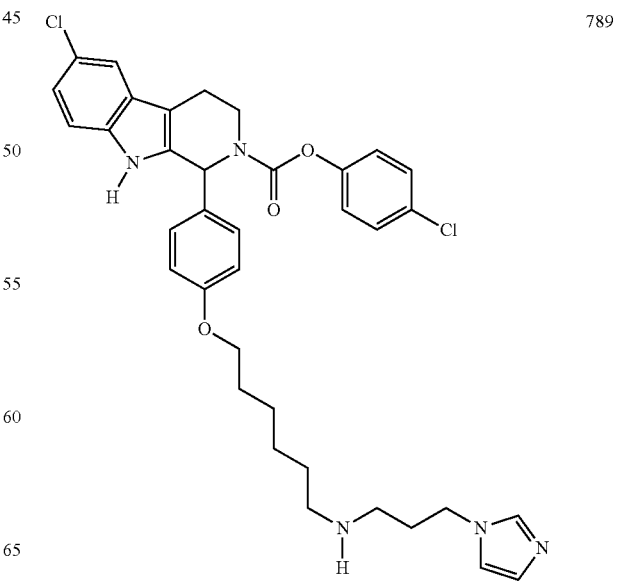

TABLE 1-continued
| | |
|---|---|
| 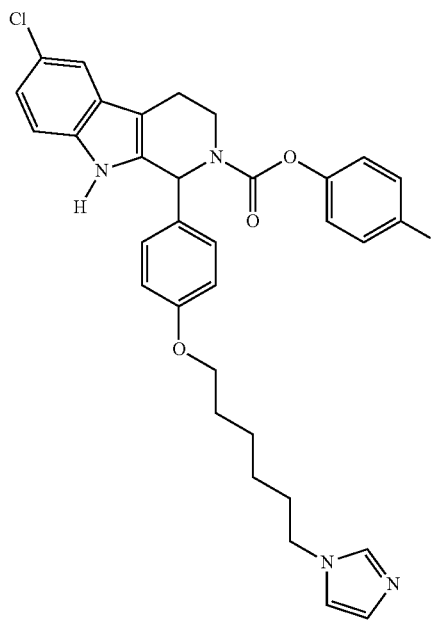 790 | 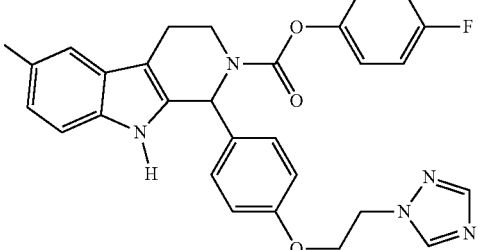 834 |
| 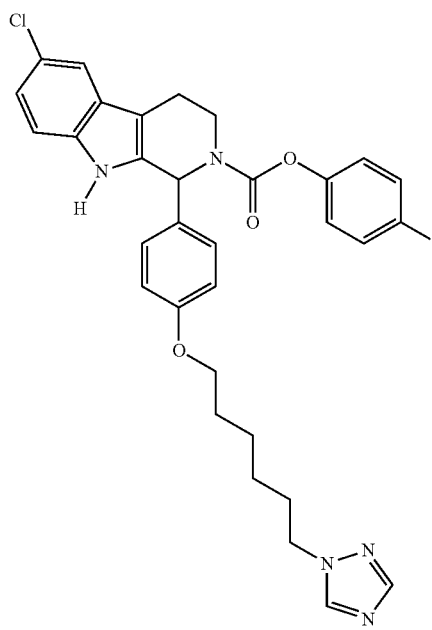 791 | 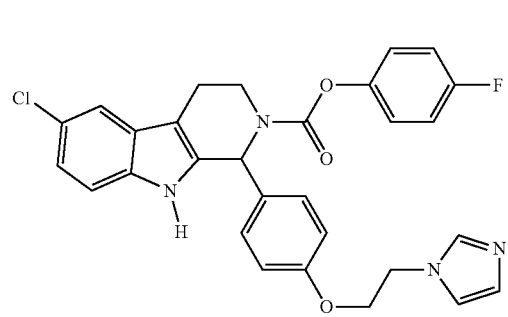 [SMILES: O=C(Oc1ccc(F)cc1)N1CCc2c([nH]c3ccc(Cl)cc23)C1c1ccc(OCCn2ccnc2)cc1] 835 |
| | 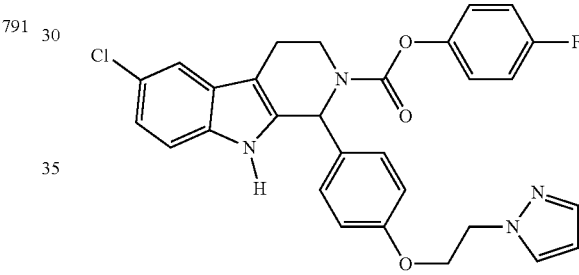 836 |
| 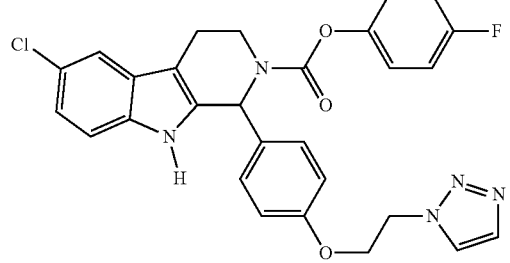 833 | 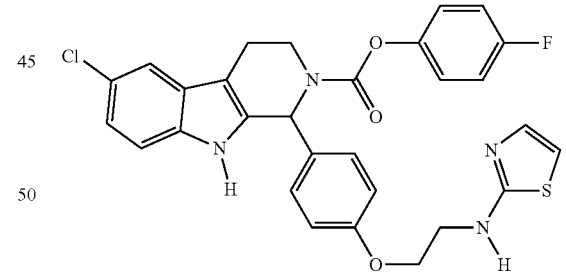 837 |
| | 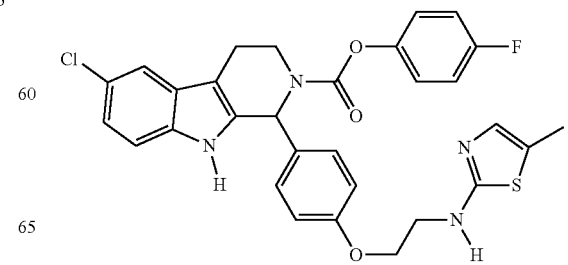 838 |

TABLE 1-continued
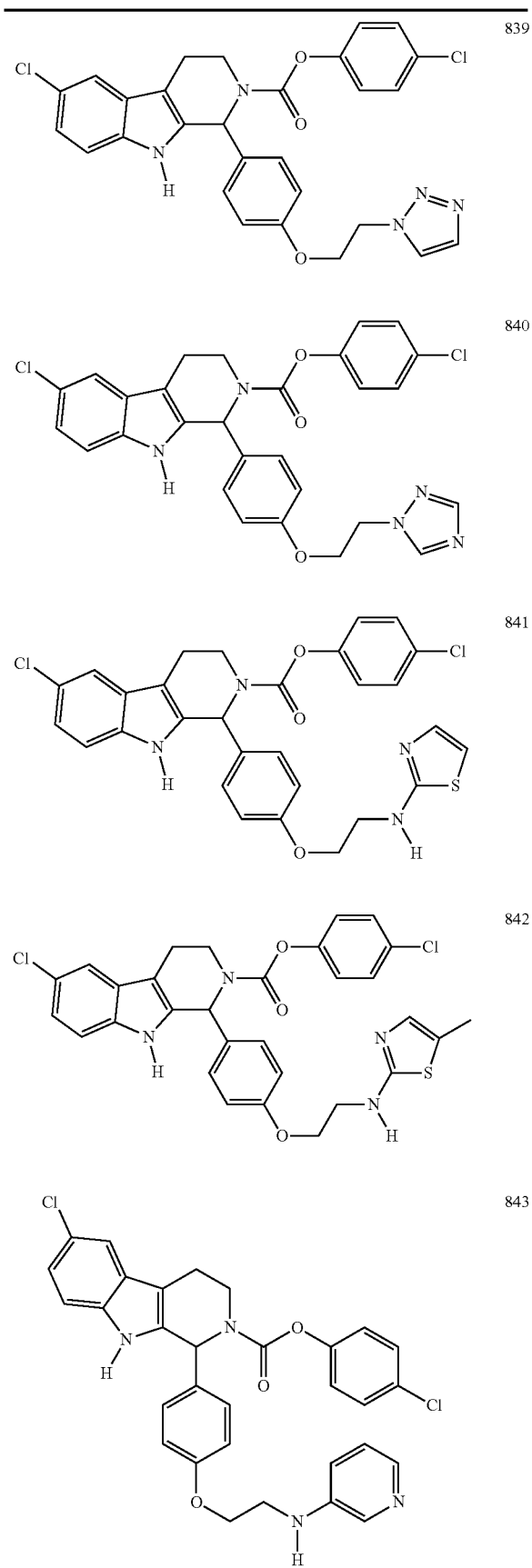
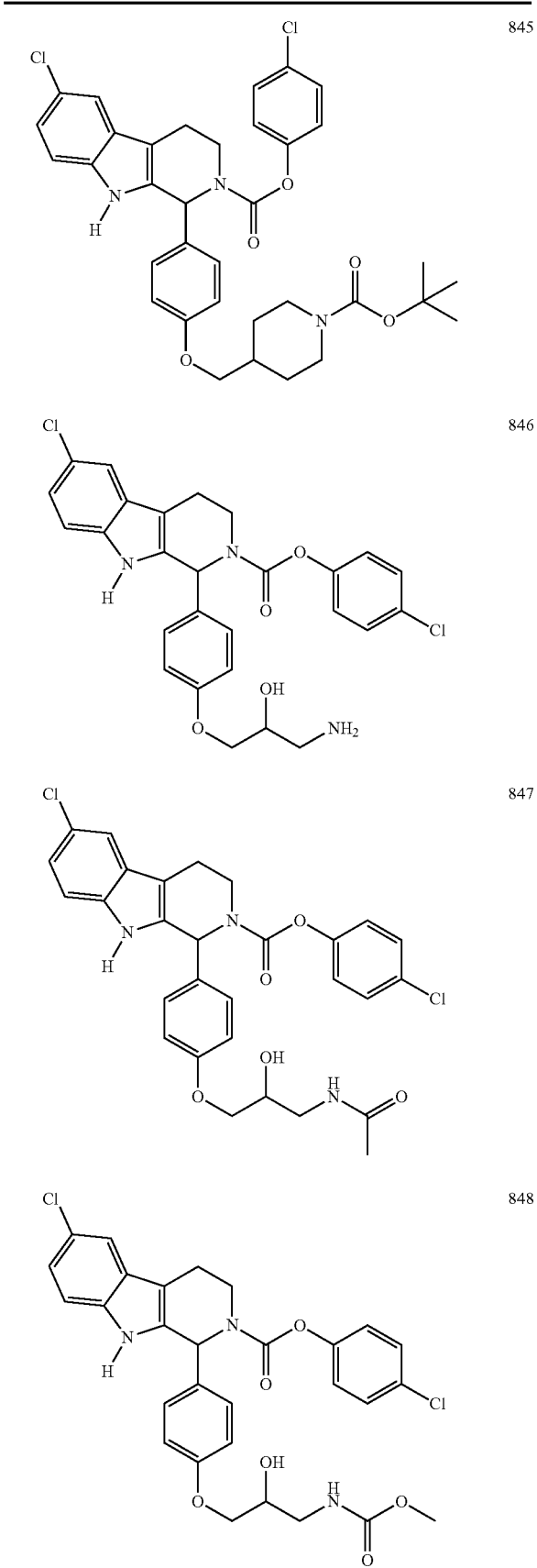

| 849 | 888 |
|---|---|
| 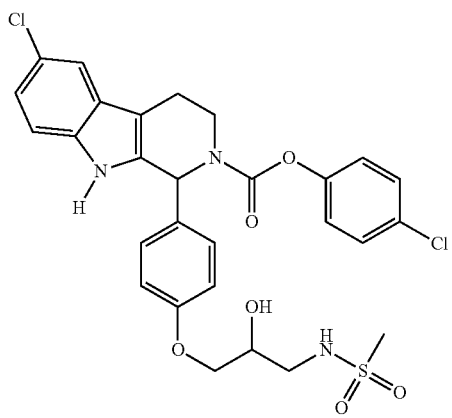 [SMILES: CS(=O)(=O)NCC(O)COc1ccc(C2c3[nH]c4ccc(Cl)cc4c3CCN2C(=O)Oc2ccc(Cl)cc2)cc1] | 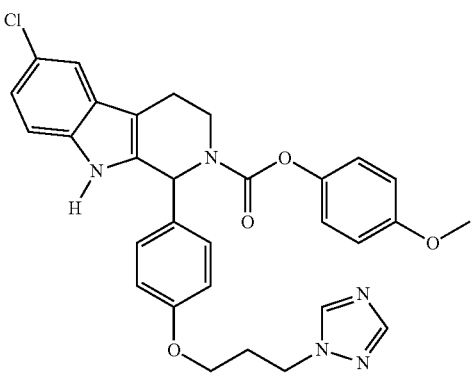 |
| 850 | 889 |
| 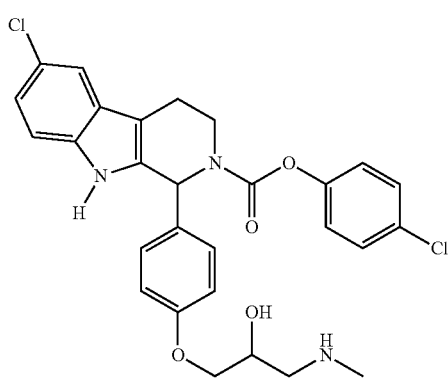 [SMILES: CNCC(O)COc1ccc(C2c3[nH]c4ccc(Cl)cc4c3CCN2C(=O)Oc2ccc(Cl)cc2)cc1] | 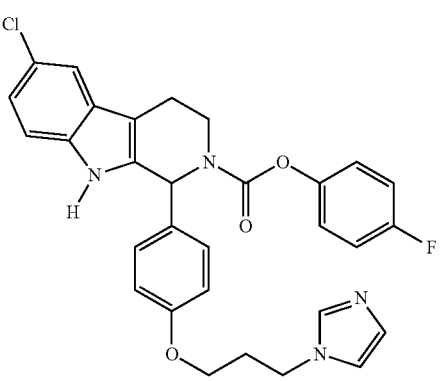 |
| 867 | 891 |
| 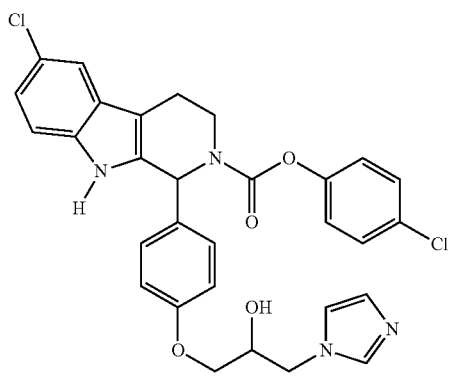 [SMILES: O=C(Oc1ccc(Cl)cc1)N1CCc2c([nH]c3ccc(Cl)cc23)C1c1ccc(OCC(O)Cn2ccnc2)cc1] | 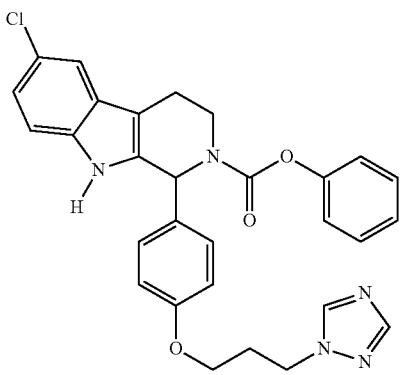 |
| 882 | 892 |
| 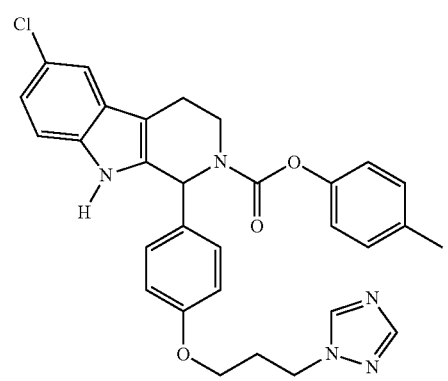 [SMILES: Cc1ccc(OC(=O)N2CCc3c([nH]c4ccc(Cl)cc34)C2c2ccc(OCCCn3cncn3)cc2)cc1] | 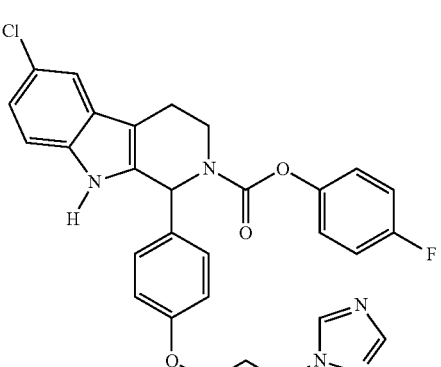 |

TABLE 1-continued
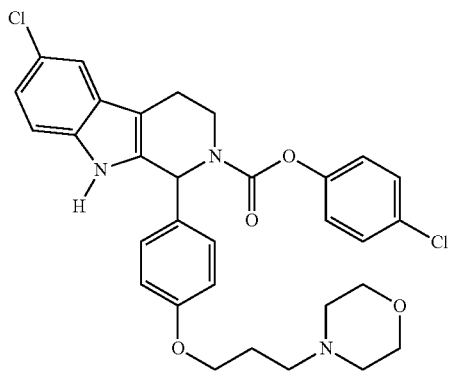 [SMILES: O=C(Oc1ccc(Cl)cc1)N1CCc2c([nH]c3ccc(Cl)cc23)C1c1ccc(OCCCN2CCOCC2)cc1]
894
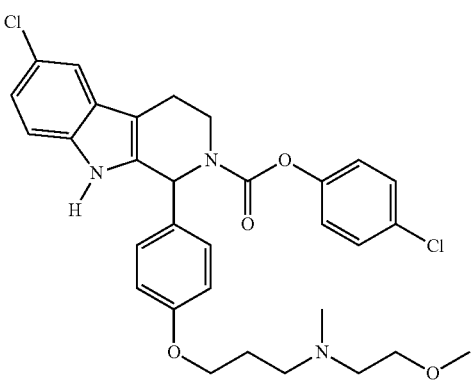
908
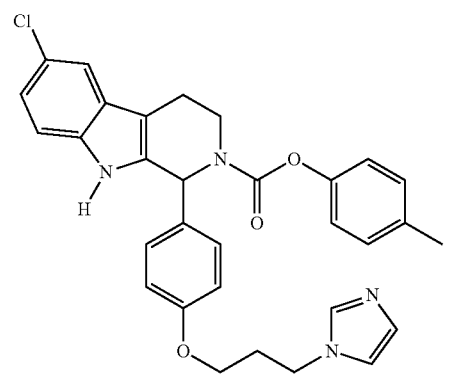 [SMILES: Cc1ccc(OC(=O)N2CCc3c([nH]c4ccc(Cl)cc34)C2c2ccc(OCCCn3ccnc3)cc2)cc1]
900
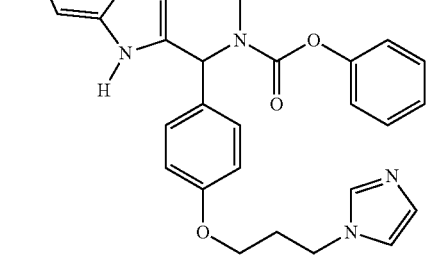
911
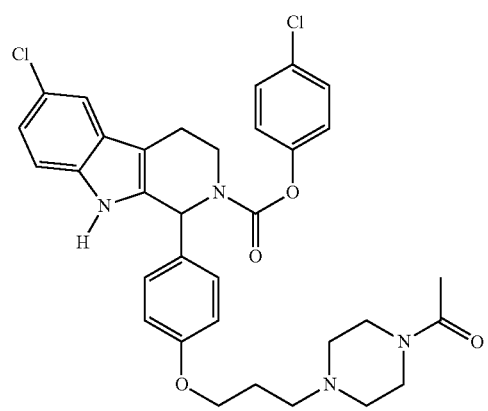 [SMILES: CC(=O)N1CCN(CCCOc2ccc(C3c4[nH]c5ccc(Cl)cc5c4CCN3C(=O)Oc3ccc(Cl)cc3)cc2)CC1]
903
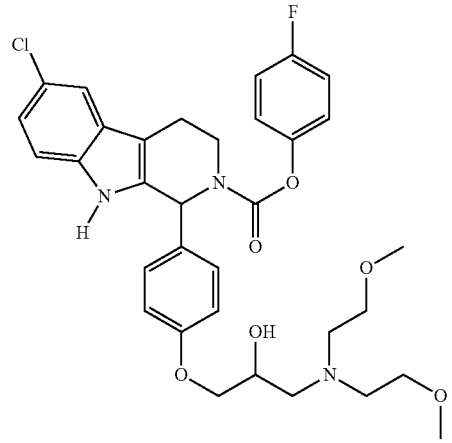
913
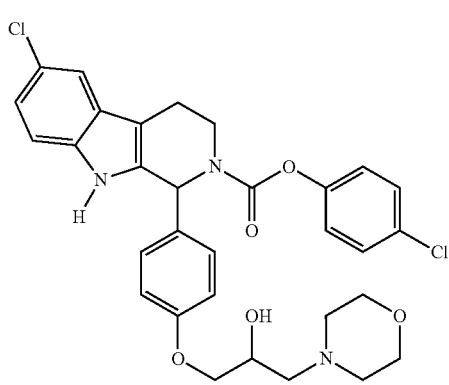 [SMILES: O=C(Oc1ccc(Cl)cc1)N1CCc2c([nH]c3ccc(Cl)cc23)C1c1ccc(OCC(O)CN2CCOCC2)cc1]
904
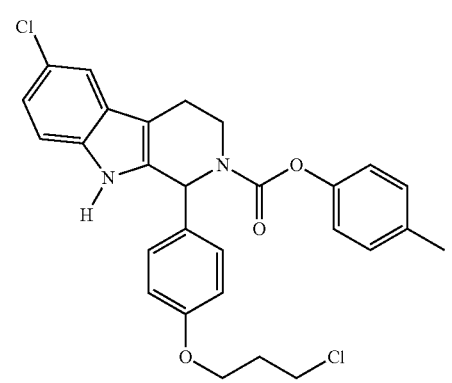 [SMILES: Cc1ccc(OC(=O)N2CCc3c([nH]c4ccc(Cl)cc34)C2c2ccc(OCCCCl)cc2)cc1]
915

TABLE 1-continued
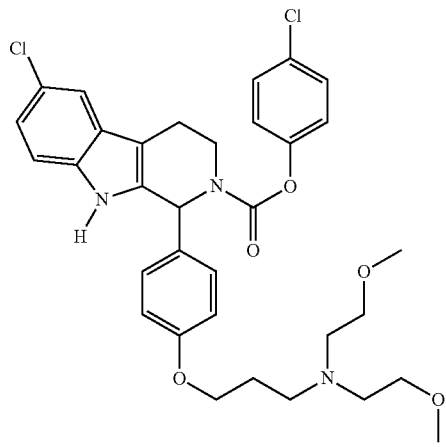 [SMILES: COCCN(CCCOc1ccc(C2c3[nH]c4ccc(Cl)cc4c3CCN2C(=O)Oc2ccc(Cl)cc2)cc1)CCOC]
916
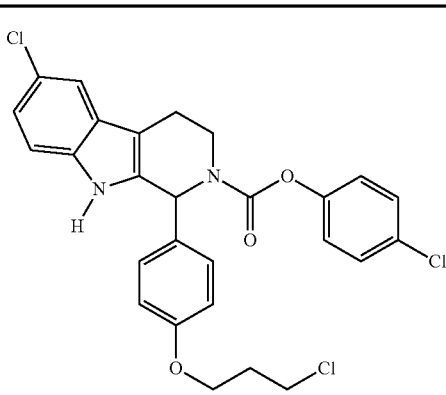
921
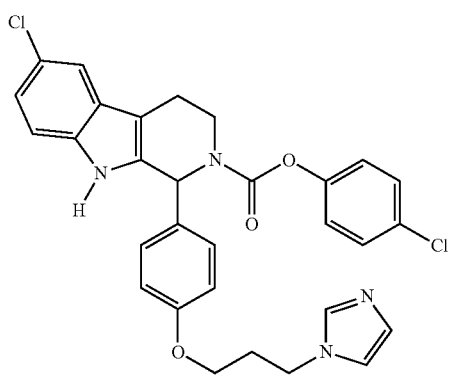 [SMILES: O=C(Oc1ccc(Cl)cc1)N1CCc2c([nH]c3ccc(Cl)cc23)C1c1ccc(OCCCn2ccnc2)cc1]
917
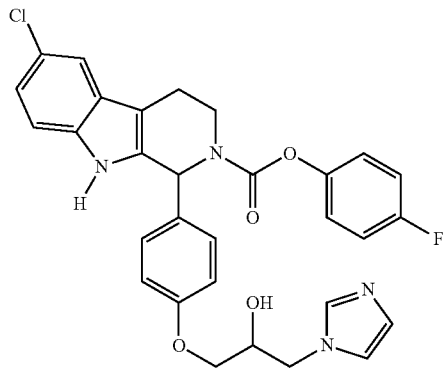
922
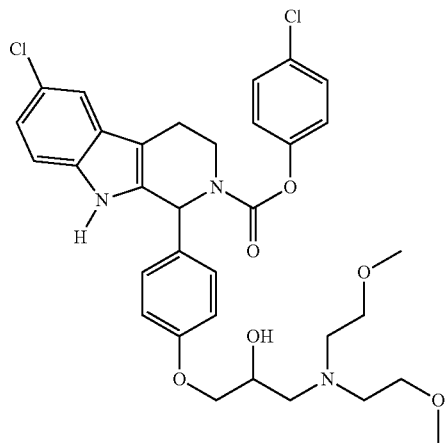 [SMILES: COCCN(CCOC)CC(O)COc1ccc(C2c3[nH]c4ccc(Cl)cc4c3CCN2C(=O)Oc2ccc(Cl)cc2)cc1]
918
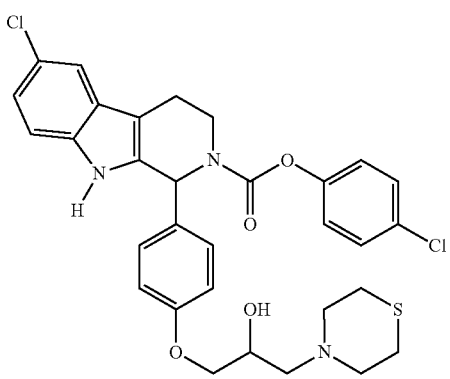
923
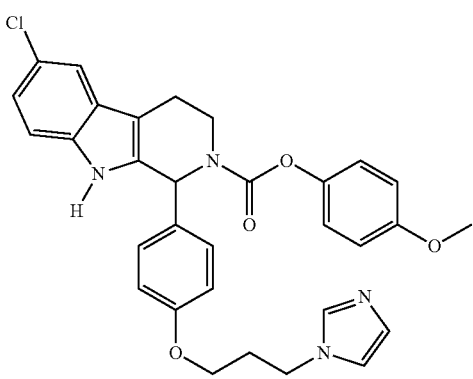 [SMILES: COc1ccc(OC(=O)N2CCc3c([nH]c4ccc(Cl)cc34)C2c2ccc(OCCCn3ccnc3)cc2)cc1]
920
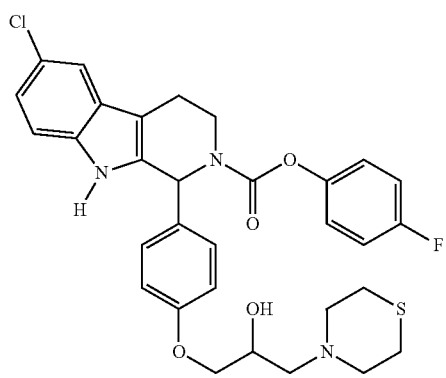
925

TABLE 1-continued
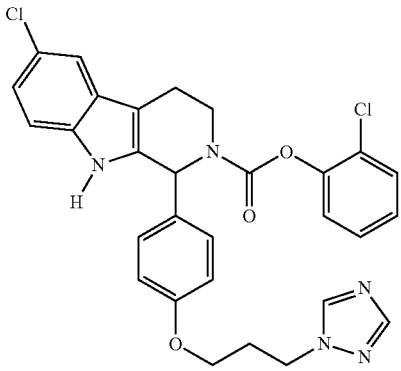 [SMILES: O=C(Oc1ccccc1Cl)N1CCc2c([nH]c3ccc(Cl)cc23)C1c1ccc(OCCCn2cncn2)cc1]
926
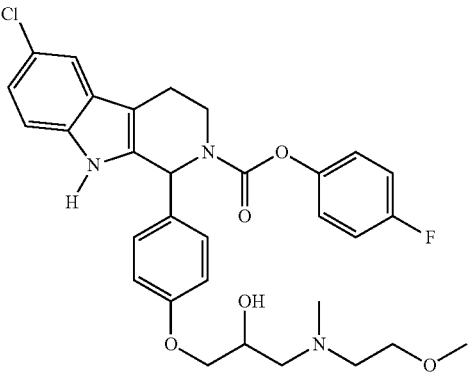
936
932
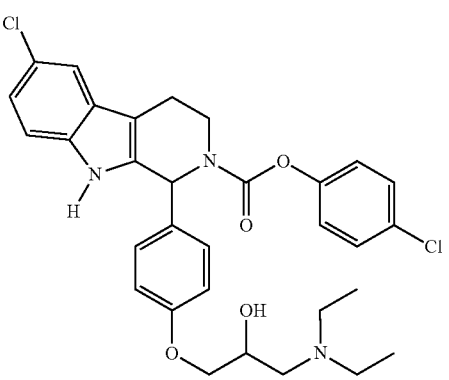 [SMILES: CCN(CC)CC(O)COc1ccc(C2c3[nH]c4ccc(Cl)cc4c3CCN2C(=O)Oc2ccc(Cl)cc2)cc1]
938
933
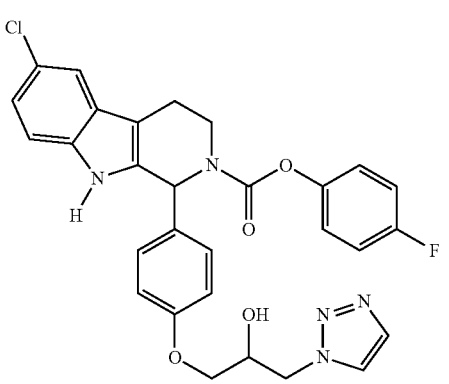 [SMILES: O=C(Oc1ccc(F)cc1)N1CCc2c([nH]c3ccc(Cl)cc23)C1c1ccc(OCC(O)Cn2ccnn2)cc1]
941
934
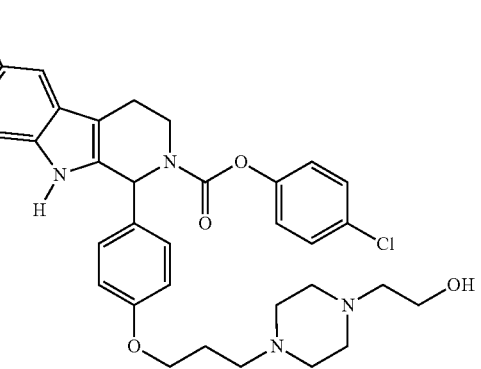
942

TABLE 1-continued
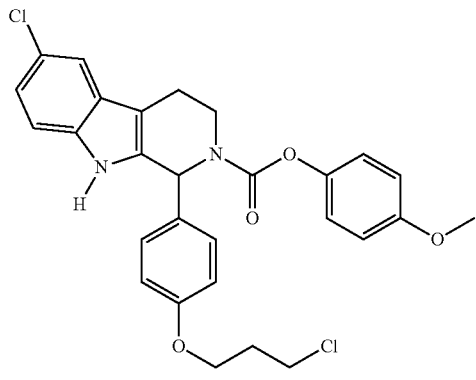 [SMILES: COc1ccc(OC(=O)N2CCc3c([nH]c4ccc(Cl)cc34)C2c2ccc(OCCCCl)cc2)cc1] 944
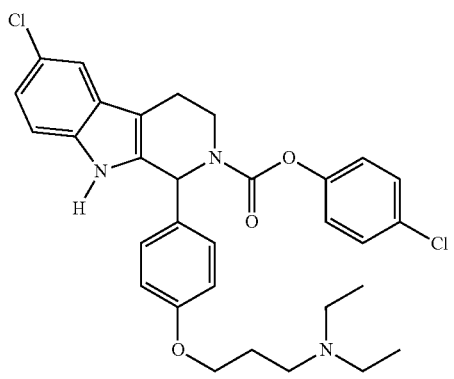 [SMILES: CCN(CC)CCCOc1ccc(C2c3[nH]c4ccc(Cl)cc4c3CCN2C(=O)Oc2ccc(Cl)cc2)cc1] 946
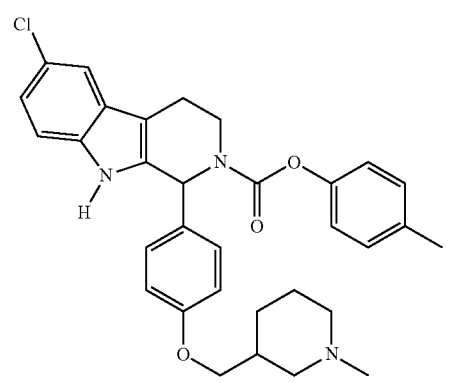 [SMILES: Cc1ccc(OC(=O)N2CCc3c([nH]c4ccc(Cl)cc34)C2c2ccc(OCC3CCCN(C)C3)cc2)cc1] 951
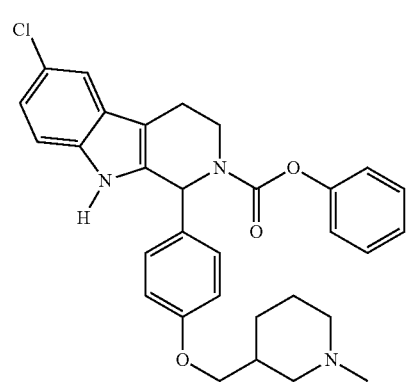 [SMILES: CN1CCCC(COc2ccc(C3c4[nH]c5ccc(Cl)cc5c4CCN3C(=O)Oc3ccccc3)cc2)C1] 952
TABLE 1-continued
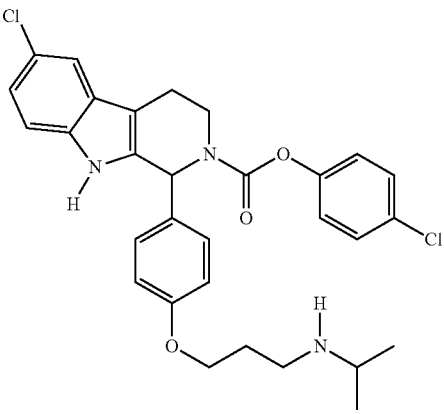 [SMILES: CC(C)NCCCOc1ccc(C2c3[nH]c4ccc(Cl)cc4c3CCN2C(=O)Oc2ccc(Cl)cc2)cc1] 953
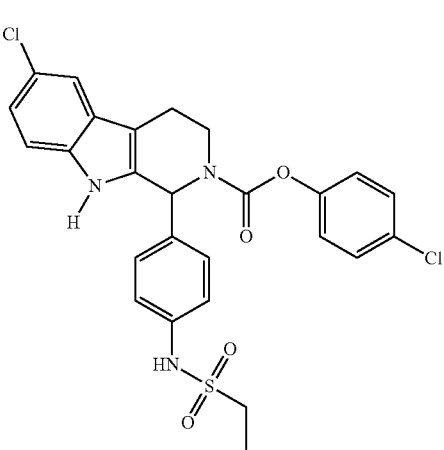 [SMILES: CCS(=O)(=O)Nc1ccc(C2c3[nH]c4ccc(Cl)cc4c3CCN2C(=O)Oc2ccc(Cl)cc2)cc1] 958
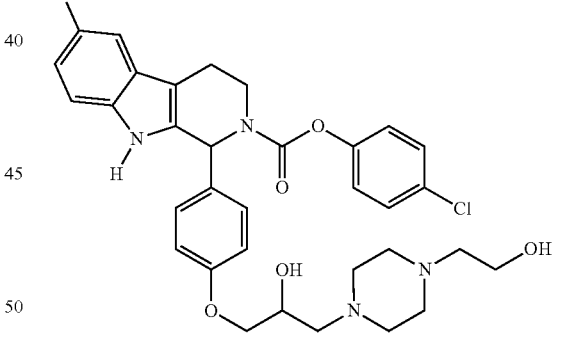 960
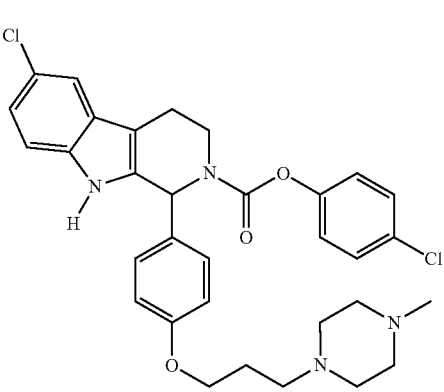 [SMILES: CN1CCN(CCCOc2ccc(C3c4[nH]c5ccc(Cl)cc5c4CCN3C(=O)Oc3ccc(Cl)cc3)cc2)CC1] 961

TABLE 1-continued
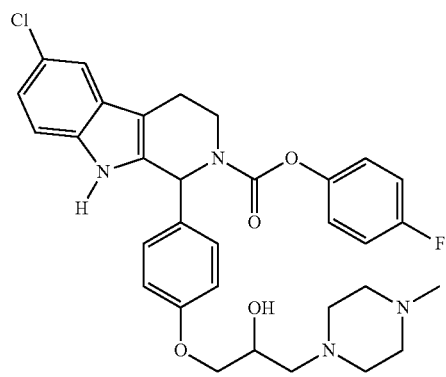 [SMILES: CN1CCN(CC(O)COc2ccc(C3c4[nH]c5ccc(Cl)cc5c4CCN3C(=O)Oc3ccc(F)cc3)cc2)CC1]
963
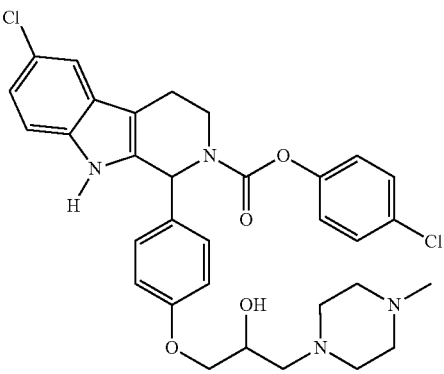
970
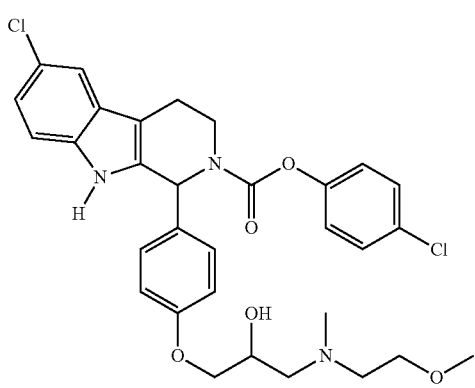 [SMILES: COCCN(C)CC(O)COc1ccc(C2c3[nH]c4ccc(Cl)cc4c3CCN2C(=O)Oc2ccc(Cl)cc2)cc1]
964
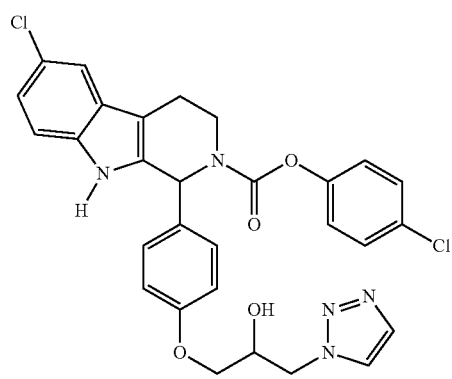
973
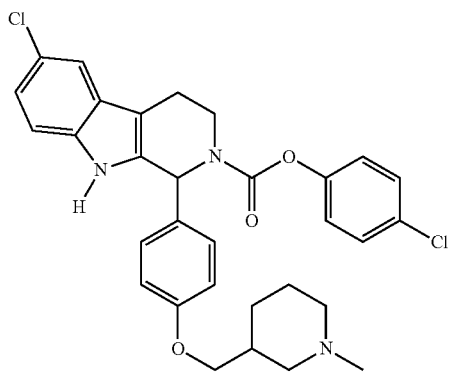 [SMILES: CN1CCCC(COc2ccc(C3c4[nH]c5ccc(Cl)cc5c4CCN3C(=O)Oc3ccc(Cl)cc3)cc2)C1]
966
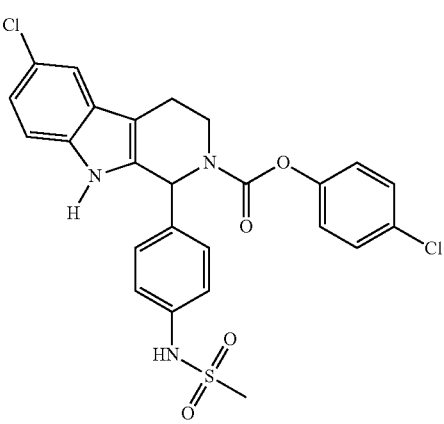
974
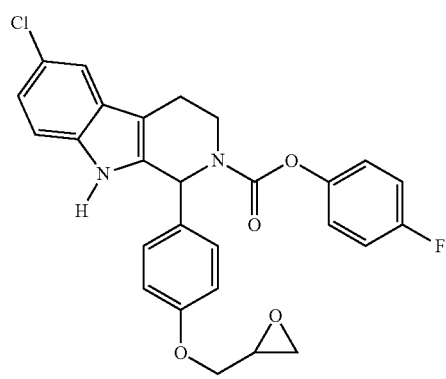 [SMILES: O=C(Oc1ccc(F)cc1)N1CCc2c([nH]c3ccc(Cl)cc23)C1c1ccc(OCC2CO2)cc1]
967
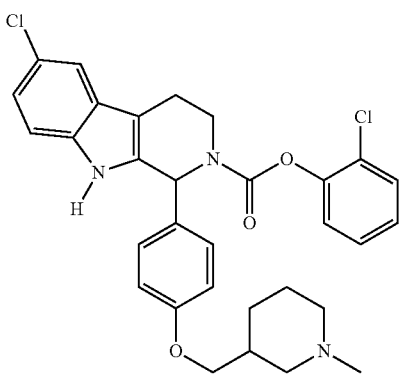 [SMILES: CN1CCCC(COc2ccc(C3c4[nH]c5ccc(Cl)cc5c4CCN3C(=O)Oc3ccccc3Cl)cc2)C1]
976

TABLE 1-continued
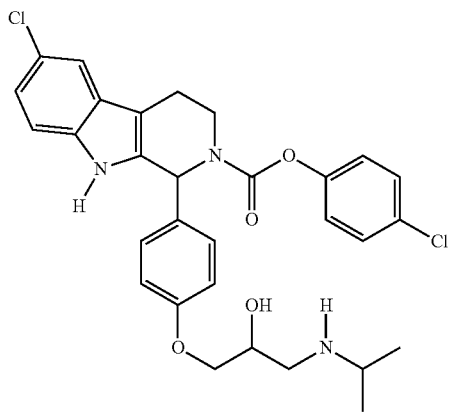 [SMILES: CC(C)NCC(O)COc1ccc(C2c3[nH]c4ccc(Cl)cc4c3CCN2C(=O)Oc2ccc(Cl)cc2)cc1]
977
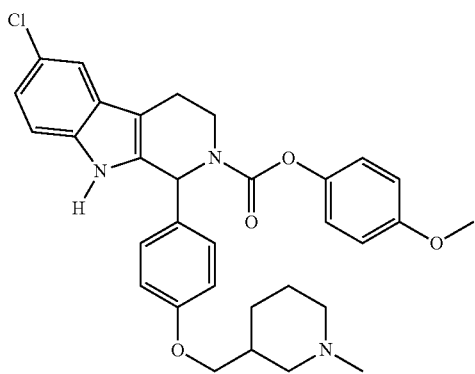 [SMILES: COc1ccc(OC(=O)N2CCc3c([nH]c4ccc(Cl)cc34)C2c2ccc(OCC3CCCN(C)C3)cc2)cc1]
981
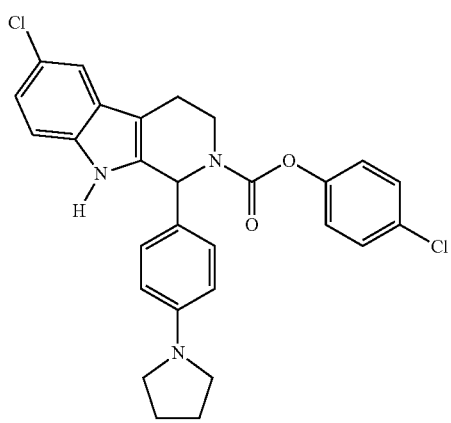 [SMILES: O=C(Oc1ccc(Cl)cc1)N1CCc2c([nH]c3ccc(Cl)cc23)C1c1ccc(N2CCCC2)cc1]
984
TABLE 1-continued
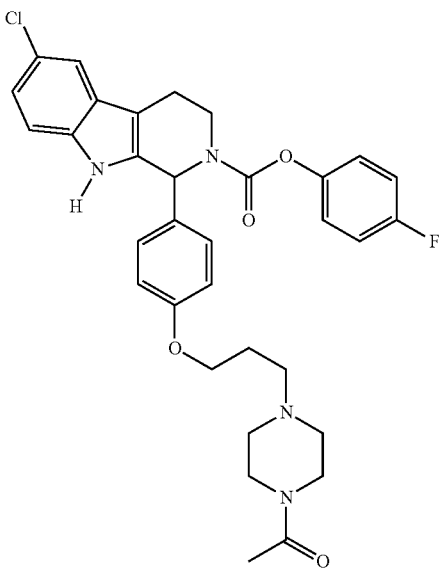 [SMILES: CC(=O)N1CCN(CCCOc2ccc(C3c4[nH]c5ccc(Cl)cc5c4CCN3C(=O)Oc3ccc(F)cc3)cc2)CC1]
988
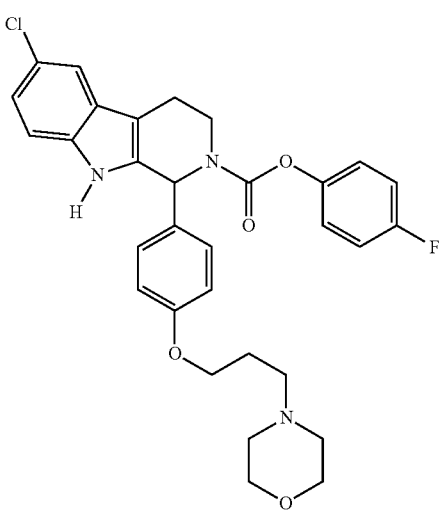 [SMILES: O=C(Oc1ccc(F)cc1)N1CCc2c([nH]c3ccc(Cl)cc23)C1c1ccc(OCCCN2CCOCC2)cc1]
989
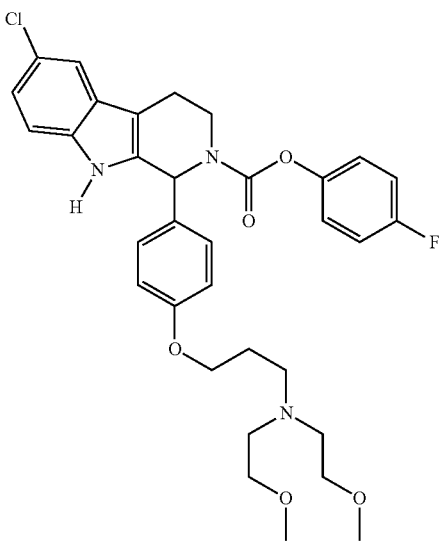 [SMILES: COCCN(CCCOc1ccc(C2c3[nH]c4ccc(Cl)cc4c3CCN2C(=O)Oc2ccc(F)cc2)cc1)CCOC]
990

TABLE 1-continued
991
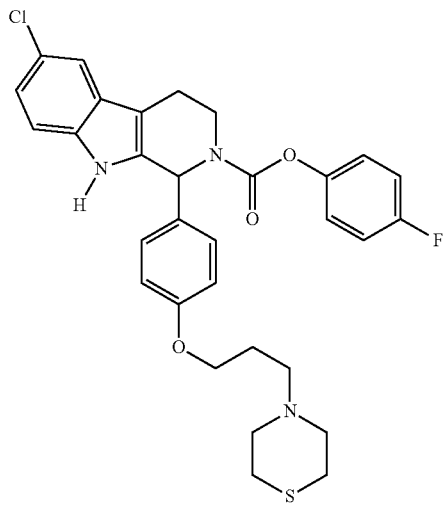 [SMILES: O=C(Oc1ccc(F)cc1)N1CCc2c([nH]c3ccc(Cl)cc23)C1c1ccc(OCCCN2CCSCC2)cc1]
992
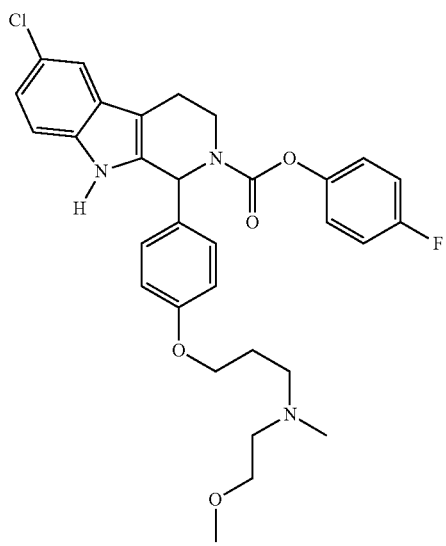 [SMILES: COCCN(C)CCCOc1ccc(C2c3[nH]c4ccc(Cl)cc4c3CCN2C(=O)Oc2ccc(F)cc2)cc1]
993
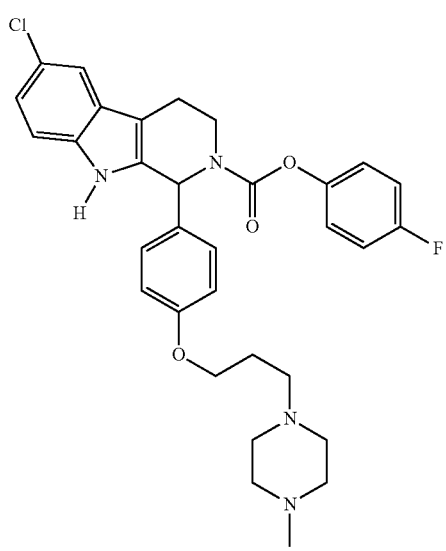 [SMILES: CN1CCN(CCCOc2ccc(C3c4[nH]c5ccc(Cl)cc5c4CCN3C(=O)Oc3ccc(F)cc3)cc2)CC1]
994
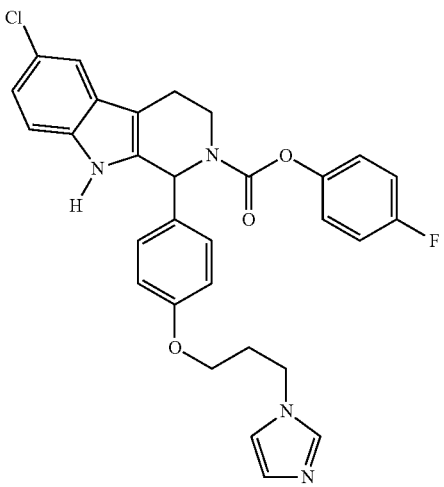 [SMILES: O=C(Oc1ccc(F)cc1)N1CCc2c([nH]c3ccc(Cl)cc23)C1c1ccc(OCCCn2ccnc2)cc1]
995
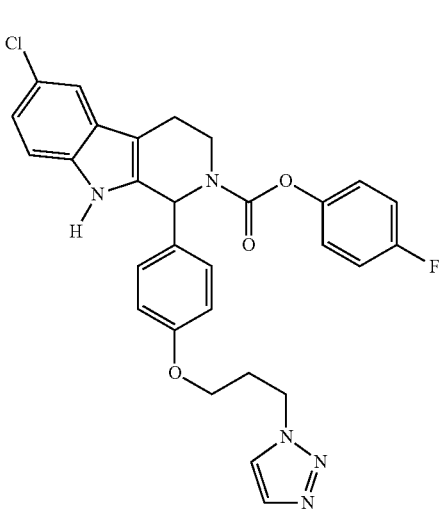 [SMILES: O=C(Oc1ccc(F)cc1)N1CCc2c([nH]c3ccc(Cl)cc23)C1c1ccc(OCCCn2ccnn2)cc1]
996

TABLE 1-continued
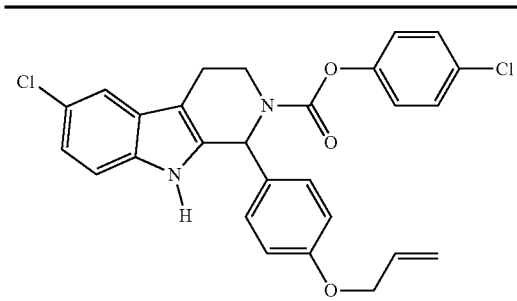
999
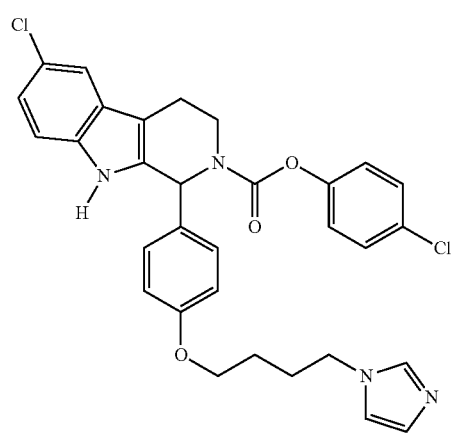 [SMILES: O=C(Oc1ccc(Cl)cc1)N1CCc2c([nH]c3ccc(Cl)cc23)C1c1ccc(OCCCCn2ccnc2)cc1]
1001
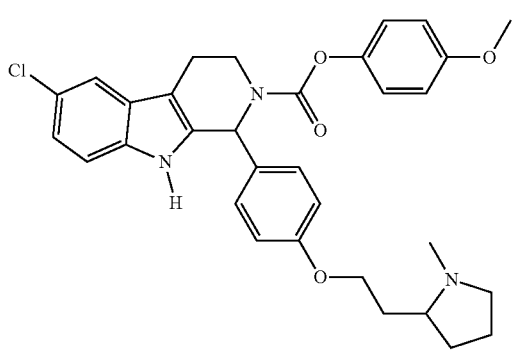 [SMILES: COc1ccc(OC(=O)N2CCc3c([nH]c4ccc(Cl)cc34)C2c2ccc(OCCC3CCCN3C)cc2)cc1]
1005
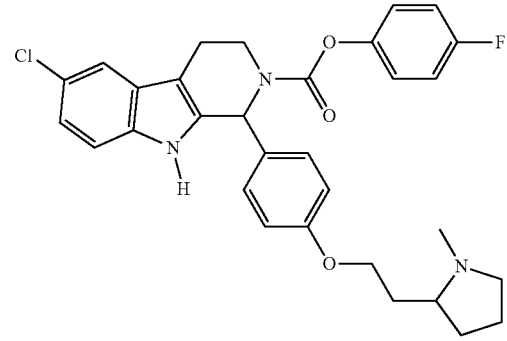 [SMILES: CN1CCCC1CCOc1ccc(C2c3[nH]c4ccc(Cl)cc4c3CCN2C(=O)Oc2ccc(F)cc2)cc1]
1008
TABLE 1-continued
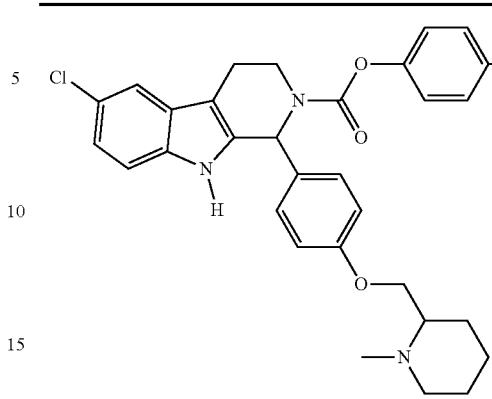
1009
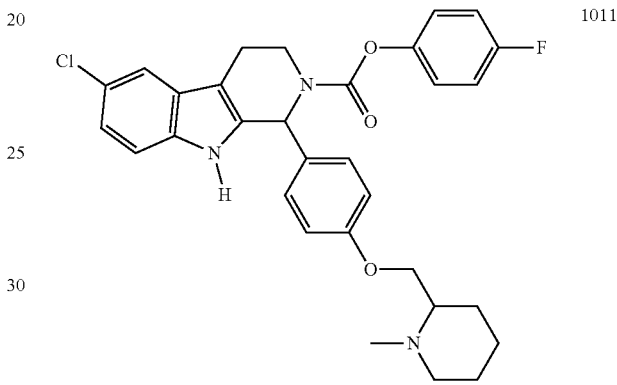
1011
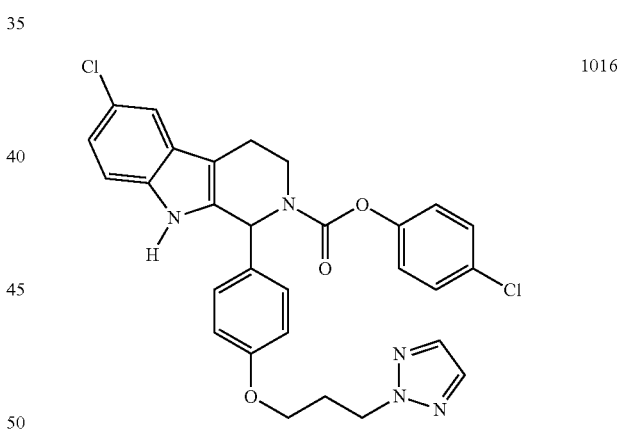
1016
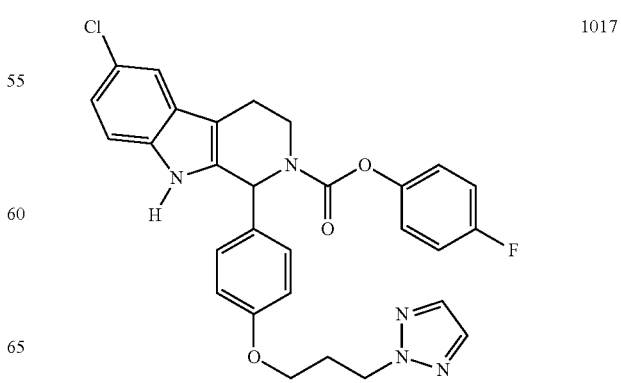
1017

TABLE 1-continued
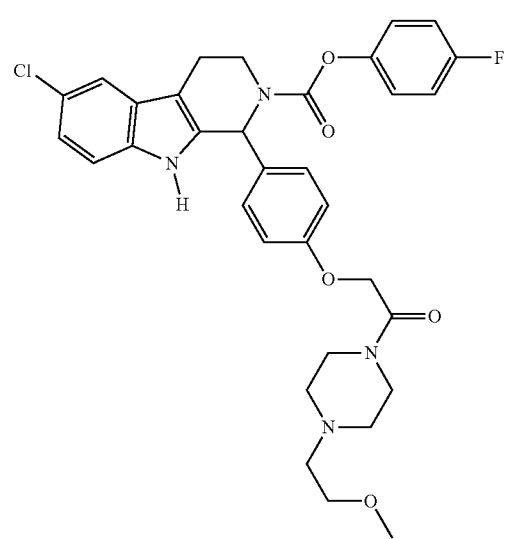 [SMILES: COCCN1CCN(C(=O)COc2ccc(C3c4[nH]c5ccc(Cl)cc5c4CCN3C(=O)Oc3ccc(F)cc3)cc2)CC1]
1021
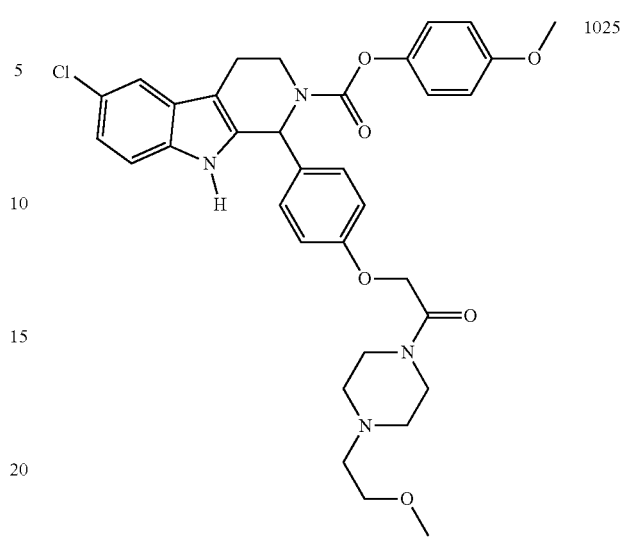
1025
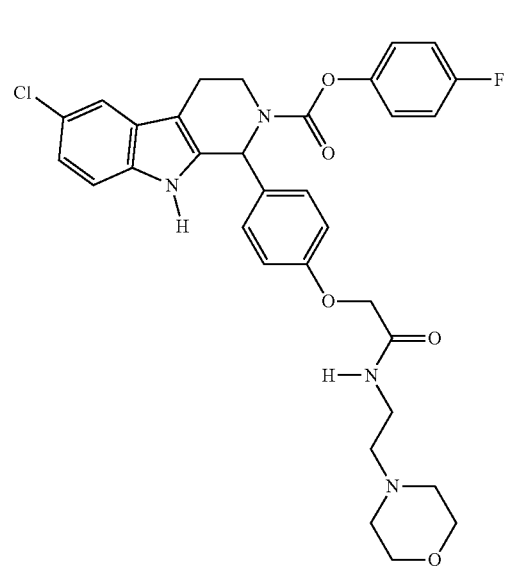 [SMILES: O=C(COc1ccc(C2c3[nH]c4ccc(Cl)cc4c3CCN2C(=O)Oc2ccc(F)cc2)cc1)NCCN1CCOCC1]
1022
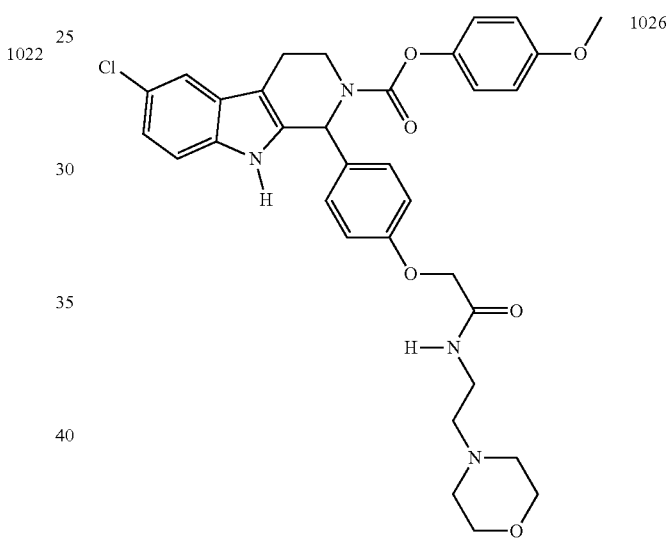
1026
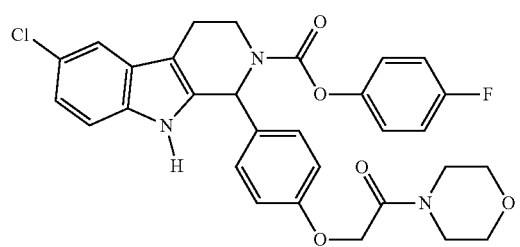 [SMILES: O=C(COc1ccc(C2c3[nH]c4ccc(Cl)cc4c3CCN2C(=O)Oc2ccc(F)cc2)cc1)N1CCOCC1]
1023
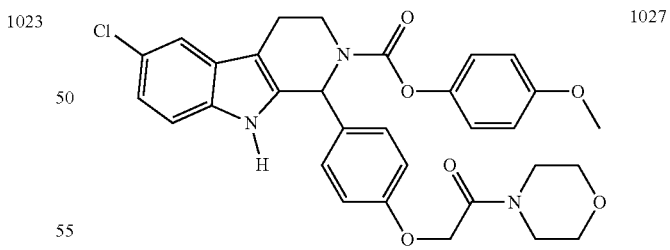
1027
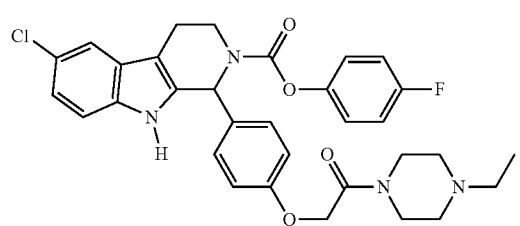 [SMILES: CCN1CCN(C(=O)COc2ccc(C3c4[nH]c5ccc(Cl)cc5c4CCN3C(=O)Oc3ccc(F)cc3)cc2)CC1]
1024
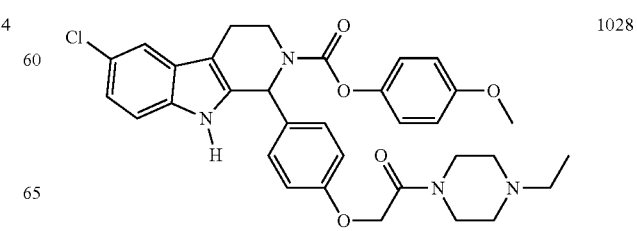
1028

101
TABLE 1-continued
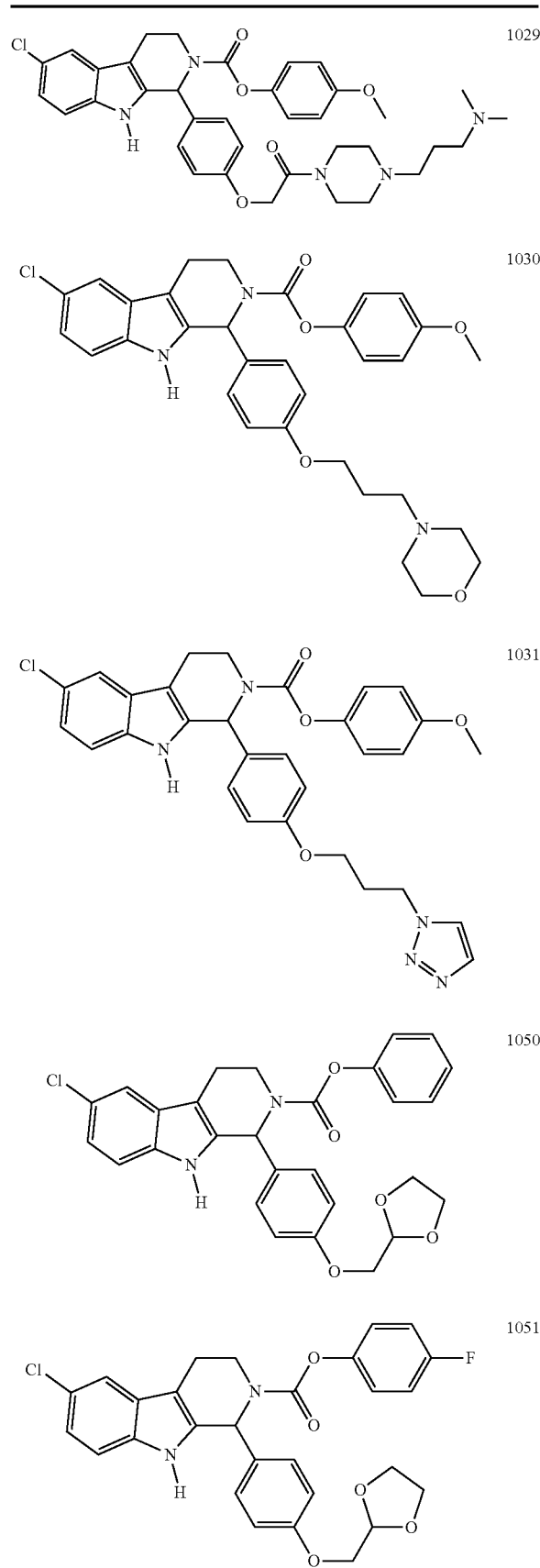
102
TABLE 1-continued
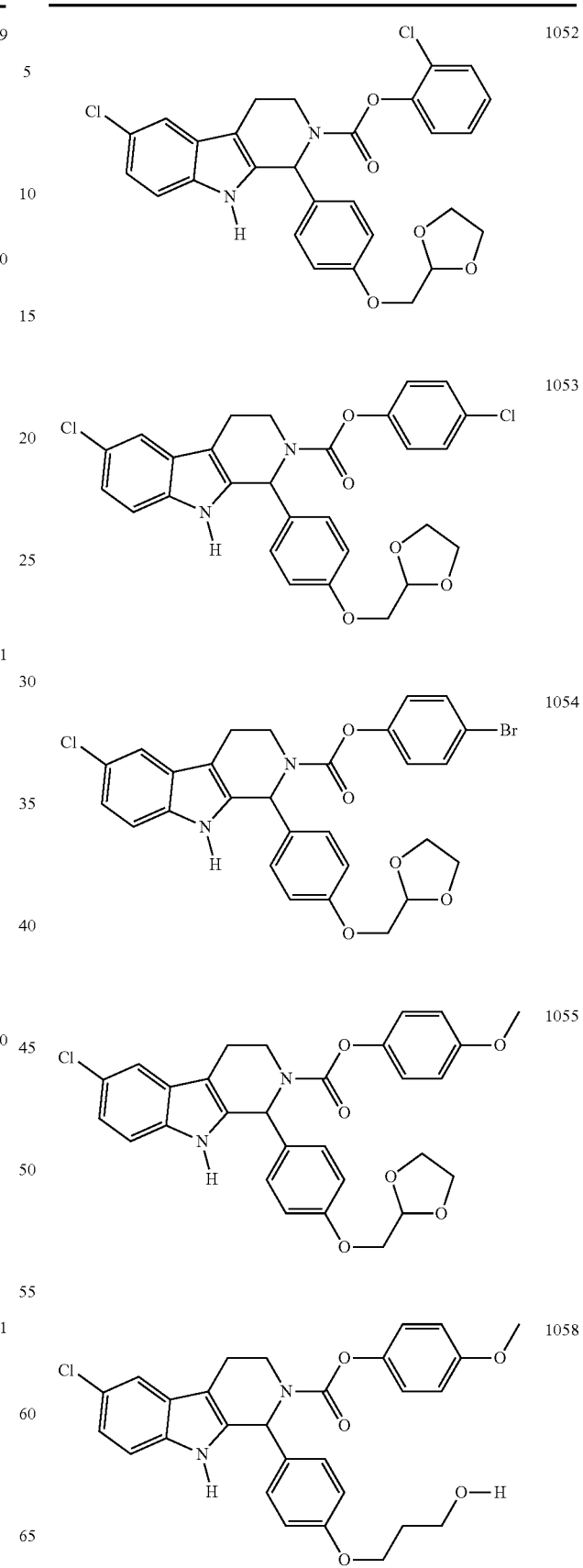

TABLE 1-continued
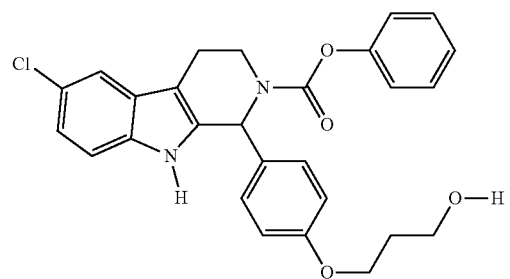 [SMILES: O=C(Oc1ccccc1)N1CCc2c([nH]c3ccc(Cl)cc23)C1c1ccc(OCCCO)cc1]
1062
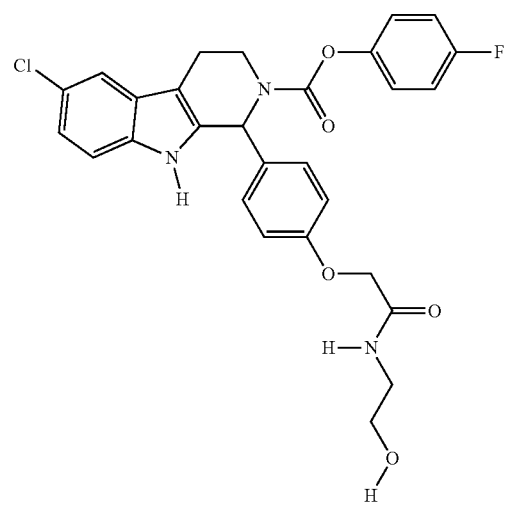 [SMILES: O=C(COc1ccc(C2c3[nH]c4ccc(Cl)cc4c3CCN2C(=O)Oc2ccc(F)cc2)cc1)NCCO]
1063
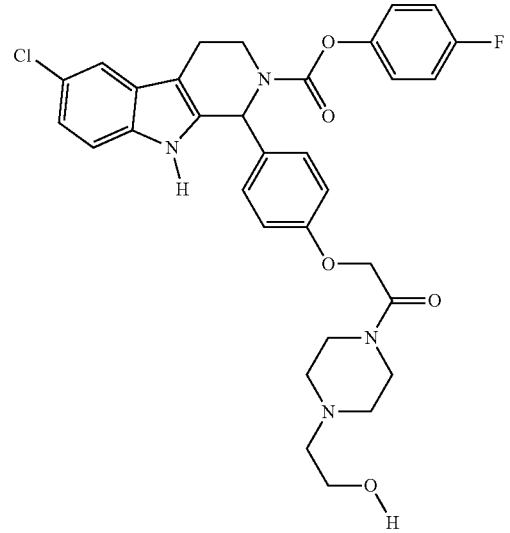 [SMILES: O=C(COc1ccc(C2c3[nH]c4ccc(Cl)cc4c3CCN2C(=O)Oc2ccc(F)cc2)cc1)N1CCN(CCO)CC1]
1064
TABLE 1-continued
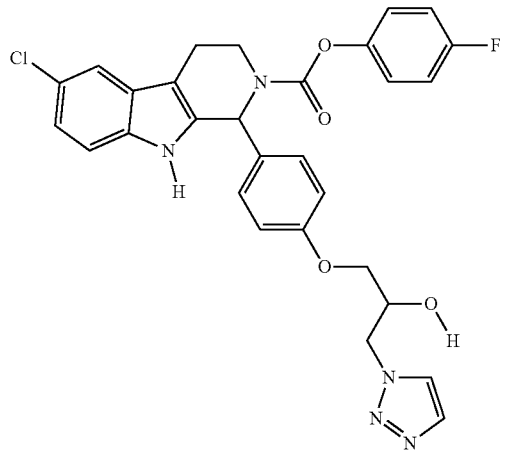 [SMILES: O=C(Oc1ccc(F)cc1)N1CCc2c([nH]c3ccc(Cl)cc23)C1c1ccc(OCC(O)Cn2ccnn2)cc1]
1066
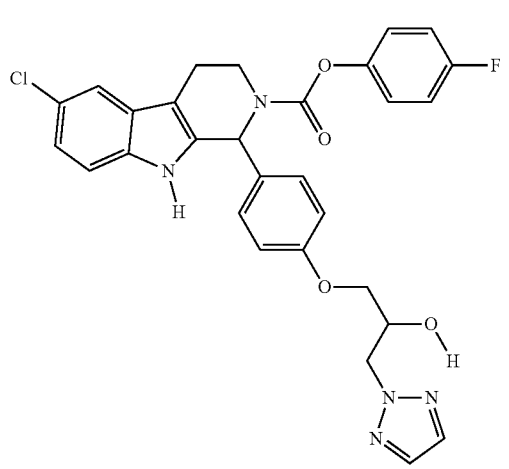 [SMILES: O=C(Oc1ccc(F)cc1)N1CCc2c([nH]c3ccc(Cl)cc23)C1c1ccc(OCC(O)Cn2nccn2)cc1]
1067
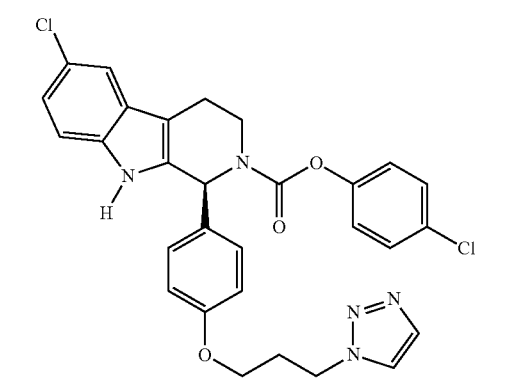 [SMILES: O=C(Oc1ccc(Cl)cc1)N1CCc2c([nH]c3ccc(Cl)cc23)[C@@H]1c1ccc(OCCCn2ccnn2)cc1]
1068
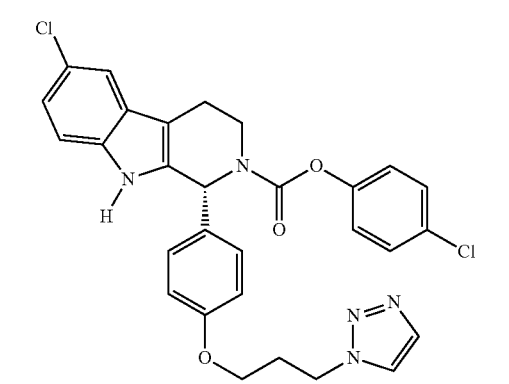 [SMILES: O=C(Oc1ccc(Cl)cc1)N1CCc2c([nH]c3ccc(Cl)cc23)[C@H]1c1ccc(OCCCn2ccnn2)cc1]
1069

TABLE 1-continued
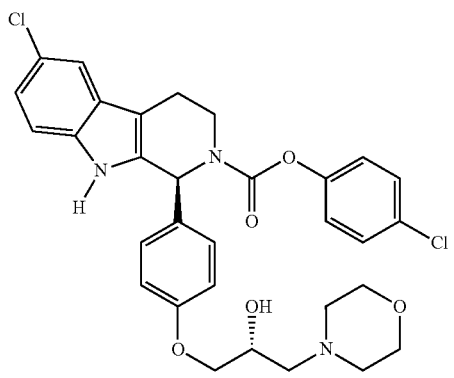 [SMILES: O=C(Oc1ccc(Cl)cc1)N1CCc2c([nH]c3ccc(Cl)cc23)[C@@H]1c1ccc(OC[C@H](O)CN2CCOCC2)cc1] 1070
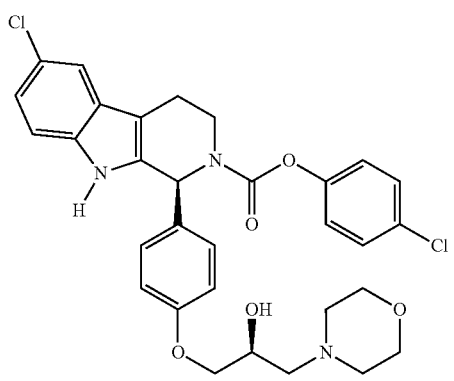 [SMILES: O=C(Oc1ccc(Cl)cc1)N1CCc2c([nH]c3ccc(Cl)cc23)[C@@H]1c1ccc(OC[C@@H](O)CN2CCOCC2)cc1] 1071
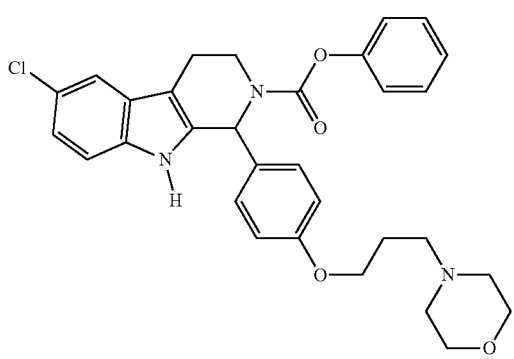 [SMILES: O=C(Oc1ccccc1)N1CCc2c([nH]c3ccc(Cl)cc23)C1c1ccc(OCCCN2CCOCC2)cc1] 1075
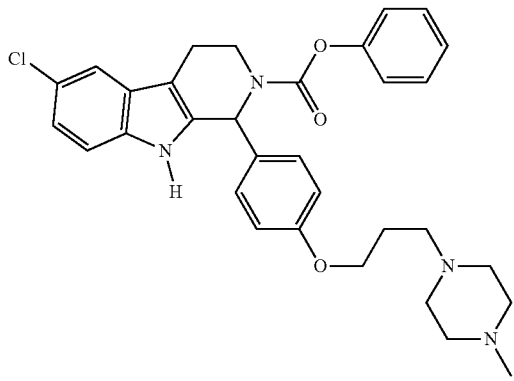 [SMILES: CN1CCN(CCCOc2ccc(C3c4[nH]c5ccc(Cl)cc5c4CCN3C(=O)Oc3ccccc3)cc2)CC1] 1076
TABLE 1-continued
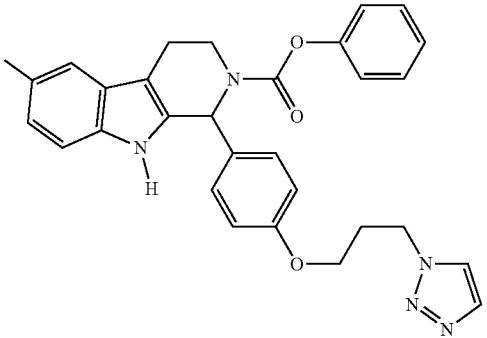 1077
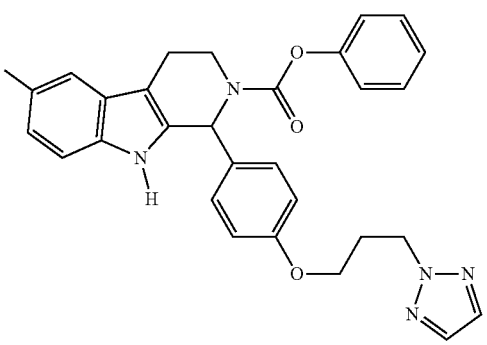 1078
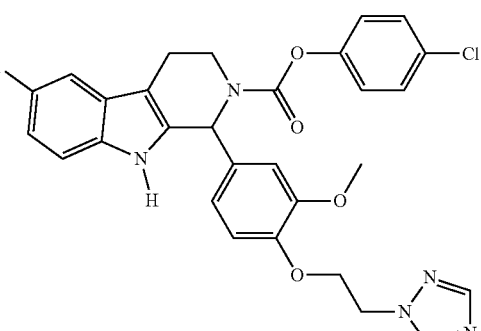 1086
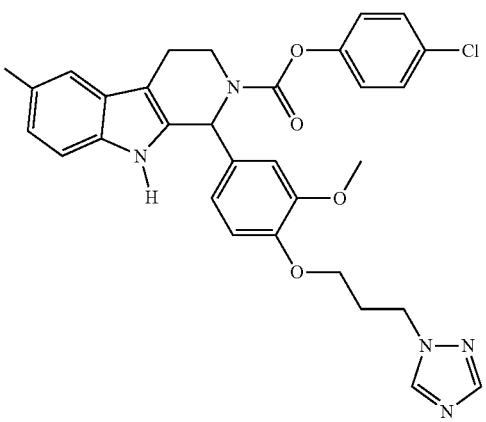 1087

TABLE 1-continued
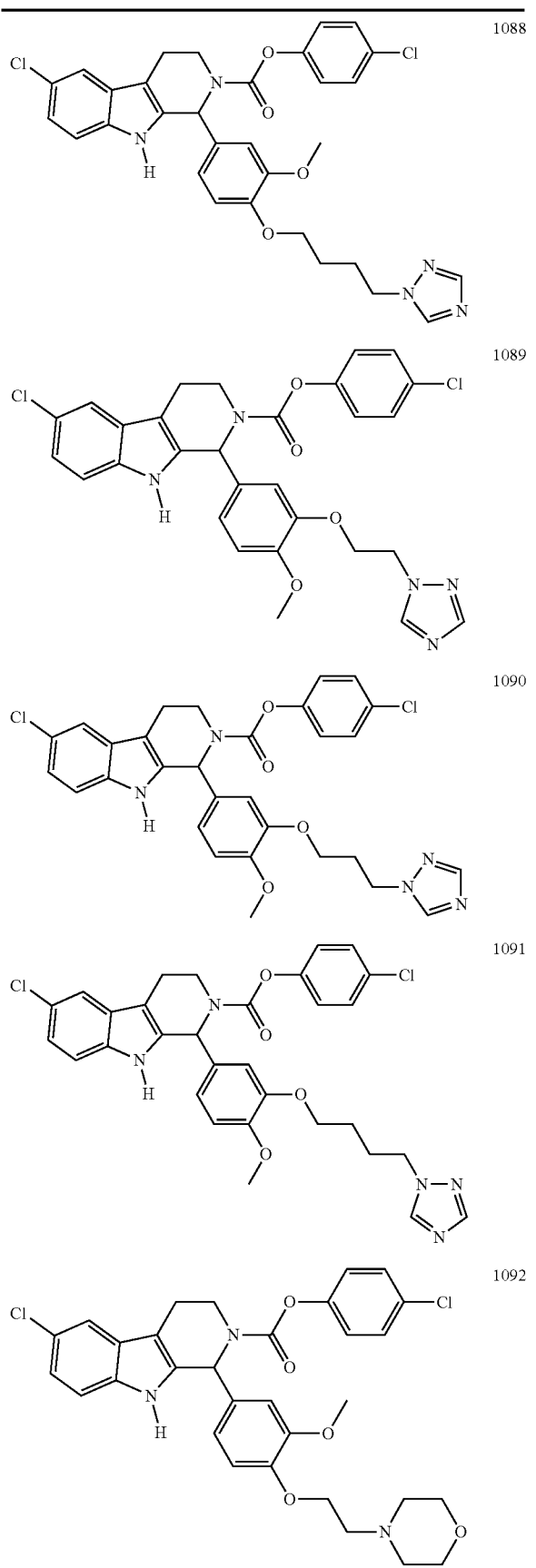
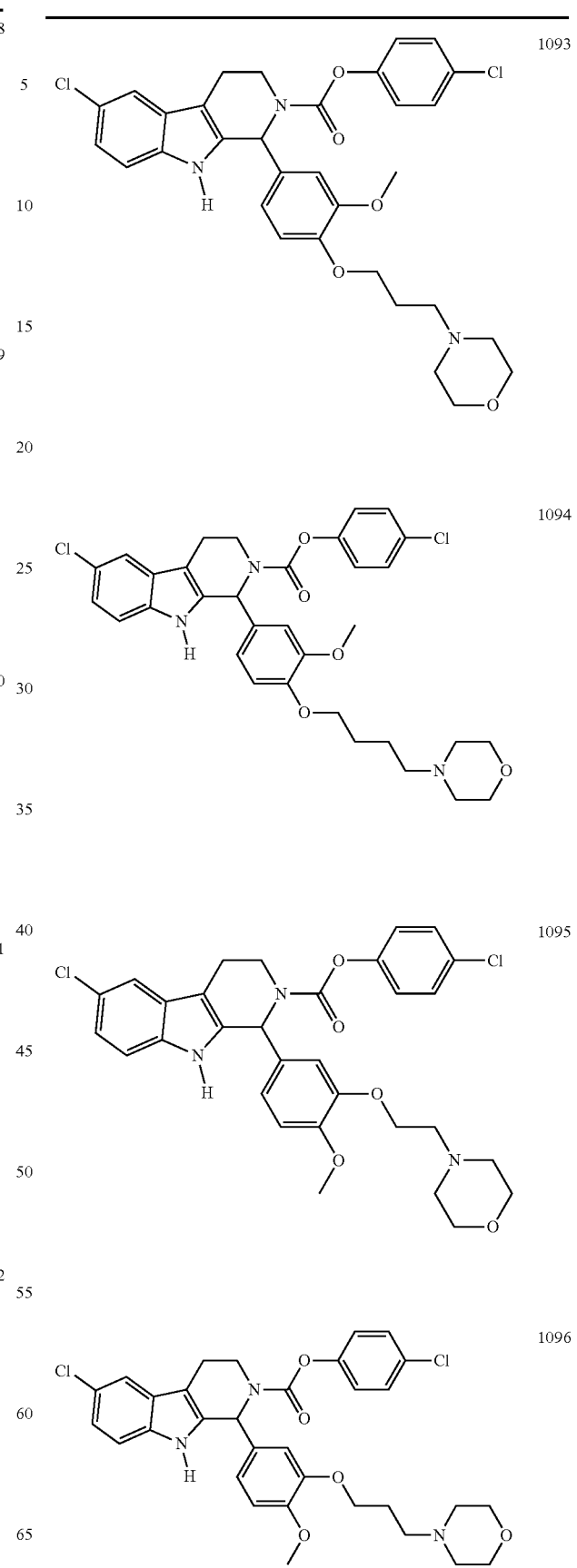

TABLE 1-continued
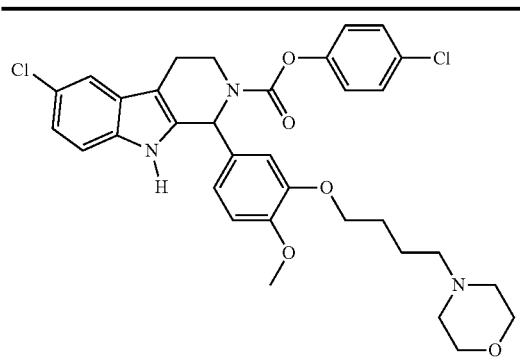
1097
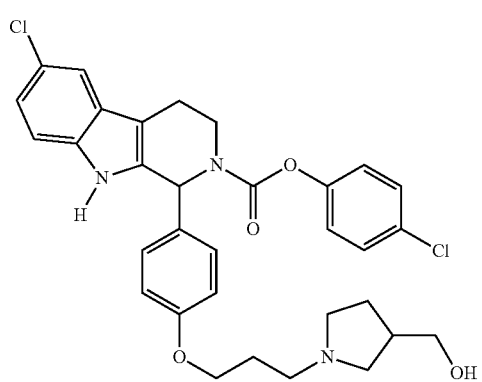 [SMILES: O=C(Oc1ccc(Cl)cc1)N1CCc2c([nH]c3ccc(Cl)cc23)C1c1ccc(OCCCN2CCC(CO)C2)cc1]
1098
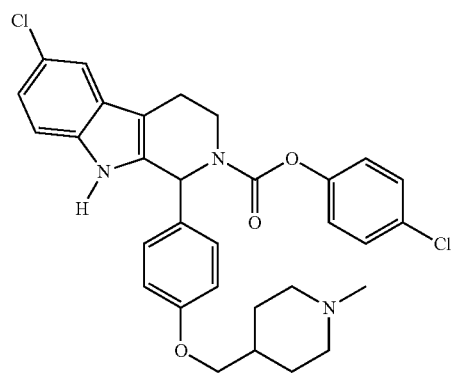 [SMILES: CN1CCC(COc2ccc(C3c4[nH]c5ccc(Cl)cc5c4CCN3C(=O)Oc3ccc(Cl)cc3)cc2)CC1]
1099
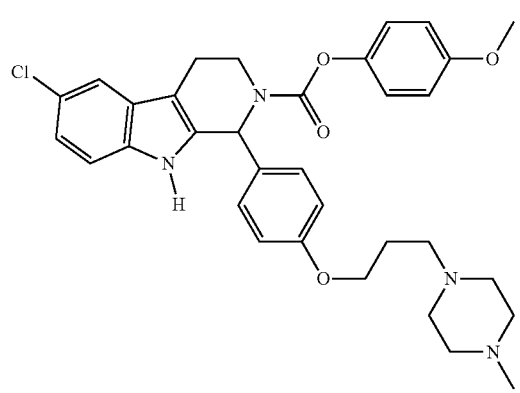 [SMILES: COc1ccc(OC(=O)N2CCc3c([nH]c4ccc(Cl)cc34)C2c2ccc(OCCCN3CCN(C)CC3)cc2)cc1]
1108
TABLE 1-continued
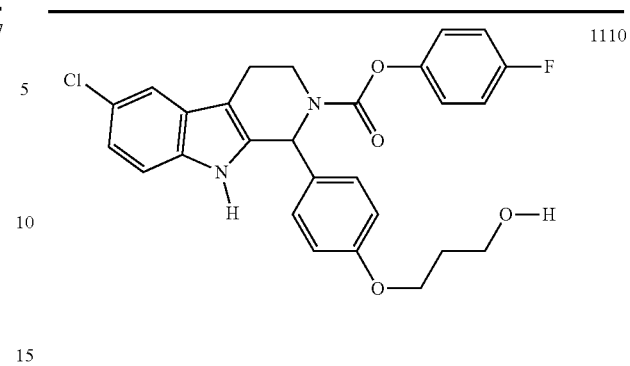
1110
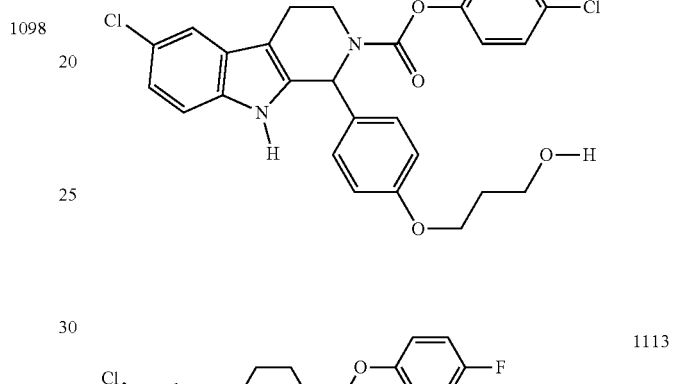
1111
1113
1115
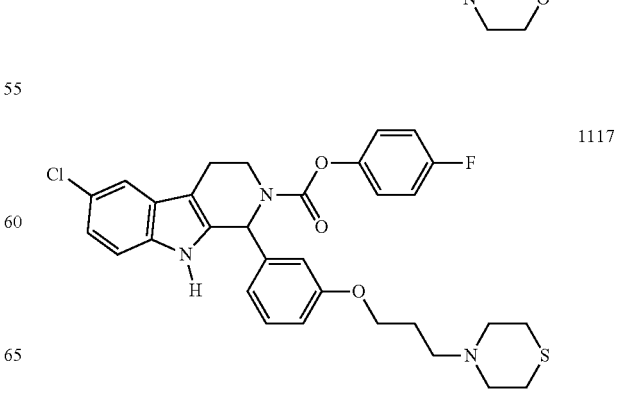
1117

TABLE 1-continued
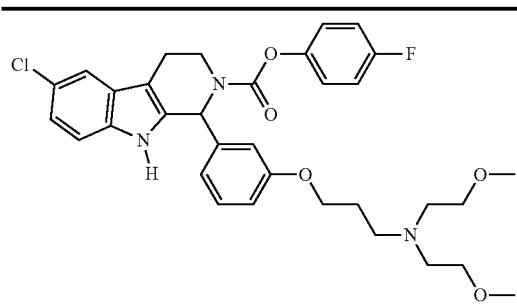
1119
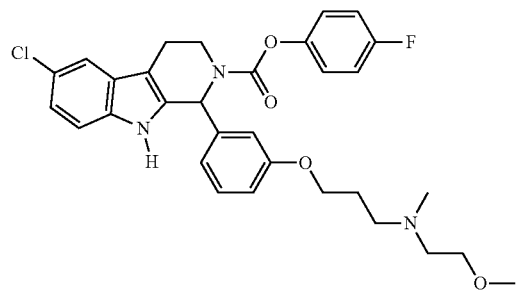 [SMILES: COCCN(C)CCCOc1cccc(C2c3[nH]c4ccc(Cl)cc4c3CCN2C(=O)Oc2ccc(F)cc2)c1]
1121
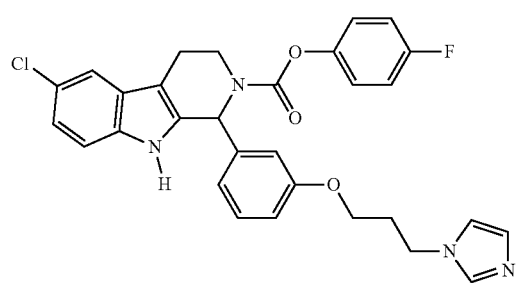 [SMILES: O=C(Oc1ccc(F)cc1)N1CCc2c([nH]c3ccc(Cl)cc23)C1c1cccc(OCCCn2ccnc2)c1]
1123
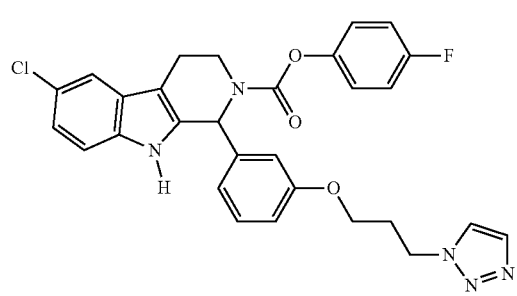 [SMILES: O=C(Oc1ccc(F)cc1)N1CCc2c([nH]c3ccc(Cl)cc23)C1c1cccc(OCCCn2ccnn2)c1]
1125
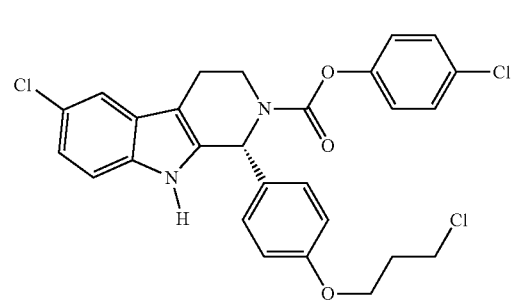
1126
TABLE 1-continued
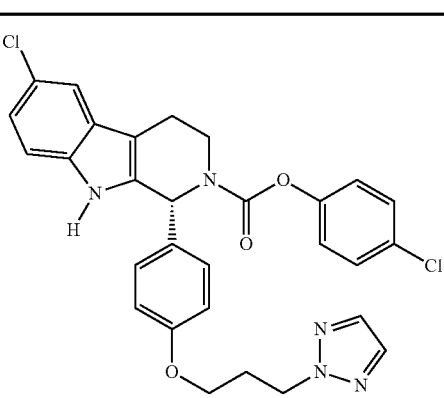
1127
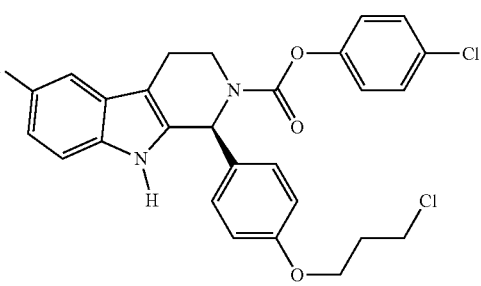
1128
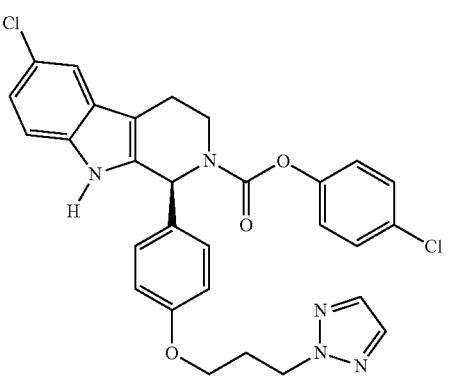 [SMILES: O=C(Oc1ccc(Cl)cc1)N1CCc2c([nH]c3ccc(Cl)cc23)[C@@H]1c1ccc(OCCCn2nccn2)cc1]
1129
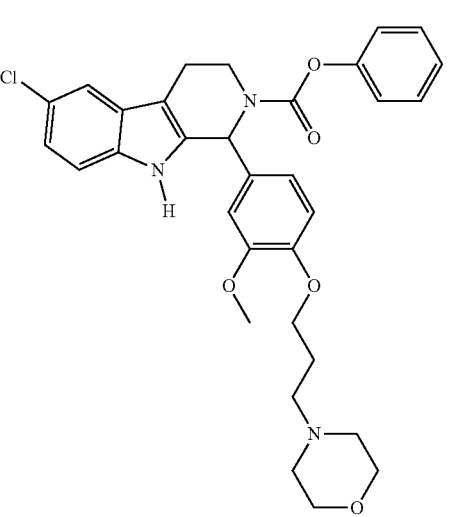 [SMILES: COc1cc(C2c3[nH]c4ccc(Cl)cc4c3CCN2C(=O)Oc2ccccc2)ccc1OCCCN1CCOCC1]
1130

TABLE 1-continued
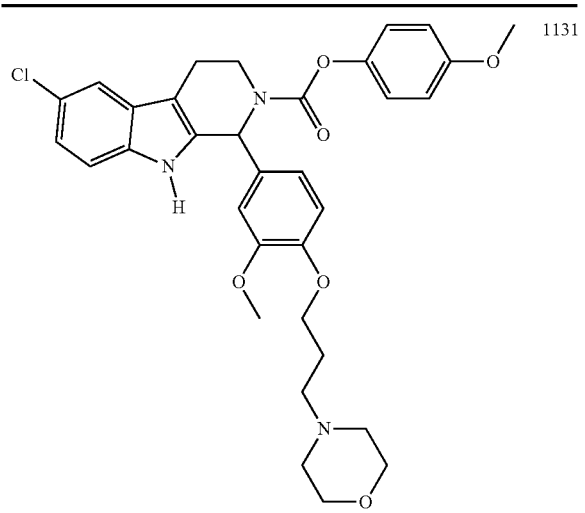
1131
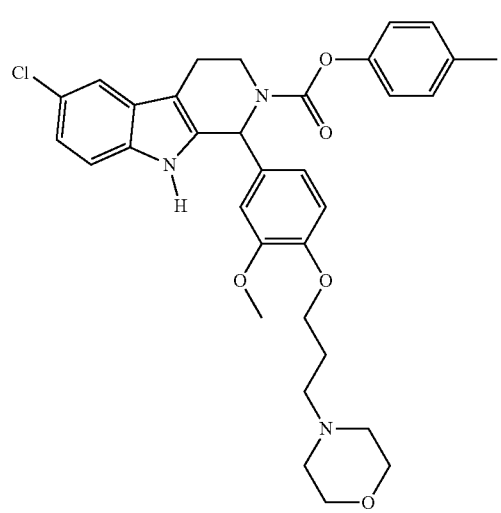 [SMILES: COc1cc(C2c3[nH]c4ccc(Cl)cc4c3CCN2C(=O)Oc2ccc(C)cc2)ccc1OCCCN1CCOCC1]
1132
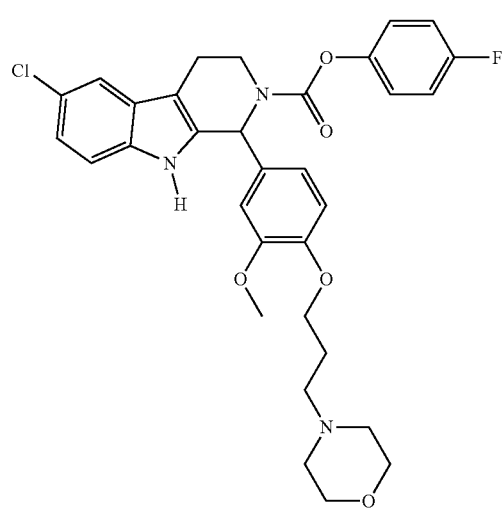 [SMILES: COc1cc(C2c3[nH]c4ccc(Cl)cc4c3CCN2C(=O)Oc2ccc(F)cc2)ccc1OCCCN1CCOCC1]
1133
TABLE 1-continued
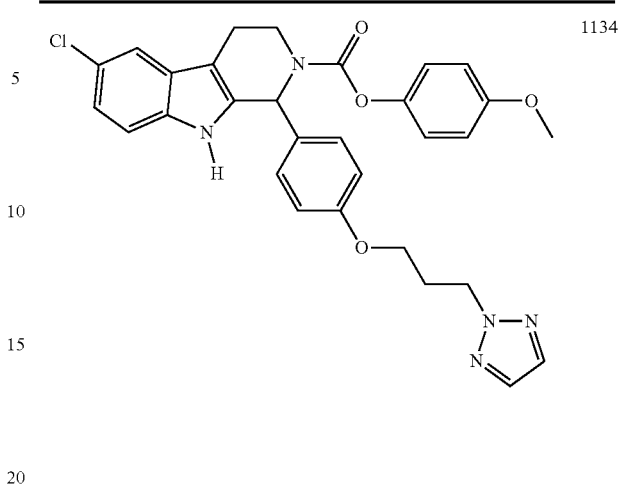
1134
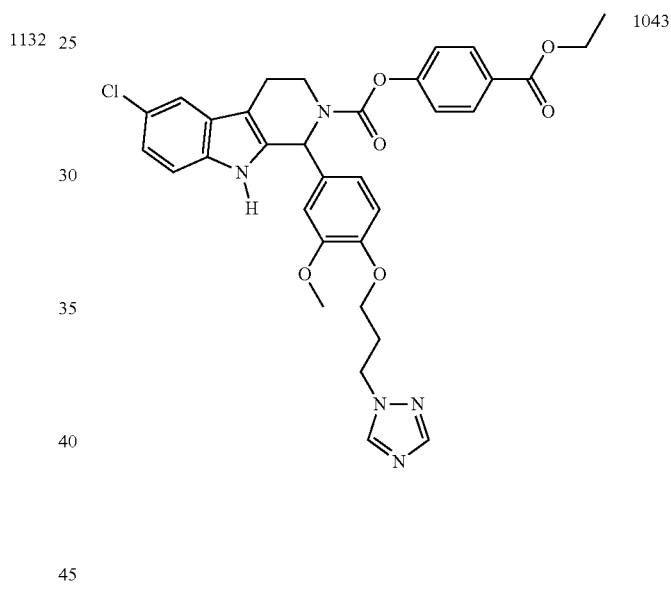
1043
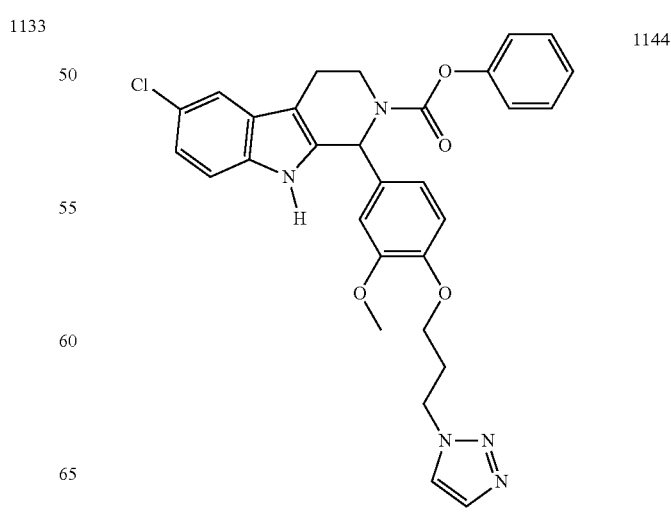
1144

TABLE 1-continued
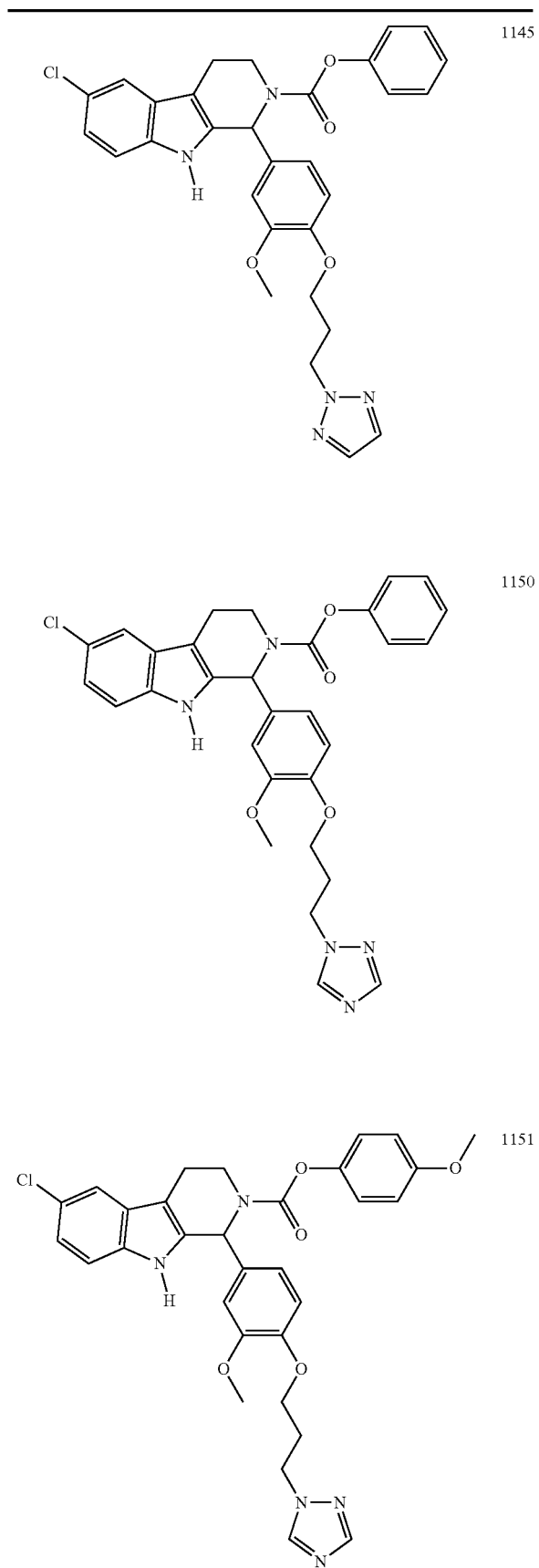
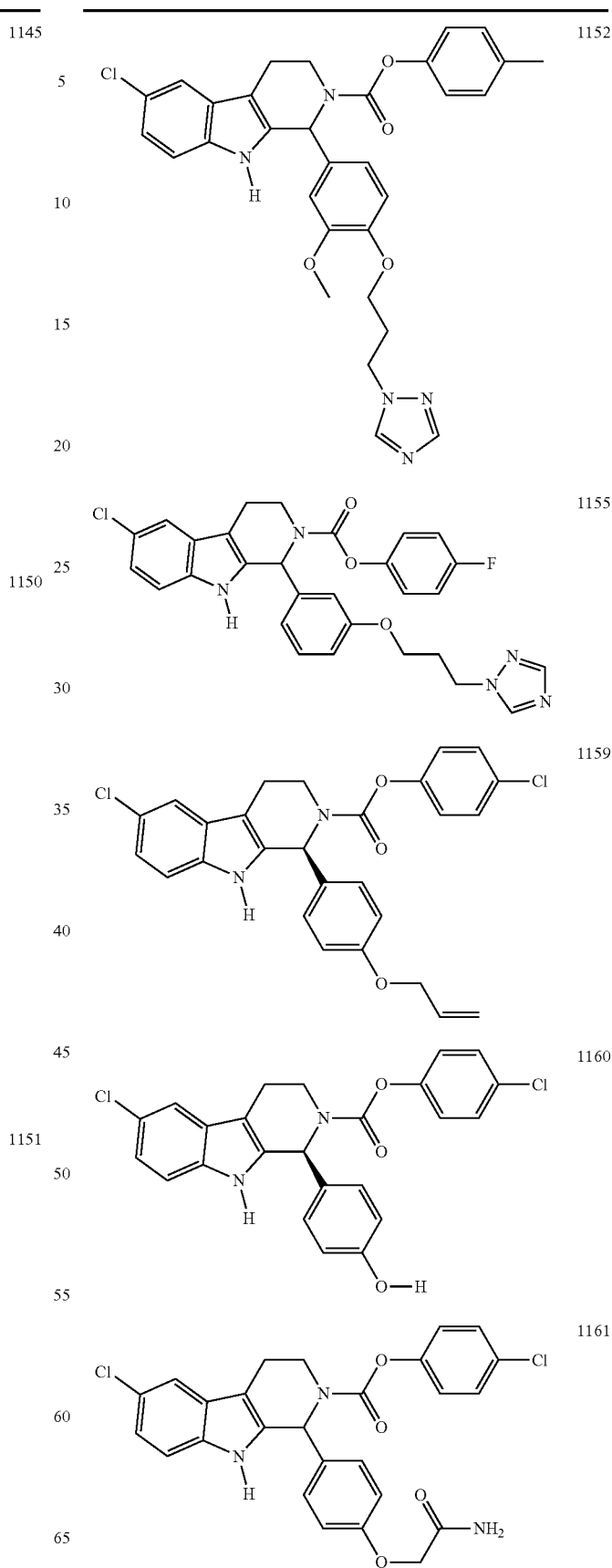

TABLE 1-continued
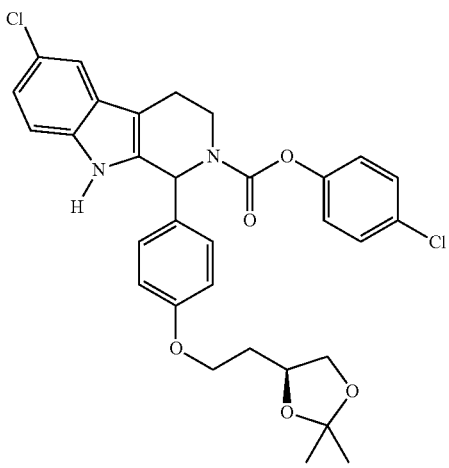 [SMILES: CC1(C)OC[C@H](CCOc2ccc(C3c4[nH]c5ccc(Cl)cc5c4CCN3C(=O)Oc3ccc(Cl)cc3)cc2)O1]
1162
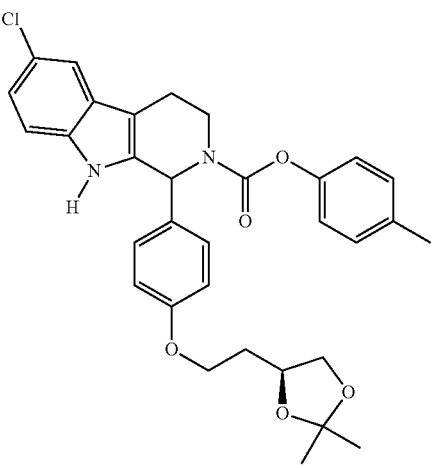
1170
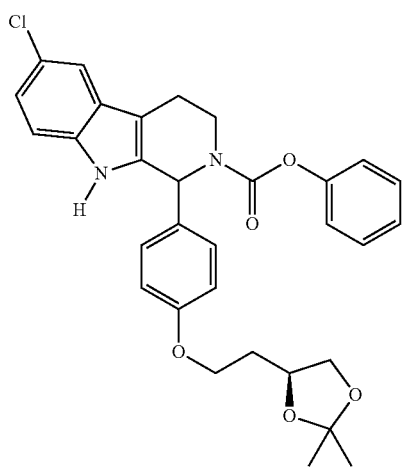 [SMILES: CC1(C)OC[C@H](CCOc2ccc(C3c4[nH]c5ccc(Cl)cc5c4CCN3C(=O)Oc3ccccc3)cc2)O1]
1168
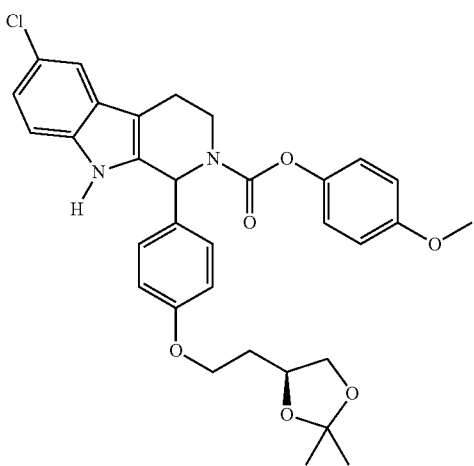
1171
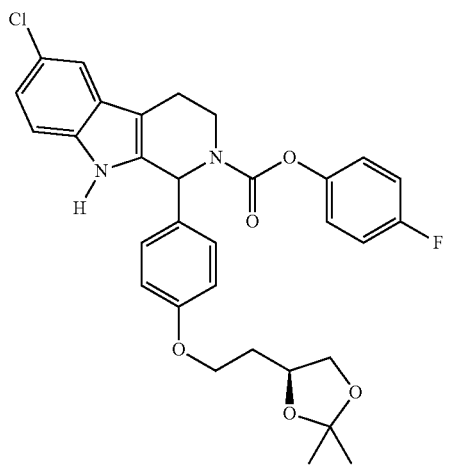 [SMILES: CC1(C)OC[C@H](CCOc2ccc(C3c4[nH]c5ccc(Cl)cc5c4CCN3C(=O)Oc3ccc(F)cc3)cc2)O1]
1169
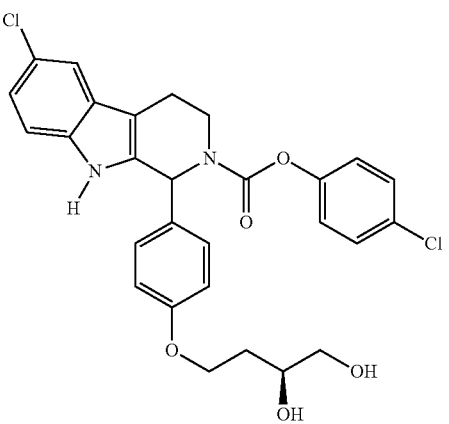 [SMILES: O=C(Oc1ccc(Cl)cc1)N1CCc2c([nH]c3ccc(Cl)cc23)C1c1ccc(OCC[C@H](O)CO)cc1]
1172

TABLE 1-continued
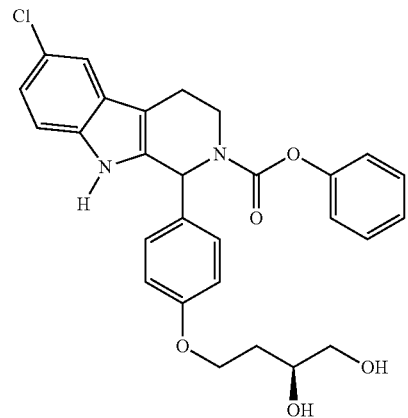 [SMILES: O=C(Oc1ccccc1)N1CCc2c([nH]c3ccc(Cl)cc23)C1c1ccc(OCC[C@H](O)CO)cc1]
1178
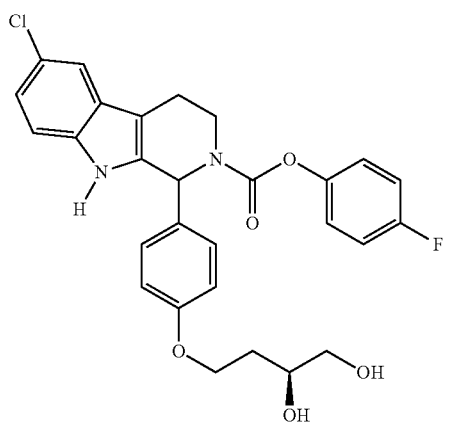 [SMILES: O=C(Oc1ccc(F)cc1)N1CCc2c([nH]c3ccc(Cl)cc23)C1c1ccc(OCC[C@H](O)CO)cc1]
1179
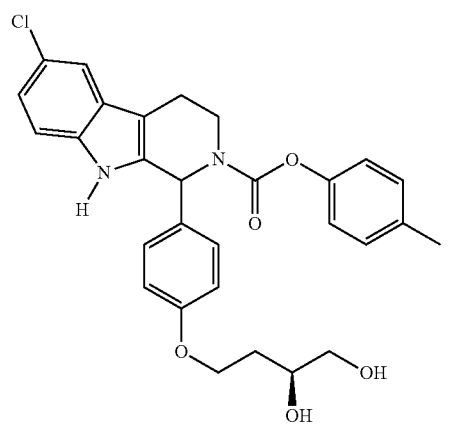 [SMILES: Cc1ccc(OC(=O)N2CCc3c([nH]c4ccc(Cl)cc34)C2c2ccc(OCC[C@H](O)CO)cc2)cc1]
1180
TABLE 1-continued
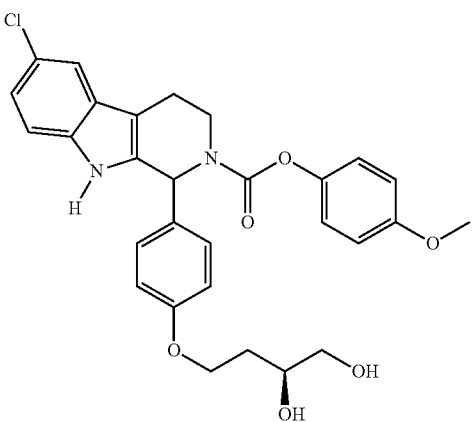 [SMILES: COc1ccc(OC(=O)N2CCc3c([nH]c4ccc(Cl)cc34)C2c2ccc(OCC[C@H](O)CO)cc2)cc1]
1181
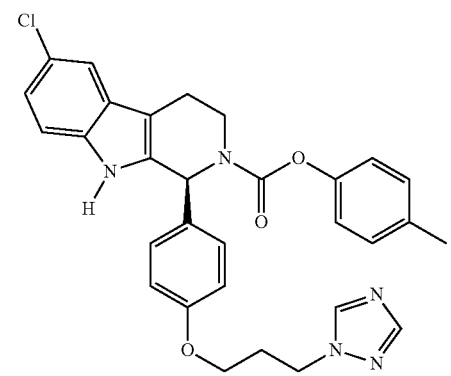 [SMILES: Cc1ccc(OC(=O)N2CCc3c([nH]c4ccc(Cl)cc34)[C@@H]2c2ccc(OCCCn3cncn3)cc2)cc1]
1182
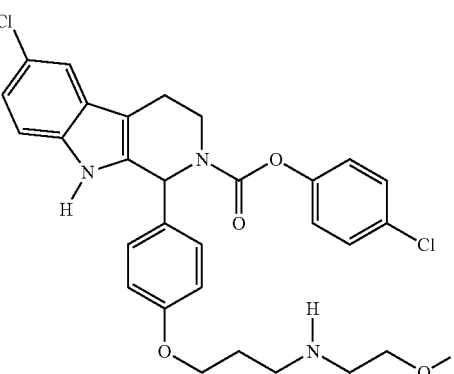
1183
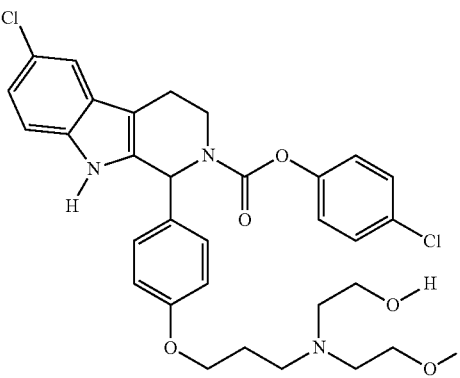
1184

TABLE 1-continued
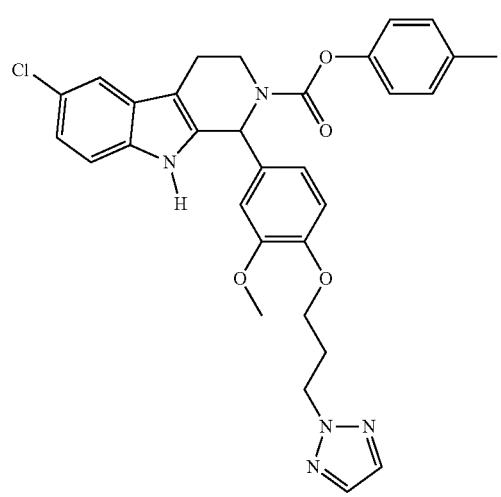 [SMILES: COc1cc(C2c3[nH]c4ccc(Cl)cc4c3CCN2C(=O)Oc2ccc(C)cc2)ccc1OCCCn1nccn1]
1194
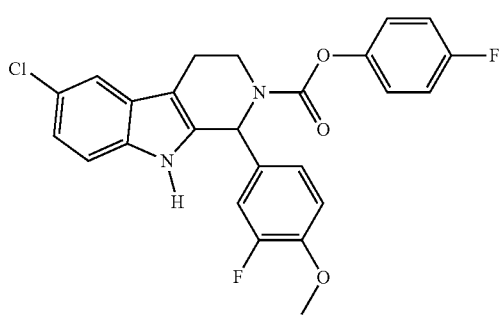 [SMILES: COc1ccc(C2c3[nH]c4ccc(Cl)cc4c3CCN2C(=O)Oc2ccc(F)cc2)cc1F]
1195
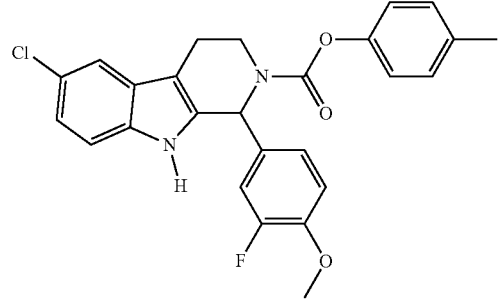 [SMILES: COc1ccc(C2c3[nH]c4ccc(Cl)cc4c3CCN2C(=O)Oc2ccc(C)cc2)cc1F]
1196
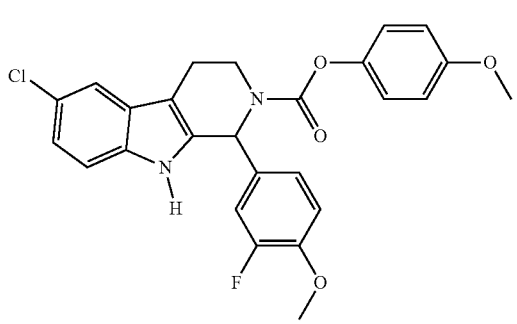 [SMILES: COc1ccc(OC(=O)N2CCc3c([nH]c4ccc(Cl)cc34)C2c2ccc(OC)c(F)c2)cc1]
1197
TABLE 1-continued
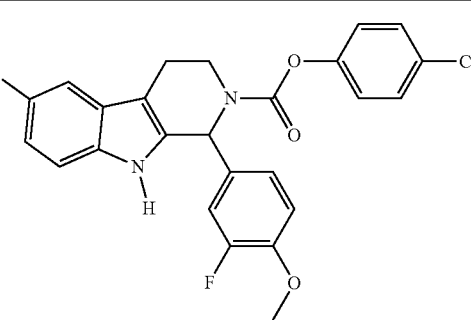
1199
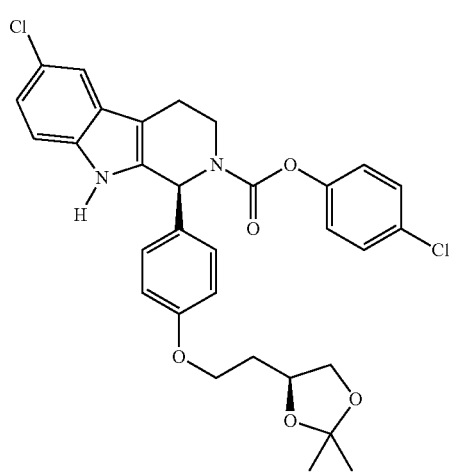 [SMILES: CC1(C)OC[C@H](CCOc2ccc([C@H]3c4[nH]c5ccc(Cl)cc5c4CCN3C(=O)Oc3ccc(Cl)cc3)cc2)O1]
1203
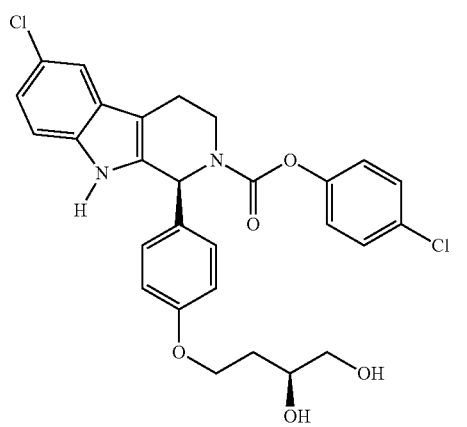 [SMILES: O=C(Oc1ccc(Cl)cc1)N1CCc2c([nH]c3ccc(Cl)cc23)[C@@H]1c1ccc(OCC[C@H](O)CO)cc1]
1205
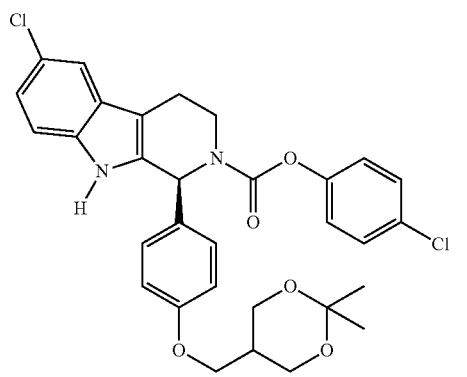 [SMILES: CC1(C)OCC(COc2ccc([C@H]3c4[nH]c5ccc(Cl)cc5c4CCN3C(=O)Oc3ccc(Cl)cc3)cc2)CO1]
1207

TABLE 1-continued
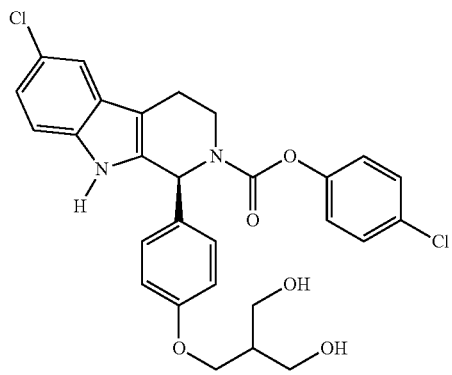 [SMILES: O=C(Oc1ccc(Cl)cc1)N1CCc2c([nH]c3ccc(Cl)cc23)[C@@H]1c1ccc(OCC(CO)CO)cc1]
1209
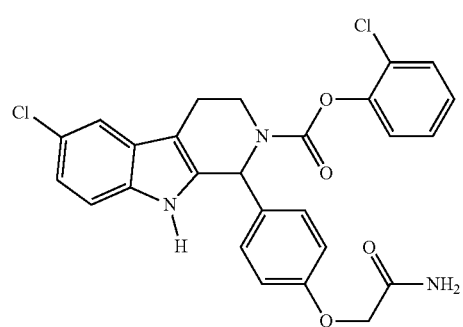 [SMILES: NC(=O)COc1ccc(C2c3[nH]c4ccc(Cl)cc4c3CCN2C(=O)Oc2ccccc2Cl)cc1]
1213
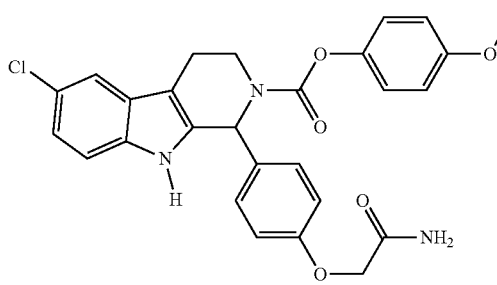
1216
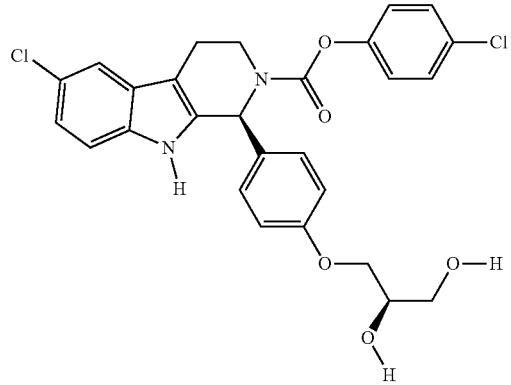 [SMILES: O=C(Oc1ccc(Cl)cc1)N1CCc2c([nH]c3ccc(Cl)cc23)[C@@H]1c1ccc(OC[C@H](O)CO)cc1]
1223
TABLE 1-continued
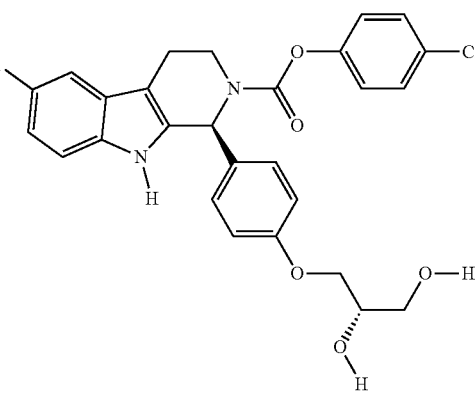
1224
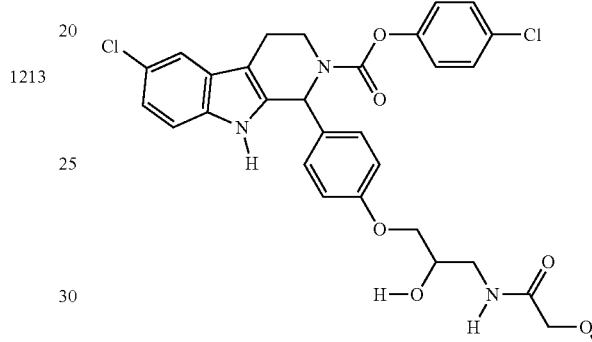
1225

1227

1228

TABLE 1-continued
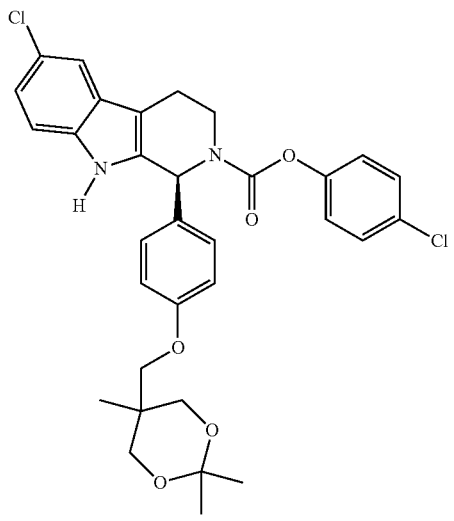 [SMILES: CC1(COc2ccc([C@H]3c4[nH]c5ccc(Cl)cc5c4CCN3C(=O)Oc3ccc(Cl)cc3)cc2)COC(C)(C)OC1]
1229
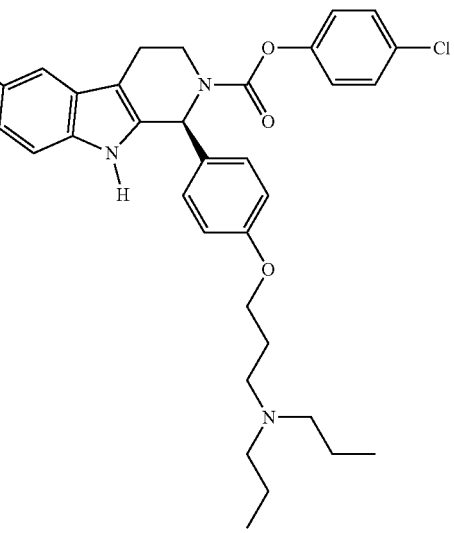
1234
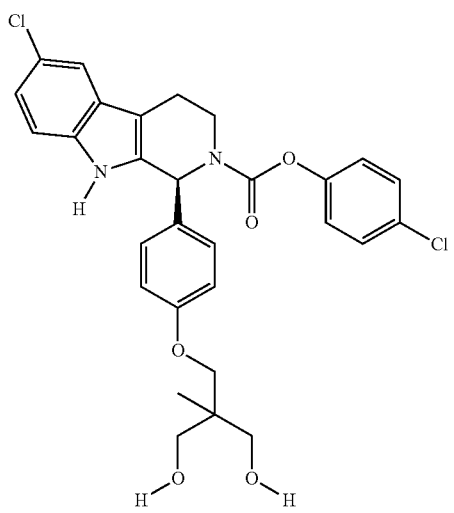 [SMILES: CC(CO)(CO)COc1ccc([C@H]2c3[nH]c4ccc(Cl)cc4c3CCN2C(=O)Oc2ccc(Cl)cc2)cc1]
1230
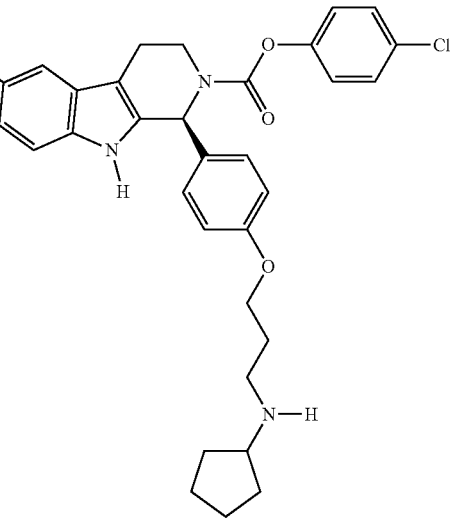
1235
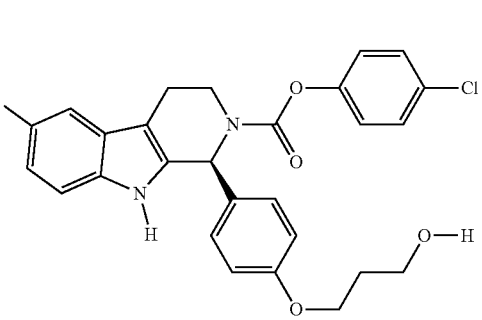
1250
1231

TABLE 1-continued
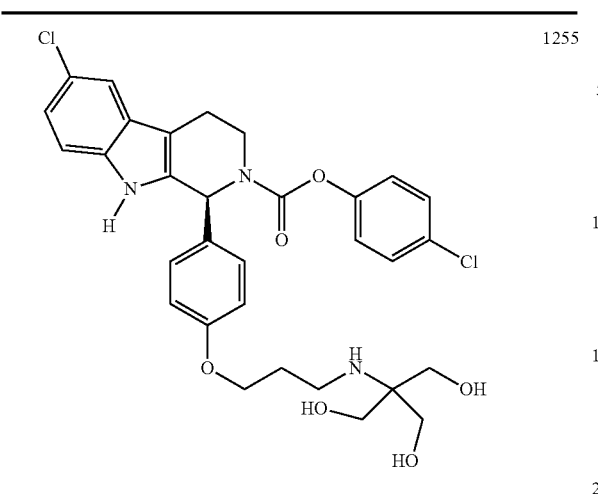
1255
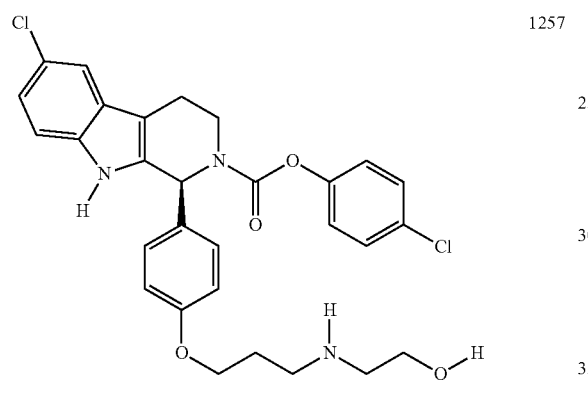
1257
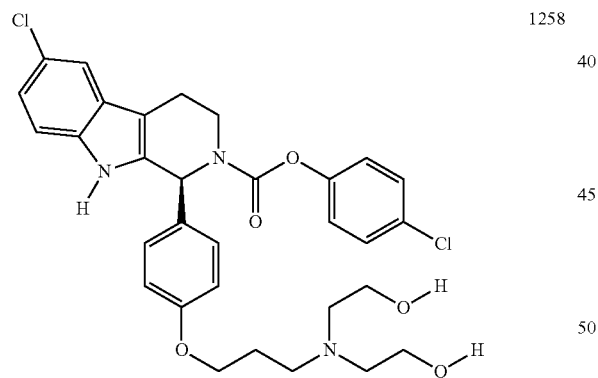
1258
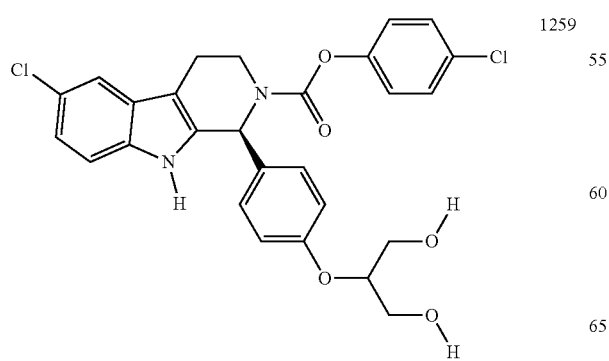
1259
TABLE 1-continued
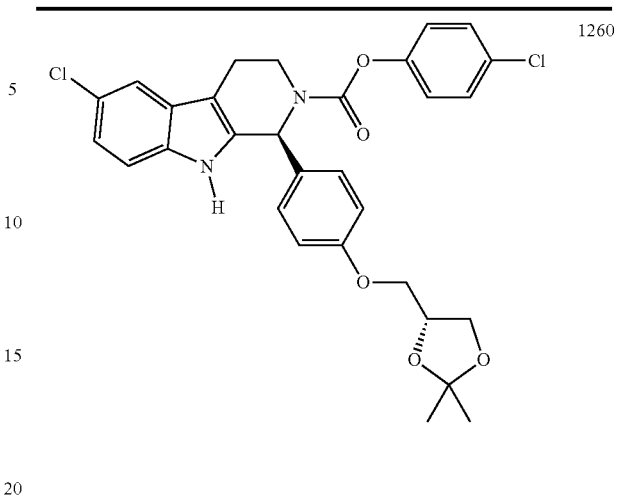
1260
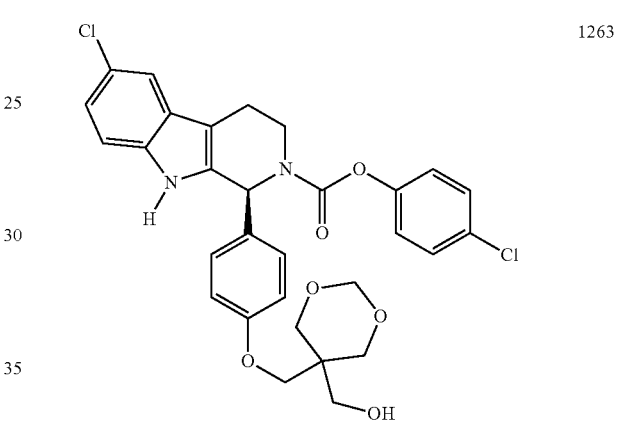
1263
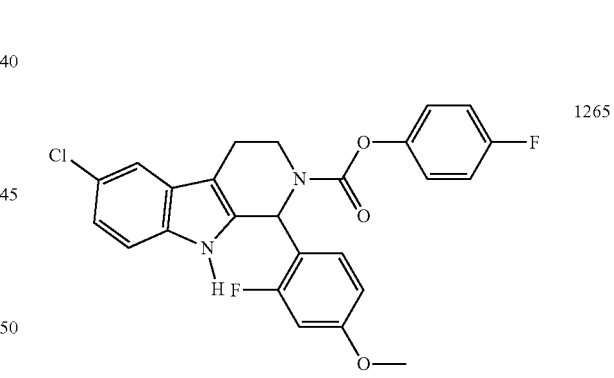
1265
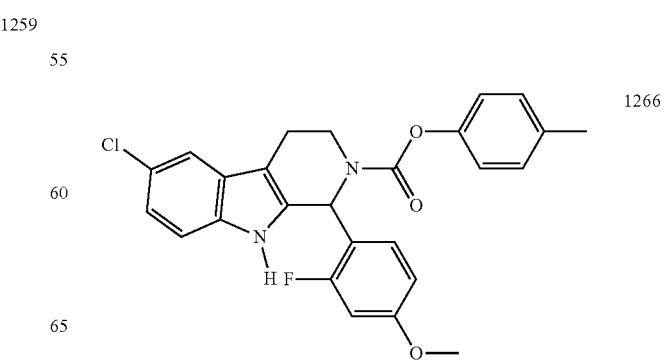
1266

TABLE 1-continued
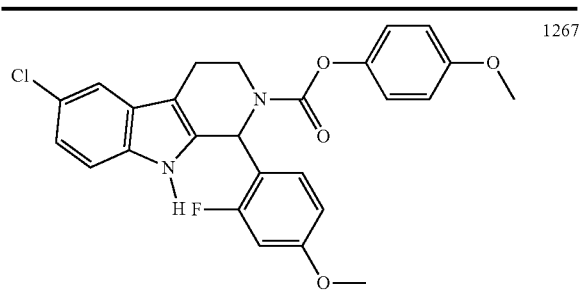
1267
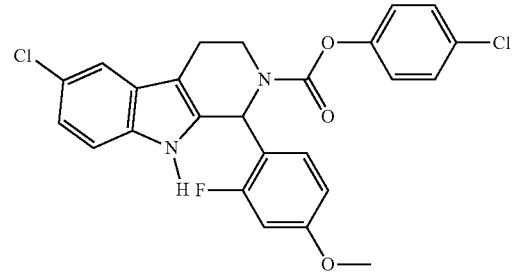 [SMILES: COc1ccc(C2c3[nH]c4ccc(Cl)cc4c3CCN2C(=O)Oc2ccc(Cl)cc2)c(F)c1]
1269
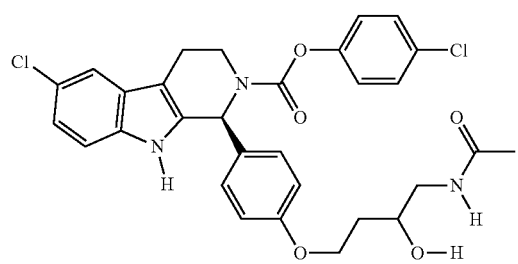 [SMILES: CC(=O)NCC(O)CCOc1ccc([C@H]2c3[nH]c4ccc(Cl)cc4c3CCN2C(=O)Oc2ccc(Cl)cc2)cc1]
1276
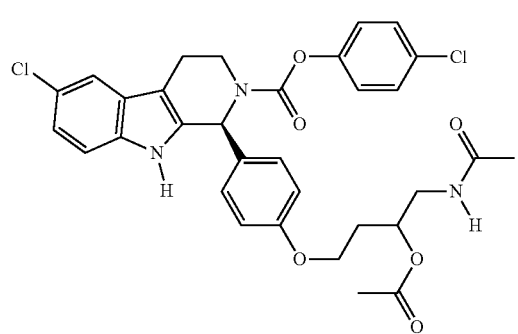 [SMILES: CC(=O)NCC(CCOc1ccc([C@H]2c3[nH]c4ccc(Cl)cc4c3CCN2C(=O)Oc2ccc(Cl)cc2)cc1)OC(C)=O]
1277
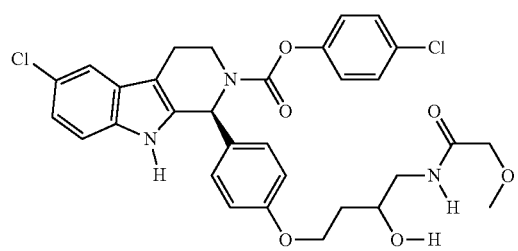 [SMILES: COCC(=O)NCC(O)CCOc1ccc([C@H]2c3[nH]c4ccc(Cl)cc4c3CCN2C(=O)Oc2ccc(Cl)cc2)cc1]
1278
TABLE 1-continued
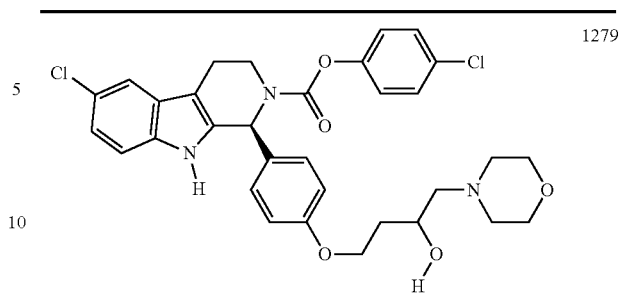
1279
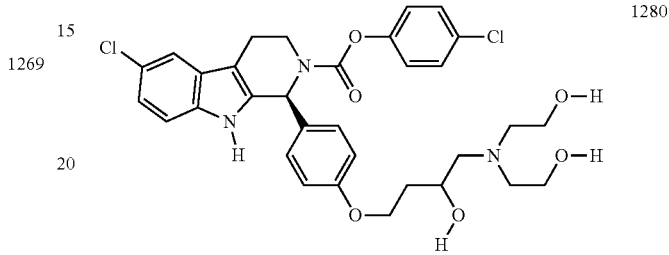
1280
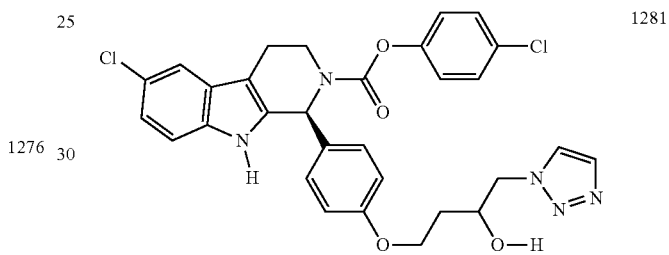
1281
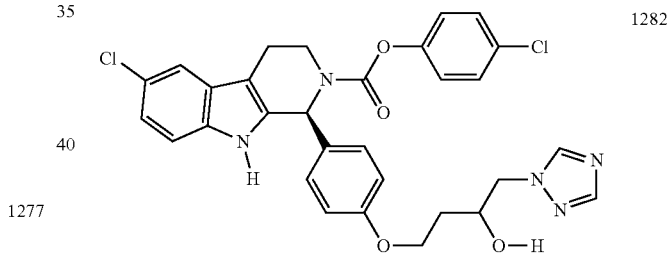
1282
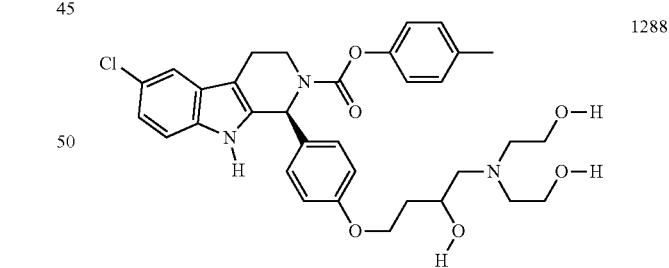
1288
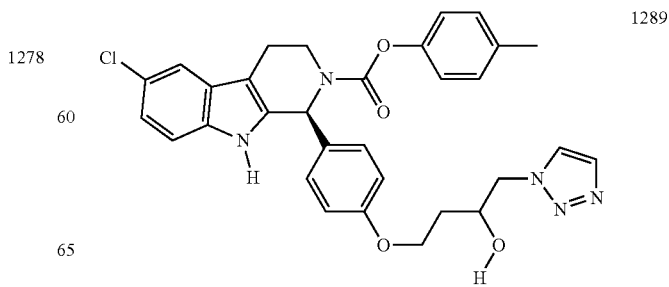
1289

TABLE 1-continued
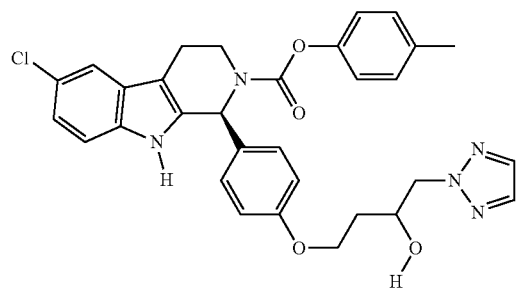 [SMILES: Cc1ccc(OC(=O)N2CCc3c([nH]c4ccc(Cl)cc34)[C@@H]2c2ccc(OCCC(O)Cn3nccn3)cc2)cc1]
1290
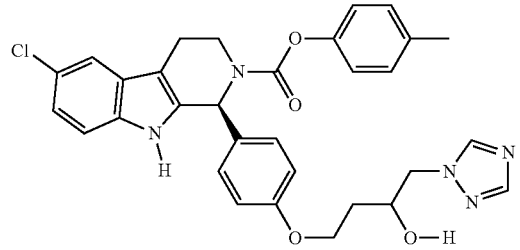 [SMILES: Cc1ccc(OC(=O)N2CCc3c([nH]c4ccc(Cl)cc34)[C@@H]2c2ccc(OCCC(O)Cn3cncn3)cc2)cc1]
1291
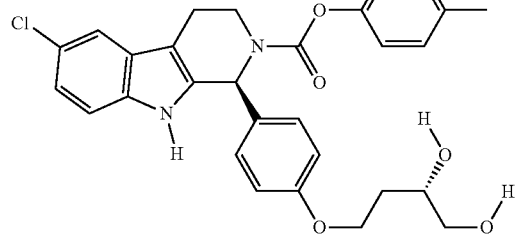
1292
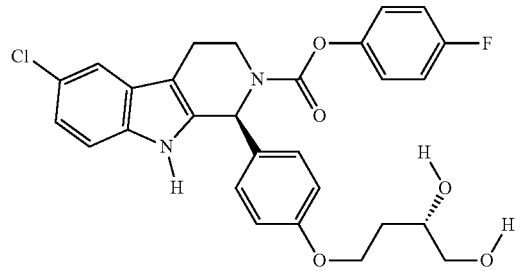 [SMILES: O=C(Oc1ccc(F)cc1)N1CCc2c([nH]c3ccc(Cl)cc23)[C@@H]1c1ccc(OCC[C@H](O)CO)cc1]
1293
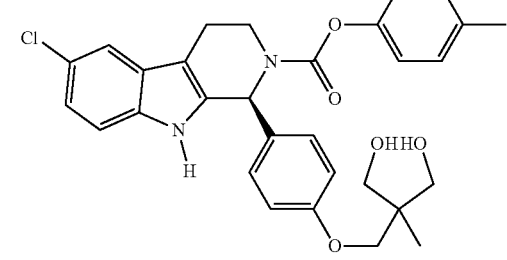
TABLE 1-continued
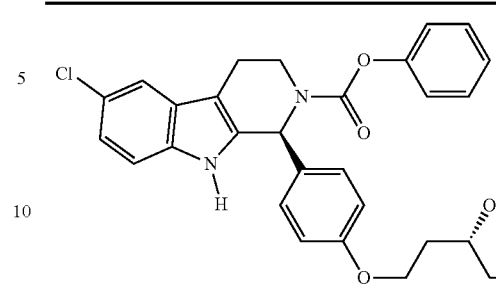
1299
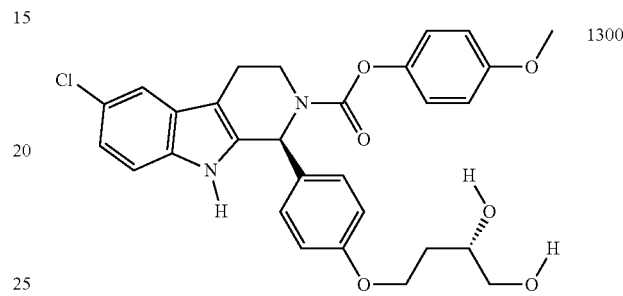
1300
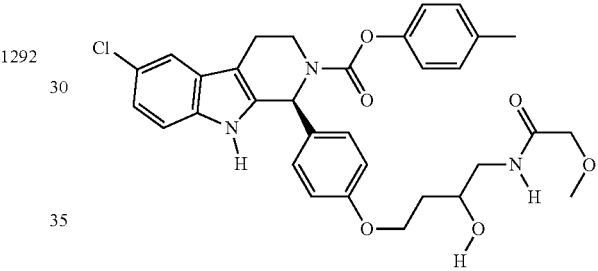
1301
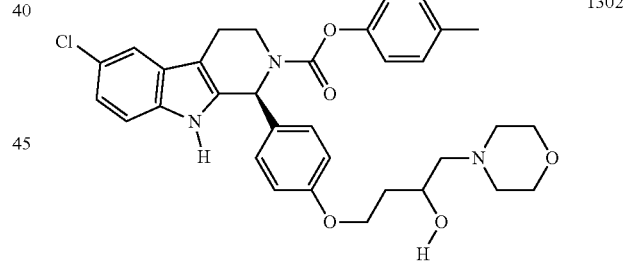
1302
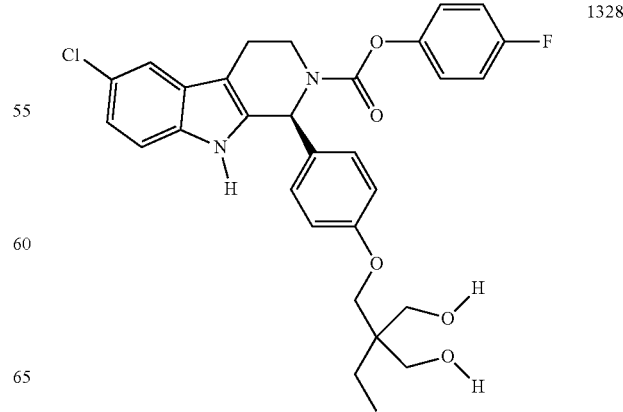
1328

TABLE 1-continued
1329
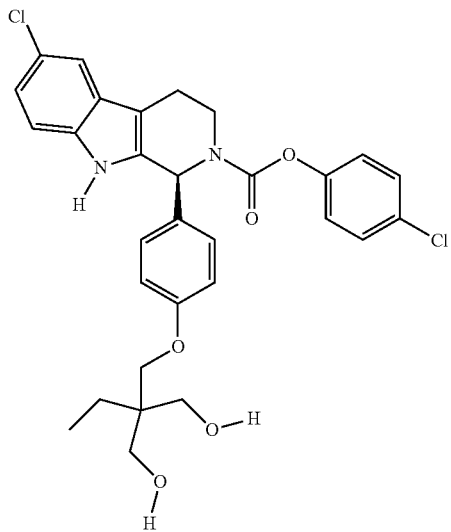 [SMILES: CCC(CO)(CO)COc1ccc([C@H]2c3[nH]c4ccc(Cl)cc4c3CCN2C(=O)Oc2ccc(Cl)cc2)cc1]
1330
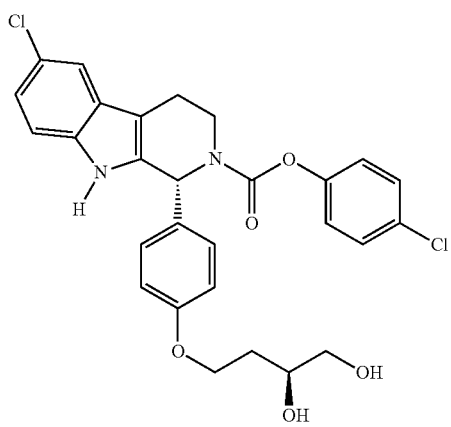
1331
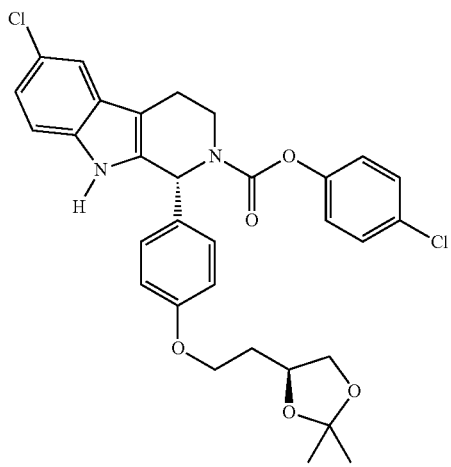 [SMILES: CC1(C)OC[C@H](CCOc2ccc([C@@H]3c4[nH]c5ccc(Cl)cc5c4CCN3C(=O)Oc3ccc(Cl)cc3)cc2)O1]
TABLE 1-continued
1332
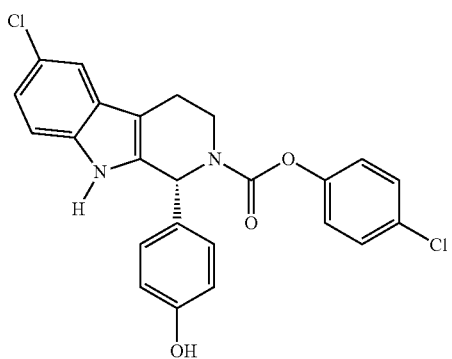 [SMILES: O=C(Oc1ccc(Cl)cc1)N1CCc2c([nH]c3ccc(Cl)cc23)[C@H]1c1ccc(O)cc1]
1333
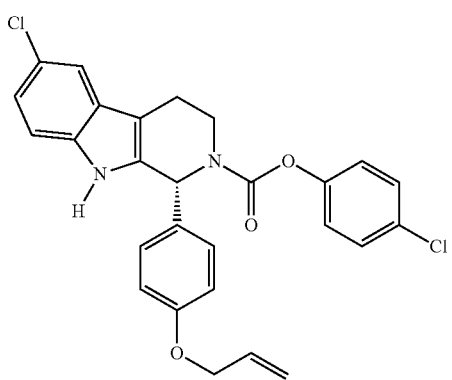 [SMILES: C=CCOc1ccc([C@@H]2c3[nH]c4ccc(Cl)cc4c3CCN2C(=O)Oc2ccc(Cl)cc2)cc1]
1335
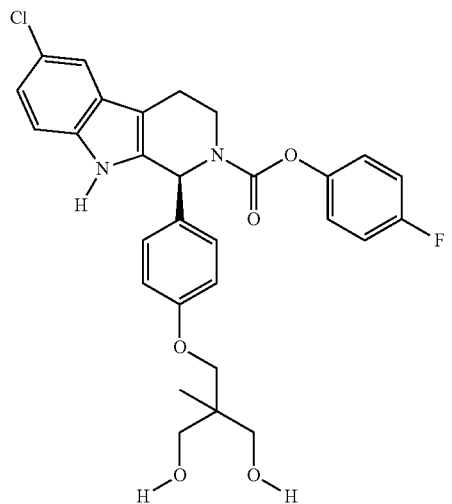 [SMILES: CC(CO)(CO)COc1ccc([C@H]2c3[nH]c4ccc(Cl)cc4c3CCN2C(=O)Oc2ccc(F)cc2)cc1]
1336
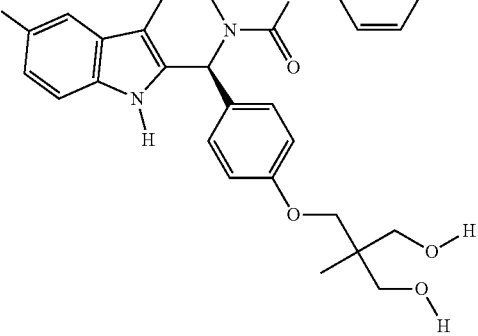

TABLE 1-continued
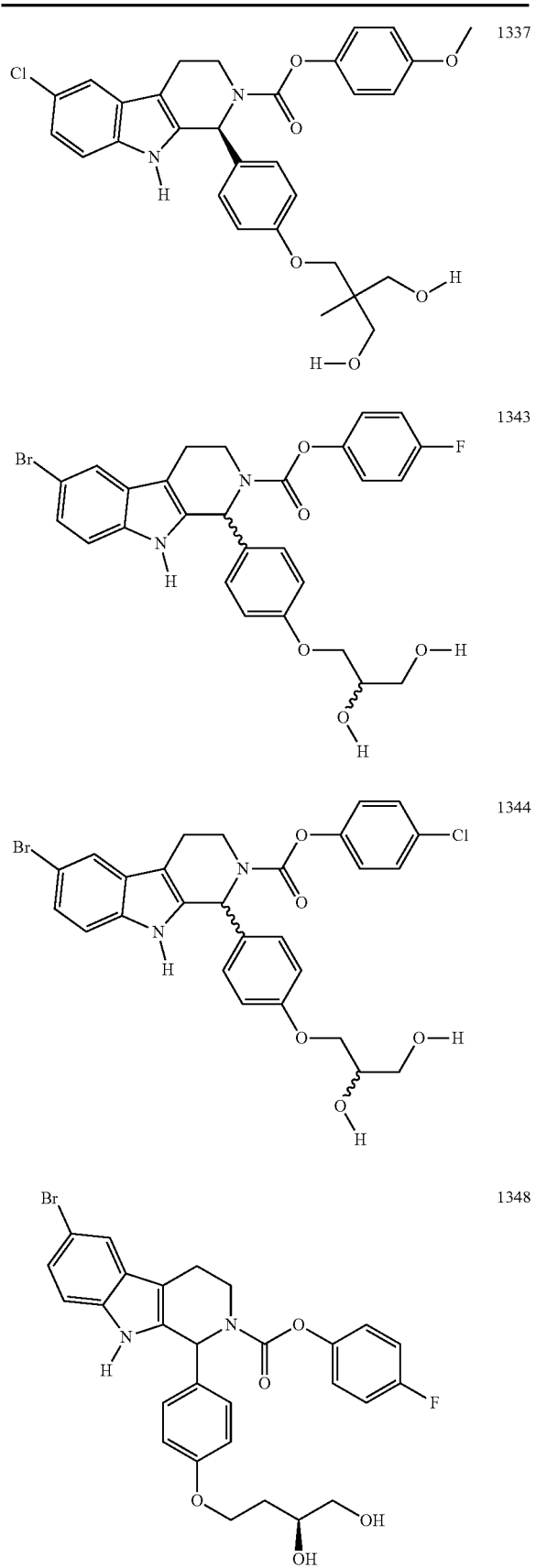
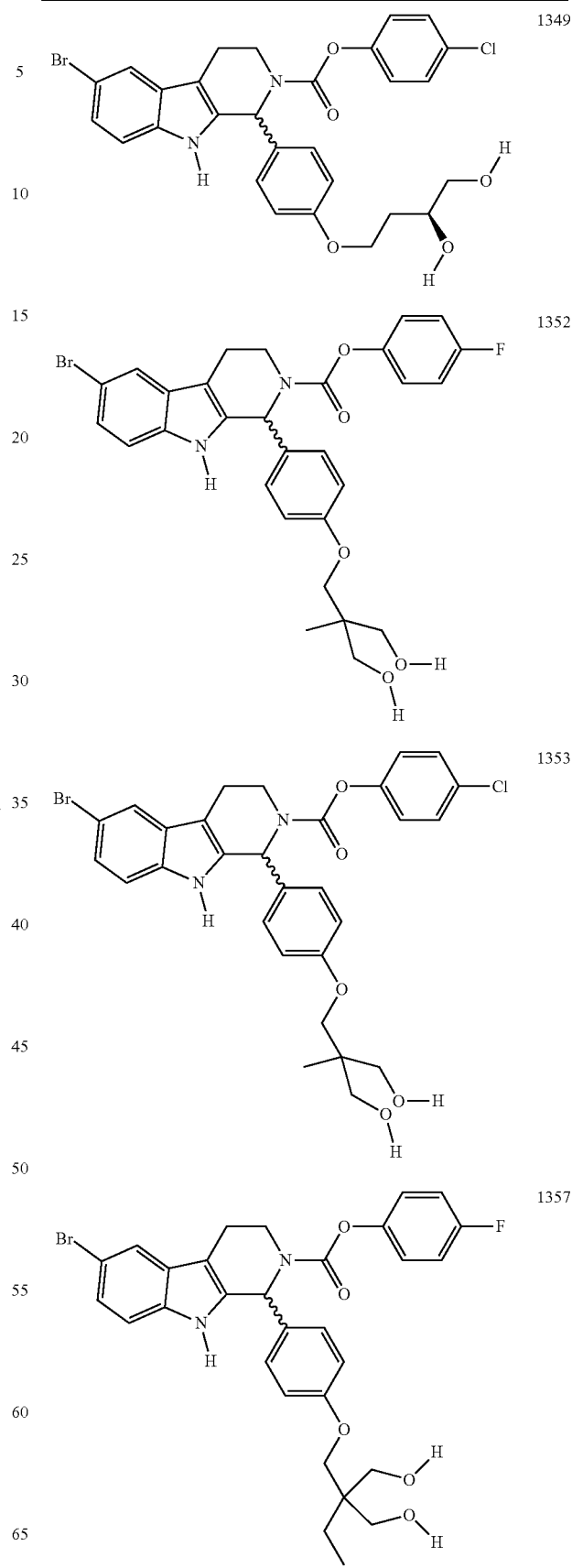

TABLE 1-continued
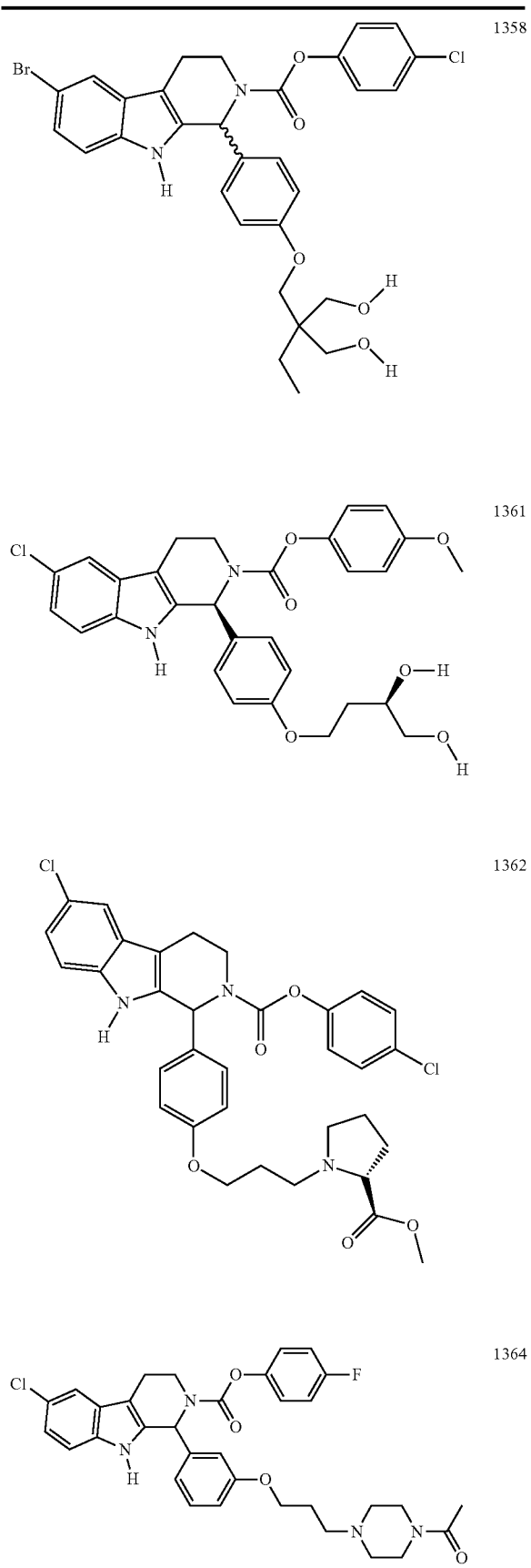
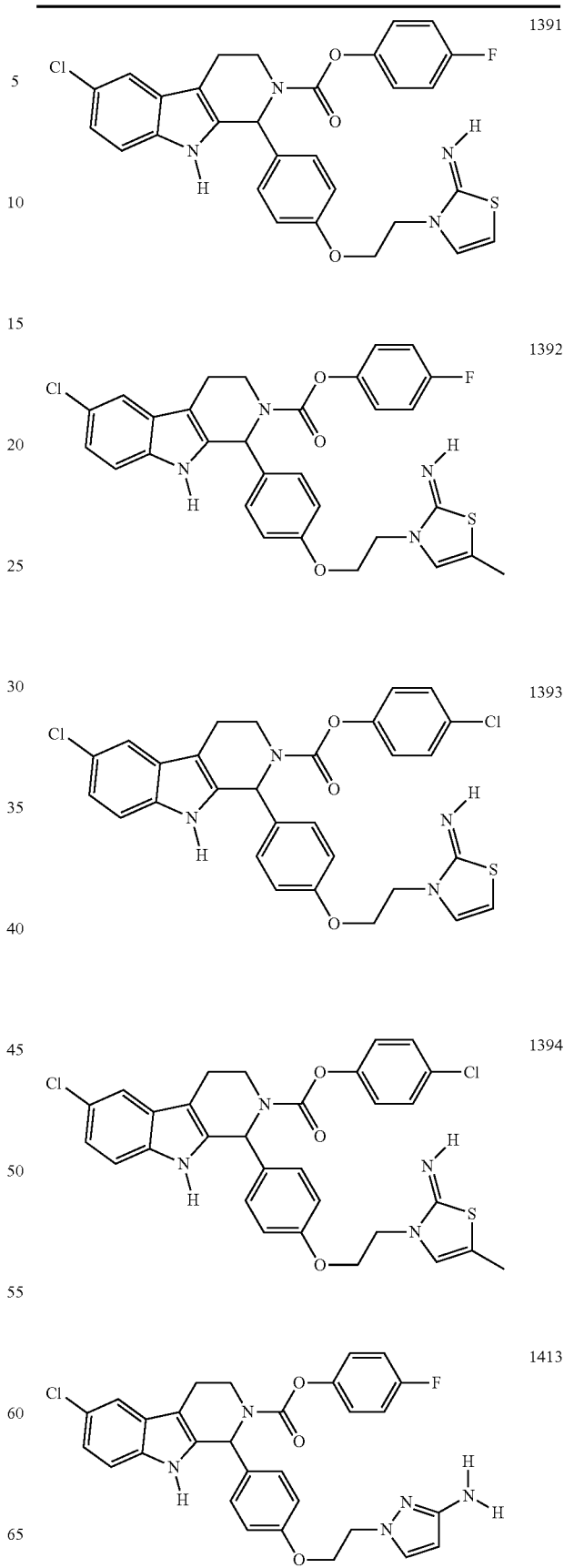

TABLE 1-continued
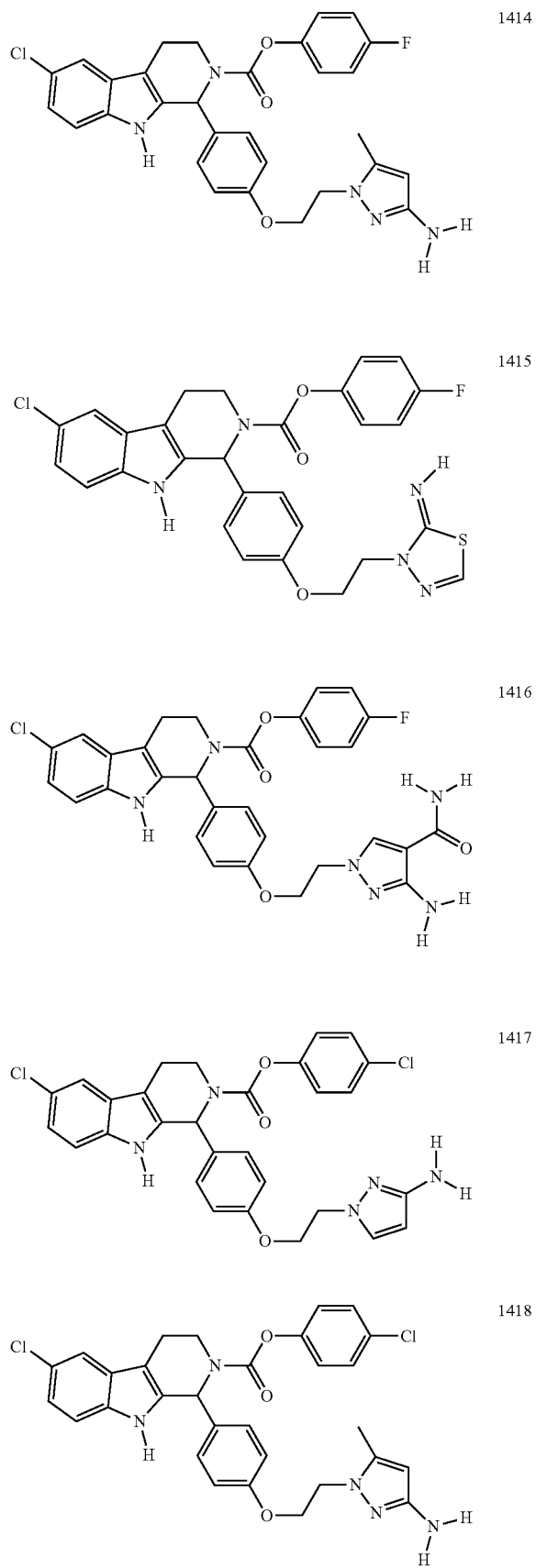
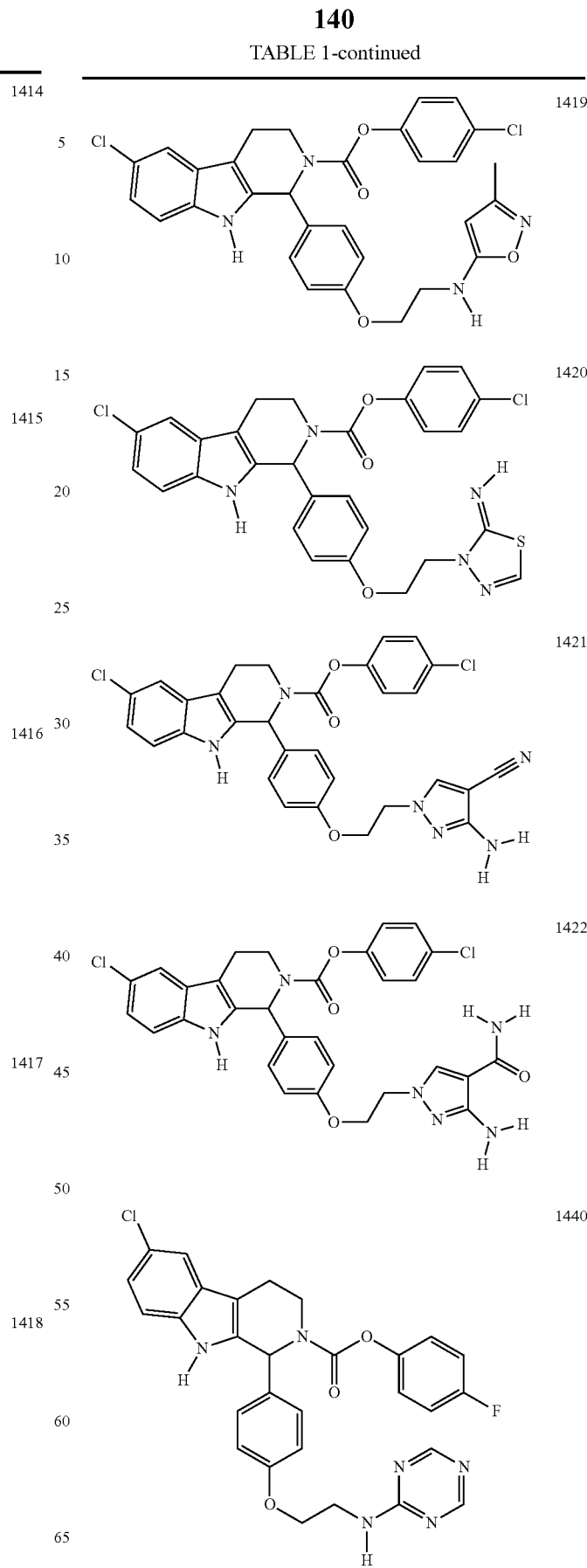

TABLE 1-continued
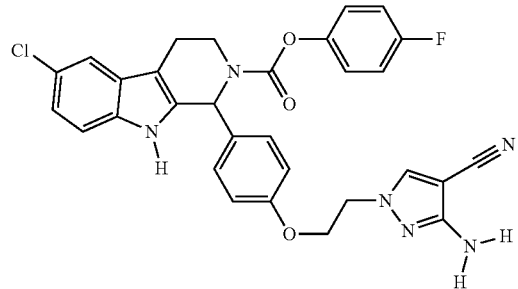 [SMILES: N#Cc1cn(CCOc2ccc(C3c4[nH]c5ccc(Cl)cc5c4CCN3C(=O)Oc3ccc(F)cc3)cc2)nc1N]
1441
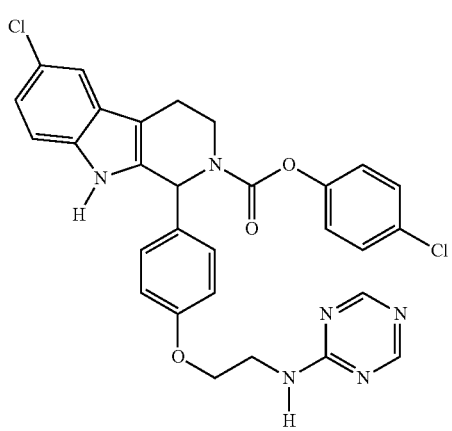 [SMILES: O=C(Oc1ccc(Cl)cc1)N1CCc2c([nH]c3ccc(Cl)cc23)C1c1ccc(OCCNc2ncncn2)cc1]
1442
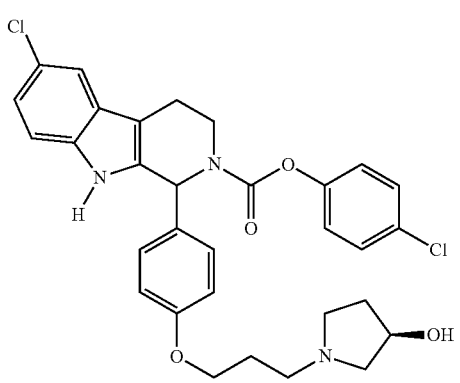 [SMILES: O=C(Oc1ccc(Cl)cc1)N1CCc2c([nH]c3ccc(Cl)cc23)C1c1ccc(OCCCN2CC[C@@H](O)C2)cc1]
1476
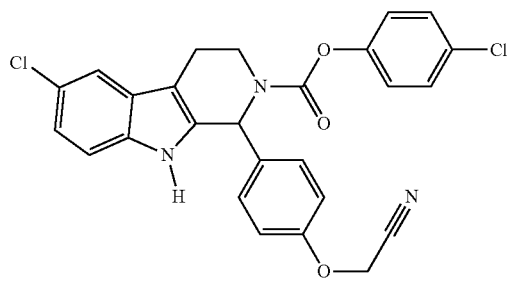 [SMILES: N#CCOc1ccc(C2c3[nH]c4ccc(Cl)cc4c3CCN2C(=O)Oc2ccc(Cl)cc2)cc1]
1520
TABLE 1-continued
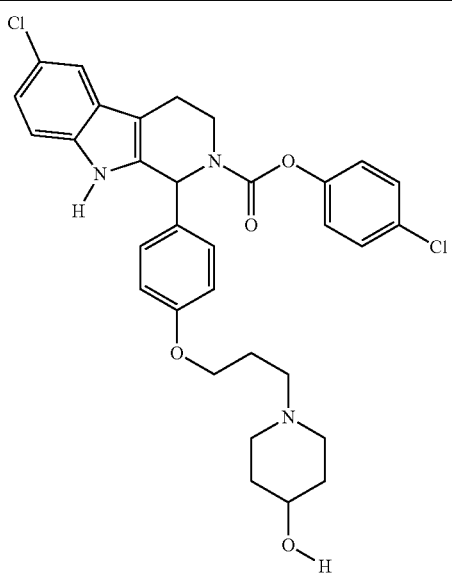
1537
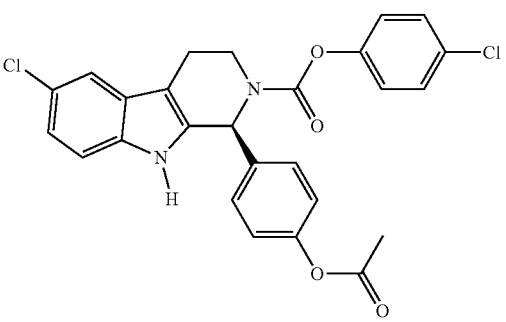 [SMILES: CC(=O)Oc1ccc([C@H]2c3[nH]c4ccc(Cl)cc4c3CCN2C(=O)Oc2ccc(Cl)cc2)cc1]
1538
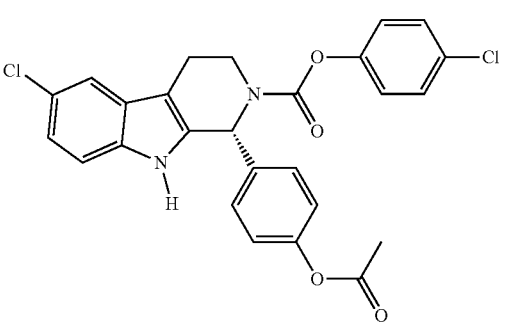 [SMILES: CC(=O)Oc1ccc([C@@H]2c3[nH]c4ccc(Cl)cc4c3CCN2C(=O)Oc2ccc(Cl)cc2)cc1]
1539
1546

TABLE 1-continued
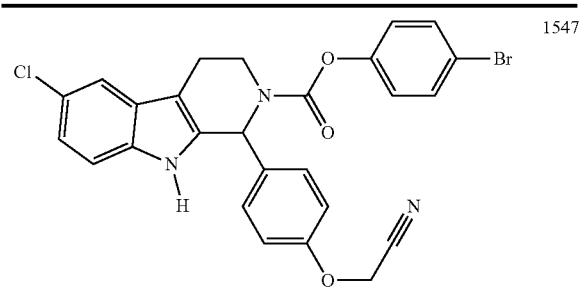
1547
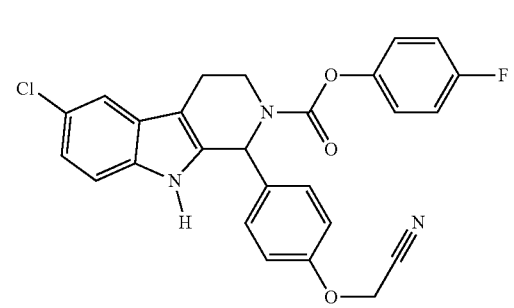 [SMILES: N#CCOc1ccc(C2c3[nH]c4ccc(Cl)cc4c3CCN2C(=O)Oc2ccc(F)cc2)cc1]
1548
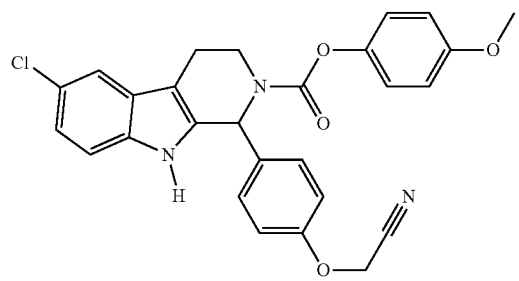 [SMILES: COc1ccc(OC(=O)N2CCc3c([nH]c4ccc(Cl)cc34)C2c2ccc(OCC#N)cc2)cc1]
1549
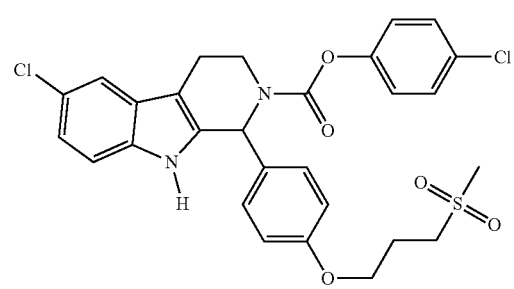 [SMILES: CS(=O)(=O)CCCOc1ccc(C2c3[nH]c4ccc(Cl)cc4c3CCN2C(=O)Oc2ccc(Cl)cc2)cc1]
1551
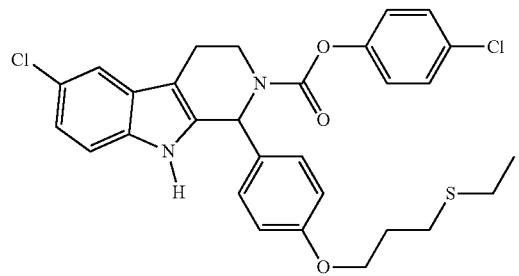 [SMILES: CC(C)SCCCOc1ccc(C2c3[nH]c4ccc(Cl)cc4c3CCN2C(=O)Oc2ccc(Cl)cc2)cc1]
1552
TABLE 1-continued
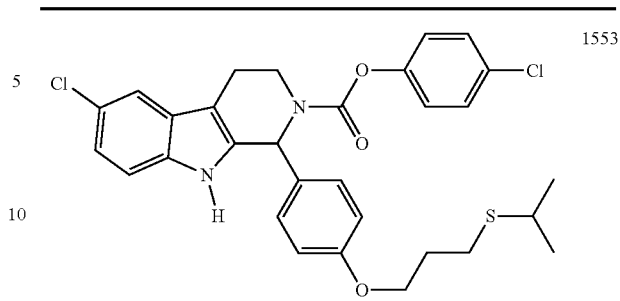
1553
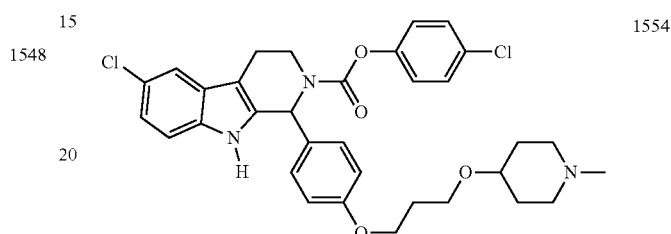
1554
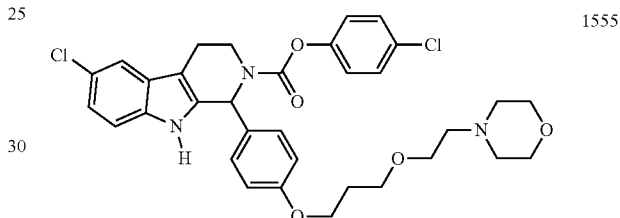
1555
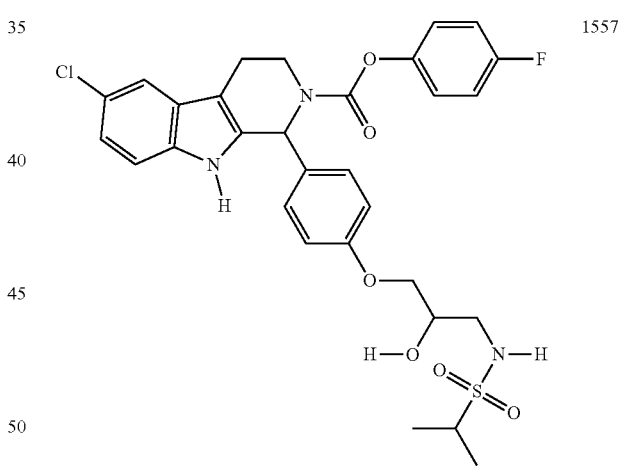
1557
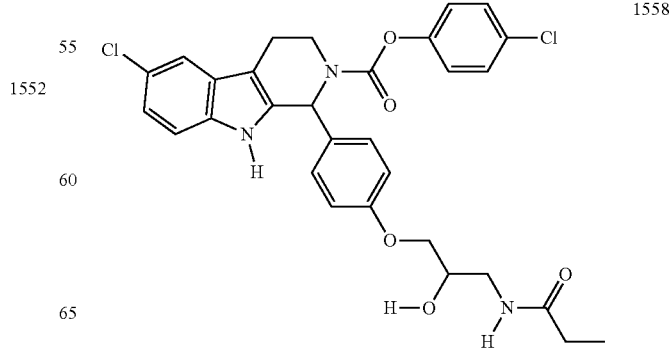
1558

TABLE 1-continued
1559
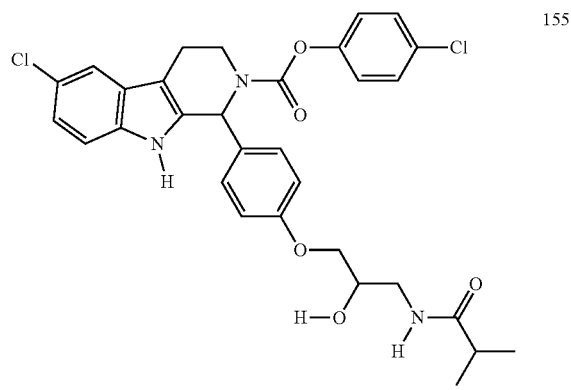
1560
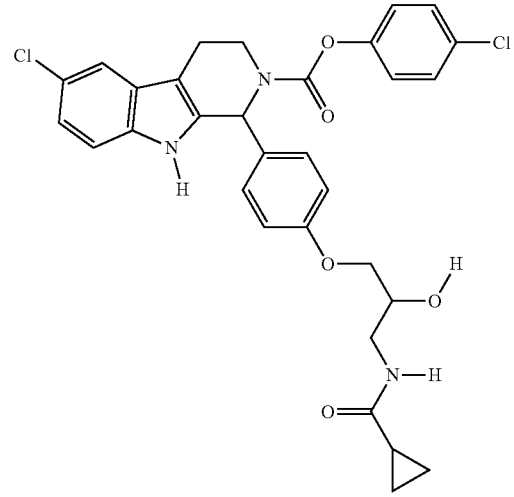 [SMILES: O=C(NCC(O)COc1ccc(C2c3[nH]c4ccc(Cl)cc4c3CCN2C(=O)Oc2ccc(Cl)cc2)cc1)C1CC1]
1561
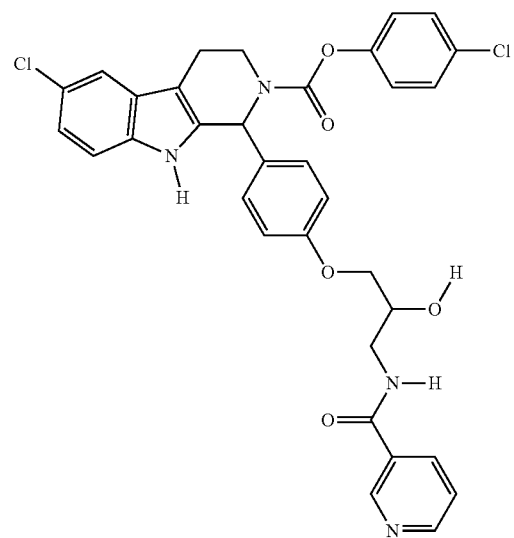 [SMILES: O=C(NCC(O)COc1ccc(C2c3[nH]c4ccc(Cl)cc4c3CCN2C(=O)Oc2ccc(Cl)cc2)cc1)c1cccnc1]
TABLE 1-continued
1562
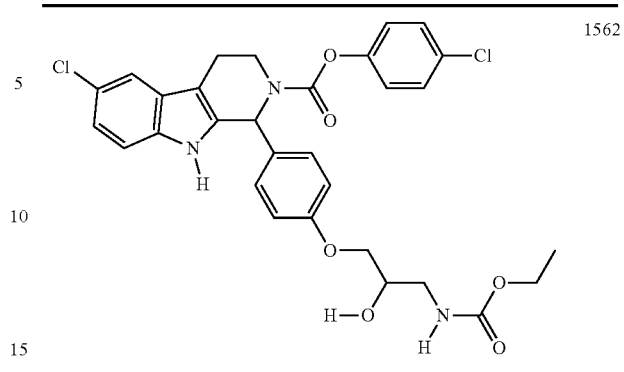
1563
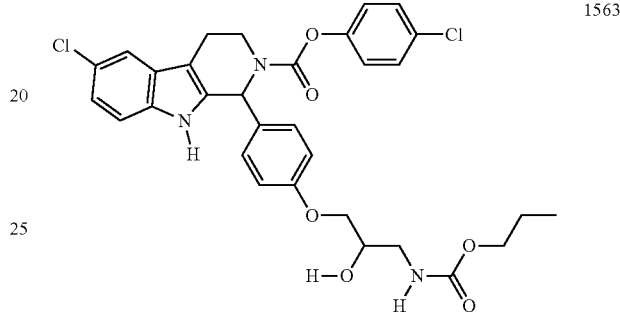
1564
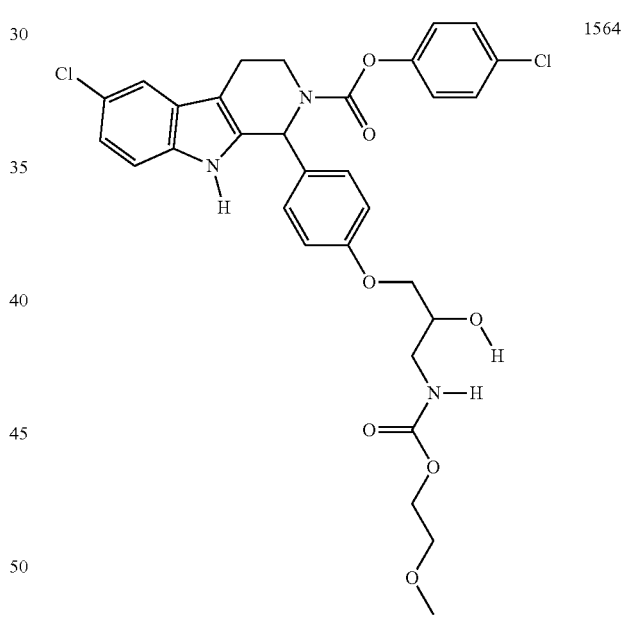
1565
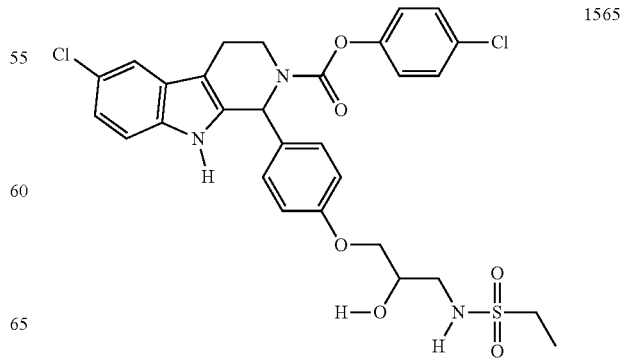

TABLE 1-continued
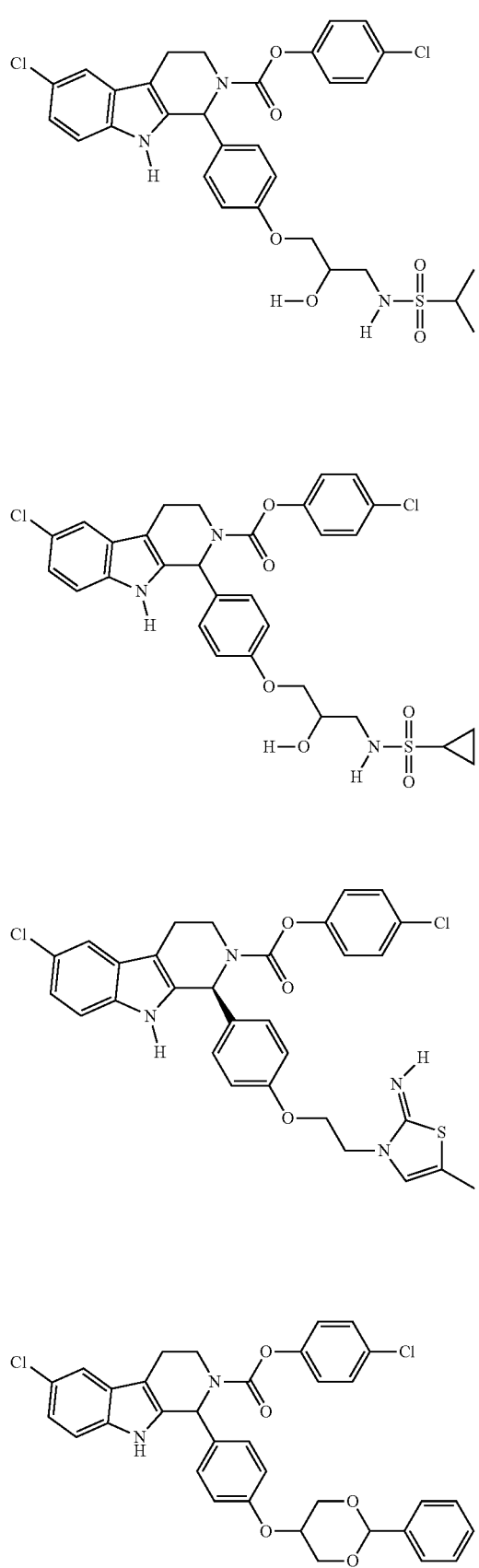
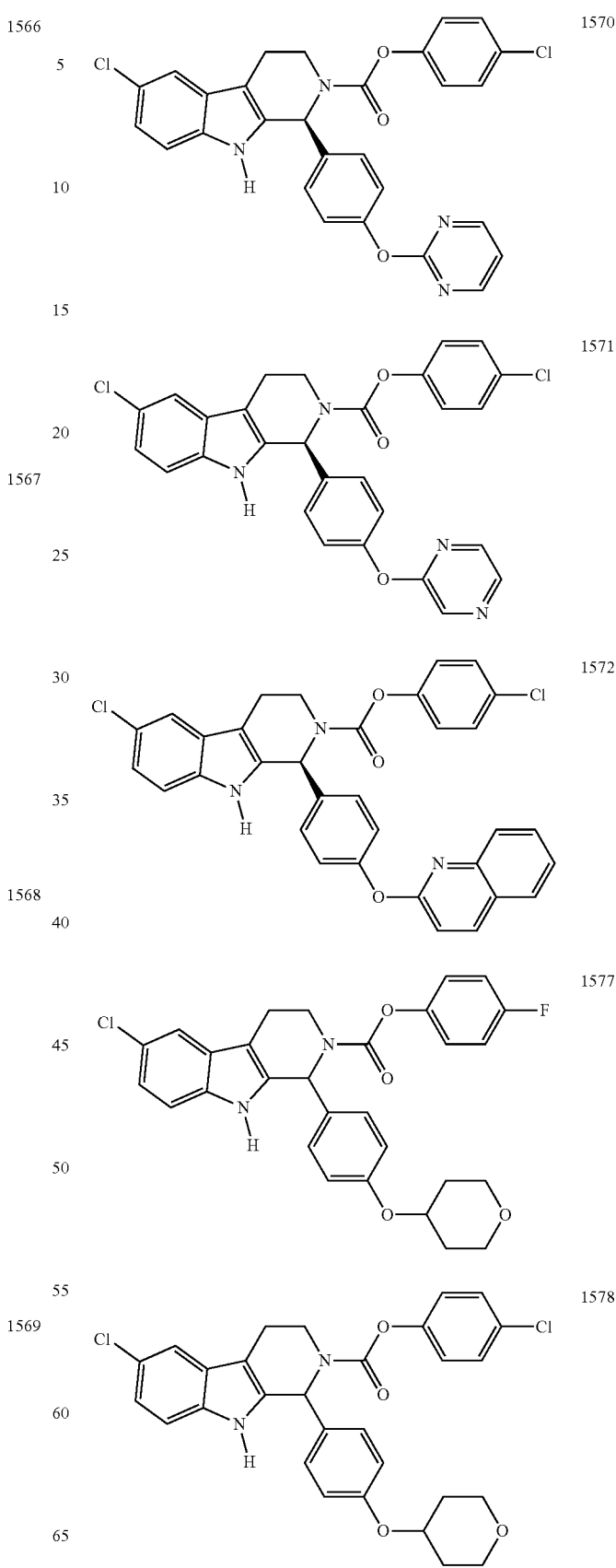

TABLE 1-continued
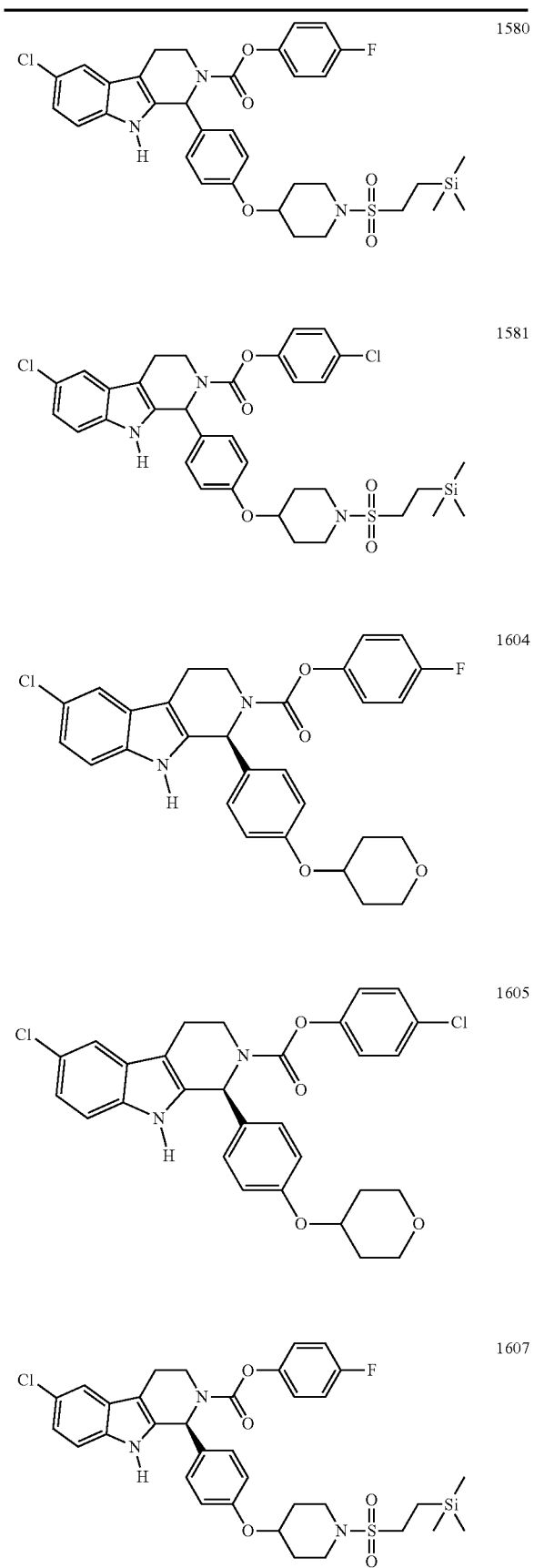
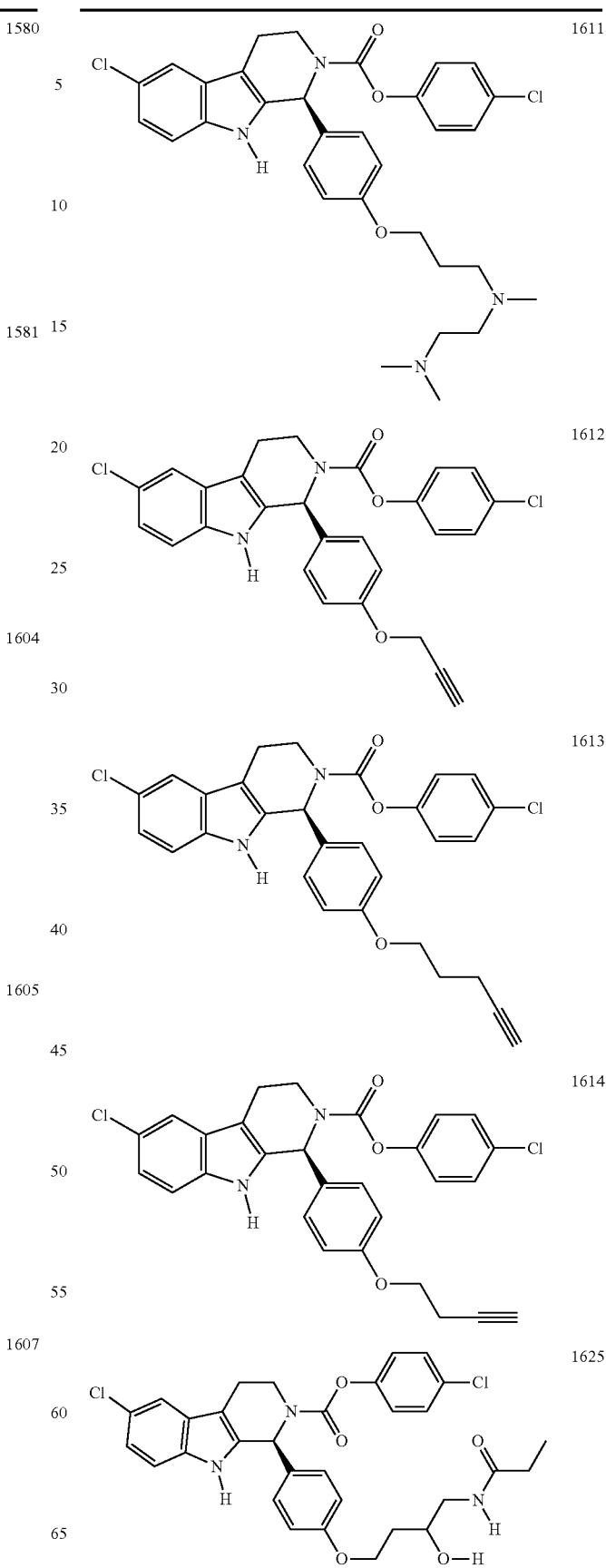

TABLE 1-continued
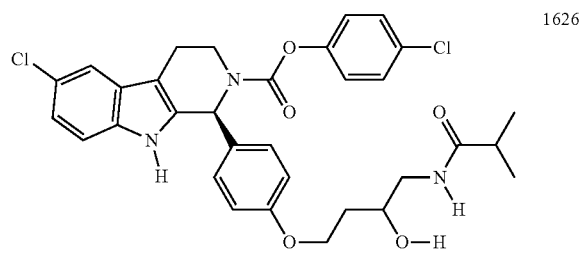
1626
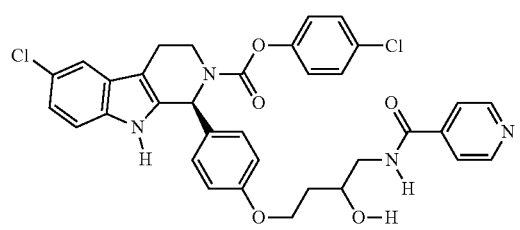 [SMILES: O=C(NCC(O)CCOc1ccc([C@H]2c3[nH]c4ccc(Cl)cc4c3CCN2C(=O)Oc2ccc(Cl)cc2)cc1)c1ccncc1]
1627
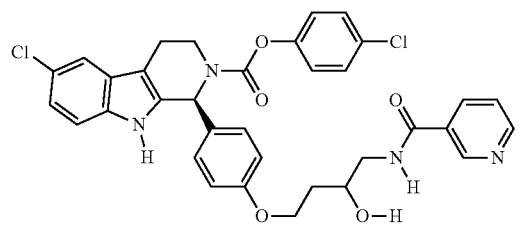 [SMILES: O=C(NCC(O)CCOc1ccc([C@H]2c3[nH]c4ccc(Cl)cc4c3CCN2C(=O)Oc2ccc(Cl)cc2)cc1)c1cccnc1]
1628
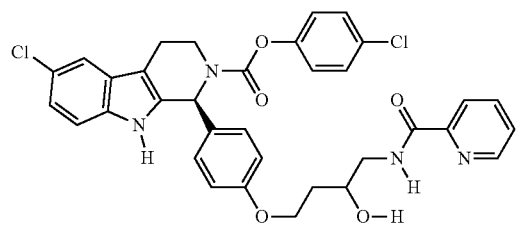 [SMILES: O=C(NCC(O)CCOc1ccc([C@H]2c3[nH]c4ccc(Cl)cc4c3CCN2C(=O)Oc2ccc(Cl)cc2)cc1)c1ccccn1]
1629
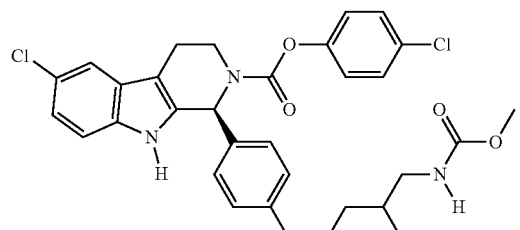
1635
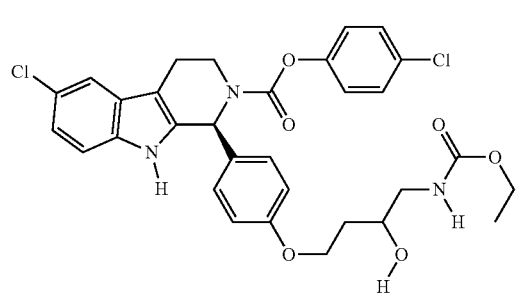
1636
TABLE 1-continued
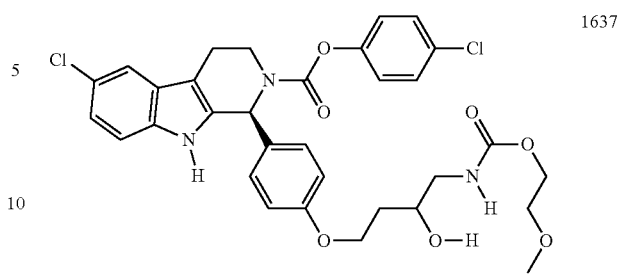
1637
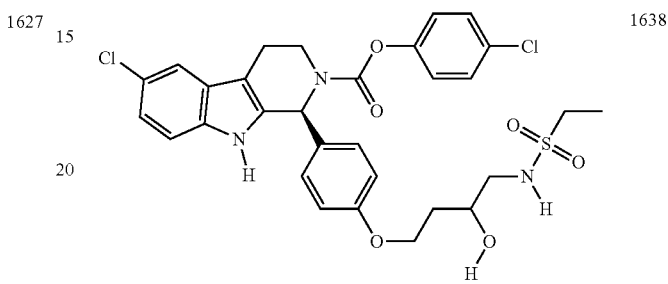
1638
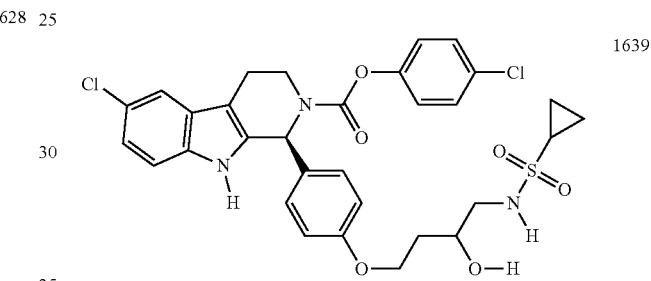
1639
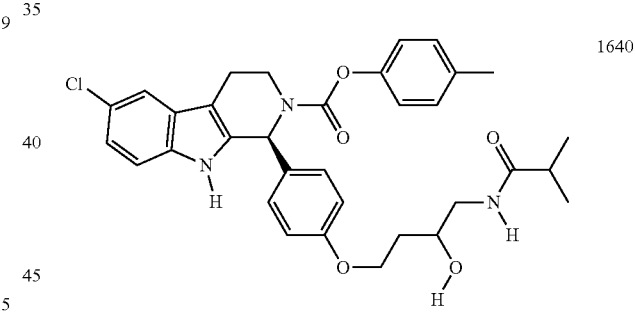
1640
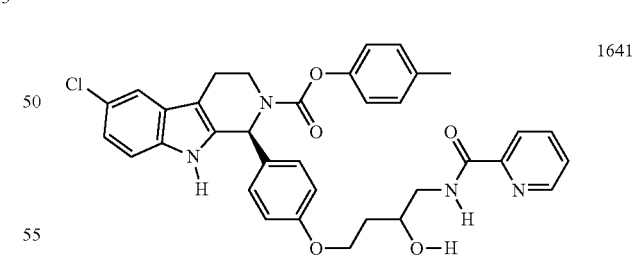
1641
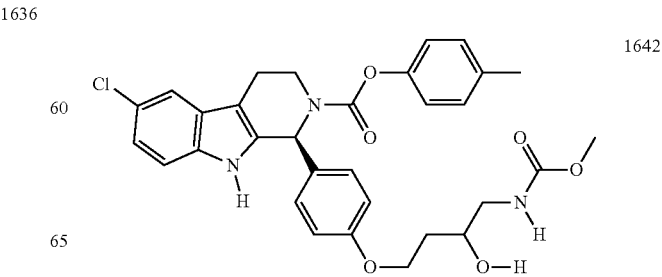
1642

TABLE 1-continued
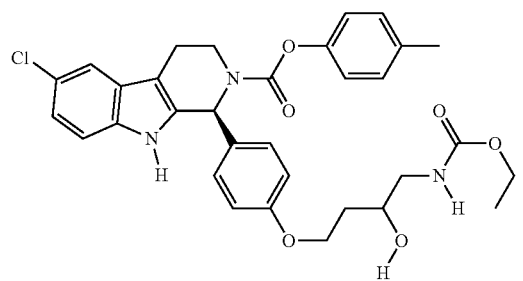 [SMILES: Cc1ccc(OC(=O)N2CCc3c([nH]c4ccc(Cl)cc34)[C@@H]2c2ccc(OCCC(O)CNC(=O)C(C)C)cc2)cc1]
1643
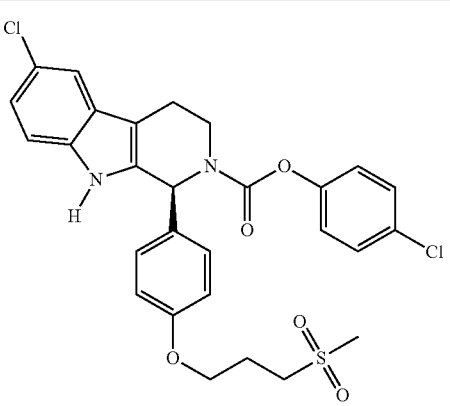 [SMILES: CS(=O)(=O)CCCOc1ccc([C@H]2c3[nH]c4ccc(Cl)cc4c3CCN2C(=O)Oc2ccc(Cl)cc2)cc1]
1648
1644
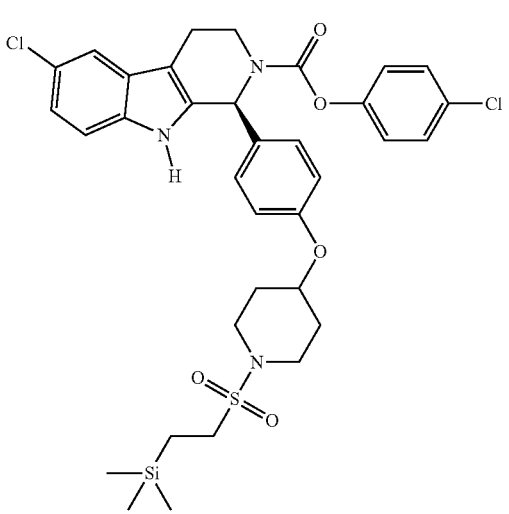 [SMILES: C[Si](C)(C)CCS(=O)(=O)N1CCC(Oc2ccc([C@H]3c4[nH]c5ccc(Cl)cc5c4CCN3C(=O)Oc3ccc(Cl)cc3)cc2)CC1]
1652
1645
1646
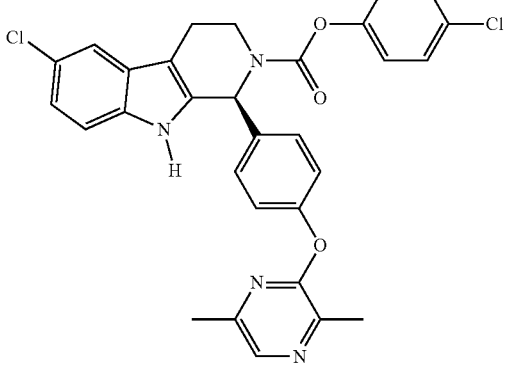
1658
1647

TABLE 1-continued
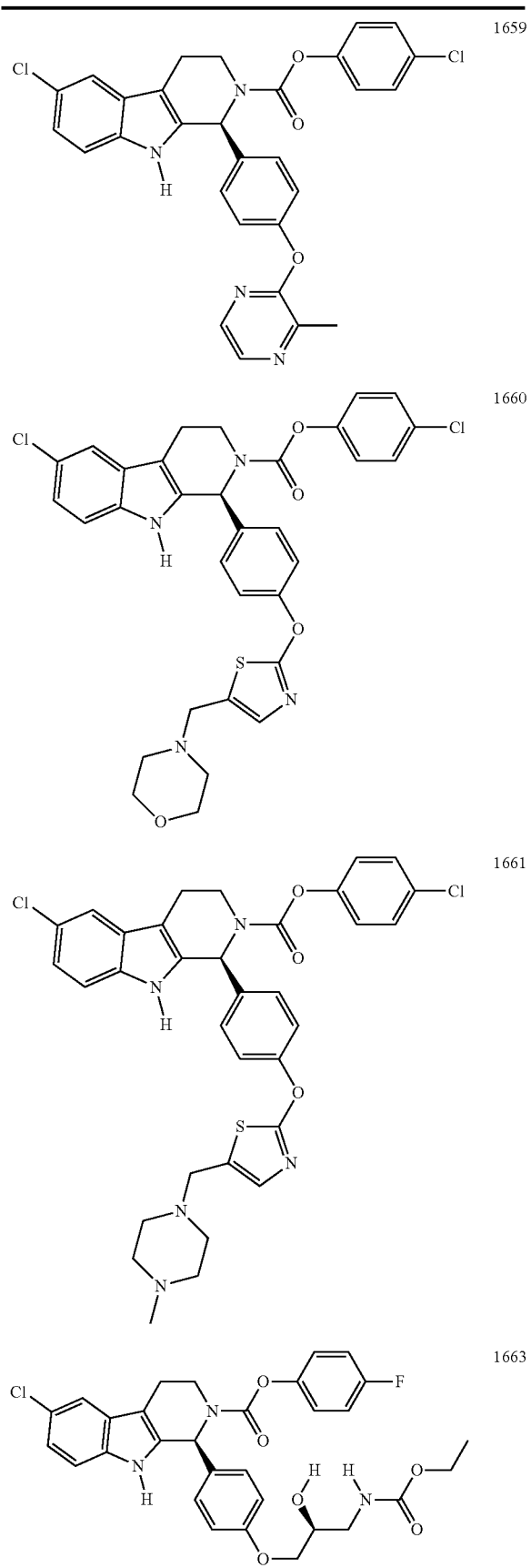
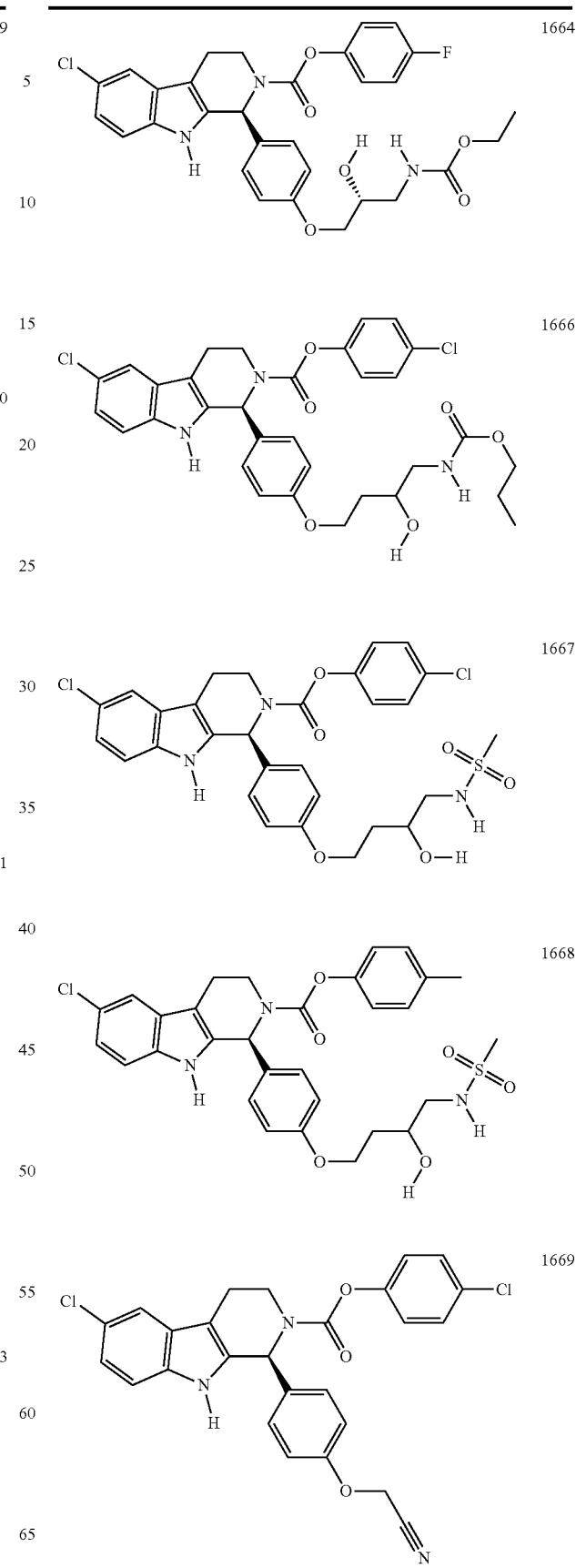

TABLE 1-continued
1671
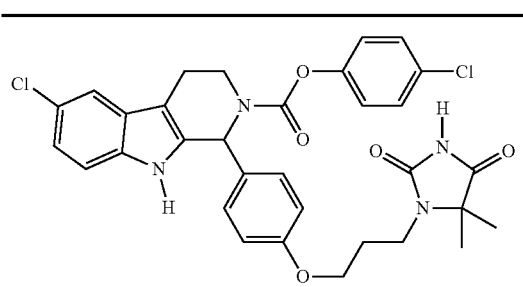
1672
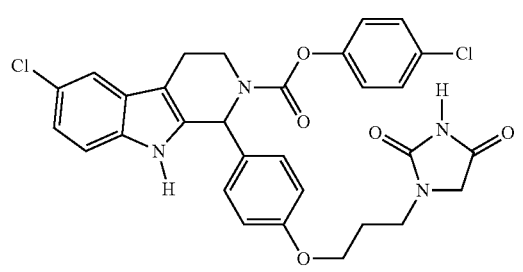 [SMILES: CN1C(=O)CN(CCCOc2ccc(C3c4[nH]c5ccc(Cl)cc5c4CCN3C(=O)Oc3ccc(Cl)cc3)cc2)C1=O]
1673
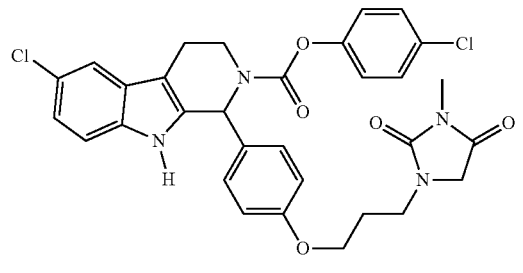
1674
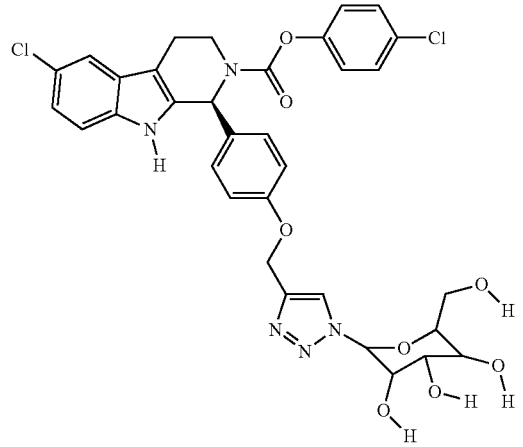 [SMILES: O=C(Oc1ccc(Cl)cc1)N1CCc2c([nH]c3ccc(Cl)cc23)[C@@H]1c1ccc(OCc2cn(C3OC(CO)C(O)C(O)C3O)nn2)cc1]
TABLE 1-continued
1675
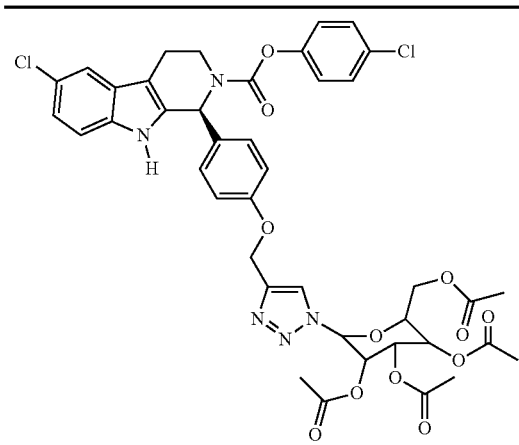
1676
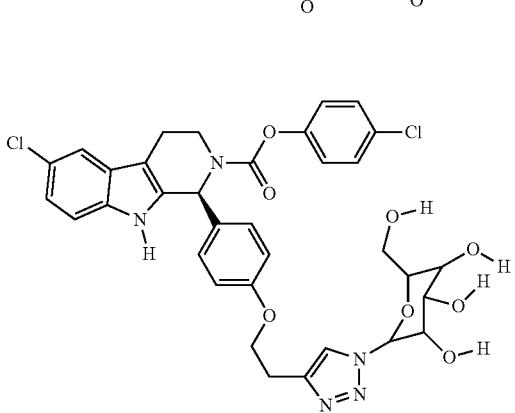
1677
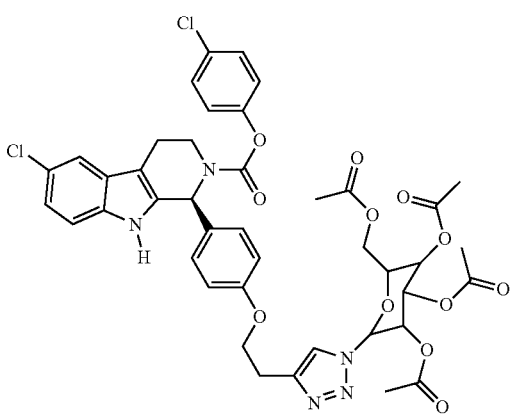 [SMILES: CC(=O)OCC1OC(n2cc(CCOc3ccc([C@H]4c5[nH]c6ccc(Cl)cc6c5CCN4C(=O)Oc4ccc(Cl)cc4)cc3)nn2)C(OC(C)=O)C(OC(C)=O)C1OC(C)=O]
1681
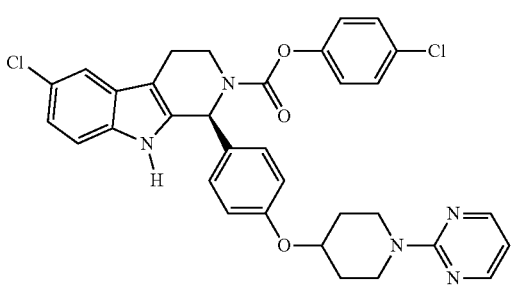 [SMILES: O=C(Oc1ccc(Cl)cc1)N1CCc2c([nH]c3ccc(Cl)cc23)[C@@H]1c1ccc(OC2CCN(c3ncccn3)CC2)cc1]

TABLE 1-continued
1682
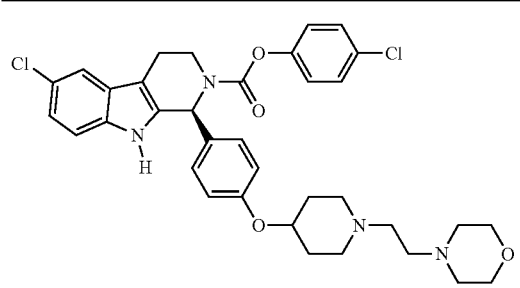
1693
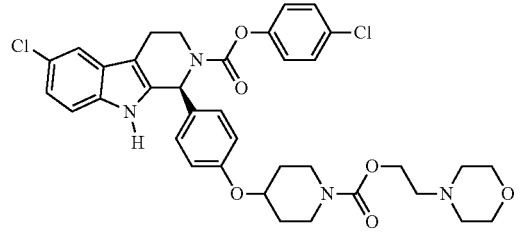 [SMILES: O=C(OCCN1CCOCC1)N1CCC(Oc2ccc([C@H]3c4[nH]c5ccc(Cl)cc5c4CCN3C(=O)Oc3ccc(Cl)cc3)cc2)CC1]
1694
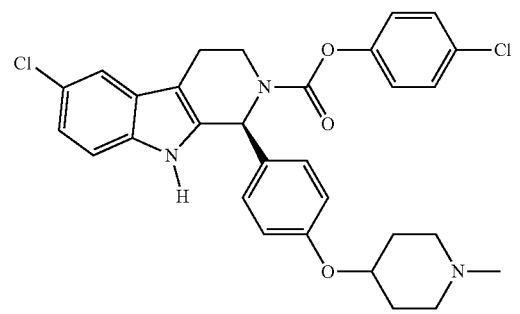 [SMILES: CN1CCC(Oc2ccc([C@H]3c4[nH]c5ccc(Cl)cc5c4CCN3C(=O)Oc3ccc(Cl)cc3)cc2)CC1]
1695
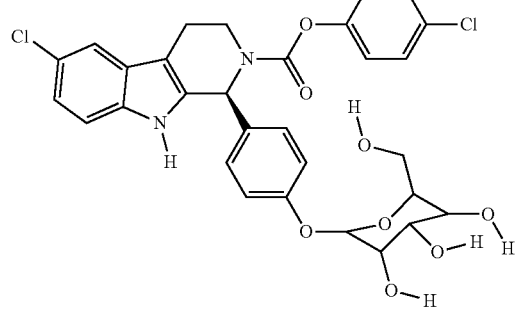
1698
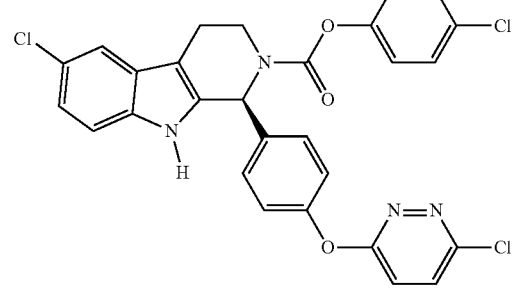
TABLE 1-continued
1701
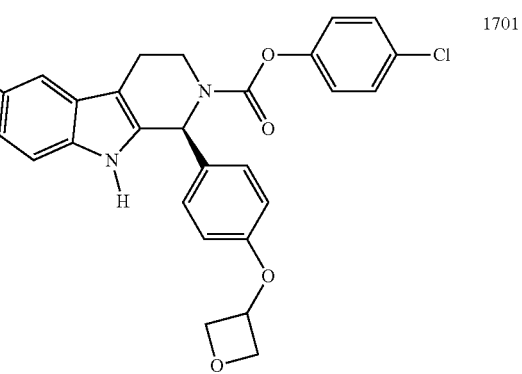
1702
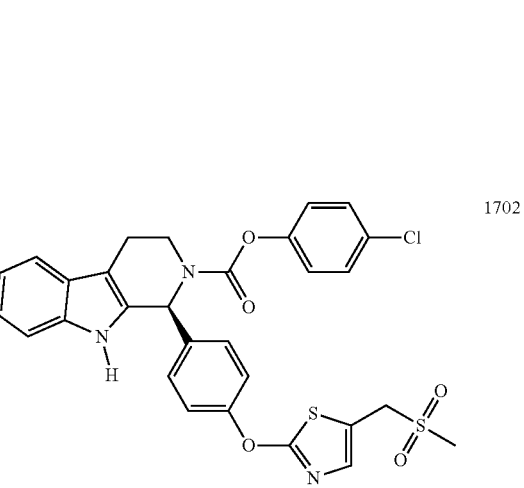
1703
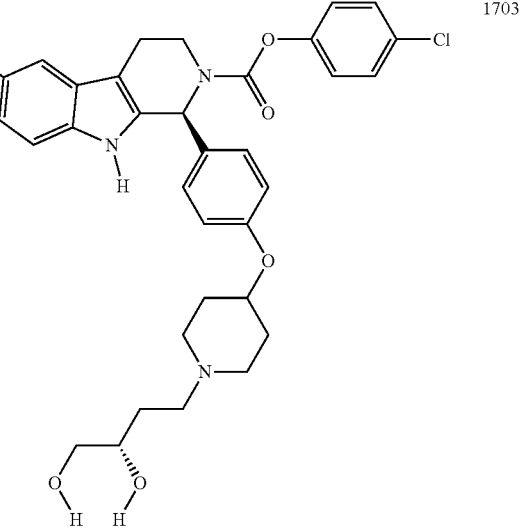

TABLE 1-continued
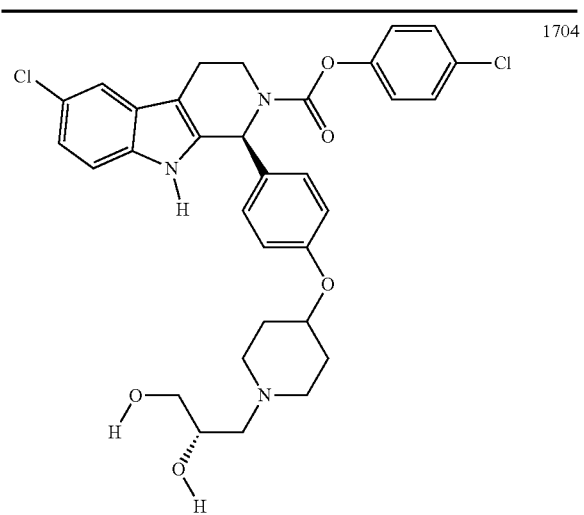
1704
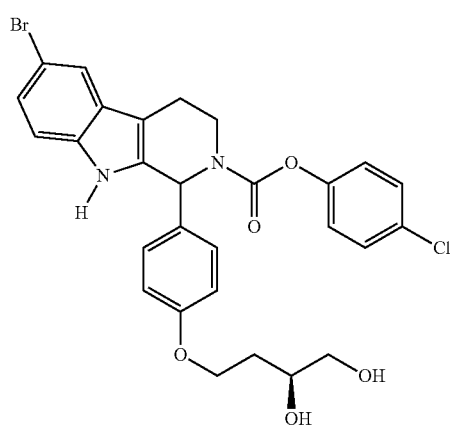
1725
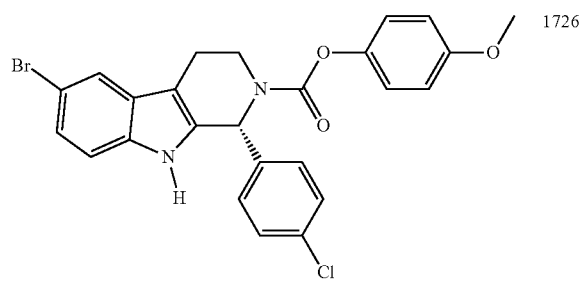
1726
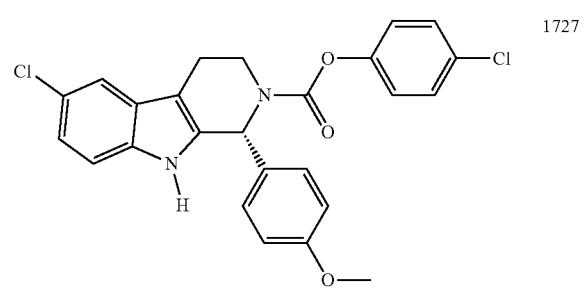
1727
TABLE 1-continued
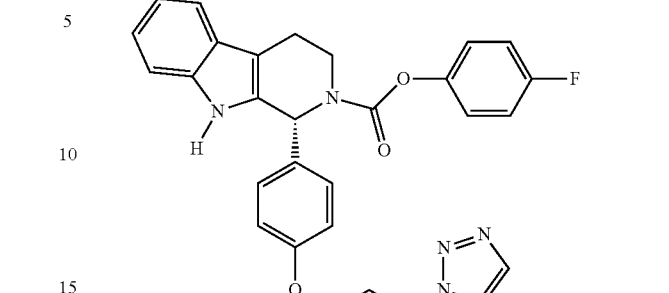
1728
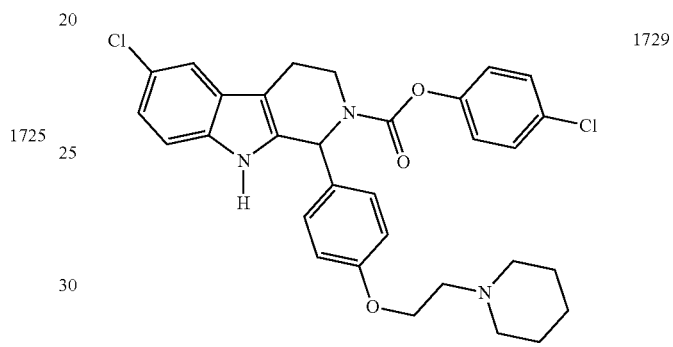
1729
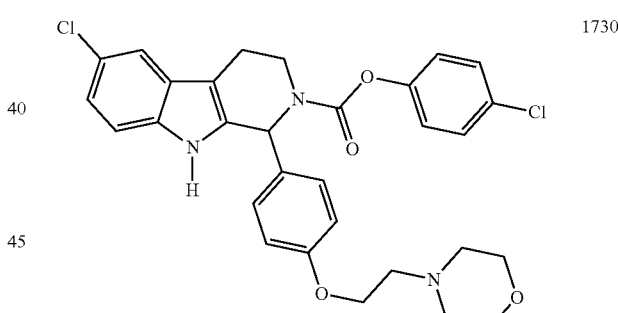
1730
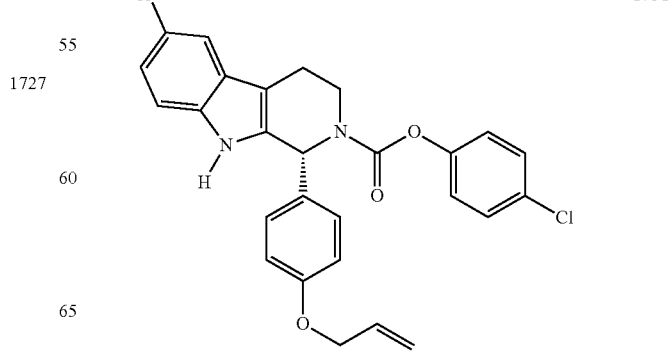
1731

TABLE 1-continued
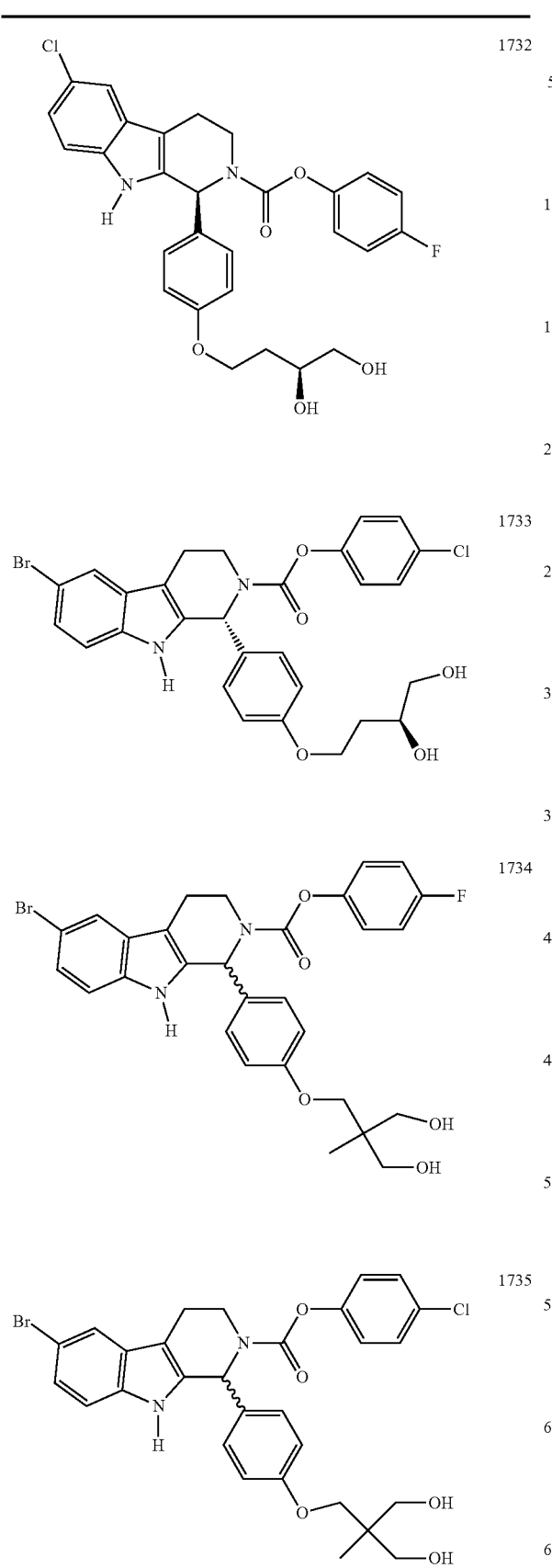
TABLE 1-continued
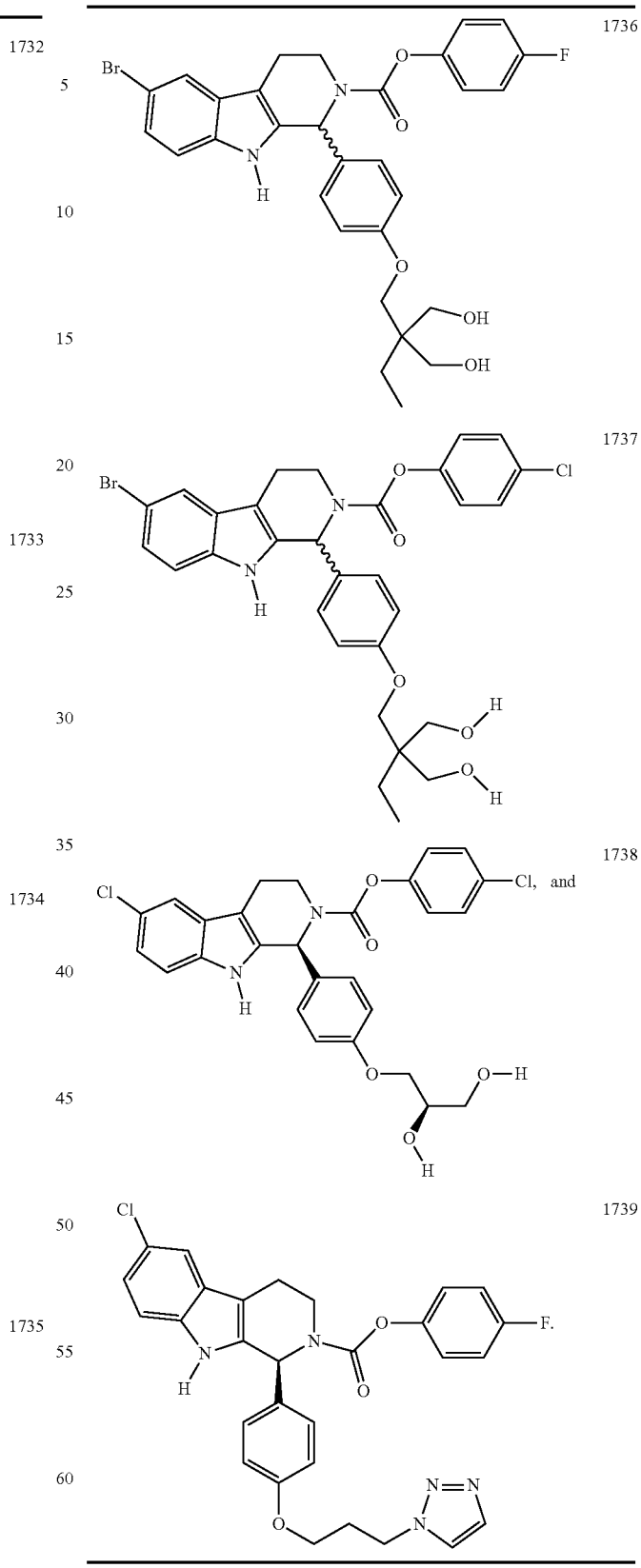
In a further embodiment, additional examples of the Compounds provided herein are disclosed in International Patent Application Publication No. WO2005/089764 ("'764 publication") on pages 26 to 98, and in copending U.S. Provisional Patent Application 61/181,653, entitled: METHODS FOR TREATING CANCER AND NON-NEOPLASTIC CONDITIONS, filed May 27, 2009, each of which are incorporated by reference herein in their entirety. Methods for preparing certain Compounds provided herein and the Compounds disclosed on pages 26 to 98 of the '764 publication are provided on pages 99 to 105 and 112 to 142 of the '764 publication and are incorporated by reference herein in their entirety and for all purposes. Methods for preparing certain Compounds provided herein and the Compounds disclosed in copending U.S. Provisional Patent Application 61/181,652, entitled: PROCESSES FOR THE PREPARATION OF SUBSTITUTED TETRAHYDRO BETA-CARBOLINES, filed May 27, 2009, are provided therein and are incorporated by reference herein in their entirety and for all purposes.

5.2 Pharmaceutical Properties and Formulations 5.2.1 Activity

Without being bound by any theory, Compounds described herein inhibit the translation of pathologically expressed human VEGF mRNA and, thus, inhibit the pathologic production of human VEGF protein. In particular, the Compounds act specifically through a mechanism dependent on the 5' untranslated region (UTR) of the human VEGF mRNA to inhibit the pathologic production of human VEGF protein. The activity of the Compounds tested is post-transcriptional since quantitative real-time polymerase chain reaction (PCR) assessments of mRNA have shown that the Compounds do not alter the levels of human VEGF mRNA. Analyses of the effects of the Compounds tested on ribosome association with VEGF transcripts indicate that the Compounds do not impede initiation of VEGF translation or promote dissociation of ribosomes from human VEGF mRNA.

5.2.1.1 Inhibition of pathological VEGF production

Compounds are described that reduce or inhibit pathologic production of human VEGF (also known as VEGF-A and vascular permeability factor (VPF)). Exemplary Compounds have been shown to reduce or inhibit tumor production of VEGF as measured in cell culture and/or preclinical tumor models. Furthermore, the Compounds tested do not affect homeostatic, physiologically produced plasma VEGF levels in healthy humans.

By way of background, the human VEGF-A gene encodes a number of different products (isoforms) due to alternative splicing. The VEGF-A isoforms include $VEGF_{121}$, $VEGF_{165}$, $VEGF_{189}$ and $VEGF_{206}$ having 121, 165, 189 and 206 amino acids, respectively. $VEGF_{165}$ and $VEGF_{121}$ isoforms are soluble, whereas $VEGF_{189}$ and $VEGF_{206}$ isoforms are sequestered within the extracellular matrix. The activity of the Compounds tested was assessed by measuring the concentrations of soluble VEGF and/or extracellular matrix bound-VEGF in cell culture systems. In preclinical tumor models, the activity of the Compounds tested was assessed by measuring the concentrations of soluble VEGF. The data indicate that the Compounds tested inhibit the production of soluble as well as matrix associated forms of tumor derived VEGF.

In particular, a Compound provided herein has been shown to selectively inhibit stress (e.g., hypoxia) induced production of soluble human VEGF isoforms in cell culture without affecting soluble human VEGF production under normoxic conditions (see Sections 9.1.1.1 and 9.1.1.2). Thus, the Compound was shown to preferentially inhibit pathological production of soluble human VEGF isoforms resulting from hypoxia while sparing homeostatic production of soluble isoforms in unperturbed cells. Accordingly, in specific embodiments, a Compound selectively inhibits or reduces the pathological production of a soluble human VEGF isoform over inhibiting or reducing physiological production of a soluble human VEGF isoform.

A Compound provided herein has also shown to selectively inhibit pathological production of VEGF in tumor cells that constitutively overproduce VEGF even under normoxic conditions. See Section 9.1.1.3. In these studies, to better assess the Compound's activity, the inhibition of the pathological production of matrix-bound human VEGF was measured. Thus, in one embodiment, a Compound selectively inhibits or reduces the pathological production of a matrix-bound human VEGF isoform over inhibiting or reducing physiological production of a matrix-bound human VEGF isoform.

The ability of a Compound provided herein to inhibit pathologic production of human VEGF in cell culture has been demonstrated for multiple human tumor cells from a variety of different tissues. See Table 4 (Section 9.1.1.4).

Exemplary Compounds inhibited intratumoral and pathologic plasma human VEGF production in animal models with pre-established human tumors. See Sections 9.1.2.1 to 9.1.2.3. In addition to reducing pathological induced human VEGF concentrations and edema, inflammation, pathological angiogenesis and tumor growth, a Compound provided herein has been shown to selectively reduce intratumoral levels of human growth factors and cytokines, such as IL-6, IL-8, osteopontin, MCP-1 and VEGF family members including human VEGF-C, VEGF-D and placental growth factor (P1GF). See Sections 9.1.2.1. In particular, the Compound shows a dose-dependent reduction in the concentration of intratumoral and pathologic plasma soluble human VEGF isoforms (see Section 9.1.2.2, in particular FIG. 5 and FIG. 6). Accordingly, in specific embodiments, a Compound provided herein, selectively inhibits or reduces the pathological production of one or more human VEGF family members. See Section 9.1.2.1.

5.2.1.2 Inhibition of Pathological Angiogenesis and Tumor Growth

Compounds are described that reduce or inhibit edema, inflammation, pathological angiogenesis and tumor growth. A Compound provided herein has been shown to have a profound effect on the architecture of the tumor vasculature in animal models with pre-established human tumors. The Compound reduced the total volume and diameter of blood vessels formed compared to vehicle treated subjects. See Section 9.2.1. The Compound also showed inhibition of tumor growth in the same model. A dose-response effect of the Compound that correlated with decreases in tumor and pathologic plasma VEGF concentrations was observed when tumor size was assessed. See Section 9.2.2. Thus, in one embodiment, the concentration of soluble pathologically produced VEGF in human plasma may be used to assess and monitor the pharmacodynamic effect of a Compound provided herein. In a specific embodiment, the concentration of either $VEGF_{121}$, $VEGF_{165}$, or both in human plasma may be used to assess and monitor the pharmacodynamic effect of a Compound provided herein.

In concert with a decrease in pathological tumor induced production of VEGF, a Compound provided herein demonstrated tumor regression or delay of tumor growth in various xenograft models, including models of breast cancer, neuroblastoma, and prostate cancer. See Section 9.2.5. Compounds that inhibit tumor growth in multiple preclinical models are more likely to have clinical efficacy. See Johnson et al., Br. J. Cancer 2001, 84(10):1424-31. Further, a Compound provided herein has shown activity in an orthotopic SY5Y neuroblastoma and SKNEP ewing sarcoma tumor model. In orthotopic tumor models, human tumor cells are implanted into the mouse in an organ that corresponds to the location of the human cells from which a tumor would arise. Such models may provide a better predictor of clinical efficacy than injection of tumors into the flanks of nude mice. See Hoffman, *Invest. New Drugs* 1999, 17(4):343-59. See Section 9.2.5.6.

An in vivo study in rats administered a $^{14}$C-radiolabeled Compound provided herein has been shown that the Compound penetrates all tissues investigated after oral administration. See Section 9.2.6 and Table 23. In one embodiment, a Compound provided herein is able to penetrate cells, tissues or organs that are surrounded by an endothelial cell barrier. In a specific embodiment, a Compound penetrates endothelial cell barriers, such as, but not limited to, the blood-brain barrier, the blood-eye barrier, the blood-testes barrier, blood-uterus barrier, or the blood-ovary barrier. The cells, tissues or organs surrounded by an endothelial cell barrier are, for example, cerebellum, cerebrum, ovary, testis, or the eye. The ability of a Compound to traverse such endothelial barriers makes it suited for the treatment of cancers, such as brain cancers, including but not limited to glioblastoma or neurofibromatosis.

5.2.1.3 Prolongation of Early $G_1$/Early S-Phase Cell Cycle Delay

Provided herein are Compounds that provoke a delay or prolongation of the cell cycle.

In addition to its effects on pathological VEGF production, a Compound provided herein induces a late $G_1$/early S-Phase cell cycle delay, i.e., between the late resting or pre-DNA synthesis phase, and the early in DNA synthesis phase in those tumor cell lines in which pathologic VEGF expression is decreased by the Compound. Further characterization indicates that this effect is concentration dependent, occurring at low nanomolar $EC_{50}$ values similar to those associated with reducing pathological VEGF production. See Section 9.3.1.1. The effect seen is reversible upon cessation of exposure to a Compound. See Section 9.3.1.2. The cell cycle delay and inhibition of pathological VEGF protein production occur in concert, linking these phenotypes in inflammation, pathological angiogenesis and tumor growth. Inhibition of pathological VEGF production in the same tumor cells used herein with small interfering RNA (siRNA) does not induce a delay or prolongation of the cell cycle (data not shown). Conversely, the use of mimosine, a DNA synthesis inhibitor that halts cell cycle progression at the $G_1$/S interface, does not delay or prolong the cell cycle or reduce VEGF production (data not shown). A Compound provided herein has demonstrated in an in vivo HT1080 xenograft model that the Compound delays cycling through the S-phase; an effect that is distinct from that of bevacizumab, which has no effect on tumor cell cycling. Thus, these experiments indicate that the effects of a Compound on the tumor cell cycle occur in parallel with its actions on pathological VEGF production in tumors.

5.2.2 Formulations 5.2.2.1 General Formulation Methods

The Compounds provided herein can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient selected from fillers or diluents, binders, disintegrants, lubricants, flavoring agents, preservatives, stabilizers, suspending agents, dispersing agents, surfactants, antioxidants or solubilizers.

Excipients that may be selected are known to those skilled in the art and include, but are not limited to fillers or diluents (e.g., sucrose, starch, mannitol, sorbitol, lactose, glucose, cellulose, talc, calcium phosphate or calcium carbonate and the like), a binder (e.g., cellulose, carboxymethylcellulose, methylcellulose, hydroxymethylcellulose, hydroxypropylmethylcellulose, polypropylpyrrolidone, polyvinylpyrrolidone, gelatin, gum arabic, polyethyleneglycol or starch and the like), a disintegrant (e.g., sodium starch glycolate, croscarmellose sodium and the like), a lubricant (e.g., magnesium stearate, light anhydrous silicic acid, talc or sodium lauryl sulfate and the like), a flavoring agent (e.g., citric acid, or menthol and the like), a preservative (e.g., sodium benzoate, sodium bisulfite, methylparaben or propylparaben and the like), a stabilizer (e.g., citric acid, sodium citrate or acetic acid and the like), a suspending agent (e.g., methylcellulose, polyvinyl pyrrolidone or aluminum stearate and the like), a dispersing agent (e.g., hydroxypropylmethylcellulose and the like), surfactants (e.g., sodium lauryl sulfate, polaxamer, polysorbates and the like), antioxidants (e.g., ethylene diamine tetraacetic acid (EDTA), butylated hydroxyl toluene (BHT) and the like) and solubilizers (e.g., polyethylene glycols, SOLUTOL®, GELUCIRE® and the like). The effective amount of the Compound provided herein in the pharmaceutical composition may be at a level that will exercise the desired effect. Effective amounts contemplated are further discussed in Section 5.4.

The dose of a Compound provided herein to be administered to a patient is rather widely variable and can be subject to the judgment of a health-care practitioner. In general, a Compound provided herein can be administered one to four times a day. The dosage may be properly varied depending on the age, body weight and medical condition of the patient and the type of administration. In one embodiment, one dose is given per day. In any given case, the amount of the Compound provided herein administered will depend on such factors as the solubility of the active component, the formulation used and the route of administration.

A Compound provided herein can be administered orally, with or without food or liquid.

The Compound provided herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, the Compound provided herein is administered orally using a capsule dosage form composition, wherein the capsule contains the Compound provided herein without an additional carrier, excipient or vehicle.

In another embodiment, provided herein are compositions comprising an effective amount of a Compound provided herein and a pharmaceutically acceptable carrier or vehicle, wherein a pharmaceutically acceptable carrier or vehicle can comprise one or more excipients, or a mixture thereof. In one embodiment, the composition is a pharmaceutical composition.

Compositions can be formulated to contain a daily dose, or a convenient fraction of a daily dose, in a dosage unit. In general, the composition is prepared according to known methods in pharmaceutical chemistry. Capsules can be prepared by mixing a Compound provided herein with one or more suitable carriers or excipients and filling the proper amount of the mixture in capsules.

5.2.2.2 Lipid-Based Formulation Methods

One embodiment, provided herein is a SEDDS or SMEDDS system comprising a Compound provided herein (e.g., an effective amount of a composition provided herein), and a carrier medium comprising a lipophilic component, a surfactant, and optionally a hydrophilic component. In certain embodiments, the present disclosure provides a SEDDS or SMEDDS system comprising a Compound provided herein, and a carrier medium comprising one or more surfactants and optionally one or more additives.

In certain embodiments, the SEDDS or SMEDDS system is suitable for oral administration.

One embodiment, provided herein is a SEDDS or SMEDDS system comprising a representative Compound provided herein and a carrier medium that comprises a lipophilic component, a surfactant, optionally a hydrophilic component and optionally an additive.

In one embodiment, the SEDDS or SMEDDS system forms an o/w (oil-in-water) microemulsion when diluted with water.

In one embodiment, of a SEDDS or SMEDDS system provided herein is a microemulsion comprising a Compound provided herein. In certain embodiments, the microemulsion is an o/w (oil-in-water) microemulsion. In one embodiment, the microemulsion comprises a Compound provided herein, a lipophilic component, a surfactant, water, and optionally a hydrophilic component and optionally an additive. In one embodiment, the microemulsion comprises a Compound provided herein, a lipophilic component, a surfactant, and water. In one embodiment, the microemulsion comprises a Compound provided herein, a surfactant, water, and optionally an additive.

The colloidal structures of the microemulsion form spontaneously or substantially spontaneously when the components of the SEDDS or SMEDDS system are brought into contact with an aqueous medium, e.g., by simple shaking by hand for a short period of time, for example for about 10 seconds. The SEDDS or SMEDDS system provided herein is thermodynamically stable, e.g., for at least 15 minutes or up to 4 hours, even to 24 hours. Typically, the system contains dispersed structures, i.e., droplets or liquid nanoparticles of a mean diameter less than about 200 nm (2,000 Å), e.g., less than about 150 nm (1,500 Å), typically less than about 100 nm (1,000 Å), generally greater than about 10 nm (100 Å) as measured by standard light scattering techniques, e.g., using a MALVERN ZETASIZER 300™ particle characterizing machine. Solid drug particles of mean diameter greater than 200 nm may also be present. The proportion of particles present may be temperature dependent.

In accordance with the present disclosure, Compounds provided herein may be present in an amount of up to about 20% by weight of the SEDDS or SMEDDS system provided herein, e.g., from about 0.05% by weight. In one embodiment, the Compound provided herein is present in an amount of from about 0.05 to about 15% by weight of the composition, or in an amount of from about 0.1 to about 5% by weight of the SEDDS or SMEDDS system.

In some embodiments, the SEDDS or SMEDDS system provided herein further comprises a carrier medium having a lipophilic component and a surfactant. In other embodiments, the carrier medium also comprises a lipophilic component, a hydrophilic component and a surfactant. In further embodiments, the carrier medium may comprise a surfactant. In some embodiments, the carrier medium also comprises a surfactant and an additive. In certain embodiments, the Compound provided herein can reside in the lipophilic component or phase.

In some embodiments, the SEDDS or SMEDDS system, the carrier medium, and the microemulsion comprise one or more lipophilic substances. In certain embodiments, the SEDDS or SMEDDS system, the carrier medium, and the microemulsion comprise one or more hydrophilic substances. In other embodiments, the SEDDS or SMEDDS system, the carrier medium, and the microemulsion comprise one or more surfactants. In further embodiments, the SEDDS or SMEDDS system, the carrier medium, and the microemulsion comprise one or more additives.

The compositions provided herein can include a variety of additives including antioxidants, antimicrobial agents, enzyme inhibitors, stabilizers, preservatives, flavors, sweeteners and further components known to those skilled in the art.

A. Lipophilic Components

Lipophilic components include, but are not limited to:

A1) Medium Chain Fatty Acid Triglyceride

These include, but are not limited to, triglycerides of saturated fatty acid having 6 to 12, e.g. 8 to 10, carbon atoms. In one embodiment, the medium chain fatty acid triglycerides include, but are not limited to, those known and commercially available under the trade names ACOMED®, LABRAFAC®, MYRITOL®, CAPTEX®, NEOBEE®M 5 F, MIGLYOL®810, MIGLYOL®812, MIGLYOL®818, MAZOL®, SEFSOL®860, SEFSOL®870. In one embodiment, the lipophilic component is LABRAFAC®. In one embodiment, the lipophilic component is LABRAFAC®CC. In another embodiment, the lipophilic component is LABRAFAC®WL1349.

A2) Propylene Glycol Mono Fatty Acid Esters

The fatty acid constituent may include, but is not limited to, both saturated and unsaturated fatty acids having a chain length of from e.g. $C_8$-$C_{12}$. In one embodiment, the fatty acid is propylene glycol mono ester of caprylic and lauric acid as commercially available, e.g. under the trade names SEFSOL® 218, Capryol®90 or LAUROGLYCOL®90, from e.g. Nikko Chemicals Co., Ltd. or Gattefosse or Capmul PG-8 from Abitec Corporation.

A3) Propylene Glycol Mono- and Di-Fatty Acid Esters

These include, but are not limited to, Laroglycol FCC and Capryol PGMC.

A4) Propylene Glycol Diesters

These include, but are not limited to, propylene glycol di-fatty acid esters such as propylene glycol dicaprylate (which is commercially available under the trade name MIGLYOL® 840 from e.g. sasol; Fiedler, H. P. "Lexikon der Hilfsstoffe für Pharmazie, Kosmetik and angrenzende Gebiete", Edition Cantor, D-7960 Aulendorf, 4th revised and expanded edition (1996), volume 2, page 1008) or Captex 200 from Abitec Corporation.

A5) Propylene Glycol Monoacetate and Propylene Glycol

A6) Transesterified Ethoxylated Vegetable Oils

Transesterified ethoxylated vegetable oils are known and are commercially available under the trade name LABRAFIL® (H. Fiedler, loc. cit., vol 2, page 880). Examples are LABRAFIL® M 2125 CS (obtained from corn oil and having an acid value of less than about 2, a saponification value of 155 to 175, an HLB value of 3 to 4, and an iodine value of 90 to 110), and LABRAFIL® M 1944 CS (obtained from kernel oil and having an acid value of about 2, a saponification value of 145 to 175 and an iodine value of 60 to 90). LABRAFIL® M 2130 CS (which is a transesterification product of a $C_{12}$-$C_{18}$ glyceride and polyethylene glycol and which has a melting point of about 35 to about 40° C., an acid value of less than about 2, a saponification value of 185 to 200 and an iodine value of less than about 3) may also be used. LABRAFIL® lipophilic components can be obtained, for example, from Gattefossé (Paramus, N.J., USA).

In one embodiment, the alkylene polyol ethers or esters include products obtainable by transesterification of glycerides, e.g. triglycerides, with poly-($C_2$-$C_4$ alkylene) glycols, e.g. poly-ethylene glycols and, optionally, glycerol. Such transesterification products are generally obtained by alcoholysis of glycerides, e.g. triglycerides, in the presence of a poly-($C_2$—$C_4$ alkylene) glycol, e.g. polyethylene glycol and, optionally, glycerol (i.e. to effect transesterification from the glyceride to the poly-alkylene glycol/glycerol component, i.e. via poly-alkylene glycolysis/glycerolysis). In general such reaction is effected by reacting the indicated components (glyceride, polyalkylene glycol and, optionally, glycerol) at elevated temperature under an inert atmosphere with continuous agitation.

In one embodiment, the glycerides are fatty acid triglycerides, e.g. ($C_{10}$-$C_{22}$ fatty acid) triglycerides, including natural and hydrogenated oils, in particular vegetable oils. In one embodiment, vegetable oils include, for example, olive, almond, peanut, coconut, palm, soybean and wheat germ oils and, in particular, natural or hydrogenated oils rich in ($C_{12}$-$C_{18}$ fatty acid) ester residues. In one embodiment, polyalkylene glycol materials are polyethylene glycols, in particular polyethylene glycols having a molecular weight of from ca. 500 to ca. 4,000, e.g. from ca. 1,000 to ca. 2,000.

In one embodiment, alkylene polyol ethers or esters include, but are not limited to, mixtures of $C_3$-$C_5$ alkylene triol esters, e.g. mono-, di- and tri-esters in variable relative amount, and poly ($C_2$-$C_4$ alkylene) glycol mono- and di-esters, together with minor amounts of free $C_3$-$C_5$ alkylene triol and free poly-($C_2$-$C_5$ alkylene) glycol. As hereinabove set forth, in one embodiment, the alkylene triol moiety is glyceryl; in another embodiment, the polyalkylene glycol moieties include, but are not limited to, polyethylene glycol, in certain embodiments, having a molecular weight of from ca. 500 to ca. 4,000; and in another embodiment, the fatty acid moieties will be $C_{10}$-$C_{22}$ fatty acid ester residues, in certain embodiments, saturated $C_{10}$-$C_{22}$ fatty acid ester residues.

In one embodiment, the alkylene polyol ethers or esters include transesterification products of a natural or hydrogenated vegetable oil and a polyethylene glycol and, optionally, glycerol; or compositions comprising or consisting of glyceryl mono-, di- and tri-$C_{10}$-$C_{22}$ fatty acid esters and polyethylene glycol mono- and di-$C_{10}$-$C_{22}$ fatty esters (optionally together with, e.g. minor amounts of free glycerol and free polyethylene glycol).

In one embodiment, the alkylene polyol ethers or esters include, but are not limited, those commercially available under the trade name GELUCIRE® from e.g. Gattefossé, in particular the products:

a) GELUCIRE® 33/01, which has an m.p.=ca. 33-37° C. and a saponification value of about 230-255;

b) GELUCIRE® 39/01, m.p.=ca. 37.5-41.5° C., saponification value of about 225-245; and c) GELUCIRE® 43/01, m.p.=ca. 42-46° C., saponification value of about 220-240.

Products (a) to (c) above all have an acid value of maximum of 3. The SEDDS or SMEDDS system provided herein may include mixtures of such ethers or esters.

B. Surfactants

The SEDDS or SMEDDS system provided herein can contain one or more surfactants to reduce the emulsion's interfacial tension thereby providing thermodynamic stability. Surfactants may be complex mixtures containing side products or unreacted starting products involved in the preparation thereof, e.g. surfactants made by polyoxyethylation may contain another side product, e.g. polyethylene glycol.

In one embodiment, surfactants include, but are not limited to:

B1) Polyoxyethylene Mono Esters of a Saturated $C_{10}$ to $C_{22}$ Polymer

These include, but are not limited to, $C_{11}$ substituted e.g. hydroxy fatty acid; e.g. 12 hydroxy stearic acid PEG ester, e.g. of PEG about e.g. 600-900, e.g. 660 Daltons MW, e.g. SOLUTOL®HS15 from BASF (Ludwigshafen, Germany). SOLUTOL®HS15, according to the BASF technical information (July 2003), comprises polyglycol mono- and di-esters of 12-hydroxystearic acid (=lipophilic part) and about 30% of free polyethylene glycol (=hydrophilic part). A small part of the 12-hydroxy group can be etherified with polyethylene glycol. SOLUTOL® HS15 has a hydrogenation value of 90 to 110, a saponification value of 53 to 63, an acid number of maximum 1, an iodine value of maximum 2, and a maximum water content of about 0.5% by weight. In one embodiment, the surfactant is SOLUTOL® HS15.

B2) Alkylene Polyol Ethers or Esters

In one embodiment, the alkylene polyol ethers or esters as described above for use in the pharmaceutical compositions provided herein include those commercially available under the trade name GELUCIRE® from e.g. Gattefossé (Paramus, N.J., USA), in particular the products:

a) GELUCIRE® 44/14, m.p.=ca. 42.5-47.5° C., saponification value of about 79-93;

b) GELUCIRE® 50/13, m.p.=ca. 46-51° C., saponification value of about 67-81;

Products (a) to (b) above both have an acid value of maximum of 2.

In one embodiment, the alkylene polyol ethers or esters have an iodine value of maximum 2. The SEDDS or SMEDDS system provided herein may further include mixtures of such ethers or esters.

GELUCIRE® products are inert semi-solid waxy materials with amphiphilic character. They are identified by their melting point and their HLB value. Most GELUCIRE® grades are saturated polyglycolised glycerides obtainable by polyglycolysis of natural hydrogenated vegetable oils with polyethylene glycols. They are composed of a mixture of mono-, di- and tri-glycerides and mono- and di-fatty acid esters of polyethylene glycol. In one embodiment, the $C_{10}$ glyceride is GELUCIRE® 44/14 which has a nominal melting point of 44° C. and an HLB of 14. GELUCIRE® 44/14 exhibits the following additional characterizing data: acid value of max. 2, iodine value of max. 2, saponification value of 79-93, hydroxyl value of 36-56, peroxide value of max. 6, alkaline impurities max. 80, water content max. 0.50, free glycerol content max. 3, monoglycerides content 3.0-8.0. (H. Fiedler, loc. cit., vol 1, page 676; manufacturer information).

In one embodiment, the surfactant is present in a range of from about 5 to about 99.9% by weight, or in a range of from about 30% to about 99.9% of the SEDDS or SMEDDS system provided herein.

In one embodiment, the surfactant comprises about 30% to about 70%, or about 40% to about 60% by weight of the carrier medium of the SEDDS or SMEDDS system provided herein.

In one embodiment, the SEDDS or SMEDDS system provided herein include additives e.g. antioxidants, flavors, sweeteners and other components known to those skilled in the art.

In one embodiment, the antioxidants include ascorbyl palmitate, butylated hydroxy anisole (BHA), 2,6-di-tert-butyl-4-methyl phenol (BHT) and tocopherols. In a further embodiment, the antioxidant is BHT.

In one embodiment, these additives may comprise about 0.005% to about 5% or about 0.01% to about 0.1% by weight of the total weight of the SEDDS or SMEDDS system. Antioxidants, or stabilizers typically provide up to about 0.005 to about 1% by weight based on the total weight of the composition. Sweetening or flavoring agents typically provide up to about 2.5% or 5% by weight based on the total weight of the composition.

The aforementioned additives can also include components that act as surfactants to solidify a liquid micro-emulsion pre-concentrate. These include solid polyethylene glycols (PEGs) and GELUCIRE® products, in one embodiment, the GELUCIRE® products include those such as GELUCIRE® 44/14 or GELUCIRE® 50/13.

When the SEDDS or SMEDDS system provided herein is combined with water or an aqueous solvent medium to obtain an emulsion, for example a microemulsion, the emulsion or microemulsion may be administered orally, for example in the form of a drinkable solution. The drinkable solution may comprise water or any other palatable aqueous system, such as fruit juice, milk and the like. In one embodiment, the relative proportion of the lipophilic component(s), the surfactant(s) and the hydrophilic component(s) lie within the "Microemulsion" region on a standard three way plot graph. The compositions will therefore be capable, on addition to an aqueous medium, of providing microemulsions, for example having a mean particle size of <200 nm.

In one embodiment, the carrier medium comprises about 30 to 70% by weight of one or more lipophilic components, wherein the one or more lipophilic components are a medium chain fatty acid triglyceride (A1), or a transesterified ethoxylated vegetable oil (A6). In a further embodiment, the medium chain fatty acid triglyceride (A1) is LABRAFAC® (Gattefossé, Paramus, N.J., USA). In another embodiment, the transesterified ethoxylated vegetable oil (A6) is LABRAFIL® (Gattefossé, Paramus, N.J., USA).

In one embodiment, the carrier medium comprises about 30 to 70% by weight of one or more surfactants, wherein the one or more surfactants are a polyoxyethylene mono ester ($C_5$), an alkylene polyol ether or ester ($C_{10}$), or a transesterified, polyoxyethylated caprylic-capric acid glyceride ($C_{13}$). In a further embodiment, the polyoxyethylene mono ester ($C_5$) is SOLUTOL® HS15 (BASF, Ludwigshafen, Germany). In another embodiment, the alkylene polyol ether or ester ($C_{10}$) is GELUCIRE®44/14 (Gattefosse, Paramus, N.J., USA). In yet another embodiment, the transesterified, polyoxyethylated caprylic-capric acid glyceride ($C_{13}$) is LABRASOL® (Gattefossé, Paramus, N.J., USA).

In one embodiment, the carrier medium comprises about 70% by weight LABRASOL®, about 18.3% by weight LABRAFAC® and about 11.7% by weight LABRAFIL®.

In one embodiment, the carrier medium comprises a range of about 65.1% to about 74.9% by weight LABRASOL®, a range of about 17.0% to about 19.6% by weight LABRAFAC® and a range of about 10.9% to about 12.5% by weight LABRAFIL®.

In one embodiment, the carrier medium comprises about 35% by weight LABRASOL®, about 35% by weight LABRAFAC® and about 30% by weight SOLUTOL® HS15.

In one embodiment, the carrier medium comprises a range of about 33.6% to about 37.4% by weight LABRASOL®, a range of about 33.6% to about 37.4% by weight LABRAFAC® and a range of about 27.9% to about 32.1% by weight SOLUTOL® HS15.

In one embodiment, the carrier medium comprises about 35% by weight LABRAFIL®, about 35% by weight LABRAFAC®, and about 30% by weight SOLUTOL®HS15.

In one embodiment, the carrier medium comprises a range of about 33.6% to about 37.4% by weight LABRAFIL®, a range of about 33.6% to about 37.4% by weight LABRAFAC®, and a range of about 27.9% to about 32.1% by weight SOLUTOL®HS15.

In one embodiment, the carrier medium comprises about 35% by weight GELUCIRE®44/14, about 35% by weight LABRAFAC®, and about 30% by weight SOLUTOL®HS15.

In one embodiment, the carrier medium comprises a range of about 33.6% to about 37.4% by weight GELUCIRE®44/14, a range of about 33.6% to about 37.4% by weight LABRAFAC®, and a range of about 27.9% to about 32.1% by weight SOLUTOL®HS15.

In one embodiment, provided herein is a SEDDS or SMEDDS system comprising a Compound provided herein, and a carrier medium comprising one or more surfactants. In one embodiment, the SEDDS or SMEDDS system additionally comprises an additive.

In one embodiment, the SEDDS or SMEDDS system comprises about 0.01% to about 5% by weight of a Compound provided herein.

In one embodiment, the dispersible pharmaceutical composition comprises about 95% to 99.09% by weight of one or more surfactants, wherein the one or more surfactants are selected from a group comprising an alkylene polyol ether or ester ($C_{10}$), and a polyoxyethylene mono ester ($C_5$). In a further embodiment, the alkylene polyol ether or ester ($C_{10}$) is GELUCIRE®44/14 (Gattefosse, Paramus, N.J., USA). In yet another embodiment, the polyoxyethylene mono ester ($C_5$) is SOLUTOL® HS15 (BASF, Ludwigshafen, Germany).

In one embodiment, the dispersible pharmaceutical composition comprises about 0.01% to about 0.1% by weight of an additive selected from a group comprising an antioxidant and a preservative. In a further embodiment, the additive is 2,6-di-tert-butyl-4-methylphenol (BHT).

In one embodiment, the SEDDS or SMEDDS system comprises about 0.28% by weight of a Compound provided herein, about 49.87% by weight of GELUCIRE®44/14, about 49.84% by weight of SOLUTOL®HS15 and about 0.01% by weight of BHT.

In one embodiment, the SEDDS or SMEDDS system comprises a range of about 0.26% to about 0.30% by weight of a Compound provided herein, a range of about 46.4% to about 53.4% by weight of GELUCIRE®44/14, a range of about 46.4% to about 53.3% by weight of SOLUTOL®HS15 and a range of about 0.009% to about 0.011% by weight of BHT.

In one embodiment, the SEDDS or SMEDDS system comprises about 1.43% by weight of a Compound provided herein, about 49.87% by weight of GELUCIRE®44/14, about 48.69% by weight of SOLUTOL®HS15 and about 0.01% by weight of BHT.

In one embodiment, the SEDDS or SMEDDS system comprises a range of about 1.33% to about 1.53% by weight of a Compound provided herein, a range of about 46.4% to about 53.4% by weight of GELUCIRE®44/14, a range of about 45.3% to about 52.1% by weight of SOLUTOL®HS15 and a range of about 0.009% to about 0.011% by weight of BHT.

In one embodiment, the SEDDS or SMEDDS system comprises about 2.67% by weight of a Compound provided herein, about 49.87% by weight of GELUCIRE®44/14, about 47.45% by weight of SOLUTOL®HS15 and about 0.01% by weight of BHT.

In one embodiment, the SEDDS or SMEDDS system comprises a range of about 2.48% to about 2.86% by weight of a Compound provided herein, a range of about 46.4% to about 53.4% by weight of GELUCIRE®44/14, a range of about 44.1% to about 50.8% by weight of SOLUTOL®HS15 and a range of about 0.009% to about 0.011% by weight of BHT.

In one embodiment, when the SEDDS or SMEDDS system provided herein is used to fill capsules for use in oral administration. The capsule may have a soft or hard capsule shell, for example, the capsule may be made of gelatine.

One group of SEDDS or SMEDDS systems provided herein may, on addition to water, provide aqueous microemulsions having an average particle size of about <200 nm (2,000 Å), about <150 nm (1,500 Å), or about <100 nm (1,000 Å).

In one embodiment, the SEDDS or SMEDDS systems provided herein exhibit advantageous properties when administered orally; for example in terms of consistency and high level of bioavailability obtained in standard bioavailability trials.

Pharmacokinetic parameters, for example, drug substance absorption and measured for example as blood levels, also can become more predictable and problems in administration with erratic absorption may be eliminated or reduced. Additionally pharmaceutical compositions provided herein are effective with biosurfactants or tenside materials, for example bile salts, being present in the gastro-intestinal tract. That is, pharmaceutical compositions provided herein are fully dispersible in aqueous systems comprising such natural tensides and thus capable of providing emulsion or microemulsion systems and/or particulate systems in situ which are stable. The function of pharmaceutical compositions provided herein upon oral administration remain substantially independent of and/or unimpaired by the relative presence or absence of bile salts at any particular time or for any given individual. Compositions provided herein may also reduce variability in inter- and intra-patient dose response.

In one embodiment, provided herein is a SEDDS or SMEDDS system comprising a Compound provided herein, and a carrier medium comprising one or more lipophilic components and one or more surfactants.

5.3 Patient Populations

In some embodiments, a subject treated for a prostate condition in accordance with the methods provided herein is a human who has or is diagnosed with a prostate condition. In other embodiments, a subject treated for a prostate condition in accordance with the methods provided herein is a human predisposed or susceptible to a prostate condition. In some embodiments, a subject treated for a prostate condition in accordance with the methods provided herein is a human at risk of developing a prostate condition. In specific embodiments, a subject treated for a prostate condition in accordance with the methods provided herein is human that meets one, two or more, or all of the criteria for subjects in the working examples in Section 11 et seq.

In some embodiments, a subject treated for a prostate condition in accordance with the methods provided herein has or is experiencing one or more of the following symptoms: the need to frequently urinate, waking up at night to urinate, unability to postpone urination, the feeling of being unable to empty bladder, a delay in starting to urinate, a weak urinary stream-straining, intermittent stream-stopping and starting urination, incontinence (loss of urinary control), painful urination, blood in urine, the inability to empty bladder (acute urinary retention), the inability to urinate, and/or prostate enlargement. In specific embodiments, a subject treated for prostate cancer in accordance with the methods provided herein has or is experiencing one or more of the following symptoms: painful ejaculation, continued pain in the bones, pain in the lower back, hips or upper thighs, liver pain, shortness of breath, loss of appetite, weight loss, cachexia, nausea, vomiting, fatigue, weakness, spinal cord compression, impaired brain function due to central nervous system metastases, prostate enlargement, and/or elevated PSA levels.

In specific embodiments, a subject treated for prostate cancer in accordance with the methods provided herein has a tumor in the prostate. In certain embodiments, a subject treated for prostate cancer in accordance with the methods provided herein has a cancer that metastasized to other areas of the body, such as the bones, lung and liver. In some embodiments, a subject treated for prostate cancer in accordance with the methods provided herein has castration-resistant prostate carcinoma. In certain embodiments, a subject treated for prostate cancer in accordance with the methods provided herein is in remission from prostate cancer. In some embodiments, a subject treated for prostate cancer in accordance with the methods provided herein that has a recurrence of prostate cancer.

In one embodiment, a subject treated for a prostate condition in accordance with the methods provided herein is a human male adult. In another embodiment, a subject treated for a prostate condition in accordance with the methods provided herein is a middle-aged human. In another embodiment, a subject treated for a prostate condition in accordance with the methods provided herein is an elderly human.

In certain embodiments, a subject treated for a prostate condition in accordance with the methods provided herein is a human that is about 18 to about 30 years old, about 25 to about 35 years old, about 35 to about 45 years old, about 40 to about 55 years old, about 50 to about 65 years old, about 60 to about 75 years old, about 70 to about 85 years old, about 80 to about 90 years old, about 90 to about 95 years old or about 95 to about 100 years old, or any age in between. In one embodiment, a subject treated for a prostate condition in accordance with the methods provided herein is a human that is 18 years old or older.

In particular embodiments, a subject treated for a prostate condition in accordance with the methods provided herein is a human male that is in an immunocompromised state or immunosuppressed state. In certain embodiments, a subject treated for a prostate condition in accordance with the methods provided herein is a human male receiving or recovering from immunosuppressive therapy. In certain embodiments, a subject treated for a prostate condition in accordance with the methods provided herein is a human male that has or is at risk of getting cancer (e.g., metastatic cancer), AIDS, or a bacterial infection. In certain embodiments, a subject treated for prostate cancer in accordance with the methods provided herein is a human male who is, will or has undergone surgery, drug therapy such as chemotherapy, anti-androgen therapy and/or radiation therapy.

In specific embodiments, a subject treated for a prostate condition in accordance with the methods provided herein is suffering from a condition, e.g., stroke or cardiovascular conditions that may require VEGF therapy, wherein the administration of anti-angiogenic therapies other than a Compound may be contraindicated. For example, in certain embodiments, a subject treated for a prostate condition in accordance with the methods provided herein has suffered from a stroke or is suffering from a cardiovascular condition. In some embodiments, a subject treated for a prostate condition in accordance with the methods provided herein is a human experiencing circulatory problems. In certain embodiments, a subject treated for a prostate condition in accordance with the methods provided herein is a human with diabetic polyneuropathy or diabetic neuropathy. In some embodiments, a subject treated for a prostate condition in accordance with the methods provided herein is a human receiving VEGF protein or VEGF gene therapy. In other embodiments, a subject treated for a prostate condition in accordance with the methods provided herein is not a human receiving VEGF protein or VEGF gene therapy.

In some embodiments, a subject treated for a prostate condition in accordance with the methods provided herein is administered a Compound or a pharmaceutical composition thereof, or a combination therapy before any adverse effects or intolerance to therapies other than the Compound develops. In some embodiments, a subject treated for a prostate condition in accordance with the methods provided herein is a refractory patient. In a certain embodiment, a refractory patient is a patient refractory to a standard therapy (e.g., surgery, radiation, anti-androgen therapy and/or drug therapy such as chemotherapy). In certain embodiments, a patient with prostate cancer, is refractory to a therapy when the cancer has not significantly been eradicated and/or the symptoms have not been significantly alleviated. The determination of whether a patient is refractory can be made either in vivo or in vitro by any method known in the art for assaying the effectiveness of a treatment of prostate cancer, using art-accepted meanings of "refractory" in such a context. In various embodiments, a patient with prostate cancer is refractory when one or more tumors associated with prostate cancer, have not decreased or have increased. In various embodiments, a patient with prostate cancer is refractory when one or more tumors metastasize and/or spreads to another organ. In some embodiments, a patient is in remission. In certain embodiments, a patient is experiencing recurrence of one or more tumors associated with prostate cancer.

In some embodiments, a subject treated for a prostate condition in accordance with the methods provided herein is a human male that has proven refractory to therapies other than treatment with a Compound, but is no longer on these therapies. In certain embodiments, a subject treated for a prostate condition in accordance with the methods provided herein is a human already receiving one or more conventional anticancer therapies, such as surgery, drug therapy such as chemotherapy, anti-androgen therapy or radiation. Among these patients are refractory patients, patients who are too young for conventional therapies, and patients with recurring tumors despite treatment with existing therapies.

In some embodiments, a subject treated for a prostate condition in accordance with the methods provided herein is a human male susceptible to adverse reactions to conventional therapies. In some embodiments, a subject treated for a prostate condition in accordance with the methods provided herein is a human male that has not received a therapy, e.g., drug therapy such as chemotherapy, surgery, anti-androgen therapy or radiation therapy, prior to the administration of a Compound or a pharmaceutical composition thereof. In other embodiments, a subject treated for a prostate condition in accordance with the methods provided herein is a human that has received a therapy prior to administration of a Compound. In some embodiments, a subject treated for a prostate condition in accordance with the methods provided herein is a human male that has experienced adverse side effects to the prior therapy or the prior therapy was discontinued due to unacceptable levels of toxicity to the human male.

In some embodiments, a subject treated for a prostate condition in accordance with the methods provided herein has had no prior exposure to another anti-angiogenic therapy (e.g., an anti-VEGF monoclonal antibody, an anti-VEGFR monoclonal antibody, a tyrosine kinase inhibitor, or other pathway modulator). In particular embodiments, a subject treated for a prostate condition in accordance with the methods provided herein does not have uncontrolled hypertension, major bleeding, HIV infection or recent acute cardiovascular event. In some embodiments, a subject treated for a prostate condition in accordance with the methods provided herein has myocardial infarction, unstable angina, coronary/peripheral artery bypass graft, congestive heart failure, cerebrovascular accident, transient ischemic attack, an arterial thromboembolic event, or pulmonary embolism.

In specific embodiments, a subject treated for prostate cancer in accordance with the methods provided herein has a body weight of about 40 kilograms to about 125 kilograms. In certain embodiments, a subject treated for prostate cancer in accordance with the methods provided herein has an Eastern Cooperative Oncology Group (ECOG) performance status of 0 or 1 or 2 or 3 or 4. In other embodiments, a subject treated for prostate cancer in accordance with the methods provided herein has a histologically or cytologically confirmed diagnosis of prostate carcinoma. In other embodiments, a subject treated for prostate cancer in accordance with the methods provided herein has locally advanced or metastatic prostate cancer, and such metastatic prostate cancer may be progressive despite castrate serum testosterone levels with primary antiandrogen intervention. In some embodiments, a subject treated for prostate cancer in accordance with the methods provided herein has had prior bilateral surgical orchiectomy or ongoing androgen suppression with a gonadotropin-releasing hormone (GnRH) agonist (e.g., leuprolide, buserelin, nafarelin, histrelin, goserelin, deslorelin, triptorelin). In certain embodiments, a subject treated for prostate cancer in accordance with the methods provided herein has evidence of progressive prostate cancer as documented by (i) 2 consecutive increases in PSA over a previous reference value based on a sequence of ≥3 PSA values obtained at ≥1-week intervals occurring ≥4 weeks after cessation of any prior antiandrogen treatment; or (ii) continued elevation of serum PSA ≥6 weeks after the washout of any antiandrogen therapy. In certain embodiments, a subject treated for prostate cancer in accordance with the methods provided herein has not had any anti-androgen therapies (e.g., flutamide, bicalutamide, nilutamide, cyproterone acetate, ketoconazole, aminoglutethimide) or corticosteroid therapy for prostate cancer for a certain period of time (e.g., 1 week, 2 weeks, 3 weeks, 4 weeks, 5 weeks, or 6 weeks or more) before initiation of treatment. In particular embodiments, a subject treated for prostate cancer in accordance with the methods provided herein has had no prior cytotoxic therapy (e.g., docetaxel and mitoxantrone) or radioisotope therapy (e.g., strontium-89 and samarium-153) for prostate cancer. In specific embodiments, a subject treated for prostate cancer in accordance with the methods provided herein has had no prior exposure to another anti-angiogenic therapy (e.g., bevacizumab, sunitinib, sorafenib, thalidomide). In particular embodiments, a subject should have sufficient concentrations of PSA and VEGF prior to start of administration with a Compound so that possible decreases may be observed during treatment with a Compound. In certain embodiments, a physician may determine for a subject that therapy with a Compound offers acceptable benefit:risk when considering current CRPC disease status, medical condition, and the potential benefits of and risks of surgery or irradiation.

In some embodiments, a subject treated for a prostate condition in accordance with the methods provided herein is not, has not and/or will not receive a drug that is primarily metabolized by CYP2D6. In particular embodiments, a subject treated for a prostate condition in accordance with the methods provided herein has not and will not received a drug that is primarily metabolized by CYP2D6 1, 2, 3 or 4 weeks before receiving a Compound or a pharmaceutical composition thereof and 1, 2, 3 or 4 weeks after receiving the Compound or pharmaceutical composition. Examples of such drugs include, without limitation, some antidepressants (e.g., tricyclic antidepressants and selective serotonin uptake inhibitors), some antipsychotics, some beta-adrenergic receptor blockers, and certain anti-arrhythmics. In specific embodiments, a subject treated for a prostate condition in accordance with the methods provided herein is not, has not and/or will not receive tamoxifen. In particular embodiments, a subject treated for a prostate condition in accordance with the methods provided herein has not and will not received tamoxifen 1, 2, 3 or 4 weeks before receiving a Compound or a pharmaceutical composition thereof and 1, 2, 3 or 4 weeks after receiving the Compound or pharmaceutical composition. In specific embodiments, a subject treated for a prostate condition in accordance with the methods provided herein has received tamoxifen, e.g., for 1, 2, 3 or 4 weeks before receiving a Compound or a pharmaceutical composition thereof.

5.4 Dosage and Administration

In accordance with the methods for treating a prostate condition provided herein, a Compound or a pharmaceutical composition thereof can be administered to a subject in need thereof by a variety of routes in amounts which result in a beneficial or therapeutic effect. A Compound or pharmaceutical composition thereof may be orally administered to a subject in need thereof in accordance with the methods for treating a prostate condition provided herein. The oral administration of a Compound or a pharmaceutical composition thereof may facilitate subjects in need of such treatment complying with a regimen for taking the Compound or pharmaceutical composition. Thus, in a specific embodiment, a Compound or pharmaceutical composition thereof is administered orally to a subject in need thereof.

Other routes of administration include, but are not limited to, intravenous, intradermal, intramuscular, subcutaneous, intranasal, inhalation, transdermal, topical, transmucosal, intracranial, intrathecal, intraurethral, intratumoral, epidural and intra-synovial. In one embodiment, a Compound or a pharmaceutical composition thereof is administered systemically (e.g., parenterally) to a subject in need thereof. In another embodiment, a Compound or a pharmaceutical composition thereof is administered locally (e.g., intratumorally) to a subject in need thereof. In one embodiment, a Compound or a pharmaceutical composition thereof is administered via a route that permits the Compound to cross the blood-brain barrier (e.g., orally).

Evaluation has indicated that Compound #10 penetrates the blood-brain barrier. Error! Reference source not found. provides brain tissue plasma concentration ratios determined by whole-body autoradiography at specified times after a single oral administration of $^{14}$C-Compound #10 to rats (50 mg/kg).

Error! Reference source not found. Blood-Brain Barrier Penetration

In accordance with the methods for treating a prostate condition provided herein that involve administration of a Compound in combination with one or more additional therapies, the Compound and one or more additional therapies may be administered by the same route or a different route of administration.

The dosage and frequency of administration of a Compound or a pharmaceutical composition thereof is administered to a subject in need thereof in accordance with the methods for treating a prostate condition provided herein will be efficacious while minimizing any side effects. The exact dosage and frequency of administration of a Compound or a pharmaceutical composition thereof can be determined by a practitioner, in light of factors related to the subject that requires treatment. Factors which may be taken into account include the severity of the disease state, general health of the subject, age, and weight of the subject, diet, time and frequency of administration, combination(s) with other therapeutic agents or drugs, reaction sensitivities, and tolerance/response to therapy. The dosage and frequency of administration of a Compound or a pharmaceutical composition thereof may be adjusted over time to provide sufficient levels of the Compound or to maintain the desired effect.

In certain embodiments, a Compound or pharmaceutical composition thereof is administered to a subject in accordance with the methods for treating a prostate condition presented herein once a day, twice a day, three times a day, or four times a day. In some embodiments, a Compound or pharmaceutical composition thereof is administered to a subject in accordance with the methods for treating a prostate condition presented herein once, twice, three times, or four times every other day (i.e., on alternate days); once, twice, three times, or four times every two days; once, twice, three times, or four times every three days; once, twice, three times, or four times every four days; once, twice, three times, or four times every 5 days; once, twice, three times, or four times every week, once, twice, three times, or four times every two weeks; once, twice, three times, or four times every three weeks; once, twice, three times, or four times every four weeks; once, twice, three times, or four times every 5 weeks; once, twice, three times, or four times every 6 weeks; once, twice, three times, or four times every 7 weeks; or once, twice, three times, or four times every 8 weeks. In particular embodiments, a Compound or pharmaceutical composition thereof is administered to a subject in accordance with the methods for treating a prostate condition presented herein in cycles, wherein the Compound or pharmaceutical composition is administered for a period of time, followed by a period of rest (i.e., the Compound or pharmaceutical composition is not administered for a period of time). In specific embodiments, a method for treating a prostate condition presented herein involves the administration of a Compound or a pharmaceutical compo-

| Tissue | 6 Hours | | 12 Hours | | 24 Hours | | 48 Hours | | 72 Hours | |
|---|---|---|---|---|---|---|---|---|---|---|
| | M | F | M | F | M | F | M | F | M | F |
| Cerebellum | 1.55 | 1.23 | 1.85 | 2.85 | 1.74 | 1.59 | 1.21 | 1.17 | NA | 2.04 |
| Cerebrum | 1.52 | 1.22 | 1.75 | 2.79 | 1.89 | 1.57 | 1.35 | 1.68 | NA | 1.56 |
| Medulla | 1.60 | 1.42 | 1.98 | 3.82 | 1.83 | 1.69 | 1.20 | 2.01 | NA | 1.88 |
| Olfactory lobe | 1.42 | 1.38 | 1.35 | 2.45 | 1.23 | 1.13 | 0.967 | NA | NA | 3.33 |
| Pituitary gland | 4.06 | 4.27 | 3.22 | 5.48 | 2.72 | 2.33 | 0.890 | 3.68 | NA | 1.58 |
| Spinal cord | 1.14 | 0.898 | 1.24 | 1.92 | 1.75 | 1.60 | 1.43 | 1.60 | 1.84 | 2.75 | sition thereof in cycles, e.g., 1 week cycles, 2 week cycles, 3 week cycles, 4 week cycles, 5 week cycles, 6 week cycles, 8 week cycles, 9 week cycles, 10 week cycles, 11 week cycles, or 12 week cycles. In such cycles, the Compound or a pharmaceutical composition thereof may be administered once, twice, three times, or four times daily. In particular embodiments, a method for treating a prostate condition presented herein involves the administration of a Compound or a pharmaceutical composition thereof twice daily in 4 week cycles.

In certain embodiments, a Compound or a pharmaceutical composition thereof is administered to a subject in need thereof in accordance with the methods for treating a prostate condition provided herein at a dosage and a frequency of administration that achieves one or more of the following: (i) decreases the production and/or concentration of VEGF or other angiogenic or inflammatory mediators in a subject with a prostate condition; (ii) decreases the concentration of one, two, three or more, or all of the following of a subject with a prostate condition: VEGF-C, VEGF-D, P1GF, VEGFR-1, VEGFR-2, IL-6 and/or IL-8; (iii) decreases the concentration of a prostate-specific marker such as PSA; (iv) reduces or ameliorates the severity of the prostate condition and/or one or more symptoms associated therewith in a subject with the prostate condition; (v) reduces the number symptoms and/or the duration of one or more symptoms associated with the prostate condition in a subject with the prostate condition; (vi) prevents the onset, progression or recurrence of a tumor of BPH or one or more symptoms associated with the prostate condition in a subject with the prostate condition; (vii) reduces the size of the prostate in a subject with the prostate condition; and/or (viii) enhances or improves the therapeutic effect of another therapy in a subject with the prostate condition.

In certain embodiments, a Compound or a pharmaceutical composition thereof is administered to a subject in need thereof in accordance with the methods for treating a prostate condition provided herein at a dosage and a frequency of administration that results in one or more of the following: (i) decrease in the PSA concentration/levels in a subject with a prostate condition or an animal model (e.g., animal model with BPH or a pre-established human tumor such as a prostate tumor); (ii) decrease in the number or concentration of CTCs in the blood of a subject with a prostate condition or an animal model (e.g., animal model with BPH or pre-established human tumor such as a prostate tumor); (iii) survival of patients with castration-resistant prostate carcinoma for about 6 months or more, about 7 months or more, about 8 months or more, about 9 months or more, or about 12 months or more; (iv) regression of a BPH or tumor associated with a prostate condition and/or inhibition of the progression of a BPH or tumor associated with a prostate condition in a subject with a prostate condition or an animal model (e.g., animal model with BPH or a pre-established human tumor such as a prostate tumor); (v) reduction in the growth of a tumor or neoplasm or BPH associated with a prostate condition and/or decrease in the size (e.g., volume or diameter) of a tumor or BPH associated with a prostate condition in a subject with a prostate condition or an animal model (e.g., animal model with BPH or a pre-established human tumor such as a prostate tumor); (vi) the size of a tumor or BPH associated with a prostate condition is maintained and/or the tumor or BPH does not increase or increases by less than the increase of a similar tumor or BPH in a subject with a prostate condition or an animal model (e.g., animal model with BPH or a pre-established human tumor such as a prostate tumor) after administration of a standard therapy as measured by conventional methods available to one of skill in the art, such as digital rectal exam, ultrasound (e.g., transrectal ultrasound), CT Scan, PET scan, DCE-MRI, and MRI; (vii) reduction in the formation of a tumor or BPH associated with a prostate condition in a subject with a prostate condition or an animal model (e.g., animal model with BPH or a pre-established human tumor such as a prostate tumor); (viii) the eradication, removal, or control of primary, regional and/or metastatic tumors associated with prostate cancer in a subject with prostate cancer or an animal model (e.g., animal model with a tumor such as a prostate tumor); (ix) a decrease in the number or size of metastases associated with prostate cancer in a subject with prostate cancer or an animal model (e.g., animal model with a pre-established human tumor such as a prostate tumor); (x) stabilization or decrease in tumor or BPH blood flow or metabolism, or peritumoral or peri-BPH inflammation or edema in a subject with a prostate condition or an animal model (e.g., animal model with BPH or a pre-established human tumor such as a prostate tumor); (xi) decreases the production and/or concentration of VEGF or other angiogenic or inflammatory mediators in a subject with a prostate condition or an animal model (e.g., animal model with BPH or a pre-established human tumor such as a prostate tumor); (xii) decreases the concentration of one, two, three or more, or all of the following of a subject with a prostate condition or an animal model (e.g., animal model with BPH or a pre-established human tumor such as a prostate tumor): VEGF-C, VEGF-D, P1GF, VEGFR-1, VEGFR-2, IL-6 and/or IL-8; and (xiii) reduction in the growth of a pre-established tumor or neoplasm or BPH and/or decrease in the size (e.g., volume or diameter) of BPH or a pre-established human tumor such as a prostate tumor in a subject with a prostate condition or an animal model (e.g., animal model with BPH or a pre-established human tumor such as a prostate tumor).

In one aspect, a method for treating a prostate condition presented herein involves the administration of a unit dosage of a Compound or a pharmaceutical composition thereof. The dosage may be administered as often as determined effective (e.g., once, twice or three times per day, every other day, once or twice per week, biweekly or monthly). In certain embodiments, a method for treating a prostate condition presented herein involves the administration to a subject in need thereof of a unit dose of a Compound or a pharmaceutical composition thereof that ranges from about 0.1 milligram (mg) to about 1000 mg, from about 1 mg to about 1000 mg, from about 5 mg to about 1000 mg, from about 10 mg to about 500 mg, from about 100 mg to about 500 mg, from about 150 mg to about 500 mg, from about 150 mg to about 1000 mg, from about 250 mg to about 1000 mg, from about 300 mg to about 1000 mg, or from about 500 mg to about 1000 mg, or any range in between. In some embodiments, a method for treating a prostate condition presented herein involves the administration to a subject in need thereof of a unit dose of a Compound or a pharmaceutical composition thereof of about 15 mg, 16, mg, 17 mg, 18 mg, 19 mg, 20 mg, 21, mg, 22 mg, 23 mg, 24 mg, 25 mg, 26 mg, 27 mg, 28 mg, 29 mg, 30 mg or 40 mg. In certain embodiments, a method for treating a prostate condition presented herein involves the administration to a subject in need thereof of a unit dose of a Compound or a pharmaceutical composition thereof of about 50 mg, 60 mg, 70 mg, 80 mg, 90 mg, 100 mg, 110 mg, 120 mg, 125 mg, 130 mg, 140 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 850 mg, or 900 mg.

In some embodiments, a method for treating a prostate condition presented herein involves the administration to a subject in need thereof of a unit dose of a Compound or a pharmaceutical composition thereof of at least about 0.1 mg, 1 mg, 5 mg, 10 mg, 20 mg, 30 mg, 40 mg, 50 mg, 60 mg, 70 mg, 80 mg, 90 mg, 100 mg, 110 mg, 120 mg, 125 mg, 130 mg, 140 mg, 150 mg, 175 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg or more. In certain embodiments, a method for treating a prostate condition presented herein involves the administration to a subject in need thereof of a unit dose of a Compound or a pharmaceutical composition thereof of less than about 35 mg, less than about 40 mg, less than about 45 mg, less than about 50 mg, less than about 60 mg, less than about 70 mg, or less than about 80 mg.

In specific embodiments, a method for treating a prostate condition presented herein involves the administration to a subject in need thereof of a unit dose of a Compound or a pharmaceutical composition thereof of about 40 mg to about 500 mg, about 40 mg to about 200 mg, about 40 mg to about 150 mg, about 75 mg to about 500 mg, about 75 mg to about 450 mg, about 75 mg to about 400 mg, about 75 mg to about 350 mg, about 75 mg to about 300 mg, about 75 mg to about 250 mg, about 75 mg to about 200 mg, about 100 mg to about 200 mg, or any range in between. In other specific embodiments, a method for treating a prostate condition presented herein involves the administration to a subject in need thereof of a unit dose of a Compound or a pharmaceutical composition thereof of about 35 mg, 40 mg, 50 mg, 60 mg, 75 mg, 100 mg, 125 mg, 150 mg, 175 mg, 200 mg, 225 mg, 250 mg or 300 mg. In some embodiments, a method for treating a prostate condition presented herein involves the administration to a subject in need thereof of a unit dose of a Compound or a pharmaceutical composition thereof of about 350 mg, 400 mg, 500 mg, 600 mg, 700 mg, 800 mg, 900 mg, or 1000 mg. In some embodiments, a unit dose of a Compound or a pharmaceutical composition thereof is administered to a subject once per day, twice per day, three times per day; once, twice or three times every other day (i.e., on alternate days); once, twice or three times every two days; once, twice or three times every three days; once, twice or three times every four days; once, twice or three times every five days; once, twice, or three times once a week, biweekly or monthly, and the dosage may be administered orally.

In certain embodiments, a method for treating a prostate condition presented herein involves the oral administration to a subject in need thereof of a unit dose of a Compound or a pharmaceutical composition thereof that ranges from about 50 mg to about 500 mg per day. In some embodiments, a method for treating a prostate condition presented herein involves the oral administration to a subject in need thereof of a unit dose of a Compound or a pharmaceutical composition thereof that ranges from about 80 mg to about 500 mg per day, about 100 mg to about 500 mg per day, about 80 mg to about 400 mg per day, about 80 mg to about 300 mg per day, about 80 mg to about 200 mg per day, about 200 mg to about 300 mg per day, about 200 mg to about 400 mg per day, about 200 mg to about 500 mg per day, or any range in between. In a specific embodiment, a method for treating a prostate condition presented herein involves the oral administration to a subject in need thereof of a unit dose of about 40 mg of a Compound or a pharmaceutical composition thereof twice per day. In another specific embodiment, a method for treating a prostate condition presented herein involves the oral administration to a subject in need thereof of a unit dose of about 80 mg of a Compound or a pharmaceutical composition thereof twice per day. In specific embodiments, a method for treating a prostate condition presented herein involves the oral administration to a subject in need thereof of a unit dose of about 150 mg to about 250 mg, about 175 mg to about 250 mg, about 200 mg to about 250 mg, or about 200 mg to about 225 mg of a Compound or a pharmaceutical composition thereof twice per day. In a specific embodiment, a method for treating prostate cancer presented herein involves the administration to a subject in need thereof of a Compound or a pharmaceutical composition at the dosage, frequency of administration and route of administration set forth in the working examples infra in Section 11 et seq.

In some embodiments, a method for treating a prostate condition presented herein involves the administration of a dosage of a Compound or a pharmaceutical composition thereof that is expressed as mg per meter squared ($mg/m^2$). The $mg/m^2$ for a Compound may be determined, for example, by multiplying a conversion factor for an animal by an animal dose in mg per kilogram (mg/kg) to obtain the dose in $mg/m^2$ for human dose equivalent. For regulatory submissions the FDA may recommend the following conversion factors: Mouse=3, Hamster=4.1, Rat=6, Guinea Pig=7.7. (based on Freireich et al., Cancer Chemother. Rep. 50(4):219-244 (1966)). The height and weight of a human may be used to calculate a human body surface area applying Boyd's Formula of Body Surface Area. In specific embodiments, a method for treating a prostate condition presented herein involves the administration to a subject in need thereof of an amount of a Compound or a pharmaceutical composition thereof in the range of from about $0.1 \text{ mg/m}^2$ to about $1000 \text{ mg/m}^2$, or any range in between.

Other non-limiting exemplary doses of a Compound or a pharmaceutical composition that may be used in the methods for treating a prostate condition provided herein include milligram (mg) or microgram (µg) amounts per kilogram (kg) of subject or sample weight per day such as from about 0.001 mg per kg to about 1500 mg per kg per day, from about 0.001 mg per kg to about 1400 mg per kg per day, from about 0.001 mg per kg to about 1300 mg per kg per day, from about 0.001 mg per kg to about 1200 mg per kg per day, from about 0.001 mg per kg to about 1100 mg per kg per day, from about 0.001 mg per kg to about 1000 mg per kg per day, from about 0.01 mg per kg to about 1500 mg per kg per day, from about 0.01 mg per kg to about 1000 mg per kg per day, from about 0.1 mg per kg to about 1500 mg per kg per day, from about 0.1 mg per kg to about 1000 mg per kg per day, from about 0.1 mg per kg to about 500 mg per kg per day, from about 0.1 mg per kg to about 100 mg per kg per day, or from about 1 mg per kg to about 100 mg per kg per day. In specific embodiments, oral doses for use in the methods provided herein are from about 0.01 mg to about 300 mg per kg body weight per day, from about 0.1 mg to about 75 mg per kg body weight per day, or from about 0.5 mg to 5 mg per kg body weight per day. In certain embodiments, oral doses for use in the methods provided herein involves the oral administration to a subject in need thereof of a dose of a Compound or a pharmaceutical composition thereof that ranges from about 80 mg to about 800 mg per kg per day, from about 100 mg to about 800 mg per kg per day, from about 80 mg to about 600 mg per kg per day, from about 80 mg to about 400 mg per kg per day, from about 80 mg to about 200 mg per kg per day, from about 200 mg to about 300 mg per kg per day, from about 200 mg to about 400 mg per kg per day, from about 200 mg to about 800 mg per kg per day, or any range in between. In certain embodiments, doses of a Compound that may be used in the methods provided herein include doses of about 0.1 mg/kg/day, 0.2 mg/kg/day, 0.3 mg/kg/day, 0.4 mg/kg/day, 0.5 mg/kg/day, 0.6 mg/kg/day, 0.7 mg/kg/day, 0.8 mg/kg/day, 0.9 mg/kg/day, 1 mg/kg/day, 1.5 mg/kg/day, 2 mg/kg/day, 2.5 mg/kg/day, 2.75 mg/kg/day, 3 mg/kg/day, 4 mg/kg/day, 5 mg/kg/day, 6 mg/kg/day, 6.5 mg/kg/day, 6.75 mg/kg/day, 7 mg/kg/day, 7.5 mg/kg/day, 8 mg/kg/day, 8.5 mg/kg/day, 9 mg/kg/day, 10 mg/kg/day, 11 mg/kg/day, 12 mg/kg/day, 13 mg/kg/day, 14 mg/kg/day or 15 mg/kg/day. In accordance with these embodiments, the dosage may be administered one, two or three times per day, every other day, or once or twice per week and the dosage may be administered orally.

In certain embodiments, a method for treating a prostate condition presented herein involves the administration to a subject in need thereof of a dosage of a Compound or a pharmaceutical composition thereof that ranges from about 0.01 mg/kg to about 100 mg/kg, from about 0.01 mg/kg to about 50 mg/kg, from about 0.01 mg/kg to about 25 mg/kg, from about 0.01 mg/kg to about 10 mg/kg, from about 0.01 mg/kg to about 5 mg/kg, from about 0.01 mg to about 1 mg/kg, or from about 0.01 mg/kg to about 0.1 mg/kg. In some embodiments, a method for treating a prostate condition presented herein involves the administration to a subject in need thereof of a dosage of a Compound or a pharmaceutical composition thereof that ranges from about 0.1 mg/kg to about 100 mg/kg, from about 0.1 mg/kg to about 50 mg/kg, from about 0.1 mg/kg to about 25 mg/kg, from about 0.1 mg/kg to about 10 mg/kg, from about 0.1 mg/kg to about 5 mg/kg, from about 0.1 mg/kg to about 4 mg/kg; from about 0.1 mg/kg to about 3 mg/kg; from about 0.1 mg/kg to about 2 mg/kg; from about 0.1 mg to about 1.5 mg/kg, from about 0.1 mg to about 1.2 mg/kg, from about 0.1 mg to about 1 mg/kg, or from about 0.5 mg/kg to about 1.5 mg/kg. In accordance with these embodiments, the dosage may be administered once, twice or three times per day, every other day, or once or twice per week and the dosage may be administered orally.

In specific embodiments, a method for treating a prostate condition presented herein involves the oral administration to a subject in need thereof of a dosage of a Compound or a pharmaceutical composition thereof of about 0.1 mg/kg to about 5 mg/kg, about 0.1 mg/kg to about 4 mg/kg, about 0.1 mg/kg to about 3 mg/kg, about 0.1 mg/kg to about 2 mg/kg, about 0.5 mg/kg to about 2 mg/kg, or about 1 mg/kg to about 1.5 mg/kg is administered twice per day. In certain embodiments, a method for treating a prostate condition presented herein involves the oral administration to a subject in need thereof of a dosage of a Compound or a pharmaceutical composition thereof of about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg or about 1 mg/kg twice per day. In certain specific embodiments, a method for treating a prostate condition presented herein involves the oral administration to a subject in need thereof of a dosage of a Compound or a pharmaceutical composition thereof of about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg or about 2 mg/kg twice per day.

In specific aspects, a method for treating a prostate condition presented herein involves the administration to a subject in need thereof of a Compound or a pharmaceutical composition thereof at a dosage that achieves a target plasma concentration of the Compound in a subject with the prostate condition or an animal model with a pre-established human tumor (e.g., tumor associated with prostate cancer). In a particular embodiment, a method for treating a prostate condition presented herein involves the administration to a subject in need thereof of a Compound or a pharmaceutical composition thereof at a dosage that achieves a plasma concentration of the Compound ranging from approximately 0.001 µg/mL to approximately 100 mg/mL, approximately 0.01 µg/mL to approximately 100 mg/mL, approximately 0.01 µg/mL to approximately 10 mg/mL, approximately 0.1 µg/mL to approximately 10 mg/mL, approximately 0.1 µg/mL to approximately 500 µg/mL, approximately 0.1 µg/mL to approximately 200 µg/mL, approximately 0.1 µg/mL to approximately 100 µg/mL, or approximately 0.1 µg/mL to approximately 75 µg/mL in a subject with the prostate condition or an animal model with pre-established human tumors (e.g., tumors associated with prostate cancer). In specific embodiments, a method for treating a prostate condition presented herein involves the administration to a subject in need thereof of a Compound or a pharmaceutical composition thereof at a dosage that achieves a plasma concentration of the Compound ranging from approximately 0.1 to approximately 50 µg/mL, approximately 0.1 µg/mL to approximately 25 µg/mL, approximately 0.1 µg/mL to approximately 20 µg/mL or approximately 5 µg/mL to approximately 10 µg/mL in a subject with the prostate condition or an animal model with pre-established human tumors (e.g., tumors associated with prostate cancer). To achieve such plasma concentrations, a Compound or a pharmaceutical composition thereof may be administered at doses that vary from 0.001 µg to 100,000 mg, depending upon the route of administration. In certain embodiments, subsequent doses of a Compound may be adjusted accordingly based on the plasma concentrations of the Compound achieved with initial doses of the Compound or pharmaceutical composition thereof administered to the subject.

In specific aspects, a method for treating a prostate condition presented herein involves the administration to a subject in need thereof of a Compound or a pharmaceutical composition thereof at a dosage that achieves a target concentration of VEGF, P1GF, VEGF-C, VEGF-D, IL-6, IL-8, VEGR1, VEGFR2, PSA and/or CTCs in a subject with the prostate condition or an animal model with a pre-established human tumor (e.g., tumor associated with prostate cancer). In a particular embodiment, a method for treating a prostate condition presented herein involves the administration to a subject in need thereof of a Compound or a pharmaceutical composition thereof at a dosage that achieves a concentration of VEGF, P1GF, VEGF-C, VEGF-D, IL-6, IL-8, VEGR1, VEGFR2, or PSA ranging from approximately 0.1 pg/mL to approximately 100 mg/mL, approximately 0.1 pg/mL to approximately 1 mg/mL, approximately 0.1 pg/mL to approximately 500 µg/mL, approximately 0.1 pg/mL to approximately 500 µg/mL, approximately 0.1 pg/mL to approximately 100 µg/mL, or approximately 5 pg/mL to approximately 10 µg/mL in a subject with a prostate condition or an animal model with a pre-established human tumor (e.g., tumor associated with prostate cancer). To achieve such concentrations, a Compound or a pharmaceutical composition thereof may be administered at doses that vary from 0.1 pg to 100,000 mg, depending upon the route of administration. In certain embodiments, subsequent doses of a Compound or a pharmaceutical composition thereof may be adjusted accordingly based on the concentrations of VEGF, P1GF, VEGF-C, VEGF-D, IL-6, IL-8, VEGR1, VEGFR2, PSA, and/or CTCs, achieved with initial doses of the Compound or pharmaceutical composition thereof administered to the subject.

In specific aspects, a method for treating a prostate condition presented herein involves the administration to a subject in need thereof a Compound or a pharmaceutical composition thereof at a dosage and/or a frequency of administration that achieves an imaging outcome indicating inhibition, stability, and/or reduction in a monitoring parameter such as size, perfusion, or metabolism of a prostate tumor or BPH, or inflammation or edema associated with a prostate condition, as assessed, e.g., by MRI scan, DCE-MRI scan, PET scan, and/or CT scan. To achieve such imaging outcome, a Compound or a pharmaceutical composition thereof may be administered at doses that vary from 0.1 pg to 100,000 mg, depending upon the route and/or frequency of administration. In certain embodiments, subsequent doses of a Compound or a pharmaceutical composition thereof may be adjusted accordingly based on the imaging outcome achieved with initial doses of the Compound or pharmaceutical composition thereof administered to the subject, as assessed, e.g., by MRI scan, DCE-MRI scan, PET scan, and/or CT scan.

In particular embodiments, a method for treating a prostate condition presented herein involves the administration to a subject in need thereof of a Compound or a pharmaceutical composition thereof at a dosage that achieves the desired tissue to plasma concentration ratios of the Compound as determined, e.g., by any imaging techniques known in the art such as whole-body autoradiography in a subject with the prostate condition or an animal model (such as an animal model with a pre-established human tumor, e.g., a tumor associated with prostate cancer). Table 23 lists exemplary tissue to plasma concentration ratios of a Compound as determined by whole-body autoradiography.

In some embodiments, a method for treating a prostate condition presented herein involves the administration to a subject in need thereof of one or more doses of an effective amount of a Compound or a pharmaceutical composition, wherein the effective amount may or may not be the same for each dose. In particular embodiments, a first dose of a Compound or pharmaceutical composition thereof is administered to a subject in need thereof for a first period of time, and subsequently, a second dose of a Compound is administered to the subject for a second period of time. The first dose may be more than the second dose, or the first dose may be less than the second dose. A third dose of a Compound also may be administered to a subject in need thereof for a third period of time.

In some embodiments, the dosage amounts described herein refer to total amounts administered; that is, if more than one Compound is administered, then, in some embodiments, the dosages correspond to the total amount administered. In a specific embodiment, oral compositions contain about 5% to about 95% of a Compound by weight.

The length of time that a subject in need thereof is administered a Compound or a pharmaceutical composition in accordance with the methods for treating a prostate condition presented herein will be the time period that is determined to be efficacious. In certain embodiments, a method for treating a prostate condition presented herein involves the administration of a Compound or a pharmaceutical composition thereof for a period of time until the severity and/or number of symptoms associated with the prostate condition decrease.

In some embodiments, a method for treating a prostate condition presented herein involves the administration of a Compound or a pharmaceutical composition thereof for up to 48 weeks. In other embodiments, a method for treating a prostate condition presented herein involves the administration of a Compound or a pharmaceutical composition thereof for up to 4 weeks, 8 weeks, 12 weeks, 16 week, 20 weeks, 24 weeks, 26 weeks (0.5 year), 52 weeks (1 year), 78 weeks (1.5 years), 104 weeks (2 years), or 130 weeks (2.5 years) or more.

In certain embodiments, a method for treating a prostate condition presented herein involves the administration of a Compound or a pharmaceutical composition thereof for an indefinite period of time. In some embodiments, a method for treating a prostate condition presented herein involves the administration of a Compound or a pharmaceutical composition thereof for a period of time followed by a period of rest (i.e., a period wherein the Compound is not administered) before the administration of the Compound or pharmaceutical composition thereof is resumed. In specific embodiments, the period of time of administration of a Compound or pharmaceutical composition thereof may be dictated by one or more monitoring parameters, e.g., concentration of VEGF or other angiogenic or inflammatory mediators (e.g., cytokines or interleukins such as IL-6 or IL-8); size, blood flow, or metabolism of a tumor of BPH; level of CTCs; concentration/level of prostate-specific markers such as PSA; or inflammation or edema associated with the prostate condition. In particular embodiments, the period of time of administration of a Compound or pharmaceutical composition thereof may be adjusted based on one or more monitoring parameters, e.g., concentration of VEGF or other angiogenic or inflammatory mediators (e.g., cytokines or interleukins such as IL-6 or IL-8); size, blood flow, or metabolism of a tumor or BPH; level of CTCs; concentration/level of prostate-specific markers such as PSA; or inflammation or edema associated with the prostate condition.

In certain embodiments, in accordance with the methods for treating a prostate condition presented herein, a Compound or a pharmaceutical composition thereof is administered to a subject in need thereof prior to, concurrently with, or after a meal (e.g., breakfast, lunch, or dinner). In specific embodiments, in accordance with the methods for treating a prostate condition presented herein, a Compound or a pharmaceutical composition thereof is administered to a subject in need thereof in the morning (e.g., between 5 am and 12 pm). In certain embodiments, in accordance with the methods for treating a prostate condition presented herein, a Compound or a pharmaceutical composition thereof is administered to a subject in need thereof at noon (i.e., 12 pm). In particular embodiments, in accordance with the methods for treating a prostate condition presented herein, a Compound or a pharmaceutical composition thereof is administered to a subject in need thereof in the afternoon (e.g., between 12 pm and 5 pm), evening (e.g., between 5 pm and bedtime), and/or before bedtime.

5.5 Combination Therapy

Presented herein are combination therapies for the treatment of a prostate condition which involve the administration of a Compound in combination with one or more additional therapies to a subject in need thereof. In a specific embodiment, presented herein are combination therapies for the treatment of a prostate condition which involve the administration of an effective amount of a Compound in combination with an effective amount of another therapy to a subject in need thereof.

As used herein, the term "in combination," refers, in the context of the administration of a Compound, to the administration of a Compound prior to, concurrently with, or subsequent to the administration of one or more additional therapies (e.g., agents, surgery, or radiation) for use in treating a prostate condition. The use of the term "in combination" does not restrict the order in which one or more Compounds and one or more additional therapies are administered to a subject. In specific embodiments, the interval of time between the administration of a Compound and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months 5 months, 6 months, 7 months, 8 months, 9 months, 10 months, 11 months, 12 months, 1 year, 2 years, or any period of time in between. In certain embodiments, a Compound and one or more additional therapies are administered less than 1 day, 1 week, 2 weeks, 3 weeks, 4 weeks, one month, 2 months, 3 months, 6 months, 1 year, 2 years, or 5 years apart.

In some embodiments, the combination therapies provided herein involve administering a Compound daily, and administering one or more additional therapies once a week, once every 2 weeks, once every 3 weeks, once every 4 weeks, once every month, once every 2 months (e.g., approximately 8 weeks), once every 3 months (e.g., approximately 12 weeks), or once every 4 months (e.g., approximately 16 weeks). In certain embodiments, a Compound and one or more additional therapies are cyclically administered to a subject. Cycling therapy involves the administration of the Compound for a period of time, followed by the administration of one or more additional therapies for a period of time, and repeating this sequential administration. In certain embodiments, cycling therapy may also include a period of rest where the Compound or the additional therapy is not administered for a period of time (e.g., 2 days, 3 days, 4 days, 5 days, 6 days, 7 days, 1 week, 2 weeks, 3 weeks, 4 weeks, 5 weeks, 10 weeks, 20 weeks, 1 month, 2 months, 3 months, 4 months, 5 months, 6 months, 7 months, 8 months, 9 months, 10 months, 11 months, 12 months, 2 years, or 3 years). In an embodiment, the number of cycles administered is from 1 to 12 cycles, from 2 to 10 cycles, or from 2 to 8 cycles.

In some embodiments, the methods for treating a prostate condition provided herein comprise administering a Compound as a single agent for a period of time prior to administering the Compound in combination with an additional therapy. In certain embodiments, the methods for treating a prostate condition provided herein comprise administering an additional therapy alone for a period of time prior to administering a Compound in combination with the additional therapy.

In some embodiments, the administration of a Compound and one or more additional therapies in accordance with the methods presented herein have an additive effect relative to the administration of the Compound or said one or more additional therapies alone. In some embodiments, the administration of a Compound and one or more additional therapies in accordance with the methods presented herein have a synergistic effect relative to the administration of the Compound or said one or more additional therapies alone.

As used herein, the term "synergistic," refers to the effect of the administration of a Compound in combination with one or more additional therapies (e.g., agents, surgery or radiation), which combination is more effective than the additive effects of any two or more single therapies (e.g., agents, surgery or radiation). In a specific embodiment, a synergistic effect of a combination therapy permits the use of lower dosages (e.g., sub-optimal doses) of a Compound or an additional therapy and/or less frequent administration of a Compound or an additional therapy to a subject. In certain embodiments, the ability to utilize lower dosages of a Compound or of an additional therapy and/or to administer a Compound or said additional therapy less frequently reduces the toxicity associated with the administration of a Compound or of said additional therapy, respectively, to a subject without reducing the efficacy of a Compound or of said additional therapy, respectively, in the treatment of a prostate condition. In some embodiments, a synergistic effect results in improved efficacy of a Compound and of each of said additional therapies in treating a prostate condition. In some embodiments, a synergistic effect of a combination of a Compound and one or more additional therapies avoids or reduces adverse or unwanted side effects associated with the use of any single therapy.

The combination of a Compound and one or more additional therapies can be administered to a subject in the same pharmaceutical composition. Alternatively, a Compound and one or more additional therapies can be administered concurrently to a subject in separate pharmaceutical compositions. A Compound and one or more additional therapies can be administered sequentially to a subject in separate pharmaceutical compositions. A Compound and one or more additional therapies may also be administered to a subject by the same or different routes of administration.

The combination therapies provided herein involve administrating to a subject to in need thereof a Compound in combination with conventional, or known, therapies for a prostate condition. Current therapies for BPH that can be used in combination with a compound described herein or pharmaceutical composition thereof include surgery and administration of alpha blockers (e.g., doxazosin, terazosin, alfuzosin and tamsulosin) and 5α-reductase inhibitors (e.g., finasteride dutasteride). Current therapies for prostate cancer, include surgery, hormonal therapy, radiation or drug therapy such as chemotherapy (e.g., docetaxel, estramustine, mitoxantrone, paclitaxel, doxorubicin). Other therapies for a prostate condition or a condition associated therewith are aimed at controlling or relieving symptoms. Accordingly, in some embodiments, the combination therapies provided herein involve administrating to a subject to in need thereof a pain reliever, or other therapies aimed at alleviating or controlling symptoms associated with a prostate condition or a condition associated therewith.

Specific examples of anti-cancer agents that may be used in combination with a Compound include: a hormonal agent (e.g., aromatase inhibitor, selective estrogen receptor modulator (SERM), and estrogen receptor antagonist), chemotherapeutic agent (e.g., microtubule dissembly blocker, antimetabolite, topisomerase inhibitor, and DNA crosslinker or damaging agent), anti-angiogenic agent (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with a Compound include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as NOLVADEX®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with a Compound include microtubule disassembly blocker, antimetabolite, topisomerase inhibitor, and DNA crosslinker or damaging agent. Chemotherapeutic agents that are microtubule dissemby blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®)).

Chemotherapeutic agents that are antimetabolites include, but are not limited to, folate antimetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capcitabine, gemcitabine (branded/marketed as GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan); class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N,N-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

Non-limiting examples of anti-angiogenic agents that may be used in combination with a Compound include VEGF antagonists, receptor antagonists, integrin antagonists (e.g., vitaxin, cilengitide, and S247), and VTAs/VDAs (e.g., fosbretabulin). VEGF antagonists include, but are not to, anti-VEGF antibodies (e.g., bevacizumab (branded/marketed as AVASTIN®) and ranibizumab (branded/marketed as LUCENTIS®)), VEGF traps (e.g., aflibercept), VEGF antisense or siRNA or miRNA, and aptamers (e.g., pegaptanib (branded/marketed as MACUGEN®)). Anti-angiogenic agents that are receptor antagonists include, but are not limited to, antibodies (e.g., ramucirumab) and kinase inhibitors (e.g., sunitinib, sorafenib, cediranib, panzopanib, vandetanib, axitinib, and AG-013958) such as tyrosine kinase inhibitors. Other non-limiting examples of anti-angiogenic agents include ATN-224, anecortave acetate (branded/marketed as RETAANE®), microtubule depolymerization inhibitor such as combretastatin A4 prodrug, and recombinant protein or protein fragment such as collagen 18 (endostatin).

Non-limiting examples of other therapies that may be administered to a subject in combination with a Compound include:
(1) a statin such as lovostatin (e.g., branded/marketed as MEVACOR®);
(2) an mTOR inhibitor such as sirolimus which is also known as Rapamycin (e.g., branded/marketed as RAPAMUNE®), temsirolimus (e.g., branded/marketed as TORISEL®), evorolimus (e.g., branded/marketed as) AFINITOR®) and deforolimus;
(3) a farnesyltransferase inhibitor agent such as tipifarnib (e.g., branded/marketed as ZARNESTRA®);
(4) an antifibrotic agent such as pirfenidone;
(5) a pegylated interferon such as PEG-interferon alpha-2b;
(6) a CNS stimulant such as methylphenidate (branded/marketed as RITALIN®);
(7) a HER-2 antagonist such as anti-HER-2 antibody (e.g., trastuzumab) or kinase inhibitor (e.g., lapatinib);
(8) an IGF-1 antagonist such as an anti-IGF-1 antibody (e.g., AVE1642 and IMC-A11) or an IGF-1 kinase inhibitor;
(9) EGFR/HER-1 antagonist such as an anti-EGFR antibody (e.g., cetuximab, panitumamab) or EGFR kinase inhibitor (e.g., erlotinib (e.g., branded/marketed as TARCEVA®), gefitinib);
(10) SRC antagonist such as bosutinib;
(11) cyclin dependent kinase (CDK) inhibitor such as seliciclib;
(12) Janus kinase 2 inhibitor such as lestaurtinib;
(13) proteasome inhibitor such as bortezomib;
(14) phosphodiesterase inhibitor such as anagrelide;
(15) inosine monophosphate dehydrogenase inhibitor such as tiazofurine;
(16) lipoxygenase inhibitor such as masoprocol;
(17) endothelin antagonist;
(18) retinoid receptor antagonist such as tretinoin or alitretinoin;
(19) immune modulator such as lenalidomide, pomalidomide, or thalidomide (e.g., branded/marketed as THALIDOMID®);
(20) kinase (eg, tyrosine kinase) inhibitor such as imatinib (e.g., branded/marketed as GLEEVEC®), dasatinib, erlotinib, nilotinib, gefitinib, sorafenib, sunitinib (e.g., branded/marketed as SUTENT®), lapatinib, AEE788, or TG100801;
(21) non-steroidal anti-inflammatory agent such as celecoxib (branded/marketed as CELEBREX®);
(22) human granulocyte colony-stimulating factor (G-CSF) such as filgrastim (branded/marketed as NEUPOGEN®);
(23) folinic acid or leucovorin calcium;
(24) integrin antagonist such as an integrin α5β1-antagonist (e.g., JSM6427);
(25) nuclear factor kappa beta (NF-κβ) antagonist such as OT-551, which is also an anti-oxidant;
(26) hedgehog inhibitor such as CUR61414, cyclopamine, GDC-0449, or anti-hedgehog antibody;
(27) histone deacetylase (HDAC) inhibitor such as SAHA (also known as vorinostat (branded/marketed as ZOLINZA®)), PCI-24781, SB939, CHR-3996, CRA-024781, ITF2357, JNJ-26481585, or PCI-24781;
(28) retinoid such as isotretinoin (e.g., branded/marketed as ACCUTANE®);
(29) hepatocyte growth factor/scatter factor (HGF/SF) antagonist such as HGF/SF monoclonal antibody (e.g., AMG 102);
(30) synthetic chemical such as antineoplaston;
(31) anti-diabetic such as rosiglitazone maleate (e.g., branded/marketed as AVANDIA®);
(32) antimalarial and amebicidal drug such as chloroquine (e.g., branded/marketed as ARALEN®);
(33) synthetic bradykinin such as RMP-7;
(34) platelet-derived growth factor receptor inhibitor such as SU-101;

(35) receptor tyrosine kinase inhibitorsof Flk-1/KDR/ VEGFR2, FGFR1 and PDGFR beta such as SU5416 and SU6668;

(36) anti-inflammatory agent such as sulfasalazine (e.g., branded/marketed as AZULFIDINE®); and

(37) TGF-beta antisense therapy.

Non-limiting examples of other therapies that may be administered to a subject in combination with a Compound include: a synthetic nonapeptide analog of naturally occurring gonadotropin releasing hormone such as leuprolide acetate (branded/marketed as LUPRON®); a nonsteroidal, anti-androgen such as flutamide (branded/marketed as EULEXIN®) or nilutamide (branded/marketed as NILANDRON®); a non-steroidal androgen receptor inhibitor such as bicalutamide (branded/marketed as CASODEX®); steroid hormone such as progesterone; anti-fungal agent such as Ketoconazole (branded/marketed as NIZORAL®); glucocorticoid such as prednisone; estramustine phosphate sodium (branded/marketed as EMCYT®); and bisphosphonate such as pamidronate, alendronate, and risedronate.

Other specific examples of therapies that may be used in combination with a Compound include, but are not limited to, antibodies that specifically bind to a tumor specific antigen or tumor associated antigen, e.g., anti-EGFR/HER-1 antibodies.

Additional specific examples of therapies that may be used in combination with a Compound include, but are not limited to, agents associated with cancer immunotherapy, e.g., cytokines, interleukins, and cancer vaccines.

Specific examples of agents alleviating side-effects associated with a prostate condition that can be used as therapies in combination with a Compound, include, but are not limited to: antiemetics, e.g., Ondansetron hydrochloride (branded/marketed as ZOFRAN®), Granisetron hydrochloride (branded/marketed as KYTRIL®), Lorazepam (branded/marketed as ATIVAN®) and Dexamethasone (branded/marketed as DECADRON®).

In certain embodiments, combination therapies provided herein for treating a prostate condition comprise administering a Compound in combination with one or more agents used to treat and/or manage one or more of the following conditions: bleeding, arterial and venous thrombosis, hypertension, delayed wound healing, asymptomatic proteinuria, nasal septal perforation, reversible posterior leukoencephalopathy syndrome in association with hypertension, lightheadedness, ataxia, headache, hoarseness, nausea, vomiting, diarrhea, rash, subungual hemorrhage, myelosuppression, fatigue, hypothyroidism, QT interval prolongation, and heart failure.

In certain embodiments, combination therapies provided herein for treating a prostate condition comprise administering a Compound in combination with one or more current anti-angiogenesis agents and one or more agents used to treat and/or manage a side effect observed with one or more of the current anti-angiogenesis agents, such as, bleeding, arterial and venous thrombosis, hypertension, delayed wound healing, asymptomatic proteinuria, nasal septal perforation, reversible posterior leukoencephalopathy syndrome in association with hypertension, light-headedness, ataxia, headache, hoarseness, nausea, vomiting, diarrhea, rash, subungual hemorrhage, myelosuppression, fatigue, hypothyroidism, QT interval prolongation, or heart failure.

In certain embodiments, a Compound is not used in combination with a drug that is primarily metabolized by CYP2D6 (such as an antidepressant (e.g. a tricyclic antidepressant, a selective serotonin reuptake inhibitor, and the like), an antipsychotic, a beta-adrenergic receptor blocker, or certain types of anti-arrhythmics) to treat a prostate condition.

6. EXAMPLE

Preparation of Compounds Provided Herein

The following examples are presented by way of illustration not limitation.

Methods for preparing certain Compounds provided herein and the Compounds disclosed on pages 26 to 98 of the '764 publication are provided on pages 112 to 142 of the '764 publication and are incorporated by reference herein on pages 99 to 105 and in their entireties and for all purposes. Methods for preparing certain Compounds provided herein and the Compounds disclosed in copending U.S. Provisional Patent Application 61/181,652, entitled: PROCESSES FOR THE PREPARATION OF SUBSTITUTED TETRAHYDRO BETA-CARBOLINES, filed May 27, 2009, are provided therein and are incorporated by reference herein in their entirety and for all purposes.

7. EXAMPLE

Formulation of Compound #10

The following example illustrates how Compound #10 may be formulated for oral administration.

For clinical use, Compound #10 has been formulated using cGMPs. Compound #10 is intended for oral administration and is provided in size 00 color coded, hard gelatin capsules. As shown in Table 2, each capsule contains 2 mg (white), 10 mg (gray), or 20 mg (orange) of the Compound formulated by w/w % (weight/weight %) in a SEDDS or SMEDDS system. The formulated product in the capsules appears as an opaque, off white soft solid at room temperature. If warmed, the encapsulated system begins to soften at temperatures of 38 to 40° C. and eventually becomes a clear, yellow liquid at ≥44° C.

TABLE 2

Composition of Compound #10 Capsules

| Component | 2 mg Capsule (w/w %) | 10 mg Capsule (w/w %) | 20 mg Capsule (w/w %) |
|---|---|---|---|
| Compound #10 | 0.28 [0.26-0.30] | 1.43 [1.33-1.53] | 2.67 [2.48-2.86] |
| GELUCIRE ® 44/14 | 49.87 [46.4-53.4] | 49.87 [46.4-53.4] | 49.87 [46.4-53.4] |
| SOLUTOL ®HS15 | 49.84 [46.4-53.3] | 48.69 [45.3-52.1] | 47.45 [44.1-50.8] |
| BHT | 0.01 [0.009-0.011] | 0.01 [0.009-0.011] | 0.01 [0.009-0.011] |
| Total Weight (100%) (mg) | 700 | 700 | 750 |

8. EXAMPLE

Assay to Evaluate Effect on Hypdxia-Inducible Endogenous VEGF Expression

The ability of the Compounds to modulate hypoxia-inducible endogenous VEGF expression may be analyzed as follows. VEGF protein levels may be monitored by an ELISA assay (R&D Systems). Briefly, HeLa cells may be cultured for 24-48 hours under hypoxic conditions (1% $O_2$, 5% $CO_2$, balanced with nitrogen) in the presence or absence of a Compound. The conditioned media may then be assayed by ELISA, and the concentration of VEGF calculated from the standard ELISA curve of each assay.

A dose-response analysis may be performed using the ELISA assay and conditions described above. The conditions for the dose-response ELISA are analogous to those described above. A series of, e.g., seven different concentrations may be analyzed. In parallel, a dose-response cytotoxicity assay may be performed using Cell Titer Glo (Promega) under the same conditions as the ELISA to ensure that the inhibition of VEGF expression was not due to the cytotoxicity. Dose-response curves may be plotted using percentage inhibition versus concentration of the Compound, and $EC_{50}$ and $CC_{50}$ values may be generated for each Compound with the maximal inhibition set as 100% and the minimal inhibition as 0%. In one embodiment, Compounds will have an $EC_{50}$ of less than 50, less than 10, less than 2, less than 0.5, or less than 0.01.

The $EC_{50}$ for a series of Compounds is provided in Table 3.

TABLE 3

| Compound | LC/MS [M + H] | LC/MS Retention Time (min) | ELISA $EC_{50}$ µM |
| --- | --- | --- | --- |
| 10 | 467.15 | 4.48 | ***** |
| #10 | 467.15 | 4.51 | ***** |
| 17 | 447.14 | 4.44 | ***** |
| 60 | 433.17 | 4.27 | **** |
| 76 | 449.26 | 4.3 | **** |
| 121 | 403.32 | 4.27 | **** |
| 142 | 462.15 | 4.11 | *** |
| 160 | 450.15 | 3.95 | *** |
| 186 | 462.19 | 3.81 | ** |
| 192 | 495.28 | 4.89 | ** |
| 331 | ~0.010 | 2.94 | * |
| #332 | ~0.010 | 4 | * |
| 341 | 447.26 | 4.25 | *** |
| 344 | 459.31 | 4.91 | **** |
| 346 | 587 | 4.04 | **** |
| 347 | 451.16 | 3.93 | ***** |
| 348 | 479.28 | 4.13 | ***** |
| 350 | 462.17 | 3.66 | ***** |
| 351 | 471.17 | 3.93 | **** |
| 353 | 497.16 | 3.94 | ***** |
| 354 | 525.2 | 4.19 | ***** |
| 355 | 511.21 | 3.81 | ***** |
| 359 | 511.25 | 3.64 | *** |
| 360 | 516 | 3.82 | **** |
| 366 | 553.3 | 4.42 | * |
| 372 | 486.9 | 4.96 | * |
| 388 | 495.4 | 3.94 | ***** |
| 391 | 562.55 | 3.63 | ***** |
| 395 | 481.32 | 3.51 | ***** |
| 397 | 535.3 | 4.29 | ***** |
| 398 | 481.3 | 4.23 | ***** |
| 400 | 493.3 | 4.43 | ***** |
| 401 | 451.3 | 3.99 | ***** |
| 403 | 479.3 | 4.23 | ***** |
| 405 | 551.17 | 4.58 | ***** |
| 409 | 477.4 | 4.18 | ***** |
| 410 | 451.3 | 3.99 | ***** |
| 413 | 459.3 | 4.16 | ***** |
| 415 | 637.64 | 2.82 | ***** |
| 417 | 562.47 | 4.15 | ***** |
| 418 | 511.3 | 4.13 | ***** |
| 421 | 553.30 | 4.05 | ***** |
| 422 | 359.29 | 4.17 | ***** |
| 426 | 535.27 | 4.29 | ***** |
| 427 | 554.3 | 4.45 | ***** |
| 428 | 563.55 | 4.64 | ***** |
| 429 | 564.42 | 2.77 | ***** |
| 432 | 489.4 | 4.14 | ***** |
| 433 | 578.44 | 2.82 | ***** |
| 436 | 477.4 | 3.93 | ***** |
| 437 | 543.4 | 3.92 | ***** |
| 440 | 536.43 | 3.95 | ***** |
| 444 | 455.28 | 3.73 | **** |
| 446 | 383.3 | 4.10 | **** |
| 448 | 501.27 | 3.65 | **** |
| 450 | 587 | 4.04 | **** |
| 452 | 439.3 | 3.56 | **** |
| 454 | 579.3 | 2.75 | **** |
| 455 | 583 | 3.84 | **** |
| 460 | 509.30 | 4.16 | **** |
| 462 | 580.56 | 2.85 | **** |
| 463 | 495.44 | 4.13 | **** |
| 465 | 507.4 | 3.98 | **** |
| 467 | 524.2 | 4.02 | **** |
| 468 | 582.2 | 2.81 | **** |
| 470 | 554.3 | 3.90 | **** |
| 471 | 620.18 | 3.85 | **** |
| 479 | 538.3 | 2.76 | *** |
| 482 | 522.3 | 3.95 | *** |
| 489 | 538.3 | 4.15 | *** |
| 491 | 537.31 | 2.64 | *** |
| 493 | 504.3 | 2.68 | *** |
| 500 | 506.29 | 3.85 | *** |
| 501 | 534.3 | 2.68 | *** |
| 502 | 518.3 | 2.76 | *** |
| 519 | 527.2 | 3.88 | ** |
| 530 | 466.28 | 3.21 | ** |
| 536 | 482.29 | 3.29 | ** |
| 540 | 428.28 | 3.43 | ** |
| 543 | 466.34 | 3.29 | ** |
| 544 | 723.58 | 3.92 | ***** |
| 545 | 466.31 | 3.28 | ** |
| 554 | 482.32 | 3.41 | ** |
| 570 | 549.22 | 4.59 | ***** |
| 571 | 497.13 | 3.50 | ** |
| 572 | 525.29 | 4.14 | ***** |
| 575 | 437.33 | 3.16 | ** |
| 576 | 575.43 | 3.71 | *** |
| 577 | 453.28 | 3.34 | *** |
| 578 | 610.45 | 3.94 | *** |
| 579 | 481.32 | 3.51 | ***** |
| 580 | 495.29 | 3.64 | ***** |
| 581 | 465.43 | 3.64 | * |
| 583 | 512.26 | 3.39 | *** |
| 584 | 466.37 | 3.34 | *** |
| 587 | 467.29 | 3.66 | *** |
| 588 | 455.26 | 3.69 | *** |
| 589 | 471.3 | 3.83 | *** |
| 590 | 495.31 | 3.64 | **** |
| 591 | 541.35 | 3.73 | ***** |
| 592 | 523.42 | 3.58 | ***** |
| 593 | 541.38 | 3.69 | **** |
| 594 | 505.38 | 3.83 | *** |
| 614 | 463 | 3.88 | ** |
| 616 | 540 | 4.17 | ** |
| 617 | 621.57 | 4.13 | **** |
| 626 | 493.6 | 3.48 | **** |
| 627 | 511.6 | 3.53 | ***** |
| 628 | 527.4 | 3.62 | *** |
| 629 | 527.5 | 3.72 | ***** |
| 630 | 573.5 | 3.75 | ***** |
| 631 | 507.6 | 3.65 | ***** |
| 632 | 538.6 | 3.53 | **** |
| 635 | 523.6 | 3.47 | **** |
| 637 | 621.62 | 2.77 | ***** |

TABLE 3-continued

| Compound | LC/MS [M + H] | LC/MS Retention Time (min) | ELISA EC$_{50}$ μM |
|---|---|---|---|
| 638 | 580.56 | 2.80 | ***** |
| 660 | 543.7 | 4.92 | ***** |
| 670 | 521.6 | 4.02 | ***** |
| 673 | 539.6 | 4.02 | **** |
| 674 | 555.6 | 4.13 | **** |
| 675 | 555.6 | 4.22 | **** |
| 677 | 535.6 | 4.15 | **** |
| 678 | 551.6 | 3.98 | *** |
| 680 | 599.5 | 4.27 | ***** |
| 681 | 566.6 | 4.02 | **** |
| 698 | 578.5 | 2.43 | **** |
| 699 | 568.5 | 2.35 | **** |
| 700 | 566.6 | 2.45 | **** |
| 701 | 596.6 | 2.47 | **** |
| 702 | 594.6 | 2.43 | **** |
| 703 | 592.6 | 2.48 | **** |
| 704 | 607.6 | 2.20 | *** |
| 705 | 575.5 | 2.47 | **** |
| 706 | 576.5 | 3.58 | ***** |
| 710 | 495.45 | 4.42 | ***** |
| 712 | 513.50 | 4.42 | ***** |
| 713 | 529.46 | 4.62 | **** |
| 719 | 527.5 | 4.47 | ***** |
| 723 | 555.4 | 4.09 (non polar) | ***** |
| 735 | 552.5 | 2.98 | ***** |
| 736 | 562.5 | 3.15 | ***** |
| 737 | 580.6 | 3.17 | **** |
| 738 | 578.5 | 3.02 | ***** |
| 739 | 576.6 | 3.17 | ***** |
| 740 | 591.6 | 2.75 | *** |
| 741 | 616.5 | 2.62 | *** |
| 742 | 559.5 | 3.13 | ***** |
| 743 | 560.5 | 3.83 | ***** |
| 772 | 580.5 | 3.03 | ***** |
| 773 | 590.6 | 3.12 | ***** |
| 774 | 578.5 | 3.12 | **** |
| 775 | 608.6 | 3.05 | ***** |
| 776 | 606.5 | 3.05 | ***** |
| 777 | 604.6 | 3.12 | ***** |
| 778 | 619.6 | 2.77 | ***** |
| 779 | 644.5 | 2.63 | *** |
| 780 | 587.5 | 3.10 | ***** |
| 781 | 588.5 | 4.05 | ***** |
| 782 | 596.5 | 3.10 | ***** |
| 783 | 606.5 | 3.18 | ***** |
| 784 | 594.5 | 3.27 | ***** |
| 785 | 624.5 | 3.22 | ***** |
| 786 | 622.5 | 3.12 | ***** |
| 787 | 620.5 | 3.20 | ***** |
| 788 | 635.6 | 2.85 | **** |
| 789 | 660.5 | 2.68 | *** |
| 790 | 603.5 | 3.22 | ***** |
| 791 | 604.5 | 4.25 | ***** |
| 833 | 532.4 | 3.50 | *** |
| 834 | 532.4 | 3.42 | **** |
| 835 | 531.4 | 2.57 | *** |
| 836 | 531.4 | 3.67 | **** |
| # 837 | 563.4 | 2.93 | ***** |
| # 838 | 577.4 | 2.82 | ***** |
| 839 | 548.3 | 3.63 | **** |
| 840 | 548.3 | 3.58 | **** |
| # 841 | 579.3 | 3.08 | ***** |
| # 842 | 593.3 | 2.95 | ***** |
| # 843 | 573.4 | 2.75 | ***** |
| 845 | 648.48 | 4.45 | *** |
| 846 | 526.45 | 2.57 | *** |
| 847 | 568.37 | 3.40 | **** |
| 848 | 585.30 | 3.57 | ***** |
| 849 | 604.37 | 3.52 | **** |
| 850 | 540.39 | 2.60 | *** |
| 851 | 495.06 | 4.37 | ***** |
| 853 | 549.09 | 4.38 | ***** |
| 854 | 523.17 | 4.73 | ***** |
| 855 | 455.19 | 4.15 | **** |
| 857 | 505.16 | 4.30 | ***** |
| 860 | 467.2 | 4.13 | ***** |
| 861 | 451.12 | 4.10 | **** |
| 862 | 471.17 | 4.32 | ***** |
| 863 | 514.55 | 4.38 | ***** |
| 867 | 577.43 | 2.85 | **** |
| 882 | 542.51 | 3.87 | ***** |
| 888 | 558.54 | 3.70 | ***** |
| 889 | 545.55 | 2.93 | ***** |
| 891 | 528.49 | 3.69 | ***** |
| 892 | 546.50 | 3.75 | ***** |
| 894 | 580.47 | 2.72 | ***** |
| 900 | 541.55 | 3.00 | ***** |
| 903 | 621.39 | 2.72 | ***** |
| 904 | 596.54 | 2.85 | ***** |
| 908 | 582.43 | 2.79 | ***** |
| 911 | 527.54 | 2.88 | ***** |
| 913 | 626.6 | 2.88 | ***** |
| 915 | 509.56 | 4.63 | ***** |
| 916 | 626.40 | 2.82 | ***** |
| 917 | 561.46 | 2.95 | ***** |
| 918 | 642.56 | 2.85 | ***** |
| 920 | 557.57 | 2.87 | ***** |
| 921 | 527.39 | 4.52 | ***** |
| 922 | 561.53 | 2.85 | ***** |
| 923 | 612.51 | 2.92 | ***** |
| 925 | 596.54 | 2.88 | ***** |
| 926 | 5.62 | 3.85 | ***** |
| 932 | 548.49 | 3.17 | ***** |
| 933 | 596.37 | 2.79 | ***** |
| 934 | 561.53 | 2.95 | ***** |
| 936 | 582.6 | 2.83 | ***** |
| 938 | 582.53 | 2.85 | ***** |
| 941 | 562.55 | 3.63 | ***** |
| 942 | 623.35 | 2.73 | **** |
| 944 | 525.56 | 4.36 | **** |
| 946 | 566.53 | 2.77 | **** |
| 951 | 544.53 | 3.27 | **** |
| 952 | 530.53 | 3.12 | **** |
| 953 | 552.46 | 2.90 | **** |
| 958 | 542.36 | 3.84 | **** |
| 960 | 639.57 | 2.70 | **** |
| 961 | 593.52 | 2.64 | **** |
| 963 | 593.61 | 2.72 | **** |
| 964 | 598.55 | 2.83 | **** |
| 966 | 564.45 | 3.32 | **** |
| 967 | 491.57 | 4.00 | **** |
| 970 | 609.54 | 2.72 | **** |
| 973 | 578.47 | 3.80 | **** |
| 974 | 528.34 | 3.79 | *** |
| 976 | 564.46 | 3.23 | *** |
| 977 | 568.53 | 2.85 | *** |
| 981 | 560.51 | 3.12 | *** |
| 984 | 5.06.19 | 3.97 | ** |
| 988 | 605.62 | 2.52 | ***** |
| 989 | 564.61 | 2.55 | ***** |
| 990 | 610.62 | 2.67 | ***** |
| 991 | 580.58 | 2.60 | *** |
| 992 | 566.61 | 2.60 | *** |
| 993 | 577.61 | 2.45 | ***** |
| 994 | 545.54 | 2.57 | ***** |
| 995 | 546.57 | 3.53 | ***** |
| 996 | 578.46 | 3.71 | ***** |
| 999 | 493.3 | 4.43 | ***** |
| 1001 | 575.5 | 2.98 | **** |
| 1005 | 560.3 | 4.55 | ** |
| 1008 | 548.2 | 4.79 | *** |
| 1009 | 468.1 | 3.90 | *** |
| 1011 | 560.2 | 5.54 | *** |
| 1016 | 560.51 | 4.23 | * |
| 1017 | 544.39 | 4.08 | ***** |
| 1021 | 621.2 | 4.35 | *** |
| 1022 | 607.2 | 5.05 | *** |
| 1023 | 586.1 | 5.93 | **** |
| 1024 | 591.2 | 5.01 | *** |
| 1025 | 633.2 | 4.29 | *** |
| 1026 | 619.2 | 4.24 | **** |
| 1027 | M − 1: 574.1 | 5.03 | *** |
| 1028 | 603.2 | 4.23 | *** |
| 1029 | 660.2 | 3.87 | * |

TABLE 3-continued

| Compound | LC/MS [M + H] | LC/MS Retention Time (min) | ELISA EC$_{50}$ μM |
|---|---|---|---|
| 1030 | 576.2 | 5.29 | **** |
| 1031 | 558.0 | 4.69 | ***** |
| 1050 | 505.33 | 3.85 | ***** |
| 1051 | 523.4 | 3.88 | ***** |
| 1052 | 539.3 | 3.97 | **** |
| 1053 | 537.5 | 4.00 | ***** |
| 1054 | 583.4 | 4.07 | ***** |
| 1055 | 535.4 | 3.82 | **** |
| 1058 | 507.0 | 5.88 | ***** |
| 1062 | 477.1 | 5.53 | ***** |
| 1063 | 560.1 | 5.47 | **** |
| 1064 | 607.1 | 4.84 | **** |
| 1066 | 562.55 | 3.63 | ***** |
| 1067 | 562.1 | 5.33 | **** |
| 1068 | 562.1 | 5.70 | ***** |
| 1069 | 562.27 | 3.9 | ***** |
| 1070 | 596.24 | 2.40 | ***** |
| 1071 | 598.21 | 2.48 | ***** |
| 1075 | 546.3 | 4.55 | **** |
| 1076 | 559.3 | 4.08 | *** |
| 1077 | 528.1 | 5.51 | **** |
| 1078 | 528.1 | 4.74 | **** |
| 1086 | 577.9 | 3.73 | **** |
| 1087 | 591.9 | 3.78 | **** |
| 1088 | 605.9 | 3.87 | **** |
| 1089 | 577.9 | 3.75 | ** |
| 1090 | 591.9 | 3.80 | ** |
| 1091 | 605.9 | 3.85 | ** |
| 1092 | 595.9 | 2.45 | **** |
| 1093 | 610.0 | 2.47 | **** |
| 1094 | 624.0 | 2.48 | **** |
| 1095 | 596.0 | 2.47 | ** |
| 1096 | 610.0 | 2.47 | ** |
| 1097 | 624.0 | 2.50 | *** |
| 1098 | 594.57 | 2.47 | **** |
| 1099 | 564.52 | 2.45 | **** |
| 1108 | 589.4 | 3.97 | **** |
| 1110 | M − 1: 493.1 | 5.48 | ***** |
| 1111 | 509.1 | 4.84 | ***** |
| 1113 | 577.4 | 34.06 | ** |
| 1115 | 564.3 | 4.61 | **** |
| 1117 | 580.3 | 4.79 | **** |
| 1119 | 610.3 | 4.85 | *** |
| 1121 | 566.3 | 4.74 | * |
| 1123 | 545.2 | 4.65 | *** |
| 1125 | 546.1 | 5.84 | ** |
| 1126 | 530.8 | 4.3 | ** |
| 1127 | 562.24 | 4.20 | *** |
| 1128 | 530.8 | 4.32 | ***** |
| 1129 | 562.26 | 4.13 | ***** |
| 1130 | 576.3 | 4.668 | **** |
| 1131 | 606.0 | 4.646 | **** |
| 1132 | 590.5 | 4.826 | **** |
| 1134 | 558.1 | 3.68 | ***** |
| 1143 | 510 | 4.300 | **** |
| 1144 | 558.5 | 4.711 | *** |
| 1145 | 558.5 | 5.05 | **** |
| 1150 | 558.5 | 4.664 | **** |
| 1151 | 588.5 | 4.616 | *** |
| 1152 | 572.5 | 4.891 | **** |
| 1155 | 546.3 | 5.54 | *** |
| 1159 | 493 | 4.22 | ***** |
| 1160 | 453 | 3.73 | ***** |
| 1161 | 492 | 3.65 | ***** |
| 1162 | 579.17 | 4.28 | ***** |
| 1168 | 547.27 | 4.18 | ***** |
| 1169 | 565.24 | 4.17 | ***** |
| 1170 | 561.28 | 4.37 | ***** |
| 1171 | 577.28 | 4.13 | ***** |
| 1172 | 539.20 | 3.58 | ***** |
| 1178 | 507.19 | 3.37 | ***** |
| 1179 | 525.25 | 3.38 | ***** |
| 1180 | 521.23 | 3.52 | ***** |
| 1181 | 537.20 | 3.35 | ***** |
| 1182 | 542.27 | 3.70 | ***** |
| 1183 | 556.26 | 2.45 | ***** |
| 1184 | 600.38 | 2.43 | ***** |
| 1194 | 572.5 | 5.237 | ***** |
| 1195 | 469.5 | 5.192 | **** |
| 1196 | 465 | 5.373 | **** |
| 1197 | 481 | 5.156 | **** |
| 1199 | 485 | 5.407 | **** |
| 1203 | 581.24 | 4.40 | ***** |
| 1205 | 539.29 | 3.58 | ***** |
| 1207 | 581.24 | 4.35 | ***** |
| 1209 | 539.26 | 3.67 | ***** |
| 1213 | 510 | 3.45 | *** |
| 1216 | 506 | 3.37 | **** |
| 1223 | 527.2 | 3.52 | ***** |
| 1224 | 527.0 | 3.53 | ***** |
| 1225 | 597.9 | 4.69 | **** |
| 1227 | 565.2 | 4.18 | ***** |
| 1228 | 567.2 | 4.37 | ***** |
| 1229 | 595.39 | 4.47 | ***** |
| 1230 | 555.24 | 3.73 | ***** |
| 1231 | 528 | 3.48 | **** |
| 1234 | 594.00 | 5.135 | ***** |
| 1235 | 578.0 | 4.785 | **** |
| 1250 | 511.07 | 3.93 | ***** |
| 1255 | 614.35 | 2.35 | *** |
| 1257 | 554.26 | 2.42 | **** |
| 1258 | 600.14 | 2.43 | ***** |
| 1259 | 527.2 | 3.50 | **** |
| 1260 | 565.2 | 4.18 | ***** |
| 1263 | 583.00 | 3.85 | ***** |
| 1265 | 469.0 | 5.478 | **** |
| 1266 | 465.0 | 5.667 | ***** |
| 1267 | 481.0 | 5.426 | **** |
| 1269 | 485.0 | 5.723 | ***** |
| 1276 | M + 23: 604.2 | 4.47 | ***** |
| 1277 | M + 23: 646.2 | 4.83 | ***** |
| 1278 | M + 23: 634.2 | 4.60 | ***** |
| 1279 | 610.2 | 5.28 | ***** |
| 1280 | 628.2 | 5.22 | **** |
| 1281 | M + 23: 614.1 | 4.65 | ***** |
| 1282 | 592.0 | 5.90 | ***** |
| 1288 | 608.2 | 4.51 | **** |
| 1289 | M + 23: 594.2 | 4.80 | ***** |
| 1290 | M + 23: 594.2 | 5.18 | ***** |
| 1291 | M + 23: 594.2 | 4.88 | **** |
| 1292 | M − 1: 519.2 | 5.53 | ***** |
| 1293 | M − 1: 523.2 | 5.34 | ***** |
| 1297 | 535.31 | 3.67 | **** |
| 1299 | M − 1: 505.2 | 5.28 | ***** |
| 1300 | M − 1: 535.2 | 4.55 | ***** |
| 1301 | M + 23: 614.2 | 5.96 | **** |
| 1302 | 590.2 | 5.37 | *** |
| 1328 | 553.4 | 3.65 | ***** |
| 1329 | 569.3 | 3.83 | ***** |
| 1330 | 539.28 | 3.60 | * |
| 1331 | 581.25 | 4.50 | * |
| 1332 | 451.27 | 3.75 | * |
| 1333 | 499.40 | 3.90 | * |
| 1335 | M − 1: 573.0 | 4.82 | **** |
| 1336 | M − 1: 519.1 | 5.76 | **** |
| 1337 | M − 1: 549.2 | 4.33 | **** |
| 1343 | 555.1 | 3.53 | ***** |
| 1344 | 571.0 | 3.70 | ***** |
| 1348 | 569.1 | 3.60 | ***** |
| 1349 | 585.0 | 3.77 | ***** |
| 1352 | 583.1 | 3.72 | ***** |
| 1353 | 599.0 | 3.88 | ***** |
| 1357 | 597.2 | 3.77 | ***** |
| 1358 | 613.2 | 3.93 | ***** |
| 1361 | M − 1: 535.2 | 5.42 | **** |
| 1362 | 622.57 | 2.53 | ***** |
| 1364 | 605.3 | 4.41 | *** |
| 1391 | 563.4 | 2.93 | ***** |
| 1392 | 577.4 | 2.82 | ***** |
| 1393 | 579.4 | 3.08 | ***** |
| 1394 | 593.3 | 2.95 | ***** |
| 1413 | 546.4 | 3.23 | ***** |
| 1414 | 560.4 | 2.83 | ***** |
| 1415 | 564.4 | 3.65 | ***** |

TABLE 3-continued

| Compound | LC/MS [M + H] | LC/MS Retention Time (min) | ELISA EC₅₀ μM |
|---|---|---|---|
| 1416 | 589.5 | 3.40 | *** |
| 1417 | 562.4 | 3.42 | ***** |
| 1418 | 576.41 | 2.95 | **** |
| 1419 | 577.4 | 4.05 | **** |
| 1420 | 580.3 | 3.83 | ***** |
| 1421 | 587.4 | 3.88 | ***** |
| 1422 | 605.4 | 3.55 | **** |
| 1440 | 558.9 | 3.65 | ***** |
| 1441 | 571.5 | 3.75 | **** |
| 1442 | 574.9 | 3.85 | ***** |
| 1476 | 580.56 | 2.43 | *** |
| 1520 | 492 | 3.87 | ***** |
| 1537 | 594.23 | 2.40 | ***** |
| 1538 | 495.2 | 3.95 | ***** |
| 1539 | 495.08 | 3.95 | *** |
| 1546 | 492 | 3.85 | *** |
| 1547 | 534.536 | 3.93 | ***** |
| 1548 | 474 | 3.75 | **** |
| 1549 | 488 | 3.77 | **** |
| 1551 | 573 | 3.83 | ***** |
| 1552 | 555 | 4.68 | ***** |
| 1553 | 569 | 4.88 | ***** |
| 1554 | 608 | 2.40 | * |
| 1555 | 624 | 3.80 | ***** |
| 1557 | M − 1: 614.2 | 4.52 | ** |
| 1558 | M − 1: 604.2 | 4.57 | **** |
| 1559 | 596.1 | 4.88 | **** |
| 1560 | M + 23: 616.2 | 4.82 | **** |
| 1561 | 631.1 | 4.15 | **** |
| 1562 | M − 1: 596.0 (cal: 597.1) | 4.98 | **** |
| 1563 | M − 1: 610.0 | 5.25 | **** |
| 1564 | M + 23: 650.2 | 4.83 | ***** |
| 1565 | M − 1: 616.1 | 4.83 | **** |
| 1566 | M − 1: 630.1 | 4.85 | *** |
| 1567 | M + 23: 652.1 | 4.93 | *** |
| 1568 | 593.2 | 2.43 | **** |
| 1569 | 615 | 4.52 | ***** |
| 1570 | 531 | 3.90 | ***** |
| 1571 | 531 | 4.00 | ***** |
| 1572 | 580 | 4.53 | ***** |
| 1577 | 521 | 3.93 | ***** |
| 1578 | 537 | 4.12 | ***** |
| 1580 | 684 | 4.32 | ***** |
| 1581 | 700 | 4.60 | ***** |
| 1604 | 521 | 3.95 | ***** |
| 1605 | 537 | 4.13 | ***** |
| 1607 | 684 | 4.30 | ***** |
| 1611 | 595.2 | 24.453 | ***** |
| 1612 | 491.365 | 5.676 | ***** |
| 1613 | 519.5 | 5.932 | ***** |
| 1614 | 505.5 | 5.775 | ***** |
| 1625 | M + 23: 618.2 | 4.61 | ***** |
| 1626 | M + 23: 632.2 | 4.76 | ***** |
| 1627 | M + 23: 667.2 | 3.96 | ***** |
| 1628 | M + 23: 667.1 | 4.03 | ***** |
| 1629 | M + 23: 667.1 | 4.92 | ***** |
| 1635 | M + 23: 620.1 | 4.73 | ***** |
| 1636 | M + 23: 634.1 | 4.92 | ***** |
| 1637 | M + 23: 664.1 | 5.03 | ***** |
| 1638 | M + 23: 654.1 | 5.03 | ***** |
| 1639 | M + 23: 666.1 | 5.10 | ***** |
| 1640 | M + 23: 612.2 | 4.93 | ***** |
| 1641 | M + 23: 647.2 | 5.13 | ***** |
| 1642 | M + 23: 600.1 | 4.92 | ***** |
| 1643 | M + 23: 614.2 | 5.12 | ***** |
| 1644 | M + 23: 628.2 | 5.35 | ***** |
| 1645 | M + 23: 644.2 | 4.91 | ***** |
| 1646 | M + 23: 634.2 | 4.88 | ***** |
| 1647 | M + 23: 646.2 | 4.99 | ***** |
| 1648 | 571 | 3.80 | ***** |
| 1652 | 700 | 4.53 | ***** |
| 1658 | 559 | 4.25 | ***** |
| 1659 | 545 | 4.12 | ***** |
| 1660 | 635 | 2.80 | ***** |
| 1661 | 650 | 2.47 | ***** |
| 1663 | 580.0 | 4.59 | ***** |
| 1664 | 579.9 | 4.84 | ***** |
| 1666 | M + 23: 648.1 | 5.44 | ***** |
| 1667 | M + 23: 640.1 | 4.55 | ***** |
| 1668 | M + 23: 620.1 | 5.45 | **** |
| 1669 | 492.1 | 13.380 | ***** |
| 1671 | 623.3 | 3.85 | ***** |
| 1672 | 593.34 | 3.70 | ***** |
| 1673 | 605.18 | 3.82 | ***** |
| 1674 | 696 | 3.33 | ** |
| 1675 | 864 | 3.88 | *** |
| 1676 | 710 | 3.33 | * |
| 1677 | 878 | 3.90 | *** |
| 1681 | 614 | 4.42 | ***** |
| 1682 | 649 | 2.33 | ***** |
| 1693 | 693 | 2.53 | ***** |
| 1694 | 550 | 2.40 | ***** |
| 1695 | 615 | 3.13 | ** |
| 1698 | 567.19 | 4.02 | ***** |
| 1701 | 509 | 3.87 | ***** |
| 1702 | 628 | 3.80 | ***** |
| 1703 | 624 | 2.35 | ** |
| 1704 | 610 | 2.40 | **** |

(S) Isomer prepared and tested.
Wherein:
1 star, >1 uM (1000 nM)
2 stars, 0.2 to 1 uM (200 nM to 1000 nM)
3 stars, 0.04 uM to 0.2 uM (40 nM to 200 nM)
4 stars, 0.008 uM to 0.04 uM (8 nM to 40 nM)
5 stars, <0.008 uM (<8 nM)

LC/MS for certain Compounds was performed on either a Waters 2795 or 2690 model separations module coupled with a Waters Micromass ZQ mass spectrometer using a Waters Xterra MS $C_{18}$ 4.6×50 mm reverse phase column (detection at 254 nM). The methods employed a gradient of acetonitrile (ACN) in water at 2 mL/min at ambient temperature as shown in Table 3a. The mobile phase was buffered with a 0.1 N formic acid.

The standard 6 minute method maintains a constant 85/5/10 ratio of water/ACN/1% aqueous formic acid from 0 minutes to 0.5 minutes. The method runs a linear gradient from 85/5/10 at 0.5 minutes to 0/90/10 at 3.5 minutes. The method holds at 0/90/10 until 4.5 minutes then immediately drops back down to 85/5/10 and holds there until 6 minutes.

The non-polar 6 minute method maintains a constant 60/30/10 ratio of water/ACN/1% aqueous formic acid from 0 minutes to 0.5 minutes. The method runs a linear gradient from 60/30/10 at 0.5 minutes to 0/90/10 at 3.5 minutes. The method holds at 0/90/10 until 4.5 minutes then immediately drops back down to 60/30/10 and holds there until 6 minutes.

The polar 6 minute method maintains a constant 90/0/10 ratio of water/ACN/1% aqueous formic acid from 0 minutes to 0.5 minutes. The method runs a linear gradient from 90/0/10 at 0.5 minutes to 20/70/10 at 3.5 minutes. The method holds at 20/70/10 until 4.5 minutes then immediately drops back down to 90/0/10 and holds there until 6 minutes.

TABLE 3a

| Time | % Acetonitrile | % Water | % 1% Aq. Formic Acid | Gradient |
|---|---|---|---|---|
| Standard | | | | |
| 0.00 | 5 | 85 | 10 | |
| 0.50 | 5 | 85 | 10 | hold |
| 3.50 | 90 | 0 | 10 | linear hold |

TABLE 3a-continued

| Time | % Acetonitrile | % Water | % 1% Aq. Formic Acid | Gradient |
|---|---|---|---|---|
| 4.50 | 5 | 85 | 10 | instant |
| 6.00 | 5 | 85 | 10 | hold |
| Non-Polar | | | | |
| 0.00 | 30 | 60 | 10 | |
| 0.50 | 30 | 60 | 10 | hold |
| 3.50 | 90 | 0 | 10 | linear hold |
| 4.50 | 30 | 60 | 10 | instant |
| 6.00 | 30 | 60 | 10 | hold |
| Polar | | | | |
| 0.00 | 0 | 90 | 10 | |
| 0.50 | 0 | 90 | 10 | hold |
| 3.50 | 70 | 20 | 10 | linear hold |
| 4.50 | 0 | 90 | 10 | instant |
| 6.00 | 0 | 90 | 10 | hold |

LC/MS for Compounds 1611 and 1669 was performed using a $C_{1-8}$-BDS 5 (250×4.6 mm) column with a 0.7 mL/min flow rate. The following solvent gradient was employed using 0.1% TFA/water as solvent A and acetonitrile as solvent B: 20% B for 0-20 minutes, 70% B for 20-30 minutes, 100% B for 30-40 minutes, 20% B for 40-50 minutes.

9. EXAMPLE

Compound Pharmacodynamics

The examples that follow demonstrate that the Compounds tested can inhibit the pathological production of human VEGF, and suppress edema, inflammation, pathological angiogenesis and tumor growth tumor growth. Compounds tested have been shown to inhibit the pathological production of human VEGF by multiple human tumor cells and/or human tumors in animal models with pre-established human tumors.

9.1 Inhibition of Pathological Production of VEGF
9.1.1 Cell Based Assays
9.1.1.1 Compound #10 and Compound 1205 Inhibit Pathological VEGF Production in Transformed Cells Grown under Hypoxic Conditions This example demonstrates the selective inhibition of Compound #10 and Compound 1205 on pathological VEGF production in transformed HeLa cells grown under stressed conditions while sparing VEGF production in HeLa cells grown under non-stressed conditions.

Experimental Design. HeLa (human cervical carcinoma) cell cultures were established under normoxic conditions (21% oxygen). HeLa cells increase VEGF production 4- to 5-fold in response to hypoxia. In one experimental design, vehicle (0.5% DMSO) alone, or a range of concentrations of Compound #10 was added to the HeLa cell cultures and the cells were incubated for 48 hours under either hypoxic (1% oxygen) or normoxic conditions. In another experimental design, vehicle (0.5% DMSO) alone, or a range of concentrations of Compound #10, Compound 1205, or Compound 1330 was added to the culture medium and the cells were incubated for 48 hours. At the completion of treatment, the conditioned media were collected and the VEGF protein levels were assayed in an enzyme-linked immunosorbent assay (ELISA) with primary antibodies that recognize the soluble $VEGF_{121}$ and $VEGF_{165}$ isoforms (R & D Systems, Minneapolis, Minn., USA). To ensure that decreases in VEGF concentration were not due to cytotoxicity, cultures were assayed using a standard assay (CELLTITER-GLO® Luminescent Cell Viability Assay; Promega, Madison, Wis., USA) that measures total cellular adenosine triphosphate (ATP) concentrations as an indicator of cell viability.

Results. FIG. 1 shows the concentrations of VEGF in conditioned media across the Compound #10 dose range tested. In the absence of Compound #10, media from hypoxic cells had substantial concentrations of VEGF (mean 1379 pg/mL). Compound #10 treatment induced dose dependent reductions in VEGF concentrations in the media, resulting in a maximal 87% decrease in VEGF concentration (to a mean of 175 pg/mL). By contrast, media from normoxic cells had relatively low concentrations of VEGF (mean 257 pg/mL) in the absence of Compound #10, and showed only a 39% decrease in VEGF concentrations (to a mean of 157 pg/mL) in the presence of Compound #10. No cytotoxicity was observed at any concentration tested. The data indicate that under stress conditions (with hypoxia), VEGF production was more sensitive to Compound #10 inhibition than under non-stress conditions (with normoxia). This data indicates that Compound #10 selectively inhibits or reduces pathological tumor-related production of soluble VEGF isoforms while sparing physiological VEGF production of the same isoforms. The (R)-enantiomer of Compound #10 showed lower activity (data not shown).

FIG. 25 shows the concentrations of VEGF in conditioned media across the dose range tested for Compound #10, Compound 1205 and Compound 1330. The data indicate that Compound #10 and Compound 1205 inhibit stress-induced VEGF production.

9.1.1.2 Compound #10 Inhibits Pathological VEGF Production in Nontransformed Cells Grown under Hypoxic Conditions This example demonstrates the inhibition of Compound #10 is selective for the pathological production of soluble VEGF isoforms in nontransformed keratinocytes grown under stressed conditions and does not affect the production of soluble VEGF isoforms in nontransformed keratinocytes grown under non-stressed conditions.

Experimental Design. Nontransformed normal human keratinocyte cell cultures were established under normoxic conditions (21% oxygen). Vehicle (0.5% DMSO) alone, or a range of concentrations of Compound #10 was added to the cultures and the cells were incubated for 72 hours under either under hypoxic (1% oxygen) or normoxic conditions. At the completion of treatment, cells were assessed for viability with an ATP assay and conditioned media were evaluated for VEGF protein levels by ELISA (as described in Section 9.1.1.1).

Results. FIG. 2 shows the concentrations of VEGF in conditioned media across the Compound #10 dose range tested. In the absence of Compound #10, media from hypoxic keratinocytes had substantial concentrations of VEGF (mean 1413 pg/mL). Compound #10 treatment induced dose dependent reductions in VEGF concentrations in the media, resulting in a maximal 57% decrease in VEGF concentration (to a mean of 606 pg/mL). By contrast, media from normoxic cells had relatively low concentrations of VEGF (mean 242 pg/mL) in the absence of Compound #10 and showed only a 21% decrease in VEGF concentrations (to a mean of 192 pg/mL) in the presence of Compound #10. No toxicity was observed at any concentration tested.

This data indicates that Compound #10 selectively inhibits or reduces pathological production of soluble VEGF isoforms in nontransformed keratinocytes grown under stressed hypoxic conditions while sparing physiological VEGF production of the same isoforms in unperturbed cells.

9.1.1.3 Compound #10 Inhibits Matrix-Bound Tumor VEGF Production

This example demonstrates that Compound #10 inhibits the pathological production of matrix bound/cell associated $VEGF_{189}$ and $VEGF_{206}$ isoforms resulting from oncogenic transformation.

Experimental Design. HT1080 (human fibrosacoma) cell cultures were established under normoxic conditions (21% oxygen). HT1080 cells constitutively overproduce VEGF even under normoxic conditions. Vehicle (0.5% DMSO) alone or a range of concentrations of Compound #10 was added to the cultures, and the cells were incubated for 48 hours under normoxic conditions. At the completion of treatment, the cells were washed and harvested. Cells were incubated with a primary antibody that recognizes the $VEGF_{189}$ and $VEGF_{206}$ isoforms. Infrared-dye labeled antibodies were applied secondarily, and the amounts of $VEGF_{189}$ and $VEGF_{206}$ were determined using the IN-CELL WESTERN® assay and ODYSSEY® infrared imaging system (Li-Cor, Lincoln, Nebr., USA); results are expressed as percentage inhibition relative to vehicle treated controls. Conventional Western blotting using the same primary antibody was also performed to confirm the presence of the matrix associated isoforms; for these experiments actin was used as a loading control. Actin is a ubiquitous housekeeping protein that is not known to be post transcriptionally regulated.

Results. As shown in FIG. 3, Compound #10 induced a potent concentration-dependent inhibition of $VEGF_{189}$ and $VEGF_{206}$ isoforms. These results demonstrate that Compound #10 inhibits the production of matrix-associated as well as soluble forms of tumor-derived VEGF. As shown in FIG. 4, immunoblotting documented the presence of 2 bands at the expected location for $VEGF_{189}$ and $VEGF_{206}$, and confirmed a concentration-dependent Compound #10 effect in reducing the amounts of these isoforms. The activity of the (R) enantiomer was relatively lower.

This data shows that Compound #10 inhibits pathological production of the matrix bound/cell associated VEGF isoforms resulting from oncogene transformation.

9.1.1.4 Compound #10 Inhibits Soluble VEGF Production in Multiple Human Tumor Cell Lines This example demonstrates that Compound #10 inhibits soluble VEGF production in multiple human tumor cell lines.

Study Design. The activity of Compound #10 in suppressing VEGF production in a number of other human tumor cell lines has been assessed. These evaluations focused on cell lines that produce sufficient soluble VEGF (>200 pg/mL in conditioned media, either constitutively or under hypoxic stress) to allow assessment of Compound #10 activity by ELISA. In these experiments, cultures were established under normoxic conditions (21% oxygen). Cultures were then incubated for 48 hours with vehicle (0.5% DMSO) alone or with Compound #10 over a range of concentrations from 0.1 nM to 10 μM. Cells requiring induction of VEGF production were incubated under hypoxic conditions (1% oxygen). At the completion of treatment, the conditioned media were collected and assayed by ELISA (as described in Section 9.1.1.1) for soluble $VEGF_{121}$ and $VEGF_{165}$ isoforms; results were calculated as percentage inhibition relative to vehicle treated controls. $EC_{50}$ values were calculated from the dose concentration response curves.

Results. Compound #10 potently inhibited the production of soluble VEGF in 18 of the human tumor cell lines tested to date. The $EC_{50}$ values for cell lines showing VEGF inhibition are generally in the low nanomolar range, as presented in Table 4. Compound #10 did not show activity in several cell lines in which there was insufficient basal or inducible production of soluble VEGF. Other human cell lines that produce sufficient soluble VEGF in vitro or in vivo may be used, with appropriate adaptations, by those skilled in the art to measure inhibition of pathologically produced soluble human VEGF.

TABLE 4

Inhibition of Soluble VEGF Production by Compound #10 in Human Cell Lines - $EC_{50}$ Values by Cell Line.

| Tumor Type | Cell Line | VEGF Inhibition Approximate $EC_{50}$ (nM) |
|---|---|---|
| Breast | MDA-MB-231[a] | 5 |
|  | MDA-MB-468[a] | 5 |
| Cervical | HeLa[a] | 2 |
| Colorectal | HCT-116 | 10 |
| Epidermoid | A431 | 10 |
| Fibrosarcoma | HT1080 | 10 |
| Gastric | SNU-1 | 0.1 |
|  | AGS | 0.1 |
|  | Kato III[a] | 10 |
| Lung | NCI H460 | 10 |
|  | A549 | 50 |
|  | Calu-6[a] | 7 |
| Melanoma | A375[a] | 50 |
| Neuroblastoma | SY5Y[a] | 5 |
| Ovarian | SKOV3[a] | 10 |
| Pancreas | Capan-1[a] | 5 |
| Prostate | LNCaP[a] | 15 |
| Renal cell | HEK293 | 10 |

[a]Cell lines requiring incubation under hypoxic conditions (1% oxygen) to induce VEGF production.
Abbreviations: $EC_{50}$ = effective concentration achieving 50% of peak activity; VEGF = vascular endothelial growth factor

9.1.2 Animal Model Systems

9.1.2.1 Compound #10 Selectively Inhibits Pathological VEGF Production Relative to Other Human Angiogenic Factors This example demonstrates that Compound #10 selectively inhibits pathological VEGF production relative to other human angiogenic factors.

Experimental Design. In a series of experiments evaluating the effects of Compound #10 on intratumoral VEGF and tumor growth, intratumoral levels of VEGF-C, P1GF (Placental Growth Factor), FGF-2 (Fibroblast growth factor 2), survivin, PDGF (Platelet derived growth factor), and endostatin were also measured to assess the selectivity of Compound #10. VEGF-C and P1GF were analyzed to determine the in vivo effects of Compound #10 on other members of the VEGF family of angiogenic factors. All of these factors can be produced at tumor sites, and all may support tumor growth and metastases. See Yoon et al., Circ Res. 2003, 93(2):87 90; Ferrara et al., Nat. Rev. Drug Discov. 2004, 3(5):391 400; Luttun et al., Biochim. Biophys. Acta 2004, 1654(1):79 94; Saharinen et al., Trends Immunol. 2004, 25(7):387 95. There is also evidence that VEGF-A may stimulate production of P1GF by a post transcriptional mechanism. See Yao et al., FEBS Lett. 2005, 579(5):1227 34. VEGF-B was not assessed. The angiogenic growth factor FGF-2 was analyzed because it promotes tumor survival (see Bikfalvi et al., Angiogenesis 1998, 1(2):155 73), and has a 5'-UTR IRES. See Vagner at al., Mol. Cell. Biol. 1995, 15(1):35 44; Hellen et al., Genes Dev. 2001, 15(13):1593 612. The survivin protein was similarly evaluated because the survivin mRNA has an IRES. PDGF was assessed because this protein has angiogenic activity and its mRNA contains an IRES. See Sella et al., Mol. Cell. Biol. 1999, 19(8):5429 40; Hellen et al., supra. Endostatin was included because antiangiogenic treatment in vivo has shown that compensatory decreases in endogenous angiogenic inhibitors such as endostatin, thrombospondin, and angiostatin, results in a more pro angiogenic environment. See Sim, Angiogenesis, 1998, 2(1):37-48.

In all of these experiments, HT1080 cells ($5 \times 10^6$ cells/mouse) were implanted subcutaneously in male athymic nude mice. When tumors had become established, mice were divided into groups (10 mice/group). Treatments comprised Compound #10 (either alone or as the racemic mixture) or the corresponding vehicle alone, administered by oral gavage BID ("bis in die"; twice a day) on Monday through Friday and QD ("quaque die"; daily) on Saturday and Sunday over periods of 7 to 21 days (Table 5). Tumor size was measured by calipers at the beginning and end of treatment. At the completion of Compound administration, the mice were sacrificed, and excised tumors were assayed by ELISA for intratumoral VEGF or other angiogenic factors using methods analogous to those described in Section 9.1.1.1.

Results. As summarized in the studies shown in Table 5, Compound #10 universally inhibited the production of intratumoral VEGF A and tumor size. Compound #10 also reduced intratumoral P1GF in the experiments where this factor was measured; the results show a variable effect on VEGF-C. Compound #10 did not have statistically significant effects on levels of the other proteins tested, except for FGF 2 levels (as shown in Study 5). In Study 5, treatment was initiated when the tumors were quite large (~600 mm$^3$). The study was continued for 15-days, and the tumors had become quite bulky by the time intratumoral protein levels were analyzed. However, Compound #10 still decreased intratumoral VEGF levels by 78%, although FGF-2 levels were noted to be significantly elevated at the time of study termination. In Studies 2 and 3, endostatin levels were depressed by 22 to 30%, although these changes were not statistically significant. Collectively, these data indicate that Compound #10 is selective for suppression of VEGF family proteins.

Table 5. Study Design and Efficacy Information for Assessments of Selectivity for VEGF Inhibition by Compound #10 in Nude Mice Bearing HT1080 Xenografts.

TABLE 5

| Parameter | | 1 | 2 | 3 | 4 | 5 | 6 | 7 |
|---|---|---|---|---|---|---|---|---|
| | | | | Study Number | | | | |
| Animal number per group | | 10 | 10 | 10 | 10 | 10 | 7 | 10 |
| Compound #10 dose (mg/kg)$^a$ | | 1 | 5 | 5 | 5 | 5/50$^b$ | 5 | 10 |
| Administration | Route | Oral | Oral | Oral | Oral | Oral | Oral | Oral |
| | Schedule | BID$^c$ | BID$^c$ | BID$^c$ | BID$^c$ | BID$^c$ | QD$^d$ | QD$^d$ |
| Vehicle | | DMSO/PEG | DMSO/PEG | DMSO/PEG | DMSO/PEG | DMSO/PEG | L21$^e$ | L21$^e$ |
| Compound #10 Treatment duration (days) | | 28 | 7 | 10 | 9 | 15 | 21 | 42 |
| Vehicle-treatment duration (days) | | 14 | 7 | 10 | 9 | 10 | 21 | 10 |
| Initial mean tumor size (mm$^3$) | | 85 | 390 | 285 | 610 | 610 | 180 | 160 |
| Final mean Compound #10-treated tumor size (mm$^3$) | | 450 | 595 | 735 | 953 | 1922 | 750 | 1770 |
| Mean % difference relative to vehicle-treated animals$^f$ in: | | | | | | | | |
| Tumor size | | −58*$^g$ | −32* | −40* | −44* | −34*$^h$ | −51* | −63*$^h$ |
| Human VEGF-A (%) | | −57* | −81* | −95* | −85* | −78* | −95* | −42 |
| Human VEGF-C (%)$^i$ | | ND | −19 | −26 | ND | ND | −38* | +10 |
| Human PlGF (%)$^i$ | | ND | −67* | −59* | ND | ND | −73 | −65* |
| FGF-2 | | +3 | +3 | +5 | +15 | +31* | ND | ND |
| Survivin | | +7 | ND | ND | −9 | ND | ND | ND |
| PDGF | | +12 | ND | −30 | +23 | +20 | ND | ND |
| Endostatin | | ND | −30 | −22 | ND | ND | ND | ND |

*p < 0.05 (Student's t-test relative to vehicle)

$^a$Some animals received racemic mixture; the dose is expressed as amount of Compound #10 in the mixture.

$^b$Mice were treated with 5 mg/kg for the first 9 days and with 50 mg/kg for the last 6 days.

$^c$Treatments were administered by oral gavage BID on Monday through Friday and QD on Saturday and Sunday for the number of days shown. All morning doses were given before 0830 hours. Evening doses were administered after 1630 hours (i.e., ≥8 hours after the morning dose).

$^d$Treatments were administered by oral gavage QD in the morning before 0830 hours on Monday through Friday for the number of days shown.

$^e$Vehicle was 35% Labrasol, 35% Labrafac and 30% Solutol).

$^f$Calculated as [1-(treated/control)] × 100%

$^g$Difference in tumor size is shown for Day 14, the day the vehicle-treated mice were taken off study.

$^h$Difference in tumor size is shown for Day 10, the day the vehicle-treated mice were taken off study.

$^i$Six mice per group in Compound #10-treated and vehicle-treated groups were analyzed Abbreviations:

BID = 2 times per day;

QD = 1 time per day;

DMSO = dimethyl sulfoxide;

PEG-300 = polyethylene glycol (molecular weight 300);

FGF-2 = basic fibroblast growth factor-2;

PDGF = platelet-derived growth factor;

PlGF = placental growth factor;

VEGF = vascular endothelial growth factor;

ND = not done

9.1.2.2 Compound #10 Dose-Dependently Reduces Tumor and Pathologically Produced Plasma Human VEGF Concentrations This example demonstrates that Compound #10 dose-dependently reduces intratumoral and pathologically produced plasma human VEGF concentrations in vivo.

Experimental Study Design. HT1080 cells ($5 \times 10^6$ cells/mouse) were implanted subcutaneously in male athymic nude mice. When tumors had become established (i.e., the mean tumor size had reached $180 \pm 75$ mm$^3$), mice were divided into 6 groups and treatment was assigned as shown in Table 6.

TABLE 6

Study Design for Dose Response Assessment in Nude Mice Bearing HT1080 Xenografts.

| Test Compound | Number of Animals M | Number of Animals F | Dose (mg/kg) | Administration[a] Route | Administration[a] Schedule | Dose Volume (mL/kg) | Dose Concentration (mg/mL) |
|---|---|---|---|---|---|---|---|
| Vehicle[b] | 10 | 0 | 0 | Oral | BID | 4 | 0 |
| Compound #10 | 10 | 0 | 0.3 | Oral | BID | 4 | 0.075 |
| Compound #10 | 10 | 0 | 1 | Oral | BID | 4 | 0.25 |
| Compound #10 | 10 | 0 | 3 | Oral | QD | 4 | 0.75 |
| Compound #10 | 10 | 0 | 3 | Oral | BID | 4 | 0.75 |
| Compound #10 | 10 | 0 | 10 | Oral | QD | 4 | 2.5 |

[a]Treatments were administered by oral gavage 7-days per week (except the 10-mg-QD regimen, which was administered daily on Monday through Friday) for a total of 18 days. All morning doses were given before 0830 hours. For BID schedules, evening doses were administered after 1630 hours (i.e., ≥8 hours after the morning dose).
[b]Vehicle was L21 (35% Labrasol, 35% Labrafac, and 30% Solutol).
Abbreviations:
BID = 2 times per day;
QD = 1 time per day Tumor size was measured using calipers at periodic intervals during the study (data shown in Section 9.2.2). Retro-orbital blood collection was performed to assess Compound #10 trough plasma concentrations after the first dose (just prior to the second dose) on Day 1, Day 4, and Day 9, and at study termination. The study was ended after 18 days, when the vehicle treated tumors reached a mean volume of ~1755 mm$^3$. Retro-orbital terminal bleeding was performed at ~8 to 16 hours (depending upon the schedule of Compound administration) after the last dose to assess pathologic plasma human VEGF concentrations and trough Compound #10 plasma concentrations. Mice were sacrificed, and excised tumors were homogenized in buffer containing protease inhibitors. Both terminal intratumoral and pathologic plasma human VEGF levels were measured using an ELISA that recognizes human VEGF$_{121}$ and VEGF$_{165}$ (as described in Section 9.1.1.1). Intratumoral VEGF levels were normalized to the total tumor protein concentration, while pathologic plasma human VEGF levels were expressed in pg/mL of plasma. Plasma Compound #10 concentrations were evaluated by high performance liquid chromatography and with tandem mass spectroscopy (HPLC-MS/MS).

Results. As shown in FIG. 5 and FIG. 6, Compound #10 significantly suppressed pathologic human VEGF levels in tumors and in plasma in all Compound #10 dose groups. At the suboptimal Compound #10 dose of 0.3 mg/kg BID, partial reductions in both tumor and pathologic plasma human VEGF concentrations were observed, while human VEGF reductions were essentially maximal at all Compound #10 dose levels of ≥1 mg/kg BID. The correlation between pathologic plasma and tumor human VEGF levels in this animal model supports the potential utility of assessing pathologic plasma human VEGF levels to serve as a mechanism-specific, pharmacodynamic marker of Compound activity in the clinic.

The data shows that Compound #10 dose-dependently reduces intratumoral and pathologically produced plasma human VEGF concentrations in vivo.

9.1.2.3 Compound 1205 Reduces Tumor and Pathologically Produced Plasma Human VEGF Concentrations This example demonstrates that Compound 1205 reduces intratumoral and pathologically produced plasma human VEGF concentrations in vivo.

Experimental Design. HT1080 cells ($5 \times 10^6$ cells/mice) were implanted subcutaneously into male athymic nude mice. Treatment with vehicle alone or Compound 1205 was initiated when the median tumor volume was approximately $311 \pm 88$ mm$^3$. Table 7 and Table 9 (study design #21 and #23) provide the study design for assessing tumor and plasma pathologic VEGF concentrations—each group in each study included eight (8) mice. When the tumors in vehicle-treated mice had reached the target size of ~1200 mm$^3$ for study #21 and ~1500 mm$^3$ for study #23, all mice in the study were sacrificed, and excised tumors were homogenized in buffer containing protease inhibitors. Both intra-tumor and pathologic plasma human VEGF levels were measured using an ELISA that recognizes human VEGF$_{121}$ and VEGF$_{165}$. Intra-tumor VEGF levels were normalized to the total tumor protein concentration and pathologic plasma VEGF levels were expressed in pg/mL. Because smaller tumors produce less VEGF per mg of tumor protein, intra-tumor VEGF levels were normalized to tumor size. Table 9 provides the study design for assessing tumor and pathologic plasma VEGF.

Results. Treatment with Compound 1205 at 0.5 or 3 mg/kg for 14-days significantly reduced the levels of pathologic human VEGF measured in excised tumors (FIG. 27A-B) and in plasma (FIG. 28) compared to levels measured in tumors and plasma from mice treated with vehicle. At the dose of 0.5 or 3 mg/kg QD, Compound 1205 inhibits both tumor and pathologic plasma human VEGF levels by more than 95%. Even with the reduction in tumor size in the treated groups, the volume normalized intra-tumor human VEGF levels were significantly reduced (FIG. 27B; Table 7).

TABLE 7

Inhibition of Intra-Tumor and Pathologic Plasma Human VEGF by Compound 1205

| | Study #21 | | Study #23 | |
|---|---|---|---|---|
| | Vehicle | Compound 1205 | Vehicle | Compound 1205 |
| 1) Dose (mg/kg) | 0 | 0.5    3 | 0 | 1 |
| 2) Regimen | QD | QD    QD | QD | QD |
| 3) Test-Compound duration (days) | 14 | 14    14 | 14 | 14 |

TABLE 7-continued

Inhibition of Intra-Tumor and Pathologic Plasma Human VEGF by Compound 1205

|  | Study #21 | | Study #23 | |
|---|---|---|---|---|
|  | Vehicle | Compound 1205 | Vehicle | Compound 1205 |
| 4) Mean difference in human tumor VEGF (%) at Day 14 (Compound 1205) or Day 18 (Compound #10) | NA | 95%** 98%** | NA | 95** |
| 5) Mean difference in human plasma VEGF (%) on Day 14 (Compound 1205) or on Day 18 (Compound #10) | NA | 97%** 99% | NA | 100%** |

**$p < 0.05$ (ANOVA vs. vehicle).

9.2 Inhibition of Pathological Angiogenesis and Tumor Growth

9.2.1 Compound #10 Inhibits Tumor Angiogenesis

This example demonstrates that Compound #10 reduces the total volume and diameter of tumor vessels.

Experimental Design. HT1080 cells ($5 \times 10^6$ cells/mouse) were implanted subcutaneously in male athymic nude mice. At a mean tumor size of 285±45 mm$^3$, mice were divided into 2 groups and treatment was administered as shown in Table 8.

At the end of treatment, the mice were sacrificed. Excised tumors were assayed by ELISA for VEGF content as described in Section 9.1.1.1, and were sectioned and immunostained with an anti murine CD31 antibody that is specific for endothelial cells.

TABLE 8

Study Design for Assessment of Intratumoral Microvessel Density in Nude Mice Bearing HT1080 Xenografts.

| Test Compound | Number of Animals | | Dose (mg/kg) | Administration$^a$ | | Dose Volume (mL/kg) | Dose Concentration (mg/mL) |
|---|---|---|---|---|---|---|---|
|  | M | F |  | Route | Schedule |  |  |
| Vehicle$^b$ | 10 | 0 | 0 | Oral | BID | 8 | 0 |
| Racemic mixture$^c$ | 10 | 0 | 5$^c$ | Oral | BID | 8 | 0.625 |

$^a$Treatments were administered by oral gavage BID on Monday through Friday and QD on Saturday and Sunday Treatments were administered by oral gavage BID on Monday through Friday and QD on Saturday and Sunday for a total of 10 days. All morning doses were given before 0830 hours. Evening doses were administered after 1630 hours (i.e., ≥8 hours after the morning dose).
$^b$Vehicle was 5% DMSO and 95% PEG 300.
$^c$Racemic material was used for this study at a dose of 10 mg/kg (1.25 mg/mL), resulting in a dose of the active Compound #10 enantiomer of 5 mg/kg (0.625 mg/mL).
Abbreviations:
BID = 2 times per day;
DMSO = dimethyl sulfoxide;
PEG 300 = polyethylene glycol (molecular weight 300);
QD = 1 time per day Results. Treatment with Compound #10 resulted in a mean 95% inhibition of tumor VEGF concentration. As shown in FIG. 7B (Compound #10 treated) in comparision to FIG. 7A (vehicle treated), this activity resulted in a profound effect on the architecture of the vasculature. Although the vessel count was unchanged, the total volume of tumor vessels and the diameters of vessels were visibly reduced. These findings are consistent with results from reports describing the effects of antiangiogenic therapies on larger tumors that have an existing vasculature. See Yuan et al., Proc. Natl. Acad. Sci. USA. 1996; 93(25):14765-70.

9.2.2 Compound #10 Inhibits Tumor Growth In Vivo

This example demonstrates that Compound #10 inhibits tumor growth in nude mice bearing HT1080 xenografts.

Experimental Design. The experimental design was reported in Section 9.1.2.2.

Results. The dose response effect of Compound #10 that correlated with decreases in tumor and pathologic human VEGF concentrations (see FIG. 5 and FIG. 6; Section 9.1.2.2) was also observed when assessing tumor size by treatment group over time. As depicted in FIG. 8, maximum antitumor activity was again observed at Compound #10 dose levels of ≥1 mg/kg BID. The dose of 1 mg/kg BID was associated with mean trough plasma concentrations of 0.13 µg/mL (0.28 µM) at 16 hours after the first day of dosing (n=3), and with steady state mean trough plasma concentrations of 0.82 µg/mL (1.76 µM) at 16 hours after the last dose on Day 18 (n=4). These data provide an indication of trough plasma concentrations that could be targeted when assessing the pharmacokinetics (PK) of a Compound in humans. In observing the animals, there was no overt toxicity associated with Compound #10 treatment. This data shows that Compound #10 inhibits tumor growth in nude mice bearing HT1080 xenografts.

9.2.3 Compound 1205 Inhibits Tumor Growth In Vivo

This example demonstrates that Compound 1205 inhibits tumor growth in nude mice bearing HT1080 xenografts.

Experimental Design. HT1080 cells ($5 \times 10^6$ cells/mouse) were implanted subcutaneously in male athymic nude mice. When tumors had become established (i.e., the mean tumor size had reached 311±88 mm$^3$), mice were divided into 5 groups and treatment was administered as shown in Table 9 and 10. Compound 1330 is a relatively inactive (R,S) diastereomer of Compound 1205, which has (S,S) configuration. For comparison, Compound #10 was included in this study.

TABLE 9

Study Design for HT1080 Xenograft Studies Assessing In vivo Efficacy of Compound 1205 and Compound #10.

| Test Compound | # of Animals Male | Dose (mg/kg) | Regimen | Dose Volume (mL/kg) | Dose Conc. (mg/mL) | Study # | Study Termination |
|---|---|---|---|---|---|---|---|
| Vehicle† | 8 | 0 | QD | 8 | 0 | 21 | All mice were taken off study |
| Compound 1205 | 8 | 0.5 | QD | 8 | 0.0625 | 21 | when tumors in vehicle |
| Compound 1205 | 8 | 3 | QD | 8 | 0.375 | 21 | reached 1200 mm$^3$ |

TABLE 9-continued

Study Design for HT1080 Xenograft Studies Assessing In vivo Efficacy of Compound 1205 and Compound #10.

| Test Compound | # of Animals Male | Dose (mg/kg) | Regimen | Dose Volume (mL/kg) | Dose Conc. (mg/mL) | Study # | Study Termination |
|---|---|---|---|---|---|---|---|
| Vehicle† | 8 | 0 | QD | 8 | 0 | 22 | (A) Vehicle-treated mice were taken off study when the average tumor size of the group wais 1500 mm$^3$. (B) Each treated mouse was taken off study when its tumor was 1500 mm$^3$ |
| Compound 1205 | 8 | 0.5 | QD | 8 | 0.0625 | 22 | |
| Compound 1205 | 8 | 3 | QD | 8 | 0.375 | 22 | |
| Vehicle† | 8 | 0 | QD | 8 | 0 | 23 | All mice were taken off study when tumors in vehicle reached 1500 mm$^3$ |
| Compound 1205 | 8 | 1 | QD | 8 | 0.125 | 23 | |
| Vehicle† | 8 | 0 | QD | 8 | 0 | 24a | A) Vehicle- and Compound 1330-treated mice were taken off study when the average tumor size of the group wais 1500 mm$^3$. (B) Each treated mouse was taken off study when its tumor was 1500 mm$^3$ |
| Compound 1205 | 8 | 10 | QD | 8 | 1.25 | 24a | |
| Compound 1330Φ | 8 | 10 | QD | 8 | 1.25 | 24a | |
| Vehicle† | 8 | 0 | QD | 8 | 0 | 24b | (A) Vehicle-treated mice were taken off study when the average tumor size of the group wais 1500 mm$^3$. (B) Each treated mouse was taken off study when its tumor was 1500 mm$^3$ |
| Compound 1205 | 8 | 0.3 | QD | 8 | 0.0375 | 24b | |

†Vehicle was 0.5% HPMC/1% Tween-80
‡ Vehicle was L21 (35% Labrasol, 35% Labrafac, and 30% Solutol).
ΦInactive (R, S) diastereomer of Compound 1205
Abbreviations:
BID = twice per day,
QD = once per day Results. The results of the studies described in Table 10 and are shown in FIG. 26 for study #24a The data indicate that Compound 1205 (S,S diastereoisomer) inhibits tumor growth in an animal model with a pre-established human tumor. As shown in FIG. 26, treatment with Compound 1205 (S,S), but not with the (R,S) diastereomer Compound 1330, significantly delayed growth of HT1080 tumor cells in vivo. The growth of the tumors in mice treated with Compound 1330 overlapped with the growth of tumors in mice treated with 0.5% HPMC vehicle. This suggests that the relatively inactive (R, S) diastereomer (Compound 1330) does not appreciably isomerize to active Compound 1205 in vivo. Compound 1205 is active at doses as low as 0.3 mg/kg.

TABLE 10

Effect of Compound 1205 and Compound #10 on Growth of HT1080 Tumor Cells In vivo.

| | Compound 1205 | | | | | | | Compound #10 |
|---|---|---|---|---|---|---|---|---|
| | 24b | 22 | 21 | 23 | 22 | 21 | 24a | 24a |
| | Study Information | | | | | | | |
| Study #$^A$ | | | | | | | | |
| Dose (mg/kg) | 0.3 | 0.5 | 0.5 | 1 | 3 | 3 | 10 | 10 |
| Regimen | QD | QD | QD | QD | QD | QD | QD | QD |
| Dose (mg/kg/week) | 2.1 | 3.5 | 3.5 | 7 | 21 | 21 | 70 | 70 |
| Study design | Xeno | Xeno | PD | PD | Xeno | PD | Xeno | Xeno |
| Number of days that test compound was administered | 16$^C$ | 28$^C$ | 14 | 14 | 32$^C$ | 14 | 30$^C$ | 27$^C$ |
| Initial mean tumor size (mm$^3$) | 204 | 170 | 167 | 157 | 170 | 167 | 311 | 311 |
| Day that vehicle-treated mice were taken off study | 15 | 11 | 14 | 14 | 11 | 14 | 11 | 11 |
| Mean tumor size in vehicle-treated mice when taken off study | 1790 | 1390 | 1210 | 1500 | 1390 | 1210 | 1500 | 1500 |
| Final mean terminal tumor size in treatment group (mm$^3$) | 1540 | 1750 | 580 | 710 | 1840 | 379 | 1400 | 1460 |

TABLE 10-continued

Effect of Compound 1205 and Compound #10 on Growth of HT1080 Tumor Cells In vivo.

| | Compound 1205 | | | | | | | Compound #10 |
|---|---|---|---|---|---|---|---|---|
| | 24b | 22 | 21 | 23 | 22 | 21 | 24a | 24a |
| | Results | | | | | | | |
| Study # Mean difference in tumor growth rate at the Day that the vehicle-treated tumors taken off study (%)$^B$ | 28% | 62%** | 61%** | 59%** | 75%** | 80%** | 76%** | 59%** |
| Difference vs. vehicle in median number of days to reach 1000 mm$^3$ (Days) | 0.7 | 11 | NA | NA | 14** | NA | 14** | 8** |

$^A$See Table 9 for additional study information.
$^B$% Difference in the rat of growth in compound-treated vs. vehicle-treated
**P < 0.05 (ANOVA vs. vehicle)
$^C$Average time on study.
NA not applicable. The time to progression could not be calculated for PD (pharmacodynamic) studies.
Xeno Xenograft 9.2.4 Time-Course Effects of Compound #10 on Tumor Size and Pathologically Produced Plasma Human VEGF Concentrations This example demonstrates that Compound #10 has a rapid onset for reducing xenograft tumor size and pathologically produced plasma human VEGF concentration.

Experimental Design. HT1080 cells (5×10$^6$ cells/mouse) were implanted subcutaneously in male athymic nude mice. When tumors had become established (i.e., the mean tumor size had reached 585±150 mm$^3$), mice were divided into 4 treatment groups, as shown in Table 11.

TABLE 11

Study Design for Time Course Assessment in Nude Mice Bearing HT1080 Xenografts

| Test Compound | Number of Animals Per Time Point$^a$ | | Dose (mg/kg) | Administration$^a$ | | Dose Volume (mL/kg) | Dose Concentration (mg/mL) |
|---|---|---|---|---|---|---|---|
| | M | F | | Route | Schedule | | |
| Vehicle$^b$ | 5 | 0 | 0 | Oral | QD | 4 | 0 |
| Compound #10 | 5 | 0 | 10 | Oral | QD | 4 | 2.50 |
| Doxorubicin | 5 | 0 | 6 | IP | Single bolus | 8 | 0.75 |
| Bevacizumab | 5 | 0 | 5 | IP | Single bolus | 8 | 0.625 |

$^a$Treatments were initiated on Day 0 with 20 mice per group. On each day, 5 mice were sacrificed per group for analysis. Mice were treated with Compound #10 daily. Mice were treated with doxorubicin or bevacizumab on Day 0 only.
$^b$Vehicle was L21 (35% Labrasol, 35% Labrafac, and 30% Solutol).
Abbreviations:
IP = intraperitoneal;
QD = 1 time per day Tumor size was measured by calipers immediately pre-treatment and at the time of sacrifice on Day 1, 2, or 3 (5 mice per group per day). At sacrifice, the plasma was collected for assay of pathologic human VEGF concentration using an ELISA that recognizes human VEGF$_{121}$ and VEGF$_{165}$ (as described in Section 9.1.1.1).

Results. FIG. 9 shows the relative change in tumor size with time. In this short term study, the untreated tumors grew rapidly. Tumors from the vehicle treated mice had grown by 22% on Day 1, 42% on Day 2, and 79% on Day 3 (p<0.05 for each day, paired Student's t-test versus Day 0). All 3 treatments significantly reduced the rate of tumor growth by more than 50% over this 3 day period.

FIG. 10A-B display an evaluation of pathologic plasma human VEGF concentrations. In Panel B, absolute values are expressed. In Panel A, values are expressed as a ratio relative to tumor volume because larger tumors tend to produce more VEGF. As shown in Panel B, pathologic plasma human VEGF concentrations from vehicle treated mice rose from Day 0 to Day 3. As indicated in Panel A, increases in pathologic plasma human VEGF in control mice were seen even when adjusting for the increase in tumor size that occurred over this time period. By contrast, pathologic plasma human VEGF levels from mice treated with Compound #10, doxorubicin, or bevacizumab were numerically lower than in control animals by Day 1. Pathologic plasma human VEGF concentrations continued to decline under the influence of Compound #10, consistent with an effect indicating the inhibition of VEGF production, while absolute and relative values in other treatment groups began to increase on Days 2 and 3. Thus, by Day 3 of treatment, Compound #10 was demonstrated to be as active as bevacizumab and more effective than doxorubicin in reducing tumor derived plasma VEGF levels. In addition, these data suggest that Compound #10 regulates tumor VEGF independent of tumor size.

9.2.5 Compound #10 Shows Antitumor Activity in Several Human Tumor Xenograft Models This example demonstrates that Compound #10 shows antitumor activity in several clinically relevant human tumor xenograft models.

Investigators at the National Cancer Institute (NCl) have shown that compounds that inhibit tumor growth in multiple nonclinical models are more likely to have clinical efficacy. See Johnson et al., Br. J. Cancer 2001, 84(10):1424 31. In each of these studies, human tumor cells were implanted and treatment was initiated some days later, only after tumors had developed a vasculature (i.e., when tumors were >100 mm$^3$). This method of waiting to begin treatment until after tumors are established is considered a more stringent and clinically relevant assessment of efficacy compared to beginning treatment immediately after tumor implantation. See Teicher, ed. Totowa, Tumor models in cancer research. Humana Press, 2002: 593-616.

9.2.5.1 Compound #10 Shows Inhibition of Tumor Growth in an T47D Estrogen-Sensitive Breast Cancer Xenograft Model This example demonstrates that Compound #10 shows antitumor activity in an T47D estrogen-sensitive breast cancer xenograft model.

Experimental Design. Estrogen pellets (0.72 mg/pellet) were implanted 30 days prior to cell implantation and again 60 days later. T47D estrogen-sensitive breast cancer cells (5×10$^6$ cells/mouse mixed 1:1 with Matrigel™) were implanted subcutaneously in female athymic nude mice. After 31 days, when the tumors had become established (i.e., the mean tumor size had reached 180±33 mm$^3$), mice were divided into 3 treatment groups, and treatment was administered as shown in Table 12. Tamoxifen was included as a positive control.

TABLE 12

Study Design for Assessment of Tumor Growth Inhibition in Nude Mice Bearing Estrogen Sensitive T47D Xenografts.

| Test Compound | Number of Animals | | Dose (mg/kg) | Administration[a] | | Dose Volume (mL/kg) | Dose Concentration (mg/mL) |
|---|---|---|---|---|---|---|---|
| | M | F | | Route | Schedule | | |
| Vehicle[b] | 0 | 10 | 0 | Oral | QD | 4 | 0 |
| Compound #10 | 0 | 10 | 10 | Oral | QD | 4 | 2.5 |
| Tamoxifen | 0 | 10 | 10 | Oral | QD | 4 | 2.5 |

[a]Treatments were administered by oral gavage QD.
[b]Vehicle was L21 (35% Labrasol, 35% Labrafac, and 30% Solutol).
Abbreviations:
QD = 1 time per day Tumor size was measured by calipers at periodic intervals. After 74 days of treatment, the mice were sacrificed. The tumors were not analyzed for intratumoral VEGF levels because of their small size at sacrifice.

Results. Results by treatment regimen are shown in Table 13. In this breast cancer xenograft model, Compound #10 resulted in a transient reduction and persistent delay in tumor growth relative to controls. Compound #10 appeared as active as tamoxifen in suppressing growth of this estrogen-sensitive cell line. In observing the animals, there was no evidence of toxicity associated with Compound #10 treatment.

TABLE 13

Efficacy Information for Assessment of Tumor Growth Inhibition in Nude Mice Bearing Estrogen Sensitive T47D Xenografts.

| Test Compound | Number of Animals | | Dose (mg/kg) | Schedule | Dose per Week (mg/kg) | Mean % Inhibition of Intratumoral VEGF vs Vehicle at Sacrifice | Mean % Inhibition of Tumor Size vs Vehicle at Day 74[a] |
|---|---|---|---|---|---|---|---|
| | M | F | | | | | |
| Vehicle[b] | 0 | 10 | 0 | QD | 0 | ND | NA |
| Compound #10 | 0 | 10 | 10 | QD | 70 | ND | 40 |
| Tamoxifen | 0 | 10 | 10 | QD | 70 | ND | 50 |

[a]Day 74 was the day on which mice were sacrificed.
[b]Vehicle was L21 (35% Labrasol, 35% Labrafac, and 30% Solutol).
Abbreviations:
NA = Not applicable;
ND = not determined;
QD = 1 time per day;
VEGF = vascular endothelial growth factor

9.2.5.2 Compound #10 Shows Inhibition of Tumor Growth in an MDA-MB 468 Estrogen Insensitive Breast Cancer Xenograft Model This example demonstrates that Compound #10 shows antitumor activity in an MDA-MB-468 estrogen-insensitive breast cancer xenograft model.

MDA-MB-468 estrogen-insensitive breast cancer cells ($5\times10^6$ cells/mouse mixed 1:1 with Matrigel™) were implanted subcutaneously in female athymic nude mice. After 6 days, tumors had become established (i.e., the mean tumor size had reached $185\pm26$ mm$^3$), mice were divided into 2 treatment groups, and treatment was administered as shown in Table 14.

TABLE 14

Study Design for Assessment of Tumor Growth Inhibition in Nude Mice Bearing Estrogen-Insensitive MDA-MB-468 Xenografts.

| Test Compound | Number of Animals M | F | Dose (mg/kg) | Administration[a] Route | Schedule | Dose Volume (mL/kg) | Dose Concentration (mg/mL) |
|---|---|---|---|---|---|---|---|
| Vehicle[b] | 0 | 10 | 0 | Oral | QD | 4 | 0 |
| Compound #10 | 0 | 10 | 10 | Oral | QD | 4 | 2.5 |

[a]Treatments were administered QD continuously by oral gavage for at least 30 days.
[b]Vehicle was L21 (35% Labrasol, 35% Labrafac, and 30% Solutol).
Abbreviations:
QD = 1 time per day Tumor size was measured by calipers at periodic intervals. When the individual tumor size in a mouse exceeded 1500 mm$^3$, that mouse was sacrificed and both tumor and plasma were assayed for pathologic VEGF concentration as described in Section 9.1.1.1.

Results. Results by treatment regimen are shown in Table 15. Compound #10 at 10 mg/kg significantly reduced intratumoral and plasma pathologic VEGF concentrations on the day on which the animals were sacrificed (range, Day 33 to 53) relative to controls (range, Day 9 to 15). In addition, Compound #10 reduced tumor size and prolonged the time to tumor progression (i.e., the time to reach $\geq1000$ mm$^3$). In observing the animals, there was no evidence of toxicity associated with Compound #10 treatment.

9.2.5.3 Compound #10 Shows Reduction in Tumor Perfusion as Assessed by Dynamic Contrast-Enhanced Magnetic Resonance Imaging This example shows that Compound #10 reduces tumor perfusion as assessed by dynamic contrast-enhanced magnetic resonance imaging.

Experimental Design. Dynamic contrast-enhanced magnetic resonance imaging can be used preclinically and clinically to evaluate the anatomy of soft tissues, including the identification and accurate measurement of tumor volumes. In addition, evaluation of the intratumoral pharmacokinetics of contrast agents containing gadolinium can be used to measure vascular permeability characteristics. Coupling gadopentetate dimeglumine gadolinium to a small molecule like bovine serum albumin can reveal information about the necrotic (non-perfused) and non-necrotic (perfused) tumor volumes, and the percentage of vascular blood volume relative to the perfused tumor volume (known as the fractional blood volume [fBV]). Use of a macromolecular tracer, gadopentetate dimeglumine, can reveal information regarding the volume transfer coefficient ($K^{trans}$), a variable that represents a combination of vascular permeability, vascular surface area, and blood flow.

MDA MB 468 breast cancer cells ($5\times10^6$ cells/mouse mixed 1:1 with Matrigel™) were implanted subcutaneously in female athymic nude mice. After 13 days, when the tumors had become established (i.e., the mean tumor size reached ~400 mm$^3$), mice were divided into 2 treatment groups, and treatment was administered as shown in Table 16.

TABLE 15

Efficacy Information for Assessment of Tumor Growth Inhibition in Nude Mice Bearing Estrogen Insensitive MDA-MB-468 Breast Cancer Xenografts.

| Test Compound | Number of Animals M | F | Schedule[a] | Dose (mg/kg) | Dose per Week (mg/kg) | Mean % Inhibition of Intratumoral VEGF vs Vehicle at Sacrifice | Mean % Inhibition of Plasma pathologic VEGF vs Vehicle at Sacrifice | Mean % Inhibition of Tumor Size vs Vehicle at Day 12[b] | Median Time to Tumor Size $\geq1000$ mm$^3$ (days) |
|---|---|---|---|---|---|---|---|---|---|
| Vehicle[c] | 0 | 10 | 0/QD | 0 | — | — | — | — | 12 |
| Compound #10 | 0 | 10 | 10/QD | 10 | 70 | 61* | 75* | 65* | 25 |

*p < 0.05 (Student's t test relative to vehicle)
[a]Treatments were administered QD continuously by oral gavage for at least 30 days.
[b]Vehicle treated animal tumors reached $\geq1500$ mm$^3$ between Day 9 and 15 and all vehicle treated animals were sacrificed by Day 15.
[c]Vehicle was L21 (35% Labrasol, 35% Labrafac, and 30% Solutol).
Abbreviations:
M = Male;
F = Female;
QD = 1 time per day;
VEGF = vascular endothelial growth factor;
M = Male;
F = Female

TABLE 16

Study Design for Assessment of Tumor Perfusion in Nude Mice Bearing MDA MB 468 Xenografts

| Test | Number of Animals | | Dose | Administration[a] | | Dose Volume | Dose Concentration |
|---|---|---|---|---|---|---|---|
| Compound | M | F | (mg/kg) | Route | Schedule | (mL/kg) | (mg/mL) |
| Vehicle[a] | 0 | 8 | 0 | Oral | QD | 4 | 0 |
| Compound #10 | 0 | 8 | 10 | Oral | QD | 4 | 2.0 |

[a]Vehicle was L21 (35% Labrasol, 35% Labrafac, and 30% Solutol).
Abbreviations:
QD = 1 time per day Before each DCE-MRI scan, mice were injected intravenously with gadolinium-containing contrast dyes (bovine serum albumin-gadopentetate dimeglumine conjugate at ~0.03 mmol/kg followed by gadopentetate dimeglumine at ~0.2 mmol/kg). Baseline DCE-MRI measurements were taken on Day −1, test Compounds were administered on Day 0 through Day 5, and additional DCE-MRI measurements were taken on Days 1, 3, and 5. Image analyses were conducted with customized software. Total tumor volumes were measured by semi-automatically segmenting a region of interest around an anatomical image of the tumor. Tumor volumes of necrotic and non-necrotic tissues were measured by applying the same semi-automated segmentation process to a contrast dyed image. fBV and $K^{trans}$ were computed using a standard Kety PK model.

Results. As shown in FIG. 19, vehicle-treated animals had an increase in mean tumor volume from Day −1 to Day 5. By contrast, Compound #10 treated animals had little mean change. Differences in total tumor volumes in vehicle treated versus treated mice were apparent by Day 1 and were statistically significant by Day 3, confirming that Compound #10 begins to impede tumor growth rapidly after treatment initiation.

As shown in FIG. 20, vehicle-treated animals had a small mean change in necrotic (non perfused) tumor volume from Day −1 to Day 5. Consistent with an antivascular effect, Compound #10 rapidly increased the mean necrotic tumor volume, resulting in differences in necrotic tumor volumes between vehicle treated and treated groups that were statistically significant by Day 1.

Conversely, as shown in FIG. 21, most of the mean tumor volume increase depicted in FIG. 19 in vehicle-treated animals was due to growth of non-necrotic tumor tissue. By contrast, mean non-necrotic tumor volume in Compound #10-treated animals decreased from Day −1 to Day 5. Differences in non necrotic tumor volumes between vehicle-treated and treated groups were statistically significant by Day 1.

Tissue regions identified as necrotic have no measurable vascular permeability, limiting analysis of fBV to non-necrotic tumor regions (primarily in the tumor rim). As shown in FIG. 22, mean tumor fBV in vehicle-treated animals increased steadily from Day 1 to Day 5. Initially, mean tumor fBV also increased in Compound #10 treated mice but then declined after Day 3, resulting in a statistically significant difference relative to the vehicle-treated values on Day 5. These data indicate that Compound #10 inhibits tumor angiogenesis, increases tumor necrosis, decreases viable tumor, and decreases tumor microvessel density.

As for fBV, analysis of $K^{trans}$ was necessarily confined to non-necrotic tissue. As shown in FIG. 23, mean $K^{trans}$ increased in vehicle treated mice between Day −1 and Day 5, while the mean $K^{trans}$ decreased in Compound #10 treated mice over this same period. The relative changes in $K^{trans}$ in vehicle-treated compared to treated animals were statistically significant by Day 1. The data are consistent with Compound #10 inhibition of vascular permeability in the non-necrotic tumor rim.

9.2.5.4 Compound #10 Shows Inhibition of Tumor Growth in an SY5Y Neuroblastoma Xenograft Model This example demonstrates that Compound #10 shows antitumor activity in an SY5Y neuroblastoma xenograft model.

Experimental Design. SY5Y cells are derived from a human neuroblastoma, a childhood tumor arising in neural crest cells. SY5Y cells ($1 \times 10^7$ cells/mouse) were implanted subcutaneously in male athymic nude mice. After 7-days, tumors had become established (i.e., the mean tumor size had reached 387±10 mm³), mice were divided into 2 groups, and treatment was administered as shown in Table 17.

TABLE 17

Study Design for Assessment of Tumor Growth Inhibition in Nude Mice Bearing SY5Y Xenografts

| Test | Number of Animals | | Dose | Administration[a] | | Dose Volume | Dose Concentration |
|---|---|---|---|---|---|---|---|
| Compound | M | F | (mg/kg) | Route | Schedule | (mL/kg) | (mg/mL) |
| Vehicle[b] | 6 | 0 | 0 | Oral | QD | 4 | 0 |
| Compound #10 | 6 | 0 | 10 | Oral | QD | 4 | 2.5 |

[a]Treatments were administered by oral gavage 5 days per week (Monday through Friday) for up to 50 days.
[b]Vehicle was L22 (35% Labrafil, 35% Labrafac, and 30% Solutol).
Abbreviation:
QD = 1 time per day Tumor size was measured by calipers at periodic intervals. When the average tumor size in a group exceeded 2000 mm³, the mice in the group were sacrificed and excised tumors were assayed for intratumoral VEGF concentration as described in Section 9.1.1.1. Animals in which tumors did not reach 2000 mm³ were sacrificed at Day 50.

Results. Results by treatment regimen are shown in Table 18. Compound #10 treatment was associated with a significant reduction in mean intratumoral VEGF concentration and essentially eliminated any increase in mean tumor size through 15-days of dosing, substantially prolonging the mean time until tumor progression (tumor size ≥1000 mm³). In contrast, tumors in many control animals exceeded 2000 mm³ by Day 17 and these animals had to be sacrificed. In view of the dramatic effect of Compound #10 treatment, Compound #10 treatment was stopped on Day 15 to determine whether these effects might be sustained after treatment withdrawal. Tumors from mice treated with Compound #10 continued to be smaller than tumors from vehicle treated mice, even after 28-days without treatment (data not shown). At Day 43, treatment with vehicle or Compound #10 was reinitiated for a further 6 days. There were not enough vehicle mice remaining in the study to assess if Compound #10 would be more effective than vehicle in terms of tumor growth inhibition after treatment reinitiation. However, as summarized in Table 18, even after the cessation of treatment for 28-days and then continued Compound #10 treatment for 6 days, intratumoral levels of VEGF were almost completely suppressed in the treated tumors. In observing the animals, there was no evidence of toxicity associated with Compound #10 treatment.

TABLE 18

Efficacy Information for Assessment of Tumor Growth Inhibition in Nude Mice Bearing SY5Y Xenografts.

| Test Compound | Number of Animals M | Number of Animals F | Dose (mg/kg) | Schedule[a] | Dose per Week (mg/kg) | Mean % Inhibition of Intratumoral VEGF vs Vehicle at Sacrifice | Mean % Inhibition of Tumor Size vs Vehicle at Day 17[b] | Median Time to Tumor Size ≥1000 mm³ (days) |
|---|---|---|---|---|---|---|---|---|
| Vehicle[c] | 6 | 0 | 0 | QD | 0 | 0 | 0 | 12 |
| Compound #10 | 6 | 0 | 50 | QD | 250 | 96* | 73* | 35 |

*p < 0.05 (Student's t-test relative to vehicle)
[a]Treatments were administered by oral gavage 5 days per week (Monday through Friday) for up to 50 days.
[b]Day 17 was day on which vehicle treated animal tumors had reached ≥2000 mm³ and the mice were sacrificed.
[c]Vehicle was L22 (35% Labrafil, 35% Labrafac, and 30% Solutol).
Abbreviations:
QD = 1 time per day;
VEGF = vascular endothelial growth factor;
M = Male;
F = Female

9.2.5.5 Compound #10 Shows Inhibition of Tumor Growth in an LNCaP Prostate Cancer Xenograft Model This example demonstrates that Compound #10 shows antitumor activity in an LNCaP prostate cancer xenograft model.

Experimental Design. The LNCaP cell line is derived from a lymph node metastasis. LNCaP cells ($1\times10^6$ cells/mouse mixed 1:1 with Matrigel™) were implanted subcutaneously in male athymic nude mice. After 43 days, tumors had become established (i.e., the mean tumor size had reached $260\pm35$ mm³), mice were divided into 2 treatment groups, and treatment was administered as shown in Table 19.

TABLE 19

Study Design for Assessment of Tumor Growth Inhibition in Nude Mice Bearing Androgen-Sensitive LNCaP Xenografts.

| Test Compound | Number of Animals M | Number of Animals F | Dose (mg/kg) | Administration[a] Route | Administration[a] Schedule | Dose Volume (mL/kg) | Dose Concentration (mg/mL) |
|---|---|---|---|---|---|---|---|
| Vehicle[b] | 10 | 0 | 0 | Oral | M-W-F | 4 | 0 |
| Compound #10 | 10 | 0 | 10 | Oral | M-W-F | 4 | 2.5 |

[a]Treatments were administered M-W-F by oral gavage for at least 35 days.
[b]Vehicle was L21 (35% Labrasol, 35% Labrafac, and 30% Solutol).
Abbreviations:
M-W-F = Monday-Wednesday-Friday Tumor size was measured by calipers at periodic intervals during the study. When the mean tumor size in a mouse exceeded 1500 mm³, mice in that group were sacrificed and both tumor and plasma were assayed for pathologic VEGF concentration as described in Section 9.1.1.1.

Results. Results by treatment regimen are shown in Table 20. Relative to controls, Compound #10 at 10 mg/kg M-W-F reduced intratumoral VEGF concentrations adjusted for tumor size on the day on which the animals were sacrificed. In addition, Compound #10 prolonged the time to tumor progression (i.e., the time to reach >1000 mm³). In observing the animals, there was no evidence of toxicity associated with Compound #10 treatment.

TABLE 20

Efficacy Information for Assessment of Tumor Growth Inhibition in Nude Mice Bearing Androgen-Insensitive LNCaP Prostate Cancer Xenografts.

| Test Compound | Number of Animals M | Number of Animals F | Dose (mg/kg) | Schedule[a] | Dose per Week (mg/kg) | Mean % Inhibition of Intratumoral VEGF vs Vehicle at Sacrifice | Mean % Inhibition of Tumor Size vs Vehicle at Day 35[b] | Median Time to Tumor Size $\geq 1000$ mm$^3$ (days) |
|---|---|---|---|---|---|---|---|---|
| Vehicle[c] | 10 | 0 | 0 | M-W-F | 0 | — | — | 27 |
| Compound #10 | 10 | 0 | 10 | M-W-F | 30 | 51[d] | 36 | 38 |

[a]Treatments were administered M-W-F by oral gavage for at least 35 days.
[b]Vehicle treated animal tumors reached ≥1500 mm3 by ~Day 30 and all vehicle-treated animals were sacrificed by Day 35.
[c]Vehicle was L21 (35% Labrasol, 35% Labrafac, and 30% Solutol).
[d]Adjusted for tumor size
Abbreviations:
M-W-F = Monday-Wednesday-Friday;
VEGF = vascular endothelial growth factor 9.2.5.6 Compound #10 Shows Inhibition of Tumor Growth in Orthotopic SY5Y Neuroblastoma and SKNEP Ewing Sarcoma Tumor Models This example demonstrates that Compound #10 shows antitumor activity in orthotopic SY5Y neuroblastoma and SKNEP Ewing sarcoma tumor models.

Experimental Design. In orthotopic tumor models, human tumor cells are implanted into the mouse in an organ that corresponds to the location from which the tumors arise. Such models may provide a better predictor of clinical efficacy than injection of tumors into the flanks of nude mice. See Hoffman, *Invest. New Drugs* 1999, 17(4):343-59. SY5Y neuroblastoma or SKNEP Ewing sarcoma tumor cells ($1\times10^6$ cells/mouse) were implanted into the kidney capsule of female athymic nude mice according to published methods. See Huang et al., *Proc. Natl. Acad. Sci. USA* 2003, 100(13):7785-90. One week after implantation of each type of tumor, mice were divided into 2 groups and were administered a test Compound as shown in Table 21.

After 5 weeks of treatment, the mice were sacrificed, and the weights of the tumors were assessed.

Results. As shown in FIG. 11A and FIG. 11B, tumors from vehicle treated mice weighed about 3 to 4 grams at 5 weeks. By contrast, treatment with Compound #10, when evaluated at the same time point, completely prevented growth of both the SY5Y (FIG. 11A) and the SKNEP tumors (FIG. 11B). In observing the animals, there was no evidence of toxicity associated with Compound #10 treatment.

9.2.6 Compound #10 Penetrates Disease Relevant Tissues

This example demonstrates that Compound #10 penetrates disease relevant tissues.

Experimental Design. The distribution of $^{14}$C-Compound #10 were evaluated following a single oral gavage administration of 50 mg/kg (~10 µCi/animal) of $^{14}$C-labeled Compound #10 to rats in a GLP study. For the quantitative whole-body autoradiography (QWBA) analysis, 1 animal/sex/timepoint was sacrificed at 6, 12, 24, 48, and 72 hours postdose as shown in Table 22.

TABLE 21

Study Design for Assessment of Tumor Growth Inhibition in Nude Mice Bearing SKNEP or SY5Y Orthotopic Xenografts.

| Tumor Type | Test Compound | Number of Animals M | Number of Animals F | Dose (mg/kg) | Administration[a] Route | Administration[a] Schedule | Dose Volume (mL/kg) | Dose Concentration (mg/mL) |
|---|---|---|---|---|---|---|---|---|
| SY5Y | Vehicle[b] | 0 | 15 | 0 | Oral | QD | 4 | 0 |
|  | Compound #10 | 0 | 15 | 30 | Oral | QD | 4 | 7.5 |
| SKNEP | Vehicle[b] | 0 | 15 | 0 | Oral | QD | 4 | 0 |
|  | Compound #10 | 0 | 15 | 30 | Oral | QD | 4 | 7.5 |

[a]Treatments were administered by oral gavage 5 days per week (Monday through Friday) for up to 5 weeks.
[b]Vehicle was L3 (70% Labrasol, 18.3% Labrafac, and 11.7% Labrafil).
Abbreviation:
QD = 1 time per day

TABLE 22

Study Design for $^{14}$C-Compound #10 Single Dose Tissue Distribution Assessment in Rats

| Number of Animals | | Compound #10 Dose[a] | Dose Volume | Dose Concentration | Number of Animals per Timepoint | Dosing Day Sampled | Timepoints Relative to Dose |
|---|---|---|---|---|---|---|---|
| M | F | (mg/kg) | (mL/kg) | (mg/mL) | | | (hours) |
| 5 | 5 | 50 | 1.25 | 40 | 1[b] | Day 1 | 6, 12, 24, 48, 72 |

[a] $^{14}$C-Compound #10 was administered as a single-dose by oral gavage in L23 vehicle (35% Gelucire, 35% Labrafac, and 30% Solutol).
[b] For 1 animal per sex at each timepoint, a blood sample was collected at the time of sacrifice for assessments of concentrations $^{14}$C-Compound #10 in blood, plasma, and tissues, and for calculation of tissue:plasma concentration ratios at the specified times postdose.
Abbreviations:
F = female;
M = male For the QWBA, the carcasses were prepared by immediately freezing them, embedding them in chilled carboxymethylcellulose, and freezing them into blocks. Appropriate cryomicrotome sections of the blocks at 40 μm thickness were collected on adhesive tape. Mounted sections were tightly wrapped and exposed on phosphorimaging screens along with plastic embedded autoradiographic standards. Exposed screens were scanned and the autoradiographic standard image data were sampled to create a calibrated standard curve. Specified tissues, organs, and fluids were analyzed. Tissue concentrations were interpolated from each standard curve as nanocuries per gram and then converted to μg equivalents/gram on the basis of the Compound #10 specific activity.

Results. All animals appeared healthy and exhibited no overt signs of toxicity throughout the study. In this study, absorbed radioactivity was rapidly distributed into the whole body with the $T_{max}$ in blood and plasma occurring at 4 hours postdose in both sexes. Excluding the gastrointestinal tract, $C_{max}$ values in most tissues occurred at 6 to 12 hours postdose, with the highest values occurring in lipomatous tissues such as adrenal gland, brown fat, and liver. By 72 hours postdose, discernable residual radioactivity remained concentrated in fatty tissues in both sexes.

As shown in Table 23, the tissue:plasma concentration ratios were greater than 1 in most tissues. At 72 hours postdose, the highest tissue:plasma concentration ratios were in fat with values ranging from 37.1 to 63.9 in both sexes. All other tissues had ratios less than 10 with the exception of female bone marrow, Harderian gland, ovary, and skin, which had values of 18.8, 12.0, 28.1, and 11.4, respectively. There were no remarkable gender related differences in absorption, distribution, and elimination of radioactivity.

TABLE 23

Tissue:Plasma Concentration Ratios Determined by Whole-Body Autoradiography at Specified Times after a Single Oral Administration of $^{14}$C-Compound #10 to Rats (50 mg/kg)

| Tissue | 6 Hours | | 12 Hours | | 24 Hours | | 48 Hours | | 72 Hours | |
|---|---|---|---|---|---|---|---|---|---|---|
| | M | F | M | F | M | F | M | F | M | F |
| Adrenal gland | 18.5 | 16.2 | 10.8 | 16.7 | 8.96 | 8.93 | 5.89 | 6.59 | 6.02 | 7.16 |
| Blood | 0.569 | 0.577 | 0.601 | 1.00 | NA | 0.613 | NA | NA | NA | 1.80 |
| Bone | NA | 0.362 | NA | 0.497 | NA | NA | NA | NA | NA | NA |
| Bone marrow | 2.71 | 4.85 | 4.01 | 13.0 | 3.48 | 4.63 | 2.91 | 7.05 | NA | 18.8 |
| Cecum | 4.18 | 7.44 | 4.80 | 5.70 | 2.56 | 2.10 | 2.39 | 3.49 | NA | 3.66 |
| Cecum contents | 98.7 | 40.5 | 21.9 | 40.3 | 4.91 | 7.20 | 4.98 | 2.74 | 5.01 | 3.04 |
| Cerebellum | 1.55 | 1.23 | 1.85 | 2.85 | 1.74 | 1.59 | 1.21 | 1.17 | NA | 2.04 |
| Cerebrum | 1.52 | 1.22 | 1.75 | 2.79 | 1.89 | 1.57 | 1.35 | 1.68 | NA | 1.56 |
| Diaphragm | 5.48 | 4.35 | 4.98 | 6.58 | 2.89 | 3.06 | 2.04 | 3.09 | 1.75 | 3.50 |
| Epididymis | 0.862 | NA | 1.22 | NA | 2.13 | NA | 3.09 | NA | 3.09 | NA |
| Esophageal contents | NA | 0.231 | NA | NA | NA | NA | NA | NA | NA | 2.21 |
| Esophagus | 1.83 | 1.25 | 1.89 | 3.64 | 1.53 | 1.59 | NA | 2.76 | NA | 1.93 |
| Exorbital lacrimal gland | 3.46 | 3.45 | 5.56 | 8.15 | 4.72 | 3.85 | 3.44 | 3.90 | 3.91 | 3.51 |
| Eye | 0.279 | 0.275 | 0.291 | 0.606 | NA | NA | 0.847 | NA | NA | 1.72 |
| Fat (abdominal) | 13.3 | 4.05 | 20.7 | 9.61 | 27.8 | 38.2 | 47.7 | 58.4 | 62.1 | 60.8 |
| Fat (brown) | 15.5 | 14.2 | 25.4 | 46.1 | 34.4 | 34.0 | 37.0 | 58.4 | 37.1 | 63.9 |
| Fat (subcutaneous) | 4.66 | 5.11 | 15.4 | 12.9 | 22.9 | 31.7 | 35.6 | 50.0 | 52.2 | 56.6 |
| Gastric mucosa | 5.47 | 5.92 | 6.58 | 6.82 | 3.35 | 3.66 | 2.86 | 4.18 | 2.97 | 4.50 |
| Harderian gland | 3.06 | 2.53 | 5.02 | 7.61 | 8.92 | 7.80 | 10.5 | 14.7 | 9.54 | 12.0 |
| Intra-orbital lacrimal gland | 3.12 | 3.33 | 5.47 | 6.21 | 4.46 | 4.11 | 3.67 | 6.13 | NA | 8.76 |
| Kidney | 5.98 | 4.50 | 4.44 | 5.82 | 3.20 | 2.72 | 2.36 | 3.23 | 2.04 | 4.09 |

TABLE 23-continued

Tissue:Plasma Concentration Ratios Determined by Whole-Body Autoradiography at Specified Times after a Single Oral Administration of $^{14}$C-Compound #10 to Rats (50 mg/kg)

| Tissue | 6 Hours | | 12 Hours | | 24 Hours | | 48 Hours | | 72 Hours | |
|---|---|---|---|---|---|---|---|---|---|---|
| | M | F | M | F | M | F | M | F | M | F |
| Large intestinal contents | 26.2 | 138 | 61.7 | 256 | 21.9 | 20.8 | 12.1 | 5.44 | 5.80 | 7.51 |
| Large intestine | 2.65 | 2.43 | 3.06 | 5.94 | 1.81 | 2.10 | 1.58 | 1.69 | NA | 3.02 |
| Liver | 7.77 | 8.49 | 5.65 | 8.82 | 4.83 | 4.79 | 4.23 | 6.01 | 4.52 | 5.74 |
| Lung | 2.52 | 2.00 | 1.80 | 2.69 | 1.54 | 1.43 | 1.38 | 1.64 | NA | 2.46 |
| Medulla | 1.60 | 1.42 | 1.98 | 3.82 | 1.83 | 1.69 | 1.20 | 2.01 | NA | 1.88 |
| Muscle | 2.65 | 2.11 | 2.81 | 3.55 | 1.70 | 1.82 | 1.47 | 1.73 | NA | 2.54 |
| Myocardium | 5.31 | 5.89 | 3.90 | 7.03 | 2.82 | 2.88 | 2.43 | 3.95 | 1.97 | 4.15 |
| Nasal turbinates | 1.19 | 1.14 | 1.40 | 2.12 | 1.55 | 1.25 | 1.52 | 2.06 | NA | 2.58 |
| Olfactory lobe | 1.42 | 1.38 | 1.35 | 2.45 | 1.23 | 1.13 | 0.967 | NA | NA | 3.33 |
| Ovary | NA | 7.48 | NA | 17.6 | NA | 12.1 | NA | 11.3 | NA | 28.1 |
| Pancreas | 6.95 | 6.25 | 6.28 | 9.58 | 4.54 | 4.79 | 3.25 | 5.08 | 3.21 | 4.96 |
| Pituitary gland | 4.06 | 4.27 | 3.22 | 5.48 | 2.72 | 2.33 | 0.890 | 3.68 | NA | 1.58 |
| Preputial gland | 4.15 | 3.45 | 6.94 | 12.3 | 11.3 | 7.93 | 20.2 | NA | NA | NA |
| Prostate | 2.62 | NA | 2.61 | NA | 2.35 | NA | 1.09 | NA | 1.78 | NA |
| Renal cortex | 6.83 | 5.65 | 4.53 | 6.48 | 3.27 | 2.96 | 2.64 | 3.49 | 2.44 | 4.40 |
| Renal medulla | 5.35 | 3.70 | 4.21 | 5.06 | 3.04 | 2.53 | 1.75 | 2.84 | 1.68 | 3.60 |
| Salivary gland | 5.69 | 4.75 | 4.80 | 7.18 | 3.38 | 3.53 | 2.45 | 3.57 | 1.90 | 3.74 |
| Seminal vesicle | 0.780 | NA | 0.646 | NA | 0.691 | NA | NA | NA | NA | NA |
| Skin | 1.66 | 1.46 | 3.33 | 5.21 | 3.98 | 4.19 | 4.49 | 5.73 | 8.06 | 11.4 |
| Small intestinal contents | 7.35 | 7.81 | 15.2 | 15.1 | 1.67 | 3.35 | 3.68 | 2.80 | 1.69 | 3.34 |
| Small intestine | 8.46 | 5.01 | 3.02 | 5.09 | 2.93 | 2.45 | 1.21 | 2.62 | 1.80 | 3.36 |
| Spinal cord | 1.14 | 0.898 | 1.24 | 1.92 | 1.75 | 1.60 | 1.43 | 1.60 | 1.84 | 2.75 |
| Spleen | 2.73 | 2.84 | 2.37 | 3.91 | 1.80 | 1.89 | 1.50 | 1.88 | NA | 2.84 |
| Stomach | 4.34 | 3.62 | 3.72 | 5.12 | 2.86 | 1.76 | 1.72 | 2.93 | 2.44 | 4.19 |
| Stomach contents | 6.51 | 3.36 | 1.10 | 1.01 | NA | NA | NA | NA | NA | NA |
| Testis | 0.642 | NA | 1.17 | NA | 1.88 | NA | 2.13 | NA | 1.90 | NA |
| Thymus | 2.11 | 1.98 | 2.50 | 3.94 | 1.98 | 1.84 | 1.58 | 1.65 | NA | 3.34 |
| Thyroid | 3.18 | 3.77 | 2.57 | 3.61 | 2.76 | 1.38 | 1.14 | 1.87 | NA | 3.05 |
| Urinary bladder | 1.63 | 1.45 | 0.786 | 1.89 | 1.56 | 1.02 | 1.23 | 1.38 | NA | 1.92 |
| Urine | 0.239 | 1.66 | 0.299 | 0.761 | NA | NA | NA | NA | NA | NA |
| Uterus | NA | 1.86 | NA | 4.97 | NA | 3.51 | NA | 3.51 | NA | 7.66 |

Abbreviations:
F = female;
M = male;
NA = not applicable

This example demonstrates that Compound #10 penetrates disease relevant tissues.

9.3 Cell Cycle Delay 9.3.1 Cell Based Assays 9.3.1.1 Compound #10 and Compound 1205 Provoke a Late $G_1$/Early S-Phase Cell Cycle Delay This example demonstrates that a Compound induces a cell cycle delay at the $G_1$/S-phase border.

Experimental Design. During in vitro evaluations of Compound #10 and Compound 1205 effects on VEGF expression, an examination of the effect on tumor cell cycling was performed. HT1080 cells were incubated under normoxic conditions (21% oxygen) for 18 hours with vehicle (0.5% DMSO) alone, or with a range of concentrations of Compound #10 from 0.3 nM to 100 nM, or 10 nM of Compound 1205. Compounds shown in Table 24 were incubated under normoxic conditions for 18 hours with vehicle or Compound #10 at a single dose of 100 nM. After treatment, cells were trypsinized, and stained with propidium iodide (PI) dye to measure DNA content of individual cells by flow cytometry. Output comprised histograms showing relative DNA content in 10,000 cells.

Figure 12:
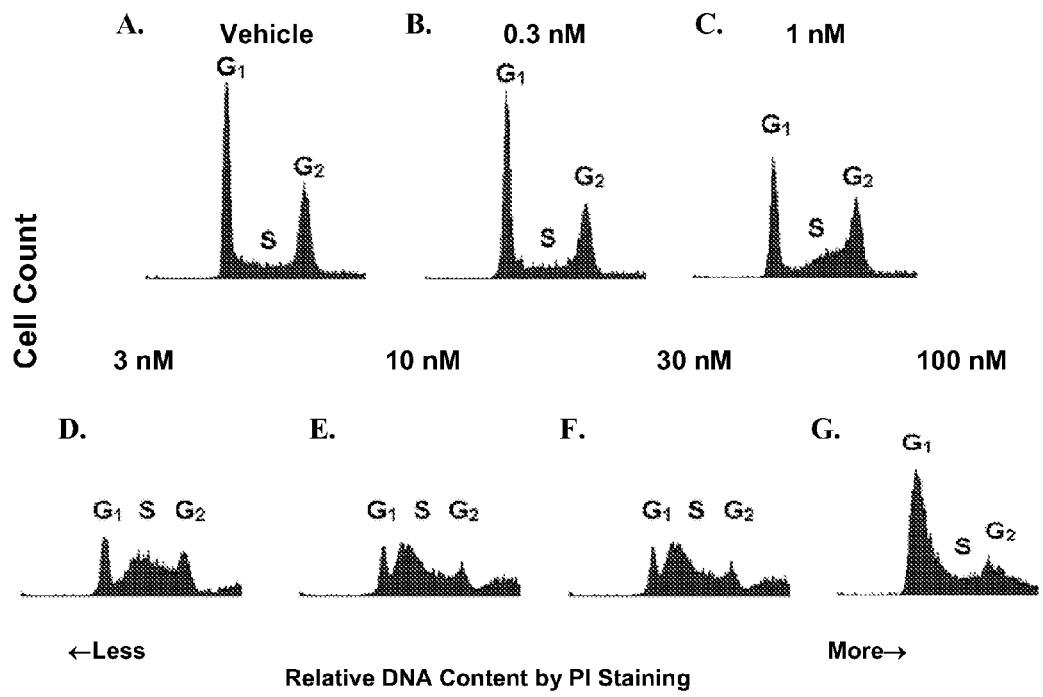

Results. As shown in FIG. 12 and FIG. 24A-B, Compound #10 and Compound 1205 induced a redistribution of the cycling characteristics of the cell population. An apparent dose response was observed for Compound #10. Starting at a concentration of 1 nM for Compound #10, an accumulation of cells in S phase can be observed. With higher concentrations of Compound #10, there is a progressive shift, such that a substantial proportion of the cells show a cell cycle delay at the $G_1$/S phase border. Concentrations of Compound #10 achieving these effects are consistent with those demonstrating inhibition of VEGF production (FIG. 1).

For additional Compounds shown in Table 24, the test results are expressed as the percentage of cells in the S-phase compared to a DMSO control (17.3% cells in S-Phase). While compounds which cause greater than 20% of the cells to accumulate in S-phase at 100 nM are considered active, a larger percentage of cells may be accumulated in S-phase at lower doses depending on the Compound, as shown in FIG. 12 for example.

TABLE 24
| Compound | % Cells In S-Phase |
|---|---|
| DMSO (Control) | 17.3 |
| 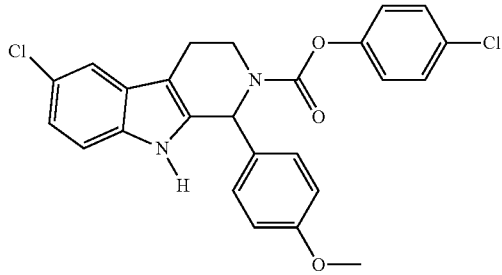 10 | 15.3 |
| 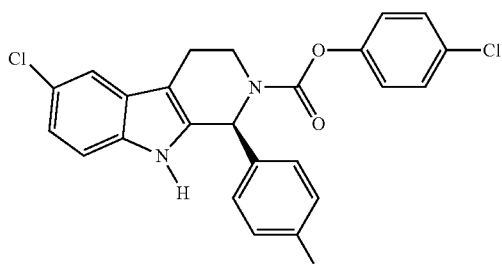 #10 | 26.1 |
| 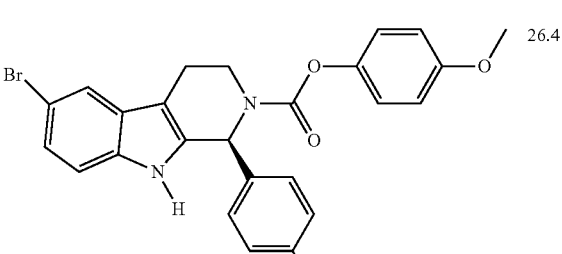 332 | 26.4 |
| 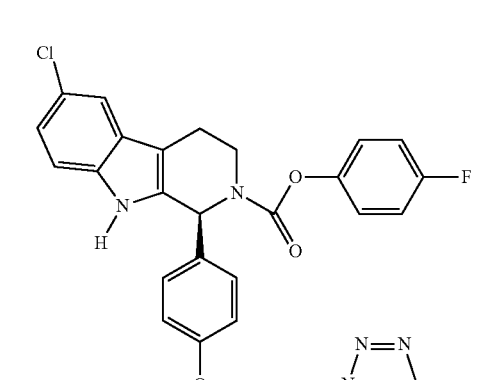 1739 | 25.7 |
TABLE 24-continued
| Compound | % Cells In S-Phase |
|---|---|
| 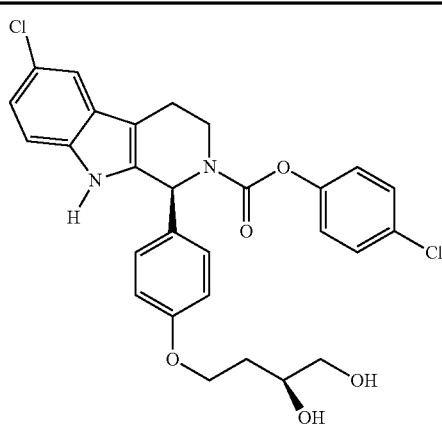 1205 | 20.0 |
| 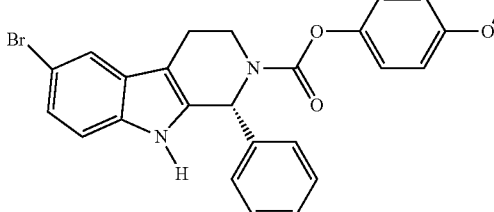 1726 | 16.5 |
| 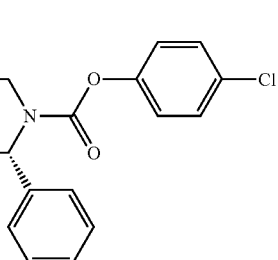 1727 | 16.8 |
| 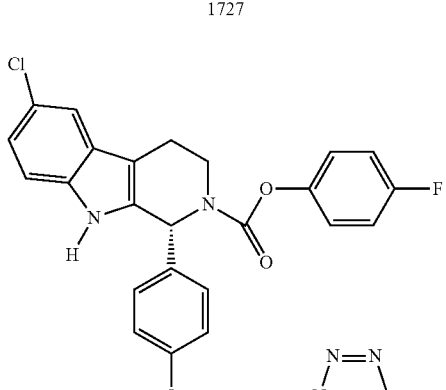 1728 | 16.4 |

TABLE 24-continued

| Compound | % Cells In S-Phase |
|---|---|
| 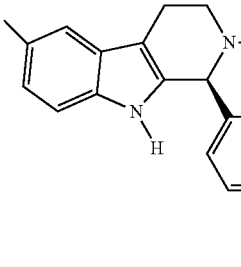 1159 | 17.2 |
| 1729 | 16.8 |
| 1730 | 16.4 |
| 1731 | 17.9 |
| 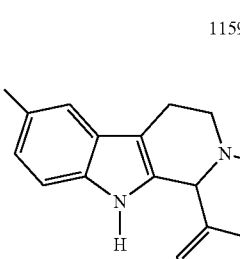 1732 | 20.6 |
| 1330 | 17 |

9.3.1.2 The Effect of Compound #10 on the Cell Cycle is Reversible

This example demonstrates that the effect of Compound #10 on cell cycle delay is reversible.

Experimental Design. HT1080 cells were incubated under normoxic conditions (21% oxygen) for 14 hours with Compound #10 (100 nM) or with vehicle (0.5% DMSO) alone. Compound #10 was then washed out of the cultures and cells were harvested and analyzed by PI staining and flow cytometry (as described in Section 9.3.1.1) at 0, 2, 5, 8, and 26 hours after discontinuation of treatment.

Figure 13:
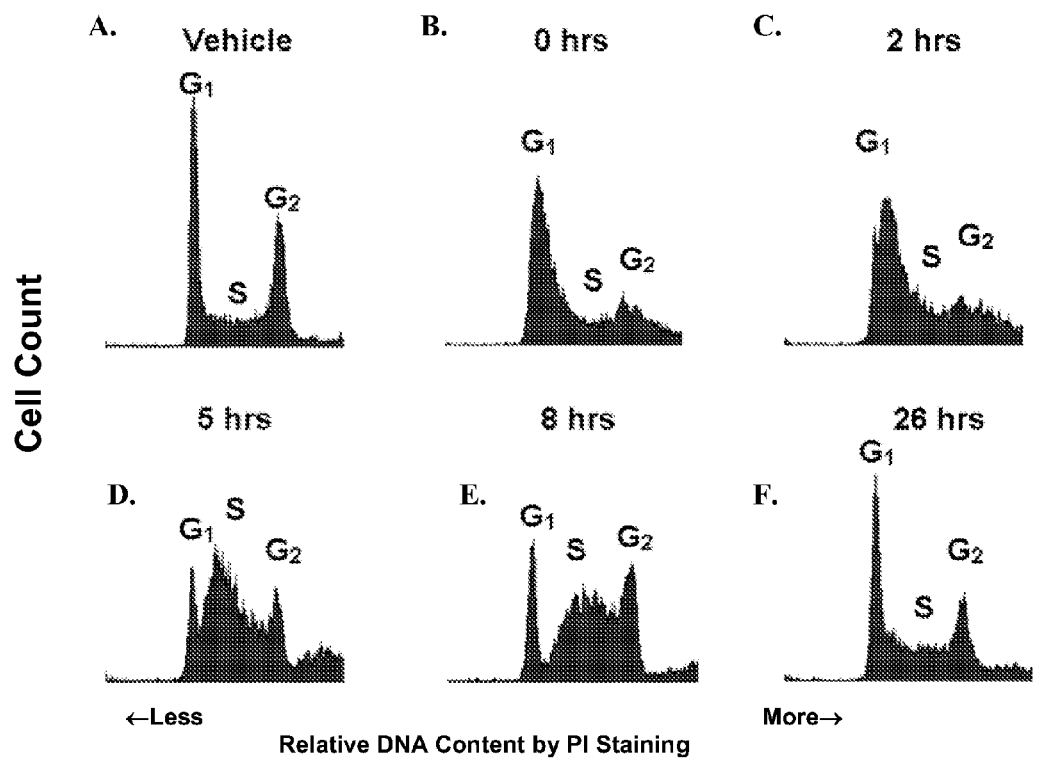

Results. As shown in FIG. 13, treatment with Compound #10 caused the expected increase in the proportion of cells in late $G_1/S$ phase of the cell cycle (Time 0). At 2 hours after Compound #10 removal, a shift was beginning to occur; however, a large percentage of the cells remained delayed in $G_1/S$. By 5 to 8 hours, cells were clearly redistributing. By 26 hours after Compound #10 washout, the cells had resumed normal cycling.

9.3.1.3 Compound #10 Cell Cycle Delay is Coincident with the Inhibition of VEGF Production This example demonstrates that Compound #10 cell cycle delay is coincident with the inhibition of VEGF production.

Experimental Design. Several VEGF secreting cell lines were assayed for cell cycle effects. Actively proliferating cells were incubated for 18 hours under normoxic conditions (21% oxygen) with vehicle (0.5% DMSO) alone or with Compound #10 at concentrations of 10 nM or 100 nM. At the completion of treatment, cells were harvested and cellular DNA content was analyzed via PI staining and flow cytometry (as described in Section 9.3.1.1).

Results. In the same cell lines, treatment was undertaken for 48 hours with a range of concentrations of Compound #10 from 0.1 nM to 30 μM or with vehicle (0.5% DMSO) alone. The conditioned media were collected and assayed by ELISA for soluble $VEGF_{121}$ and $VEGF_{165}$ isoforms (as described in Section 9.1.1.1); results were calculated as percentage inhibition relative to vehicle treated controls. $EC_{50}$ values were calculated from the concentration response curves.

As shown in Table 25, Compound #10 cell cycle delay was coincident with the inhibition of VEGF production in all of the tested tumor types.

TABLE 25

Correlation of VEGF Inhibition and Cell Cycle Delay in Human Tumor Cell Lines

| Tumor Type | Cell Line | VEGF Inhibition $EC_{50}$ (nM) | Cell Cycle Delay at VEGF Inhibition $EC_{50}$ |
|---|---|---|---|
| Cervical | HeLa | 2 | Yes |
| Fibrosarcoma | HT1080 | 10 | Yes |
| Colorectal | HCT116 | 10 | Yes |
| Renal cell | HEK293 | 10 | Yes |
| Lung | NCI H460 | 10 | Yes |
| Glioblastoma | U-87MG | >30,000 | No |
| Pancreas | ASPC-1 | >30,000 | No |
|  | PL-45 | >30,000 | No |
|  | HPAF-2 | >30,000 | No |
|  | PC-3 | >30,000 | No |

Abbreviations: $EC_{50}$ = effective concentration achieving 50% of peak activity; VEGF = vascular endothelial growth factor

9.3.1.4 The Kinetics of S-Phase Transit Employing BrdU Incorporation Into DNA This example demonstrates the rate and number of cells transiting the S-phase of the cell cycle.

Experimental Design. HT 1080 cells are exposed to BrdU (bromodeoxyuridine, a synthetic nucleoside that is an analogue of thymidine and is incorporated into DNA during the S phase of cell division) (FITC BrdU Flow Kit, BD Pharmingen catalog #552598). Cells are grown and treated as described in Section 9.3.1.3 above with the exception that one hour prior to harvesting by trypsinization, BrdU (final concentration 1 μM) is added to each culture for 1 hour. Cells actively replicating DNA during this brief time incorporate the BrdU into the DNA, which can then be quantitated. BrdU content is quantitated with using the FITC BrdU Flow Kit as instructed by the manufacturer. The process includes fixation (paraformaldehyde) and DNA staining with 7-AAD (7-amino-actinomycin D) followed by incubation with a fluoro-tagged anti-BrdU antibody that specifically recognizes BrdU incorporated into DNA. Dual channel FACS analysis permits assessment of both the DNA content of individual cells and the rate of transit across the S-phase, which is assessed based upon BrdU incorporation over the one hour treatment period.

Results. FIG. 29A-F indicate that an 18-hour treatment with increasing doses of Compound #10 causes a net increase in the percentage of cells residing in S-phase; however, individual cells incorporated less BrdU during the one-hour treatment period compared to DMSO control cells. The percentage of cells incorporating BrdU and the relative level of BrdU at each Compound #10 concentration is shown in FIG. 30A and FIG. 30B, respectively. These results suggest that Compound #10 slows the transit of cells through the S-phase of the cell cycle.

9.3.1.5 The Effect of Compound #10 on the 3-Dimensional Growth of HT 1080 Cells This example demonstrates the effect of a Compound provided herein on the 3-dimensional growth of HT1080 cells.

Experimental Design. HT1080 cells grown as a monolayer were trypsinized and seeded onto a 0.75% agar noble base to prevent the cells from attaching to the bottom of the tissue culture plate and to allow/promote the cells to self-adhere and grow as 3-dimensional spheroids. After 4 days the spheroids were established and the liquid growth medium was replaced with medium containing either 0.5% DMSO vehicle, or 10 nM or 50 nM of Compound #10 with 0.5% DMSO vehicle. The cells were incubated for 22 and 45 hours at 37° C., in the presence of a 10% $CO_2$ atmosphere. Spheroids were visually checked daily for morphological changes and a medium was replenished two times per week. At 22 and 45 hours after exposure to Compound #10, BrdU was added to a subset of the wells designated for FACS analysis and then returned to the incubator for 3 hours to permit cells synthesizing DNA (i.e. cells in S-phase) to incorporate the BrdU into the nascent strands of DNA. These pulse labeled spheroids were then harvested, washed and trypsinized (triple action solution, Gibco), pelleted and prepared for FACS analysis with a FITC BrdU Flow Kit, (BD Pharmingen). Cells were fixed and permeabilized with paraformadehyde and DNA stained with 7-AAD followed by incubation with an antibody which specifically recognizes BrDV incorporated into DNA. As described in Section 9.3.1.4. Cells were analyzed and sorted by 7-AAD signal (DNA content) to determine cell cycle phase, and BrdU content (percent actively synthesizing DNA).

Results. HT1080 spheroids prepared as above were treated with a Compound provided herein for 24 (FIG. 31A-C) or 48 hours (FIG. 32A-C). FIG. 31A-C and FIG. 32A-C show: (A) a histogram of DNA content demonstrating that the cell cycle distribution is not affected by exposure to the Compound provided herein; (B) BrdU quantification indicating the fraction of cells actively synthesizing DNA; and (C) a graphical representation of the percentage of cells that incorporated BrdU (i.e., the cells in S-phase), indicating that the percentage is not significantly altered by compound #10 treatment.

Spheroids, prepared as above, were treated with either vehicle alone (0.5% DMSO v/v final) added to the media or a Compounds provided herein (10 nM or 50 nM final concentration) in media to which vehicle has been added. The cells were photographed on day 5 of treatment to assess any gross morphological differences caused by exposure to Compound #10. Spheroids from all treatment groups looked indistinguishable from one another (data not shown). In addition, spheroids maintained in the presence of Compound #10 provided herein for three weeks also display no obvious morphological changes (data not shown).

9.3.1.6 Effect of Compound #10 on HT1080 Cell Viability and Mobility

This example demonstrates that Compound #10 inhibits or reduces the ability of cells to migrate out of spheroids of HT1080 cells.

Experimental Design. To assess the viability and motility of HT 1080 cells exposed to Compound #10, spheroids of HT1080 cells were prepared as in Section 9.3.1.5. The cells were cultured in media with vehicle only (0.5% DMSO) or in the presence of 50 nM Compound #10 present in media with vehicle added. After three weeks of treatment, treated spheroids were re-plated into wells without an agar base, thus allowing cells to migrate out onto the coated surface and grow as a two-dimensional (2-D) monolayer in the presence or absence of Compound #10 at 50 nM. Pictures were then taken 48 hours to assess the migration and proliferation of the cells across the well's surface.

Results. Cells from vehicle treated spheroids plated out in the absence of Compound #10 migrate to cover the entire surface of the tissue culture plate within the 48 hours. Spheroids grown for 3 weeks in the presence of Compound #10 and re-plated in the absence of the compound also migrate out of the spheroid to cover the surface of the tissue culture plate within 48 hours. This indicates that a three-week exposure to Compound #10 does not reduce either the proliferative or the migratory capacity of HT1080 cells.

Cells from control spheroids grown in the absence of Compound #10 and subsequently re-plated in the presence of 50 nM of Compound #10 are blocked in their ability to migrate out of the spheroid, and do not cover the surface of the tissue culture plate. Similarly, cells grown as spheroids in tissue culture media containing 50 nM of Compound #10 herein and re-plated in the presence of Compound #10 migrate much less than other groups. The data suggests that, even after three weeks of growth in three dimensions (3-D), the cell cycle delay and migratory inhibition of Compound #10 herein are still intact once the cells move into 2-D culture. The data further suggests that Compound #10 can act to inhibit the metastasis of cells from tumors.

9.3.1.7 Effect of Compound #10 on Anchorage-Independent Colony Formation in HT1080 Cells This example demonstrates that Compound #10 may reduce formation of colonies from HT1080 cells treated with Compound #10.

Experimental Design. HT1080 cells growing in monolayer were trypsinized, counted and suspended in a 0.35% agar noble/1× complete DMEM solution at 37° C. at a concentration of 2,500 cells/mL. One ml of this solution was layered over a semisolid base consisting of 0.5 mL of 0.75% agar noble/1× complete DMEM in a six well tissue culture plate. The top layer was permitted to solidify at room temperature, whereupon 1.5 mL of liquid medium (complete DMEM) containing 0.5% DMSO and 0, 5, 20 or 100 nM of Compound #10 was added to achieve a final concentration of 0, 2.5, 10 or 50 nM of Compound #10. Tissue culture plates were then returned to the incubator and colonies were allowed to form. The top medium layer was replaced periodically (every 3-4 days) with complete DMEM containing either 0.5% DMSO or Compound #10 (0, 2.5, 10 or 50 nm) and 0.5% DMSO. On day 18 the vehicle-treated wells had colonies of sufficient size to count (>50 cells/colony). At this time, for increased visualization, 1.5 mL of a 2× working volume of (3-(4,5-Dimethylthiazol-2-yl)-2,5-diphenyltetrazolium bromide, a tetrazole) (MTT, Invitrogen, Cat #C35007) was added and the plates were returned to the incubator for 2 hours until colonies were stained by conversion of the MTT to purple formazan crystals. Colonies were then visually counted under a dissecting microscope.

Results. FIG. 33 is a graphical representation of the average for each treatment group, which consists of two or three wells per group. There was a modest trend toward a reduced number of colonies formed from cells treated with 10 and 50 nM of Compound #10, but the results do not reach statistical significance (P=0.29 and 0.07, respectively).

9.3.2 Animal Model Systems 9.3.2.1 Compound #10 Induces S-phase Cell Delay in Dividing Tumor Cells In vivo This example demonstrates that Compound #10 induces a S-phase cell delay in dividing tumor cells in vivo.

Experimental Design. HT1080 cells ($5 \times 10^6$ cells/mouse) were implanted subcutaneously in male athymic nude mice. When tumors had become established (i.e., the mean tumor size had reached 585±150 mm$^3$), mice were divided into 4 treatment groups, as shown in Table 26. Positive and negative controls for effects on tumor cell cycling included doxorubicin and bevacizumab, respectively.

After 1, 2, or 3 days of treatment with Compound #10, mice were injected with BrdU, a synthetic nucleoside that is an analogue of thymidine and is incorporated into DNA during the S phase of cell division. The mice were sacrificed 3 hours later, and the tumors collected. A single cell suspension was prepared from the tumor cells. The cells were permeabilized and an antibody to BrdU was used to stain cells that had entered S phase during the labeling period. The proportion of cells actively synthesizing DNA was determined by cell sorting.

TABLE 26

Study Design for Cell Cycle Effect Assessment in Nude Mice Bearing HT1080 Xenografts

| Test Compound | Number of Animals Per Time Point[a] | | Dose (mg/kg) | Administration[a] | | Dose Volume (mL/kg) | Dose Concentration (mg/mL) |
|---|---|---|---|---|---|---|---|
| | M | F | | Route | Schedule | | |
| Vehicle[b] | 5 | 0 | 0 | Oral | QD | 4 | 0 |
| Compound #10 | 5 | 0 | 10 | Oral | QD | 4 | 2.50 |
| Doxorubicin | 5 | 0 | 6 | IP | Single bolus | 8 | 0.75 |
| Bevacizumab | 5 | 0 | 5 | IP | Single bolus | 8 | 0.625 |

[a]Treatments were initiated on Day 0 with 20 mice per group. On each day, 5 mice were sacrificed per group for analysis. Mice were treated with Compound #10 daily. Mice were treated with doxorubicin or bevacizumab on Day 0 only.
[b]Vehicle was L21 (35% Labrasol, 35% Labrafac, and 30% Solutol).
Abbreviations:
IP = intraperitoneal;
QD = 1 time per day As shown in FIG. 14, approximately 7 to 12% of the tumor cells from vehicle-treated mice were in S phase as indicated by the amount of BrdU incorporation. As the size of the tumors from vehicle treated mice increased with each succeeding treatment day, the percentage of cells showing BrdU incorporation decreased. On each treatment day, tumor cells from mice treated with Compound #10 demonstrated increased BrdU staining, consistent with a higher fraction of cells delayed in S phase. By contrast, treatment with doxorubicin decreased the percentage of tumor cells staining with BrdU, consistent with the arrest in the G1 phase of the cell cycle that is expected with this type of DNA-damaging agent. As also expected, bevacizumab had no effect on the proportion of cells in S phase.

When taken together with reductions in tumor derived plasma VEGF in these same animals (Section 9.2.3), these results are consistent with the previous in vitro results for Compound #10, suggesting that Compound #10 selectively induces a S phase cell delay in rapidly dividing tumor cells.

10. EXAMPLE

Clinical and Pre-Clinical Studies Compound #10

10.1 Pre-clinical Studies

In vitro and in vivo safety pharmacology studies with Compound #10 demonstrate a favorable safety profile. Based on the safety pharmacology studies and results of electrocardiograms (ECGs) and blood pressures collected during 7- and 28-day toxicity studies in dogs, Compound #10 is unlikely to cause serious adverse effects on the central nervous, cardiovascular, and respiratory systems.

A functional observation battery in Sprague Dawley rats dosed daily for 7-days by oral gavage at dose levels of 40, 120, and 400 mg/kg revealed no adverse behavioral or neurological effects at any dose level.

Compound #10 was considered negative for meaningful inhibition of human-ether-a-go-go-related gene (hERG) current in a higher throughput hERG assay. In a cardiovascular safety pharmacology study in awake telemeterized male beagle dogs, single oral doses of 30, 60, and 120 mg/kg of Compound #10 induced no meaningful changes in cardiovascular or electrocardiographic (including QT interval) parameters. In addition, ECG analysis and blood pressure assessments were performed as part of 2 GLP toxicity and toxicokinetic studies of Compound #10 in beagle dogs, one with 7-days of dosing and one with 28-days of dosing followed by a 15-day recovery period. In these studies, oral dosing with Compound #10 at dose levels through 120 mg/kg/day for 7-days and through 60 mg/kg/day for 28-days did not have any toxicological effects on ECG or blood pressure results in dogs. At the end of dosing in the 28-day toxicity study in dogs, males in the 60 mg/kg/day group had a slightly higher (7%) mean uncorrected QT value which also was statistically significant in comparison to controls. However, QTc (QT interval corrected for heart rate) values in males in the 60 mg/kg/day group were comparable to controls.

In a respiratory safety pharmacology study in awake telemeterized male beagle dogs, single oral doses of 30, 60, and 120 mg/kg of Compound #10 induced no dose dependent or biologically significant changes in respiratory rate, core body temperature, arterial blood gases, arterial pH, or arterial bicarbonate.

10.1.1 Pharmacokinetics and Compound Metabolism in Animals

The absorption of Compound #10 was evaluated in nude mice, C57BL/6 mice, Sprague Dawley rats, and beagle dogs dosed by the oral route. The pharmacokinetic evaluations in mice were adjuncts to the primary pharmacodynamic xenograft studies. The evaluations in rats included toxicokinetic assessments in single-dose, 7-day, and 28-day toxicology studies as well as a mass-balance study after a single oral dose of $^{14}$C-Compound #10. The evaluations in dogs included toxicokinetic assessments in 7-day and 28-day toxicology studies. In the studies performed, rodents were dosed once daily with Compound #10 formulated in vehicle and administered via oral gavage. Dogs were dosed BID at ~12-hour intervals between doses with Compound #10 formulated in vehicle and loaded into gelatin capsules that were administered orally.

The results of the PK studies demonstrate that Compound #10 is orally bioavailable in mice, rats, and dogs. Compound #10 pharmacokinetic parameters have been evaluated in mice at the 1-mg/kg dose level that, when given BID, was associated with maximal antitumor activity in the HT1080 human tumor xenograft model. At Day 1, Compound #10 plasma trough concentration of ~0.10 to 0.15 µg/mL at 24 hours was established as the minimal mean target plasma concentration to be achieved in pharmacokinetic studies.

In all mice, rats, and dogs, the relationship between Compound #10 dose and plasma exposure describes a "bell-shaped curve," i.e., plasma exposures initially rise with dose but then decrease despite further increases in dose. These bell-shaped dose-exposure relationships are consistent with absorption saturation and/or possible precipitation of the Compound within the gastrointestinal tract at the highest dose levels. The dose exposure curves were used in the dose selection for the rat and dog toxicology studies and in the interpretation of the No-Observed-Adverse-Effect Levels (NOAELs) from these studies. In both rat and dog toxicology species, $C_{max}$ and AUC values at the NOAELs exceed those expected in subjects to be enrolled to the proposed Phase 1b clinical study in patients with advanced breast cancer.

In vitro plasma protein binding for $^{14}$C-radiolabeled Compound #10 was determined from plasma samples obtained from mice, rats, dogs, monkeys, and humans. $^{14}$C-radiolabeled Compound #10 was highly bound to proteins in the plasma in vitro, with an overall mean of ≥99.5% for all species. Protein binding was independent of concentration over the range of 0.05 to 50 µg/mL of $^{14}$C-radiolabeled Compound #10. Given the similarities in protein binding across species, these data suggest that cross-species exposure comparisons do not need to be adjusted to take protein binding into account.

When evaluated in human hepatic microsomes or in assays using human recombinant cytochrome P450 (CYP) isoenzymes, Compound #10 inhibits the activity of the CYP2D6 isoenzyme. No meaningful inhibition of CYP3A4, CYP1A2, CYP2C9, or CYPC19 was observed. These data suggest the possibility that Compound #10 may slow or alter the clearance of drugs that are primarily metabolized by CYP2D6. It is possible that in certain clinical trial subjects, such agents may need to be adjusted for dosing or replaced by alternative agents that are not metabolized by CYP2D6, particularly when such agents may have a low therapeutic index.

10.1.2 Toxicology

A comprehensive toxicology program has been completed for Compound #10, consisting of a single-dose oral study in rats, 7-day oral studies in rats and dogs, and 28-day oral studies in rats and dogs each with a 2-week recovery period. A battery of genotoxicity studies was also performed. For the toxicology studies conducted in vivo, the study design consisted of a vehicle control group and 3 dose levels of Compound #10. The L23 vehicle was used. In rats, the vehicle or Compound #10 formulated in vehicle was administered by oral gavage. In dogs, the vehicle alone or Compound #10 formulated in vehicle was loaded into gelatin capsules for oral administration of 2 equal doses ~12 hours apart (BID). All studies in the toxicology program were conducted according to GLP regulations.

In rats given single oral gavage doses of Compound #10 at doses of 100, 200, or 400 mg/kg, no notable clinical or clinical pathological toxicities were observed at any dose level.

Because maximal exposure occurred at 100 mg/kg, this dose is considered the NOAEL for 1 day of dosing.

In the subsequent 7-day study, rats administered oral gavage Compound #10 doses of 40, 120, and 400 mg/kg/day. Maximal exposures occurred at a dose of 120 mg/kg/day. At this dose, notable changes included increases in mean prothrombin time (PT) and mean activated partial thromboplastin time (aPTT) in males but not in females. Elevations of about ~2.5-fold to about 3-fold in mean cholesterol levels and about 1.3-fold in mean glucose levels were also noted in males and females receiving Compound #10. Based on the collective toxicity and toxicokinetic findings, the NOAEL for 7-days of Compound #10 administration for male rats is 40 mg/kg/day and for female rats is 120 mg/kg/day.

In the 28-day study (with a 14-day recovery period), rats received oral gavage Compound #10 doses of 12, 40, and 120 mg/kg/day. Exposures were maximal at 120 mg/kg/day. Consistent with the 7-day study, the 28-day study showed reversible increases in mean PT and aPTT at Compound #10 doses of 40 and 120 mg/kg/day in males but not in females. Other chemistry changes included about 2- to about 3-fold elevations in mean cholesterol levels in all Compound #10 dose groups, and minimally increased glucose and alkaline phosphatase values in females and minimally increased chloride and minimally decreased potassium values in males dosed with Compound #10 at 40 and 120 mg/kg/day. Increased adrenal weights were observed at all dose levels; these changes correlated with adrenal cortical hypertrophy that was observed in males and females. The findings indicate an NOAEL for 28-days of Compound #10 administration in rats of 12 mg/kg/day.

In dogs given Compound #10 at doses of 10, 30, or 60 mg/kg/dose BID (20, 60, and 120 mg/kg/day) orally in L23 gelatin capsules for 7 consecutive days, exposures were maximal at 30 mg/kg/dose BID. Animals receiving Compound #10 had an increased incidence and frequency of soft stools in both males and females but no other notable treatment-related drug-related effects. Considering exposure values, the NOAEL for 7-days is considered to be 30 mg/kg/dose BID (60 mg/kg/day).

In the 28-day study (with a 15-day recovery period), dogs were administered Compound #10 doses of 5, 15, and 30 mg/kg/dose BID (10, 30, or 60 mg/kg/day) in gelatin capsules. Maximal exposures occurred at 30 mg/kg/dose BID (60 mg/kg/day). Compound #10 was clinically well tolerated in male and female dogs at the low- and mid-dose levels but at the high dose, adverse clinical findings, and decreased food consumption resulting in decreased body weights were observed. The target organ of toxicity was the small intestine. Microscopic findings of erosion, necrosis and/or ulceration of the mucosa, submucosal inflammation, epithelial hyperplasia of the mucosa of the crypts, and/or congestion of the Peyer's patches in the small intestine were seen in several dogs at the high dose. The findings in the small intestine did not reverse at the end of the 15-day recovery period. Based on the findings, the NOAEL for 28-days of Compound #10 administration in dogs is considered to be 15 mg/kg/dose BID (30 mg/kg/day).

Genotoxicity was assessed in a battery of in vitro and in vivo studies that included a bacterial reverse mutation study, a chromosome aberration study in Chinese hamster ovary (CHO) cells, and a micronucleus study in rats by the oral route. The in vitro studies were performed in the presence and absence of an exogenous metabolic activation system. There was no evidence of genotoxic effects with Compound #10 in these studies.

10.2 Clinical Studies:

Compound #10 has been evaluated in a Phase 1, escalating multiple-dose, safety, tolerability and PK study in healthy adult volunteers.

The study was performed under the oversight of the French health authorities. The study was not performed under an IND. The primary objective of the study was to determine a dose range and regimen for Compound #10 that safely achieves and maintains pharmacologically active target plasma concentrations (as determined from xenograft studies) and would be appropriate for use in subsequent Phase 1 or Phase 2 studies in patients with cancer. The secondary objective was to evaluate the safety profile of multiple doses of Compound #10 administered 2 times per day (BID) (Stage 1) or 3 times per day (TID) (Stage 2) in oral capsules, to characterize the multiple dose PK profile of Compound #10, and to assess the effect of Compound #10 on plasma and serum physiological VEGF concentrations.

Methods. The trial was a Phase 1, randomized, escalating multiple dose, single center study conducted in 2 stages. Stage 1 comprised a double blind, placebo controlled dose escalation with Compound #10 given BID. Stage 2 comprised a double blind, placebo controlled escalation of Compound #10 given TID. The number of subjects planned and enrolled for Stage 1: 24 subjects as 3 cohorts of 8 subjects, with each cohort comprising 4 males (3 Compound #10, 1 placebo) and 4 females (3 Compound #10, 1 placebo). The number of subjects planned and enrolled for Stage 2: 1 cohort of 8 subjects comprising 4 males (3 Compound #10, 1 placebo) and 4 females (3 Compound #10, 1 placebo).

Diagnosis and Main Criteria for Inclusion:

Subjects were required to be healthy males or females, 18 to 65 years old, weighing 41 to 90 kg. Female subjects were required to be surgically sterile or post menopausal (as documented by an absence of menses for >1 year before screening).

Test and Reference Products

In Stage 1, Compound #10 was provided in gelatin capsules for oral administration. Capsules contained 2 mg or 20 mg of active substance. Cohorts of subjects assigned to active treatment received progressively higher Compound #10 doses of 0.3, 0.6, and 1.2 mg/kg BID (0.6, 1.2, and 2.4 mg/kg/day).

In Stage 2, Compound #10 was provided in gelatin capsules for oral administration. Capsules contained 20 mg or 25 mg of active substance. The cohort of subjects assigned to active treatment received a Compound #10 dose of 1.6 mg/kg TID (4.8 mg/kg/day).

Placebo gelatin capsules for oral administration were used as the reference product in both Stage 1 and Stage 2 of the study.

Duration of Treatment: Stage 1: Compound #10 or placebo was administered orally BID for 7 days (Day 1 through Day 7). Stage 2: Compound #10 or placebo was administered orally TID for 7 days (Day 1 through Day 7).

Criteria for Evaluation: Maximum tolerated dose; Safety as characterized by type, frequency, severity, timing, and relationship to study treatment of any adverse events, laboratory abnormalities, or electrocardiogram (ECG) abnormalities; PK profile of Compound #10 as described by plasma concentration time curves and by derived PK parameters; Plasma and serum VEGF concentrations.

Statistical Methods: The results were summarized by study stage, treatment, and dose.

Pharmacokinetics: Compound #10 concentrations and PK parameters were presented descriptively. Noncompartmental methods were used to compute $T_{max}$, $C_{max}$, and AUC. Dose proportionality and sex effect were evaluated using ANOVA on log transformed PK parameters using dose, sex, and dose by sex as fixed factors.

Plasma VEGF Concentrations: Plasma and serum VEGF concentrations and concentration changes from baseline were presented descriptively.

Results. As planned, 32 subjects were included in the study. In Stage 1, 8 subjects were enrolled to each of the 3 dose groups (3 males and 3 females receiving Compound #10 and 1 male and 1 female receiving placebo) resulting in enrollment of 24 subjects (12 males and 12 females). In Stage 2, 8 subjects (3 males and 3 females receiving Compound #10 and 1 male and 1 female receiving placebo) completed their participation in the study. No subject discontinued prematurely and all subjects completed the study. Subject characteristics for Stage 1 and Stage 2 are described in Table 27 below. Demographic characteristics in Stage 1 were generally similar between the Compound #10 and placebo groups. Characteristics in Stage 2 were generally similar to those in Stage 1.

a ~30 minute lag time. On Day 1, mean maximum concentration ($C_{max}$) values after the second dose were almost double those of the first dose, while by Day 7, the mean Cmax values of the first and second daily doses appeared similar; this pattern suggests accumulation of Compound #10 concentrations over time rather than diurnal variation in exposures. At all dose levels, the target trough plasma concentration of ~0.1 to 0.15 µg/mL established as maximally active in the HT1080 animal tumor model was achieved.

PK parameters for Compound #10 in plasma are shown in Table 28 below. The mean $T_{max}$ was in the range of ~3 hours. During Stage 1 and Stage 2, increases in mean values for $C_{max}$ and area under the concentration time curve over 24 hours ($AUC_{0-24}$) were generally dose proportional. When comparing Day 1 to Day 7, there was an increase in the mean $C_{max}$ and $AUC_{0-24}$ over time at all dose levels, indicating accumulation (~2-fold) when Compound #10 was dosed continu-

TABLE 27

Subject Characteristics: Stage 1 and Stage 2 of Multiple-dose Study

| Characteristic | Stage 1 | | Stage 2 | |
|---|---|---|---|---|
| | Compound #10 N = 18 | Placebo N = 6 | Compound #10 N = 6 | Placebo N = 2 |
| Gender, n | | | | |
| Male:Female | 9:9 | 3:3 | 3:3 | 1:1 |
| Median age, years [range] | | | | |
| Males | 34 [25-62] | 32 [21-38] | 38 [33-46] | 31 [NA] |
| Females | 57 [44-64] | 56 [53-62] | 56 [54-65] | 58 [NA] |
| Mean body weight, kg [range] | | | | |
| Males | 73 [67-90] | 88 [80-90] | 66 [52-70] | 78 [NA] |
| Females | 62 [46-72] | 55 [52-77] | 66 [51-67] | 70 [NA] |
| Race, n (%) | | | | |
| Caucasian | 14 (78) | 3 (50) | 5 (83) | 2 (100) |
| African/West Indian | 2 (11) | 2 (33) | — | — |
| Other | 2 (11) | 1 (17) | 1 (17) | — |

Abbreviations: BID = 2 times per day, TID = 3 times per day

Pharmacokinetics: Mean plasma concentration time profiles for Compound #10 are shown in FIG. 15 for Stage 1 and FIG. 16 or Stage 2. Compound #10 appeared in plasma after ously. A 2-compartment model could be readily fit to all of the individual subject data throughout the 7 day course of treatment.

TABLE 28

Mean (SD) Compound #10 Pharmacokinetic Parameters: Stage 1 and Stage 2 Multiple dose Study

| | Stage 1 Compound #10 Dose mg/kg BID | | | | | | Stage 2 Compound #10 Dose mg/kg TID | |
|---|---|---|---|---|---|---|---|---|
| | 0.3 N = 6 | | 0.6 N = 6 | | 1.2 N = 6 | | 1.6 N = 6 | |
| Parameter, units | Day 1 | Day 7 | Day 1 | Day 7 | Day 1 | Day 7 | Day 1 | Day 7 |
| $T_{max}$ (after PM dose), hours | 3.16 (0.41) | 3.33 (0.52) | 3.17 (0.41) | 3.33 (0.52) | 3.00 (0.00) | 3.33 (0.52) | 2.50 (1.05) | 2.33 (1.37) |
| $C_{max}$ (after PM dose), µg/mL | 0.48 (0.15) | 0.59 (0.18) | 0.97 (0.24) | 1.16 (0.27) | 1.97 (0.29) | 2.47 (0.57) | 2.36 (0.46) | 4.65 (1.86) |
| $C_{24h}$, µg/mL | 0.094 (0.036) | 0.21 (0.09) | 0.26 (0.095) | 0.54 (0.21) | 0.41 (0.17) | 0.85 (0.32) | 1.33 (0.40) | 2.37 (0.62) |
| $AUC_{0-24}$, µg · hr/mL | 4.31 (1.20) | 8.44 (2.84) | 10.1 (2.60) | 18.6 (4.85) | 18.0 (3.97) | 32.9 (9.43) | 37.2 (5.90) | 78.6 (19.4) |
| Dose-normalized $C_{max}$, µg/mL/mg/kg | 0.79 (0.24) | 0.99 (0.29) | 0.81 (0.20) | 0.97 (0.22) | 0.82 (0.12) | 1.03 (0.24) | 0.51 (0.10) | 0.98 (0.38) |
| Dose-normalized | 7.2 | 14.1 | 8.4 | 15.5 | 7.5 | 13.7 | 7.7 | 16.4 |

TABLE 28-continued

Mean (SD) Compound #10 Pharmacokinetic Parameters: Stage 1 and Stage 2 Multiple dose Study

| | Stage 1 Compound #10 Dose mg/kg BID | | | | | | Stage 2 Compound #10 Dose mg/kg TID | |
|---|---|---|---|---|---|---|---|---|
| | 0.3 N = 6 | | 0.6 N = 6 | | 1.2 N = 6 | | 1.6 N = 6 | |
| Parameter, units | Day 1 | Day 7 | Day 1 | Day 7 | Day 1 | Day 7 | Day 1 | Day 7 |
| $AUC_{0-24}$, µg · hr/mL/mg/kg | (2.0) | (4.7) | (2.2) | (4.1) | (1.6) | (3.9) | (1.2) | (4.0) |

Values represent male and female subjects combined.
Abbreviations:
AUC = area under the concentration-time curve,
$C_{24}$ = concentration at 24 hours after first daily dose,
$C_{max}$ = maximum concentration,
$T_{max}$ = time of maximum concentration;
BID = 2 times per day,
TID = 3 times per day Gender related differences were analyzed by ANOVA. In this study, no significant differences in $C_{max}$ or $AUC_{0-24}$ values were observed between males and females.

Circulating VEGF Concentrations: Plasma and serum VEGF A concentrations were assayed in all subjects. Mean absolute values and changes from baseline in plasma and serum VEGF A concentrations are plotted in FIG. 17A and FIG. 17B for Stage 1 and in FIG. 18A and FIG. 18B for Stage 2. When considering both stages of the study, no clear dose dependent effects of Compound #10 on physiological concentrations of circulating VEGF A were noted.

Results: In this Phase 1 dose study of Compound #10 in healthy volunteer males and females, administration of Compound #10 for 7 consecutive days at doses of 0.3, 0.6, and 1.2 mg/kg BID (0.6, 1.2, and 2.4 mg/kg/day) and at 1.6 mg/kg TID (4.8 mg/kg/day) was well tolerated. Treatment emergent adverse events and laboratory abnormalities were generally Grade 1. The incidence or severity of these findings was not clearly greater in the Compound #10 group than in the placebo group and no dose dependency was apparent. Frequent ECG evaluations revealed no concerning rhythm, waveform, or interval changes. In particular, no meaningful QTc prolongation was observed. No serious adverse events or premature discontinuations due to adverse events occurred. Interventions for adverse events were minimal. None of the safety findings were deemed clinically significant by the investigator. No MTD was established and no dose limiting toxicities were observed through the highest dose level tested (1.6 mg/kg TID).

PK data indicated that Compound #10 is orally bioavailable. The mean $T_{max}$ was in the range of ~3 hours. Increases in $C_{max}$ and AUC were generally proportional with dose. There was ~2 fold accumulation when Compound #10 was dosed continuously. In this study, no significant differences in $C_{max}$ or $AUC_{0-24}$ values were observed between males and females. Target trough plasma concentrations of ≥100 to 150 ng/mL derived from preclinical human tumor xenograft models were achieved and maintained at all dose levels in the current study.

No significant alterations in plasma or serum physiological VEGF-A concentrations were observed at any of the Compound #10 doses tested in this multiple dose study. The finding that Compound #10 did not affect physiological plasma or serum VEGF levels in healthy volunteers appears consistent with in vitro results suggesting that Compound #10 does not perturb physiological VEGF production, but acts selectively to inhibit pathological VEGF production (induced by hypoxia or tumor transformation). Lack of changes in circulating VEGF concentrations may correlate with the lack of Compound #10 toxicities (e.g., hypertension, bleeding, proteinuria) in this trial. Such toxicities have been classically associated with currently used drugs that inhibit VEGF signaling at endothelial cells.

Collectively, the safety and PK findings of this study in healthy volunteers indicate that the dosing regimens tested in this study can readily attain target trough plasma concentrations known to be active in nonclinical models of human disease and that oral BID administration of Compound #10 may offer safety and ease of use advantages over existing clinical methods of inhibiting VEGF signaling.

11. EXAMPLE

Protocol for Treating Patients

Subjects with prostate cancer may receive a Compound in repeated 4-week cycles comprising daily oral administration of 100 mg per dose, two times a day (BID). In a specific embodiment, the Compound is Compound #10 or Compound #1205.

Clinical Objectives: Efficacy of a Compound for treating prostate cancer may be assessed by determining the effects of a Compound on serum PSA as a marker of prostate cancer tumor burden. The efficacy of a Compound for treating prostate cancer may also be assessed by: (i) determining the effects of a Compound on tumor burden as measured radiographically; (ii) evaluating the effects of a Compound on tumor metabolism as assessed by [$^{18}$F] 2 fluorodeoxyglucose or [$^{11}$C] choline positron emission tomography (FDG- or choline-PET); (iii) determining the effect of a Compound on numbers of circulating tumor cells (CTCs); (iv) determining the effects of a Compound on concentrations of circulating angiogenic factors and cytokines; (v) describing a Compound's safety profile; (vi) evaluating compliance with treatment with a Compound; (vii) evaluating effects on tumor blood flow, and/or peritumoral inflammation or edema; and (viii) determining a Compound's plasma exposure over time.

Clinical Endpoints: A primary clinical endpoint for efficacy of a Compound for treating prostate cancer may be PFS-6 rate (proportion of subjects who are progression-free at 6 months [24 weeks] of monotherapy with a Compound).

Other clinical endpoints for efficacy of a Compound for treating prostate cancer may include:

1. Antitumor activity as documented by PSA-PFS, changes in serum PSA, the proportion of subjects with a serum PSA response, and changes in serum PSA doubling time (Arlen et al. J Urol. 2008 June; 179(6):2181-5; discussion 2185-6);
2. antitumor activity as evaluated by changes in tumor size, proportion of subjects with a tumor response, and tumor PFS;
3. tumor metabolism as assessed by changes in FDG- or choline-PET standardized uptake value (SUV) in target tumor lesions;
4. antitumor activity as documented by changes in the number of CTC and in the proportion of subjects with a CTC response (defined as a reduction from ≥5 to <5 CTC with the decrease persisting for ≥3 weeks during treatment);
5. antiangiogenic or anti-inflammatory activity as documented by changes in the blood concentrations of VEGF, VEGF-C, VEGF-D, P1GF, VEGFR-1, VEGFR-2, IL-6, and IL-8;
6. overall safety profile of treatment with a Compound characterized in terms of the type, frequency, severity, timing, and relationship to the therapy of any adverse events or abnormalities of physical findings, laboratory tests, or ECGs; treatment discontinuations due to adverse events; or serious adverse events;
7. trough and peak (4-hour samples) plasma concentrations of a Compound as assessed by a validated bioanalytical method; and
8. peritumoral inflammation or edema which may be assessed by CT scan, MRI scan, or PET scan.

Evaluation of Clinical Endpoints

Radiographic assessments: Radiographic assessments of evaluable soft-tissue disease offer the opportunity to document changes that can substantiate other findings (Scher et al. J Clin Oncol. 2008 Mar. 1; 26(7):1148-59). In addition, changes in radiographic tumor measures (in conjunction with serum PSA and subject symptoms) also define criteria for disease progression that may assist in determining the appropriate duration of treatment for a subject. The Response Evaluation Criteria in Solid Tumors (RECIST) method of tumor size assessment may be employed, which is consistent with current recommendations (Scher et al. J Clin Oncol. 2008 Mar. 1; 26(7):1148-59).

Tumor metabolism using FDG-or choline-PET: Accelerated metabolism (e.g., glycolysis) is characteristic of cancer cells and is associated with increased proliferative indices, elevated VEGF expression, and poor prognosis (Airley et al. Chemotherapy. 2007; 53(4):233-56). FDG-PET or choline-PET offers sensitive means to assess changes in tumor metabolism through assessment of alterations in the uptake of a tracer. Because of correlations between tumor blood flow and tumor metabolism, the effects of anti-angiogenic therapy can be reflected in decreased FDG or choline uptake that is detectable by FDG- or choline-PET (Kim et al. Cancer Res. 2007 Oct. 1; 67(19):9337-45; Mullamitha et al. Clin Cancer Res. 2007 Apr. 1; 13(7):2128-35; Tuncel et al. Nucl Med Biol. 2008 August; 35(6):689-95). Thus, FDG-or choline-PET in addition to standard CT scanning may used to evaluate proof of mechanism and tumor control by a Compound (Lind et al. Eur J Nucl Med Mol Imaging. 2004 June; 31 Suppl 1:S125-34).

Circulating Tumor Cells: Levels of circulating tumor cells (CTCs) may be assessed in subjects. The levels of circulating CTCs may provide predictive and prognostic information useful in assessing the efficacy of a Compound for treating prostate cancer (Tibbe et al. Nat Biotechnol. 1999 December; 17(12):1210-3; Allard et al. Clin Cancer Res. 2004 Oct. 15; 10(20):6897-904; Cristofanilli et al. N Engl J Med. 2004 Aug. 19; 351(8):781-91).

Anti-angiogenic activity: Assessing circulating VEGF concentrations provides a relevant and convenient mechanism-specific marker of treatment activity. Appropriate methods for the measurement of circulating VEGF concentrations have been determined (see, e.g., Jelkmann et al., Clin. Chem., April 2001, 47(4):617-23.), and such methods may be used to evaluate the effects of treatment with a Compound. For example, clinically validated ELISA kits (e.g., from R&D Systems, Minneapolis, Minn.) may be used to measure circulating concentrations of VEGF-A, VEGF-C, P1GF, VEGFR, and inflammatory mediators such as IL-6 and IL-8. CT scan and MRI scan may also be used to assess peritumoral inflammation or edema.

Safety: Toxicities that may be encountered in treatment with a Compound, such as, e.g., hypertension, bleeding, and proteinuria, may be monitored. For consistency of interpretation, adverse events may be coded using the standard Medical Dictionary for Regulatory Activities (MedDRA), and the severity of these events may be graded using the well-defined Common Terminology Criteria for Adverse Events (CTCAE) Version 3.0. Standard definitions for seriousness may be applied.

Subject Selection: The following eligibility criteria may be used to select subjects for whom treatment with a Compound is considered appropriate. All relevant medical and non-medical conditions are taken into consideration when deciding whether this treatment protocol is suitable for a particular subject.

Subjects should meet the following conditions to be eligible for the treatment protocol:

1. Eastern Cooperative Oncology Group (ECOG) performance status of 0 or 1;
2. Histologically or cytologically confirmed diagnosis of prostate carcinoma;
3. Presence of locally advanced or metastatic prostate cancer (may be progressive despite castrate serum testosterone levels with primary antiandrogen intervention);
4. Prior bilateral surgical orchiectomy or ongoing androgen suppression with a gonadotropin-releasing hormone (GnRH) agonist (eg, leuprolide, buserelin, nafarelin, histrelin, goserelin, deslorelin, triptorelin); and
5. Evidence of progressive prostate cancer as documented by 2 consecutive increases in PSA over a previous reference value based on a sequence of ≥3 PSA values obtained at ≥1-week intervals occurring ≥4 weeks after cessation of any prior antiandrogen treatment; or evidence of continued elevation of serum PSA ≥6 weeks after the washout of any antiandrogen therapy.

Administration of Compound: A Compound may be orally administered each day on a BID schedule at approximately the same times each day. Ideally doses should be taken at ~12-hour intervals (e.g., at ~7:00 AM and at ~7:00 PM). If convenient for the subject, a Compound may be taken during or within ~30 minutes after a meal; however, administration with food is not required. Subjects may continue receiving repeated 4-week cycles of treatment with a Compound indefinitely or until termination. Compound administration may be terminated because of, e.g., tumor progression or other progression of prostate cancer, or a dose-limiting toxicity (DLT).

The dosage administered to a subject may be reduced to 80 mg/dose BID, 60 mg/dose BID, or 40 mg/dose if a dose-limiting toxicity (DLT) occurs. The dosage may be successively reduced if a DLT occurs. In other words, if a DLT occurs at 100 mg/dose BID, then the dosage may first be reduced to 80 mg/dose BID, and if a DLT occurs again then the dosage may be reduced to 60 mg/dose BID. A DLT may be defined as the occurrence of any of the following:

1. Grade ≥2: Compound-related vomiting despite maximal oral antiemetic therapy, or a requirement for intravenous antiemetics to control Compound-related nausea and vomiting.
2. Grade ≥2: proteinuria.
3. Other Grade ≥3: Compound-related toxicities.

Schedule of Events and Procedures: The types and timing of data that may be collected to assess the efficacy of a Compound for treating prostate cancer are described below.

Screening Plasma VEGF: Ideally, subjects should have blood samples obtained for assessment of plasma VEGF-A before administration of a Compound (e.g., within 28 days prior to initiating administration of a Compound). The sample for plasma collection may comprises 3 mL of venous blood drawn into a VACUTAINER® tube with $K_2$EDTA as the anticoagulant. Immediately after collection, the tube may be gently inverted 8 to 10 times to mix the anticoagulant with the blood sample. The tube may be stored upright at room temperature until centrifugation; centrifugation and sample processing may be performed within 30 minutes of sample collection. The plasma fraction may be separated by placing the collection tube into a room-temperature (18 to 25° C.) horizontal rotor (with a swing-out head) for 15 minutes at 1000 relative centrifugal force (RCF). Immediately following the completion of centrifugation, the plasma fraction may be withdrawn by pipette and divided into 2 polypropylene freezing tubes (with each tube receiving approximately equal aliquots). After processing, the sample may be placed into a freezer at approximately −70° C. (up to 3 months) until analyzed. Repeated freeze-thaw cycles should be avoided. A clinically validated ELISA kit may be used to measure plasma VEGF-A level.

Vital Signs: Vital signs (pulse and blood pressure) may be monitored prior to initial administration of a Compound, and at other times as clinically indicated. For example, vital signs may be monitored within 14 days prior to the initiation of a Compound administration, and prior to the AM dose and at approximately 4 hours after the morning dose on Day 1 of Cycle 1; prior to the AM dose of a Compound on Day 1 administration and every subsequent cycle. Vital signs may also be collected after treatment with a Compound ends.

Height, Body Weight, and Performance Status: Height (in cm) can be measured once prior to initial administration of a Compound. Body weight and ECOG performance status may be assessed. For example, body weight and ECOG performance status may be assessed within 14 days prior to the initial administration of a Compound, prior to the AM dose of a Compound on Day 1 every cycle, and after the a Compound treatment ends.

Hematology Laboratory Assessment: Hematology laboratory assessments may include white blood cell count with differential, hemoglobin, hematocrit, other red cell parameters, and platelet count. These parameters may be monitored prior to initial administration of a Compound, and during the treatment protocol as necessary. For example, these parameters may be monitored prior to initial administration of a Compound, prior to the AM dose of a Compound on Day 1 of each cycle, and after the treatment with a Compound ends.

Biochemistry Laboratory Assessment: Biochemistry laboratory assessments may include sodium, potassium, chloride, bicarbonate, blood urea nitrogen, creatinine, calcium, phosphorus, uric acid, glucose, total protein, albumin, globulin, albumin:globulin ratio, bilirubin (direct and indirect), aspartate aminotransferase, alanine aminotransferase, gamma glutamyl transferase, alkaline phosphatase, lactate dehydrogenase, total cholesterol, triglycerides, low-density lipoprotein, and high-density lipoprotein. These parameters may be monitored prior to initial administration of a Compound, and during the treatment protocol as necessary. For example, these parameters may be monitored prior to initial administration of a Compound, prior to the AM dose of a Compound on Day 1 of each cycle, and after the treatment with a Compound ends. To the extent possible, all samples for biochemistry parameter analysis should be taken after an overnight fast.

Coagulation Laboratory Assessment: Coagulation laboratory assessments may include prothrombin time ("PT") and activated partial thromboplastin time ("aPTT"). These parameters can be monitored prior to, or at various times during, the treatment protocol. For example, these parameters may be monitored within 14 days prior to the initiation of a Compound administration, prior to the AM dose of a Compound on Day 1 of each cycle, and after the treatment with a Compound ends.

Urinalysis: Urinalyses may include dipstick or quantitative analysis for pH, specific gravity, glucose, ketones, blood, protein, urobilinogen, bilirubin, and microscopic examination. These parameters can be monitored prior to initiation of the treatment protocol or at various times during the treatment protocol. For example, these parameters may be monitored within 14 days prior to the initiation of administration with a Compound, prior to the AM dose of a Compound on Day 1 of each cycle, and after the treatment with a Compound ends.

12-Lead ECG: A 12-lead ECG can be obtained prior to initiation of the treatment protocol or at various times during the treatment protocol.

Blood for Compound's Exposure: Blood for determination of a Compound's plasma concentrations may be collected immediately pre-dose and at ~4 hours on Day 1 of each cycle. Each sample may comprise 2 mL of venous blood drawn into a VACUTAINER® tube with $K_2$-EDTA as the anticoagulant. Immediately after collection, the tube may be gently inverted 8 to 10 times to mix the anticoagulant with the blood sample. The tube may be stored upright on ice until centrifugation; centrifugation and sample processing may be performed within 1 hour of sample collection. The plasma fraction may be separated by placing the collection tube into a refrigerated centrifuge (4° C. to 8° C.) in a horizontal rotor (with a swing-out head) for a minimum of 15 minutes at 1500 RCF. The plasma fraction may be withdrawn by pipette and divided into 2 polypropylene freezing tubes (with each tube receiving approximately equal aliquots). After processing, samples may be placed into a freezer at approximately −70° C. Analyses of the PK samples for a Compound may be performed using validated LC-MS/MS methods. Plasma samples collected for PK analysis may be preserved for future metabolite analysis, as appropriate.

Blood for Circulating VEGF, VEGFR, and Cytokines: Two blood samples (1 for plasma and 1 for serum) may obtained for assessment of circulating VEGF, VEGFR, and cytokine levels. Each sample for plasma collection may comprise 3 mL of venous blood drawn into a VACUTAINER® tube with $K_2$EDTA as the anticoagulant. Immediately after collection, the tube may be gently inverted 8 to 10 times to mix the anticoagulant with the blood sample. The tube may be stored upright at room temperature until centrifugation; centrifugation and sample processing may be performed within 30 minutes of sample collection. The plasma fraction may be separated by placing the collection tube into a room-temperature (18 to 25° C.) horizontal rotor (with a swing-out head) for 15 minutes at 1000 RCF. Immediately following the completion of centrifugation, the plasma fraction may be withdrawn by pipette and divided into 2 polypropylene freezing tubes (with each tube receiving approximately equal aliquots)

Each sample for serum collection may comprise 4 mL of venous blood drawn into a VACUTAINER® SSTT™ Tube. After collection, the tube may be stored upright at room temperature for 30 minutes to allow the sample to clot prior to centrifugation. The serum fraction may be separated by placing the collection tube into a room-temperature (18 to 25° C.), horizontal rotor (with a swing-out head) for 15 minutes at 1000 RCF. Immediately following the completion of centrifugation, the serum fraction may be withdrawn by pipette and divided into 2 polypropylene freezing tubes (with each tube receiving approximately equal aliquots).

After processing, samples may be placed into a freezer at approximately −70° C. Repeated freeze-thaw cycles should be avoided. Clinically validated ELISA kits may be used to measure plasma VEGF and cytokine levels.

Serum Prostate-Specific Antigen: Serum may be obtained for assessment of the circulating PSA levels. Serum PSA may be assayed consistent with the routine practices. PSA response may be defined as a reduction by ≥50% in the tumor marker value relative to baseline. In this protocol, the ≥50% decline of serum PSA may be confirmed by a second serum PSA value ≥4 weeks later. The serum PSA response commences on the date of first 50% decline in serum PSA. Serum PSA progression may be defined as the occurrence of either of the following: (i) relative to the measurements at the lowest on-treatment serum PSA level in a subject with an on-treatment serum PSA decline: An increase in the serum PSA by ≥25% and ≥2 ng/mL above the on-treatment nadir, and which is confirmed by a second value obtained 4 weeks later; or (ii) relative to pretreatment measurements in a subject with no on-treatment serum PSA decline from baseline: An increase in the serum PSA by ≥25% and ≥2 ng/mL after 12 weeks of treatment.

Due to the potential cytostatic activity of a Compound, subjects with serum PSA progression in the absence of objective tumor progression or substantial symptomatic worsening may stay on treatment with a Compound for ≥12 additional weeks before.

Circulating Tumor Cells: Blood for assessment of CTCs may be obtained. Each sample for plasma collection may comprise 7.5 mL of venous blood drawn into a CellSave® tube. It is preferred that the tubes are filled completely in order to be processed for CTCs. After collection, the tube may be inverted eight times to prevent clotting and then can be stored at room temperature.

Tumor Metabolism With FDG- or choline-PET: Ideally, all subjects should undergo FDG- or choline PET (Weber 2006 J. Clin. Oncol. 24(20): 3282-3292; Tuncel et al. Nucl Med Biol. 2008 August; 35(6):689-95). for target lesion(s) of interest prior to initiation of administration with a Compound and during the treatment protocol.

Radiological Tumor Assessment: Evaluation of tumor soft-tissue metastases may be performed according to the RECIST system of unidimensional evaluation. All baseline imaging-based tumor assessments may be performed prior to initial administration with a Compound. Thereafter, tumor assessments may be performed at the end of every 3 cycles (Cycle 3, 6, 9, and 12).

The same method of assessment and the same technique should be used to characterize each identified and reported lesion at baseline and during follow-up. Imaging-based evaluation is preferred to evaluation by clinical examination when both methods have been used to assess the antitumor effect of treatment. Ideally, patients should, at a minimum, have a CT scan of the chest, abdomen, and pelvis and a bone scan at each radiological tumor assessment.

CT, FDG- or choline-PET/CT, or MRI scans are the preferred methods for assessment of nodal or visceral disease. CT, PET/CT, or MRI may be performed with cuts of 10 mm or less in slice thickness contiguously. This applies to the chest, abdomen, and pelvis.

Chest x-ray is acceptable as a method to measure pulmonary lesions when they are clearly defined and surrounded by aerated lung. However, chest CT or PET/CT is preferable for assessment of pulmonary lesions.

Bone scans may not be considered appropriate for quantitative measurement of disease but may be used to provide a qualitative assessment of regression or progression.

Ultrasound may not be used to measure tumor lesions that are clinically not easily accessible for objective response evaluation, e.g., visceral lesions. However, it may be an alternative to clinical measurements of local pelvic disease of the prostate, superficial palpable nodes, subcutaneous lesions, and thyroid nodules. Ultrasound might also be useful to confirm the complete disappearance of superficial lesions usually assessed by clinical examination.

Clinical lesions may only be considered measurable when they are superficial (e.g., palpable lymph nodes). In the case of skin lesions, documentation by color photography including a ruler to estimate the size of the lesion is recommended.

Endoscopy or laparoscopy may not be used for response assessment.

At baseline, tumor lesions may be categorized by the investigator as measurable or non-measurable by the RECIST method. Measurable lesions may be those that can be accurately measured in at least 1 dimension (longest diameter to be recorded) as ≥20 mm with conventional techniques or as ≥10 mm with spiral CT scan. Clinical lesions may be only be considered measurable when they are superficial (e.g., skin nodules, palpable lymph nodes). Non-measurable lesions comprise all other lesions, including small lesions (longest diameter <20 mm with conventional techniques or <10 mm with spiral CT scan) and bone lesions, leptomeningeal disease, ascites, pleural or pericardial effusions, lymphangitis of the skin or lung, abdominal masses that are not confirmed and followed by imaging techniques, cystic lesions, previously irradiated lesions, and disease documented by indirect evidence only (e.g., by laboratory tests such as alkaline phosphatase).

All measurable lesions up to a maximum of 10 lesions representative of all involved organs may be identified as target lesions, and measured and recorded at baseline and at the stipulated intervals during treatment. Target lesions may be selected based on size (lesions with the longest diameters) and their suitability for accurate repetitive measurements (either by imaging techniques or clinically). It is recommended that target lymph nodes be ≥20 mm in longest diameter. Visceral lesions and nodal lesions may be reported separately.

The longest diameter may be recorded for each target lesion. The sum of the longest diameter for all target lesions may be calculated and recorded as the baseline sum longest diameter to be used as reference to further characterize the objective tumor response of the measurable dimension of the disease during treatment. All measurements may be performed using a caliper or ruler and should be recorded in centimeters.

All other lesions (or sites of disease) may be identified as non-target lesions and may be recorded at baseline. Measurements may not required and these lesions may be followed as "present" or "absent."

Definitions of Tumor Response:

For target lesions: Complete response (CR) may defined as the disappearance of all target lesions. Partial response (PR) may be defined as a ≥30% decrease in the sum of the longest dimensions of the target lesions, taking as a reference the baseline sum of the longest dimensions. Progressive disease (PD) may be defined as a ≥20% increase in the sum of the longest dimensions of the target lesions taking as a reference the smallest sum of the longest dimensions recorded since the treatment started, or the appearance of 1 or more new soft-tissue lesions. Stable disease (SD) may be defined as neither sufficient shrinkage to qualify for PR nor sufficient increase to qualify for PD, taking as a reference the smallest sum of the longest dimensions since the treatment started.

For non-target lesions: CR may be defined as the disappearance of all non-target lesions. Non-complete response (Non-CR)/non-progressive disease (Non-PD) is defined as a persistence of ≥1 non-target lesions. PD may be defined as unequivocal progression of existing non-target lesions, or the appearance of ≥1 new soft-tissue lesion or ≥2 new bone lesions (with confirmation on a repeat scan obtained ≥6 weeks later). The cytological confirmation of the neoplastic origin of any effusion that appears or worsens during treatment when the measurable tumor has met criteria for response or SD may be mandatory to differentiate between response or SD and PD.

Confirmation of Tumor Response. To be assigned a status of CR or PR, changes in tumor measurements in subjects with responding tumors are preferably confirmed by repeat studies that should be performed ≥3 weeks after the criteria for response are first met. In the case of SD, follow-up measurements preferably meet the SD criteria at least once after administration with a Compound at a minimum interval of 6 weeks.

Determination of Overall Response by RECIST. When both target and non-target lesions are present, individual assessments may be recorded separately. The overall assessment of response may involve some or all of the parameters as recited in Table 29.

TABLE 29

Tumor Response Criteria

| Target lesions[a] | Non-Target lesions[b] | New Lesions[c] | Overall Response |
|---|---|---|---|
| CR | CR | No | CR |
| CR | Non-CR/Non-PD | No | PR |
| PR | Non-PD | No | PR |
| SD | Non-PD | No | SD |
| PD | Any response | Yes or No | PD |

TABLE 29-continued

Tumor Response Criteria

| Target lesions[a] | Non-Target lesions[b] | New Lesions[c] | Overall Response |
|---|---|---|---|
| Any response | PD | Yes or No | PD |
| Any response | Any response | Yes | PD |

[a]Measurable lesions only
[b]May include measurable lesions not followed as target lesions or non-measurable lesions
[c]Measurable or non-measurable lesions
Abbreviations: CR = complete response, PD = progressive disease, PR = partial response, SD = stable disease The best overall response is the best response recorded from the start of the treatment until disease progression/recurrence (taking as reference for tumor progression the smallest measurements recorded since the treatment started). The subject's best response assignment may depend on the achievement of both measurement and confirmation criteria.

Subjects may be defined as being not evaluable for response (NE) if there is no post randomization oncologic assessment. These subjects may be counted as failures in the analysis of tumor response data. Subjects with a global deterioration of health status requiring discontinuation of treatment without objective evidence of disease progression at that time may be reported as having "symptomatic deterioration". Every effort should be made to document the objective progression even after discontinuation of treatment.

12. EXAMPLE

Treatment in Disease Model 12.1 Effect of a Compound as Monotherapy and in Combination with Docetaxel on the Growth of LNCaP Tumors In vivo This example demonstrates that Compound #10 is effective in delaying the growth of LNCaP prostate tumor cells in vivo.

Male C.B.17 SCID mice (Charles River Laboratory; Wilmington, Mass.) were inoculated with LNCaP prostate tumor cells ($6.1 \times 10^6$ cells/mouse) obtained from the ATCC (Manassas, Va.). Tumor cells were mixed 1:1 with BD MATRIGEL™ (BD Biosciences, San Jose, Calif.) prior to inoculation. Mice were inoculated using a 25 gauge needle in the right flank in a volume of 0.2 mL. A total of 95 mice were injected, of which 32 were used.

Thirty seven days after inoculation, the mice were randomized into 4 groups as outlined in Table 30. Animals were distributed into groups such that the average tumor size did not differ among groups. Treatment started on Day 0 and continued through Day 31. Dosing volumes are summarized in Table 31.

Compound #10 was prepared in a lipid based vehicle, L21 (35% Labrasol®, 35% Labrafac®, and 30% Solutol H515®). Docetaxel (Sanofi-Aventis; Bridgewater, N.J.) was prepared on Day 1 for the first injection by the addition of a diluent provided by the manufacturer (13% ethanol in water) and then further diluted in 0.9% sodium chloride (NaCl). This docetaxel stock was stored at 4° C. and then diluted with 0.9% NaCl on Day 8 for the second injection as suggested by the manufacturer. Formulated Compound #10 was stored at room temperature in ambient humidity and protected from light.

TABLE 30

Group Designation

| | | Oral Dosing | | IV Dosing | | |
|---|---|---|---|---|---|---|
| Group | Treatment | Route, Dose, and Regimen | Treatment | Route, Dose, and Regimen | | Number of Mice |
| 1 | L21 vehicle | PO, QD daily | None | None | | 8 |
| 2 | Compound #10 | PO, 10 mg/kg QD daily | None | None | | 8 |

TABLE 30-continued

| | | Group Designation | | | |
|---|---|---|---|---|---|
| | | Oral Dosing | | IV Dosing | |
| Group | Treatment | Route, Dose, and Regimen | Treatment | Route, Dose, and Regimen | Number of Mice |
| 3 | L21 vehicle | PO, QD daily | Docetaxel | IV, 3 mg/kg on Day 1 and Day 8 | 8 |
| 4 | Compound #10 | PO, 10 mg/kg QD daily | Docetaxel | IV, 3 mg/kg Day 1 and Day 8 | 8 |

Abbreviations: IV = intravenous, PO = oral, QD = once per day

TABLE 31

| | Dosing Volumes | | |
|---|---|---|---|
| Test Compound | Dose (mg/kg) | Dosing Volume | Dose Concentration (mg/mL) |
| Compound #10 | 10 | 0.1 mL/mouse[1] | 2.1 |
| Docetaxel | 3 | 10 mL/kg | 0.3 |

[1]The concentration of the dosing solution was adjusted as necessary so that a volume of 0.1 mL delivered a dose of 10 mg/kg.

Procedures & Analysis:

Body Weight: One day prior to the initiation of the study, the mice were weighed. Thereafter, mice were weighed every week and on the day that the study was terminated.

Tumor Size: Tumors were measured every 3 to 4 days using digital calipers. To calculate tumor volume, the following calculation was used, where L equals the longest dimension measurement and W equals the shortest dimension measurement:

$$\text{Tumor Volume} = \frac{L \times (W)^2}{2}$$

Clinical Observations: Each animal was observed once daily for mortality and signs of pain or distress. Findings of overt toxicity were recorded as they were observed.

Data Analysis: Tumor growth was calculated as:

[1-[(final tumor size minus initial tumor size in test compound treated-mice)/(final tumor size minus initial tumor size in vehicle-treated mice)]×100%

Values were calculated for individual mice and then averaged across the group.

Percent change in body weight was calculated as:

[(Body weight on Day of study)−(initial body weight)/ (initial body weight)]×100%

Values were calculated for individual mice and then averaged across the group.

Differences in tumor size, tumor growth, and body weight change among groups were analyzed by ANOVA (analysis of variance) (SigmaStat 3.0).

Results: All mice survived until the scheduled necropsy. Data are summarized in Table 32.

TABLE 32

Summary of Data

| | | Percent Inhibition Relative to Vehicle | | |
|---|---|---|---|---|
| Group | Treatment | Tumor Volume at Day 31 | Tumor Growth From Day 0 to 31 | Maximal Body Weight Loss From Initial Weight (Day of Maximal Loss) |
| 1 | Vehicle, QD, daily | NA | NA | −9.9% (Day 27) |
| 2 | Compound #10, 10 mg/kg QD, daily | 38%* | 54%* | −3.9% (Day 27) |
| 3 | Docetaxel, 3 mg/kg IV on Days 1 and 8 Vehicle, QD, daily | 12% | 17% | −15% (Day 13) |
| 4 | Compound #10, 10 mg/kg QD, daily Docetaxel, 3 mg/kg IV on Days 1 and 8 | 39%* | 55%* | −10% (Day 6) |

*p < 0.05 (ANOVA, multiple comparisons versus vehicle)
Abbreviations: IV = intravenous, PO = oral dosing, QD = once per day.

Effect of Treatment on Tumor Growth: A total of 32/95 mice that were inoculated with LNCaP cells developed tumors that were within the appropriate range at the start of this study. The mean±SD tumor volume for mice used in this study was 342±105 mm3 at the initiation of treatment. Treatment continued until Day 31. FIG. 34 shows the mean tumor size over time.

Tumor Growth in Vehicle-Treated Mice: Tumors in vehicle-treated mice grew from a mean±SD of 342±95 mm3 to 1159±316 mm3 by Day 31.

Tumor Growth in Compound #10-Treated Mice: Tumors in Compound #10 treated mice were significantly smaller than the tumors in vehicle-treated mice by Day 17, remaining smaller than tumors in vehicle-treated mice through the study (p<0.05, ANOVA, multiple comparisons versus vehicle). On Day 31, the mean±SD tumor size was 722±267 mm3, or 38% inhibition of tumor size and 54% inhibition of the increase in tumor size (p<0.05, ANOVA, multiple comparisons versus vehicle).

Tumor Growth in Docetaxel-Treated Mice: Tumors in docetaxel-treated mice were significantly smaller than tumors in vehicle-treated mice by Day 13 but subsequently grew such that they were nearly the same size as tumors in vehicle treated mice by Day 31. At Day 31, the mean±SD tumor size was 1017±458 mm3. No statistically significant differences in inhibition of tumor size versus vehicle or inhibition in the increase in tumor size versus vehicle were observed.

Tumor Growth in Mice Treated with the Combination of Compound #10 and Docetaxel: Tumors in mice treated with the combination of Compound #10 and docetaxel were significantly smaller than tumors in vehicle-treated mice by Day 13 and were similar in size to tumors in Compound #10-treated mice through Day 31. At Day 31, the mean±SD tumor size was 713±204 mm3, or 39% inhibition of tumor size and 55% inhibition of the increase in tumor size (p<0.05, ANOVA, multiple comparisons versus vehicle). There was no statistically significant difference in tumor growth between mice treated with the combination of Compound #10 and docetaxel and Compound #10-treated mice.

Effect of Treatment on Body Weight: Mice were not randomized by body weight but by initial tumor size. The effect of treatment was determined by normalizing the body weight over time to initial body weight (i.e., by determining the percent change from the initial body weight). FIG. 35 shows the changes in body weight over time.

Vehicle-treated mice lost weight over the course of the study, exhibiting tumor-induced cachexia. At Day 6, mean body weight was significantly reduced compared to mean initial body weight (p<0.05, Student's paired t test) and remained so through Day 31. At Day 30, mean body weight was 9.9% lower than mean initial body weight.

Compound #10-treated mice tended to lose weight over the course of the study, with significantly less weight loss than vehicle-treated mice on Day 6, 13, and 21. At no point during the study was mean body weight significantly reduced compared to mean initial body weight, indicating that Compound #10-treated mice did not exhibit tumor-induced cachexia.

Docetaxel-treated mice lost more weight over the course of the study than vehicle-treated mice, indicating that docetaxel-treatment was likely associated with toxicity. The difference in weight loss between docetaxel- and vehicle-treated mice was significant by Day 6 and maximal at Day 13. At Day 13, mean body weight was 15% lower than mean initial body weight. By Day 21, docetaxel-treated mice had regained weight, possibly because mice were only dosed on Day 1 and Day 8.

Mice treated with the combination of Compound #10 and docetaxel lost weight, but they lost less weight than docetaxel-treated mice. By Day 13, the mice dosed with the combination had lost as much weight as the vehicle-treated mice (more weight than the Compound #10-only treated mice but less than the docetaxel-only treated mice). Therefore, Compound #10 reduced docetaxel-induced cachexia. It should be noted that there were no differences in mean tumor size at Day 13 in docetaxel-treated mice and in Compound #10- and docetaxel-treated mice, suggesting that the effect on cachexia was independent of tumor size reduction.

Serum Exposure: Blood was obtained by cardiac puncture at sacrifice on Day 31, 7 hours after the last dose, and the serum analyzed by liquid chromatography with tandem mass spectrometry (LC-MS/MS) to confirm exposure of Compound #10. The mean±SD level of Compound #10 in Compound #10-treated mice was 5.23±0.88 µg/mL (n=7). The mean±SD levels of Compound #10 in mice treated with a combination of Compound #10 and docetaxel was 6.41±0.75 µg/mL (n=8), which was significantly higher than levels in mice treated with Compound #10 only (p<0.05, Student's t-test). However, it should be noted that serum concentrations were only measured at a single timepoint and may not be representative of the total exposure. Additional studies would be necessary to determine if there is an interaction between docetaxel and Compound #10. Levels of docetaxel were not monitored, thus the effect of Compound #10 on docetaxel could not be evaluated.

Thus, treatment of mice with Compound #10 delays the growth of LNCaP prostate tumor cells in vivo. Compound #10 also prevented tumor-induced cachexia and reduced docetaxel-induced cachexia. The effect on cachexia appeared to be independent of the effect on tumor growth. Compound #10 was more effective at delaying tumor growth than docetaxol. The combination of docetaxel and Compound #10 was not more effective than Compound #10 alone in delaying tumor growth.

12.2 Effect of Compound #10 as Monotherapy and in Combination with Bicalutamide on the Growth of LNCaP Tumors In vivo This example demonstrates that Compound #10 is effective in delaying the growth of LNCaP prostate tumor cells in vivo.

Male C.B.17 SCID mice (Charles River Laboratory; Wilmington, Mass.) were inoculated with LNCaP prostate tumor cells ($6.1 \times 10^6$ cells/mouse) obtained from the ATCC (Manassas, Va.). Tumor cells were mixed 1:1 with BD MATRIGEL™ (Becton, Dickinson and Company, San Jose, Calif.) prior to inoculation. Mice were inoculated using a 25 gauge needle in the right flank in a volume of 0.2 mL. A total of 95 mice were injected, of which 32 were used.

Twenty-seven days after inoculation, the mice were randomized into 4 groups as outlined in Table 33. Animals were distributed into groups such that the average tumor size did not differ among groups. Treatment started on Day 0 and continued through Day 30. Dosing volumes are summarized in Table 34.

Compound #10 was prepared in a lipid based vehicle, L21 (35% LABRASOL®, 35% LABRAFAC®, and 30% Solutol HS15®. Bicalutamide (AstraZeneca, Wilmington, Del.) was prepared in 0.5% carboxymethylcellulose (CMC) from clinical-grade tablets. Formulated Compound #10 and bicalutamide were stored at room temperature in ambient humidity and protected from light.

TABLE 33

| | | Group Designation | | | |
|---|---|---|---|---|---|
| | | Oral Dosing | | Oral Dosing | |
| Group | Treatment | Route, Dose, and Regimen | Treatment | Route, Dose, and Regimen | Number of Mice |
| 1 | L21 vehicle | PO, QD, daily | None | None | 8 |
| 2 | Compound #10 | PO, 10 mg/kg QD, daily | None | None | 8 |

TABLE 33-continued

| | | Group Designation | | | |
|---|---|---|---|---|---|
| | | Oral Dosing | | Oral Dosing | |
| Group | Treatment | Route, Dose, and Regimen | Treatment | Route, Dose, and Regimen | Number of Mice |
| 3 | L21 vehicle | PO, QD, daily | Bicalutamide | PO, 25 mg/kg on Days 0, 1, 2, 3, 6, 7, 8, 9, and 10 | 8 |
| 4 | Compound #10 | PO, 10 mg/kg QD, daily | Bicalutamide | PO, 25 mg/kg on Days 0, 1, 2, 3, 6, 7, 8, 9, and 10 | 8 |

Abbreviations: QD = Once per day, PO = ora

TABLE 34

| | Dosing Volumes | | |
|---|---|---|---|
| Test Compound | Dose (mg/kg) | Dosing Volume[1] (mL/mouse) | Dose Concentration (mg/mL) |
| Compound #10 | 10 | 0.1 | 2.10 |
| Bicalutamide | 25 | 0.1 | 5.25 | a) The concentration of the dosing solution was adjusted as necessary so that a volume of 0.1 mL delivered a dose of 10 mg/kg or 25 mg/kg for Compound #10 or bicalutamide, respectively.

Procedures and Analysis

Body Weight: One day prior to the initiation of the study, the mice were weighed. Thereafter, mice were weighed every week and on the day that the study was terminated.

Tumor Size: Tumors were measured every 3 to 4 days using digital calipers. To calculate tumor volume, the following calculation was used, where L equals the longest dimension measurement and W equals the shortest dimension measurement:

$$\text{Tumor Volume} = \frac{L \times (W)^2}{2}$$

Clinical Observations: Each animal was observed once daily for mortality and signs of pain or distress. Findings of overt toxicity were recorded as they were observed.

Data Analysis:

Tumor growth was calculated as:

[1−[(final tumor size minus initial tumor size in test compound treated-mice)/(final tumor size minus initial tumor size in vehicle-treated mice)]×100%

Values were calculated for individual mice and then averaged across the group.

Percent change in body weight was calculated as:

[(Body weight on Day of study)−(initial body weight)/ (initial body weight)]×100%

Values were calculated for individual mice and then averaged across the group.

Differences in tumor size, tumor growth, and body weight change among groups were analyzed by ANOVA (analysis of variance) (SigmaStat 3.0).

Results: One vehicle mouse was found dead on Day 29 in the morning prior to dosing, possibly due to tumor-induced cachexia. This mouse had weighed 17 g on Day 27, when the mean body weight for that group was 20 g. All other mice survived until necropsy. Data are summarized in Table 35.

TABLE 35

| | | Summary of Data | | |
|---|---|---|---|---|
| | | Percent Inhibition Relative to Vehicle | | |
| Group | Treatment (Oral Dosing) | Tumor Volume at Day 31 | Tumor Growth From Day 0 to 31 | Maximal Body Weight Loss From Initial Weight (Day of Maximal Loss) |
| 1 | L21 vehicle, QD | NA | NA | −7.0% (Day 13) |
| 2 | Compound #10, 10 mg/kg QD | 38%* | 49%* | −2.6% (Day 6) |
| 3 | Bicalutamide, 25 mg/kg QD on Days 0, 1, 2, 3, 6, 7, 8, 9, and 10 L21 vehicle, QD | 7.2% | 9.3% | −5.3% (Day 20) |
| 4 | Compound #10, 10 mg/kg QD Bicalutamide, 25 mg/kg QD on Days 0, 1, 2, 3, 6, 7, 8, 9, and 10 | 32%* | 41%* | −1.7% (Day 27) |

*p < 0.05 (Multiple comparisons versus vehicle)
Abbreviations: QD = Once per day Effect of Treatment on Tumor Growth: A total of 32/95 mice that were inoculated with LNCaP cells developed tumors that were within the appropriate range at the start of this study. The mean±SD tumor volume was 262±69 mm3 at the initiation of treatment. Treatment continued until Day 30, at which time the mice were sacrificed 5.5 hours after the last dose. FIG. 36 shows the mean tumor size over time.

Tumor Growth in Vehicle-Treated Mice: Tumors in vehicle-treated mice grew from a mean±SD of 262±78 mm3 to 1141±385 mm3 by Day 30.

Tumor Growth in Compound #10-Treated Mice: Tumors in Compound #10 treated mice were significantly smaller than tumors in vehicle-treated mice by Day 20 (p<0.05, ANOVA, multiple comparisons to vehicle) and remained smaller than tumors in vehicle-treated mice through Day 30. At Day 30, the mean±SD tumor size was 712±241 mm3, or 38% inhibition of tumor size and 49% inhibition of the increase in tumor size (p<0.05, ANOVA, multiple comparisons versus vehicle).

Tumor Growth in Bicalutamide-Treated Mice: Tumors in bicalutamide treated mice treated were significantly smaller than tumors in vehicle treated mice by Day 20 but subsequently increased such that they were nearly the same size as tumors in vehicle-treated mice by Day 30. At Day 30, the mean±SD tumor size was 1059±321 mm3. No statistically significant differences in inhibition of tumor size versus vehicle or inhibition in the increase in tumor size versus vehicle were observed.

Tumor Growth in Mice Treated with the Combination of Compound #10 and Bicalutamide: Tumors in mice treated with the combination of Compound #10 and bicalutamide were significantly smaller than tumors in vehicle-treated mice by Day 20 and were of similar size to tumors in Compound #10-treated mice through Day 30. At Day 30, the mean±SD tumor size was 781±157 mm3, or 32% inhibition of tumor size and 41% inhibition of the increase in tumor size (p<0.05, ANOVA, multiple comparisons versus vehicle). There was no statistically significant difference in tumor growth between mice treated with the combination of Compound #10 and bicalutamide and Compound #10-treated mice.

Effect of Treatment on Body Weight: Mice were not randomized by body weight but by initial tumor size. The effect of treatment was determined by normalizing body weight over time to initial body weight (i.e., by determining the percent change from the initial body weight). FIG. 37 shows the changes in body weight over time.

Vehicle-treated mice lost weight over the course of the study, exhibiting tumor-induced cachexia. By Day 6, mean body weight was significantly reduced compared to mean initial body weight (p<0.05, Student's paired t test) and remained so through Day 30. Maximal weight loss was observed at Day 13, at which point mean body weight was 7% lower than mean initial body weight. At Day 30, mean body weight was 5.2% lower than mean initial body weight.

Compound #10-treated mice lost weight over the course of the study, but they tended to lose less weight than vehicle-treated mice and did not exhibit tumor-induced cachexia. At Day 6 and Day 13, mean body weight was significantly reduced compared to mean initial body weight (p<0.05, Student's paired t-test). Maximal weight loss was noted at Day 6, at which point mean body weight was 2.6% lower than mean initial body weight.

Bicalutamide-treated lost weight over the course of the study, but they lost less weight than vehicle-treated mice and did not exhibit tumor-induced cachexia. this difference was significant at Day 6 by ANOVA. Maximal weight loss was noted at Day 20, at which point mean body weight was 5.3% lower than mean initial body weight.

Mice treated with the combination of Compound #10 and bicalutamide tended to lose less weight than the mice treated with either agent as monotherapy, although this difference did not reach significance at any day; these data indicate that the combination of Compound #10 and bicalutamide tended to be most effective at preventing tumor-induced cachexia.

Plasma Exposure: Plasma was obtained by terminal cardiac puncture at sacrifice on Day 30, 5.5 hours after the last dose, and analyzed by liquid chromatography with tandem mass spectrometry (LC-MS/MS) to confirm exposure of Compound #10. The mean±SD level of Compound #10 in Compound #10-treated mice was 4.8±0.88 µg/mL (n=7). The mean±SD level of Compound #10 in mice treated with a combination of Compound #10 and bicalutamide was 5.4±0.51 µg/mL (n=8), which was not significantly higher than levels in mice treated with Compound #10 only (p=0.098, Student's t-test). Levels of bicalutamide were not monitored, thus the effect of Compound #10 on bicalutamide could not be evaluated.

Thus, treatment of mice with Compound #10 delays the growth of LNCaP prostate tumor cells in vivo. Compound #10 also prevents tumor-induced cachexia, and the combination of Compound #10 and bicalutamide tends to be more effective than either agent as monotherapy in preventing tumor induced cachexia. Compound #10 was more effective at delaying tumor growth than bicalutamide. The combination of bicalutamide and Compound #10 was not more effective than Compound #10 alone in delaying tumor growth.

12.3 Effect of a Compound as Monotherapy and in Combination with Docetaxel on the Growth of PC3 Tumors In vivo This example demonstrates the effect of Compound #10 on the growth of PC3 prostate tumor cells in vivo. PC3 cells are a human androgen-independent cancer cell line that does not produce prostate specific antigen (PSA).

Male C.B.17 SCID mice (Charles River Laboratory; Wilmington, Mass.) were inoculated with LNCaP prostate tumor cells ($6.1 \times 10^6$ cells/mouse) obtained from the ATCC (Manassas, Va.). Tumor cells were mixed 1:1 with BD MATRIGEL™ (BD Biosciences, San Jose, Calif.) prior to inoculation. Mice were inoculated using a 25 gauge needle in the right flank in a volume of 0.2 mL. A total of 95 mice were injected, of which 32 were used.

Thirty seven days after inoculation, the mice were randomized into 4 groups as outlined in Table 36. Animals were distributed into groups such that the average tumor size did not differ among groups. Treatment started on Day 0 and continued through Day 31. Dosing volumes are summarized in Table 31.

Thirty seven days after inoculation, the mice were randomized into 4 groups as outlined in Table 30. Animals were distributed into groups such that the average tumor size did not differ among groups. Treatment started on Day 0 and continued through Day 31. Dosing volumes are summarized in Table 31.

Compound #10 was prepared in a lipid based vehicle, L21 (35% Labrasol®, 35% Labrafac®, and 30% Solutol H515®). Docetaxel (Sanofi-Aventis; Bridgewater, N.J.) was prepared on Day 1 for the first injection by the addition of a diluent provided by the manufacturer (13% ethanol in water) and then further diluted in 0.9% sodium chloride (NaCl). This docetaxel stock was stored at 4° C. and then diluted with 0.9% NaCl on Day 8 for the second injection as suggested by the manufacturer. Formulated Compound #10 was stored at room temperature in ambient humidity and protected from light.

TABLE 36

Dosing Volumes

| Cpd | Dose (mg/kg)[a] | Route[a] | Administration Regimen | Dose Volume (mL/kg) | Dose Concentration (mg/mL) |
|---|---|---|---|---|---|
| Cpd #10 | 10 | PO | QD | 4 | 2.50 |
| Cpd #10 | 10 | PO | BID | 4 | 2.50 |
| Cpd #10 | 20 | PO | BID | 4 | 5.00 |
| Cpd #10 | 3 | PO | BID | 4 | 0.75 |
| Cpd #10 | 6 | PO | BID | 4 | 1.50 |
| Docetaxel | 3 | IV | Day 1 and 8 | 10 | 0.30 |
| Docetaxel | 10 | IV | Day 29 | 10 | 0.30 |

Abbreviations BID = twice daily, IV = intravenous, PO = Per os (oral dosing), QD = once daily.
[a]The concentration of the dosing solution was adjusted as necessary so that a volume of 0.1 mL delivered a dose of 10 mg/kg.

PC3 cells (CRL 1435) obtained from the American Type Tissue Collection (ATCC, Manassas, Va.) were thawed and seeded at $0.5 \times 10^7$ cells per 175 mm² flask. Cells were fed and expanded on a regular schedule to reach a given density prior to passage. Flasks were between 80-90% confluent, but not >95% confluent on the day of harvest. Harvest occurred ~48 hr after the previous split to allow for full recovery.

To harvest the cells, medium was removed from the flasks and the cell layers rinsed with 37° C. PBS. A volume of 3 mL trypsin-EDTA was added per 175 cm² surface area and incubated at room temperature for 5 minutes until the cells detached. The cells were collected in 7-10 mL ice cold complete medium and were transferred to a conical tube. The tube was placed immediately on ice. After all flasks were harvested, the cells were pelleted by centrifugation at 4° C. Cells were re-suspended at 2.5×10⁷ cells/mL in Hank's Salt Solution and 10 mM HEPES. Cells were stored on ice until the time of tumor inoculation (which was less than 1 h later).

Tumor Implantation: Details of the tumor cell inoculation are summarized in Table 37.

TABLE 37

Cell Inoculation

| Parameters | Methods |
| --- | --- |
| Cells | PC3 cells obtained from ATCC (CRL 1435) |
| Target cell concentration | 5 × 10⁶ cells/0.2 mL = 2.5 × 10⁷ cells/mL |
| Cell inoculation medium | Hank's Salt Solution with 10 mM HEPES mixed 1:1 with Matrigel ™ (Biosciences; San Jose, CA) |
| Cell inoculation | 0.2 mL/mouse |

Tumor Cell Injection: Tumor cells were kept on ice at all times. Tumor cells were mixed 1:1 with BD MATRIGEL™ (Biosciences; San Jose, Calif.) prior to inoculation. A 25-gauge needle was used for tumor cell injections. Tumor cells were injected in a volume of 0.2 mL subcutaneously. A total of 100 mice were inoculated, of which 69 were used in the study.

Seventeen days after inoculation, the mice were randomized into six groups. At this time, the majority of the tumors had reached a volume of 170-415 mm³. Randomization of the mice was performed by using the formula RAND ( )*5000 from Microsoft Excel. Animals were distributed into groups such that the average tumor size did not differ among groups. Animals with tumors that were not within the 170-415 mm³ range were excluded from the study.

As shown in Table 38, mice were distributed among the designated dosing groups, so that at the initiation of dosing, all groups had the same average tumor volume (average±SD, 266±59.7 mm³ for the 69 mice in the study). Furthermore, all animals in a group were taken off study when the mean tumor size in that group reached 1000 mm³.

TABLE 38

Group Designation

| | | Dose Level and Schedule | | |
| --- | --- | --- | --- | --- |
| Group | Cmpd | Weekday | Weekend | # Mice |
| 1 | L21 | 0 BID PO | 0 QD PO | 13 |
| 2 | Cpd #10 | 10 mg/kg QD PO | | 13 |
| 3 | Docetaxel[a] | 3 mg/kg IV Day 1 and 8 10 mg/kg on Day 29 | | 10 |
| 4 | Cpd #10 and Docetaxel | 10 mg/kg QD PO 3 mg/kg IV Day 1 and 8 10 mg/kg Day 29 | | 10 |
| 5 | Cpd #10 | 10 mg/kg BID | 20 mg/kg QD | 13 |
| 6 | Cpd #10 | 3 mg/kg BID | 6 mg/kg QD | 10 |

[a]The dose of docetaxel was based upon regimens reported in the literature (Fujimoto-Ouchi et al, 2001).

Tumor Size: Tumors were measured every 3 to 4 days using digital calipers. To calculate tumor volume, the following calculation was used, where L equals the longest dimension measurement and W equals the shortest dimension measurement:

$$\text{Tumor Volume} = \frac{L \times (W)^2}{2}$$

Differences in mean tumor size, tumor growth, and body weight change were compared across groups using analysis of variance (ANOVA) (SigmaStat 3.0).

To calculate the time to progression, defined as the number of days for a tumor to reach 1000 mm³, tumor growth vs time was individually plotted for each animal. The time to reach 1000 mm³ estimated for each animal. In cases where the tumor size did not reach 1000 mm³, the duration of the study was used as the time for progression for the animal. The median and mean time for each treatment group to reach 1000 mm³ was then calculated and groups were compared using ANOVA (SigmaStat 3.0).

Body Weight: One day prior to the initiation of the study, the mice were weighed. Thereafter, mice were weighed every week and on the day that the study was terminated.

Clinical Observations: Each animal was observed once daily for mortality and signs of pain or distress. Findings of overt toxicity were recorded as they were observed.

Plasma Exposure: Plasma was collected by cardiac puncture when mice are taken off study and on day 43 for mice treated with Compound #10 at 10 mg/kg QD, Day 54 for Compound #10 at 10 mg/kg or 3 mg/kg BID and Day 60 for Compound #10 at 10 mg/kg QD and docetaxel (3 mg/kg on Day 1, 8 and at 10 mg/kg on Day 29) (see Appendix E). Plasma samples were analyzed by LC/MS/MS for Compound #10. Levels of docetaxel were not measured.

Effects on Tumor Growth: A total of 69 of the 100 mice that were inoculated with PC3 cells developed tumors that were within the appropriate range at the start of the study. The mean tumor volume±the standard deviation for mice used in this study was 266±59.7 mm³ at the initiation of treatment. Treatment continued until Day 60 (for the last group of treated animals that were taken off). FIG. 38A shows the effect on mean tumor growth over the study time period for mice treated by oral gavage with Compound #10 at 10 mg/kg QD (once per day), 10 mg/kg BID (twice per day) and 3 mg/kg BID. FIG. 38B shows the effect on mean tumor growth over the study time period for mice treated by oral gavage with Compound #10 (10 mg/kg QD), docetaxel (3 mg/kg IV (intravenous injection) Day 1, and at 8 and 10 mg/kg Day 29) and the combination of Compound #10 and docetaxel.

Figure 38:
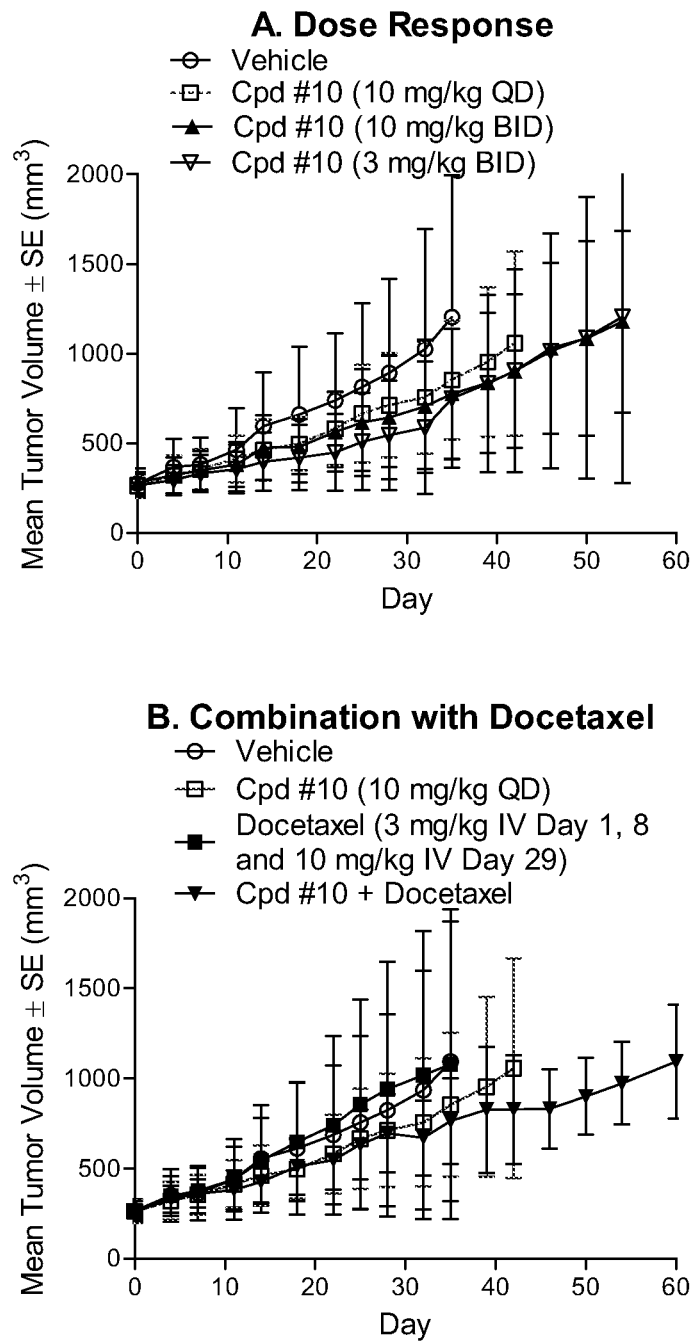

Tumor Growth in Mice Treated with Vehicle: As shown in FIG. 38, tumors in vehicle-treated mice grew from 266 mm³ to 1095 mm³ by Day 35. The median time to progression (the time for the tumor to reach a size ≥1000 mm³) was 23 days.

Tumor Growth in Mice Treated with Compound #10 Alone: As shown in FIG. 38, tumors in mice treated with Compound #10 at 10 mg/kg QD, 10 mg/kg BID or 3 mg/kg BID by oral gavage administration tended to be smaller than tumors in mice treated with vehicle by Day 20 up to Day 35 (the time at which the vehicle-treated mice were taken off study). There was no difference between these three doses of Compound #10. As shown in FIG. 38A at Day 35, the mean tumor sizes were 781 mm³, 776 mm³ and 750 mm³ for the mice treated with Compound #10 at 10 mg/kg QD, 10 mg/kg BID or 3 mg/kg BID respectively. Associated with the decrease in tumor size was a significant delay in median time to progression (p<0.05, vs vehicle). As shown in Table 39, the median time to progression in mice treated with Compound #10 at 10 mg/kg QD, 10 mg/kg BID, or 3 mg/kg BID was 38 days, 39 days and 34 days respectively (vs 23 days in vehicle.

Tumor Growth in Mice Treated with Docetaxel Alone: Docetaxel was intravenously administered at 3 mg/kg on Day 1 and at 8 and 10 mg/kg on Day 29. Because the dose at 3 mg/kg IV had no effect, the dose was increased to 10 mg/kg. As shown in FIG. 38A, tumors from mice treated with docetaxel by IV tail administration were not significantly different from the tumors in vehicle-treated mice up to Day 35. As shown in Table 39, the median time to progression in docetaxel-treated mice was 22 days, (vs 23 days in vehicle.

Tumor Growth in Mice Treated with Combination Therapy: As shown in Table 39, the dose of docetaxel (at 3 mg/kg on Day 1, and at 8 and 10 mg/kg on Day 29) was not effective as monotherapy for reducing tumors size or in delaying the time to tumor progression. When tumor size in mice treated with Compound #10 (10 mg/kg QD) alone was compared to the tumor size in mice treated with the combination of Compound #10 and docetaxel (3 mg/kg IV and 10 mg/kg IV), tumors in mice treated with the combination tended to be smaller. The median time to progression was increased from 38 days with Compound #10 to 51 days with the combination of Compound #10 and 3 mg/kg IV docetaxel ($p<0.05$, vs Compound #10 alone).

TABLE 39

Time to Progression (Time to Reach 1000 mm$^3$)

| Group | Average Time on Therapy (days)$^a$ | Median Time to Reach 1000 mm$^3$ |
|---|---|---|
| Vehicle | 22 | 23 |
| Compound #10 (10 mg/kg QD) | 33 | 38 |
| Docetaxel (3 mg/kg IV Day 1, 8 and 10 mg/kg Day 29) | 23 | 22 |
| Compound #10 (10 mg/kg BID) | 36* | 39 |
| Compound #10 (3 mg/kg BID) | 34* | 34 |
| Compound #10 (10 mg/kg BID and Docetaxel (3 mg/kg IV) | 45* | 51 |

$^a$When the tumor size did not reach 1000 mm$^3$, the last day the mice were on study was used to calculate the mean.
*$p < 0.05$ vs. vehicle (ANOVA on Ranks, multiple comparisons vs. vehicle); when the tumor size did not reach 1000 mm$^3$, the last day the mice were on study was used for the statistical analysis.
Abbreviations: ANOVA = analysis of variance, BID = two times per day, IV = intravenous injection, QD = one time per day Effects on Body Weight: Vehicle-treated mice lost weight over the course of the study. At Day 7, the body weight of the vehicle-treated mice was ~7% less than their pre-dose weight. By Day 35, the mean body weight was ~10% less than the pre-dose weight. On Day 35 the weight was significantly less than on Day 0 ($p<0.05$ Paired Student's t-test)

As shown in FIG. 39A, mice treated with various doses of Compound #10 (10 mg/kg QD, 10 mg/kg BID and 3 mg/kg BID) tended to gain weight from Day 7 up to Day 42 in comparison to the vehicle control-treated mice. However, the difference in weight gain in mice treated with Compound #10 was not significant compared to the vehicle-treated mice. There was no significant weight loss between Day 0 and Day 42 (Paired Student's t-test). Therefore, Compound #10 prevented tumor-induced weight loss.

As shown in FIG. 39B, docetaxel did not elicit significantly greater loss in body weight than that noted in vehicle-treated mice up to Day 28. However, at Day 35, significantly more weight loss was noted in docetaxel-treated mice than in vehicle-treated mice. There was no significant weight loss between Day 0 and Day 35 (Paired Student's t-test).

As shown in FIG. 39B, for mice treated with Compound #10 (10 mg/kg QD) in combination with docetaxel (3 mg/kg IV Day 1, and at 8 and 10 mg/kg IV Day 29), loss in body weight was prevented in comparison to mice treated with docetaxel only at Day 35.

Plasma Concentrations: To confirm exposure of Compound #10, plasma samples were taken from animals treated with Compound #10 only and/or the combination Compound #10 and docetaxel at trough (18-22 h post dosing) on the day of sacrifice.

As shown in Table 40, plasma levels of Compound #10 in mice dosed with Compound #10 (10 mg/kg QD) alone or in combination with docetaxel were not significantly different at trough although the groups cannot be directly compared because mice were taken off on different days and at different times. These results suggest that docetaxel does not affect the pharmacokinetics of Compound #10. Plasma levels of docetaxel were not measured, so the effect of Compound #10 on docetaxel could not be assessed.

TABLE 40

Plasma Concentrations of Compound #10 and Combination With Docetaxel

| Treatment | Day/Time Points (hr post dosing) | Compound #10 Plasma Concentration (µg/mL) |
|---|---|---|
| Compound #10 (3 mg/kg BID PO) | Day 50; 18 hr | 3.4 ± 1.1 |
| Compound #10 (10 mg/kg QD PO) | Day 42; 22 hr | 6.0 ± 1.5* |
| Compound #10 (10 mg/kg BID PO) | Day 50; 18 hr | 8.0 ± 1.5*# |
| Compound #10 (10 mg/kg QD PO) and Docetaxel (3 mg/kg IV) | Day 54; 19 hr | 6.0 ± 2.4 |

*$p < 0.05$ vs Compound #10 (3 mg/kg BID);
$p < 0.05$ vs Compound #10 (10 mg/kg QD)

Results: As monotherapy, Compound #10 tended to prevent growth of PC3 tumor cells in vivo when compared to vehicle-treated mice. However, efficacy at 3 mg/kg BID was similar to 10 mg/kg BID. As monotherapy at the dose utilized, docetaxel neither prevented nor delayed the growth of PC3 tumor in mice. Compound #10 (10 mg/kg QD) in combination with docetaxel at doses of 3 mg/kg IV (Day 1, and at 8 and 10 mg/kg on Day 29) significantly increased the time to progression when compared to vehicle-treated mice or docetaxel administered alone (as monotherapy).

Vehicle-treated mice lost ~10% of their body weight compared to their initial weight. This weight loss was not markedly exacerbated by docetaxel administered as monotherapy. However, weight loss tended to be prevented by the combination therapy of docetaxel with Compound #10. Compound #10 as a monotherapy prevented tumor-induced weight loss. There was no overt toxicity associated with Compound #10 treatment as monotherapy or in combination with docetaxel. Compound #10 was well-tolerated and efficacious in this model as monotherapy or when dosed in combination with docetaxel.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method for treating a prostate cancer or benign prostatic hyperplasia, comprising administering to a human having the prostate cancer or benign prostatic hyperplasia an effective amount of a compound of Formula (II):

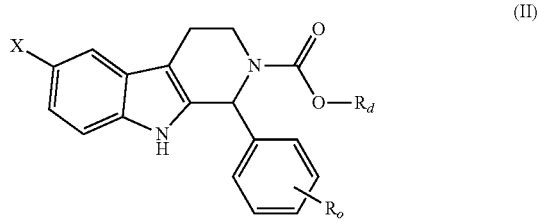

or a pharmaceutically acceptable salt, racemate or stereoisomer thereof, wherein, X is hydrogen; $C_1$ to $C_6$ alkyl optionally substituted with one or more halogen substituents; hydroxyl; halogen; or $C_1$ to $C_5$ alkoxy optionally substituted with phenyl;

$R_o$ is halogen; cyano; nitro; sulfonyl substituted with $C_1$ to $C_6$ alkyl or morpholinyl; amino optionally substituted with $C_1$ to $C_6$ alkyl, —C(O)—$R_b$, —C(O)O—$R_b$, alkylsulfonyl, morpholinyl or tetrahydropyranyl; $C_1$ to $C_8$ alkyl optionally substituted with one or more substituents independently selected from the group consisting of hydroxyl, halogen and amino; —C(O)—$R_n$; or —O$R_a$;

$R_a$ is hydrogen; $C_2$ to $C_8$ alkenyl; —C(O)—$R_n$; —C(O)O—$R_b$; —C(O)—NH—$R_b$; $C_1$ to $C_8$ alkyl optionally substituted with one or more substituents independently selected from the group consisting of hydroxyl, halogen, $C_1$ to $C_4$ alkoxy, ($C_1$ to $C_4$)alkyl-O—($C_1$ to $C_4$)alkyl-O—, amino, alkylamino, dialkylamino, acetamide, —C(O)—$R_b$, —C(O)O—$R_b$, aryl, morpholinyl, thiomorpholinyl, pyrrolidinyl, piperidinyl, piperazinyl, 1,3-dioxolan-2-one, oxiranyl, tetrahydrofuranyl, tetrahydropyranyl, 1,2,3-triazole, 1,2,4-triazole, furan, imidazole, isoxazole, isothiazole, oxazole, pyrazole, thiazole, thiophene and tetrazole;

wherein amino is optionally substituted with $C_1$ to $C_4$ alkoxycarbonyl, imidazole, isothiazole, pyrazole, pyridine, pyrazine, pyrimidine, pyrrole, thiazole or sulfonyl substituted with $C_1$ to $C_6$ alkyl, wherein pyridine and thiazole are each optionally substituted with $C_1$ to $C_4$ alkyl;

wherein alkylamino and dialkylamino are each optionally substituted on alkyl with hydroxyl, $C_1$ to $C_4$ alkoxy, imidazole, pyrazole, pyrrole or tetrazole; and, wherein morpholinyl, thiomorpholinyl, pyrrolidinyl, piperidinyl, piperazinyl and oxiranyl are each optionally substituted with —C(O)—$R_n$, —C(O)O—$R_n$ or $C_1$ to $C_4$ alkyl, wherein $C_1$ to $C_4$ alkyl is optionally substituted with hydroxyl;

$R_b$ is hydroxyl; amino; alkylamino, optionally substituted on alkyl with hydroxyl, amino, alkyl amino or $C_1$ to $C_4$ alkoxy; $C_1$ to $C_4$ alkoxy; $C_2$ to $C_8$ alkenyl; $C_2$ to $C_8$ alkynyl; aryl optionally substituted with one or more substituents independently selected from the group consisting of halogen and $C_1$ to $C_4$ alkoxy; furan; or $C_1$ to $C_8$ alkyl optionally substituted with one or more substituents independently selected from the group consisting of $C_1$ to $C_4$ alkoxy, aryl, amino, morpholinyl, piperidinyl and piperazinyl;

$R_d$ is aryl optionally substituted with one or more substituents independently selected from the group consisting of halogen, nitro, $C_1$ to $C_6$ alkyl, —C(O)O—$R_e$, and —O$R_e$;

$R_e$ is hydrogen; $C_1$ to $C_6$ alkyl optionally substituted with one or more substituents independently selected from the group consisting of halogen and alkoxy; or phenyl, wherein phenyl is optionally substituted with one or more substituents independently selected from the group consisting of halogen and alkoxy; and $R_n$ is hydroxyl, $C_1$ to $C_4$ alkoxy, amino or $C_1$ to $C_6$ alkyl;

wherein administering the compound to the human produces at least two of the results selected from the group consisting of:

(i) decrease in the number of circulating tumor cells in the blood;
(ii) increase in survival of the human;
(iii) regression of the prostate cancer or benign prostatic hyperplasia;
(iv) reduction in growth of the prostate cancer or benign prostatic hyperplasia;
(v) inhibition or decrease in prostate-specific antigen levels in the range of about 30% to 100% relative to the prostate-specific antigen level prior to administration of the compound;
(vi) decrease in tumor or benign prostatic hyperplasia metabolism or perfusion;
(vii) stabilization or decrease in tumor or benign prostatic hyperplasia blood flow or metabolism; and
(viii) stabilization or decrease in peritumoral or peri-benign prostatic hyperplasia inflammation or edema.

2. The method of claim 1, wherein the prostate cancer is castration-resistant prostate cancer.

3. The method of claim 1, wherein the effective amount is in a range of from about 0.001 mg per kg per day to about 1500 mg per kg per day.

4. The method of claim 1, wherein the compound is administered during or within about 30 minutes after a meal.

5. The method of claim 1, wherein the effective amount of the compound is administered two times per day at a time interval of from about 12 hours to about 18 hours between doses.

6. The method of claim 1, wherein the effective amount of the compound is administered two times per day at a time interval of about 12 hours between doses.

7. The method of claim 1, wherein the effective amount of the compound is administered three times per day at a time interval of from about 8 hours to about 12 hours between doses.

8. The method of claim 1, wherein the effective amount of the compound is administered three times per day at a time interval of about 8 hours between doses.

9. The method of claim 1, wherein the compound has the Formula (II):

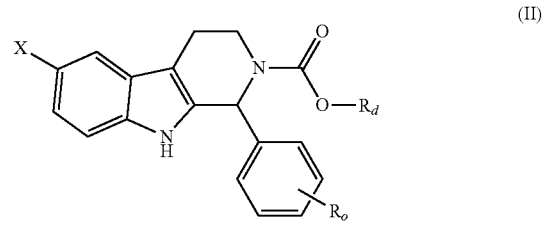

or a pharmaceutically acceptable salt, racemate or stereoisomer thereof, wherein, X is halogen;

$R_o$ is halogen; $C_1$ to $C_8$ alkyl optionally substituted with one or more substituents independently selected from the group consisting of hydroxyl, halogen and amino; or —$OR_a$;

$R_a$ is hydrogen, $C_1$ to $C_8$ alkyl optionally substituted with one or more substituents independently selected from the group consisting of hydroxyl and halogen; and $R_d$ is phenyl optionally substituted with one or more —$O(C_1$ to $C_6$ alkyl) or halogen substituents.

10. The method of claim 1, wherein the compound has the Formula (II):

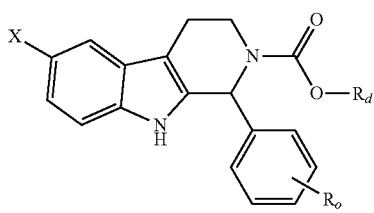

(II)

or a pharmaceutically acceptable salt, racemate or stereoisomer thereof, wherein, X is halogen;

$R_o$ is halogen; $C_1$ to $C_8$ alkyl optionally substituted with one or more substituents independently selected from the group consisting of hydroxyl, halogen and amino; or —$OR_a$;

$R_a$ is hydrogen, or $C_1$ to $C_8$ alkyl optionally substituted with one or more substituents independently selected from the group consisting of hydroxyl and halogen; and $R_d$ is phenyl optionally substituted with one or more halogen substituents.

11. The method of claim 1, wherein the compound has the Formula (III):

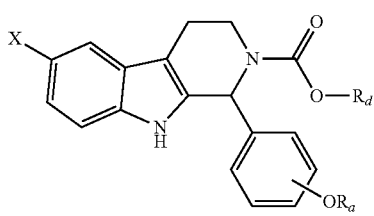

(III)

or a pharmaceutically acceptable salt, racemate or stereoisomer thereof, wherein, X is halogen;

$R_a$ is hydrogen, $C_1$ to $C_8$ alkyl optionally substituted with one or more substituents independently selected from the group consisting of hydroxyl and halogen; and $R_d$ is phenyl substituted with one or more halogen substituents.

12. The method of claim 1, wherein the compound has the Formula (IV):

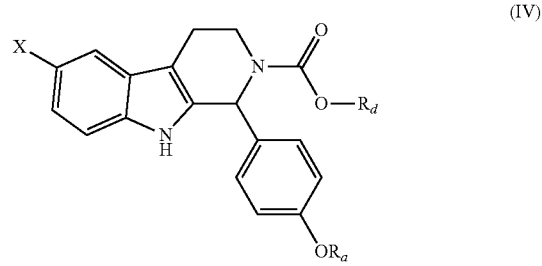

(IV)

or a pharmaceutically acceptable salt, racemate or stereoisomer thereof, wherein, X is halogen;

$R_a$ is hydrogen, $C_1$ to $C_8$ alkyl optionally substituted with one or more substituents independently selected from the group consisting of hydroxyl and halogen; and $R_d$ is phenyl substituted with one or more halogen substituents.

13. The method of claim 1, wherein the compound has the Formula (IV):

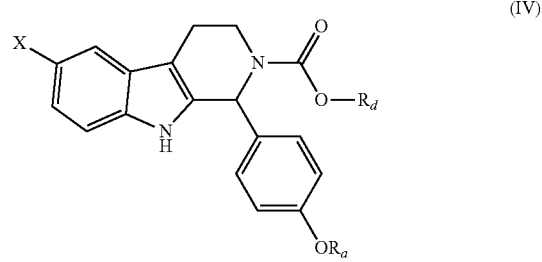

(IV)

or a pharmaceutically acceptable salt, racemate or stereoisomer thereof, wherein, X is halogen;

$R_a$ is hydrogen, $C_1$ to $C_8$ alkyl optionally substituted with one or more substituents independently selected from the group consisting of hydroxyl and halogen; and $R_d$ is phenyl substituted on a para position with a halogen substituent.

14. A method for treating a prostate cancer or benign prostatic hyperplasia, comprising administering to a human having the prostate cancer or benign prostatic hyperplasia an effective amount of a compound selected from the group consisting of:

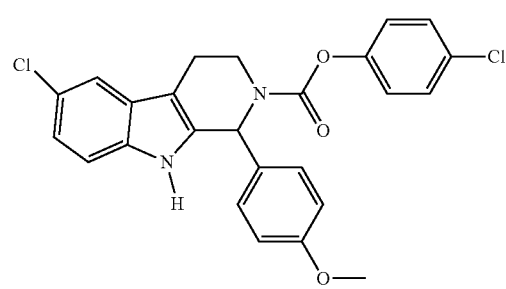

10

271
-continued
10
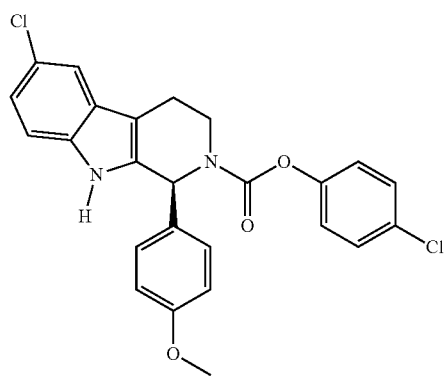
17
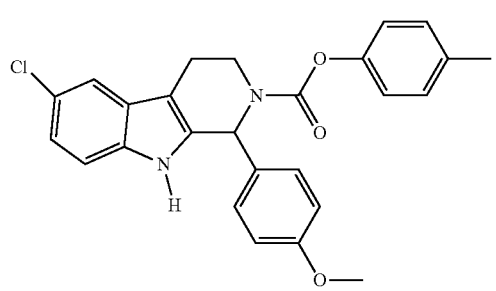
60
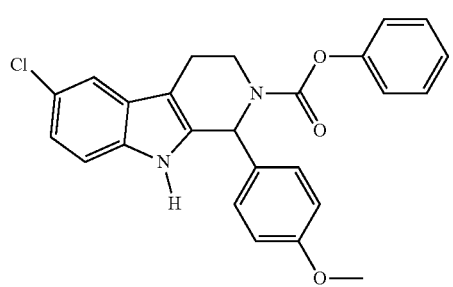
76
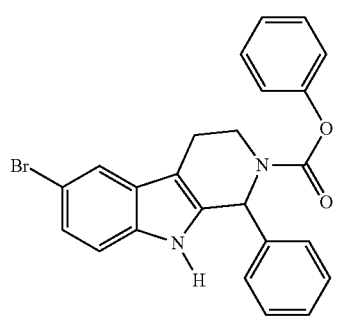
121
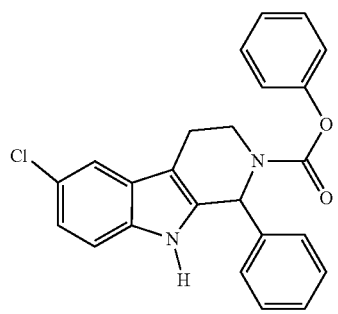
272
-continued
331
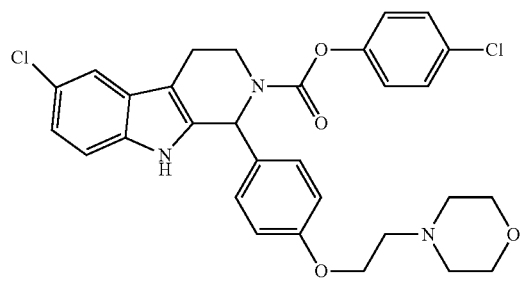
332
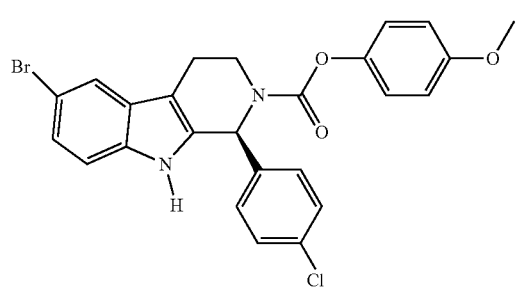
341
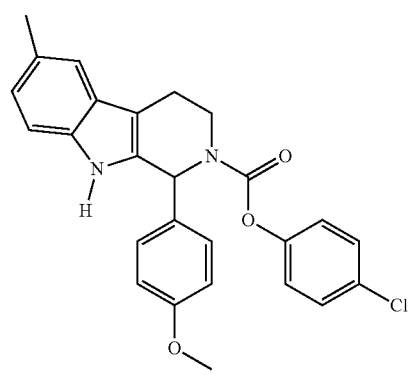
344
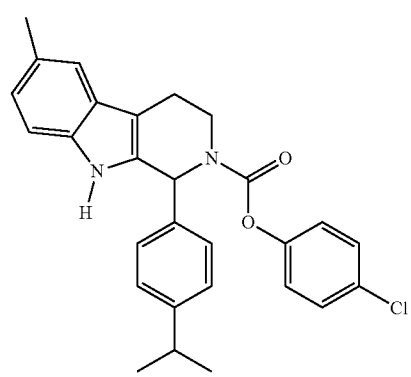

273
-continued
346
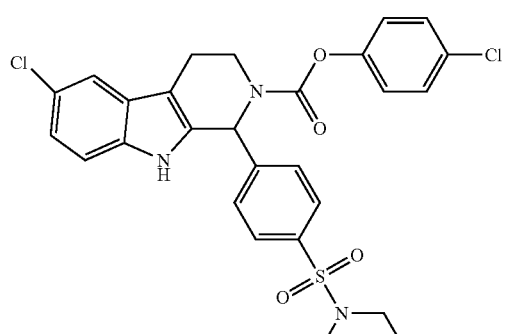
347
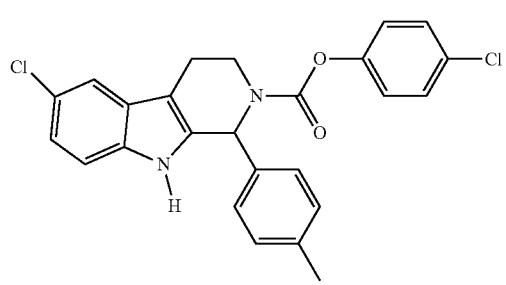
348
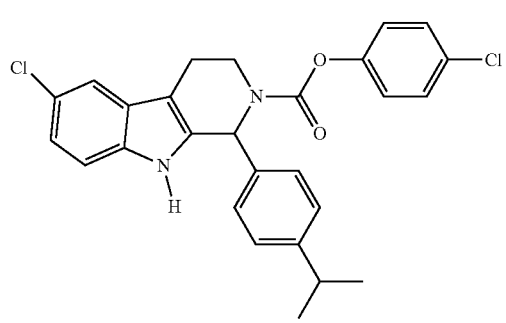
350
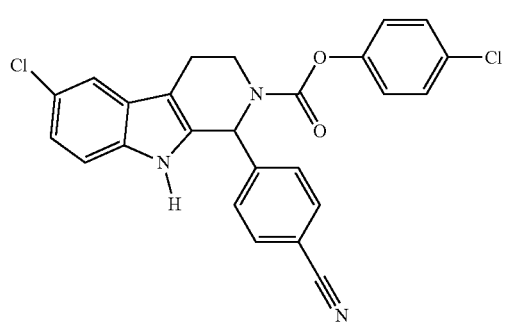
274
-continued
351
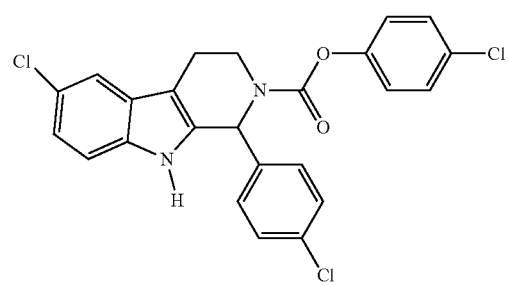
353
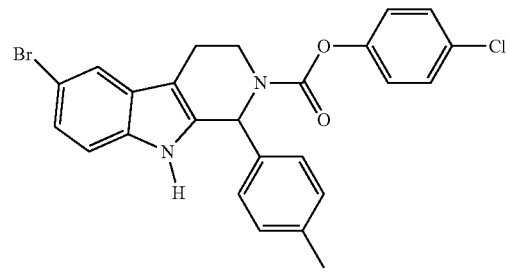
354
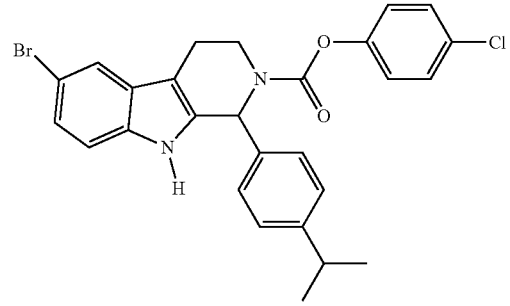
355
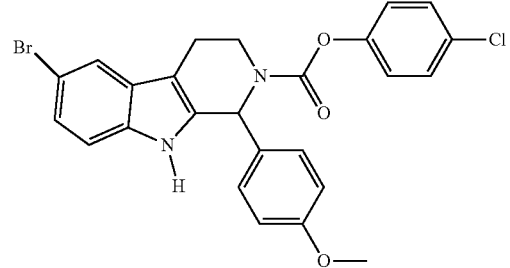
359
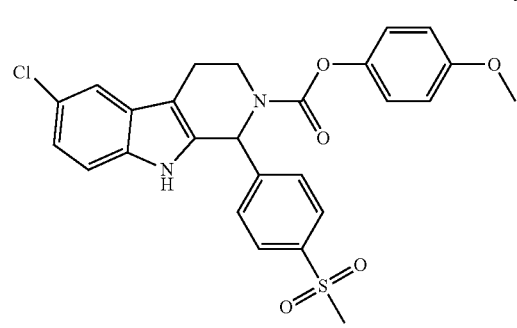

275
-continued
360
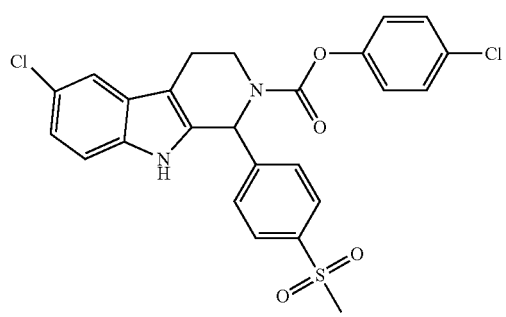
366
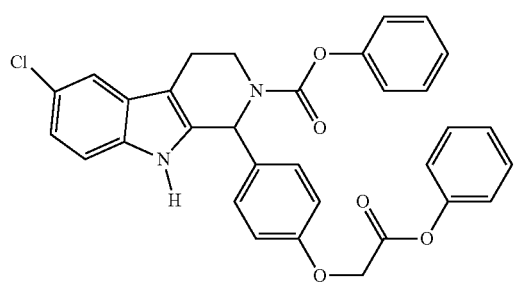
388
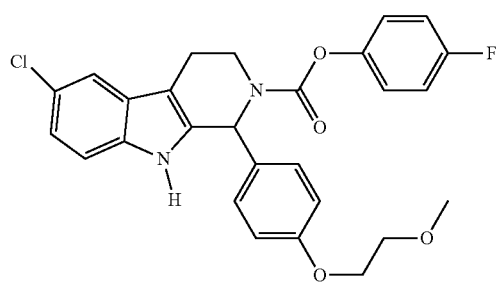
391
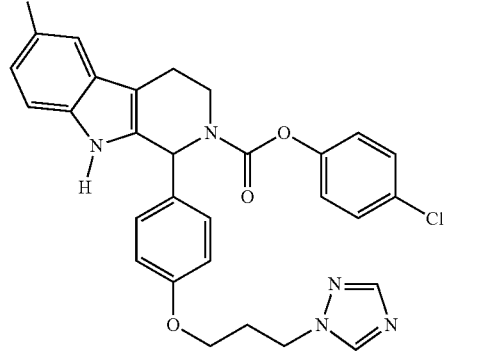
395
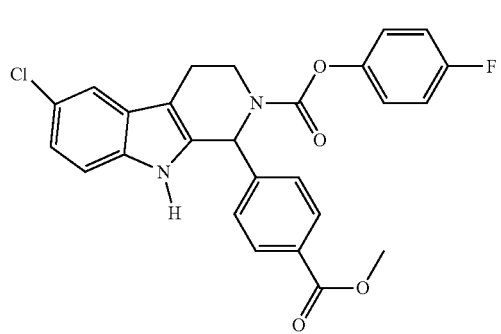
276
-continued
397
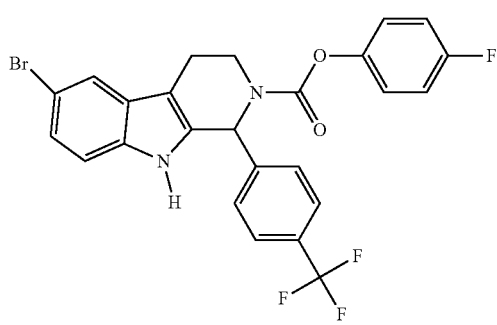
398
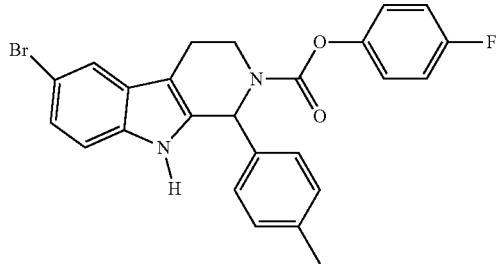
400
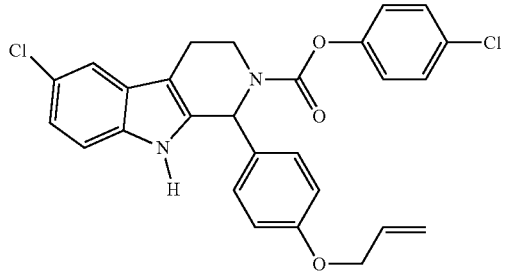
401
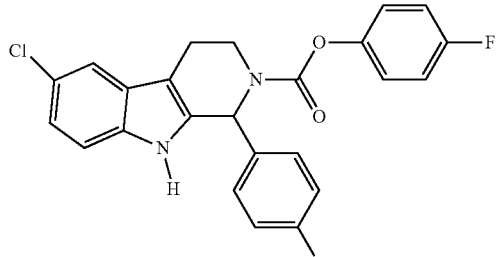
403
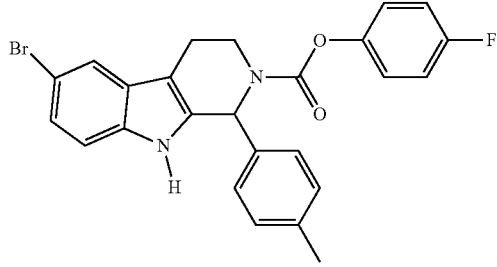

-continued
405
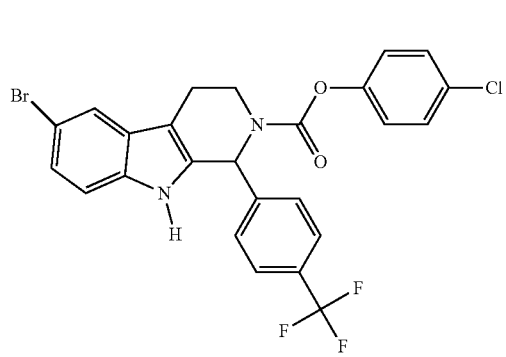
409
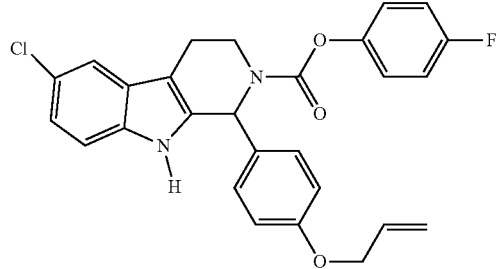
410
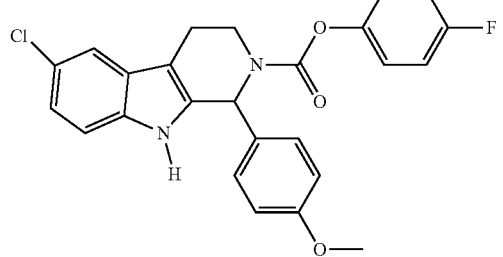
413
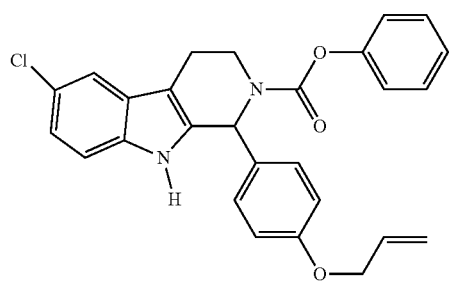
-continued
415
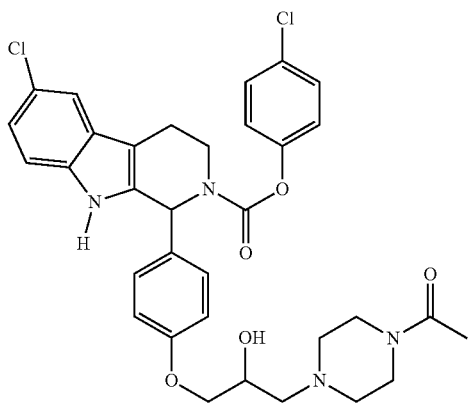
417
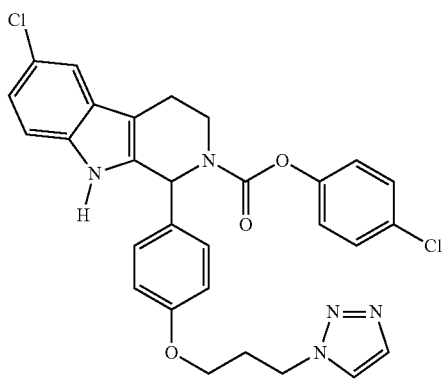
418
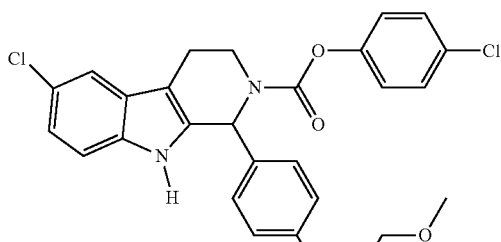
421
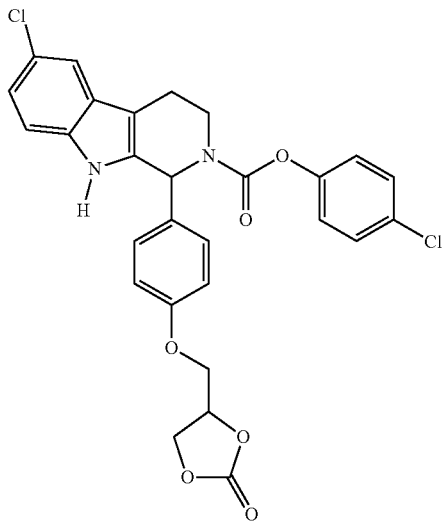

279
-continued
422
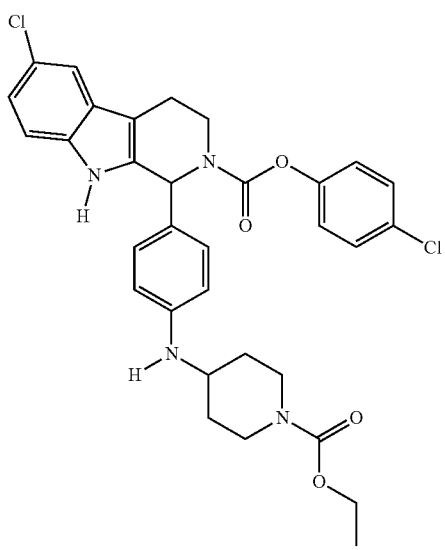
426
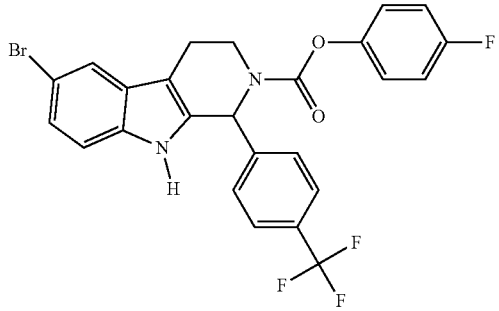
427
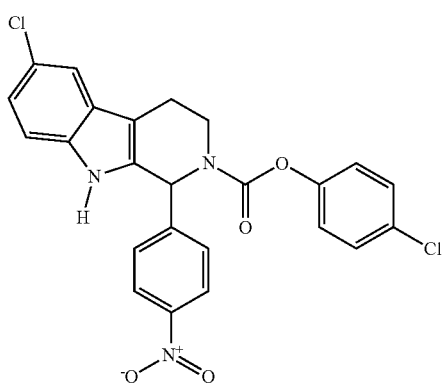
428
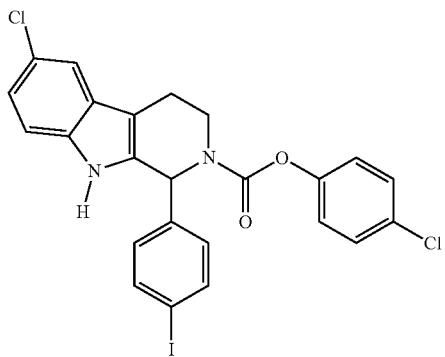
280
-continued
429
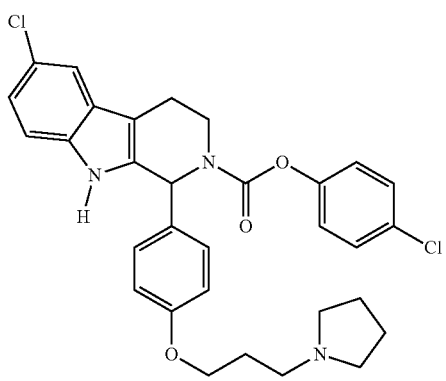
432
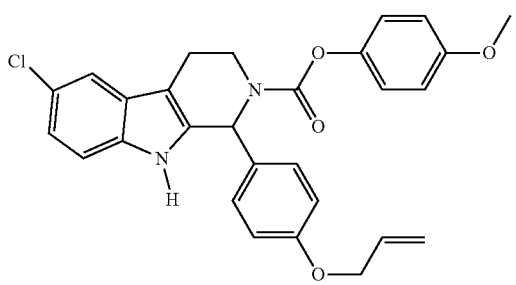
433
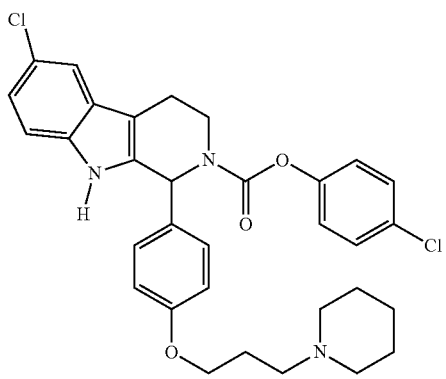
436
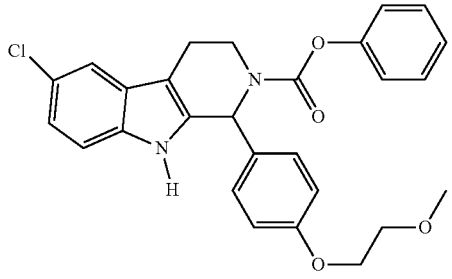

437
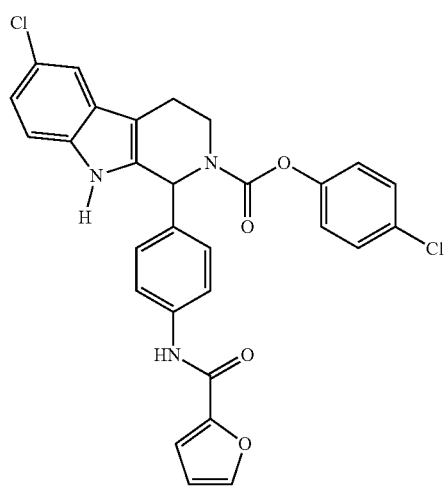
440
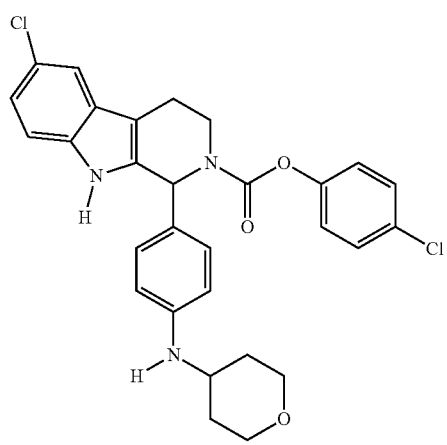
444
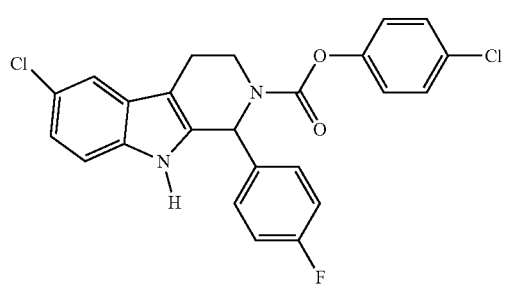
446
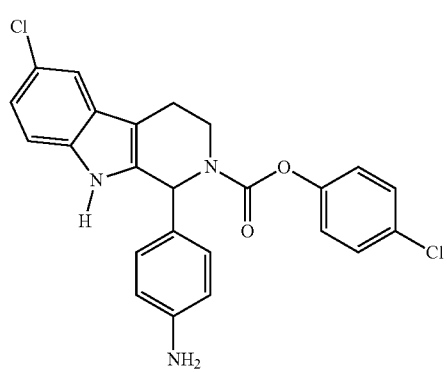
448
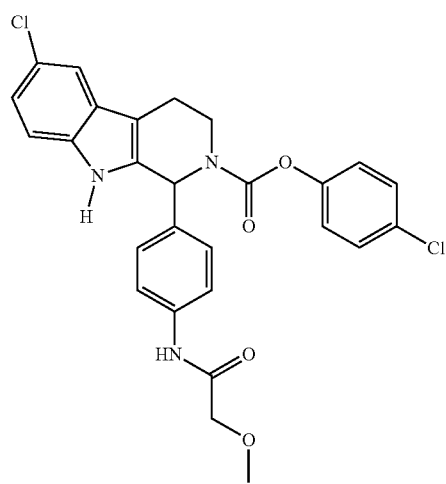
450
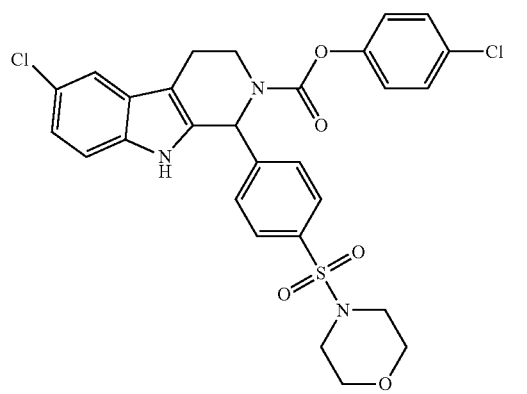
452
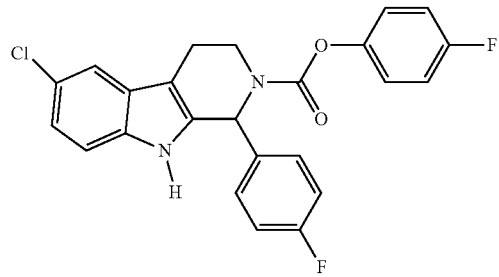

283
-continued
454
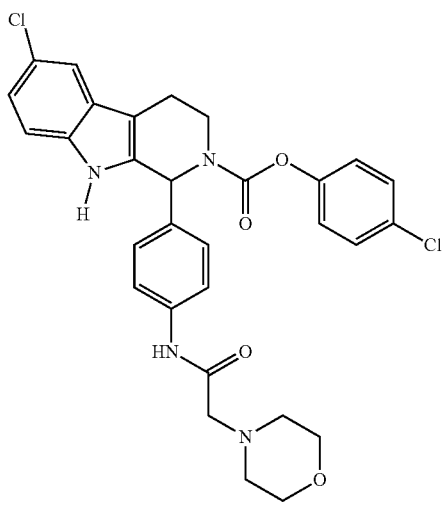
455
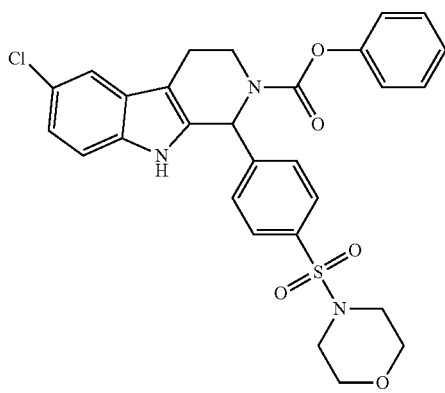
460
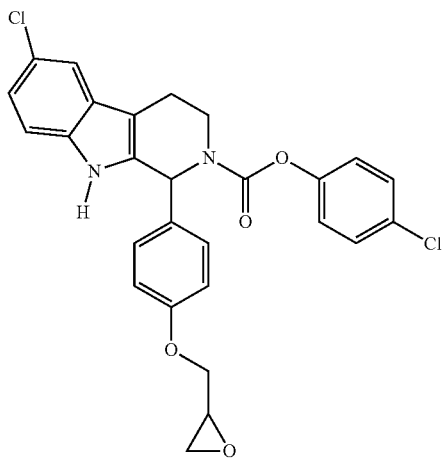
284
-continued
462
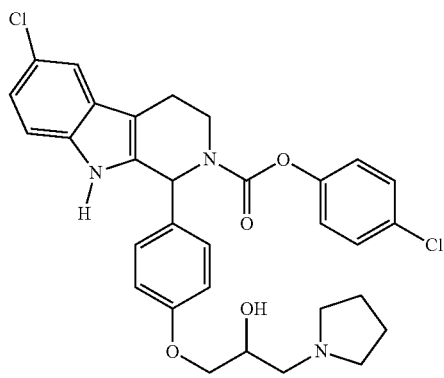
463
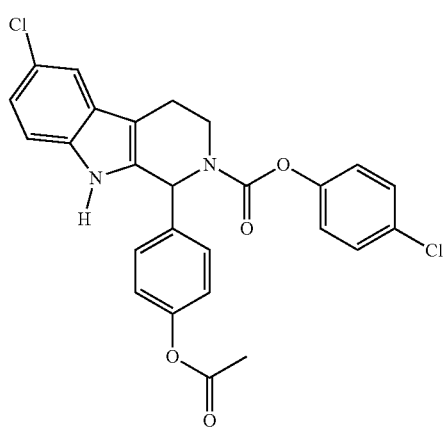
465
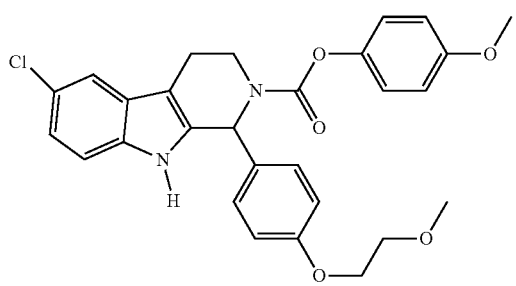
467
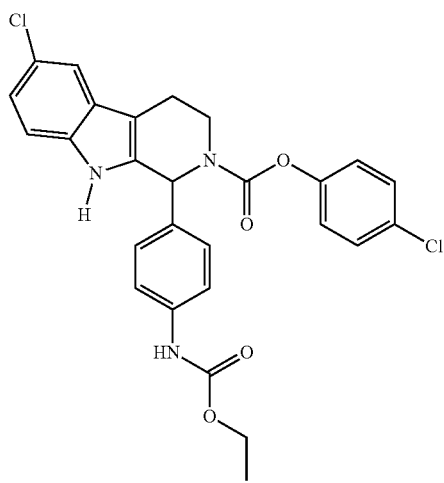

285
-continued
468
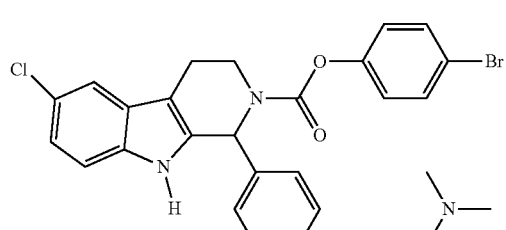
470
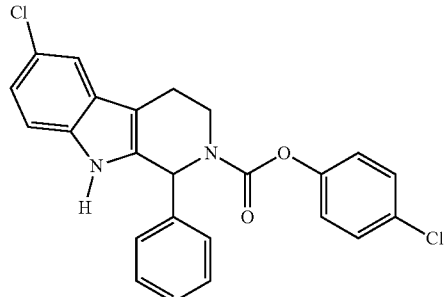
471
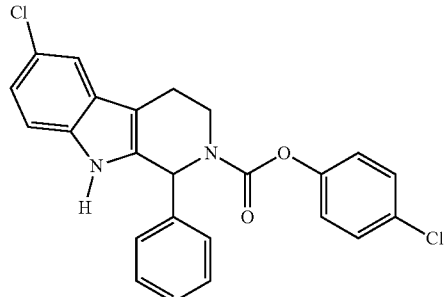
479
286
-continued
482
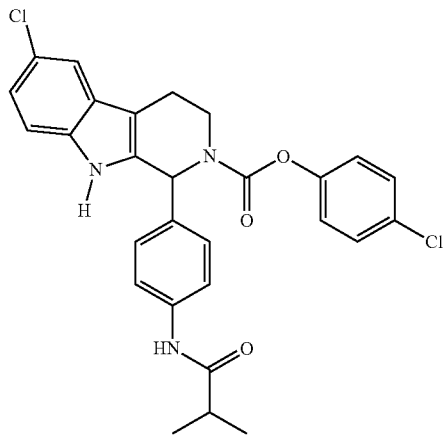
489
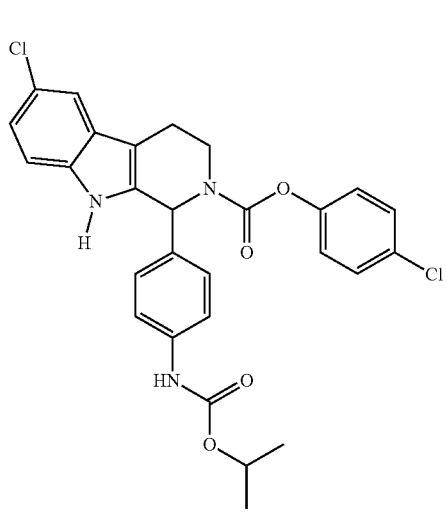
491
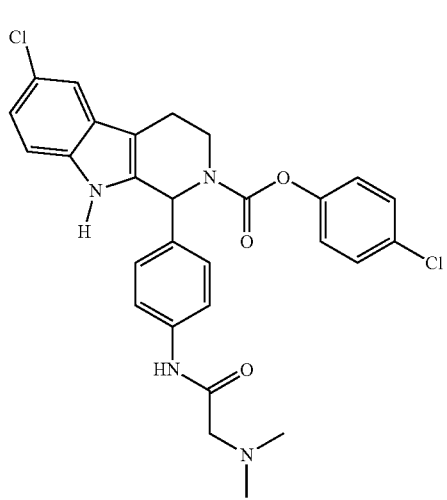

287
-continued
493
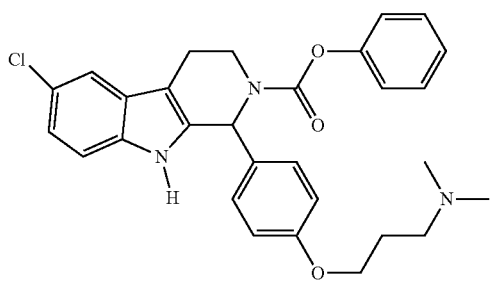
500
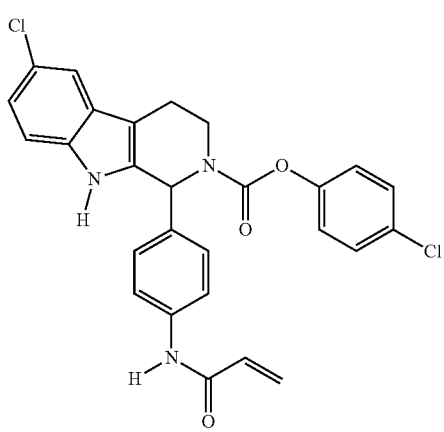
501
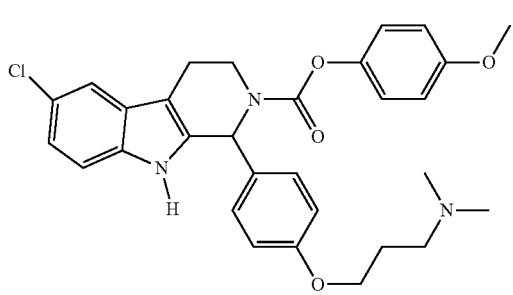
502
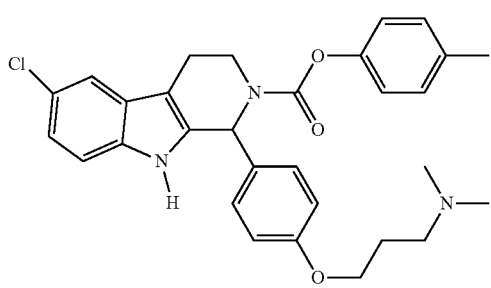
288
-continued
519
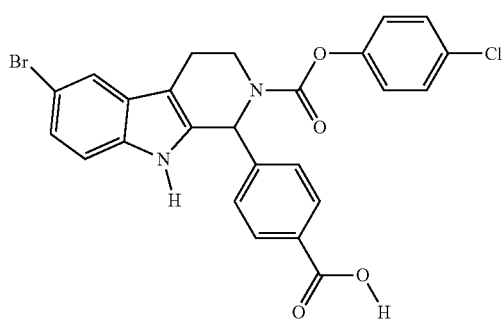
544
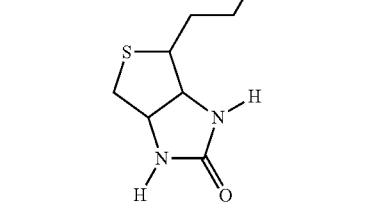
570
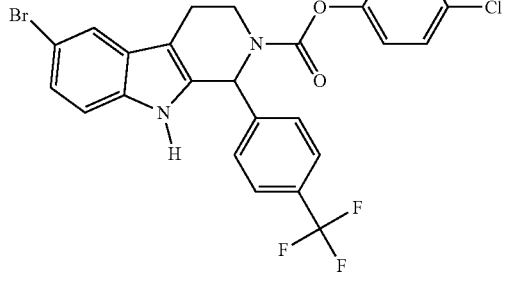

289
-continued
571
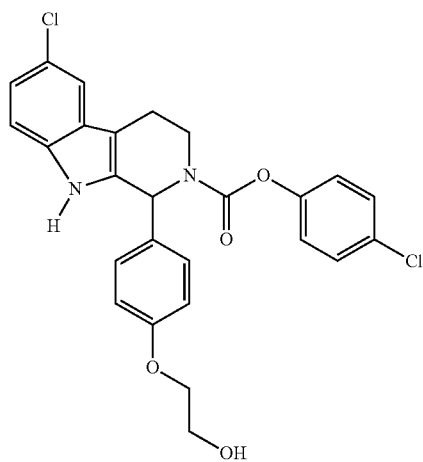
572
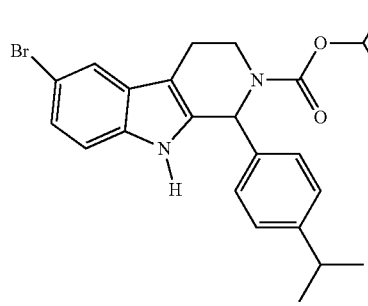
575
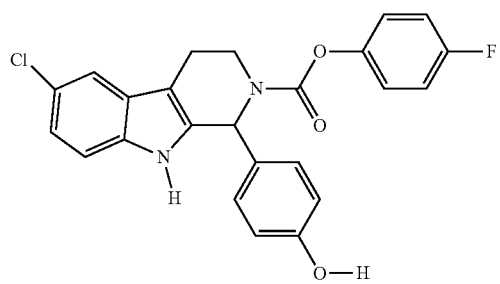
576
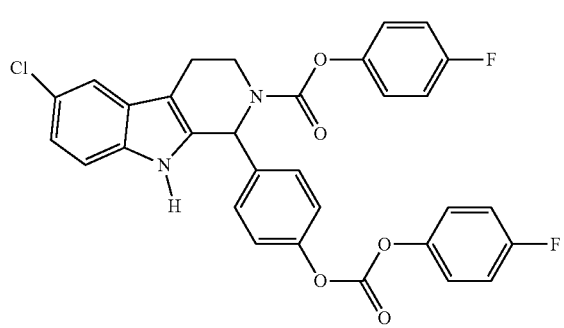
290
-continued
577
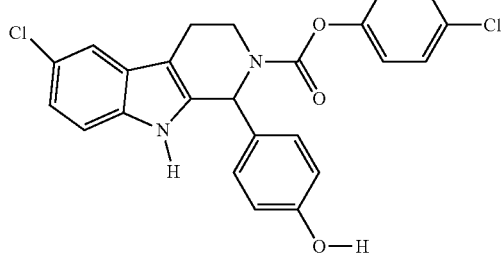
578
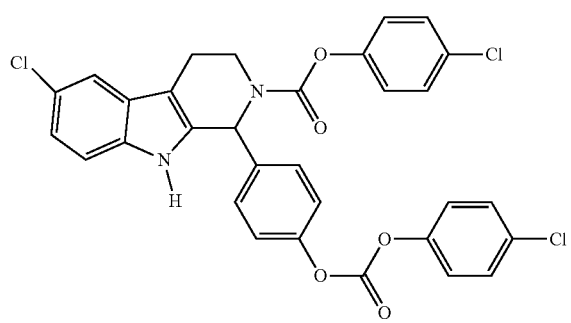
579
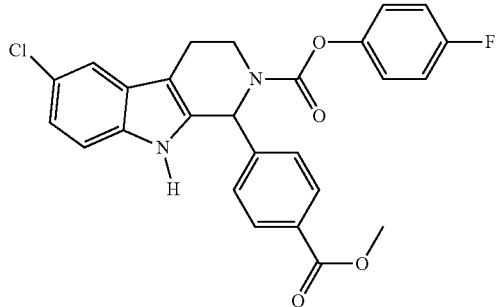
580
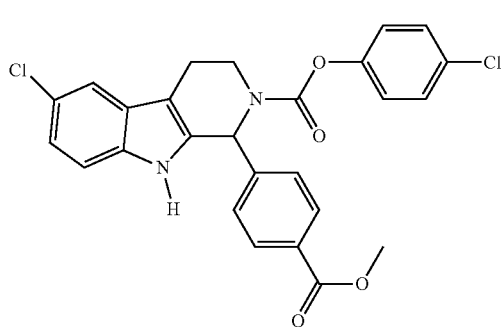
581
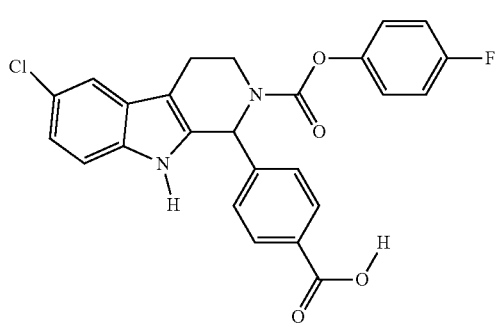

587 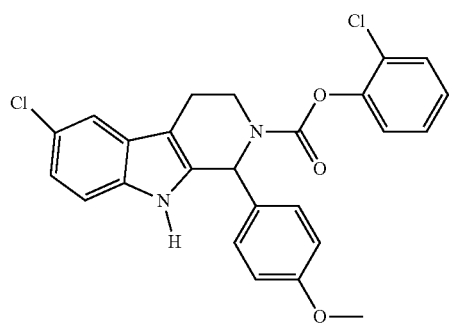
588 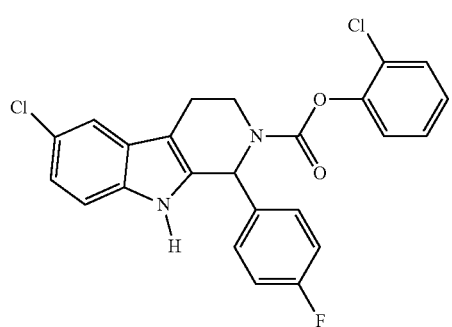
591 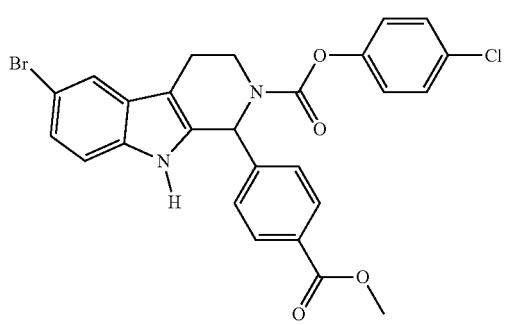
592 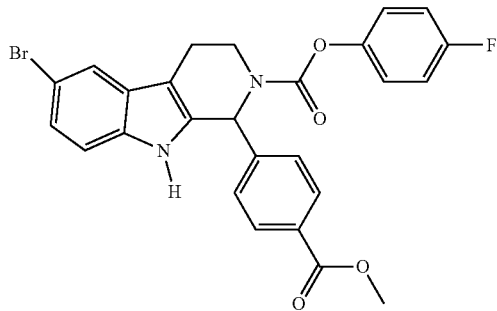
589 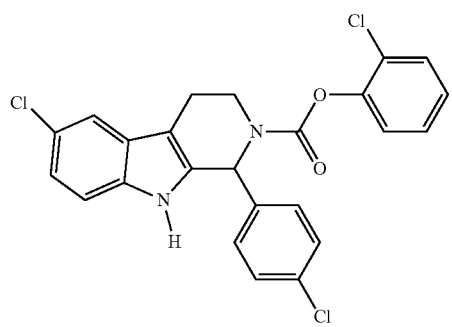
593 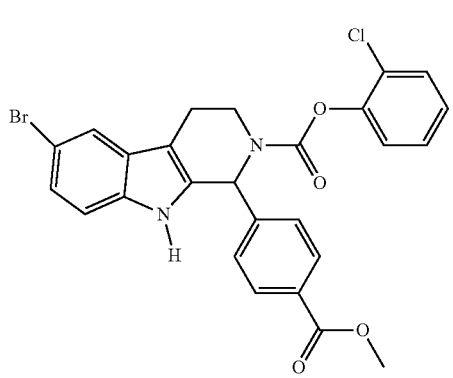
590 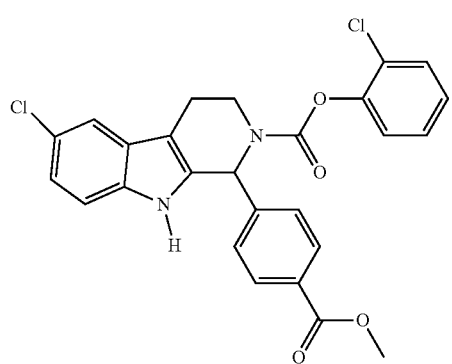
594 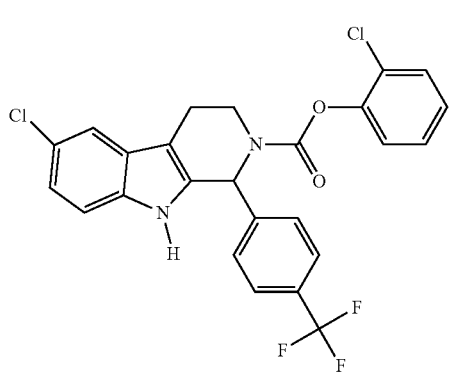

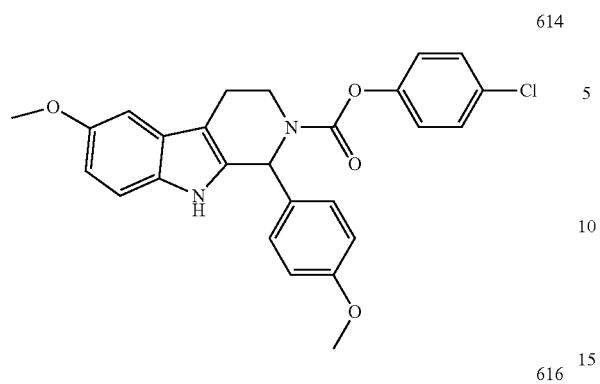
614
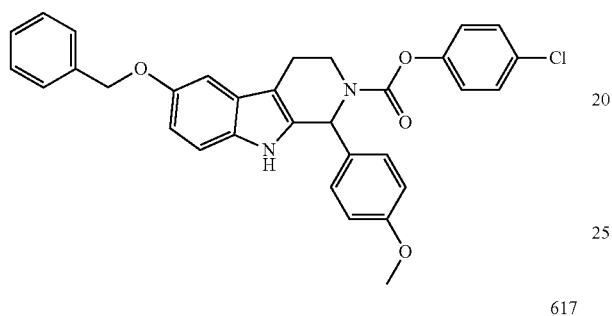
616
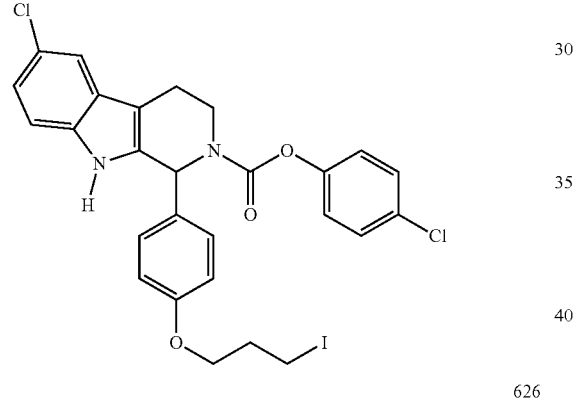
617
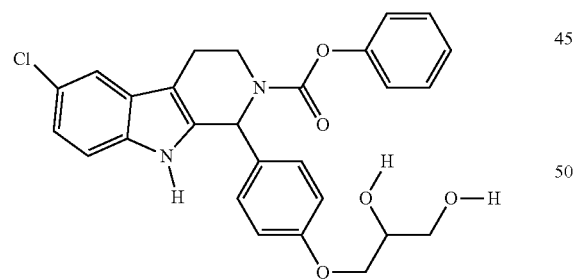
626
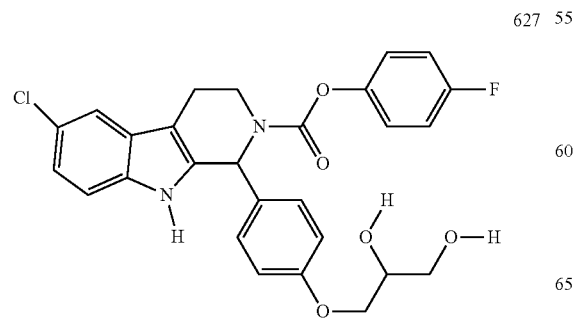
627
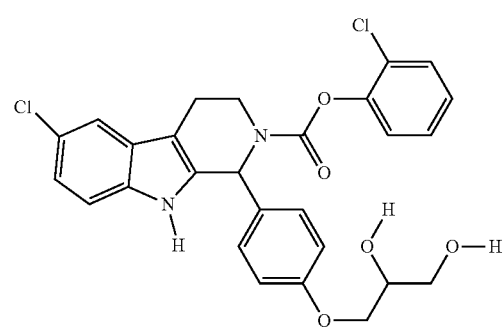
628
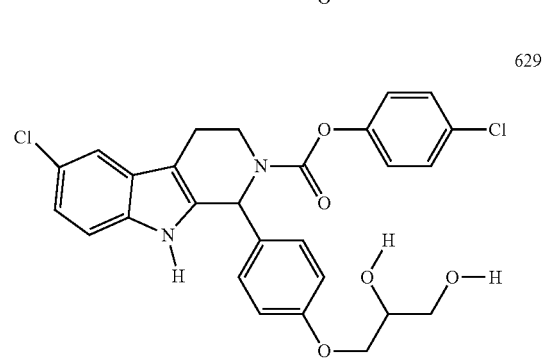
629
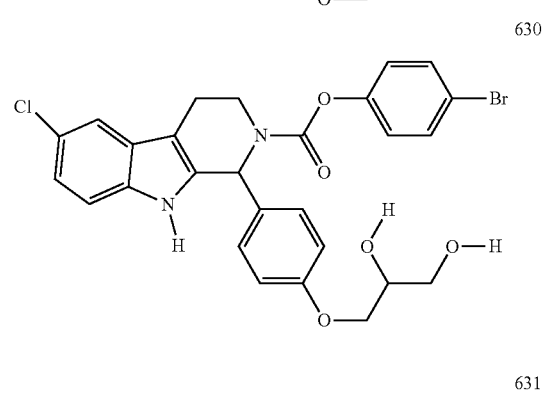
630
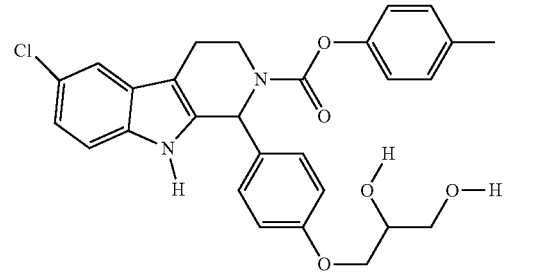
631
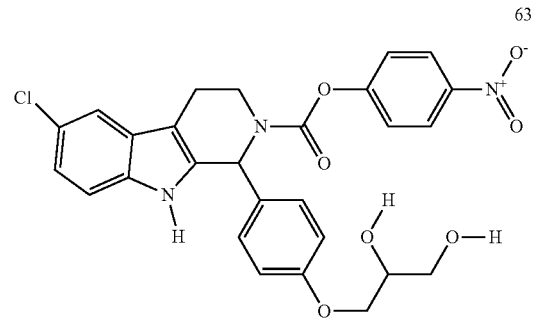
632

635
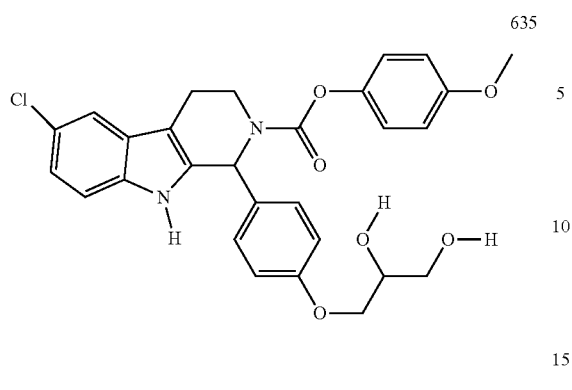
637
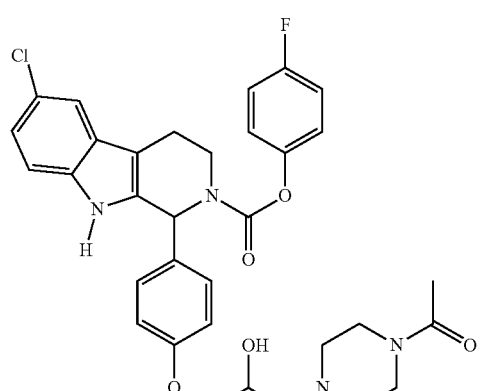
638
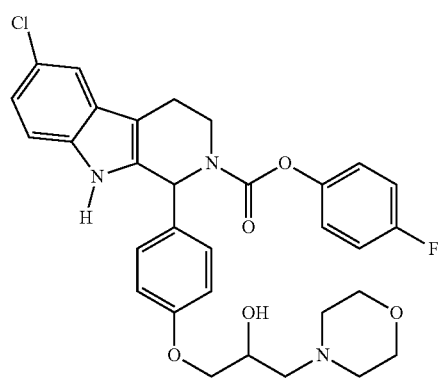
660
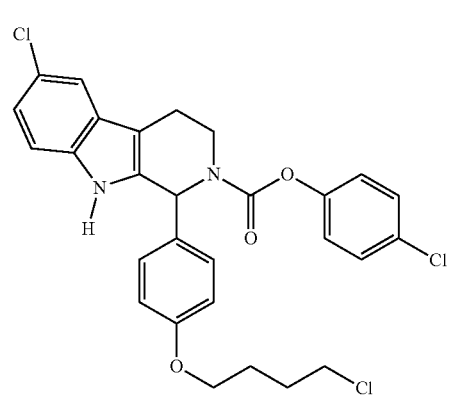
670
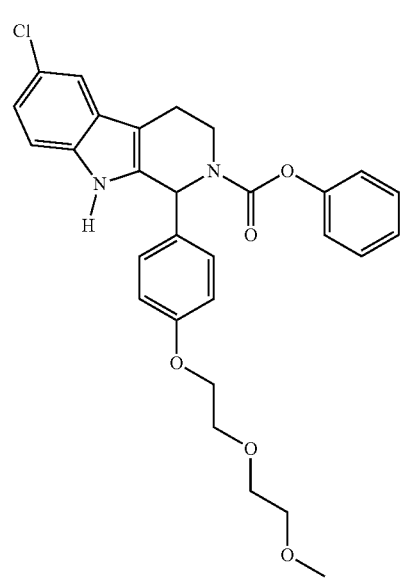
673
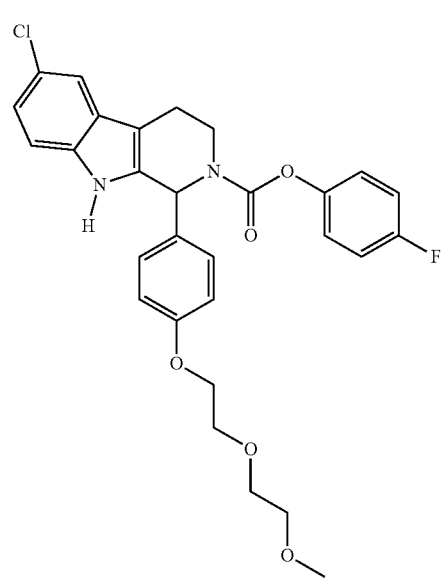

297
-continued
674
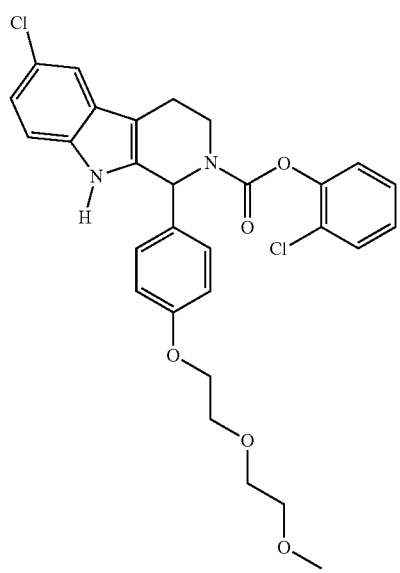
675
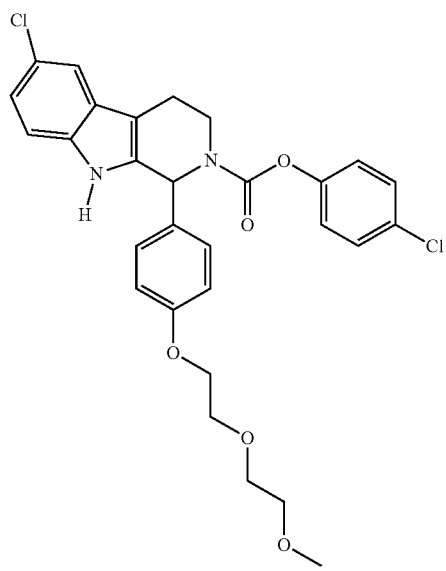
298
-continued
677
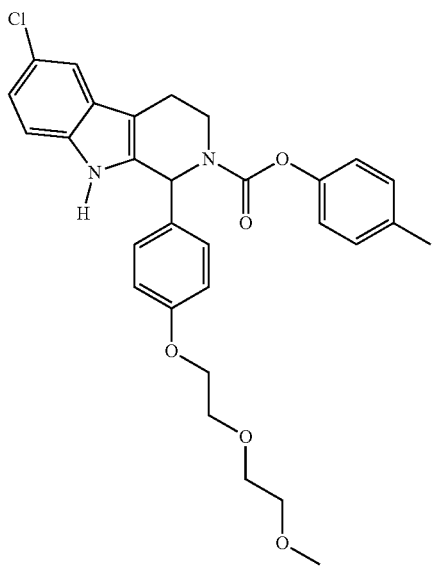
678
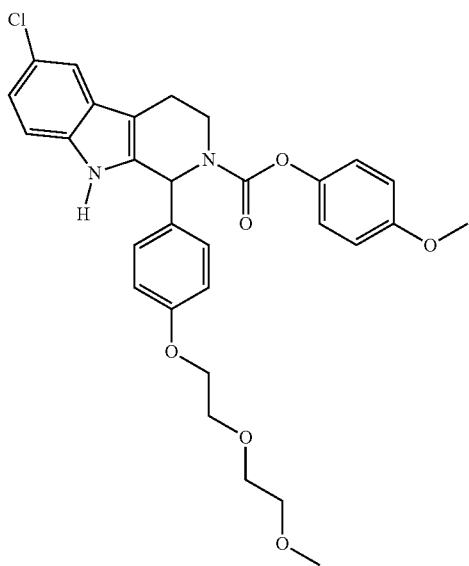

299
-continued
300
-continued
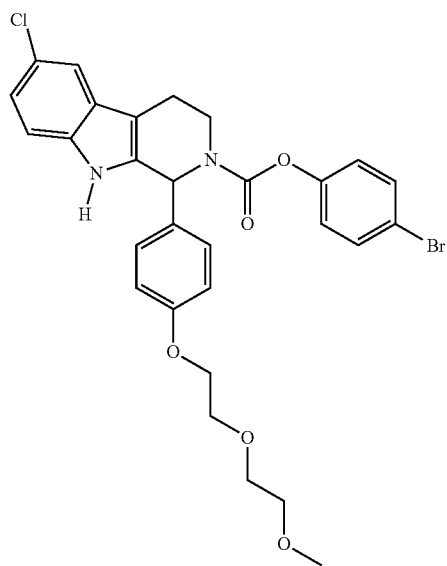
680
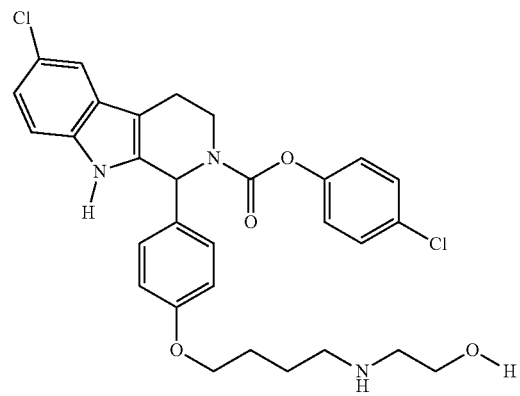
699
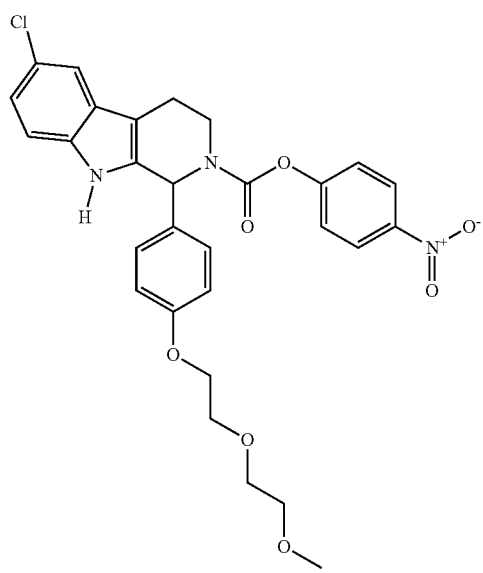
681
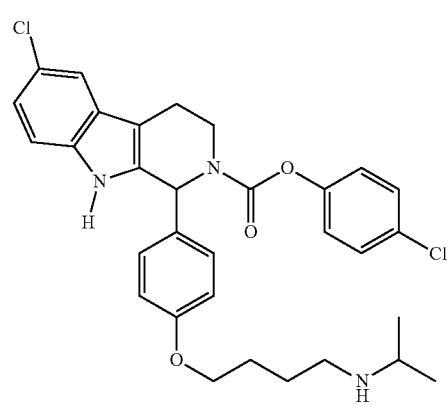
700
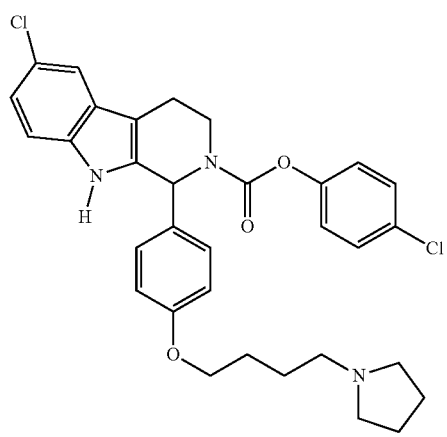
698
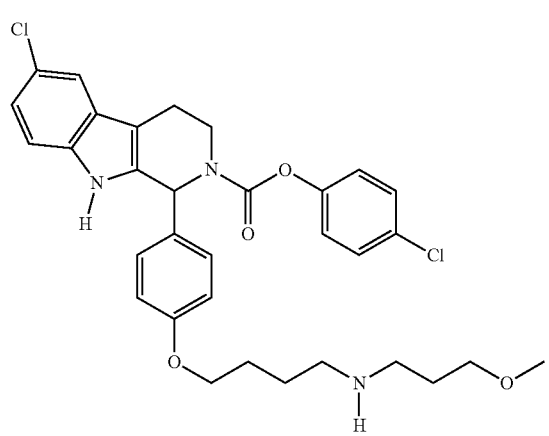
701

301
-continued
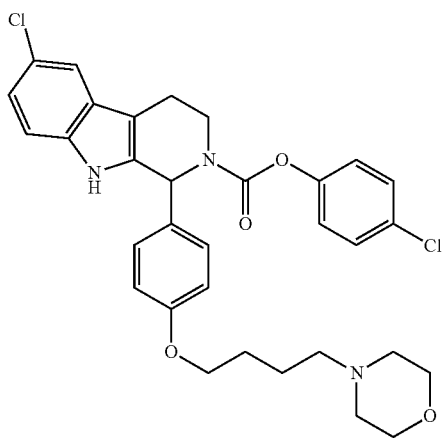
702
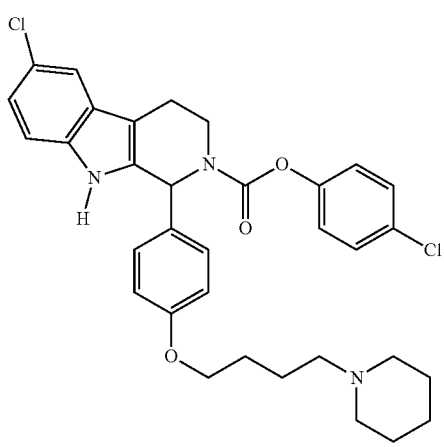
703
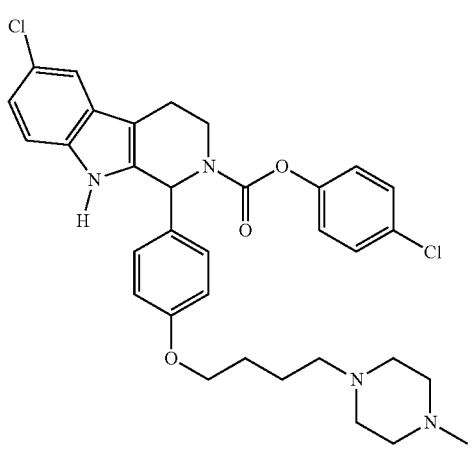
704
302
-continued
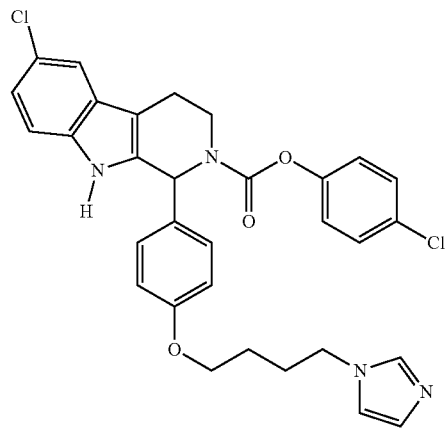
705
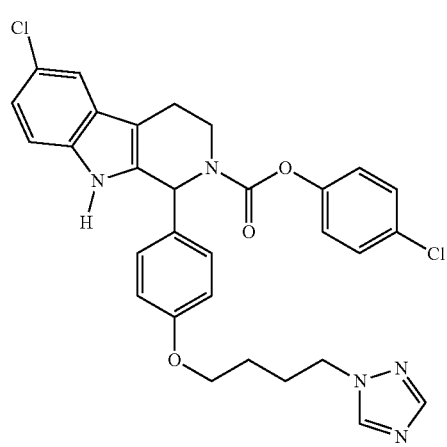
706
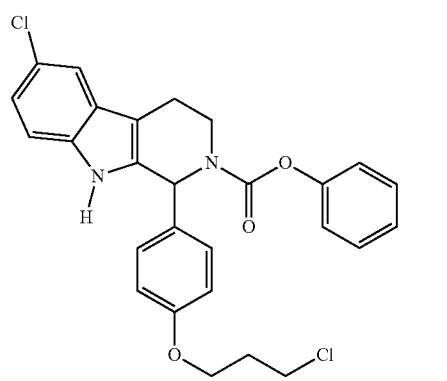
710
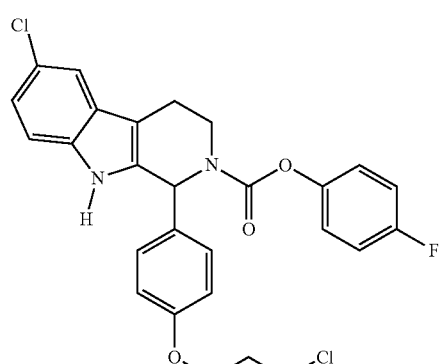
712

303
-continued
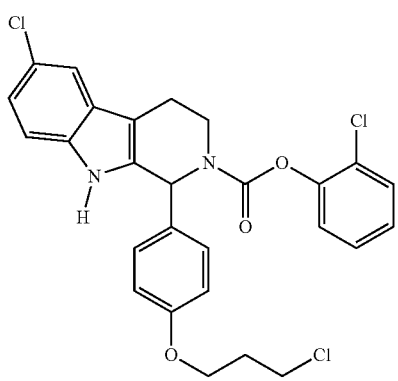
713
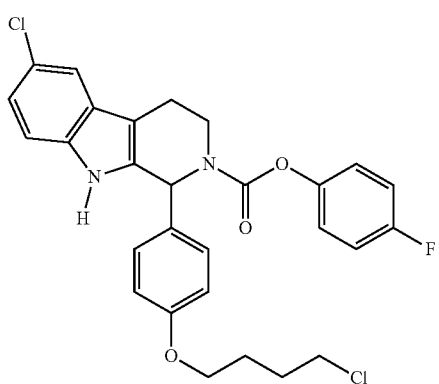
719
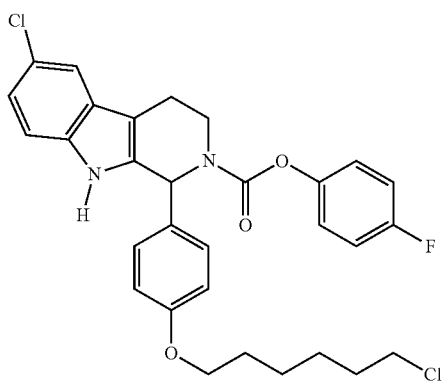
723
304
-continued
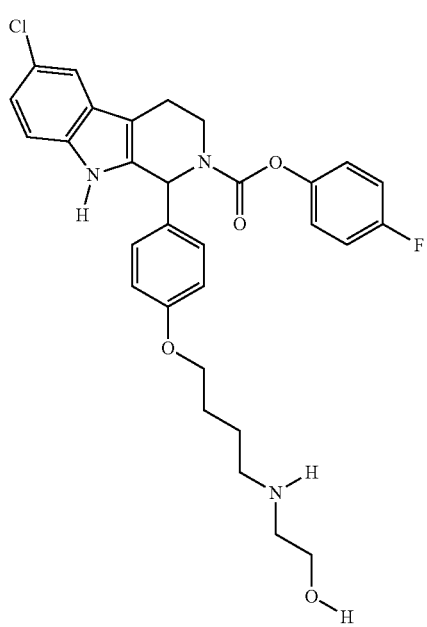
735
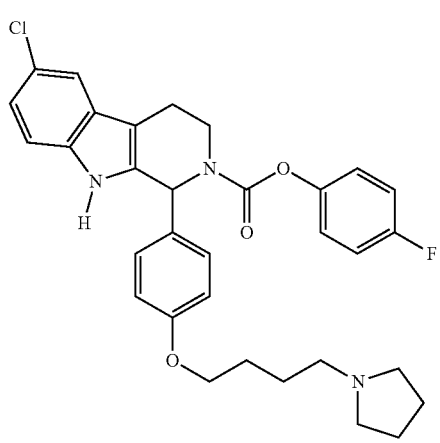
736
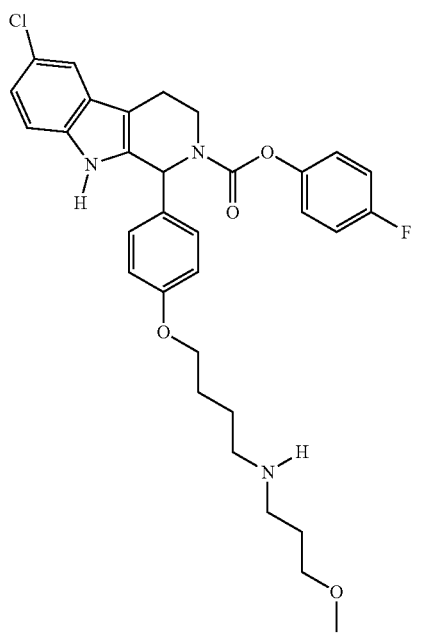
737

305
-continued
738
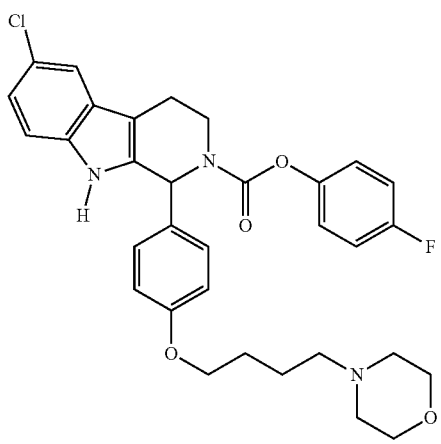
739
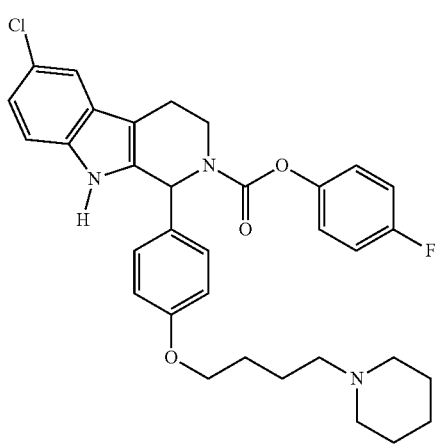
740
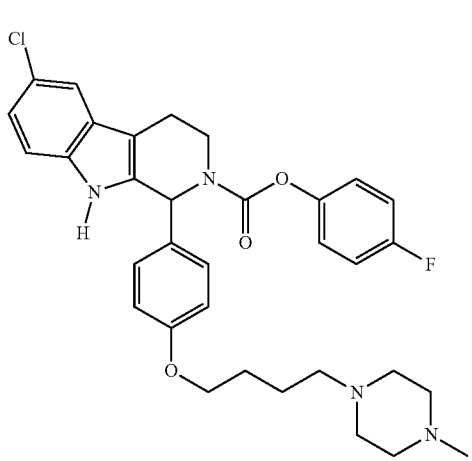
306
-continued
741
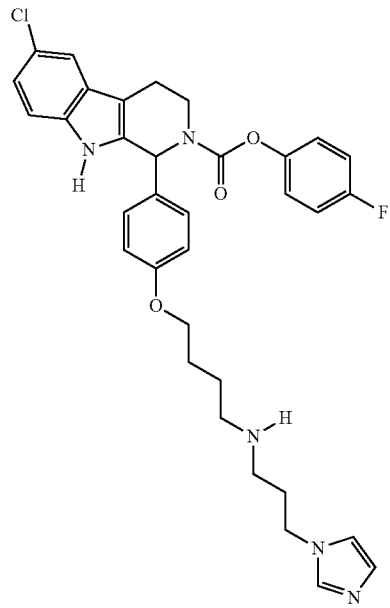
742
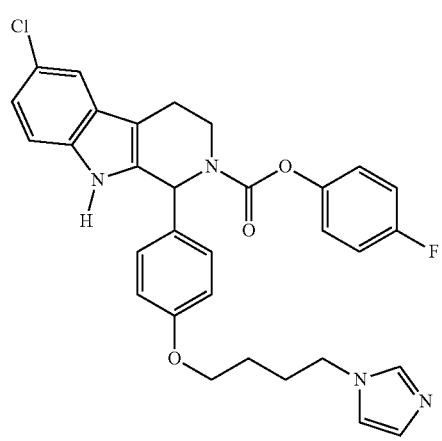
743

307
-continued
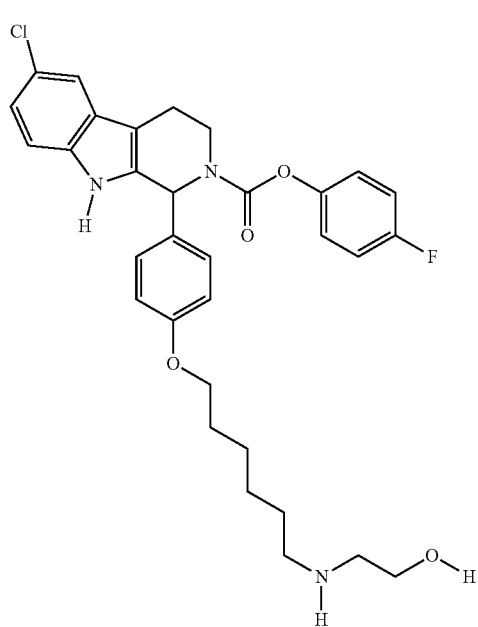
772
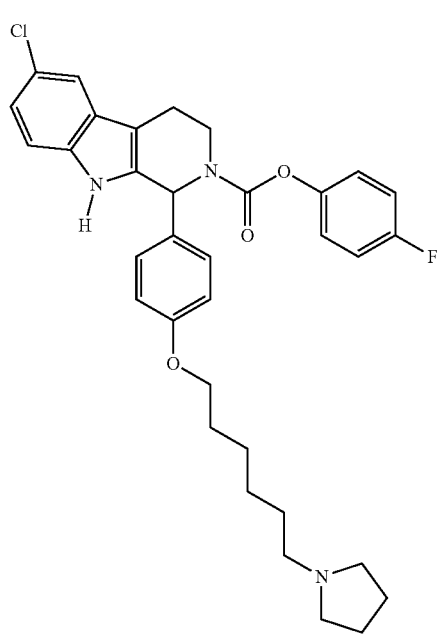
773
308
-continued
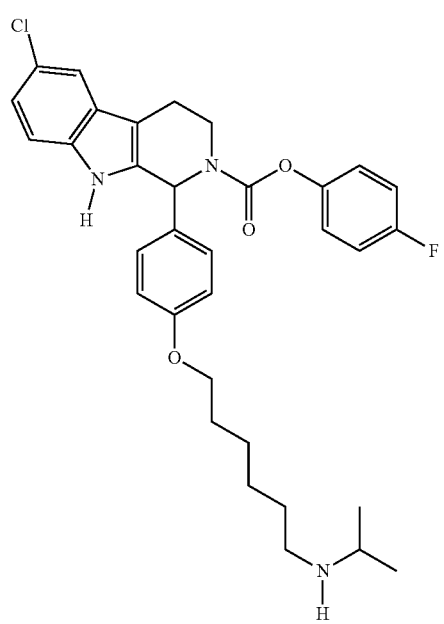
774
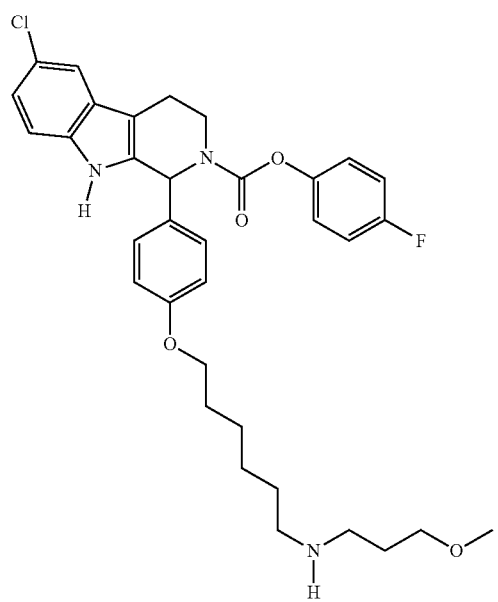
775

309
-continued
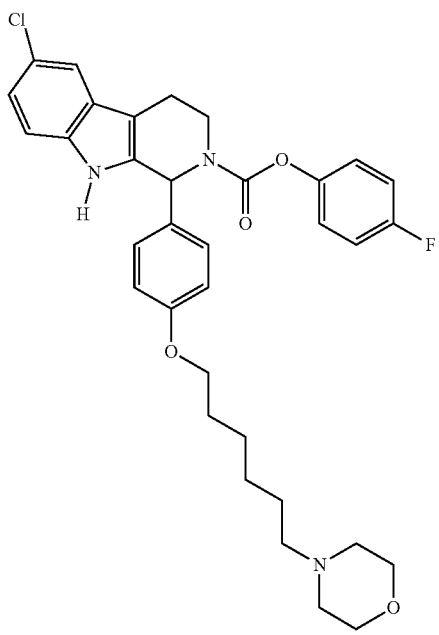
776
310
-continued
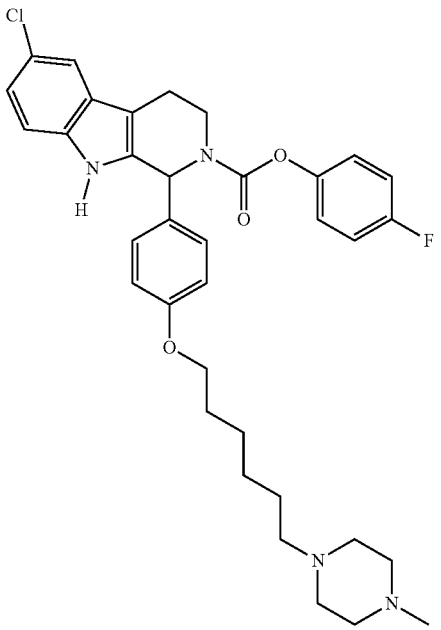
778
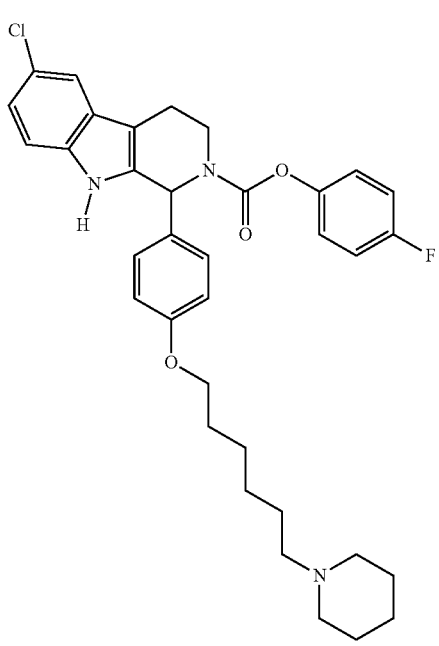
777
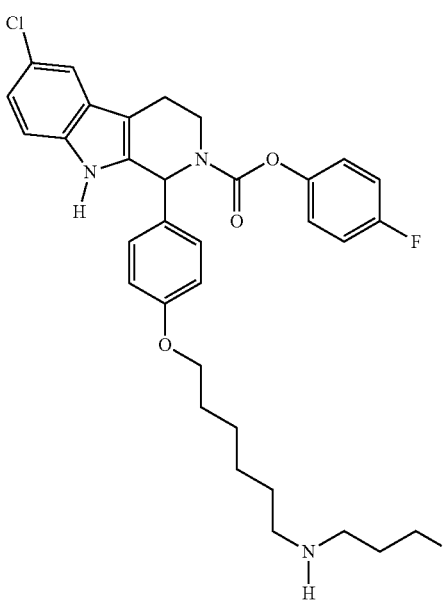
779

311
-continued
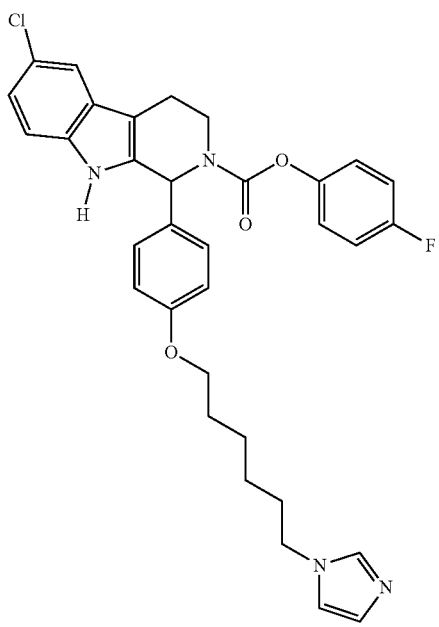
780
312
-continued
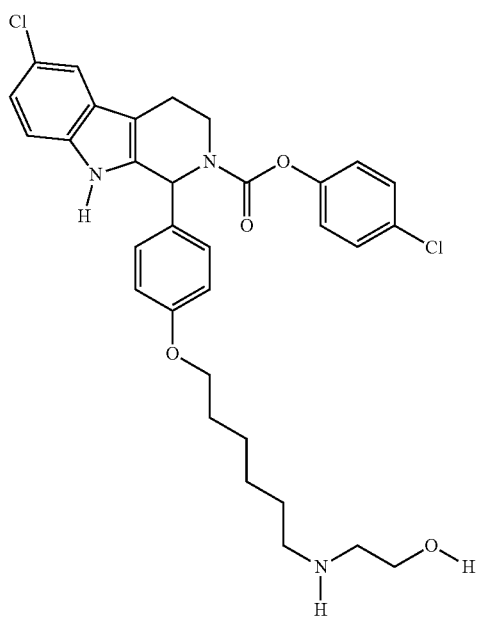
782
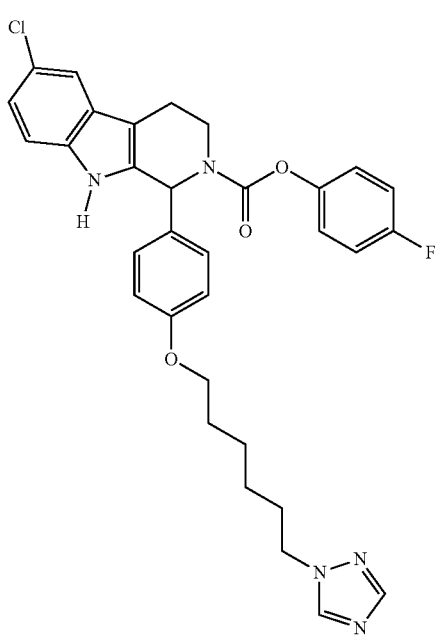
781
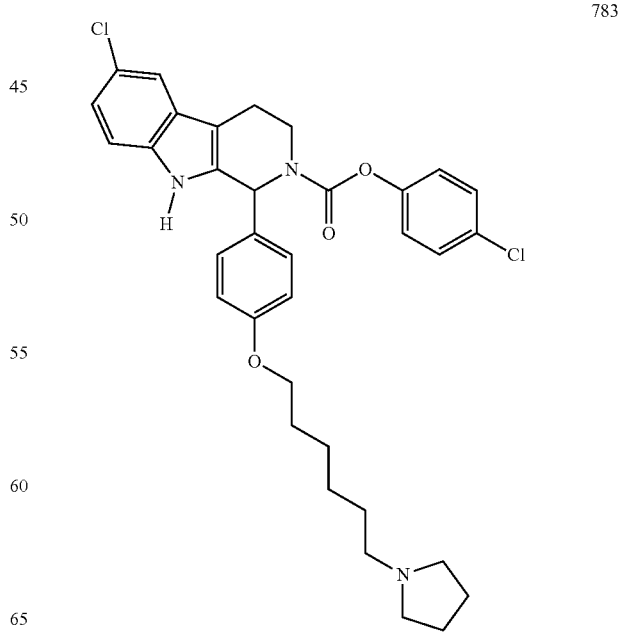
783

313
-continued
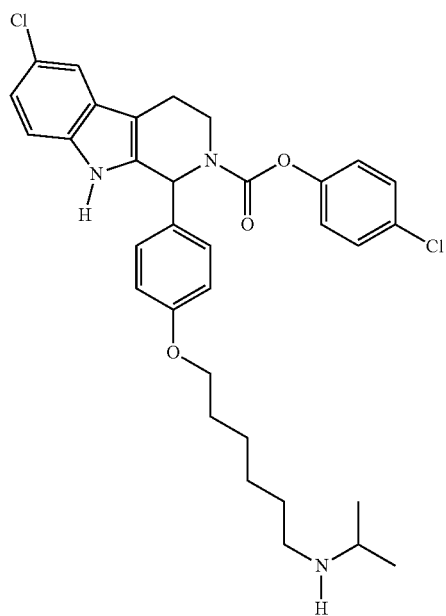
784
314
-continued
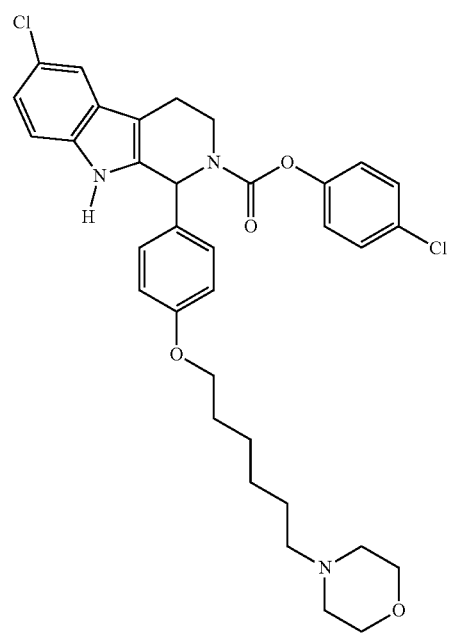
786
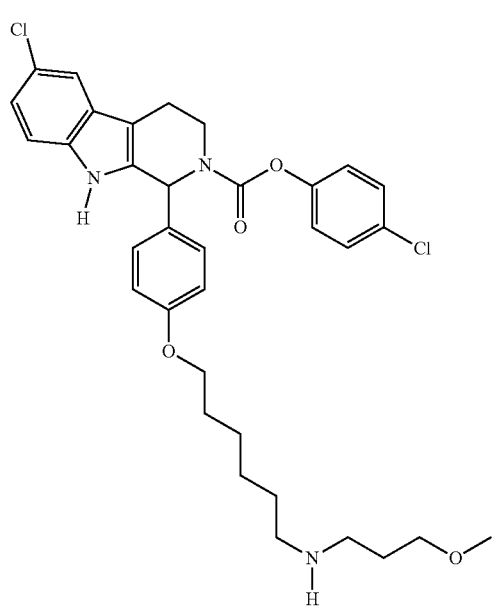
785
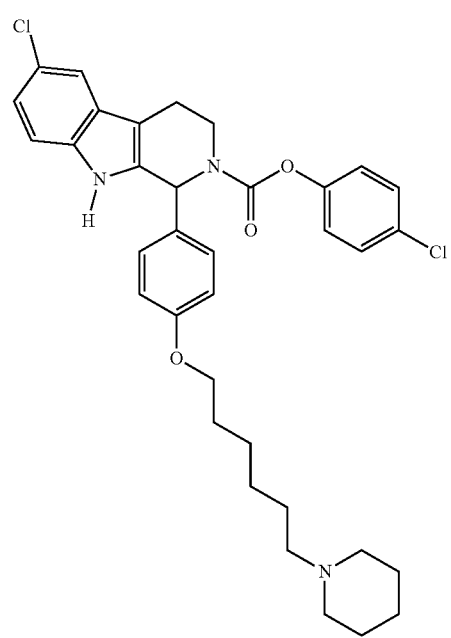
787

315
-continued
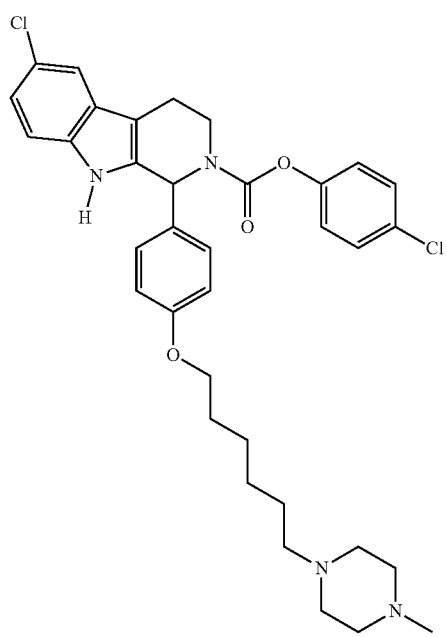
788
316
-continued
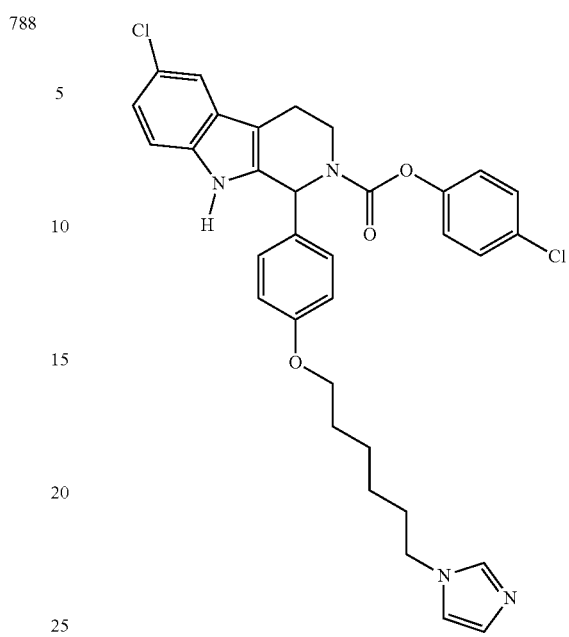
790
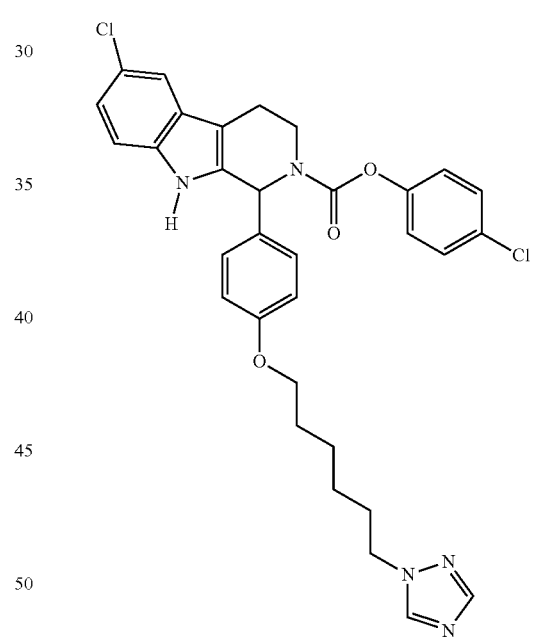
791
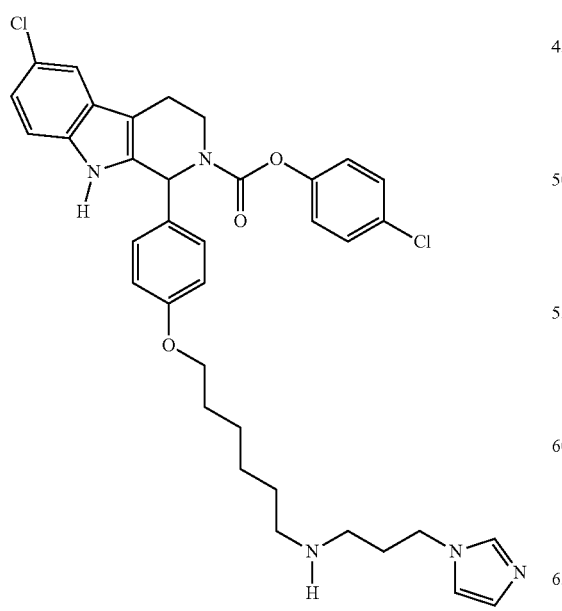
789
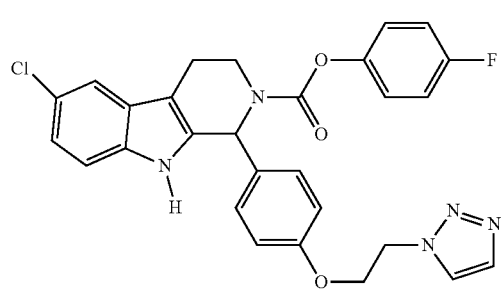
833

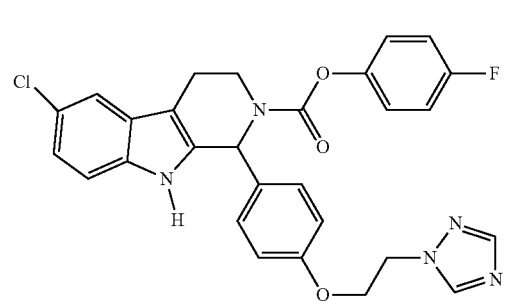
834
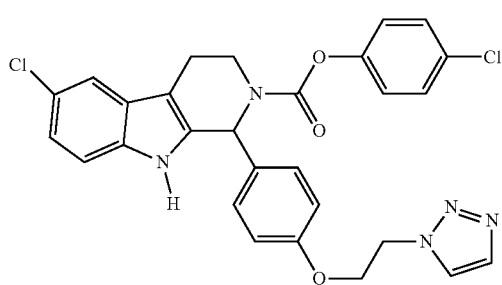
839
835
840
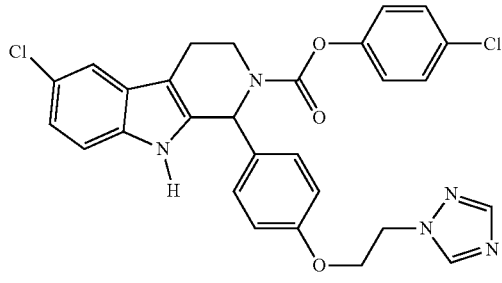
841
836
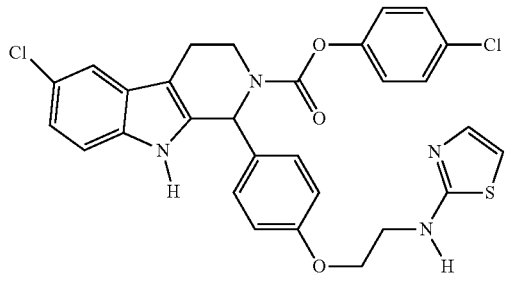
842
837
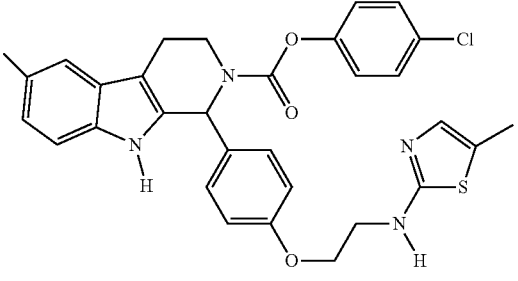
843
838
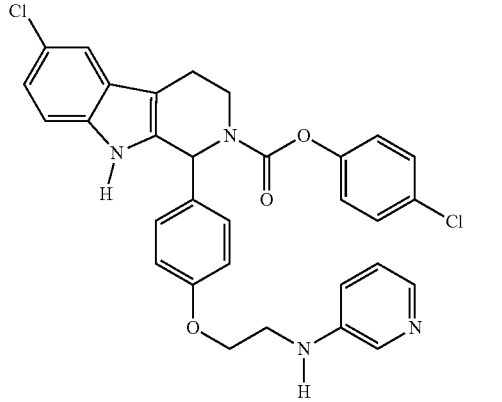

845 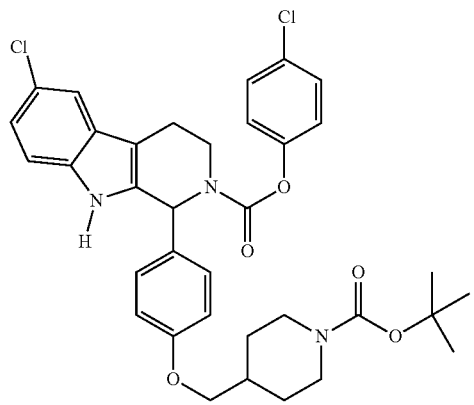
846 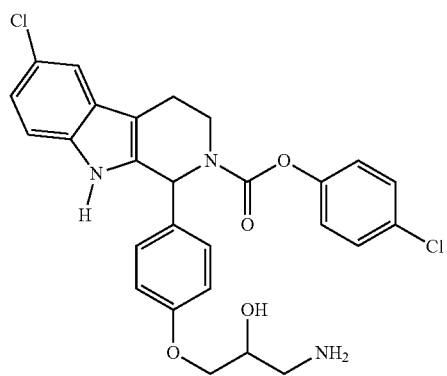
847 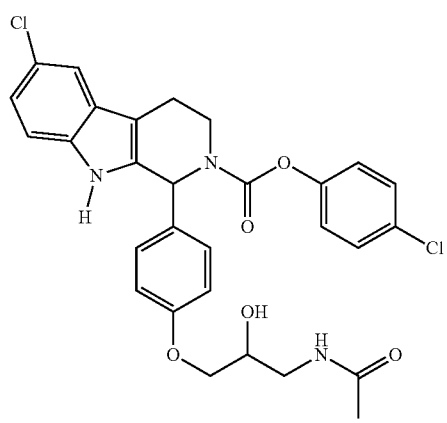
848 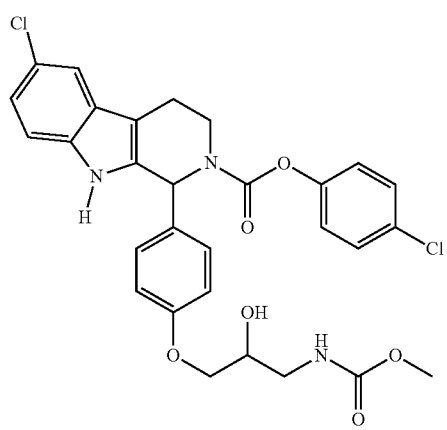
849 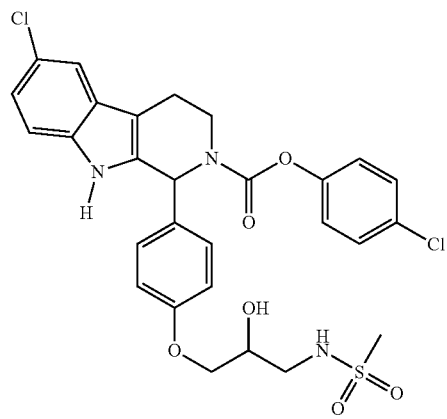
850 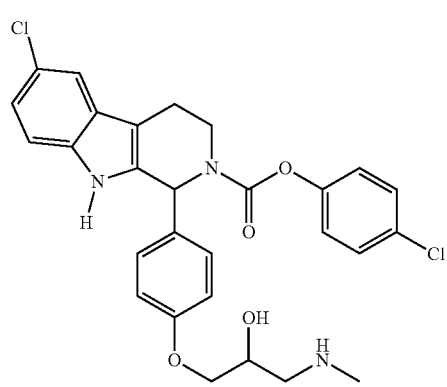
867 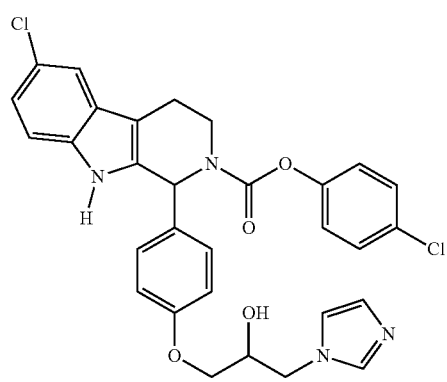
882 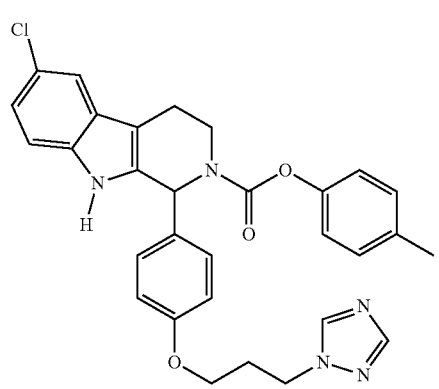

| 888 | 894 |
|---|---|
| 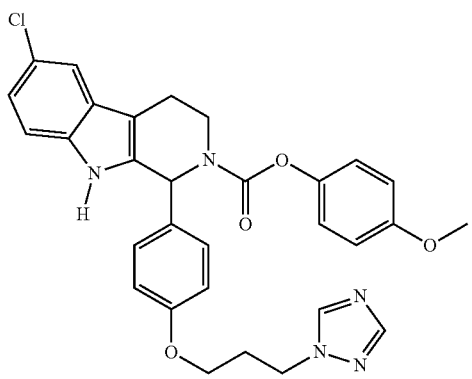 | 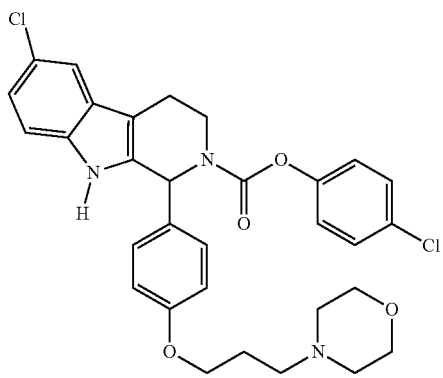 |
| 889 | 900 |
|---|---|
| 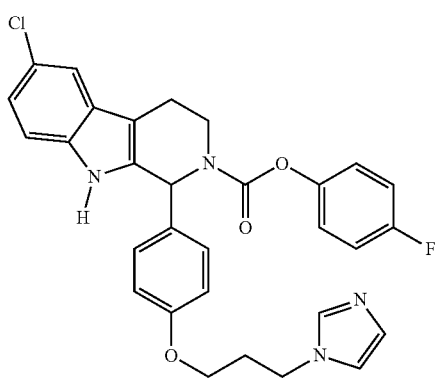 | 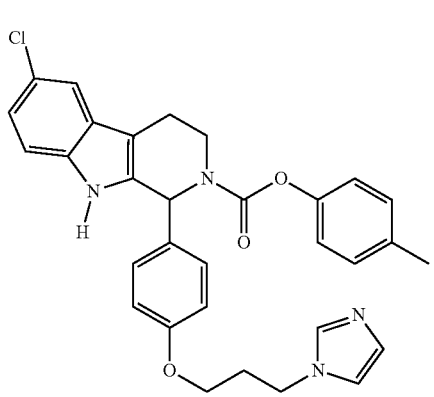 |
| 891 | 903 |
|---|---|
| 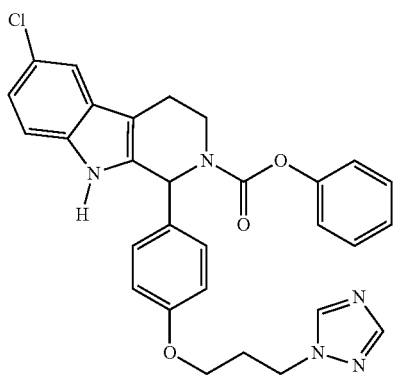 | 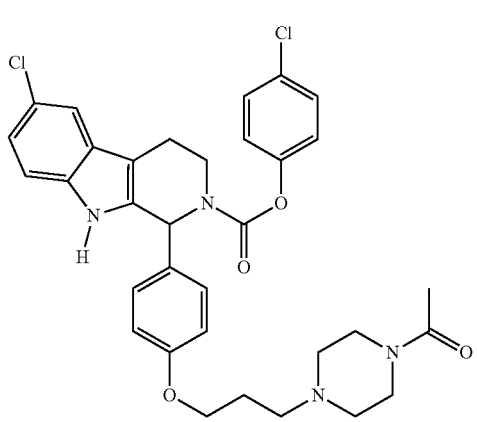 |
| 892 | 904 |
|---|---|
| 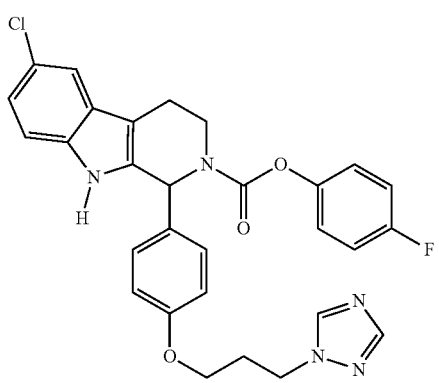 | 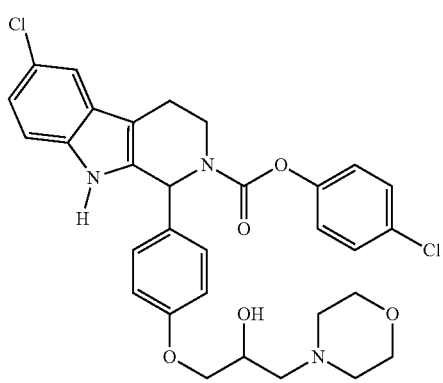 |

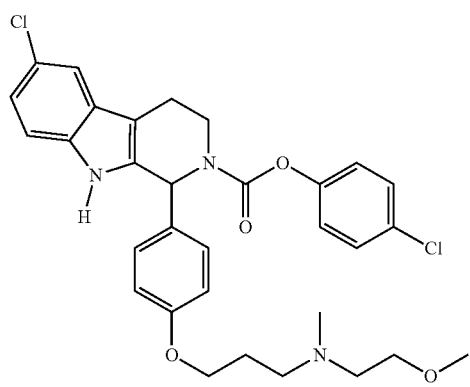
908
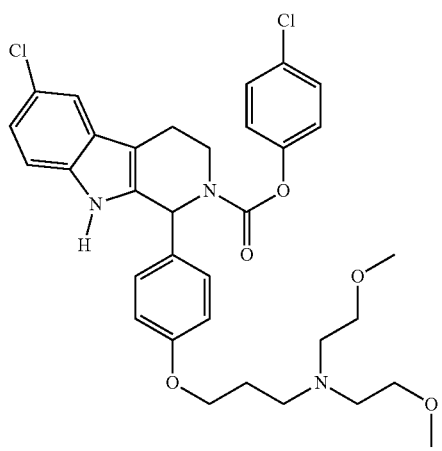
916
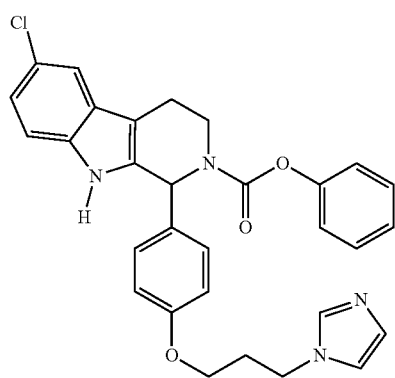
911
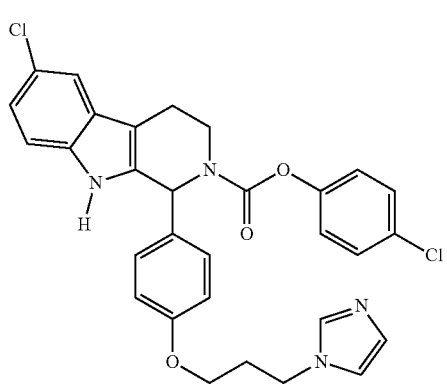
917
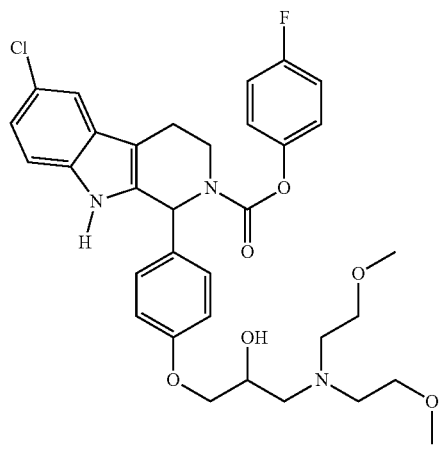
913
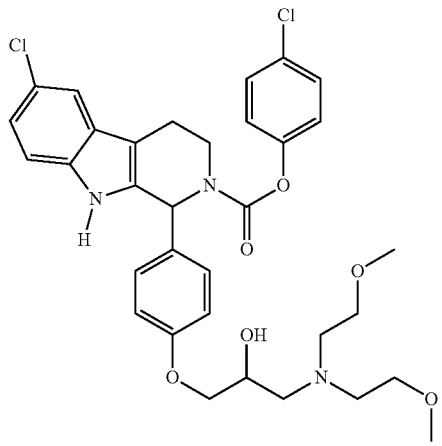
918
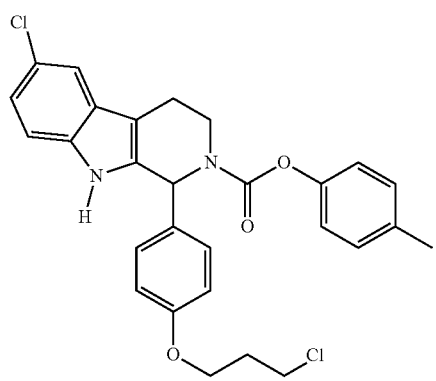
915
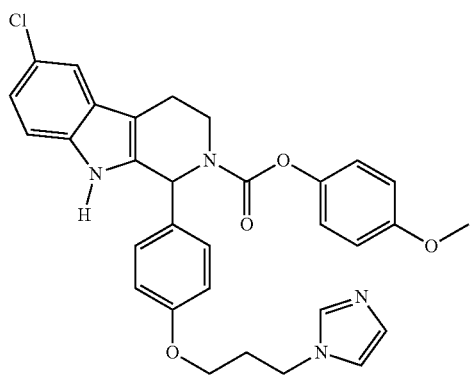
920

325
-continued
921
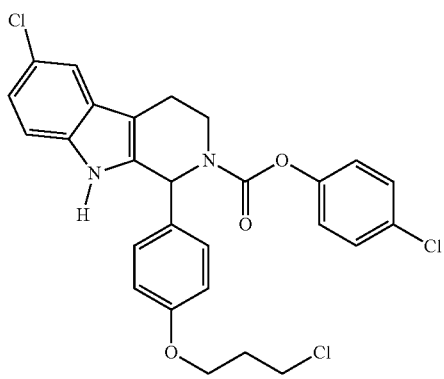
922
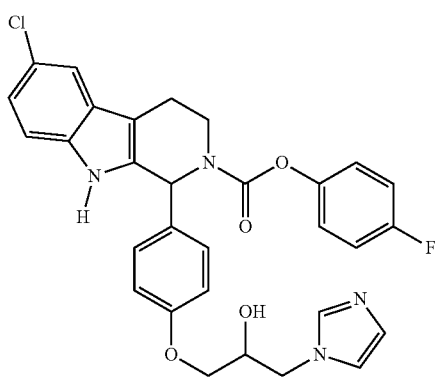
923
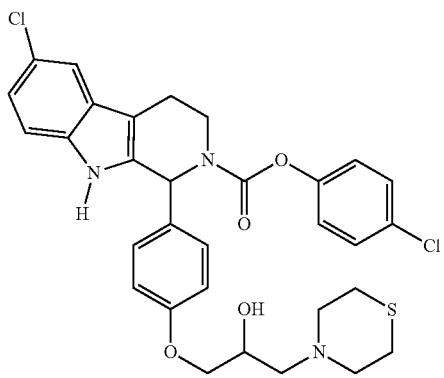
925
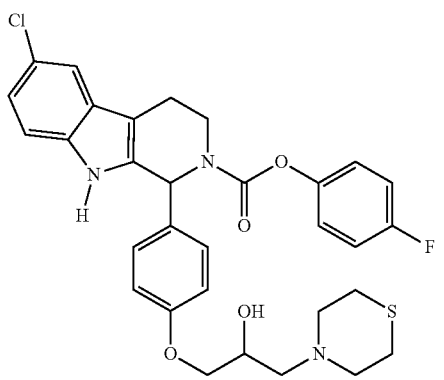
326
-continued
926
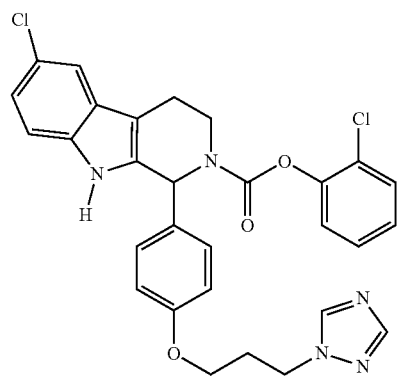
932
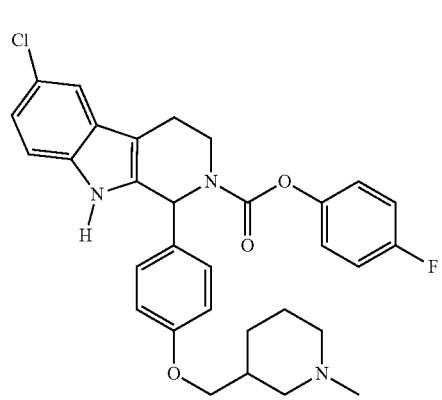
933
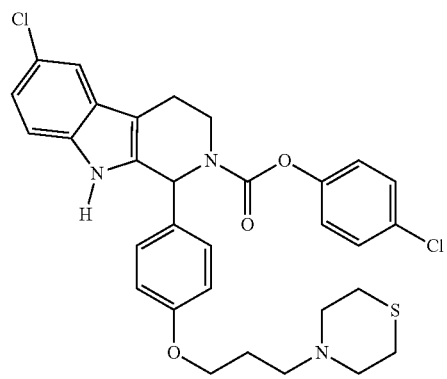
934
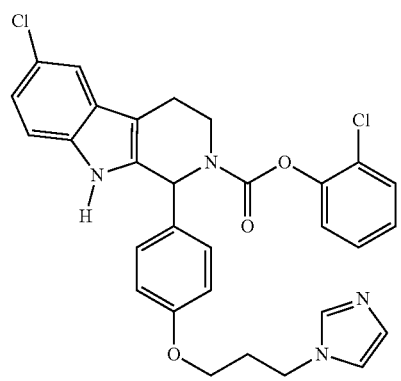

327
-continued
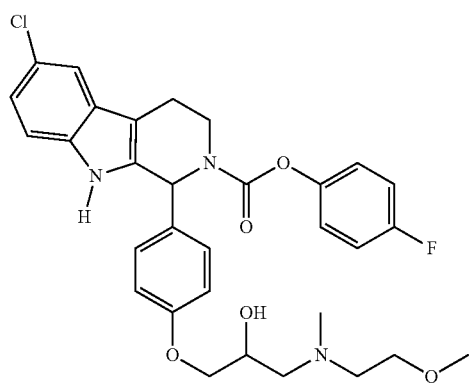
936
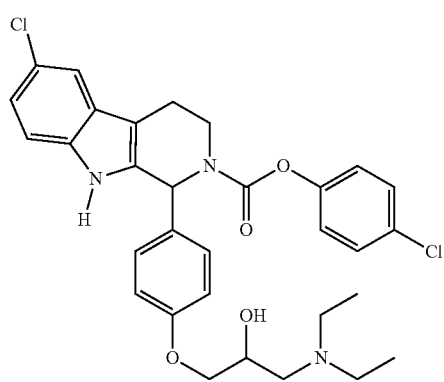
938
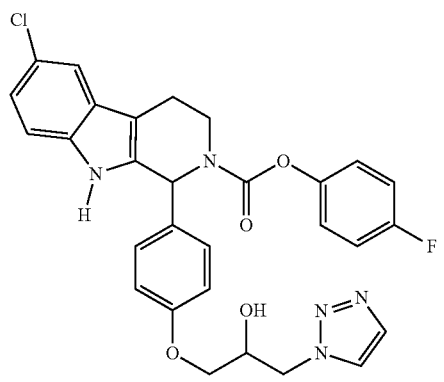
941
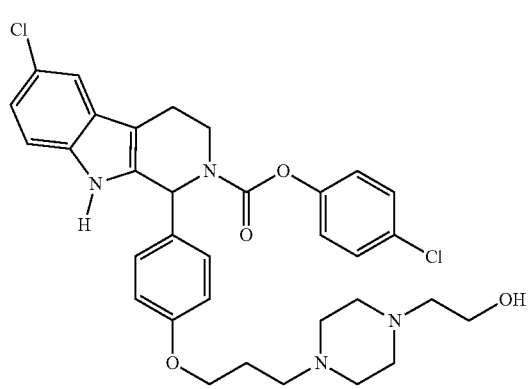
942
328
-continued
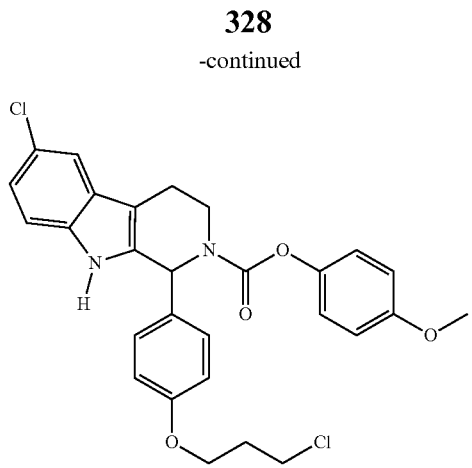
944
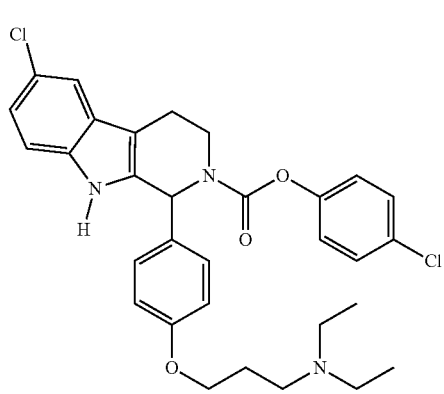
946
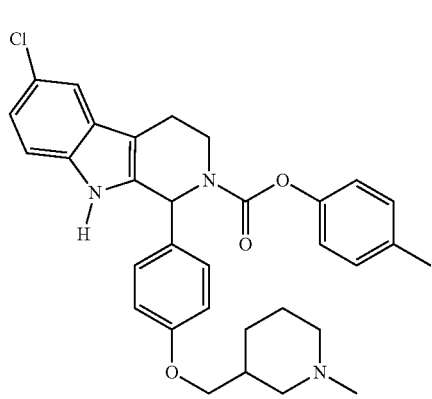
951
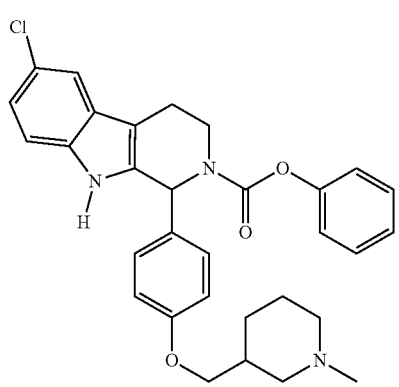
952

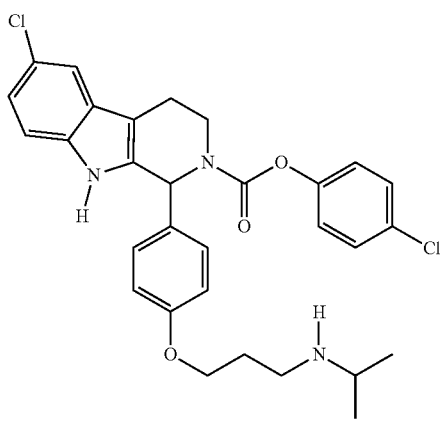
953
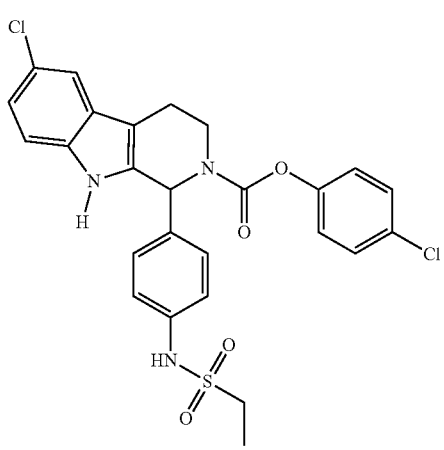
958
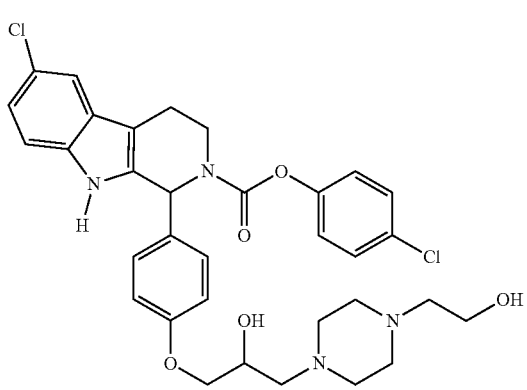
960
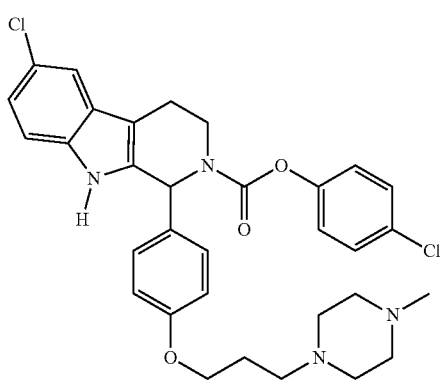
961
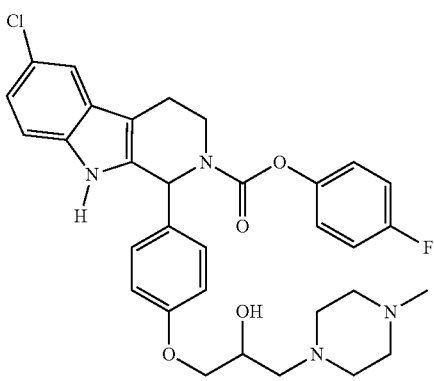
963
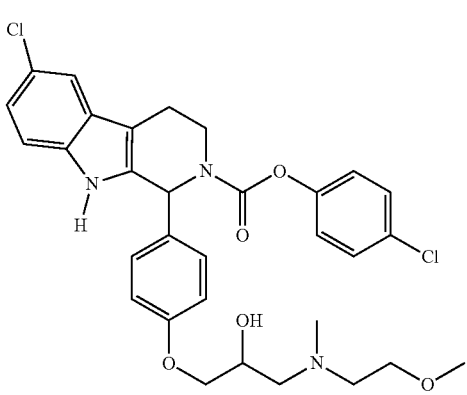
964
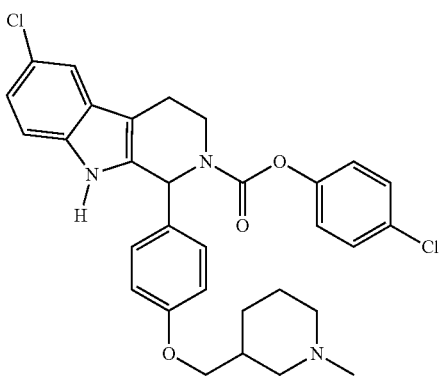
966
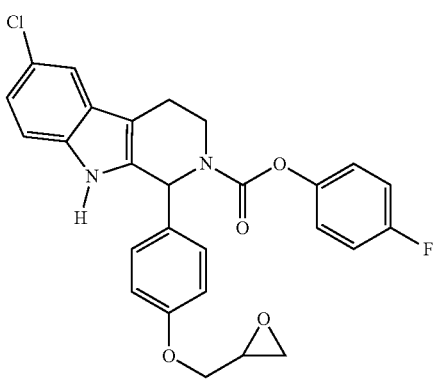
967

331
-continued
970
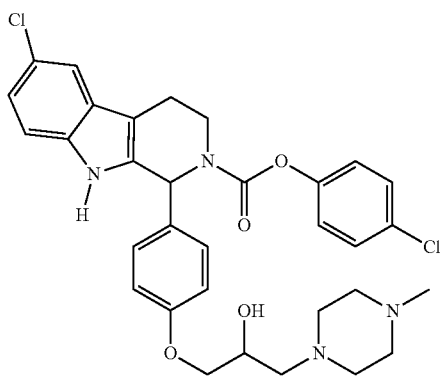
973
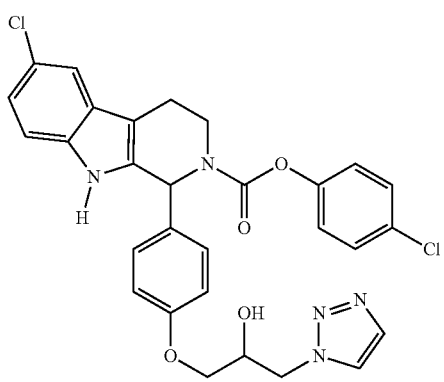
974
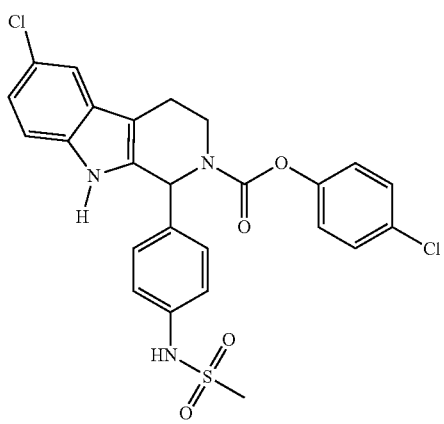
976
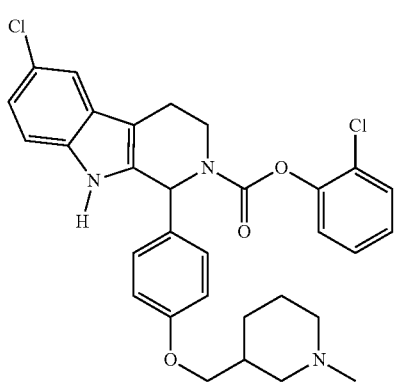
332
-continued
977
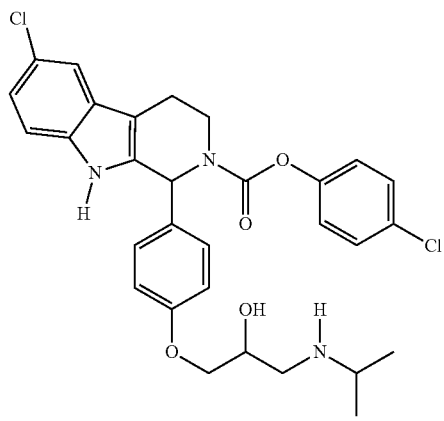
981
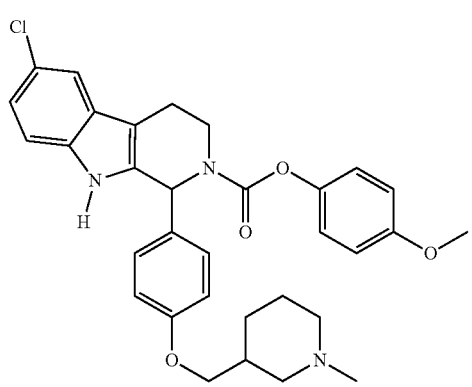
984
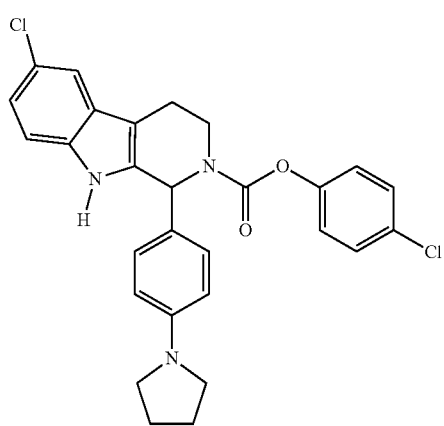

333
-continued
334
-continued
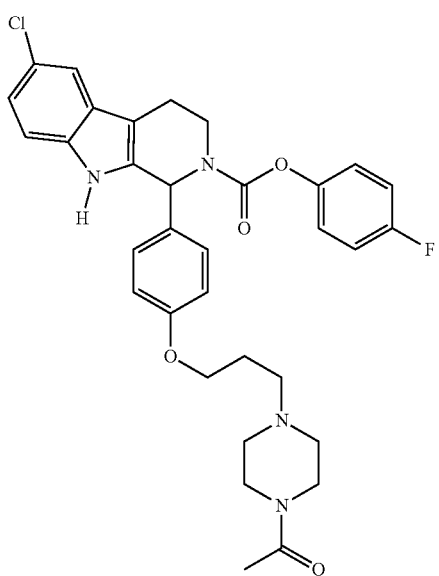
988
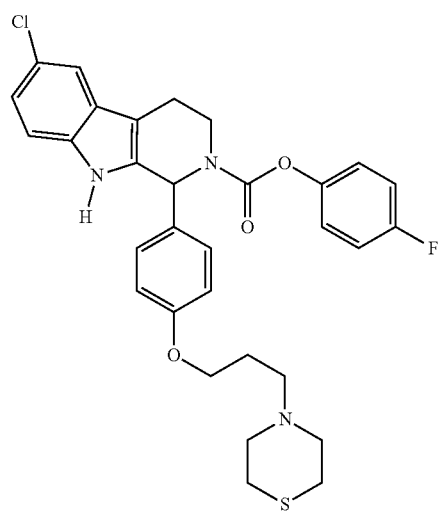
991
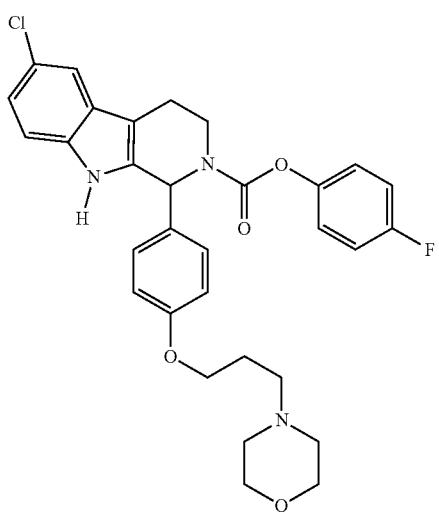
989
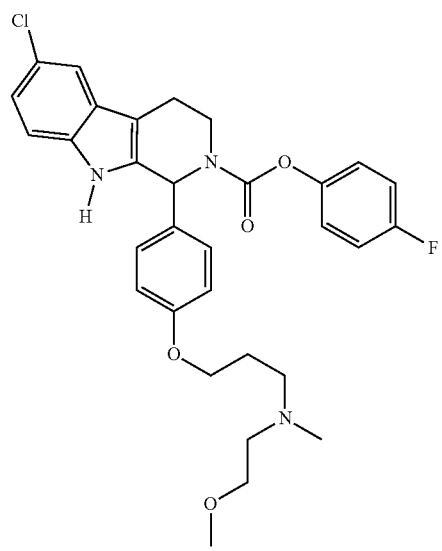
992
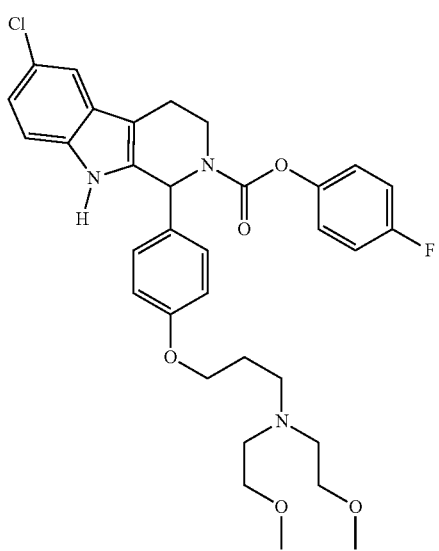
990
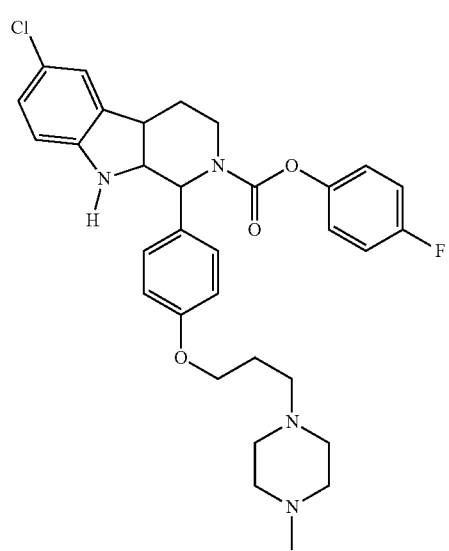
993

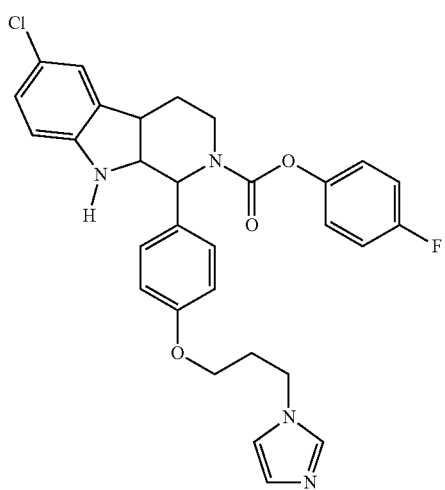
994
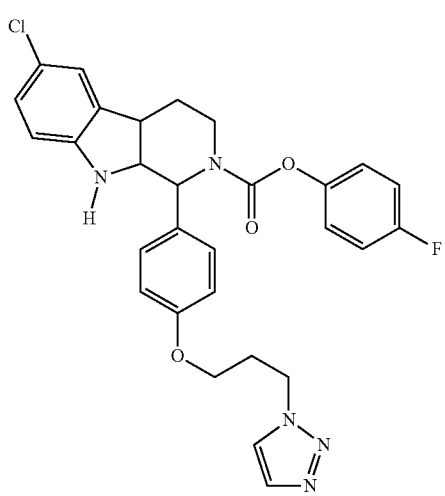
995
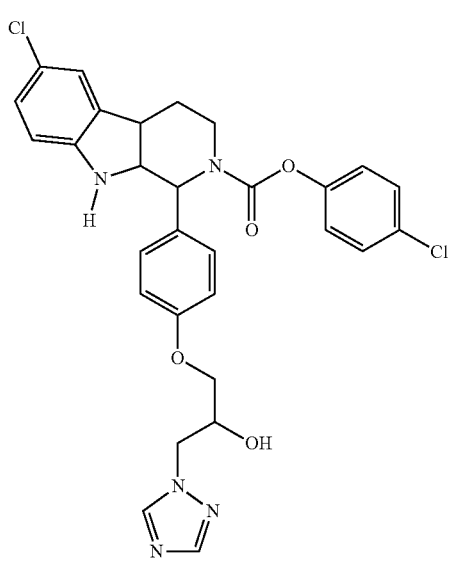
996
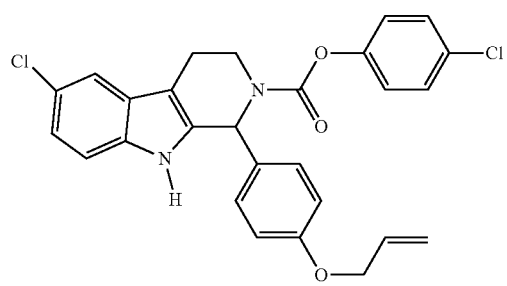
999
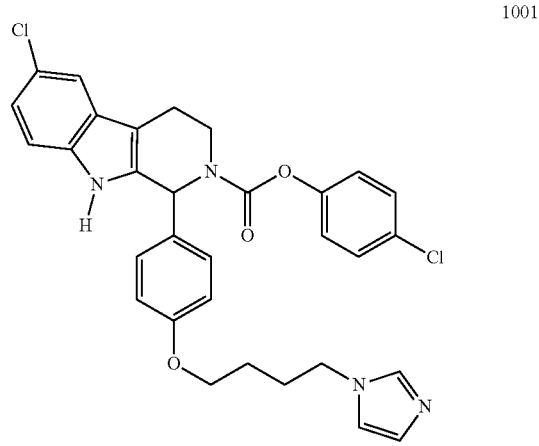
1001
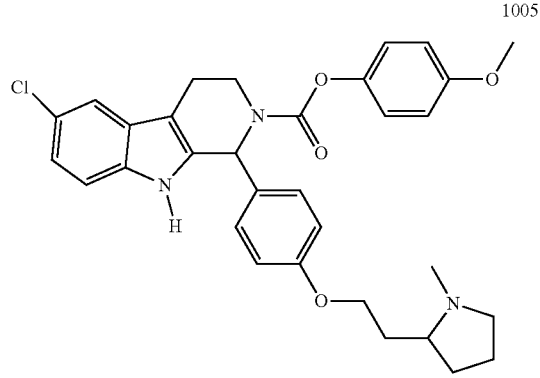
1005
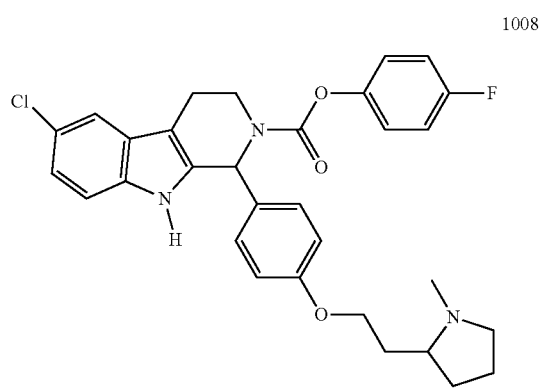
1008

337
-continued
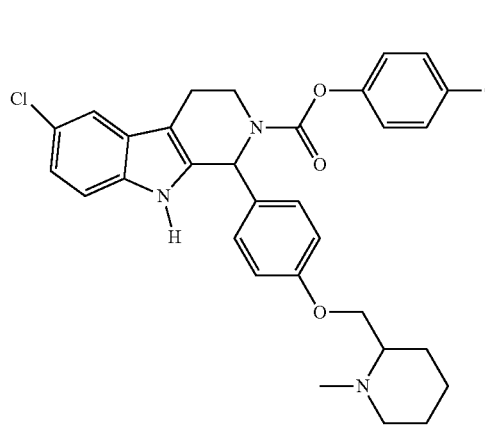
1009
1011
1016
1017
338
-continued
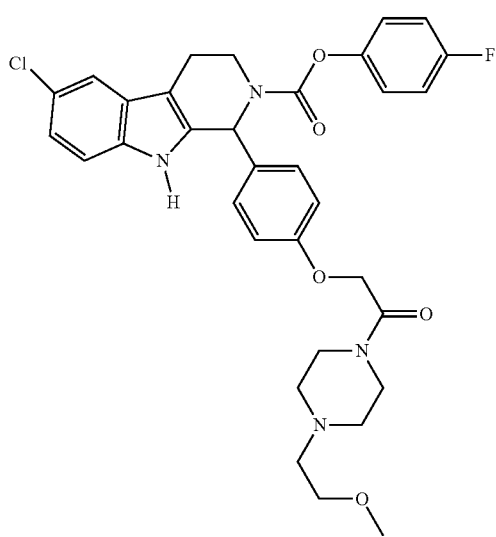
1021
1022
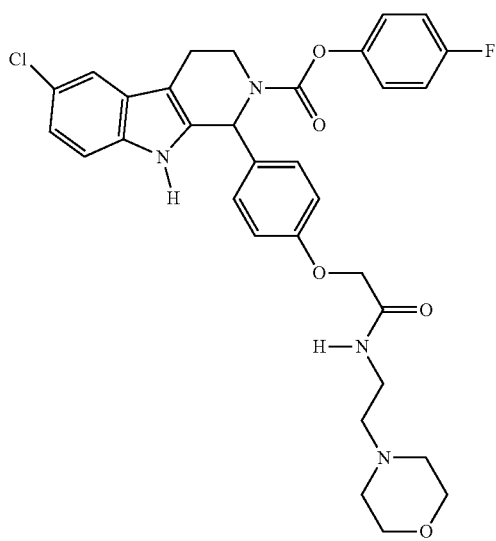
1023
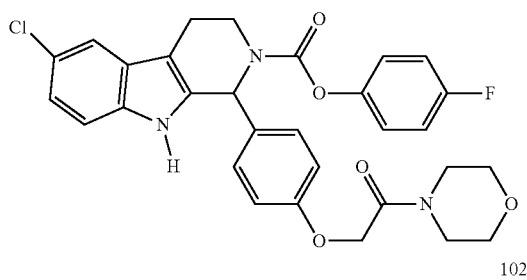
1024
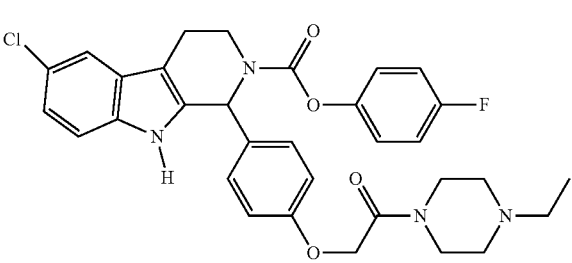

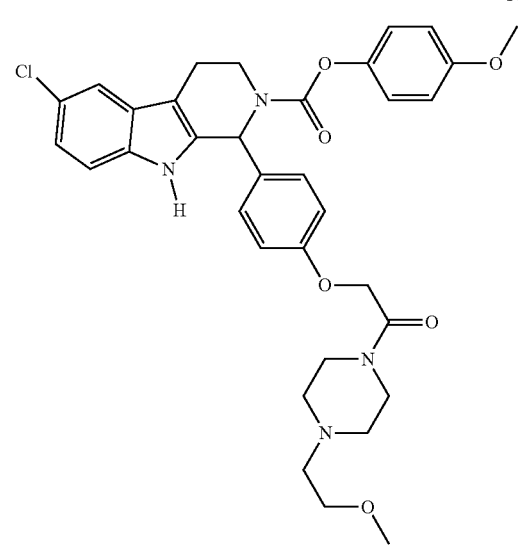
1025
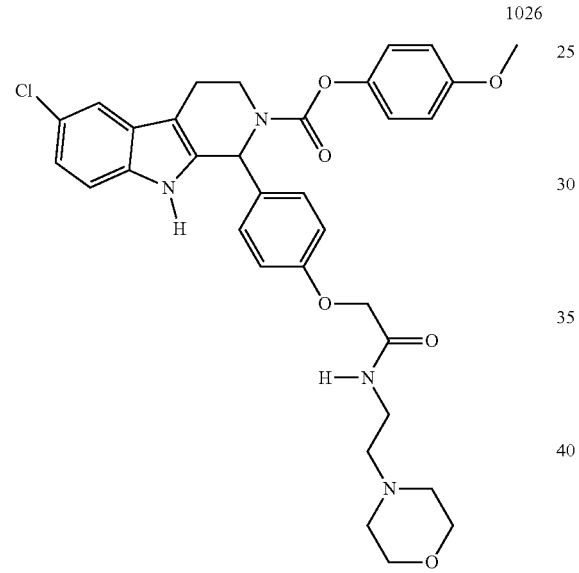
1026
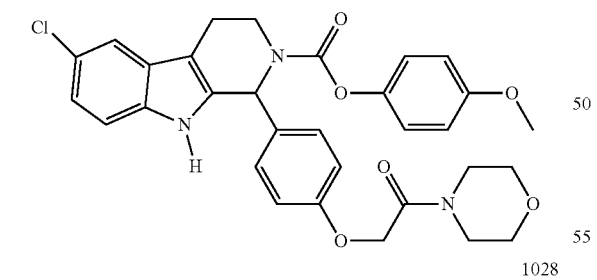
1027
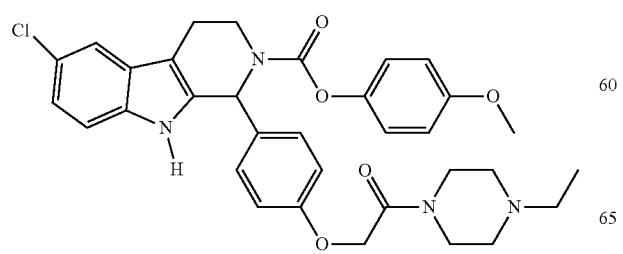
1028
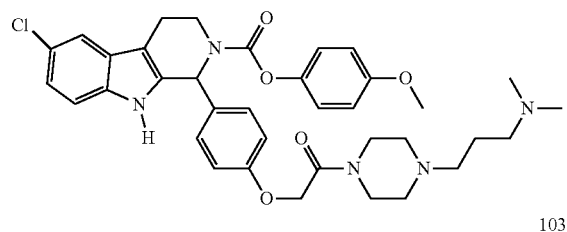
1029
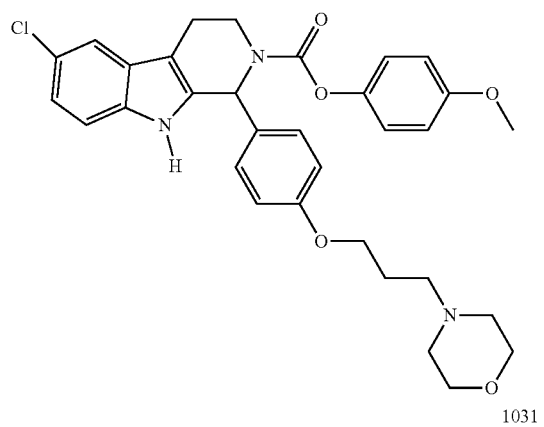
1030
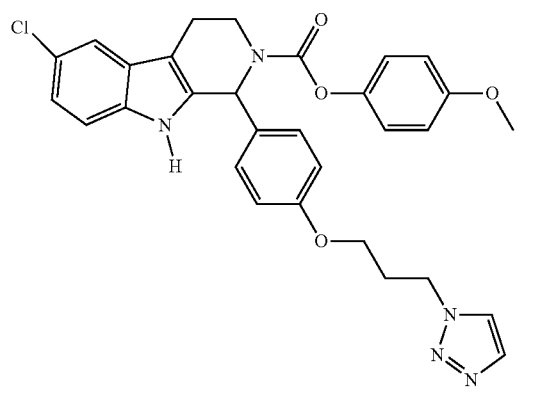
1031
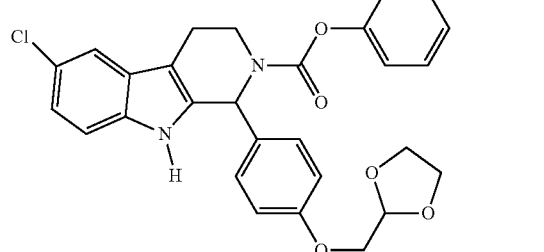
1050
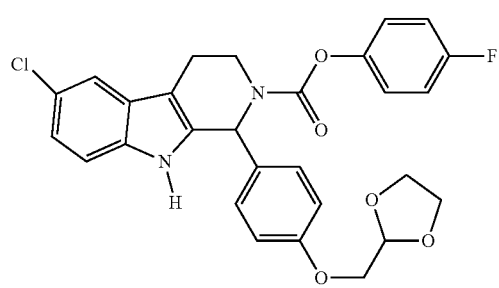
1051

1052
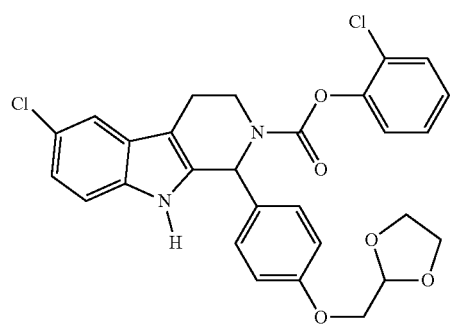
1053
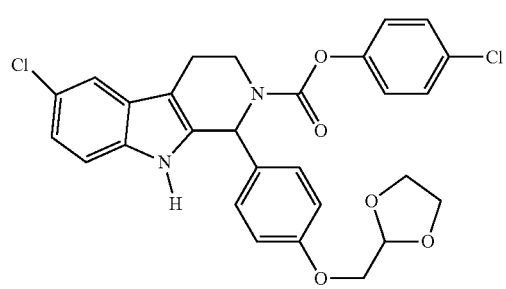
1054
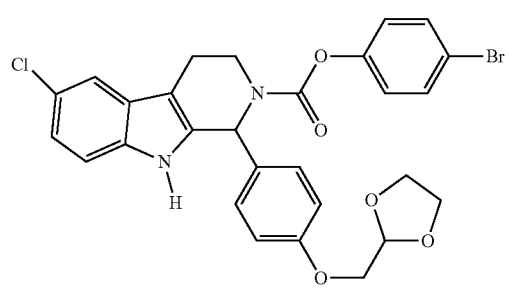
1055
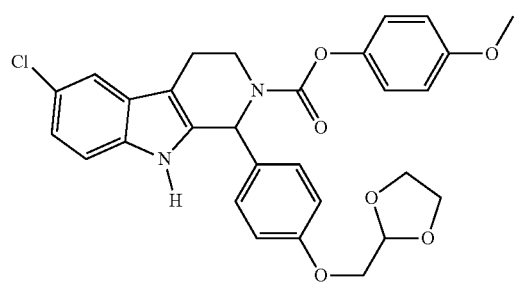
1058
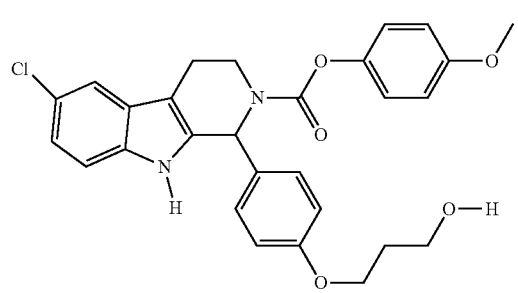
1062
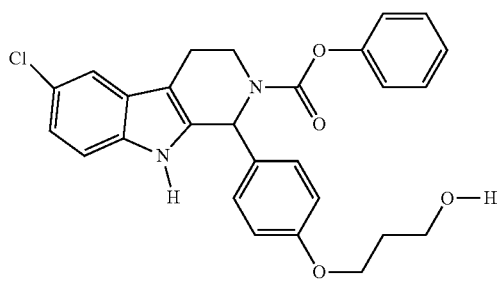
1063
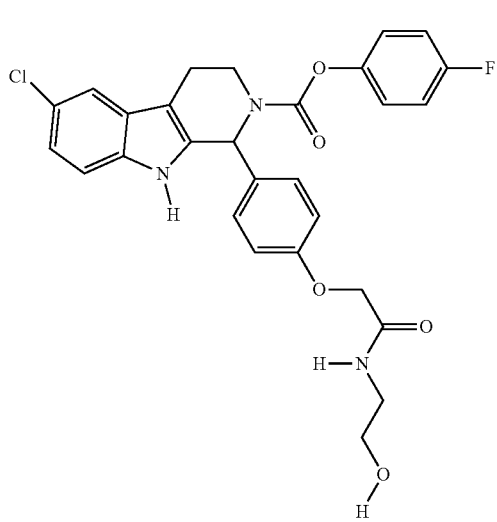
1064
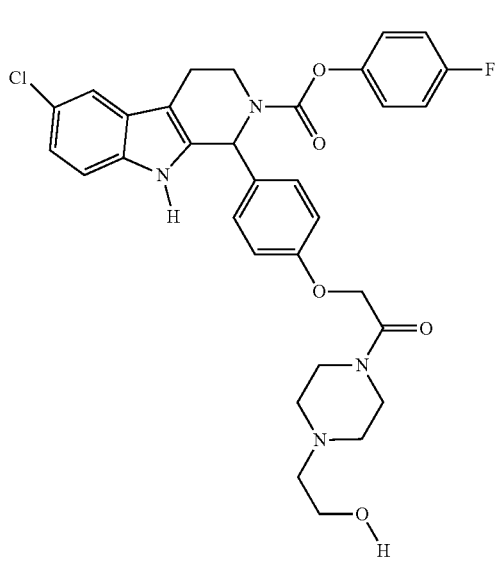

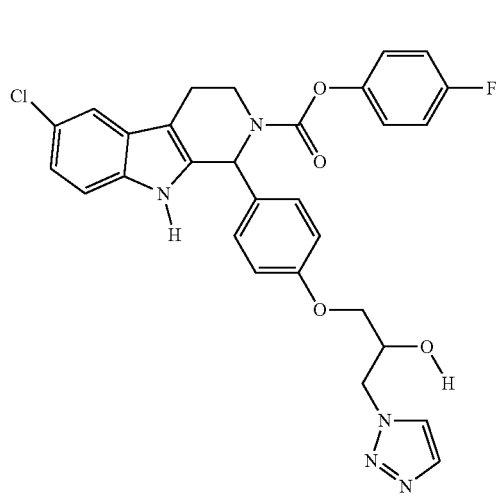
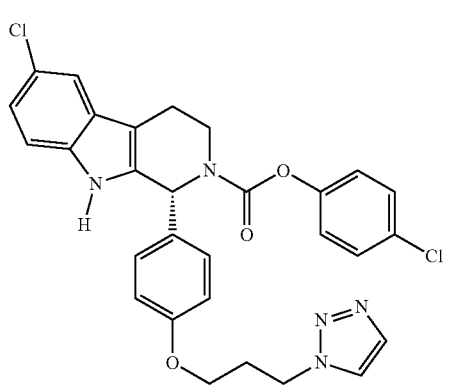
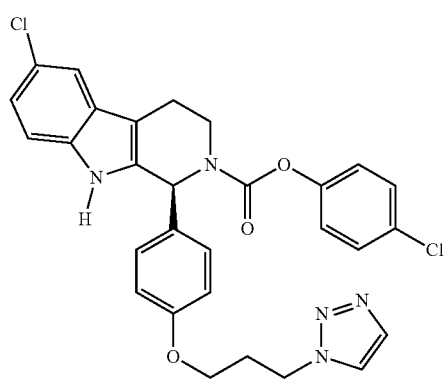
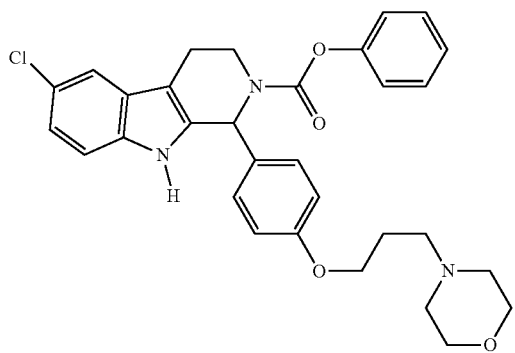

1076
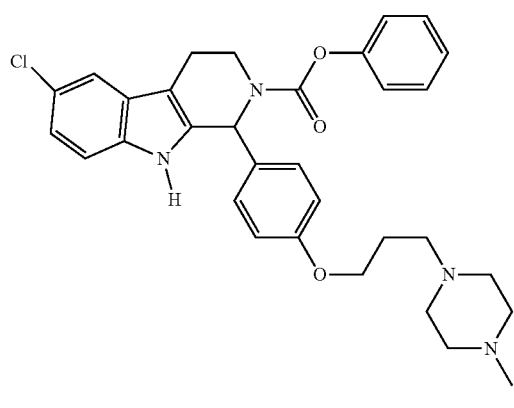
1077
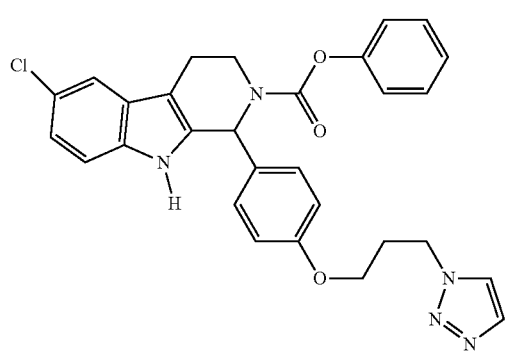
1078
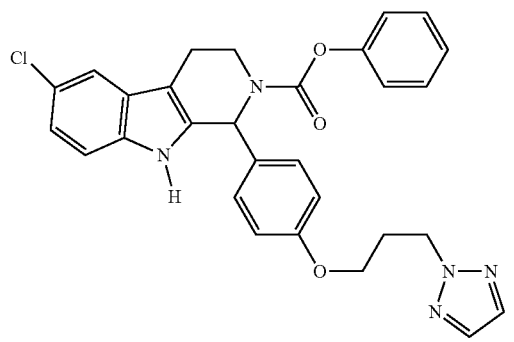
1086
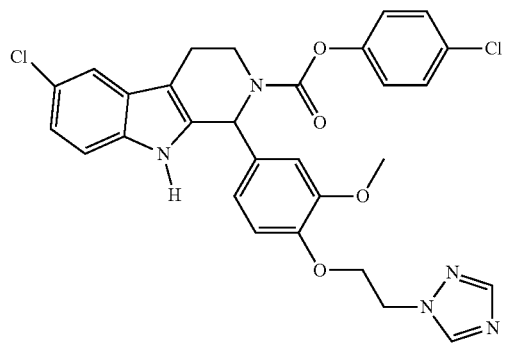
1087
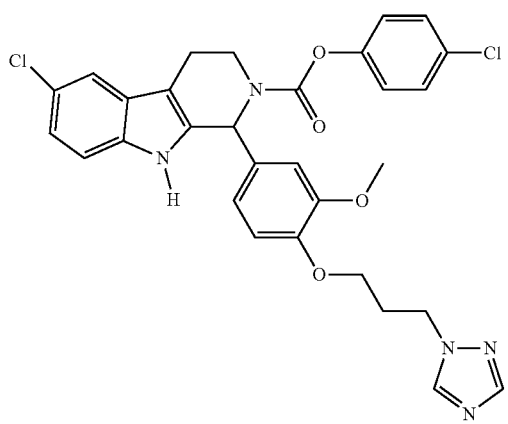
1088
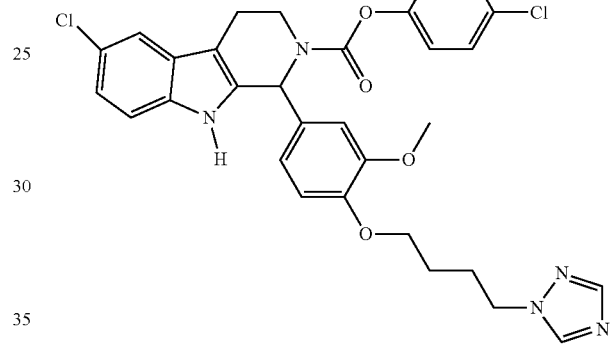
1089
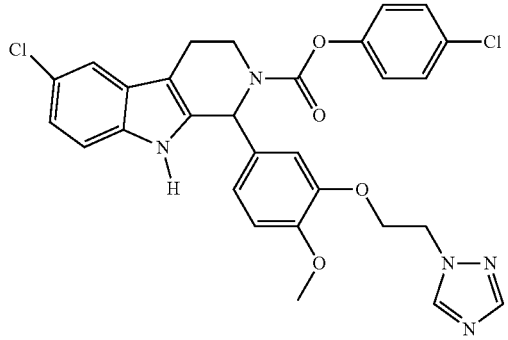
1090
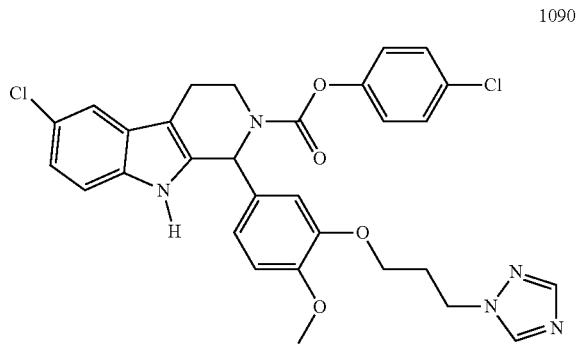

347
-continued
1091
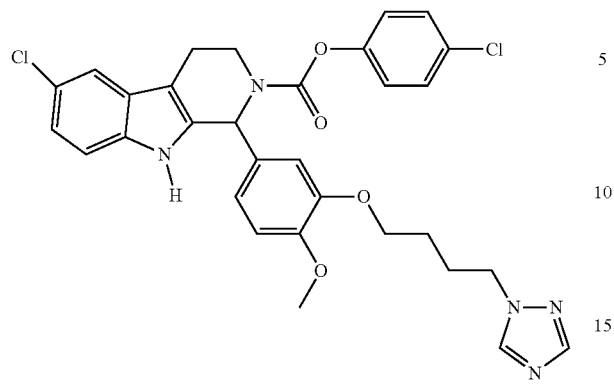
1092
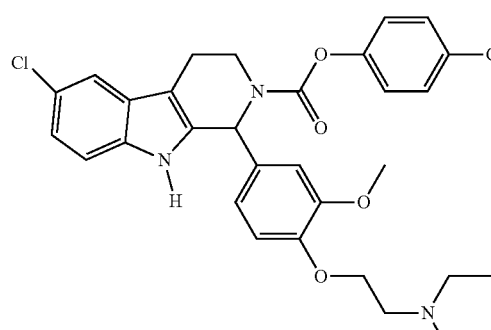
1093
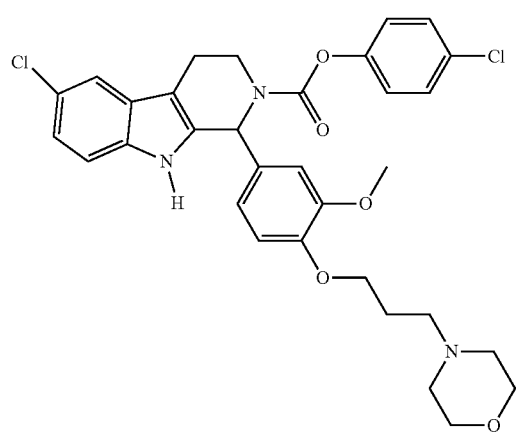
1094
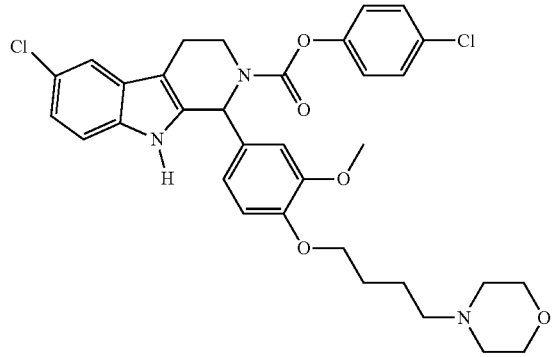
348
-continued
1095
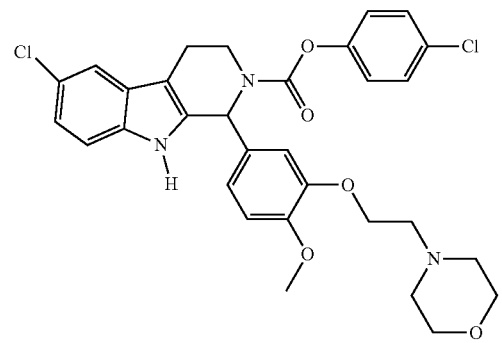
1096
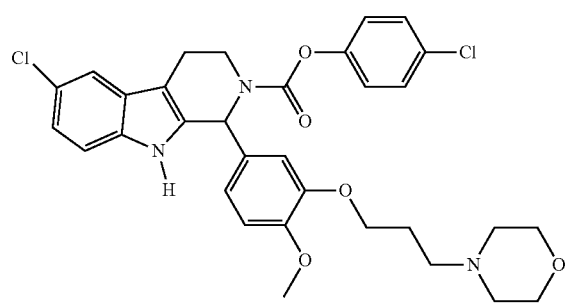
1097
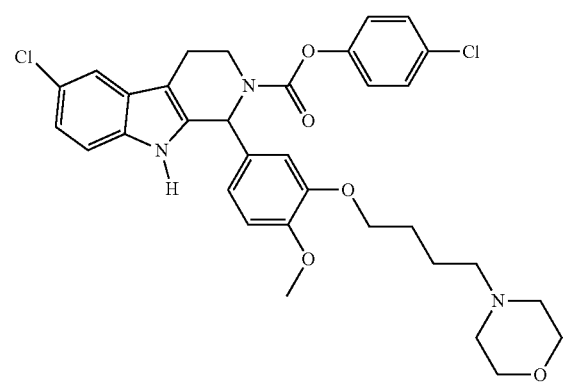
1098
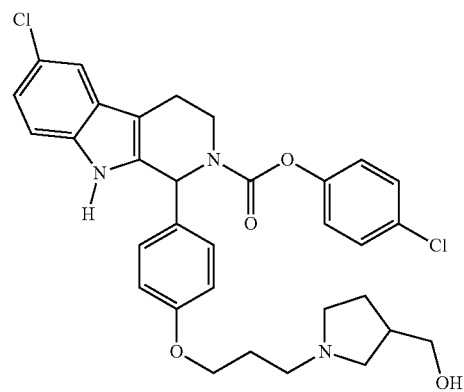

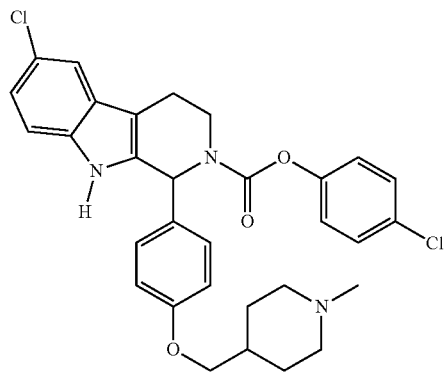
1099
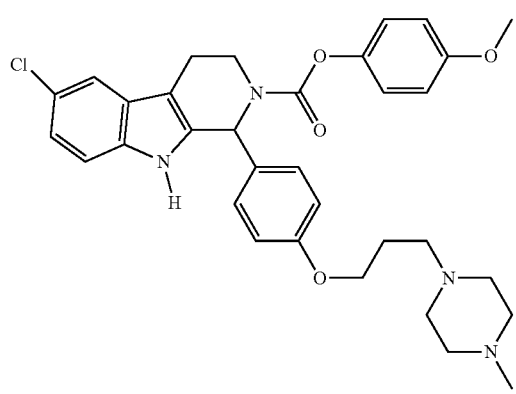
1108
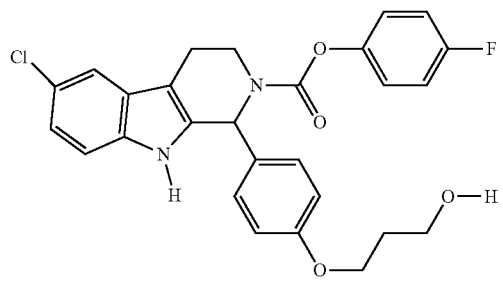
1110
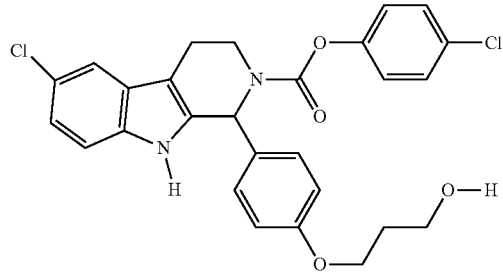
1111
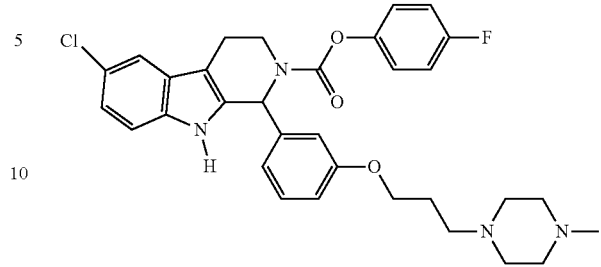
1113

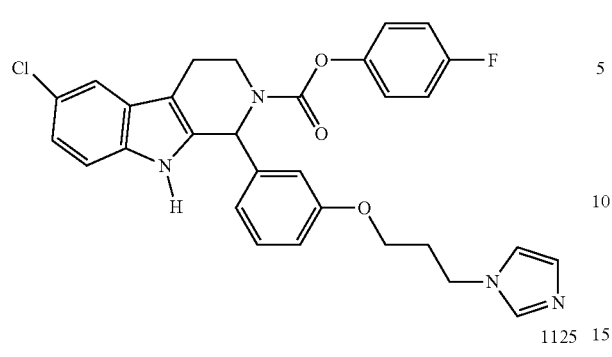
1123
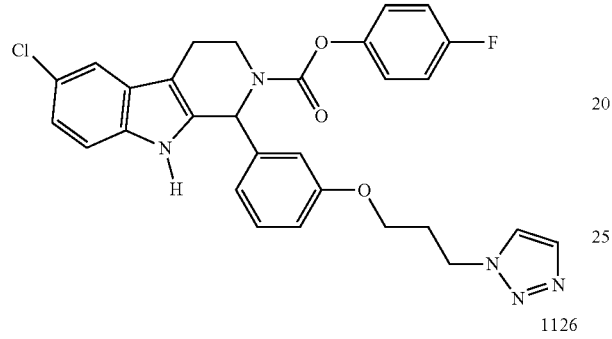
1125
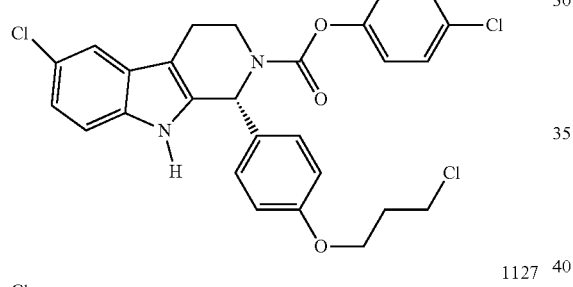
1126
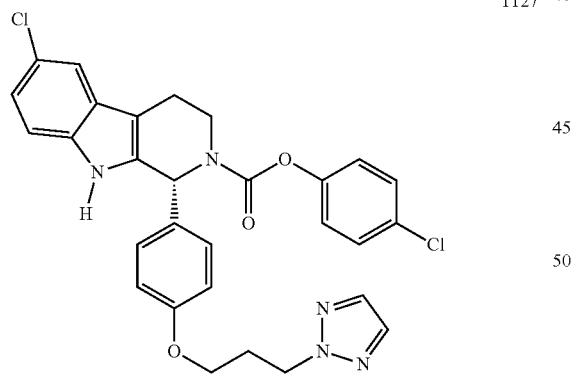
1127
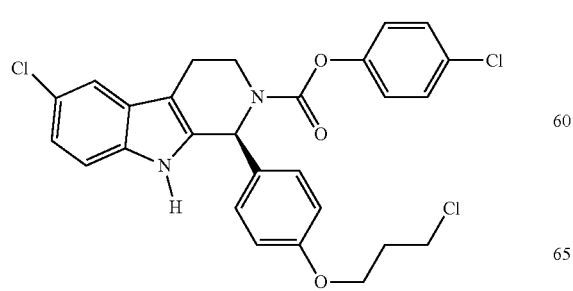
1128
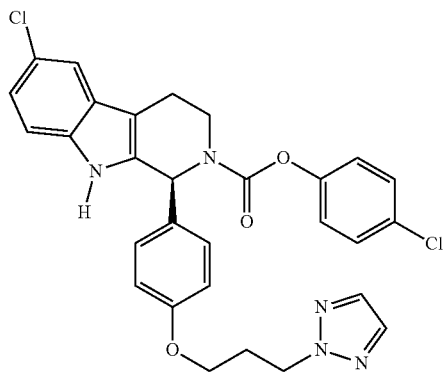
1129
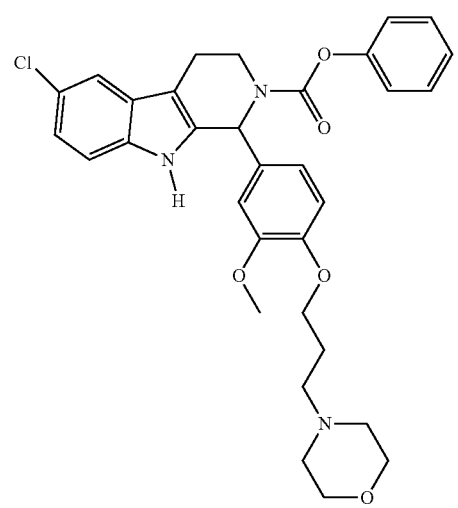
1130
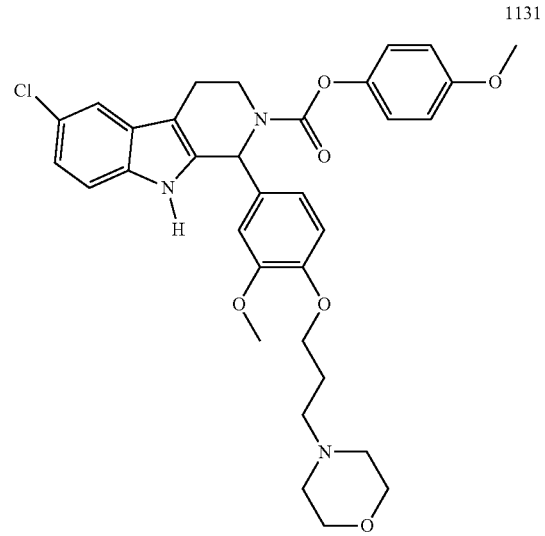
1131

353
-continued
1132
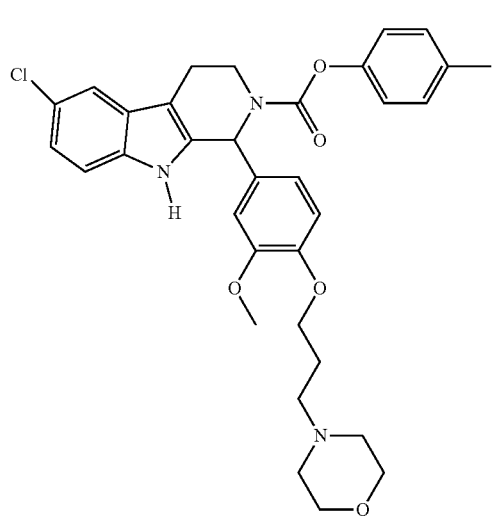
1133
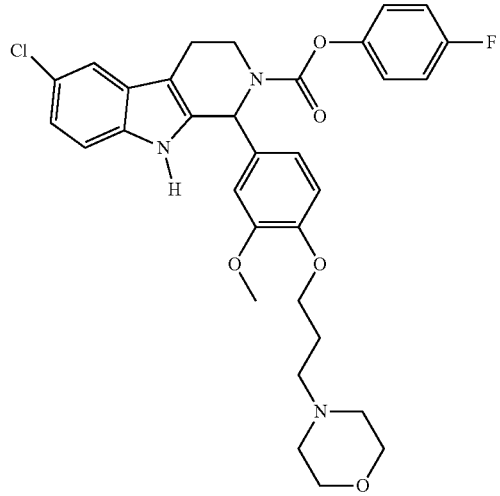
1134
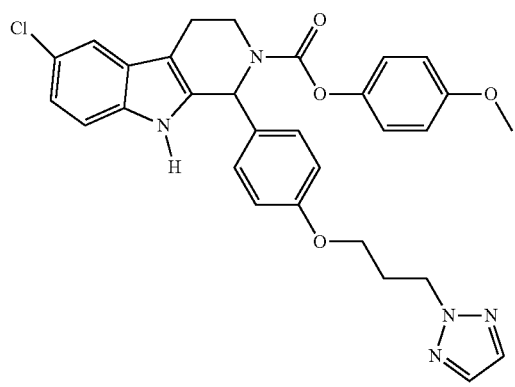
354
-continued
1043
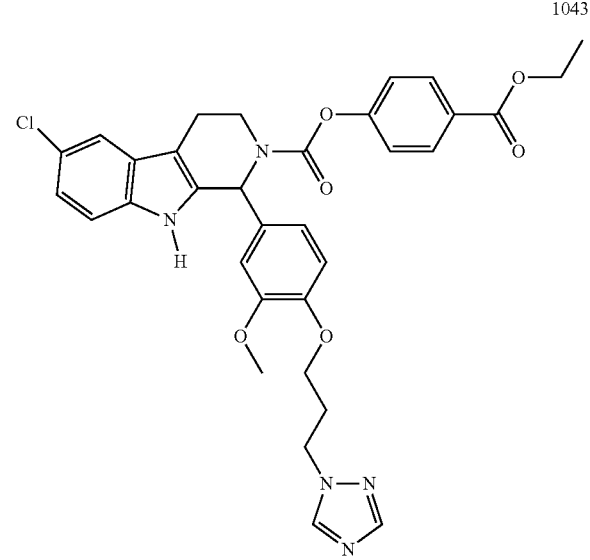
1144
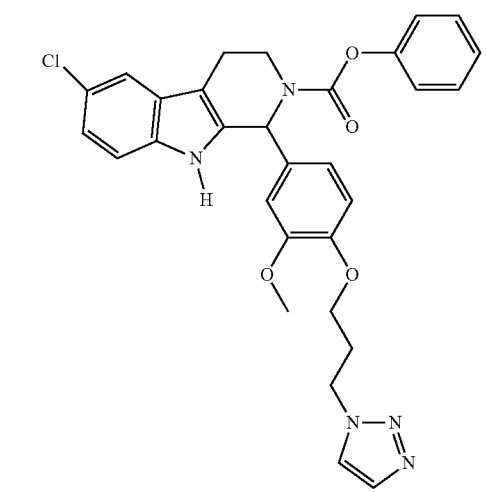
1145
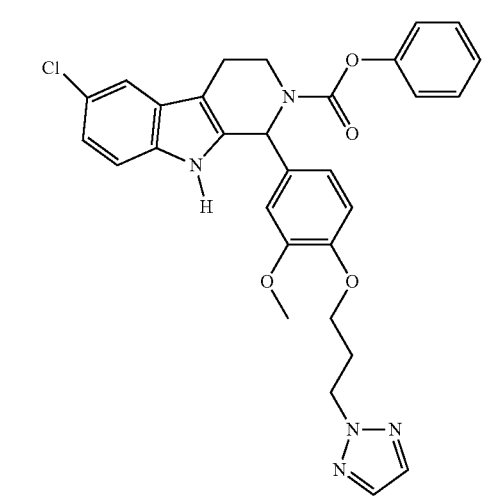

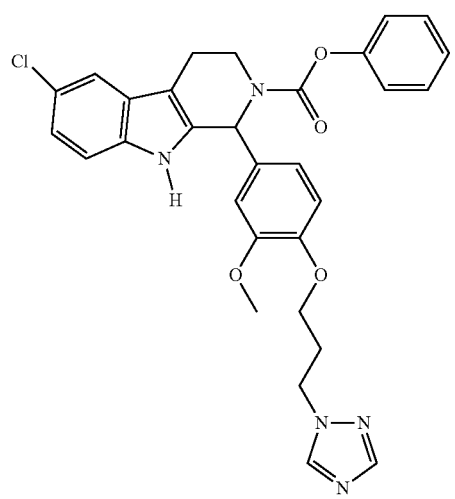
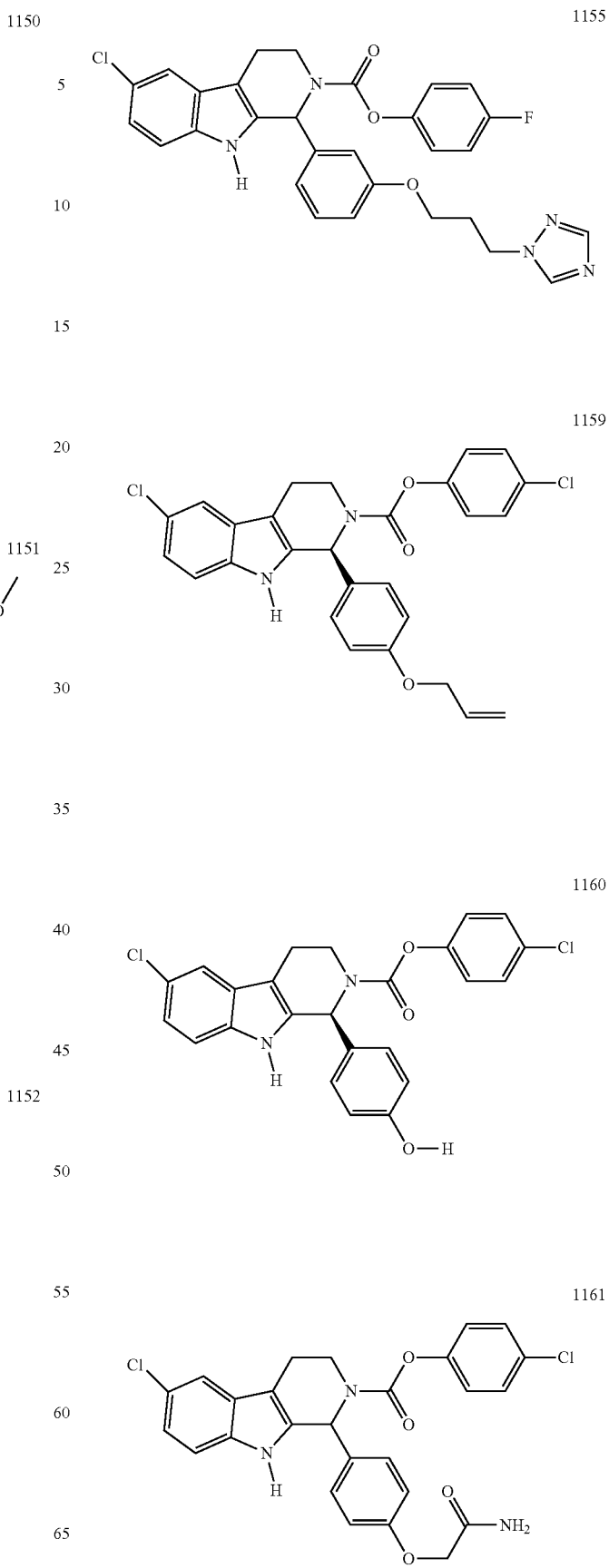

357
-continued
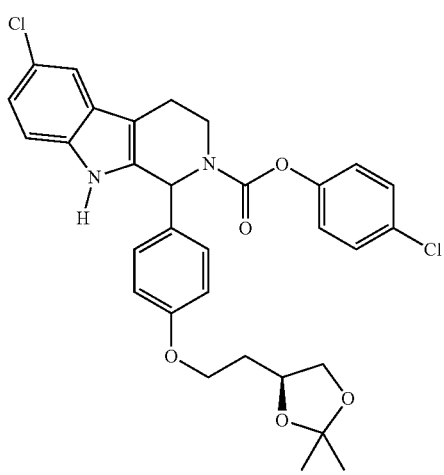
1162
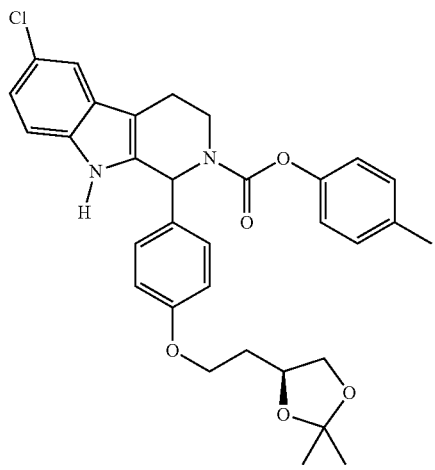
358
-continued
1170
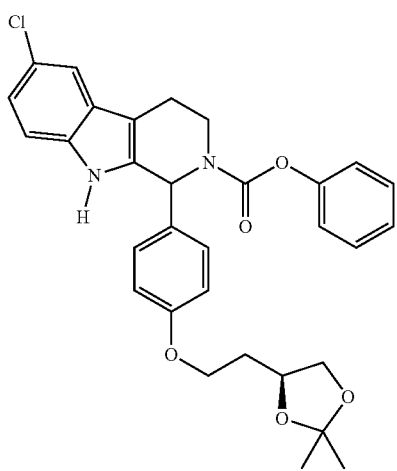
1168
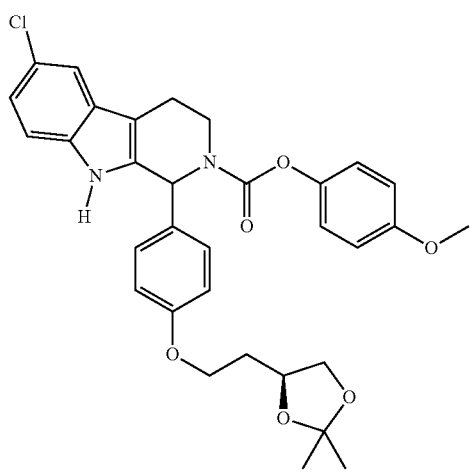
1171
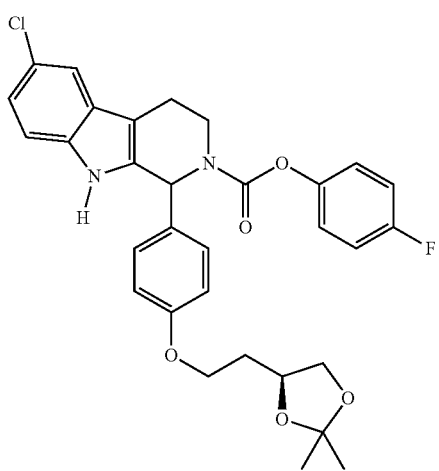
1169
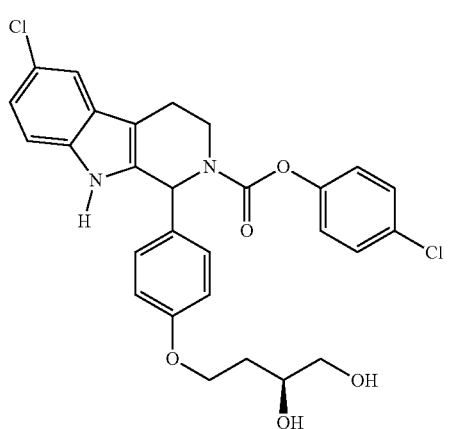
1172

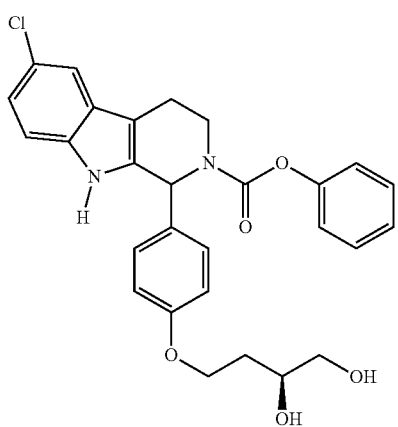
1178
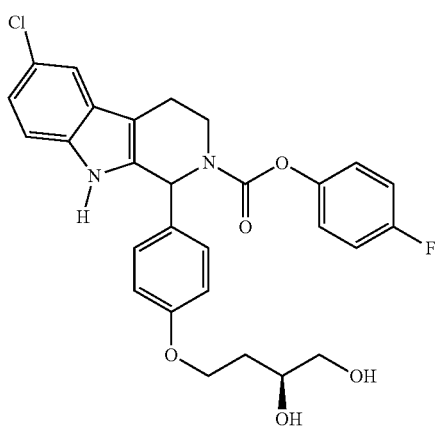
1179
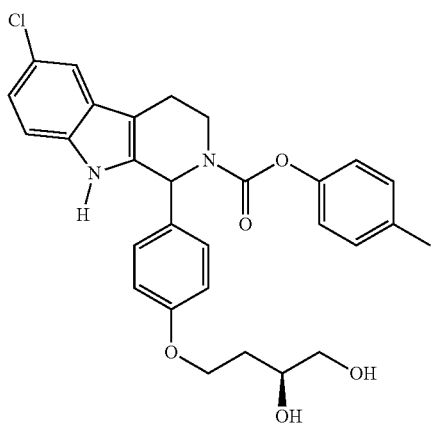
1180
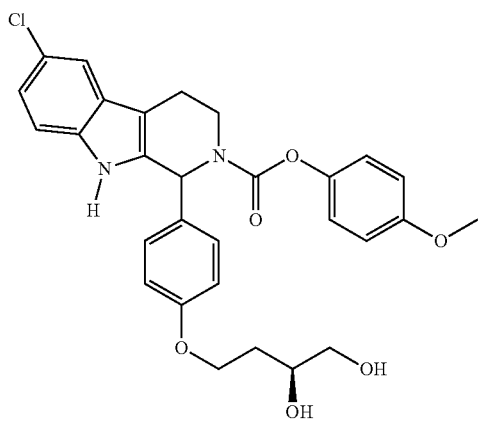
1181
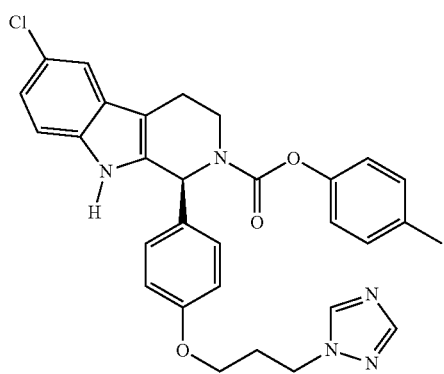
1182
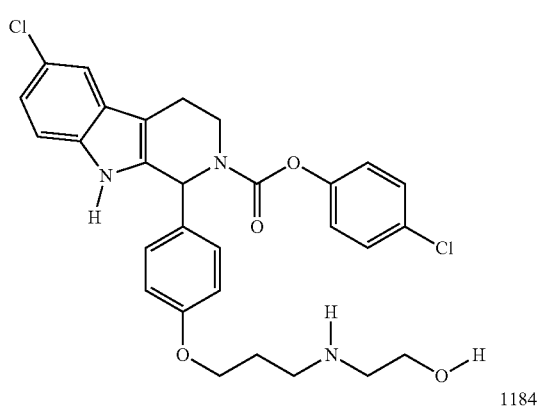
1183
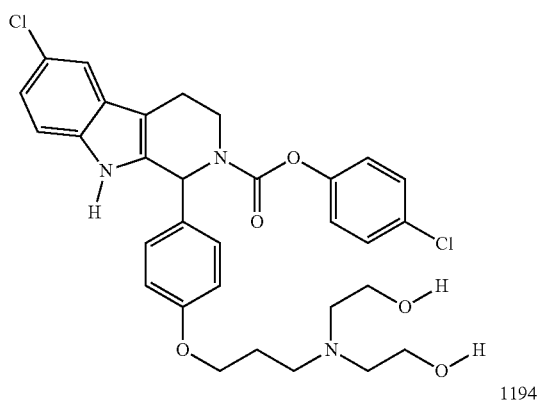
1184
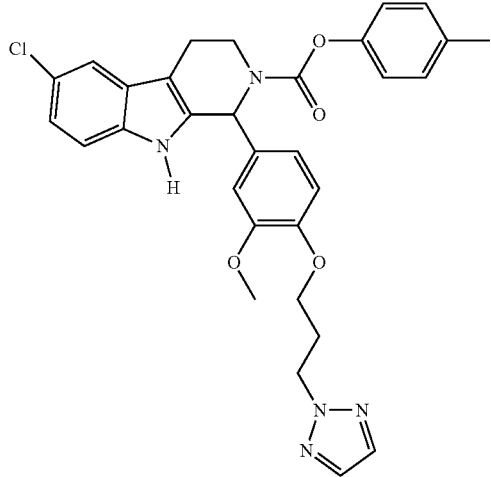
1194

361
-continued
1195
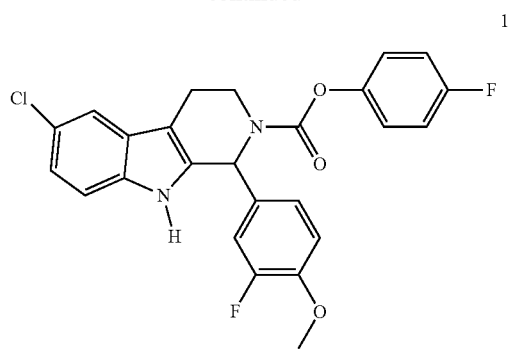
1196
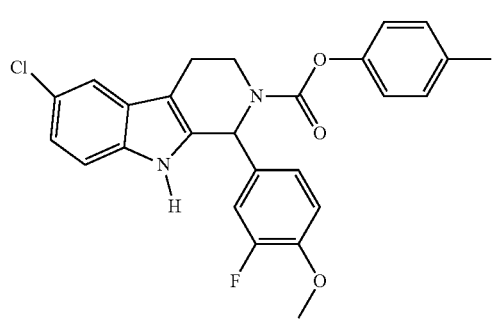
1197
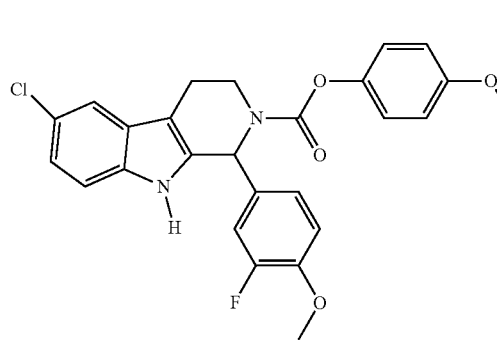
1199
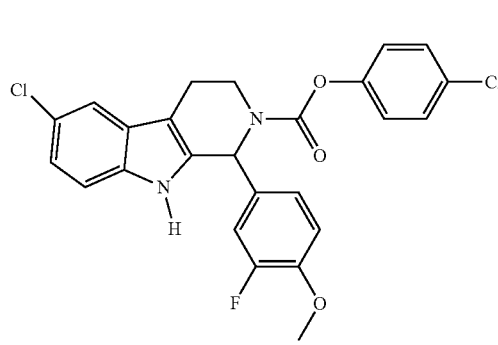
362
-continued
1203
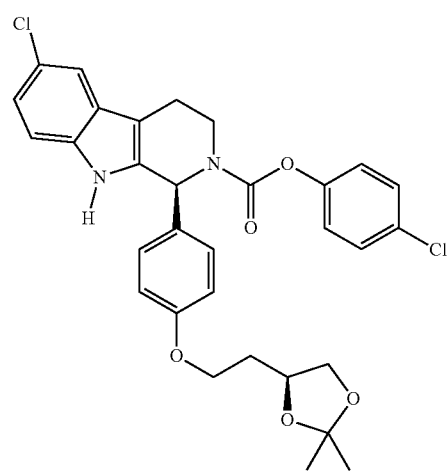
1205
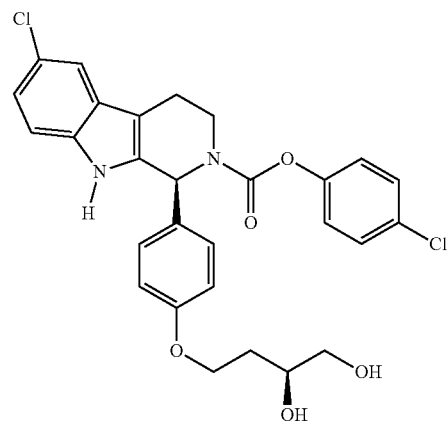
1207
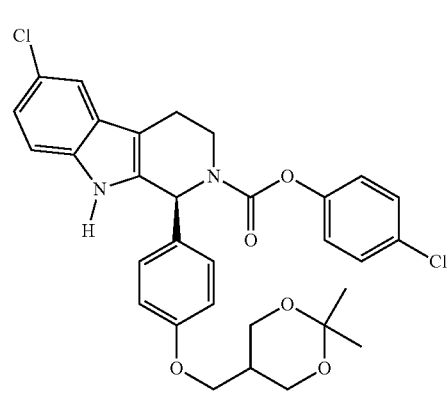
1209
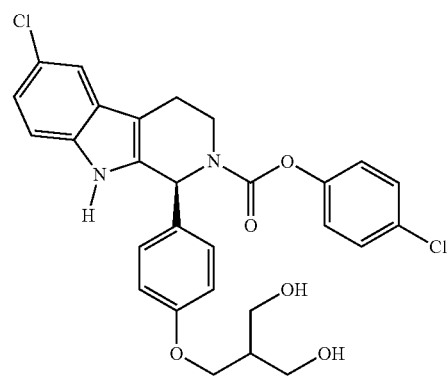

1213
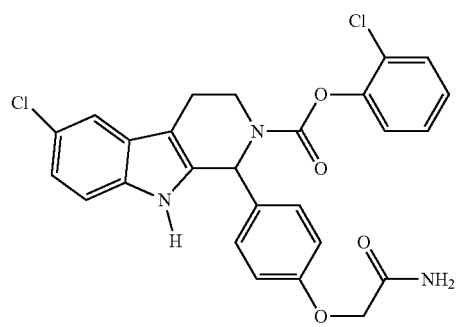
1216
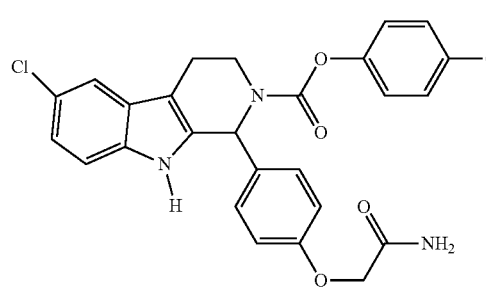
1223
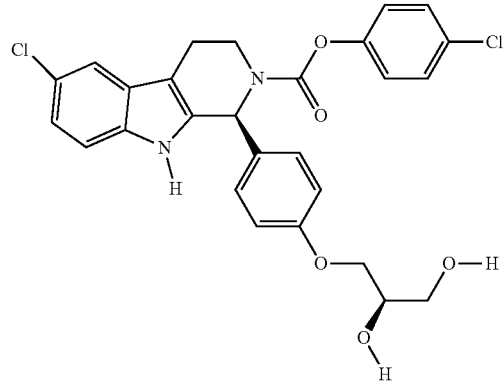
1224
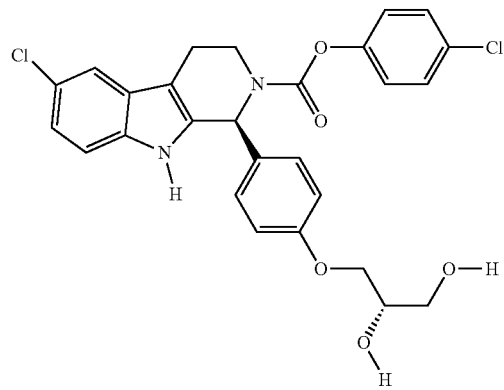
1225
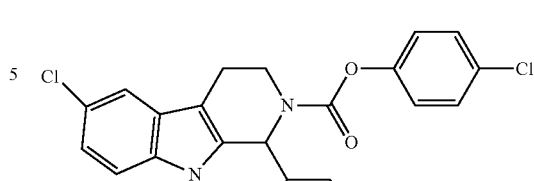
1227
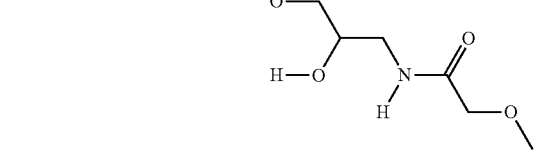
1228
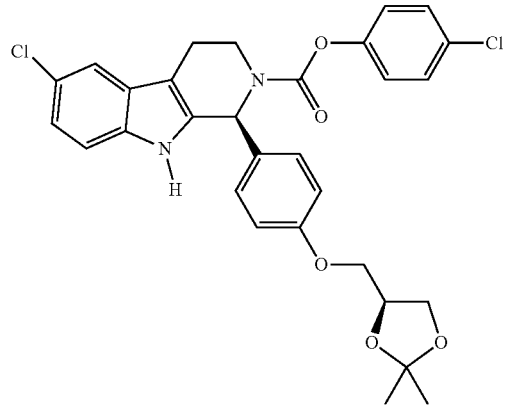

365
-continued
366
-continued
1229
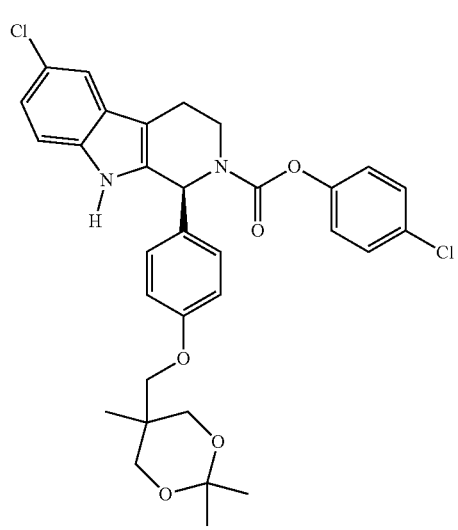
1234
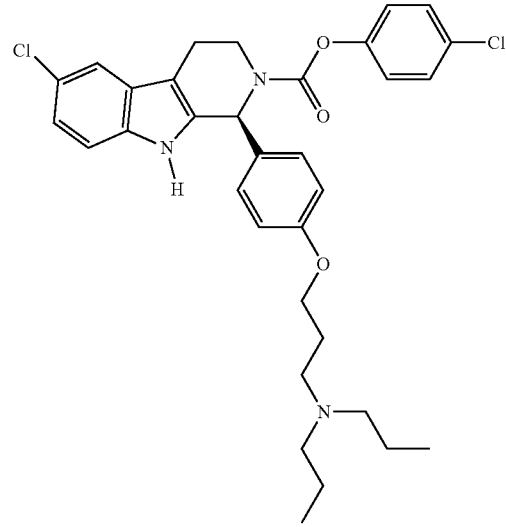
1230
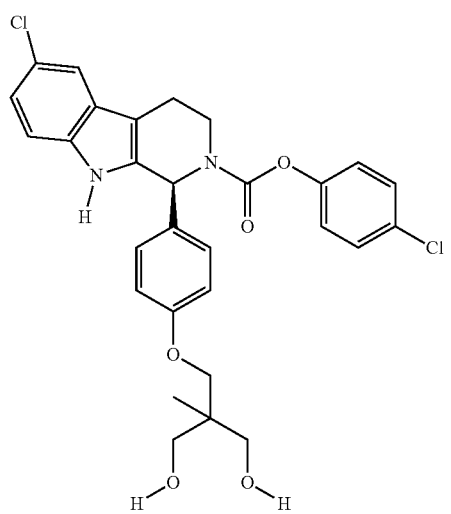
1235
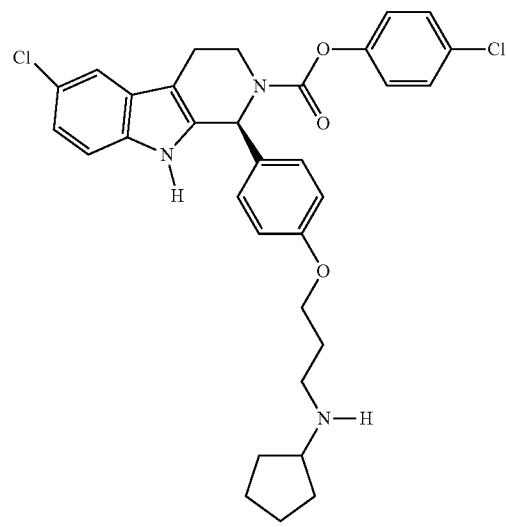
1231
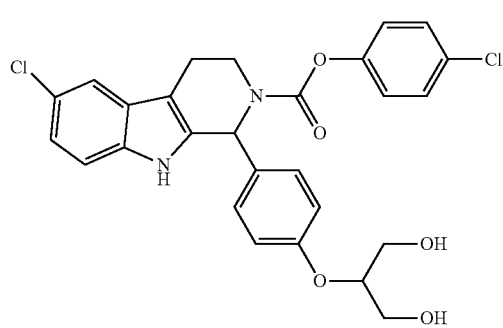
1250
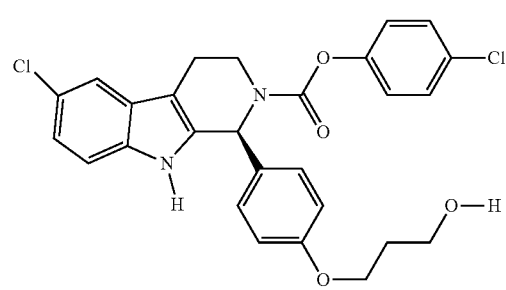

1255
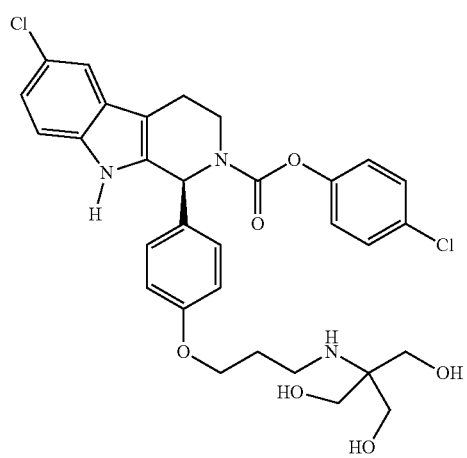
1257
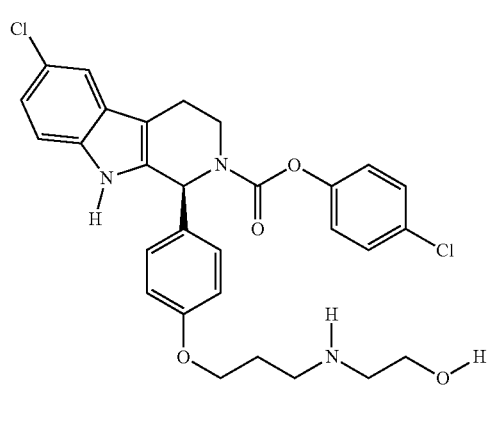
1258
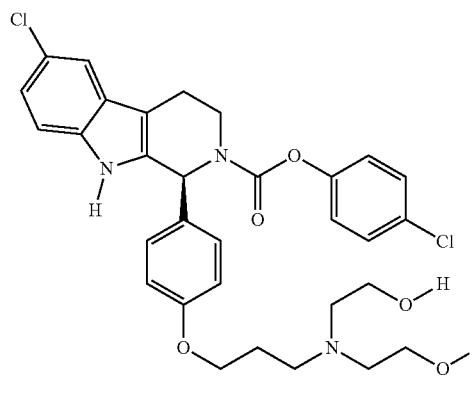
1259
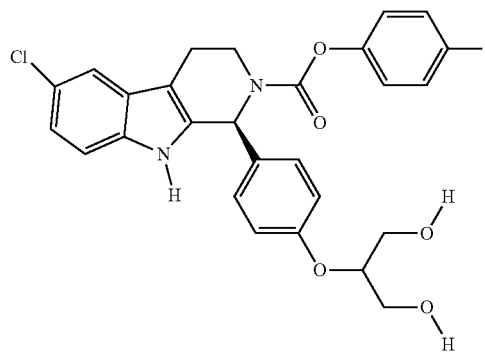
1260
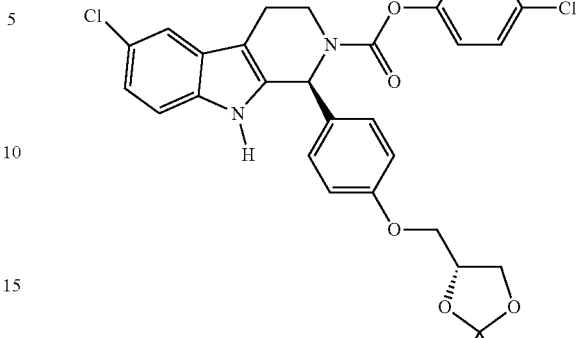
1263
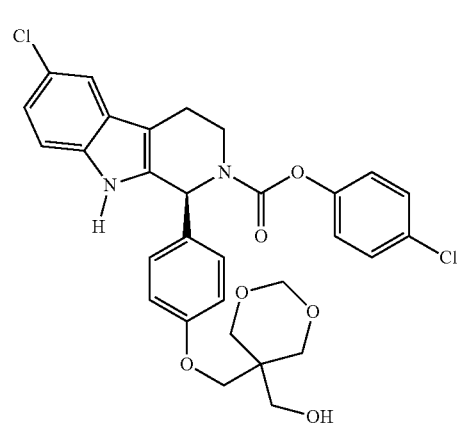
1265
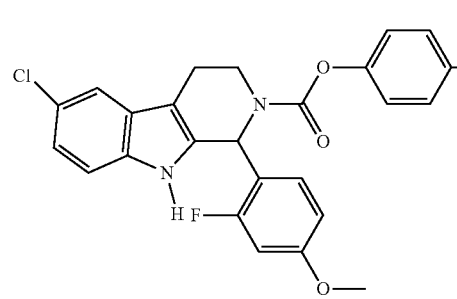
1266
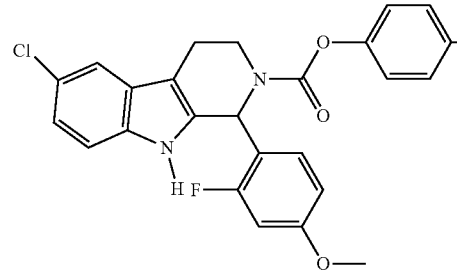

1267 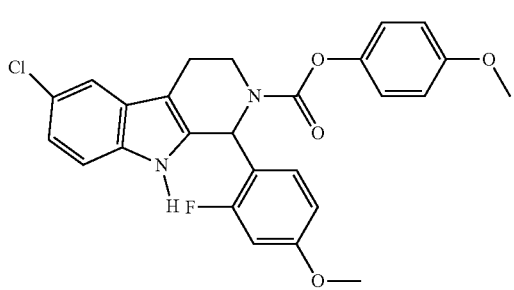
1269 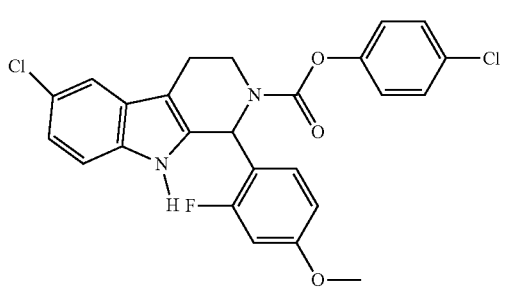
1276 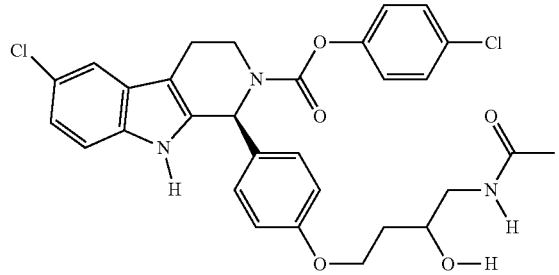
1277 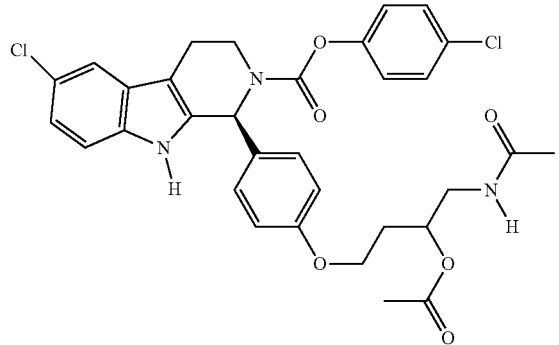
1278 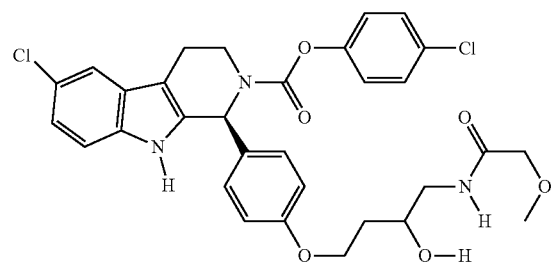
1279 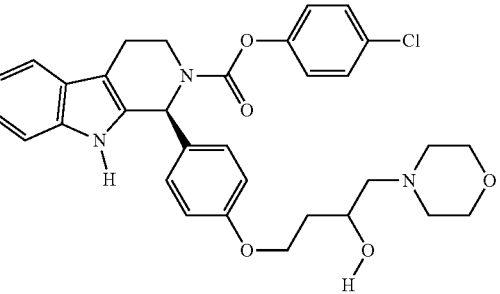
1280 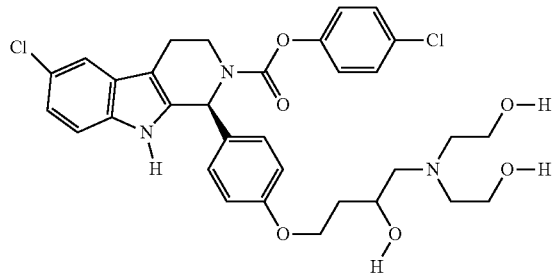
1281 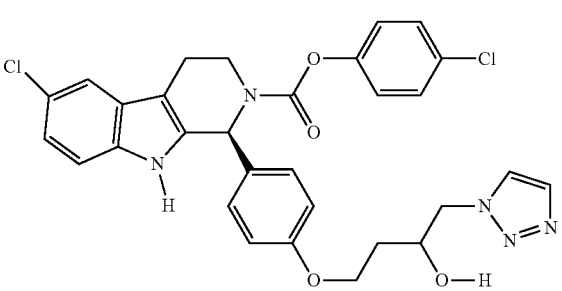
1282 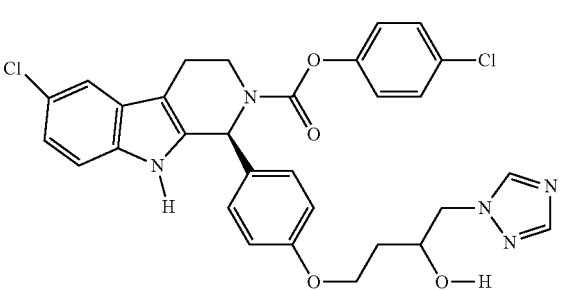
1288 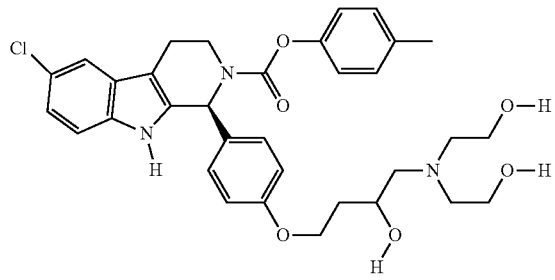

1289
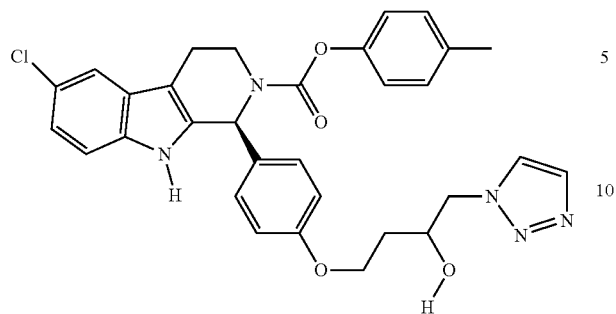
1297
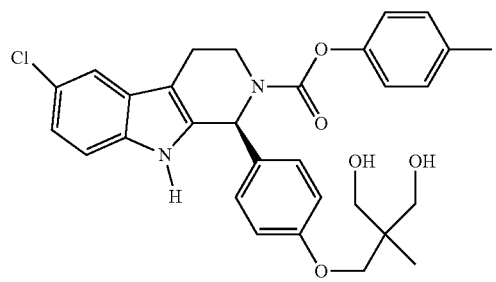
1290
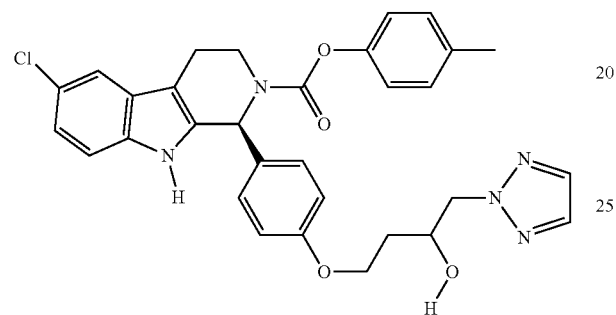
1299
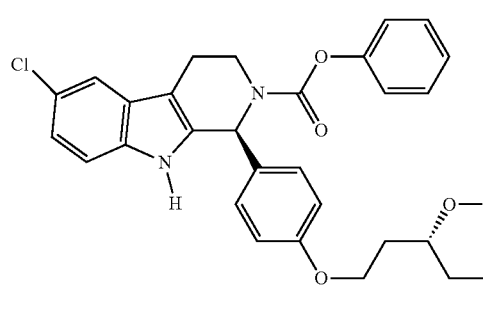
1291
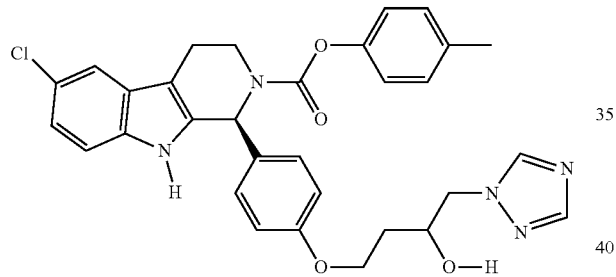
1300
1292
1301
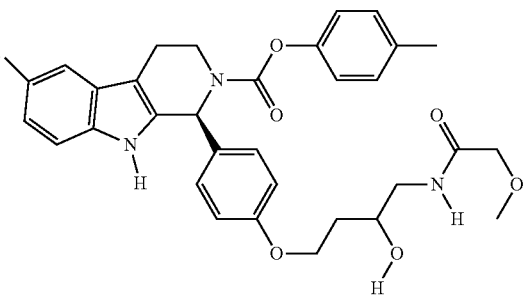
1293
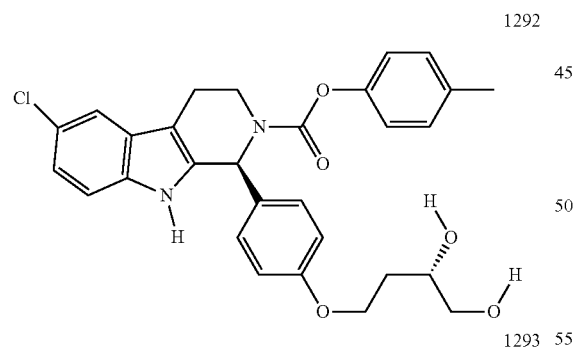
1302
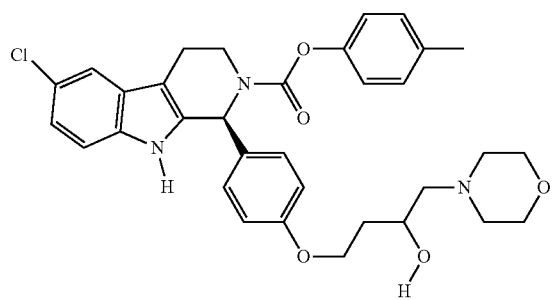
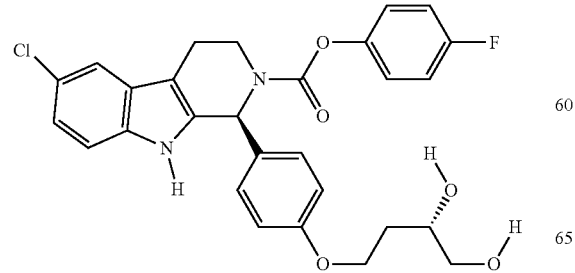

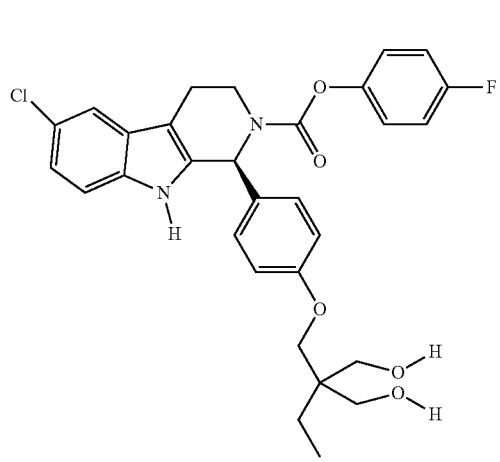
1328
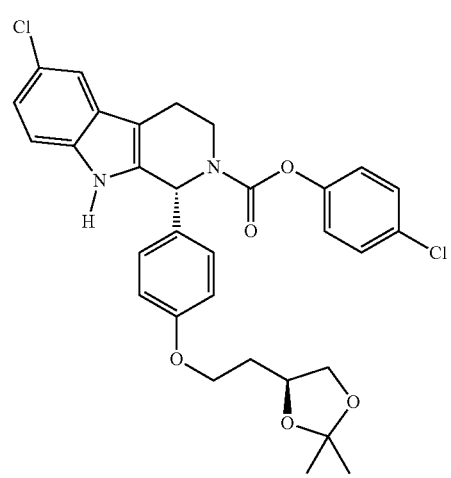
1331
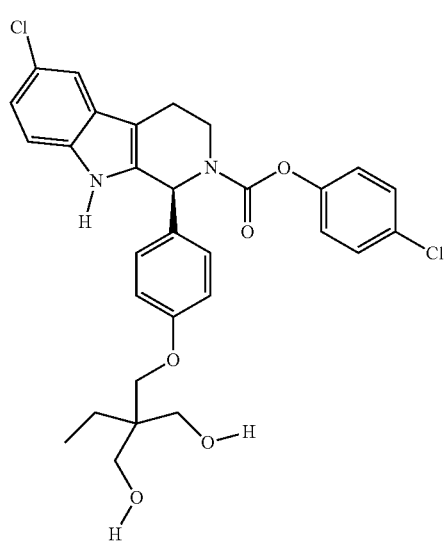
1329
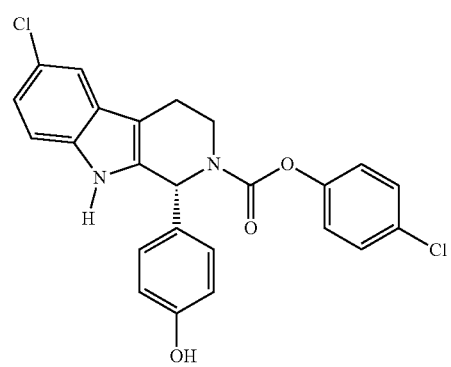
1332
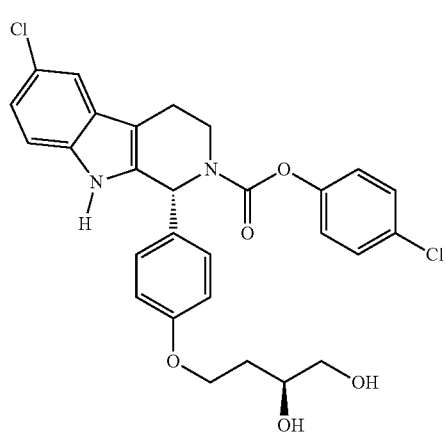
1330
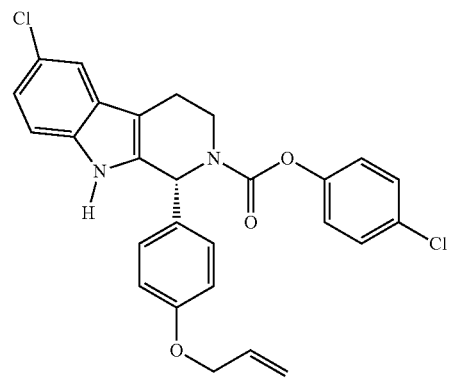
1333

1335
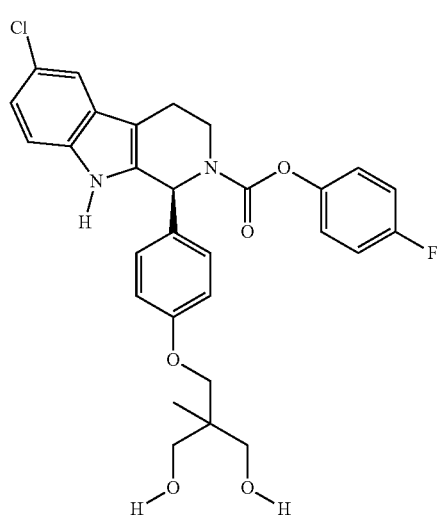
1336
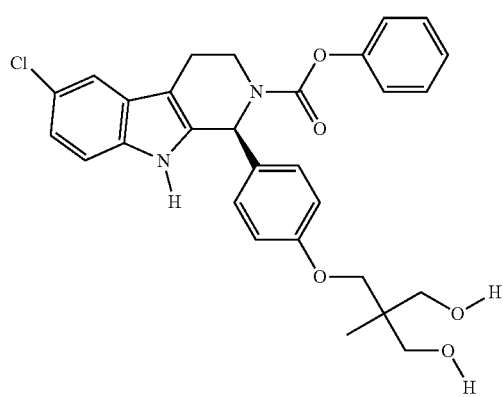
1337
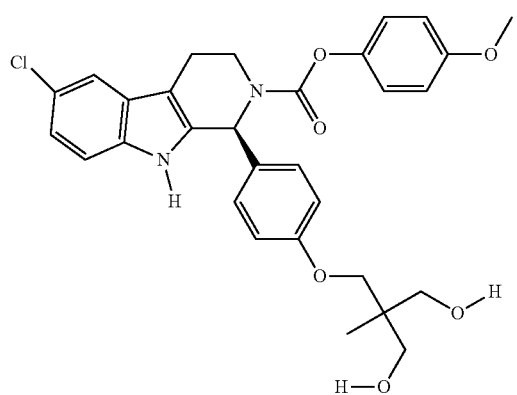
1343
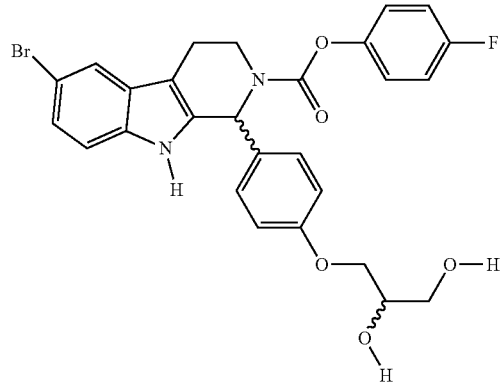
1344
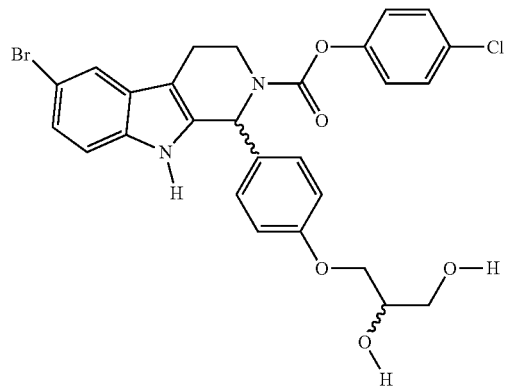
1348
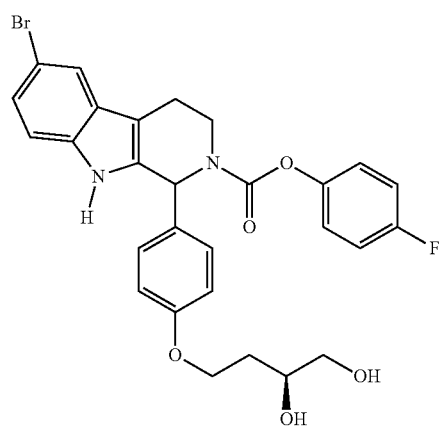
1349
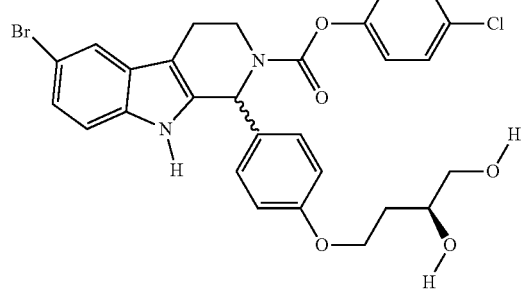

1352
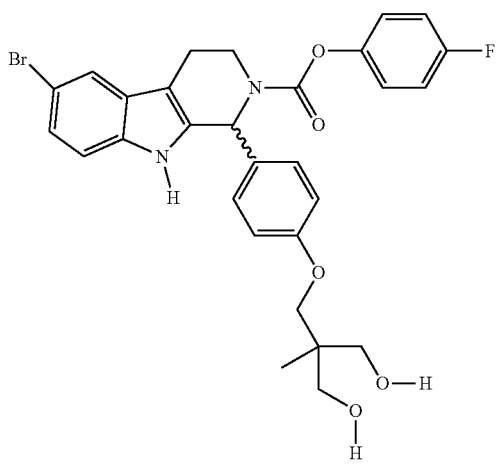
1353
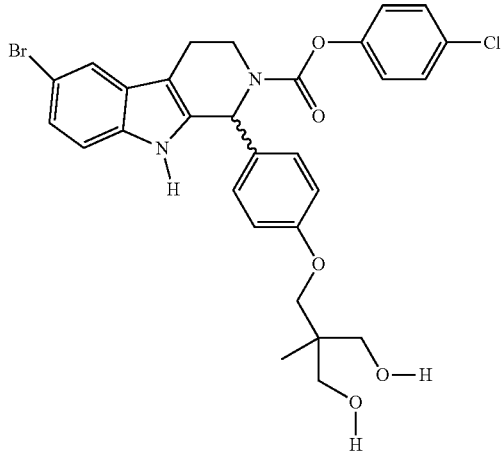
1357
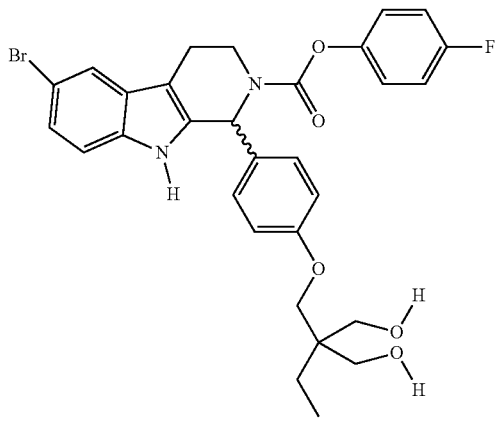
1358
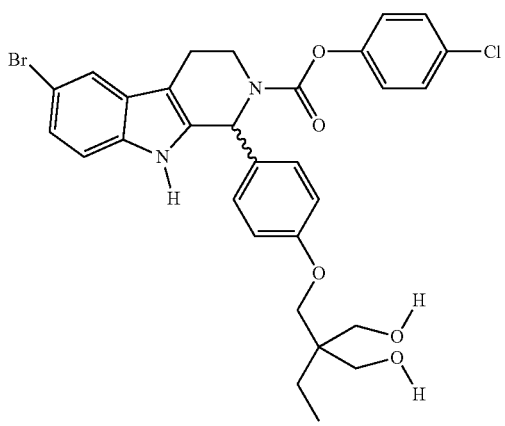
1361
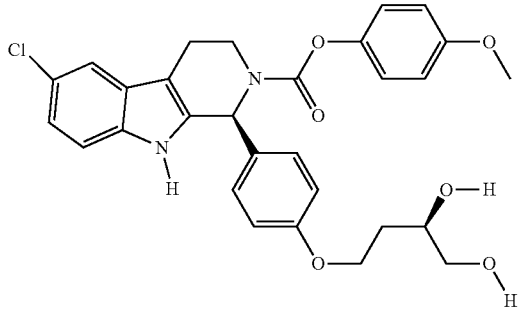
1362
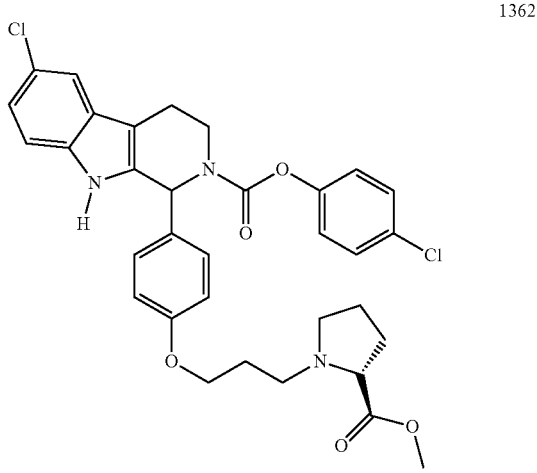
1364
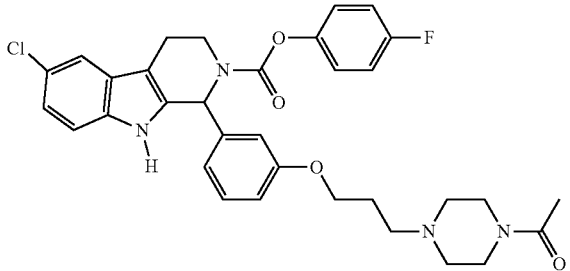

-continued
1391
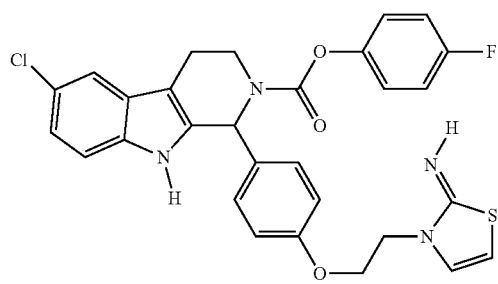
1392
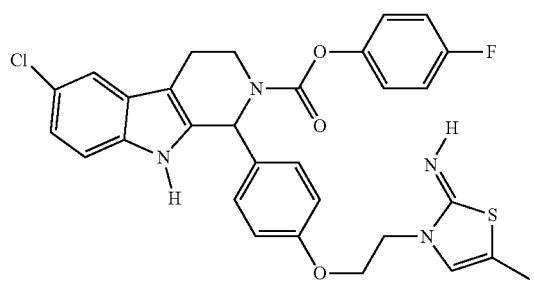
1393
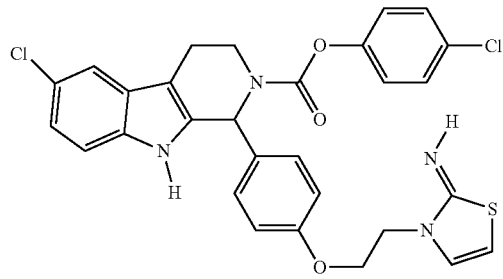
1394
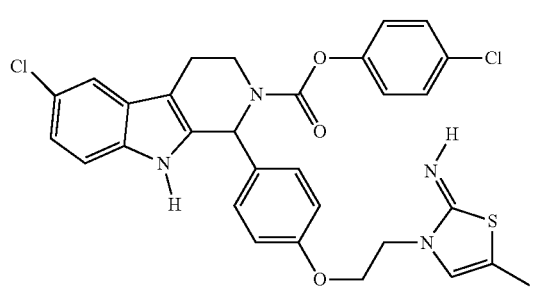
1413
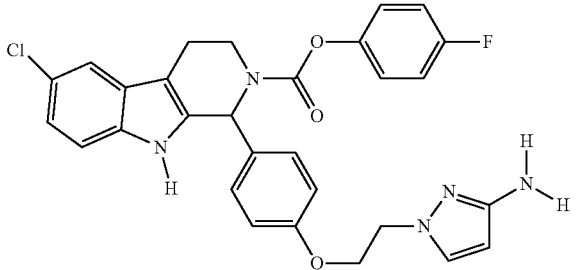
-continued
1414
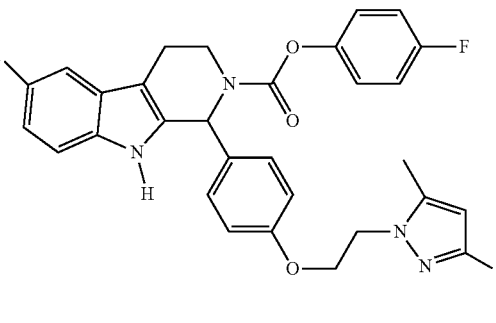
1415
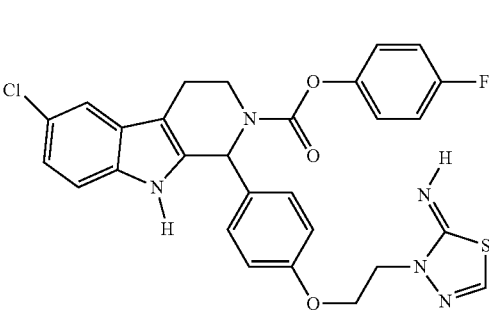
1416
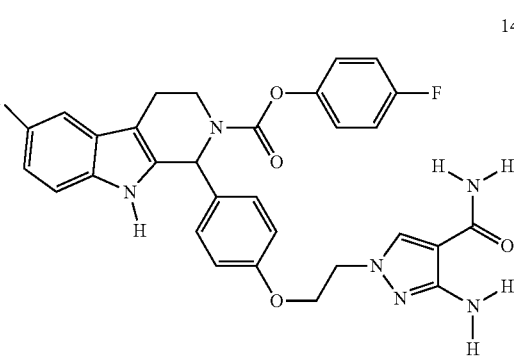
1417
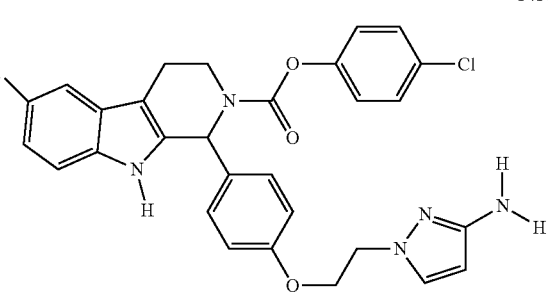
1418
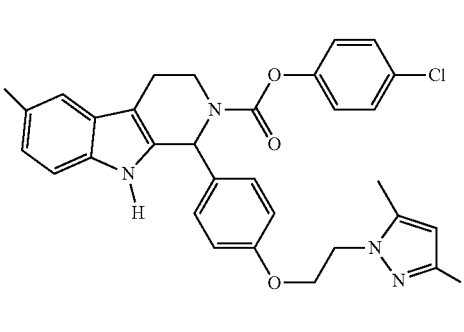

1419
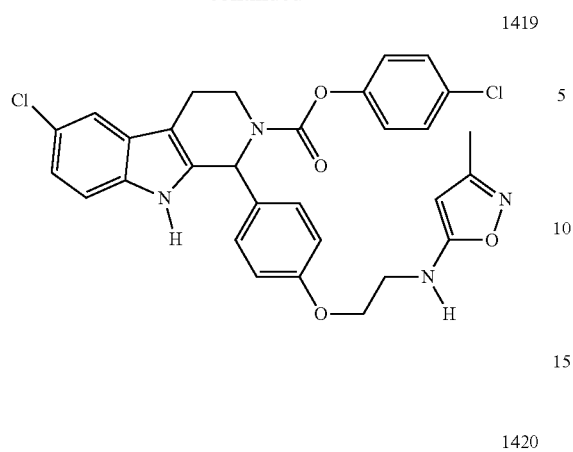
1420
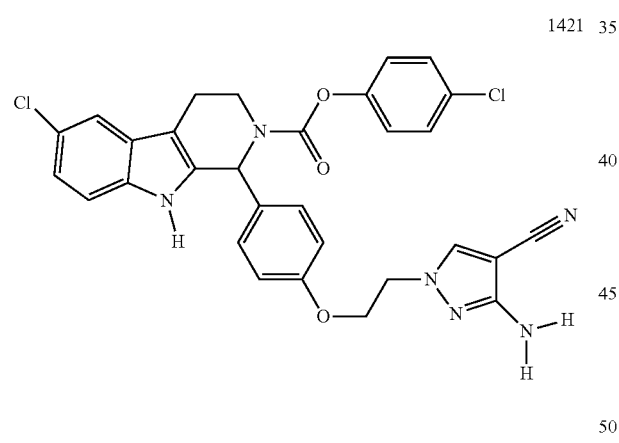
1421
1422
1440
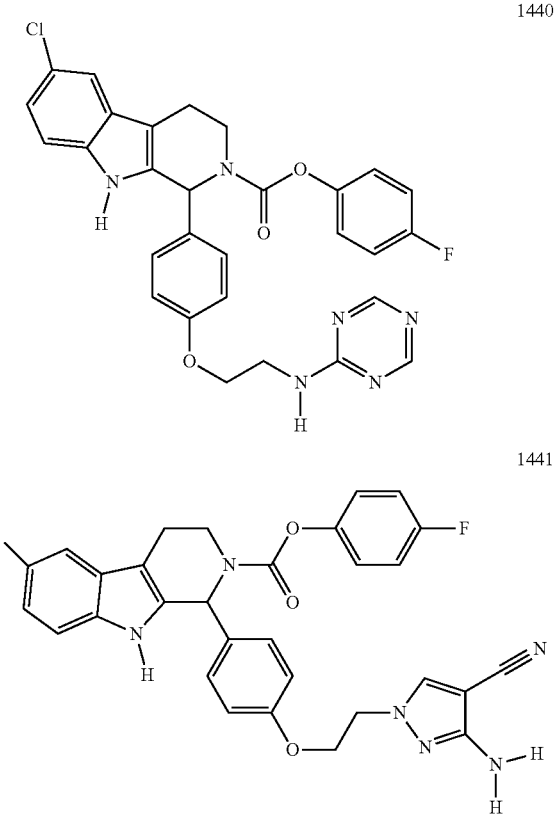
1441
1442
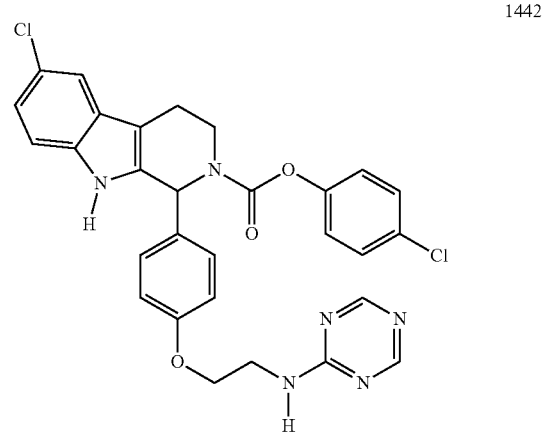
1476
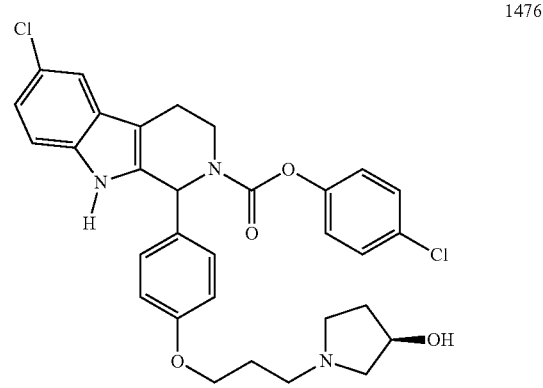

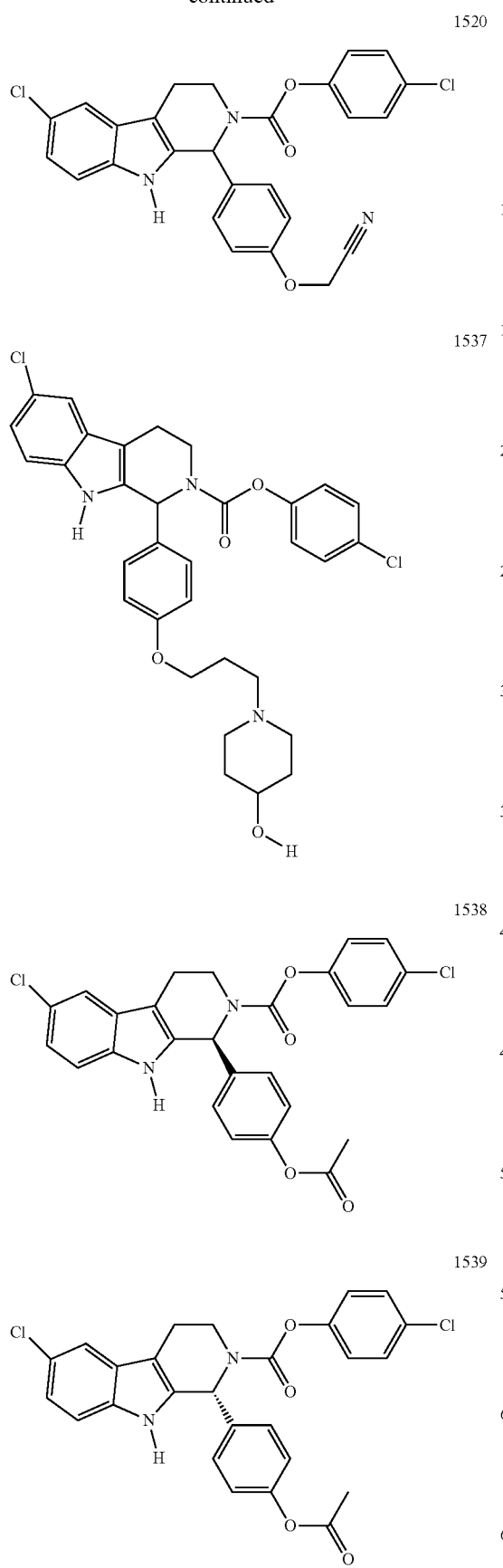
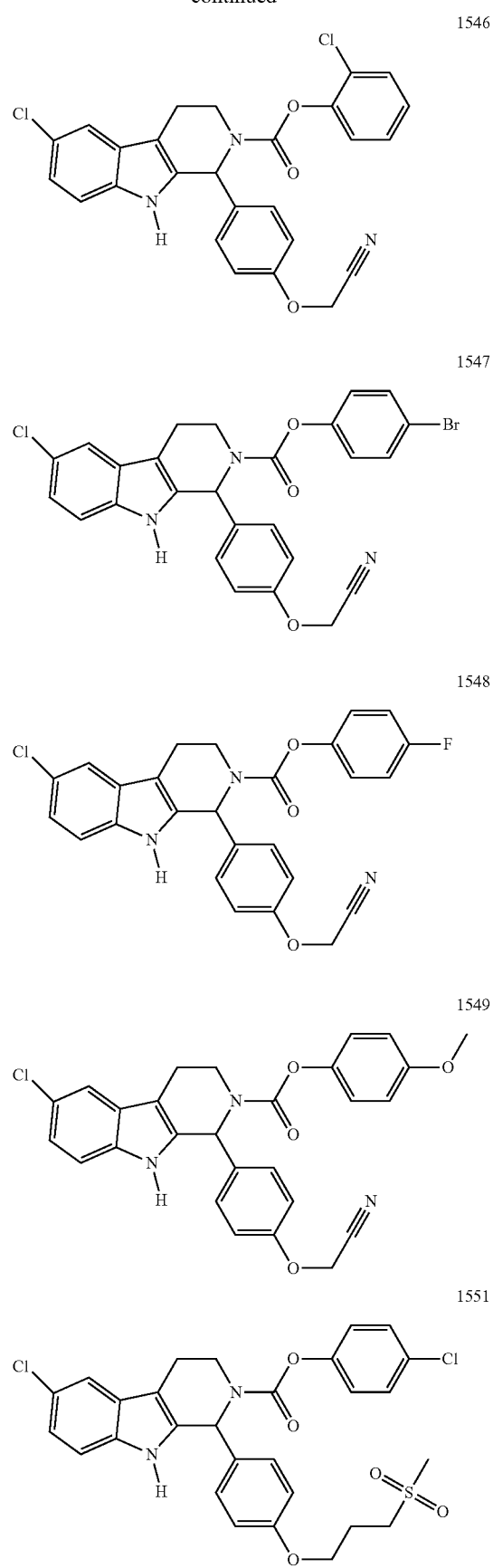

1552
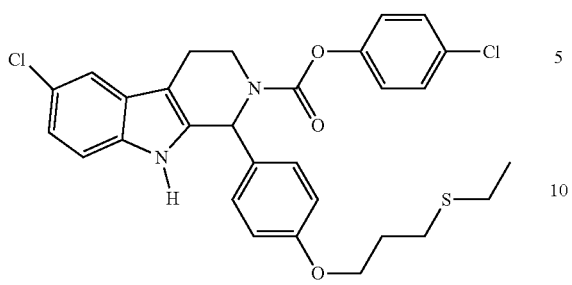
1553
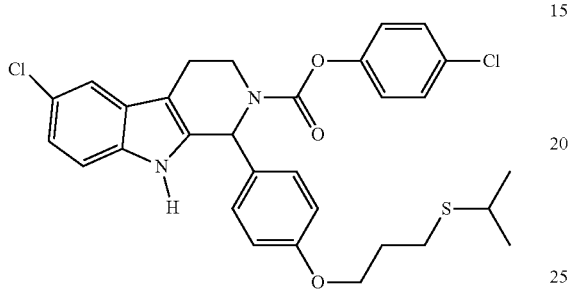
1554
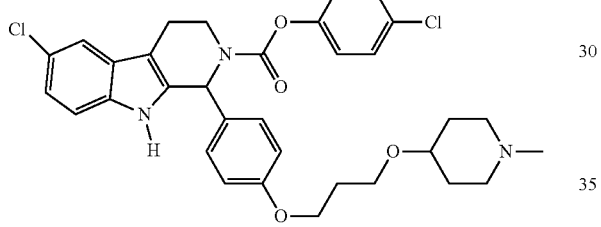
1555
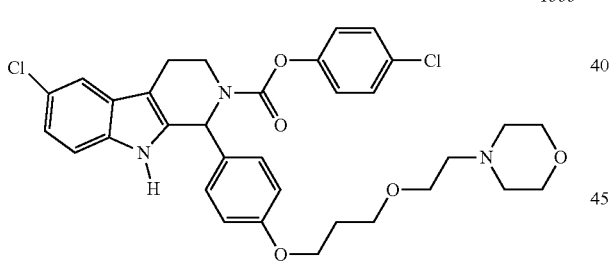
1557
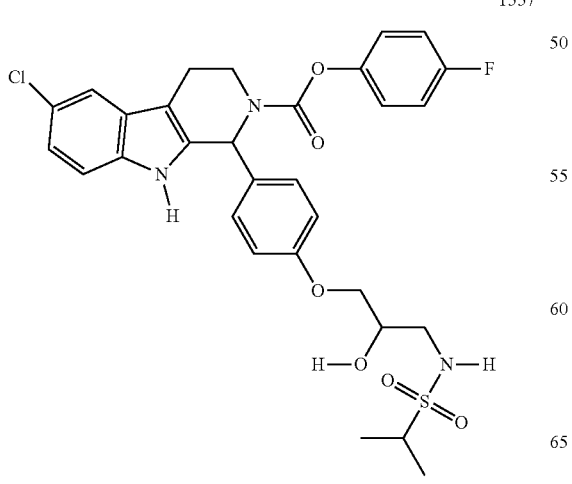
1558
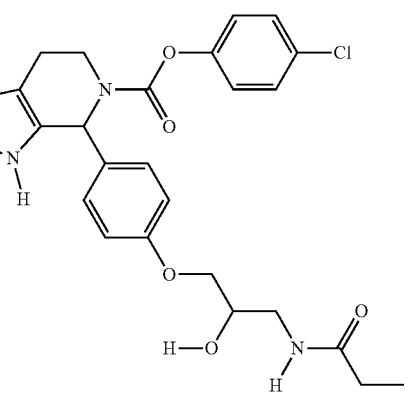
1559
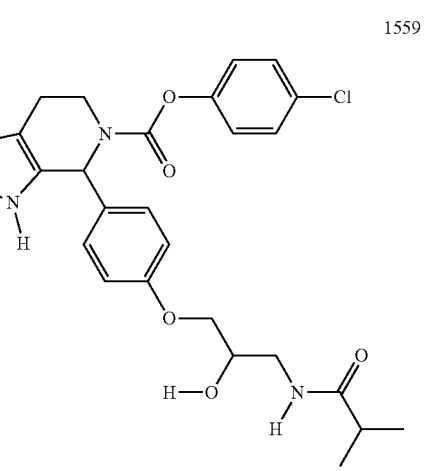
1560
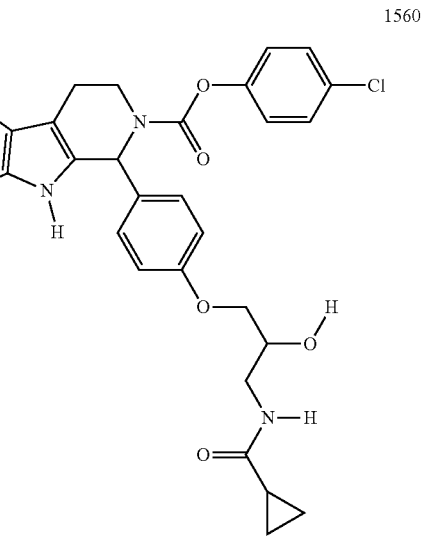

387
-continued
1561
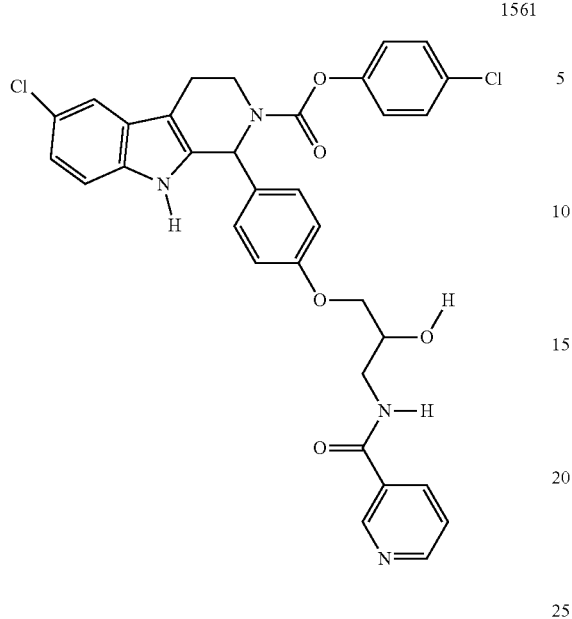
1562
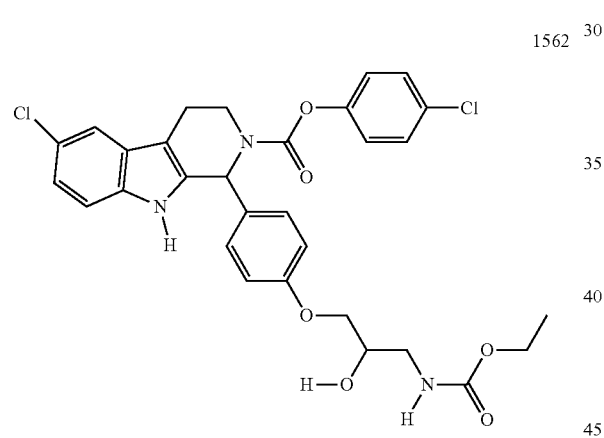
1563
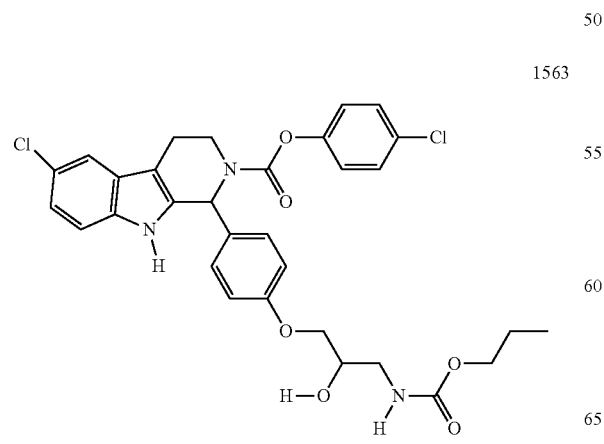
388
-continued
1564
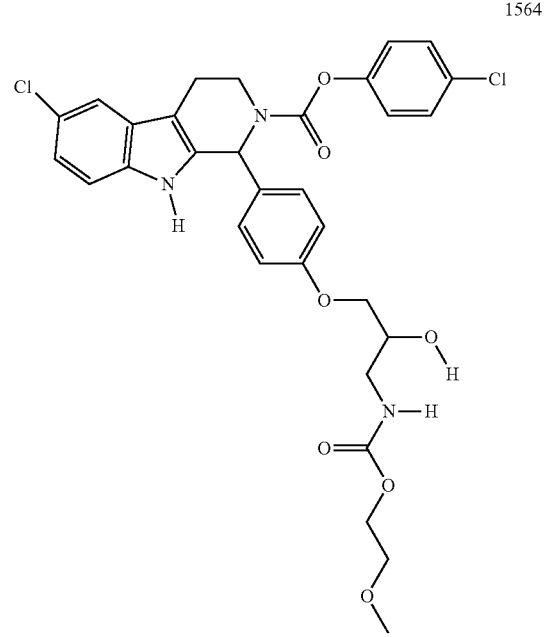
1565
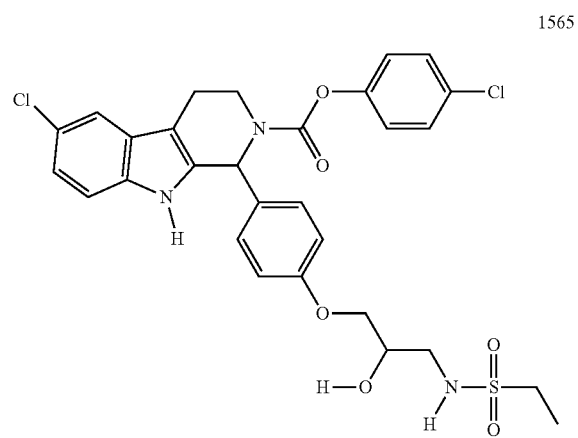
1566
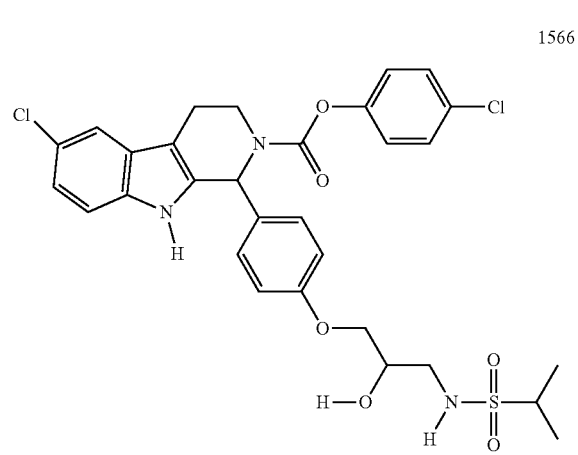

1567
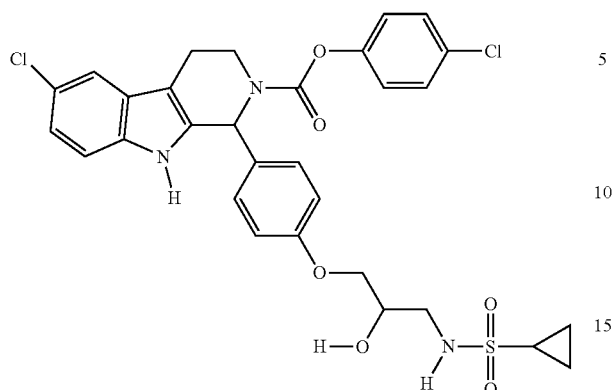
1568
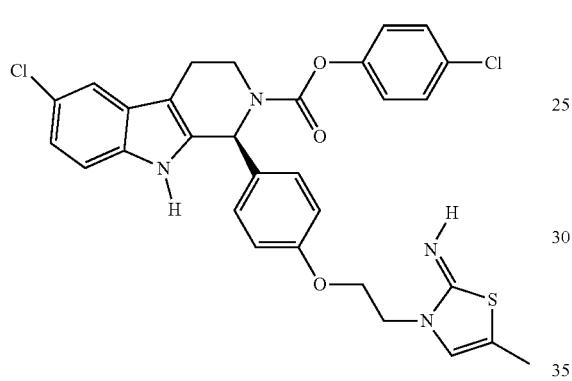
1569
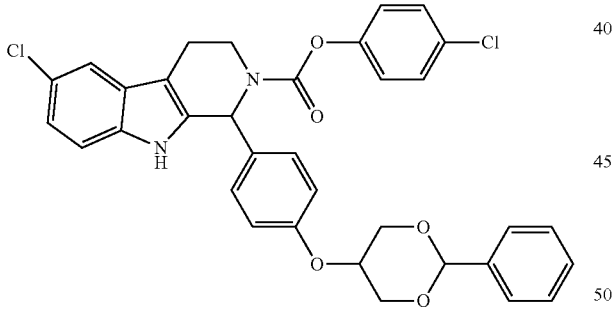
1570
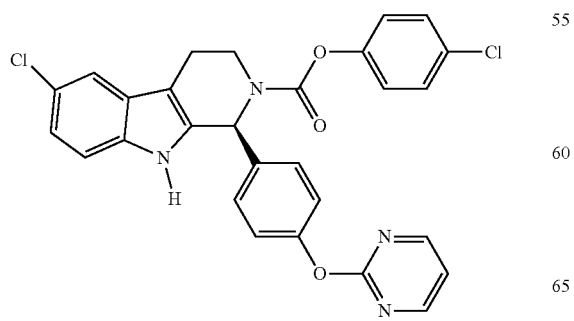
1571
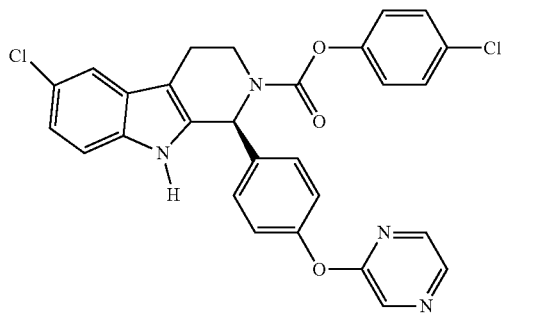
1572
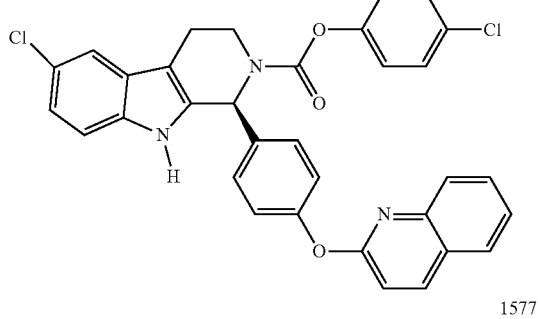
1577
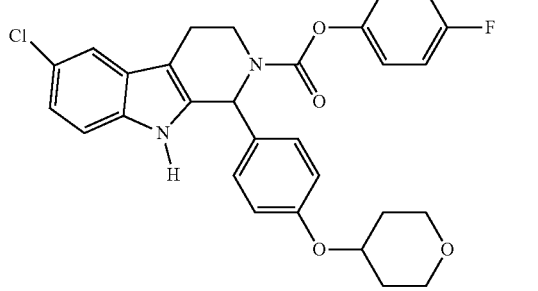
1578
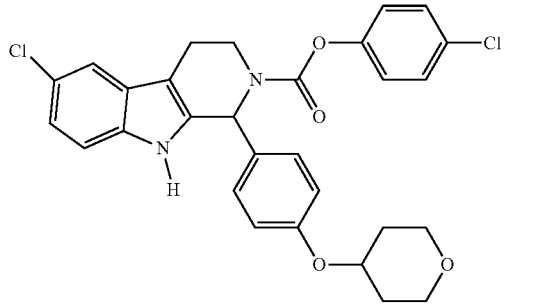
1580
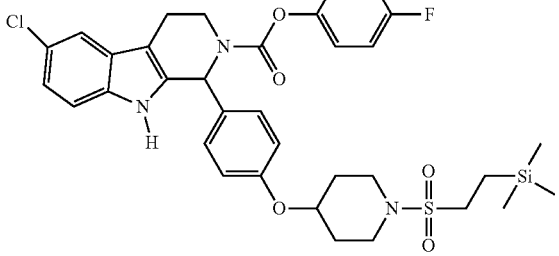

1581
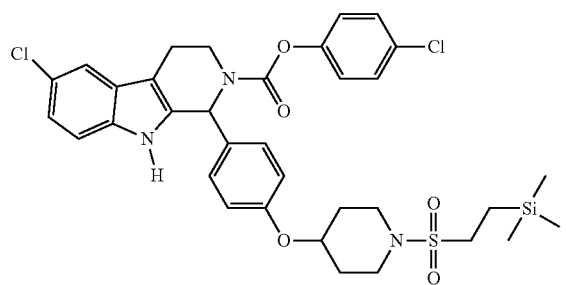
1604
1605
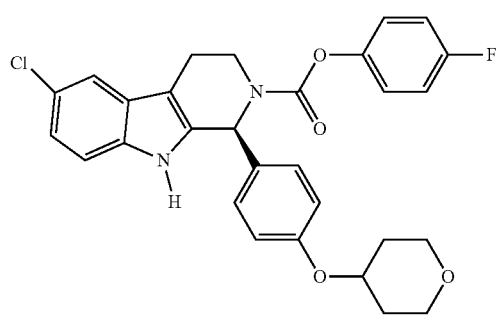
1607
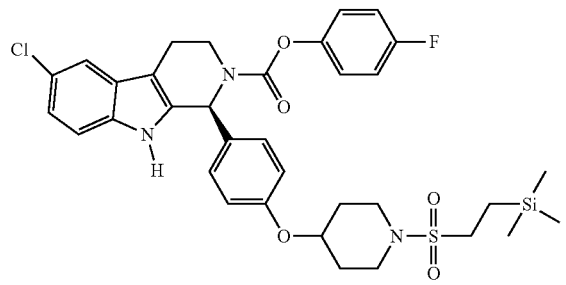
1611
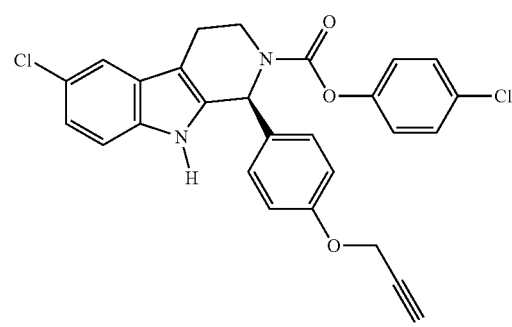
1612
1613
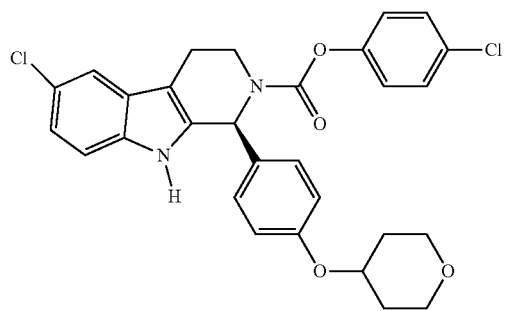
1614
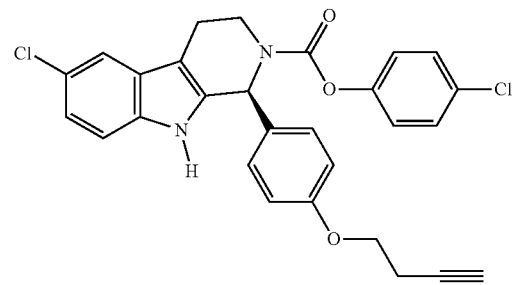

393
-continued
1625
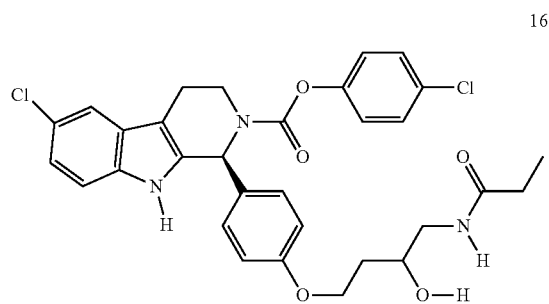
1626
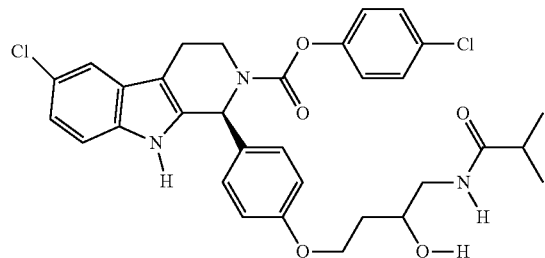
1627
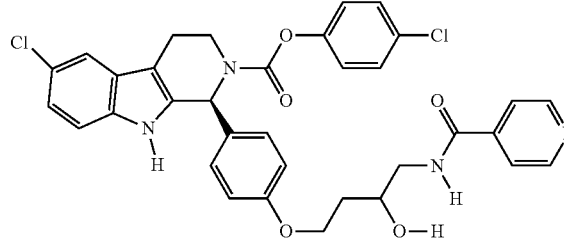
1628
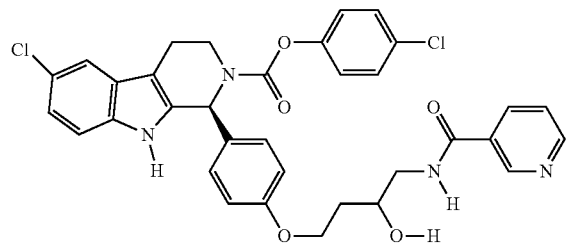
1629
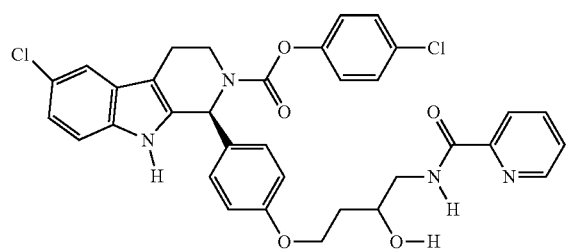
394
-continued
1635
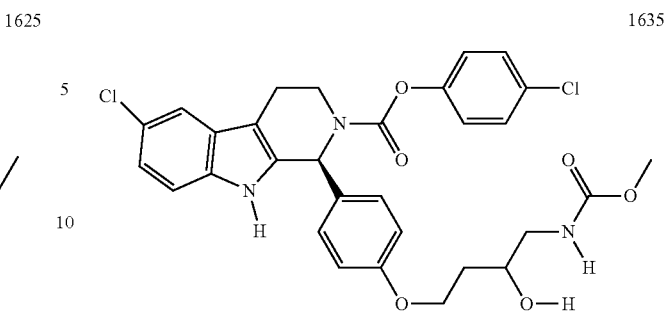
1636
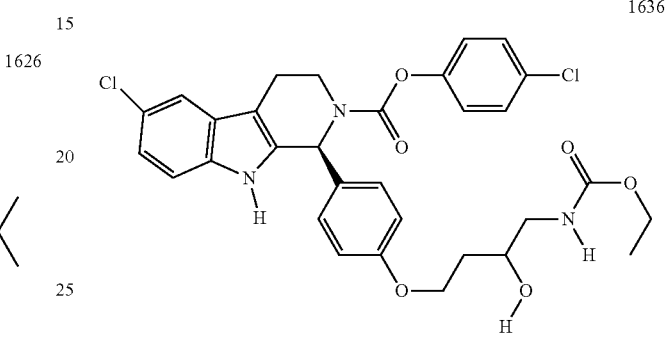
1637
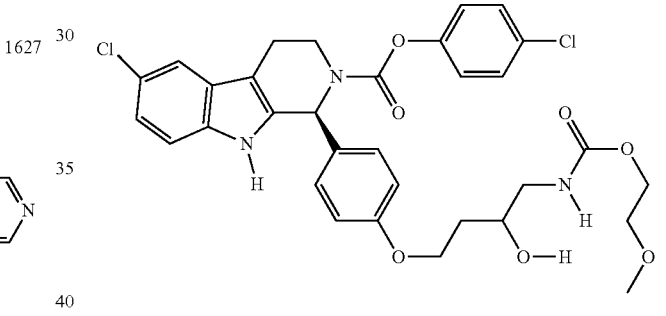
1638
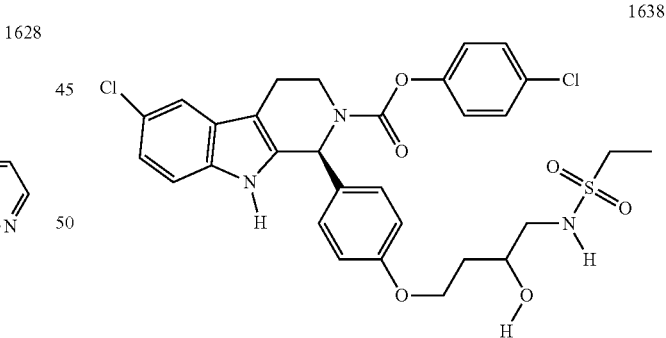
1639
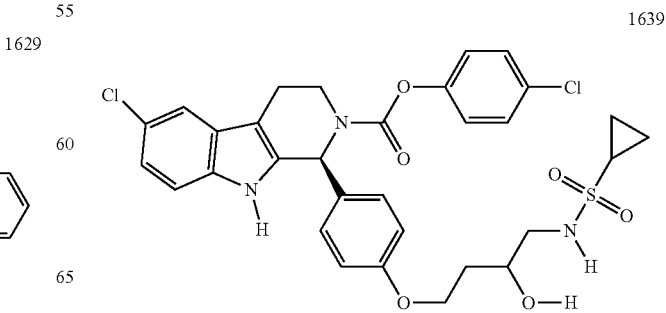

1640
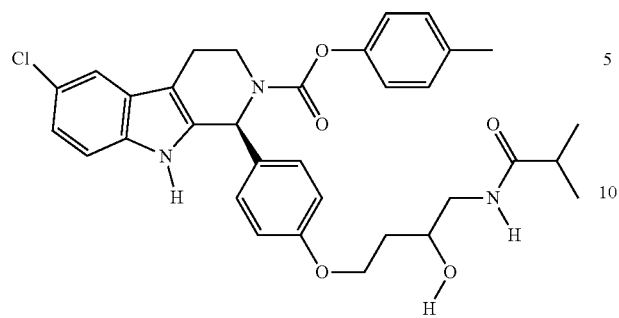
1641
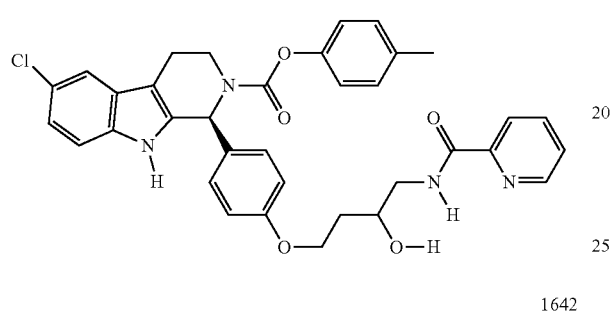
1642
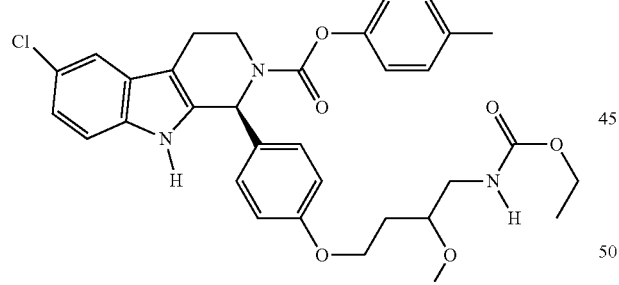
1643
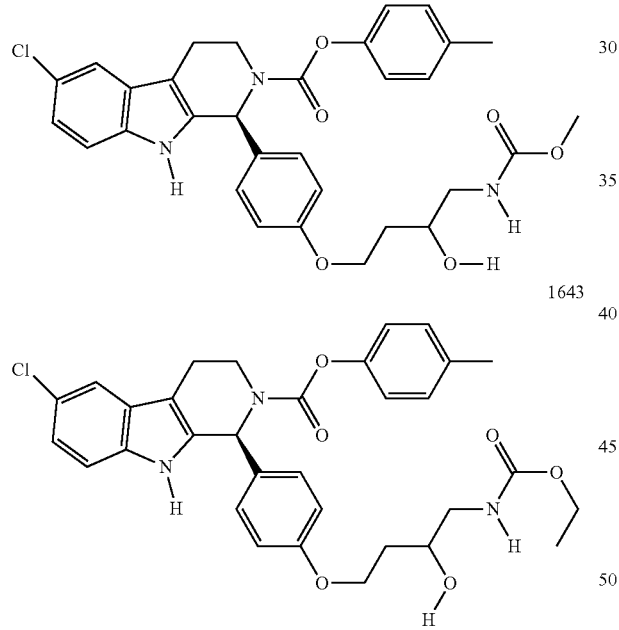
1644
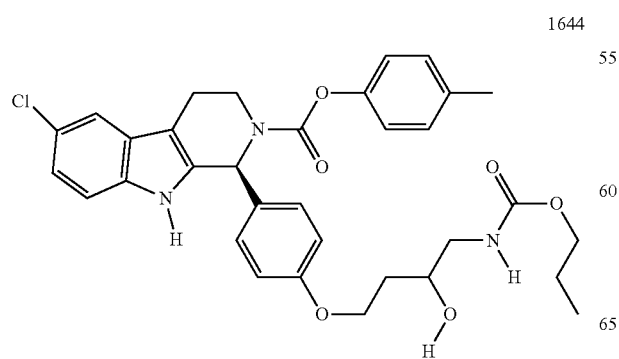
1645
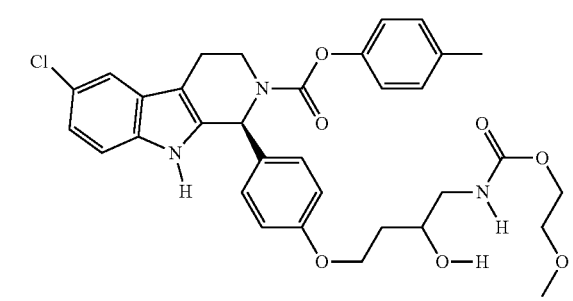
1646
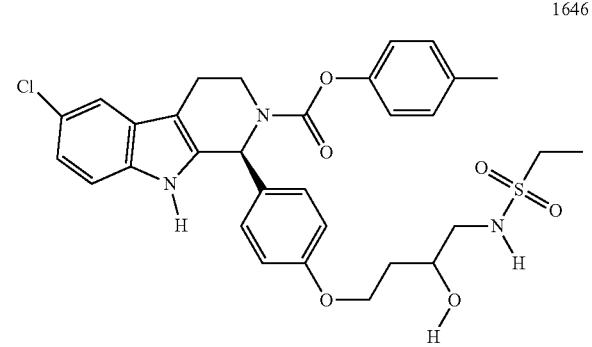
1647
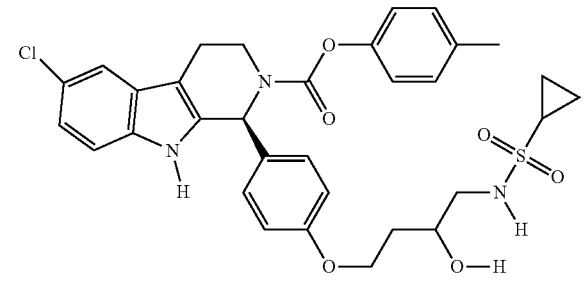
1648
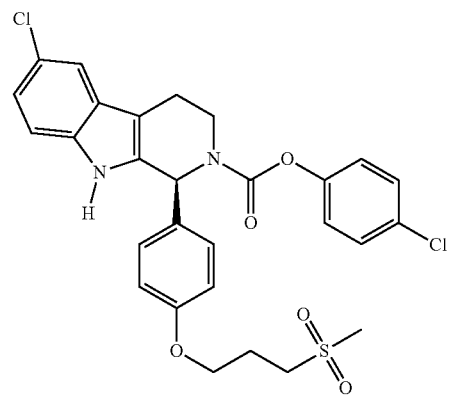

397
-continued
1652
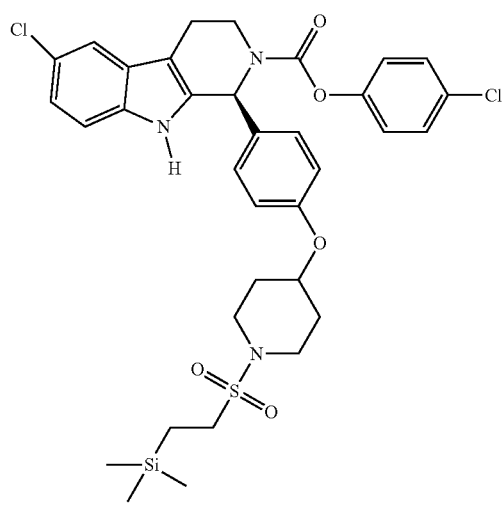
1658
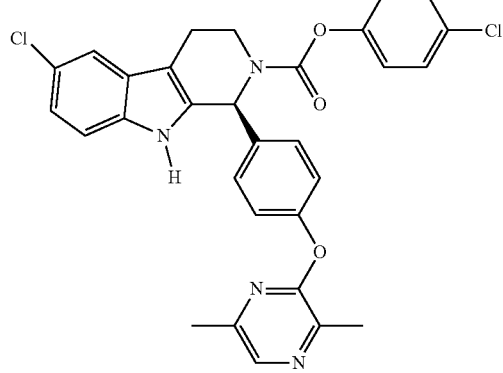
1659
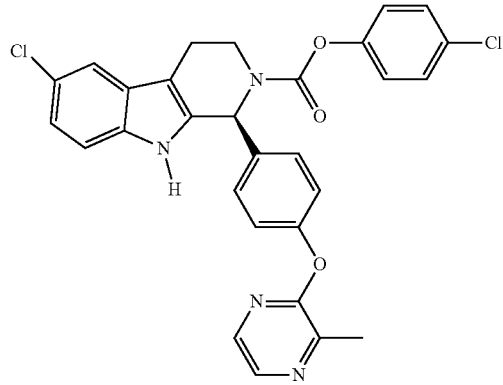
398
-continued
1660
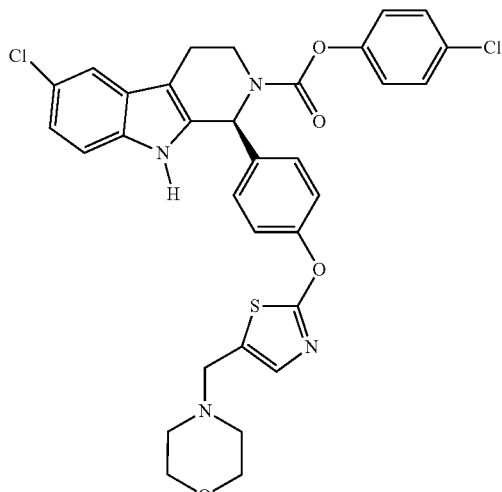
1661
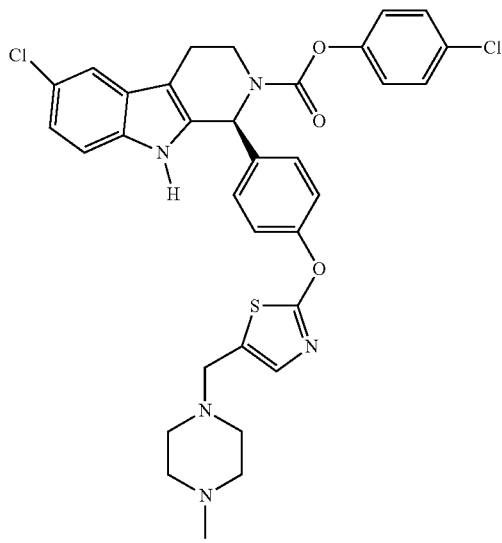
1663
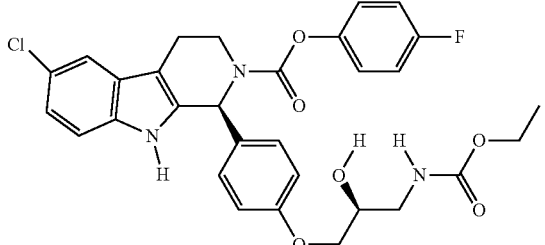
1664
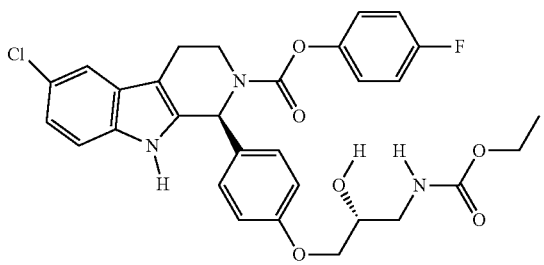

1666
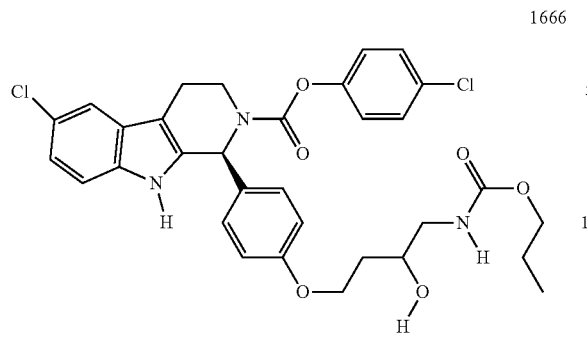
1667
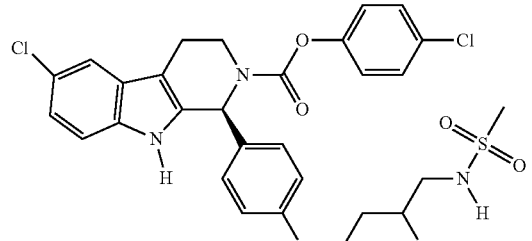
1668
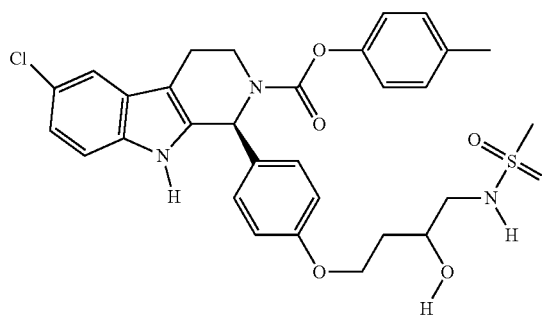
1669
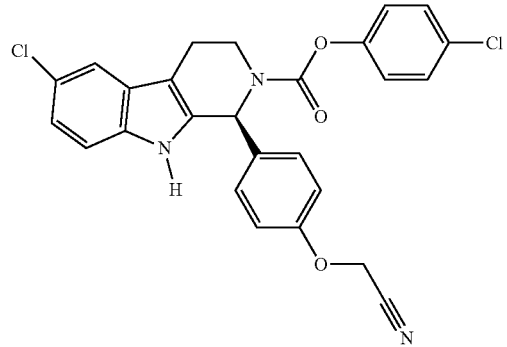
1670
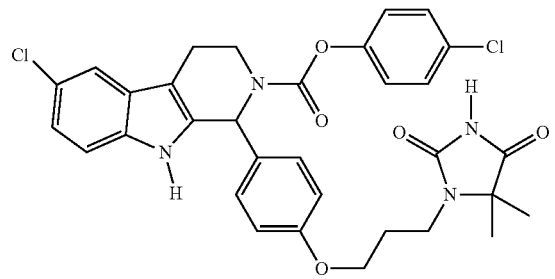
1671
1672
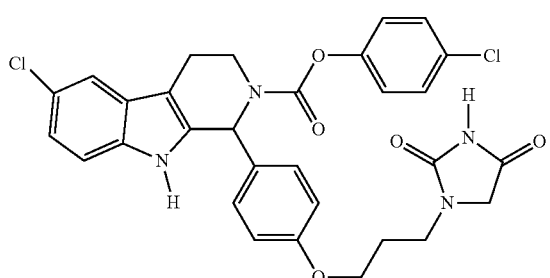
1673
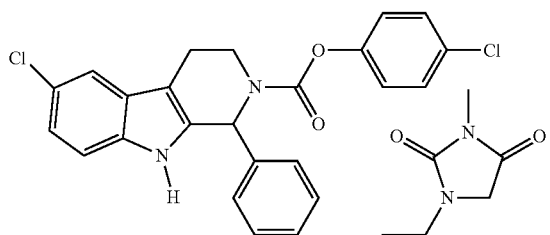
1674
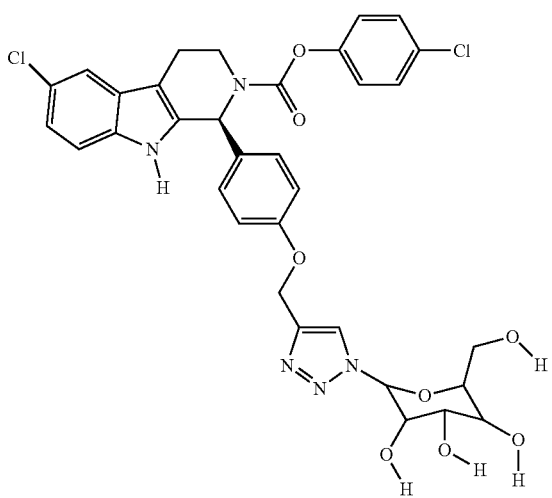
1675
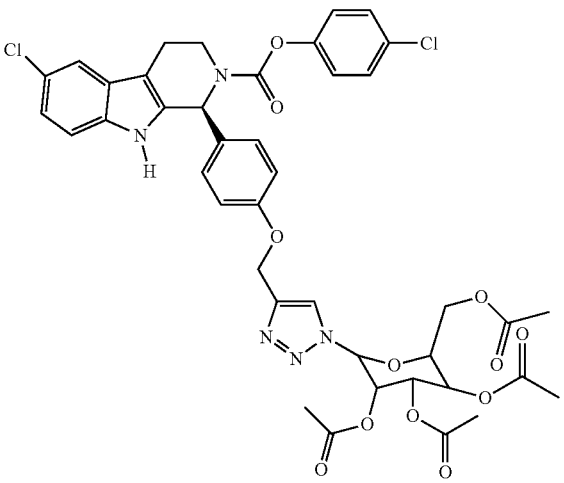

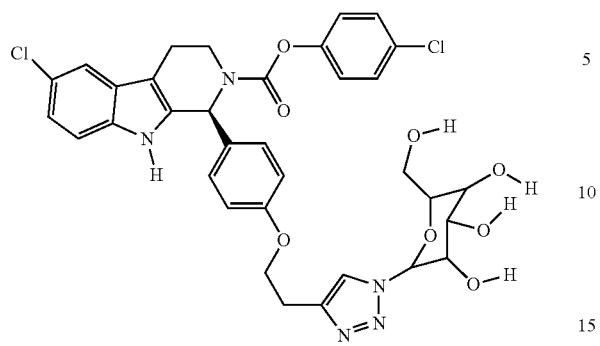
1676
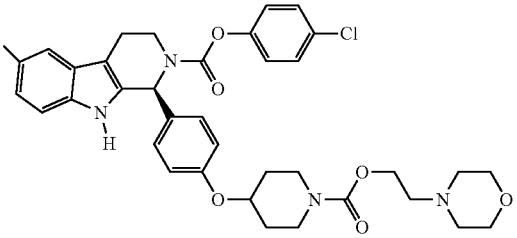
1693
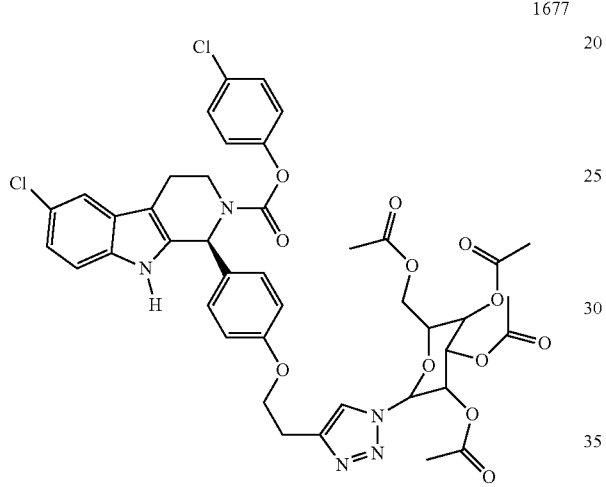
1677
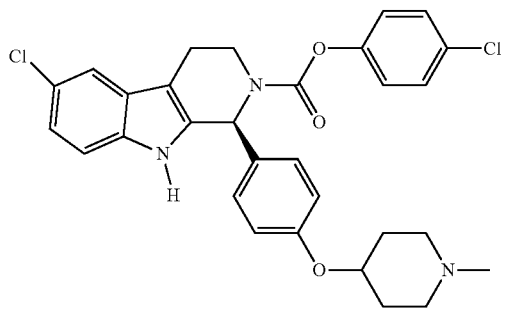
1694
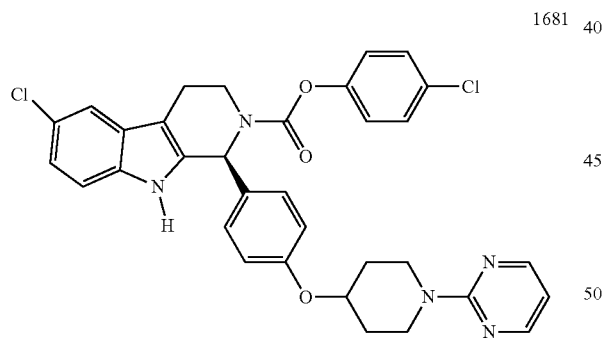
1681
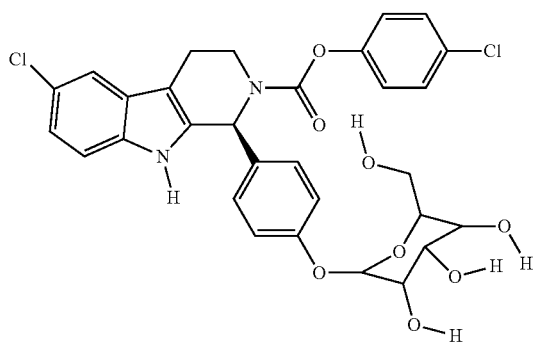
1695
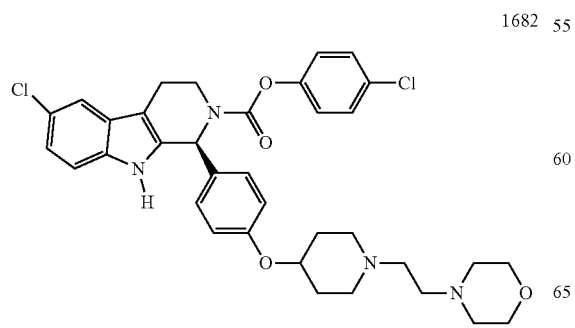
1682
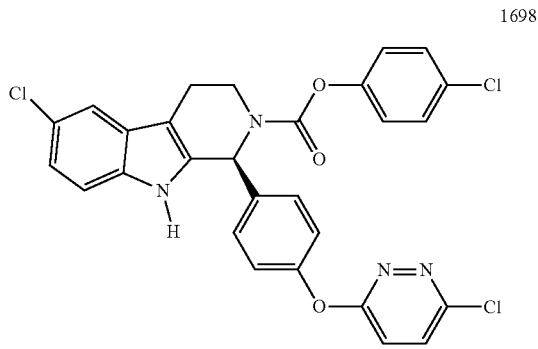
1698

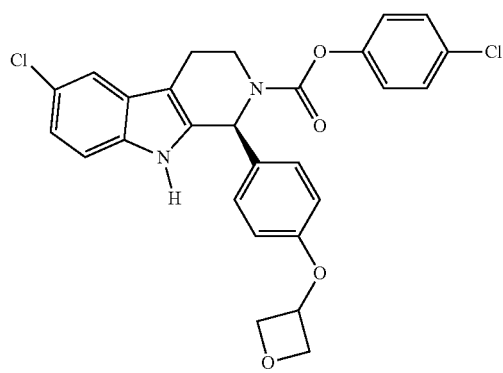 [SMILES: O=C(Oc1ccc(Cl)cc1)N1CCc2c([nH]c3ccc(Cl)cc23)[C@@H]1c1ccc(OC2COC2)cc1]
1701
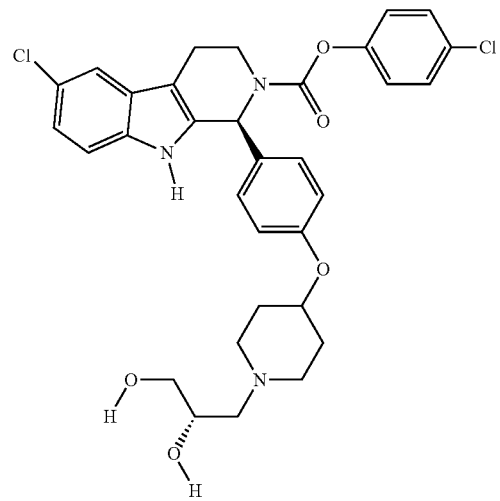
1704
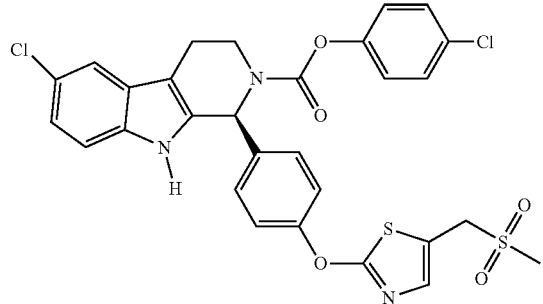
1702
1725
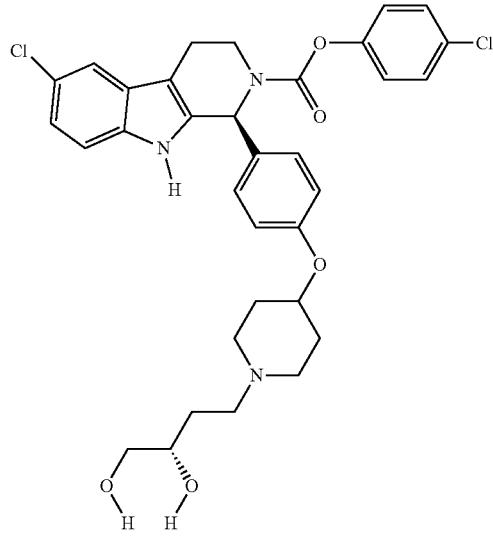
1703
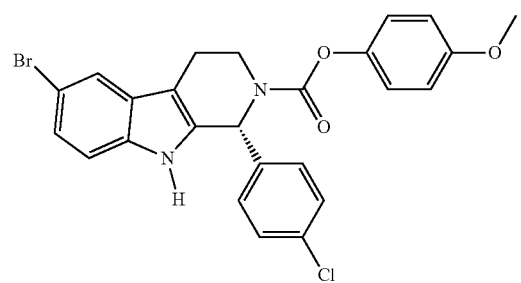
1726
1727

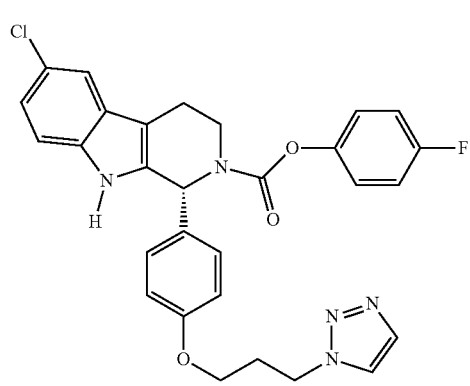 [SMILES: O=C(Oc1ccc(F)cc1)N1CCc2c([nH]c3ccc(Cl)cc23)[C@H]1c1ccc(OCCCn2ccnn2)cc1]
1728
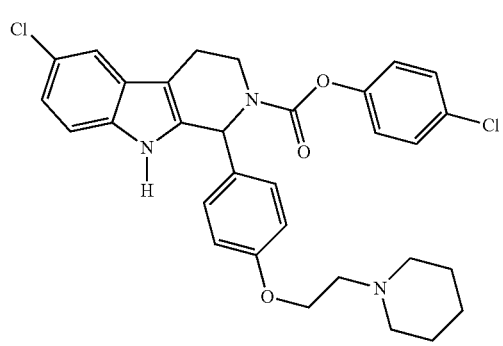
1729
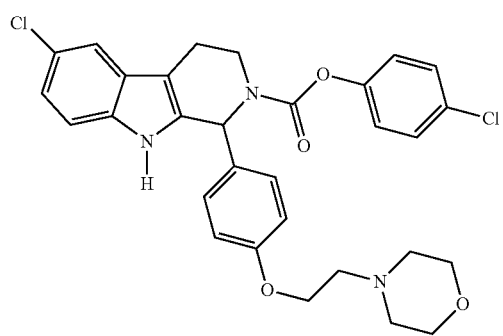
1730
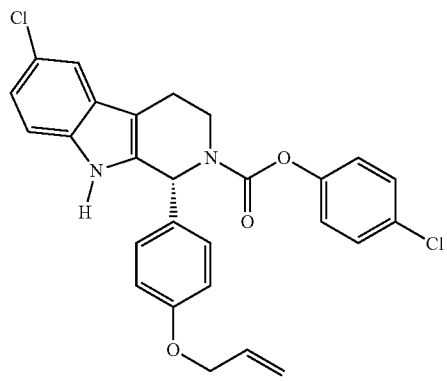
1731
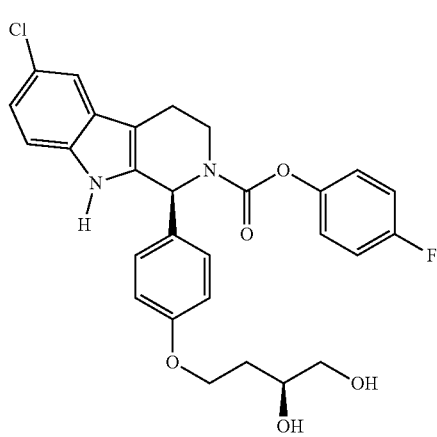
1732
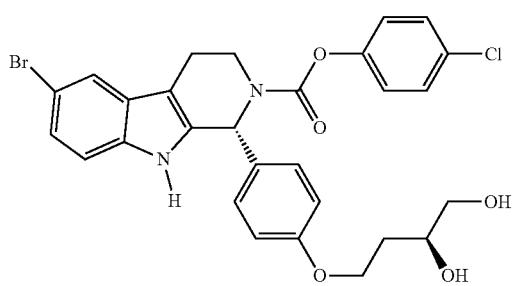
1733
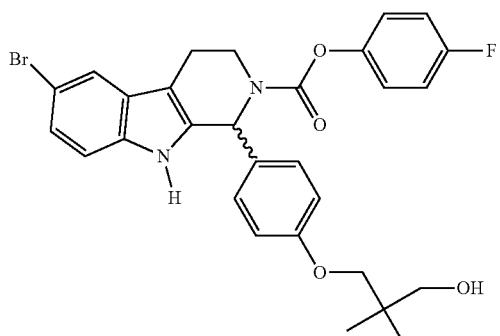
1734
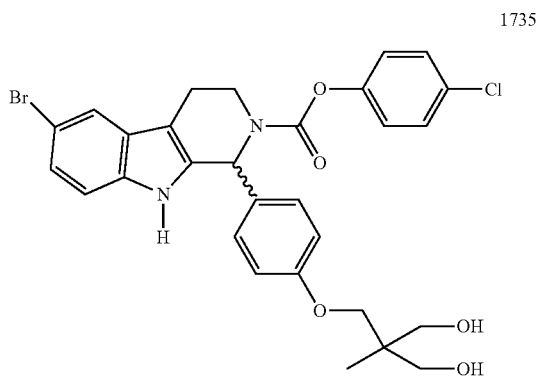
1735

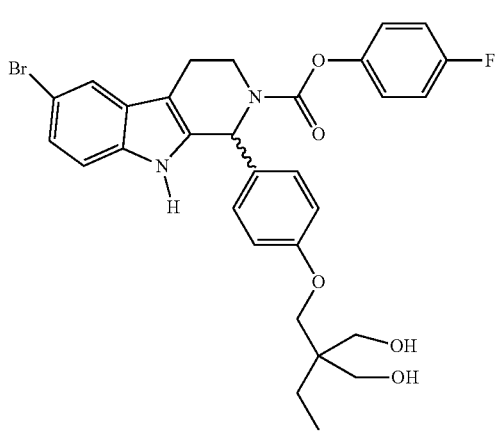

1736

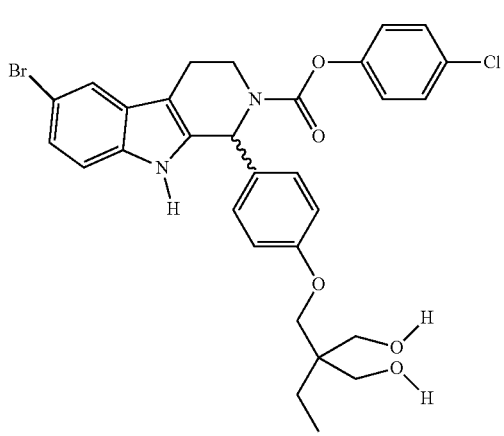

1737

1738

1739 or a pharmaceutically acceptable salt, racemate or stereoisomer thereof;

wherein administering the compound to the human produces at least two of the results selected from the group consisting of:

(i) decrease in the number of circulating tumor cells in the blood;

(ii) increase in survival of the human;

(iii) regression of the prostate cancer or benign prostatic hyperplasia;

(iv) reduction in growth of the prostate cancer or benign prostatic hyperplasia;

(v) inhibition or decrease in prostate-specific antigen levels in the range of about 30% to 100% relative to the prostate-specific antigen level prior to administration of the compound;

(vi) decrease in tumor or benign prostatic hyperplasia metabolism or perfusion;

(vii) stabilization or decrease in tumor or benign prostatic hyperplasia blood flow or metabolism; and (viii) stabilization or decrease in peritumoral or peri-benign prostatic hyperplasia inflammation or edema.

15. The method of any one of claims 1, 11, 12, 13, and 14, wherein said compound is a stereoisomer having a chiral carbon atom at the substituted carbon atom in the beta-position to the nitrogen atom of the five-membered ring of the tricyclic core, and said compound is an (S) stereoisomer at said chiral carbon atom.

* * * * *

UNITED STATES PATENT AND TRADEMARK OFFICE
CERTIFICATE OF CORRECTION

| | |
|---|---|
| PATENT NO. | : 8,703,726 B2 |
| APPLICATION NO. | : 13/321213 |
| DATED | : April 22, 2014 |
| INVENTOR(S) | : Cao et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 6 days.

Signed and Sealed this
Fourth Day of August, 2015

Michelle K. Lee
*Director of the United States Patent and Trademark Office*